(12) United States Patent
Bruenker et al.

(10) Patent No.: US 11,242,390 B2
(45) Date of Patent: Feb. 8, 2022

(54) PROTEASE-ACTIVATED T CELL BISPECIFIC MOLECULES

(71) Applicant: Hoffmann-La Roche Inc., Little Falls, NJ (US)

(72) Inventors: Peter Bruenker, Hittnau (CH); Rebecca Croasdale-Wood, Preston (GB); Christian Klein, Bonstetten (CH); Juergen Michael Schanzer, Munich (DE); Kay-Gunnar Stubenrauch, Penzberg (DE); Pablo Umana, Wollerau (CH); Martina Geiger, Obfelden (CH); Eric Sullivan, Pleasanton, CA (US); Jigar Patel, Pleasanton, CA (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/138,417

(22) Filed: Sep. 21, 2018

(65) Prior Publication Data

US 2019/0119383 A1 Apr. 25, 2019

Related U.S. Application Data

(63) Continuation of application No. PCT/EP2017/056556, filed on Mar. 20, 2017.

(60) Provisional application No. 62/433,327, filed on Dec. 13, 2016.

(30) Foreign Application Priority Data

Mar. 22, 2016 (EP) ..................... 16161740

(51) Int. Cl.
| | | |
|---|---|---|
| *C07K 16/28* | (2006.01) | |
| *A61P 35/00* | (2006.01) | |
| *C07K 16/42* | (2006.01) | |
| *A61K 39/00* | (2006.01) | |

(52) U.S. Cl.
CPC .......... *C07K 16/2809* (2013.01); *A61P 35/00* (2018.01); *C07K 16/28* (2013.01); *C07K 16/2863* (2013.01); *C07K 16/4208* (2013.01); *A61K 2039/505* (2013.01); *C07K 2317/31* (2013.01); *C07K 2317/524* (2013.01); *C07K 2317/526* (2013.01); *C07K 2317/55* (2013.01); *C07K 2317/622* (2013.01); *C07K 2317/64* (2013.01); *C07K 2317/71* (2013.01); *C07K 2317/73* (2013.01); *C07K 2319/50* (2013.01)

(58) Field of Classification Search
CPC ............ C07K 16/2809; C07K 16/4208; C07K 16/28; C07K 16/2863; C07K 2317/526; C07K 2317/524; C07K 2317/31; C07K 2317/55; C07K 2317/64; C07K 2317/71; C07K 2319/50; C07K 2317/73; C07K 2317/622; C07K 7/06; C07K 7/08; A61P 35/00; A61K 2039/505

See application file for complete search history.

(56) References Cited

U.S. PATENT DOCUMENTS

| | | |
|---|---|---|
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,809,185 B1 | 10/2004 | Schoonjans et al. |
| 7,332,581 B2 | 2/2008 | Presta |
| 7,695,936 B2 | 4/2010 | Carter et al. |
| 8,227,577 B2 | 7/2012 | Klein et al. |
| 8,242,247 B2 | 8/2012 | Klein et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,969,526 B2 | 3/2015 | Baehner et al. |
| 9,068,008 B2 | 6/2015 | Mossner et al. |

(Continued)

FOREIGN PATENT DOCUMENTS

| | | |
|---|---|---|
| EP | 0404097 B1 | 9/1996 |
| EP | 1870459 A1 | 12/2007 |

(Continued)

OTHER PUBLICATIONS

Paul, Fundamental Immunology, 3rd Edition, pp. 292-295 (Year: 1993).*

(Continued)

*Primary Examiner* — Phuong Huynh

(74) *Attorney, Agent, or Firm* — Clark & Elbing LLP; Karen L. Elbing

(57) ABSTRACT

The present invention generally relates to novel protease-activatable T cell activating bispecific molecules and idiotype-specific polypeptides. The present invention also relates to polynucleotides encoding such protease-activatable T cell activating bispecific molecules and idiotype-specific polypeptides, and vectors and host cells comprising such polynucleotides. The invention further relates to methods for producing the protease-activatable T cell activating bispecific molecules and idiotype-specific polypeptides of the invention, and to methods of using these protease-activatable T cell activating bispecific molecules and idiotype-specific polypeptides in the treatment of disease.

5 Claims, 95 Drawing Sheets

Specification includes a Sequence Listing.

(56) References Cited

U.S. PATENT DOCUMENTS

| | | |
|---|---|---|
| 9,207,238 B2 | 12/2015 | Ando et al. |
| 9,266,938 B2 | 2/2016 | Ast et al. |
| 9,266,967 B2 | 2/2016 | Klein et al. |
| 9,382,323 B2 | 7/2016 | Brinkmann et al. |
| 9,447,159 B2 | 9/2016 | Ast et al. |
| 9,522,196 B2 | 12/2016 | Matsuyama et al. |
| 9,526,797 B2 | 12/2016 | Gerdes et al. |
| 2007/0111281 A1 | 5/2007 | Sondermann et al. |
| 2008/0241152 A1 | 10/2008 | Alitalo et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0233079 A1* | 9/2010 | Jakob .................. A61P 11/06 424/1.49 |
| 2010/0310571 A1* | 12/2010 | Cheung ............. A61K 51/1078 424/141.1 |
| 2010/0316645 A1 | 12/2010 | Imhof-Jung et al. |
| 2011/0293613 A1 | 12/2011 | Brinkmann et al. |
| 2012/0225071 A1 | 9/2012 | Klein et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2013/0266579 A1* | 10/2013 | Wei ...................... A61P 25/00 424/158.1 |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0205610 A1 | 7/2014 | Ando et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0308285 A1 | 10/2014 | Yan et al. |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0079088 A1* | 3/2015 | Lowman ............. C07K 16/2809 424/135.1 |
| 2015/0166661 A1 | 6/2015 | Chen et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0175397 A1 | 6/2016 | Umana et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209625 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |

FOREIGN PATENT DOCUMENTS

| | | | |
|---|---|---|---|
| EP | 1870459 A4 | 9/2010 | |
| EP | 2578230 A1 | 4/2013 | |
| EP | 2647707 A1 | 10/2013 | |
| EP | 2647707 A4 | 4/2014 | |
| EP | 2982694 A1 | 2/2016 | |
| EP | 1870459 B1 | 6/2016 | |
| WO | WO-91/03493 A1 | 3/1991 | |
| WO | WO-93/16185 A2 | 8/1993 | |
| WO | WO-96/01126 A1 | 1/1996 | |
| WO | WO-96/27011 A1 | 9/1996 | |
| WO | WO-96/40210 A1 | 12/1996 | |
| WO | WO-98/50431 A2 | 11/1998 | |
| WO | WO-98/50431 A3 | 1/1999 | |
| WO | WO-02/09573 A2 | 2/2002 | |
| WO | WO-2005/044859 A2 | 5/2005 | |
| WO | WO-2006/082515 A2 | 8/2006 | |
| WO | WO-2006/099141 A2 | 9/2006 | |
| WO | WO-2007/024715 A2 | 3/2007 | |
| WO | WO-2007/042261 A2 | 4/2007 | |
| WO | WO-2007/075270 A2 | 7/2007 | |
| WO | WO-2007/110205 A2 | 10/2007 | |
| WO | WO-2007/146968 A2 | 12/2007 | |
| WO | WO-2007/147901 A1 | 12/2007 | |
| WO | WO-2007/024715 A3 | 10/2008 | |
| WO | WO-2008/119566 A2 | 10/2008 | |
| WO | WO-2008/119567 A2 | 10/2008 | |
| WO | WO-2007/024715 A9 | 4/2009 | |
| WO | WO-2009/070642 A1 | 6/2009 | |
| WO | WO-2009/080251 A1 | 7/2009 | |
| WO | WO-2009/080252 A1 | 7/2009 | |
| WO | WO-2009/080253 A1 | 7/2009 | |
| WO | WO-2009/080254 A1 | 7/2009 | |
| WO | WO-2009/089004 A1 | 7/2009 | |
| WO | WO-2010096838 A2 * | 8/2010 | ............. C07K 14/00 |
| WO | WO-2010/115589 A1 | 10/2010 | |
| WO | WO-2010/129304 A2 | 11/2010 | |
| WO | WO-2010/136172 A1 | 12/2010 | |
| WO | WO-2010/145792 A1 | 12/2010 | |
| WO | WO-2010/145793 A1 | 12/2010 | |
| WO | WO-2010/129304 A3 | 2/2011 | |
| WO | WO-2011/028952 A1 | 3/2011 | |
| WO | WO-2011/090754 A1 | 7/2011 | |
| WO | WO-2011/090762 A1 | 7/2011 | |
| WO | WO-2011/143545 A1 | 11/2011 | |
| WO | WO-2012/058768 A1 | 5/2012 | |
| WO | WO-2012/058768 A8 | 6/2012 | |
| WO | WO-2012/073985 A1 | 6/2012 | |
| WO | WO-2012/130831 A1 | 10/2012 | |
| WO | WO-2012/158818 A2 | 11/2012 | |
| WO | WO-2012/162067 A2 | 11/2012 | |
| WO | WO-2013/026831 A1 | 2/2013 | |
| WO | WO-2013/026833 A1 | 2/2013 | |
| WO | WO-2013/026837 A1 | 2/2013 | |
| WO | WO-2013/072406 A1 | 5/2013 | |
| WO | WO-2013/096291 A2 | 6/2013 | |
| WO | WO-2013/157953 A1 | 10/2013 | |
| WO | WO-2013/157954 A1 | 10/2013 | |
| WO | WO-2014/004549 A2 | 1/2014 | |
| WO | WO-2014/022540 A1 | 2/2014 | |
| WO | WO-2014/028560 A2 | 2/2014 | |
| WO | WO-2014/047231 A1 | 3/2014 | |
| WO | WO-2014/028560 A3 | 5/2014 | |
| WO | WO-2014/081955 A1 | 5/2014 | |
| WO | WO-2014/087863 A1 | 6/2014 | |
| WO | WO-2014/104270 A1 | 7/2014 | |
| WO | WO-2014/122143 A1 | 8/2014 | |
| WO | WO-2014/122144 A1 | 8/2014 | |
| WO | WO-2014/122251 A2 | 8/2014 | |
| WO | WO-2014/131694 A1 | 9/2014 | |
| WO | WO-2014/141152 A1 | 9/2014 | |
| WO | WO-2014/144722 A2 | 9/2014 | |
| WO | WO-2014/151910 A1 | 9/2014 | |
| WO | WO-2014/153002 A1 | 9/2014 | |
| WO | WO-2014/122251 A3 | 10/2014 | |
| WO | WO-2014/161845 A1 | 10/2014 | |
| WO | WO-2014/167022 A1 | 10/2014 | |
| WO | WO-2014/141152 A3 | 12/2014 | |

(56) References Cited

FOREIGN PATENT DOCUMENTS

| WO | WO-2014/191113 A1 | 12/2014 |
|---|---|---|
| WO | WO-2014/191113 A8 | 12/2014 |
| WO | WO-2015/001085 A1 | 1/2015 |
| WO | WO-2015/013671 A1 | 1/2015 |
| WO | WO-2015/018085 A1 | 2/2015 |
| WO | WO-2015/048272 A1 | 4/2015 |
| WO | WO-2015/150447 A1 | 10/2015 |
| WO | WO-2016/014974 A2 | 1/2016 |
| WO | WO-2016/020065 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/077505 A2 | 5/2016 |
| WO | WO-2016/079076 A1 | 5/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/146894 A1 | 9/2016 |
| WO | WO-2016/179003 A1 | 11/2016 |
| WO | WO-2017/021450 A1 | 2/2017 |

OTHER PUBLICATIONS

Rudikoff et al., Proc. Natl. Acad. Sci. USA, 79:1979-1983 (Year: 1982).*
Lloyd et a., Protein Engineering, Design & Selection 22:159-168 (Year: 2009).*
Edwards et al., J Mol Biol. 334(1): 103-118 (Year: 2003).*
Stancovski et al., Proceedings of the National Academy of Science USA 88: 8691-8695 (Year: 1991).*
Riemer et al., Mol. Immunol. 42: 1121-1124 (Year: 2005).*
Carreno et al., "First step toward the marine idiotypic network generated by OKT3," Human Immunology. 32:12 (1991) (Abstract only) (1 page).
Cui et al., "Chemically programmed bispecific antibodies that recruit and activate T cells," J Biol Chem. 287(34):28206-14 (10 Pages) (2012).
Mezzanzanica et al., "Human ovarian carcinoma lysis by cytotoxic T cells targeted by bispecific monoclonal antibodies: analysis of the antibody components," Int J Cancer. 41(4):609-15 (1988).
Atwell et al., "Stable heterodimers from remodeling the domain interface of a homodimer using a phage display library," J Mol Biol. 270(1):26-35 (1997).
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).
Carter, "Bispecific human IgG by design," J Immunol Methods. 248(1-2):7-15 (2001).
Chan et al., "Variable region domain exchange in human IgGs promotes antibody complex formation with accompanying structural changes and altered effector functions," Mol Immunol. 41(5):527-38 (2004).
Edelman et al., "The covalent structure of an entire gammaG immunoglobulin molecule," Proc Natl Acad Sci U S A. 63(1):78-85 (1969).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).

Hudson et al., "Engineered antibodies," Nat Med. 9(1):129-34 (2003).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Pessano et al., "The T3/T cell receptor complex: antigenic distinction between the two 20-kd T3 (T3-delta and T3-epsilon) subunits," EMBO J. 4(2):337-44 (1985).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM × anti-CD3) as a targeted cancer immunotherapy," Cancer Treat Rev. 36(6):458-67 (2010).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BiTE antibody that engages patient-derived T cells," J Immunother. 34(8):597-605 (2011).
Tutt et al., "Trispecific F(ab')3 derivatives that use cooperative signaling via the TCR/CD3 complex and CD2 to activate and redirect resting cytotoxic T cells," J Immunol. 147(1):60-9 (1991).
Wolf et al., "BiTEs: bispecific antibody constructs with unique anti-tumor activity," Drug Discov Today. 10(18):1237-44 (2005).
Zhu et al., "Identification of heavy chain residues in a humanized anti-CD3 antibody important for efficient antigen binding and T cell activation," J Immunol. 155(4):1903-10 (1995).
Carreno et al., "Cross-species reactivity of the anti-idiotype anti-OKT3 cascade between mice and humans," Hum Immunol. 33(4):249-58 (1992).
Edwards et al., "The remarkable flexibility of the human antibody repertoire; isolation of over one thousand different antibodies to a single protein, BLyS," J Mol Biol. 334(1):103-18 (2003).
Katayose et al., "MUC1-specific targeting immunotherapy with bispecific antibodies: inhibition of xenografted human bile duct carcinoma growth," Cancer Res. 56(18):4205-12 (1996) (9 pages).
Lloyd et al., "Modelling the human immune response: performance of a $10^{11}$ human antibody repertoire against a broad panel of therapeutically relevant antigens". Protein Eng Des Sel 22(3):159-68 (2009).
Paul, Chapter 9: Structure and Function of Immunoglobulins, *Fundamental Immunology, Third Edition*. Raven Press Ltd., 292-295 (1993) (6 pages).

(56) References Cited

OTHER PUBLICATIONS

Rudikoff et al., "Single amino acid substitution altering antigen-binding specificity," Proc Natl Acad Sci U S A. 79(6):1979-83 (1982).
Office Action for U.S. Appl. No. 16/138,417, dated May 18, 2020 (20 pages).
Search Report and Written Opinion for Singaporean Patent Application No. 11201808085, dated Mar. 3, 2020 (10 pages).
English Translation of Office Action and Search Report for Chinese Patent Application No. 201580059475.0, dated Jun. 22, 2020 (15 pages).
English Translation of Office Action and Search Report for Chinese Patent Application No. 201580073564.0, dated Jul. 21, 2020 (5 pages).
English Translation of Office Action for Chinese Patent Application No. 201580073062.8, dated Jul. 3, 2020 (21 pages).
Office Action for U.S. Appl. No. 15/600,011, dated Sep. 17, 2019 (43 pages).
Search Report and Written Opinion for Brazilian Patent Application No. BR112017007086-3, dated Oct. 4, 2020 (4 pages).
Second Written Opinion for Singaporean Patent Application No. 11201702976T, dated Apr. 15, 2020 (10 pages).

* cited by examiner

| Clone ID | Isotype | Temp | $k_a$ (1/Ms) | $k_d$ (1/s) | $t_{1/2}$ diss. (min) | $K_D$ (nM) |
|---|---|---|---|---|---|---|
| A9263 | IgG1, kappa | 25°C | 1.96E+05 | 1.05E-04 | 110 | 1 |
|  |  | 37°C | 3.46E+05 | 6.52E-04 | 18 | 2 |
| A9577 | IgG1, kappa | 25°C | 1.66E+05 | 2.09E-04 | 55 | 1 |
|  |  | 37°C | 2.68E+05 | 6.96E-04 | 17 | 3 |
| A9KBB | IgG2b, kappa | 25°C | 2.71E+05 | 1.87E-03 | 6 | 7 |
|  |  | 37°C | 4.28E+05 | 3.24E-03 | 4 | 8 |
| A2472 | IgG1, kappa | 25°C | 8.72E+04 | 1.18E-03 | 10 | 14 |
|  |  | 37°C | 1.55E+05 | 4.45E-03 | 3 | 29 |
| A2178 | IgG1, kappa | 25°C | 1.31E+05 | 3.06E-03 | 4 | 23 |
|  |  | 37°C | 4.25E+05 | 9.28E-03 | 1 | 22 |
| A15AA | IgG2b, kappa | 25°C | 2.61E+04 | 2.50E-03 | 5 | 96 |
|  |  | 37°C | 1.44E+05 | 1.35E-02 | 1 | 94 |

FIG. 2

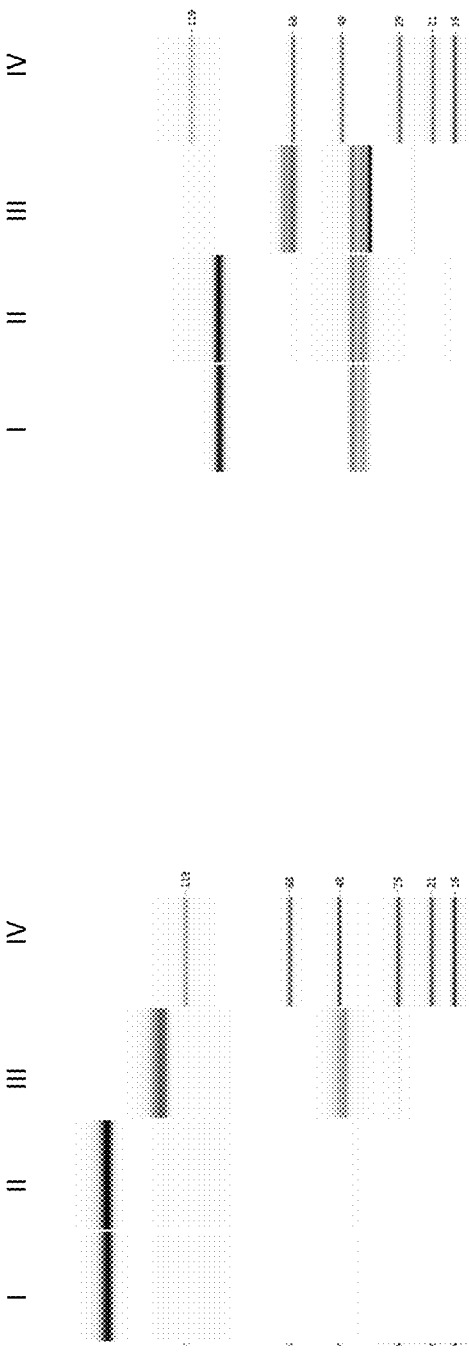

| EC50 | | |
|---|---|---|
| 7859 scFv 4.15.64 MK062 protease site | 4710 | 16 fold more than 7861 |
| 7861 | 286 | 16 fold less than 7859 |
| 7860 scFv 4.32.63 MK062 protease site | 15538 | 54 fold more than 7861 |
| 7861 | 286 | 54 fold less than 7860 |

| Human cell lines | FolR1 density |
|---|---|
| Hela | 2'240'716 |
| Skov3 | 91'510 |
| HT29 | 10'135 |
| MKN45 | 54 |
| Human Renal Cortical Epithelial Cells (HRCEpiC) | 312 |

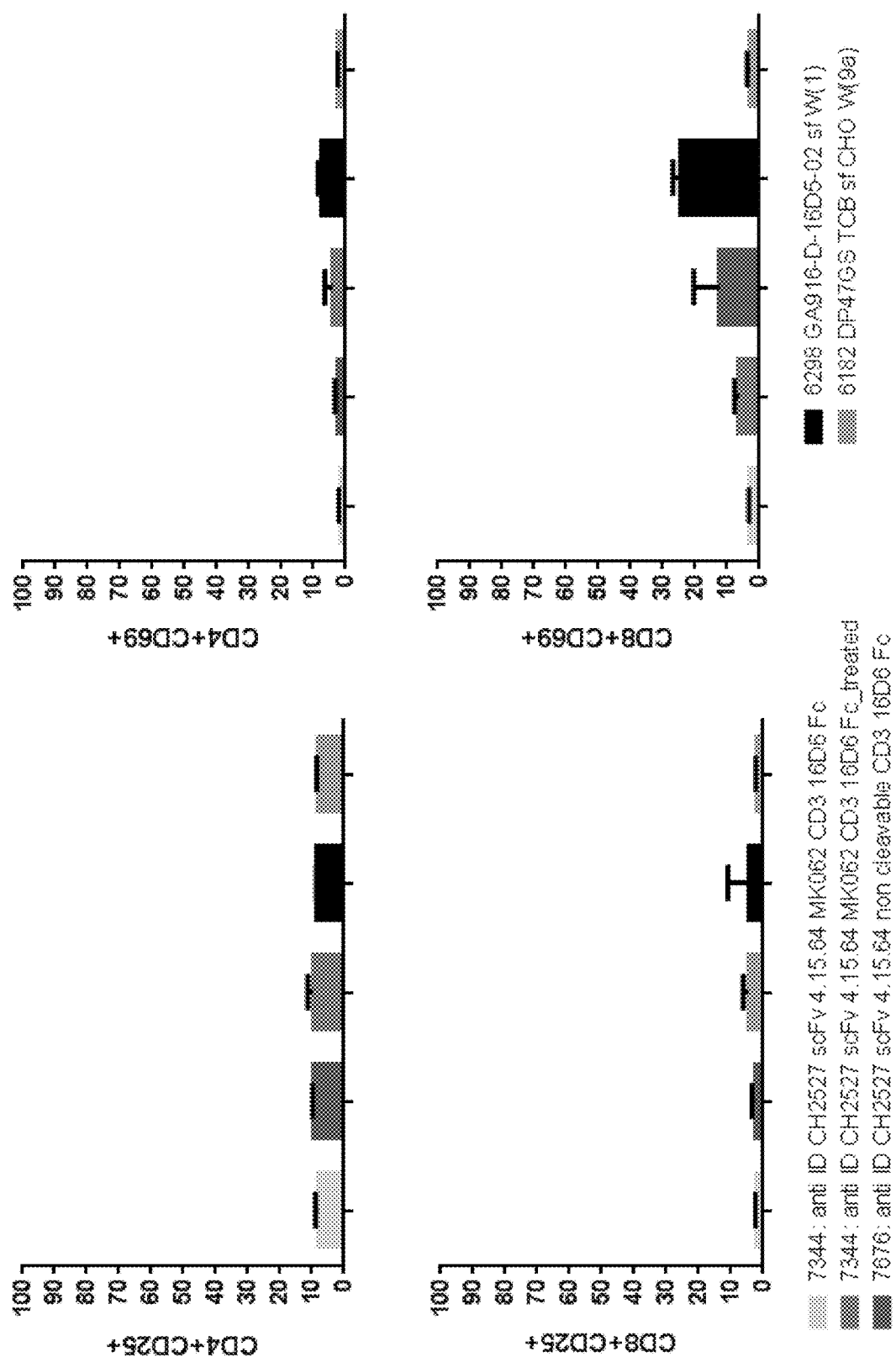

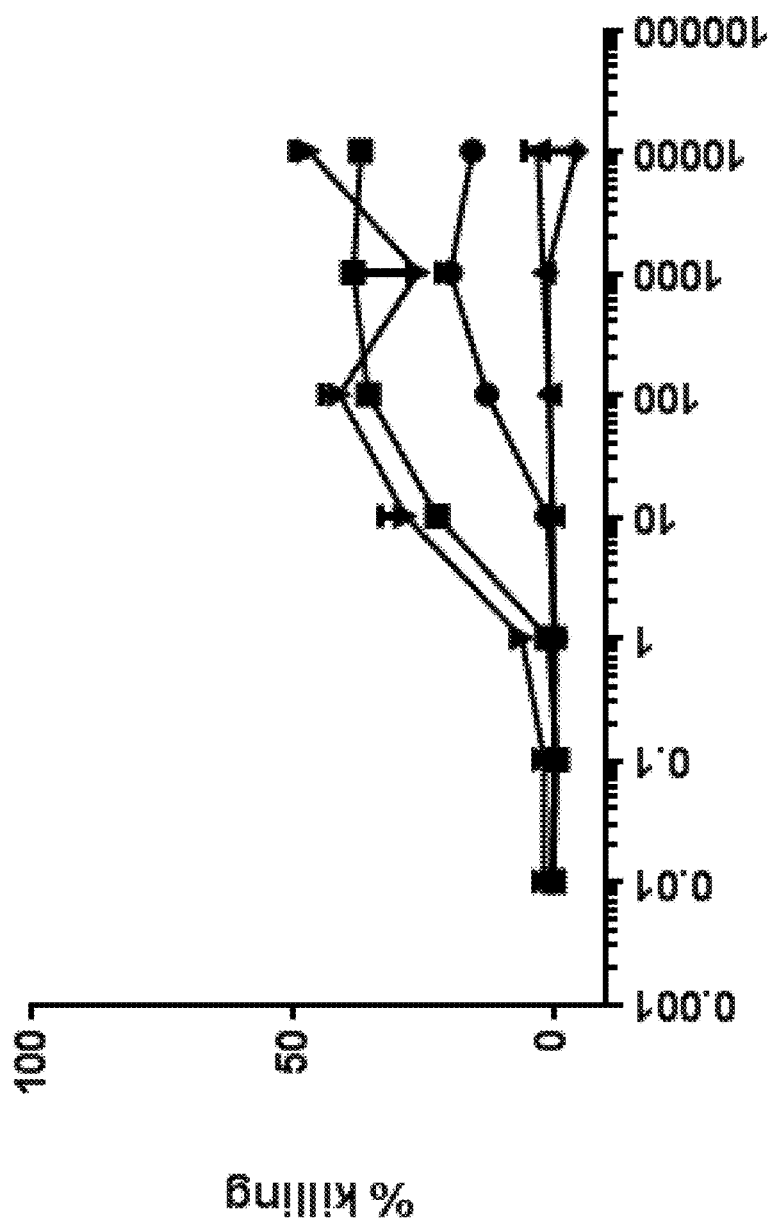

| Molecule | Isotype | Temp. | $k_a$ (1/Ms) | $k_d$ (1/s) | $K_D$ (nM) |
|---|---|---|---|---|---|
| GA201 | IgG1, kappa | 37°C | 1.68E+05 | 1.20E-04 | 1 |
| GA201-anti-GA201-scFv MMP2 cleaved | IgG1, kappa | 37°C | 1.03E+05 | 1.63E-04 | 2 |
| GA201-anti-GA201-scFv without MMP2 | IgG1, kappa | 37°C | - | - | - |

SEQUENCE LISTING

<160> NUMBER OF SEQ ID NOS: 170

<210> SEQ ID NO 1
<211> LENGTH: 215
<212> TYPE: PRT
<213> ORGANISM: Artificial Sequence
<220> FEATURE:
<223> OTHER INFORMATION: Synthetic Construct

<400> SEQUENCE: 1

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175
```

```
Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 2
<211> LENGTH: 971
<212> TYPE: PRT
<213> ORGANISM: Artificial Sequence
<220> FEATURE:
<223> OTHER INFORMATION: Synthetic Construct

<400> SEQUENCE: 2

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Asp Tyr
            20                  25                  30

Ser Ile His Trp Val Lys Gln Ala Pro Gly Lys Cys Leu Lys Trp Met
        35                  40                  45

Gly Trp Ile Asn Thr Glu Thr Gly Glu Pro Ala Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Phe Phe Cys
                85                  90                  95

Ala His Pro Tyr Asp Tyr Asp Val Leu Asp Tyr Trp Gly Gln Gly Thr
            100                 105                 110

Ser Val Thr Val Ser Ser Gly Gly Gly Ser Gly Gly Gly Gly Ser
        115                 120                 125

Gly Gly Gly Gly Ser Gly Gly Gly Ser Asp Thr Val Leu Thr Gln
    130                 135                 140

Ser Pro Ala Ser Leu Gly Val Ser Leu Gly Gln Arg Ala Thr Ile Ser
145                 150                 155                 160

Cys Arg Ala Ser Lys Ser Val Ser Thr Ser Asn Tyr Ser Tyr Ile His
                165                 170                 175

Trp Tyr Gln Gln Lys Pro Gly Gln Pro Pro Lys Leu Leu Ile Lys Tyr
            180                 185                 190

Val Ser Tyr Leu Glu Ser Gly Val Pro Ala Arg Phe Ser Gly Ser Gly
        195                 200                 205

Ser Gly Thr Asp Phe Thr Leu Asn Ile His Pro Val Glu Glu Glu Asp
    210                 215                 220

Ala Ala Thr Tyr Tyr Cys Gln His Ser Arg Glu Phe Pro Trp Thr Phe
225                 230                 235                 240

Gly Cys Gly Thr Lys Leu Glu Ile Lys Gly Gly Gly Ser Gly Gly
                245                 250                 255

Gly Gly Ser Arg Gln Ala Arg Val Val Asn Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Ala Ser Gly Phe Thr Phe Ser Thr Tyr Ala Met Asn Trp Val Arg
305                 310                 315                 320
```

```
Gln Ala Pro Gly Lys Gly Leu Glu Trp Val Ser Arg Ile Arg Ser Lys
                325                 330                 335

Tyr Asn Asn Tyr Ala Thr Tyr Ala Asp Ser Val Lys Gly Arg Phe
            340                 345                 350

Thr Ile Ser Arg Asp Asp Ser Lys Asn Thr Leu Tyr Leu Gln Met Asn
                355                 360                 365

Ser Leu Arg Ala Glu Asp Thr Ala Val Tyr Tyr Cys Val Arg His Gly
            370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
            405                 410                 415

Pro Leu Ala Pro Ser Ser Lys Ser Thr Ser Gly Gly Thr Ala Ala Leu
            420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
            450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
            485                 490                 495

Ser Asn Thr Lys Val Asp Lys Lys Val Glu Pro Lys Ser Cys Asp Gly
            500                 505                 510

Gly Gly Gly Ser Gly Gly Gly Gly Ser Glu Val Gln Leu Val Glu Ser
            515                 520                 525

Gly Gly Gly Leu Val Lys Pro Gly Gly Ser Leu Arg Leu Ser Cys Ala
            530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
                565                 570                 575

Asp Gly Gly Thr Thr Asp Tyr Ala Ala Pro Val Lys Gly Arg Phe Thr
                580                 585                 590

Ile Ser Arg Asp Asp Ser Lys Asn Thr Leu Tyr Leu Gln Met Asn Ser
                595                 600                 605

Leu Lys Thr Glu Asp Thr Ala Val Tyr Tyr Cys Thr Thr Pro Trp Glu
            610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
                645                 650                 655

Lys Ser Thr Ser Gly Gly Thr Ala Ala Leu Gly Cys Leu Val Lys Asp
                660                 665                 670

Tyr Phe Pro Glu Pro Val Thr Val Ser Trp Asn Ser Gly Ala Leu Thr
            675                 680                 685

Ser Gly Val His Thr Phe Pro Ala Val Leu Gln Ser Ser Gly Leu Tyr
            690                 695                 700

Ser Leu Ser Ser Val Val Thr Val Pro Ser Ser Ser Leu Gly Thr Gln
705                 710                 715                 720

Thr Tyr Ile Cys Asn Val Asn His Lys Pro Ser Asn Thr Lys Val Asp
                725                 730                 735
```

-continued

```
Lys Lys Val Glu Pro Lys Ser Cys Asp Lys Thr His Thr Cys Pro Pro
            740                 745                 750

Cys Pro Ala Pro Glu Ala Ala Gly Gly Pro Ser Val Phe Leu Phe Pro
        755                 760                 765

Pro Lys Pro Lys Asp Thr Leu Met Ile Ser Arg Thr Pro Glu Val Thr
    770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                805                 810                 815

Glu Glu Gln Tyr Asn Ser Thr Tyr Arg Val Val Ser Val Leu Thr Val
            820                 825                 830

Leu His Gln Asp Trp Leu Asn Gly Lys Glu Tyr Lys Cys Lys Val Ser
        835                 840                 845

Asn Lys Ala Leu Gly Ala Pro Ile Glu Lys Thr Ile Ser Lys Ala Lys
    850                 855                 860

Gly Gln Pro Arg Glu Pro Gln Val Tyr Thr Leu Pro Pro Cys Arg Asp
865                 870                 875                 880

Glu Leu Thr Lys Asn Gln Val Ser Leu Trp Cys Leu Val Lys Gly Phe
                885                 890                 895

Tyr Pro Ser Asp Ile Ala Val Glu Trp Glu Ser Asn Gly Gln Pro Glu
            900                 905                 910

Asn Asn Tyr Lys Thr Thr Pro Pro Val Leu Asp Ser Asp Gly Ser Phe
        915                 920                 925

Phe Leu Tyr Ser Lys Leu Thr Val Asp Lys Ser Arg Trp Gln Gln Gly
    930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
                965                 970

<210> SEQ ID NO 3
<211> LENGTH: 450
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 4
<211> LENGTH: 971
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30
```

```
Gly Val Ser Trp Val Arg Gln Pro Gly Lys Cys Leu Glu Trp Leu
         35                  40                  45

Gly Ile Ile Trp Gly Asp Gly Ser Thr Asn Tyr His Ser Ala Leu Ile
 50                  55                  60

Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
             85                  90                  95

Lys Gly Ile Thr Thr Val Val Asp Tyr Tyr Ala Met Asp Tyr Trp
                100                 105                 110

Gly Gln Gly Thr Ser Val Thr Val Ser Ser Gly Gly Gly Ser Gly
             115                 120                 125

Gly Gly Gly Ser Gly Gly Gly Ser Gly Gly Gly Ser Asp Ile
         130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
             180                 185                 190

Ala Thr Phe Leu Ala Asp Asp Val Pro Ser Arg Phe Ser Gly Ser Gly
         195                 200                 205

Ser Gly Thr Gln Tyr Ser Leu Lys Ile Asn Ser Leu Gln Ser Glu Asp
     210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Arg Gln Ala Arg Val Val Asn Gly Gly Gly Gly Ser
             260                 265                 270

Gly Gly Gly Gly Ser Gly Gly Gly Ser Glu Val Gln Leu Leu Glu
         275                 280                 285

Ser Gly Gly Gly Leu Val Gln Pro Gly Gly Ser Leu Arg Leu Ser Cys
290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Tyr Ala Asp Ser Val Lys Gly Arg Phe
             340                 345                 350

Thr Ile Ser Arg Asp Asp Ser Lys Asn Thr Leu Tyr Leu Gln Met Asn
         355                 360                 365

Ser Leu Arg Ala Glu Asp Thr Ala Val Tyr Tyr Cys Val Arg His Gly
     370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
                405                 410                 415

Pro Leu Ala Pro Ser Ser Lys Ser Thr Ser Gly Gly Thr Ala Ala Leu
             420                 425                 430

Gly Cys Leu Val Lys Asp Tyr Phe Pro Glu Pro Val Thr Val Ser Trp
         435                 440                 445

Asn Ser Gly Ala Leu Thr Ser Gly Val His Thr Phe Pro Ala Val Leu
```

```
                450                 455                 460
Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
                485                 490                 495

Ser Asn Thr Lys Val Asp Lys Lys Val Glu Pro Lys Ser Cys Asp Gly
            500                 505                 510

Gly Gly Gly Ser Gly Gly Gly Ser Glu Val Gln Leu Val Glu Ser
        515                 520                 525

Gly Gly Gly Leu Val Lys Pro Gly Gly Ser Leu Arg Leu Ser Cys Ala
    530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
                565                 570                 575

Asp Gly Gly Thr Thr Asp Tyr Ala Ala Pro Val Lys Gly Arg Phe Thr
            580                 585                 590

Ile Ser Arg Asp Asp Ser Lys Asn Thr Leu Tyr Leu Gln Met Asn Ser
        595                 600                 605

Leu Lys Thr Glu Asp Thr Ala Val Tyr Tyr Cys Thr Thr Pro Trp Glu
    610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
                645                 650                 655

Lys Ser Thr Ser Gly Gly Thr Ala Ala Leu Gly Cys Leu Val Lys Asp
            660                 665                 670

Tyr Phe Pro Glu Pro Val Thr Val Ser Trp Asn Ser Gly Ala Leu Thr
        675                 680                 685

Ser Gly Val His Thr Phe Pro Ala Val Leu Gln Ser Ser Gly Leu Tyr
    690                 695                 700

Ser Leu Ser Ser Val Val Thr Val Pro Ser Ser Ser Leu Gly Thr Gln
705                 710                 715                 720

Thr Tyr Ile Cys Asn Val Asn His Lys Pro Ser Asn Thr Lys Val Asp
                725                 730                 735

Lys Lys Val Glu Pro Lys Ser Cys Asp Lys Thr His Thr Cys Pro Pro
            740                 745                 750

Cys Pro Ala Pro Glu Ala Ala Gly Gly Pro Ser Val Phe Leu Phe Pro
        755                 760                 765

Pro Lys Pro Lys Asp Thr Leu Met Ile Ser Arg Thr Pro Glu Val Thr
    770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                805                 810                 815

Glu Glu Gln Tyr Asn Ser Thr Tyr Arg Val Val Ser Val Leu Thr Val
            820                 825                 830

Leu His Gln Asp Trp Leu Asn Gly Lys Glu Tyr Lys Cys Lys Val Ser
        835                 840                 845

Asn Lys Ala Leu Gly Ala Pro Ile Glu Lys Thr Ile Ser Lys Ala Lys
    850                 855                 860

Gly Gln Pro Arg Glu Pro Gln Val Tyr Thr Leu Pro Pro Cys Arg Asp
865                 870                 875                 880
```

```
Glu Leu Thr Lys Asn Gln Val Ser Leu Trp Cys Leu Val Lys Gly Phe
            885                 890                 895

Tyr Pro Ser Asp Ile Ala Val Glu Trp Glu Ser Asn Gly Gln Pro Glu
            900                 905                 910

Asn Asn Tyr Lys Thr Thr Pro Pro Val Leu Asp Ser Asp Gly Ser Phe
            915                 920                 925

Phe Leu Tyr Ser Lys Leu Thr Val Asp Lys Ser Arg Trp Gln Gln Gly
            930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
            965                 970

<210> SEQ ID NO 5
<211> LENGTH: 971
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
            85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
            165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Gly Gly
            245                 250                 255

Gly Gly Ser Gly Gly Gly Gly Ser Gly Gly Gly Gly Gly Gly Gly Ser
            260                 265                 270
```

-continued

Gly Gly Gly Gly Ser Gly Gly Gly Ser Glu Val Gln Leu Leu Glu
            275                 280                 285

Ser Gly Gly Gly Leu Val Gln Pro Gly Gly Ser Leu Arg Leu Ser Cys
290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Tyr Ala Asp Ser Val Lys Gly Arg Phe
                340                 345                 350

Thr Ile Ser Arg Asp Asp Ser Lys Asn Thr Leu Tyr Leu Gln Met Asn
            355                 360                 365

Ser Leu Arg Ala Glu Asp Thr Ala Val Tyr Tyr Cys Val Arg His Gly
            370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
                405                 410                 415

Pro Leu Ala Pro Ser Ser Lys Ser Thr Ser Gly Gly Thr Ala Ala Leu
                420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
            450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
                485                 490                 495

Ser Asn Thr Lys Val Asp Lys Lys Val Glu Pro Lys Ser Cys Asp Gly
            500                 505                 510

Gly Gly Gly Ser Gly Gly Gly Ser Glu Val Gln Leu Val Glu Ser
            515                 520                 525

Gly Gly Gly Leu Val Lys Pro Gly Gly Ser Leu Arg Leu Ser Cys Ala
            530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
                565                 570                 575

Asp Gly Gly Thr Thr Asp Tyr Ala Ala Pro Val Lys Gly Arg Phe Thr
                580                 585                 590

Ile Ser Arg Asp Asp Ser Lys Asn Thr Leu Tyr Leu Gln Met Asn Ser
            595                 600                 605

Leu Lys Thr Glu Asp Thr Ala Val Tyr Tyr Cys Thr Thr Pro Trp Glu
            610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
                645                 650                 655

Lys Ser Thr Ser Gly Gly Thr Ala Ala Leu Gly Cys Leu Val Lys Asp
            660                 665                 670

Tyr Phe Pro Glu Pro Val Thr Val Ser Trp Asn Ser Gly Ala Leu Thr
            675                 680                 685

```
Ser Gly Val His Thr Phe Pro Ala Val Leu Gln Ser Ser Gly Leu Tyr
    690             695                 700
Ser Leu Ser Ser Val Val Thr Val Pro Ser Ser Ser Leu Gly Thr Gln
705             710                 715                 720
Thr Tyr Ile Cys Asn Val Asn His Lys Pro Ser Asn Thr Lys Val Asp
            725                 730                 735
Lys Lys Val Glu Pro Lys Ser Cys Asp Lys Thr His Thr Cys Pro Pro
        740                 745                 750
Cys Pro Ala Pro Glu Ala Ala Gly Gly Pro Ser Val Phe Leu Phe Pro
            755                 760                 765
Pro Lys Pro Lys Asp Thr Leu Met Ile Ser Arg Thr Pro Glu Val Thr
770                 775                 780
Cys Val Val Val Asp Val Ser His Glu Asp Pro Glu Val Lys Phe Asn
785                 790                 795                 800
Trp Tyr Val Asp Gly Val Glu Val His Asn Ala Lys Thr Lys Pro Arg
                805                 810                 815
Glu Glu Gln Tyr Asn Ser Thr Tyr Arg Val Val Ser Val Leu Thr Val
                820                 825                 830
Leu His Gln Asp Trp Leu Asn Gly Lys Glu Tyr Lys Cys Lys Val Ser
                835                 840                 845
Asn Lys Ala Leu Gly Ala Pro Ile Glu Lys Thr Ile Ser Lys Ala Lys
850                 855                 860
Gly Gln Pro Arg Glu Pro Gln Val Tyr Thr Leu Pro Pro Cys Arg Asp
865                 870                 875                 880
Glu Leu Thr Lys Asn Gln Val Ser Leu Trp Cys Leu Val Lys Gly Phe
                885                 890                 895
Tyr Pro Ser Asp Ile Ala Val Glu Trp Glu Ser Asn Gly Gln Pro Glu
                900                 905                 910
Asn Asn Tyr Lys Thr Thr Pro Pro Val Leu Asp Ser Asp Gly Ser Phe
                915                 920                 925
Phe Leu Tyr Ser Lys Leu Thr Val Asp Lys Ser Arg Trp Gln Gln Gly
                930                 935                 940
Asn Val Phe Ser Cys Ser Val Met His Glu Ala Leu His Asn His Tyr
945                 950                 955                 960
Thr Gln Lys Ser Leu Ser Leu Ser Pro Gly Lys
                965                 970

<210> SEQ ID NO 6
<211> LENGTH: 971
<212> TYPE: PRT
<213> ORGANISM: Artificial Sequence
<220> FEATURE:
<223> OTHER INFORMATION: Synthetic Construct

<400> SEQUENCE: 6

Gln Ile Gln Leu Val Gln Ser Gly Pro Glu Leu Lys Lys Pro Gly Glu
1               5                   10                  15
Thr Val Arg Ile Ser Cys Lys Ala Ser Gly Tyr Thr Phe Thr Asp Tyr
                20                  25                  30
Ser Ile His Trp Val Lys Gln Ala Pro Gly Lys Cys Leu Lys Trp Met
            35                  40                  45
Gly Trp Ile Asn Thr Glu Thr Gly Glu Pro Ala Tyr Ala Asp Asp Phe
        50                  55                  60
Lys Gly Arg Phe Ala Phe Ser Leu Glu Thr Ser Ala Ser Thr Ala Tyr
65                  70                  75                  80
```

```
Leu Gln Ile Asn Asn Leu Lys Asn Glu Asp Thr Ala Thr Phe Phe Cys
                85                  90                  95
Ala His Pro Tyr Asp Tyr Asp Val Leu Asp Tyr Trp Gly Gln Gly Thr
            100                 105                 110
Ser Val Thr Val Ser Ser Gly Gly Gly Ser Gly Gly Gly Gly Ser
            115                 120                 125
Gly Gly Gly Gly Ser Gly Gly Gly Ser Asp Thr Val Leu Thr Gln
            130                 135                 140
Ser Pro Ala Ser Leu Gly Val Ser Leu Gly Gln Arg Ala Thr Ile Ser
145                 150                 155                 160
Cys Arg Ala Ser Lys Ser Val Ser Thr Ser Asn Tyr Ser Tyr Ile His
                165                 170                 175
Trp Tyr Gln Gln Lys Pro Gly Gln Pro Pro Lys Leu Leu Ile Lys Tyr
                180                 185                 190
Val Ser Tyr Leu Glu Ser Gly Val Pro Ala Arg Phe Ser Gly Ser Gly
                195                 200                 205
Ser Gly Thr Asp Phe Thr Leu Asn Ile His Pro Val Glu Glu Glu Asp
            210                 215                 220
Ala Ala Thr Tyr Tyr Cys Gln His Ser Arg Glu Phe Pro Trp Thr Phe
225                 230                 235                 240
Gly Cys Gly Thr Lys Leu Glu Ile Lys Gly Gly Gly Ser Gly Gly
                245                 250                 255
Gly Gly Ser Gly Gly Gly Ser Gly Gly Gly Gly Gly Gly Ser
            260                 265                 270
Gly Gly Gly Gly Ser Gly Gly Gly Ser Glu Val Gln Leu Leu Glu
            275                 280                 285
Ser Gly Gly Gly Leu Val Gln Pro Gly Gly Ser Leu Arg Leu Ser Cys
290                 295                 300
Ala Ala Ser Gly Phe Thr Phe Ser Thr Tyr Ala Met Asn Trp Val Arg
305                 310                 315                 320
Gln Ala Pro Gly Lys Gly Leu Glu Trp Val Ser Arg Ile Arg Ser Lys
                325                 330                 335
Tyr Asn Asn Tyr Ala Thr Tyr Tyr Ala Asp Ser Val Lys Gly Arg Phe
                340                 345                 350
Thr Ile Ser Arg Asp Asp Ser Lys Asn Thr Leu Tyr Leu Gln Met Asn
                355                 360                 365
Ser Leu Arg Ala Glu Asp Thr Ala Val Tyr Tyr Cys Val Arg His Gly
                370                 375                 380
Asn Phe Gly Asn Ser Tyr Val Ser Trp Phe Ala Tyr Trp Gly Gln Gly
385                 390                 395                 400
Thr Leu Val Thr Val Ser Ser Ala Ser Thr Lys Gly Pro Ser Val Phe
                405                 410                 415
Pro Leu Ala Pro Ser Ser Lys Ser Thr Ser Gly Gly Thr Ala Ala Leu
                420                 425                 430
Gly Cys Leu Val Lys Asp Tyr Phe Pro Glu Pro Val Thr Val Ser Trp
                435                 440                 445
Asn Ser Gly Ala Leu Thr Ser Gly Val His Thr Phe Pro Ala Val Leu
            450                 455                 460
Gln Ser Ser Gly Leu Tyr Ser Leu Ser Ser Val Val Thr Val Pro Ser
465                 470                 475                 480
Ser Ser Leu Gly Thr Gln Thr Tyr Ile Cys Asn Val Asn His Lys Pro
                485                 490                 495
Ser Asn Thr Lys Val Asp Lys Lys Val Glu Pro Lys Ser Cys Asp Gly
```

```
                500                 505                 510
Gly Gly Gly Ser Gly Gly Gly Ser Glu Val Gln Leu Val Glu Ser
            515                 520                 525
Gly Gly Gly Leu Val Lys Pro Gly Gly Ser Leu Arg Leu Ser Cys Ala
        530                 535                 540
Ala Ser Gly Phe Thr Phe Ser Asn Ala Trp Met Ser Trp Val Arg Gln
545                 550                 555                 560
Ala Pro Gly Lys Gly Leu Glu Trp Val Gly Arg Ile Lys Ser Lys Thr
                565                 570                 575
Asp Gly Gly Thr Thr Asp Tyr Ala Ala Pro Val Lys Gly Arg Phe Thr
            580                 585                 590
Ile Ser Arg Asp Asp Ser Lys Asn Thr Leu Tyr Leu Gln Met Asn Ser
        595                 600                 605
Leu Lys Thr Glu Asp Thr Ala Val Tyr Tyr Cys Thr Thr Pro Trp Glu
    610                 615                 620
Trp Ser Trp Tyr Asp Tyr Trp Gly Gln Gly Thr Leu Val Thr Val Ser
625                 630                 635                 640
Ser Ala Ser Thr Lys Gly Pro Ser Val Phe Pro Leu Ala Pro Ser Ser
                645                 650                 655
Lys Ser Thr Ser Gly Gly Thr Ala Ala Leu Gly Cys Leu Val Lys Asp
            660                 665                 670
Tyr Phe Pro Glu Pro Val Thr Val Ser Trp Asn Ser Gly Ala Leu Thr
        675                 680                 685
Ser Gly Val His Thr Phe Pro Ala Val Leu Gln Ser Ser Gly Leu Tyr
    690                 695                 700
Ser Leu Ser Ser Val Val Thr Val Pro Ser Ser Ser Leu Gly Thr Gln
705                 710                 715                 720
Thr Tyr Ile Cys Asn Val Asn His Lys Pro Ser Asn Thr Lys Val Asp
                725                 730                 735
Lys Lys Val Glu Pro Lys Ser Cys Asp Lys Thr His Thr Cys Pro Pro
            740                 745                 750
Cys Pro Ala Pro Glu Ala Ala Gly Gly Pro Ser Val Phe Leu Phe Pro
        755                 760                 765
Pro Lys Pro Lys Asp Thr Leu Met Ile Ser Arg Thr Pro Glu Val Thr
    770                 775                 780
Cys Val Val Val Asp Val Ser His Glu Asp Pro Glu Val Lys Phe Asn
785                 790                 795                 800
Trp Tyr Val Asp Gly Val Glu Val His Asn Ala Lys Thr Lys Pro Arg
                805                 810                 815
Glu Glu Gln Tyr Asn Ser Thr Tyr Arg Val Val Ser Val Leu Thr Val
            820                 825                 830
Leu His Gln Asp Trp Leu Asn Gly Lys Glu Tyr Lys Cys Lys Val Ser
        835                 840                 845
Asn Lys Ala Leu Gly Ala Pro Ile Glu Lys Thr Ile Ser Lys Ala Lys
    850                 855                 860
Gly Gln Pro Arg Glu Pro Gln Val Tyr Thr Leu Pro Pro Cys Arg Asp
865                 870                 875                 880
Glu Leu Thr Lys Asn Gln Val Ser Leu Trp Cys Leu Val Lys Gly Phe
                885                 890                 895
Tyr Pro Ser Asp Ile Ala Val Glu Trp Glu Ser Asn Gly Gln Pro Glu
            900                 905                 910
Asn Asn Tyr Lys Thr Thr Pro Pro Val Leu Asp Ser Asp Gly Ser Phe
        915                 920                 925
```

```
Phe Leu Tyr Ser Lys Leu Thr Val Asp Lys Ser Arg Trp Gln Gln Gly
        930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
                965                 970

<210> SEQ ID NO 7
<211> LENGTH: 33
<212> TYPE: PRT
<213> ORGANISM: Artificial Sequence
<220> FEATURE:
<223> OTHER INFORMATION: Synthetic Construct

<400> SEQUENCE: 7

Gly Gly Gly Gly Ser Gly Gly Gly Gly Ser Arg Gln Ala Arg Val Val
1               5                   10                  15

Asn Gly Gly Gly Gly Ser Gly Gly Gly Gly Ser Gly Gly Gly Gly
                20                  25                  30

Ser

<210> SEQ ID NO 8
<211> LENGTH: 28
<212> TYPE: PRT
<213> ORGANISM: Artificial Sequence
<220> FEATURE:
<223> OTHER INFORMATION: Synthetic Construct

<400> SEQUENCE: 8

Gly Gly Gly Gly Ser Val His Met Pro Leu Gly Phe Leu Pro Gly
1               5                   10                  15

Arg Ser Arg Gly Ser Phe Pro Gly Gly Gly Ser
                20                  25

<210> SEQ ID NO 9
<211> LENGTH: 41
<212> TYPE: PRT
<213> ORGANISM: Artificial Sequence
<220> FEATURE:
<223> OTHER INFORMATION: Synthetic Construct

<400> SEQUENCE: 9

Gly Gly Gly Gly Ser Gly Gly Gly Gly Ser Arg Gln Ala Arg Val Val
1               5                   10                  15

Asn Gly Gly Gly Gly Ser Val Pro Leu Ser Leu Tyr Ser Gly Gly
                20                  25                  30

Gly Gly Gly Ser Gly Gly Gly Gly Ser
        35                  40

<210> SEQ ID NO 10
<211> LENGTH: 36
<212> TYPE: PRT
<213> ORGANISM: Artificial Sequence
<220> FEATURE:
<223> OTHER INFORMATION: Synthetic Construct

<400> SEQUENCE: 10

Gly Gly Gly Gly Ser Gly Gly Gly Gly Ser Arg Gln Ala Arg Val Val
1               5                   10                  15

Asn Gly Val Pro Leu Ser Leu Tyr Ser Gly Gly Gly Gly Ser Gly
                20                  25                  30
```

```
Gly Gly Gly Ser
        35

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Thr Tyr Ala Met Asn
1               5

<210> SEQ ID NO 12
<211> LENGTH: 19
<212> TYPE: PRT
<213> ORGANISM: Artificial Sequence
<220> FEATURE:
<223> OTHER INFORMATION: Synthetic Construct

<400> SEQUENCE: 12

Arg Ile Arg Ser Lys Tyr Asn Asn Tyr Ala Thr Tyr Tyr Ala Asp Ser
1               5                   10                  15

Val Lys Gly

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

His Gly Asn Phe Gly Asn Ser Tyr Val Ser Trp Phe Ala Tyr
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Asn Ala Trp Met Ser
1               5

<210> SEQ ID NO 15
<211> LENGTH: 19
<212> TYPE: PRT
<213> ORGANISM: Artificial Sequence
<220> FEATURE:
<223> OTHER INFORMATION: Synthetic Construct

<400> SEQUENCE: 15

Arg Ile Lys Ser Lys Thr Asp Gly Gly Thr Thr Asp Tyr Ala Ala Pro
1               5                   10                  15

Val Lys Gly

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 16

Pro Trp Glu Trp Ser Trp Tyr Asp Tyr
1               5

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Gly Ser Ser Thr Gly Ala Val Thr Thr Ser Asn Tyr Ala Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Gly Thr Asn Lys Arg Ala Pro
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Ala Leu Trp Tyr Ser Asn Leu Trp Val
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Asp Tyr Ser Ile His
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Trp Ile Asn Thr Glu Thr Gly Glu Pro Ala Tyr Ala Asp Asp Phe Lys
1               5                   10                  15

Gly

<210> SEQ ID NO 22
<211> LENGTH: 9
<212> TYPE: PRT
<213> ORGANISM: Artificial Sequence
<220> FEATURE:

```
<223> OTHER INFORMATION: Synthetic Construct

<400> SEQUENCE: 22

Pro Tyr Asp Tyr Asp Val Leu Asp Tyr
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic Construct

<400> SEQUENCE: 23

Arg Ala Ser Lys Ser Val Ser Thr Ser Asn Tyr Ser Tyr Ile His
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Tyr Val Ser Tyr Leu Glu Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Gln His Ser Arg Glu Phe Pro Trp Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Ser Tyr Gly Val Ser
1               5

<210> SEQ ID NO 27
<211> LENGTH: 16
<212> TYPE: PRT
<213> ORGANISM: Artificial Sequence
<220> FEATURE:
<223> OTHER INFORMATION: Synthetic Construct

<400> SEQUENCE: 27

Ile Ile Trp Gly Asp Gly Ser Thr Asn Tyr His Ser Ala Leu Ile Ser
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Synthetic Construct
```

<400> SEQUENCE: 28

Gly Ile Thr Thr Val Val Asp Asp Tyr Tyr Ala Met Asp Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Construct

<400> SEQUENCE: 29

Arg Ala Ser Glu Asn Ile Asp Ser Tyr Leu Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Ala Ala Thr Phe Leu Ala Asp
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Gln His Tyr Tyr Ser Thr Pro Tyr Thr
1               5

<210> SEQ ID NO 32
<211> LENGTH: 450
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
   450

<210> SEQ ID NO 33
<211> LENGTH: 213
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
         35                  40                  45

Tyr Asn Thr Asn Asn Leu Gln Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Phe Pro Thr
                 85                  90                  95

Phe Gly Gln Gly Thr Lys Leu Glu Ile Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 34
<211> LENGTH: 492
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Glu Gln Ser Gly Pro Val Leu Val Lys Pro Gly Thr
1               5                   10                  15

Ser Val Lys Met Ser Cys Lys Ala Ser Gly Tyr Thr Phe Thr Asp Tyr
            20                  25                  30

Tyr Ile Asn Trp Ile Ile Gln Ser His Gly Lys Cys Leu Glu Trp Ile
         35                  40                  45

Gly Val Ile Asn Pro Asp Ser Gly Gly Thr Tyr Asn Gln Asn Phe
 50                  55                  60

Lys Gly Lys Ala Thr Leu Thr Val Asp Lys Ser Ser Thr Thr Ala Tyr
 65                  70                  75                  80

Met Glu Leu Thr Ser Leu Thr Ser Glu Asp Ser Ala Val Tyr Tyr Cys
                 85                  90                  95

Ala Arg Arg Asp Ser Tyr Gly Phe Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Ser Gly Gly Gly Gly Ser Asp Ile Val Leu Thr Gln Thr
    130                 135                 140

Pro Lys Phe Leu Leu Val Pro Ala Gly Asp Arg Ile Thr Met Thr Cys
145                 150                 155                 160

Lys Ala Ser Leu Ser Val Thr Asn Asp Val Ala Trp Tyr Gln Gln Lys
                165                 170                 175

```
Pro Gly Gln Ser Pro Lys Leu Leu Leu Tyr Tyr Ala Ser Asn Arg Asn
            180                 185                 190

Ala Gly Val Pro Asp Arg Phe Thr Gly Ser Gly Tyr Gly Thr Asp Phe
        195                 200                 205

Thr Phe Thr Ile Thr Thr Leu Gln Ala Glu Asp Leu Ala Val Tyr Phe
    210                 215                 220

Cys Gln Gln Asp Tyr Thr Ser Pro Pro Thr Phe Gly Cys Gly Thr Lys
225                 230                 235                 240

Leu Glu Ile Arg Gly Gly Gly Ser Gly Gly Gly Ser Gly Pro
                245                 250                 255

Leu Gly Leu Trp Ser Gln Gly Gly Gly Ser Gly Gly Gly Gly Ser
            260                 265                 270

Gly Gly Gly Gly Ser Gly Gly Asp Ile Gln Met Thr Gln Ser Pro Ser
        275                 280                 285

Ser Leu Ser Ala Ser Val Gly Asp Arg Val Thr Ile Thr Cys Arg Ala
    290                 295                 300

Ser Gln Gly Ile Asn Asn Tyr Leu Asn Trp Tyr Gln Gln Lys Pro Gly
305                 310                 315                 320

Lys Ala Pro Lys Arg Leu Ile Tyr Asn Thr Asn Asn Leu Gln Thr Gly
                325                 330                 335

Val Pro Ser Arg Phe Ser Gly Ser Gly Ser Gly Thr Glu Phe Thr Leu
            340                 345                 350

Thr Ile Ser Ser Leu Gln Pro Glu Asp Phe Ala Thr Tyr Tyr Cys Leu
        355                 360                 365

Gln His Asn Ser Phe Pro Thr Phe Gly Gln Gly Thr Lys Leu Glu Ile
    370                 375                 380

Lys Arg Thr Val Ala Ala Pro Ser Val Phe Ile Phe Pro Pro Ser Asp
385                 390                 395                 400

Glu Gln Leu Lys Ser Gly Thr Ala Ser Val Val Cys Leu Leu Asn Asn
                405                 410                 415

Phe Tyr Pro Arg Glu Ala Lys Val Gln Trp Lys Val Asp Asn Ala Leu
            420                 425                 430

Gln Ser Gly Asn Ser Gln Glu Ser Val Thr Glu Gln Asp Ser Lys Asp
        435                 440                 445

Ser Thr Tyr Ser Leu Ser Ser Thr Leu Thr Leu Ser Lys Ala Asp Tyr
    450                 455                 460

Glu Lys His Lys Val Tyr Ala Cys Glu Val Thr His Gln Gly Leu Ser
465                 470                 475                 480

Ser Pro Val Thr Lys Ser Phe Asn Arg Gly Glu Cys
                485                 490

<210> SEQ ID NO 35
<211> LENGTH: 35
<212> TYPE: PRT
<213> ORGANISM: Artificial Sequence
<220> FEATURE:
<223> OTHER INFORMATION: Synthetic Construct

<400> SEQUENCE: 35

Gly Gly Gly Gly Ser Gly Gly Gly Ser Pro Leu Gly Leu Trp
1               5                   10                  15

Ser Gln Gly Gly Gly Gly Ser Gly Gly Gly Ser Gly Gly Gly Gly
                20                  25                  30

Ser Gly Gly
        35
```

```
<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Arg Gln Ala Arg Val Val Asn Gly
1               5

<210> SEQ ID NO 37
<211> LENGTH: 18
<212> TYPE: PRT
<213> ORGANISM: Artificial Sequence
<220> FEATURE:
<223> OTHER INFORMATION: Synthetic Construct

<400> SEQUENCE: 37

Val His Met Pro Leu Gly Phe Leu Gly Pro Gly Arg Ser Arg Gly Ser
1               5                   10                  15

Phe Pro

<210> SEQ ID NO 38
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: X
<222> LOCATION: (9)..(13)
<223> OTHER INFORMATION: X is an amino acid
<220> FEATURE:
<221> NAME/KEY: X
<222> LOCATION: (9)..(13)
<223> OTHER INFORMATION: X or Xaa is an amino acid

<400> SEQUENCE: 38

Arg Gln Ala Arg Val Val Asn Gly Xaa Xaa Xaa Xaa Xaa Val Pro Leu
1               5                   10                  15

Ser Leu Tyr Ser Gly
            20

<210> SEQ ID NO 39
<211> LENGTH: 16
<212> TYPE: PRT
<213> ORGANISM: Artificial Sequence
<220> FEATURE:
<223> OTHER INFORMATION: Synthetic Construct

<400> SEQUENCE: 39

Arg Gln Ala Arg Val Val Asn Gly Val Pro Leu Ser Leu Tyr Ser Gly
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Pro Leu Gly Leu Trp Ser Gln
1               5
```

```
<210> SEQ ID NO 41
<211> LENGTH: 249
<212> TYPE: PRT
<213> ORGANISM: Artificial Sequence
<220> FEATURE:
<223> OTHER INFORMATION: Synthetic Construct

<400> SEQUENCE: 41
```

| | | | | | | | | | | | | | | |
|---|---|---|---|---|---|---|---|---|---|---|---|---|---|---|
| Gln | Ile | Gln | Leu | Val | Gln | Ser | Gly | Pro | Glu | Leu | Lys | Lys | Pro | Gly | Glu |
| 1 | | | | 5 | | | | | 10 | | | | | 15 | |

| Thr | Val | Arg | Ile | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Ser | Ile | His | Trp | Val | Lys | Gln | Ala | Pro | Gly | Lys | Cys | Leu | Lys | Trp | Met |
|---|---|---|---|---|---|---|---|---|---|---|---|---|---|---|---|
| | | 35 | | | | | 40 | | | | | 45 | | | |

| Gly | Trp | Ile | Asn | Thr | Glu | Thr | Gly | Glu | Pro | Ala | Tyr | Ala | Asp | Asp | Phe |
|---|---|---|---|---|---|---|---|---|---|---|---|---|---|---|---|
| 50 | | | | | 55 | | | | | 60 | | | | | |

| Lys | Gly | Arg | Phe | Ala | Phe | Ser | Leu | Glu | Thr | Ser | Ala | Ser | Thr | Ala | Tyr |
|---|---|---|---|---|---|---|---|---|---|---|---|---|---|---|---|
| 65 | | | | | 70 | | | | | 75 | | | | | 80 |

| Leu | Gln | Ile | Asn | Asn | Leu | Lys | Asn | Glu | Asp | Thr | Ala | Thr | Phe | Phe | Cys |
|---|---|---|---|---|---|---|---|---|---|---|---|---|---|---|---|
| | | | | 85 | | | | | 90 | | | | | 95 | |

| Ala | His | Pro | Tyr | Asp | Tyr | Asp | Val | Leu | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Ser | Val | Thr | Val | Ser | Ser | Gly | Gly | Gly | Ser | Gly | Gly | Gly | Gly | Gly | Ser |
|---|---|---|---|---|---|---|---|---|---|---|---|---|---|---|---|
| | | 115 | | | | | 120 | | | | | 125 | | | |

| Gly | Gly | Gly | Gly | Ser | Gly | Gly | Gly | Ser | Asp | Thr | Val | Leu | Thr | Gln |
|---|---|---|---|---|---|---|---|---|---|---|---|---|---|---|
| | 130 | | | | | 135 | | | | | 140 | | | |

| Ser | Pro | Ala | Ser | Leu | Gly | Val | Ser | Leu | Gly | Gln | Arg | Ala | Thr | Ile | Ser |
|---|---|---|---|---|---|---|---|---|---|---|---|---|---|---|---|
| 145 | | | | | 150 | | | | | 155 | | | | | 160 |

| Cys | Arg | Ala | Ser | Lys | Ser | Val | Ser | Thr | Ser | Asn | Tyr | Ser | Tyr | Ile | His |
|---|---|---|---|---|---|---|---|---|---|---|---|---|---|---|---|
| | | | | 165 | | | | | 170 | | | | | 175 | |

| Trp | Tyr | Gln | Gln | Lys | Pro | Gly | Gln | Pro | Pro | Lys | Leu | Leu | Ile | Lys | Tyr |
|---|---|---|---|---|---|---|---|---|---|---|---|---|---|---|---|
| | | | 180 | | | | | 185 | | | | | 190 | | |

| Val | Ser | Tyr | Leu | Glu | Ser | Gly | Val | Pro | Ala | Arg | Phe | Ser | Gly | Ser | Gly |
|---|---|---|---|---|---|---|---|---|---|---|---|---|---|---|---|
| | | 195 | | | | | 200 | | | | | 205 | | | |

| Ser | Gly | Thr | Asp | Phe | Thr | Leu | Asn | Ile | His | Pro | Val | Glu | Glu | Glu | Asp |
|---|---|---|---|---|---|---|---|---|---|---|---|---|---|---|---|
| | 210 | | | | | 215 | | | | | 220 | | | | |

| Ala | Ala | Thr | Tyr | Tyr | Cys | Gln | His | Ser | Arg | Glu | Phe | Pro | Trp | Thr | Phe |
|---|---|---|---|---|---|---|---|---|---|---|---|---|---|---|---|
| 225 | | | | | 230 | | | | | 235 | | | | | 240 |

| Gly | Cys | Gly | Thr | Lys | Leu | Glu | Ile | Lys |
|---|---|---|---|---|---|---|---|---|
| | | | | 245 | | | | |

```
<210> SEQ ID NO 42
<211> LENGTH: 249
<212> TYPE: PRT
<213> ORGANISM: Artificial Sequence
<220> FEATURE:
<223> OTHER INFORMATION: Synthetic Construct

<400> SEQUENCE: 42
```

| Gln | Val | Gln | Leu | Lys | Glu | Ser | Gly | Pro | Gly | Leu | Val | Ala | Pro | Ser | Gln |
|---|---|---|---|---|---|---|---|---|---|---|---|---|---|---|---|
| 1 | | | | 5 | | | | | 10 | | | | | 15 | |

| Ser | Leu | Ser | Ile | Thr | Cys | Thr | Val | Ser | Gly | Phe | Ser | Leu | Thr | Ser | Tyr |
|---|---|---|---|---|---|---|---|---|---|---|---|---|---|---|---|
| | | | 20 | | | | | 25 | | | | | 30 | | |

| Gly | Val | Ser | Trp | Val | Arg | Gln | Pro | Pro | Gly | Lys | Cys | Leu | Glu | Trp | Leu |
|---|---|---|---|---|---|---|---|---|---|---|---|---|---|---|---|
| | | 35 | | | | | 40 | | | | | 45 | | | |

| Gly | Ile | Ile | Trp | Gly | Asp | Gly | Ser | Thr | Asn | Tyr | His | Ser | Ala | Leu | Ile |
|---|---|---|---|---|---|---|---|---|---|---|---|---|---|---|---|
| 50 | | | | | 55 | | | | | 60 | | | | | |

Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
            115                 120                 125

Gly Gly Gly Ser Gly Gly Gly Gly Ser Gly Gly Gly Gly Ser Asp Ile
        130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
                180                 185                 190

Ala Thr Phe Leu Ala Asp Asp Val Pro Ser Arg Phe Ser Gly Ser Gly
            195                 200                 205

Ser Gly Thr Gln Tyr Ser Leu Lys Ile Asn Ser Leu Gln Ser Glu Asp
        210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys
                245

<210> SEQ ID NO 43
<211> LENGTH: 125
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 44
<211> LENGTH: 5
<212> TYPE: PRT
<213> ORGANISM: Artificial Sequence
<220> FEATURE:
<223> OTHER INFORMATION: Synthetic Construct

<400> SEQUENCE: 44

```
Thr Tyr Ala Met Asn
1               5

<210> SEQ ID NO 45
<211> LENGTH: 19
<212> TYPE: PRT
<213> ORGANISM: Artificial Sequence
<220> FEATURE:
<223> OTHER INFORMATION: Synthetic Construct

<400> SEQUENCE: 45

Arg Ile Arg Ser Lys Tyr Asn Asn Tyr Ala Thr Tyr Tyr Ala Asp Ser
1               5                   10                  15

Val Lys Gly

<210> SEQ ID NO 46
<211> LENGTH: 14
<212> TYPE: PRT
<213> ORGANISM: Artificial Sequence
<220> FEATURE:
<223> OTHER INFORMATION: Synthetic Construct

<400> SEQUENCE: 46

His Gly Asn Phe Gly Asn Ser Tyr Val Ser Trp Phe Ala Tyr
1               5                   10

<210> SEQ ID NO 47
<211> LENGTH: 120
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
        115                 120

<210> SEQ ID NO 48
<211> LENGTH: 5
<212> TYPE: PRT
<213> ORGANISM: Artificial Sequence
<220> FEATURE:
<223> OTHER INFORMATION: Synthetic Construct

<400> SEQUENCE: 48

Asp Tyr Tyr Ile Asn
1               5
```

<210> SEQ ID NO 49
<211> LENGTH: 17
<212> TYPE: PRT
<213> ORGANISM: Artificial Sequence
<220> FEATURE:
<223> OTHER INFORMATION: Synthetic Construct

<400> SEQUENCE: 49

Val Ile Asn Pro Asp Ser Gly Gly Thr Asp Tyr Asn Gln Asn Phe Lys
1               5                   10                  15

Gly

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Arg Asp Ser Tyr Gly Phe Asp Tyr
1               5

<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Lys Ala Ser Leu Ser Val Thr Asn Asp Val Ala
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Tyr Ala Ser Asn Arg Asn Ala
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Gln Gln Asp Tyr Thr Ser Pro Pro Thr
1               5

<210> SEQ ID NO 54
<211> LENGTH: 207
<212> TYPE: PRT
<213> ORGANISM: Artificial Sequence
<220> FEATURE:
<223> OTHER INFORMATION: Synthetic Construct

<400> SEQUENCE: 54

Met Gln Ser Gly Thr His Trp Arg Val Leu Gly Leu Cys Leu Leu Ser
1               5                   10                  15

```
Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
 50                  55                  60

Asn Ile Gly Gly Asp Glu Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205

<210> SEQ ID NO 55
<211> LENGTH: 109
<212> TYPE: PRT
<213> ORGANISM: Artificial Sequence
<220> FEATURE:
<223> OTHER INFORMATION: Synthetic Construct

<400> SEQUENCE: 55

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 56
<211> LENGTH: 5
<212> TYPE: PRT
<213> ORGANISM: Artificial Sequence
<220> FEATURE:
<223> OTHER INFORMATION: Synthetic Construct

<400> SEQUENCE: 56

Asp Tyr Lys Ile His
```

<210> SEQ ID NO 57
<211> LENGTH: 17
<212> TYPE: PRT
<213> ORGANISM: Artificial Sequence
<220> FEATURE:
<223> OTHER INFORMATION: Synthetic Construct

<400> SEQUENCE: 57

Tyr Phe Asn Pro Asn Ser Gly Tyr Ser Thr Tyr Ala Gln Lys Phe Gln
1               5                   10                  15

Gly

<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

Leu Ser Pro Gly Gly Tyr Tyr Val Met Asp Ala
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic Construct

<400> SEQUENCE: 59

Arg Ala Ser Gln Gly Ile Asn Asn Tyr Leu Asn
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct

<400> SEQUENCE: 60

Asn Thr Asn Asn Leu Gln Thr
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Leu Gln His Asn Ser Phe Pro Thr
1               5

<210> SEQ ID NO 62
<211> LENGTH: 648
<212> TYPE: DNA
<213> ORGANISM: Artificial Sequence
<220> FEATURE:
<223> OTHER INFORMATION: Synthetic Construct

<400> SEQUENCE: 62

```
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca acaagagagc cctggcacc      180 cctgccagat tcagcggatc tctgctggga ggaaaggccg ccctgacact gtctggcgcc     240
cagccagaag atgaggccga gtactactgc gccctgtggt acagcaacct gtgggtgttc     300
ggcggaggca ccaagctgac agtcctaggt caacccaagg ctgcccccag cgtgaccctg     360
ttccccccca gcagcgagga actgcaggcc aacaaggcca cctggtctg cctgatcagc      420 gacttctacc caggcgccgt gaccgtggcc tggaaggccg acagcagccc cgtgaaggcc     480
ggcgtggaga ccaccacccc cagcaagcag agcaacaaca gtacgccgc cagcagctac      540 ctgagcctga cccccgagca gtggaagagc acaggtcct acagctgcca ggtgacccac      600
gagggcagca ccgtggagaa aaccgtggcc cccaccgagt gcagctga                  648

<210> SEQ ID NO 63
<211> LENGTH: 2916
<212> TYPE: DNA
<213> ORGANISM: Artificial Sequence
<220> FEATURE:
<223> OTHER INFORMATION: Synthetic Construct

<400> SEQUENCE: 63
cagatccagc tggtgcagag cggccctgag ctgaagaaac cggcgagac agtgcggatc       60 agctgcaagg ccagcggcta caccttcacc gactacagca tccactgggt caagcaggcc    120
cctggcaagt gcctgaagtg gatgggctgg atcaacaccg agacaggcga gcccgcctac    180
gccgacgatt tcaagggcag attcgccttc agcctggaaa ccagcgccag caccgcctac    240
ctgcagatca caaacctgaa gaacgaggac accgccacct ttttctgcgc ccaccccta     300 gactacgacg tgctggatta ttggggccag ggcaccagcg tgaccgtgtc tagcggaggc    360
ggaggatctg gcggcggagg aagtggcgga ggggatctg ggggaggcgg atctgatacc     420
gtgctgacac agagccctgc cagcctggga gtgtccctgg acagagagc caccatcagc     480 tgtcgggcca gcaagagcgt gtccaccagc aactacagct atatccactg gtatcagcag    540
aagcccggcc agcccccaa gctgctgatc aaatacgtgt cctacctgga aagcggcgtg     600
cccgccagat tttctggctc tggcagcggc accgacttca ccctgaacat caccccgtg    660 gaagaggaag atgccgccac ctactactgc cagcacagca gagagttccc ttggaccttc    720
ggctgcggca ccaagctgga aatcaaaggc ggggaggct ccggaggcgg cggaagtaga    780
caggccagag tcgtgaacgg gggaggggg ggaagtgggg gcggaggcag tggggggga     840 ggatccgagg tgcagctgct ggaatctggc ggcggactgg tgcagcctgg cggatctctg    900
agactgagct gtgccgccag cggcttcacc ttcagcacct acgccatgaa ctgggtgcgc    960
caggcccctg gcaaaggcct ggaatgggtg tccggatca aagcaagta caacaactac    1020 gccacctact acgccgacag cgtgaagggc cggttcacca tcagccggga cgacagcaag    1080
aacaccctgt acctgcagat gaacagcctg cgggccgagg acaccgccgt gtactattgt    1140
gtgcggcacg gcaacttcgg caacagctat gtgtcttggt ttgcctactg gggccagggc    1200
accctcgtga ccgtgtcaag cgctagcaca aagggcccta gcgtgttccc tctggccccc    1260
agcagcaaga gcacaagcgg cggaacagcc gccctgggct gcctcgtgaa ggactacttc    1320
cccgagcccg tgacagtgtc cttggaacagc ggagccctga caagcggcgt gcacaccttc    1380
cctgccgtgc tgcagagcag cggcctgtac tccctgagca gcgtggtcac cgtgcctagc    1440
```

```
agcagcctgg gcacccagac ctacatctgc aacgtgaacc acaagcccag caacaccaaa    1500
gtggacaaga aggtggagcc caagagctgt gatggcggag gagggtccgg aggcggagga    1560
tccgaggtgc aattggttga atctggtggt ggtctggtaa aaccgggcgg ttccctgcgt    1620
ctgagctgcg cggcttccgg attcaccttc tccaacgcgt ggatgagctg ggttcgccag    1680
gccccgggca aaggcctcga gtgggttggt cgtatcaagt ctaaaactga cggtggcacc    1740
acggattacg cggctccagt taaaggtcgt tttaccattt cccgcgacga tagcaaaaac    1800
actctgtatc tgcagatgaa ctctctgaaa actgaagaca ccgcagtcta ctactgtact    1860
accccgtggg aatggtcttg gtacgattat tggggccagg gcacgctggt tacggtgtct    1920
agcgctagta ccaagggccc cagcgtgttc cccctggcac ccagcagcaa gagcacatct    1980
ggcggaacag ccgctctggg ctgtctggtg aaagactact cccccgagcc cgtgaccgtg    2040
tcttggaact ctggcgccct gaccagcggc gtgcacacct tccagccgt gctgcagagc     2100 agcggcctgt actccctgtc ctccgtggtc accgtgccct ctagctccct gggaacacag    2160
acatatatct gtaatgtcaa tcacaagcct tccaacacca agtcgataa gaaagtcgag     2220 cccaagagct gcgacaaaac tcacacatgc ccaccgtgcc cagcacctga gctgcaggg     2280 ggaccgtcag tcttcctctt ccccccaaaa cccaaggaca ccctcatgat ctcccggacc    2340
cctgaggtca catgcgtggt ggtggacgtg agccacgaag accctgaggt caagttcaac    2400
tggtacgtgg acggcgtgga ggtgcataat gccaagacaa agccgcggga ggagcagtac    2460
aacagcacgt accgtgtggt cagcgtcctc accgtcctgc accaggactg gctgaatggc    2520
aaggagtaca agtgcaaggt ctccaacaaa gccctcggcg cccccatcga gaaaaccatc    2580
tccaaagcca aagggcagcc ccgagaacca caggtgtaca ccctgccccc atgccgggat    2640
gagctgacca agaaccaggt cagcctgtgg tgcctggtca aaggcttcta tcccagcgac    2700
atcgccgtgg agtgggagag caatgggcag ccggagaaca actacaagac cacgcctccc    2760
gtgctggact ccgacggctc cttcttcctc tacagcaagc tcaccgtgga caagagcagg    2820
tggcagcagg ggaacgtctt ctcatgctcc gtgatgcatg aggctctgca caaccactac    2880
acgcagaaga gcctctccct gtctccgggt aaatga                             2916
```

<210> SEQ ID NO 64  
<211> LENGTH: 1353  
<212> TYPE: DNA  
<213> ORGANISM: Artificial Sequence  
<220> FEATURE:  
<223> OTHER INFORMATION: Synthetic Construct

<400> SEQUENCE: 64

```
gaggtgcaat tggttgaatc tggtggtggt ctggtaaaac cgggcggttc cctgcgtctg     60
agctgcgcgg cttccggatt caccttctcc aacgcgtgga tgagctgggt tcgccaggcc    120
ccgggcaaag gcctcgagtg ggttggtcgt atcaagtcta aaactgacgg tggcaccacg    180
gattacgcgg ctccagttaa aggtcgtttt acctatttccc gcgacgatag caaaaacact    240
ctgtatctgc agatgaactc tctgaaaact gaagacaccg cagtctacta ctgtactacc    300
ccgtgggaat ggtcttggta cgattattgg ggccagggca cgctggttac ggtgtcttcc    360
gctagcacca agggcccctc cgtgttcccc ctggccccca gcagcaagag caccagcggc    420
ggcacagccg ctctgggctg cctggtcaag gactacttcc ccgagcccgt gaccgtgtcc    480
tggaacagcg gagccctgac ctccggcgtg cacaccttcc ccgccgtgct gcagagttct    540
```

| | |
|---|---|
| ggcctgtata gcctgagcag cgtggtcacc gtgccttcta gcagcctggg cacccagacc | 600 |
| tacatctgca acgtgaacca caagcccagc aacaccaagg tggacaagaa ggtggagccc | 660 |
| aagagctgcg acaaaactca cacatgccca ccgtgcccag cacctgaagc tgcaggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcggcgccc catcgagaa aaccatctcc | 1020 |
| aaagccaaag ggcagccccg agaaccacag gtgtgcaccc tgcccccatc ccgggatgag | 1080 |
| ctgaccaaga accaggtcag cctctcgtgc gcagtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctcgtg agcaagctca ccgtggacaa gagcaggtgg | 1260 |
| cagcagggga acgtcttctc atgctccgtg atgcatgagg ctctgcacaa ccgcttcacg | 1320 |
| cagaagagcc tctccctgtc tccgggtaaa tga | 1353 |

<210> SEQ ID NO 65
<211> LENGTH: 2916
<212> TYPE: DNA
<213> ORGANISM: Artificial Sequence
<220> FEATURE:
<223> OTHER INFORMATION: Synthetic Construct

<400> SEQUENCE: 65

| | |
|---|---|
| caagtgcagc tgaaagagtc cggccctgga ctggtggccc ctagccagag cctgagcatc | 60 |
| acctgtaccg tgtccggctt cagcctgacc agctacggcg tgtcatgggt gcgccagcct | 120 |
| ccaggcaagt gtctggaatg gctgggcatc atctggggcg acggcagcac caattaccac | 180 |
| agcgccctga tcagcagact gagcatctcc aaggacaaca gcaagagcca ggtgttcctg | 240 |
| aagctgaaca gcctgcagac cgacgacacc gccacctact actgcgccaa gggcatcacc | 300 |
| accgtggtgg acgactacta cgctatggac tactgggggcc agggcaccag cgtgacagtg | 360 |
| tctagcggag gcggaggatc tggcggcgga ggaagtggcg agggggatc tggggaggc | 420 |
| ggaagcgata tccagatgac ccagagccct gccagcctgt ctgcctctgt gggcgagaca | 480 |
| gtgaccatca catgccgggc cagcgagaac atcgacagct acctggcctg gtatcagcag | 540 |
| aagcagggca gagcccccca gctgctggtg tacgccgcca cctttctggc cgacgatgtg | 600 |
| cccagcagat tcagcggcag cggaagcggc acacagtaca gcctgaagat caactccctg | 660 |
| cagagcgagg acgtggcccg gtactactgc cagcactact acagcacccc ctacaccttc | 720 |
| ggctgcggca ccaagctgga aatcaaaggc ggggaggct ccggaggcgg cggaagtaga | 780 |
| caggccagag tcgtgaacgg gggaggggg ggaagtgggg gcggaggcag tggggcggga | 840 |
| ggatccgagg tgcagctgct ggaatctggc ggcggactgg tgcagcctgg cggatctctg | 900 |
| agactgagct gtgccgccag cggcttcacc ttcagcacct acgccatgaa ctgggtgcgc | 960 |
| caggcccctg gcaagggcct ggaatgggtg tcccggatca gcaagagta caacaactac | 1020 |
| gccacctact acgccgacag cgtgaagggc cggttcacca tcagccggga cgacagcaag | 1080 |
| aacaccctgt acctgcagat gaacagcctg cgggccgagg acaccgccgt gtactattgt | 1140 |
| gtgcggcacg gcaacttcgg caacagctat gtgtcttggt ttgcctactg gggccagggc | 1200 |
| accctcgtga ccgtgtcaag cgctagcaca aagggcccta gcgtgttccc tctggccccc | 1260 |

```
agcagcaaga gcacaagcgg cggaacagcc gccctgggct gcctcgtgaa ggactacttc    1320
cccgagcccg tgacagtgtc ttggaacagc ggagccctga caagcggcgt gcacaccttc    1380
cctgccgtgc tgcagagcag cggcctgtac tccctgagca gcgtggtcac cgtgcctagc    1440
agcagcctgg gcacccagac ctacatctgc aacgtgaacc acaagcccag caacaccaaa    1500
gtggacaaga aggtggagcc caagagctgt gatggcggag agggtccgg gggcggagga    1560 tccgaggtgc aattggttga atctggtggt ggtctggtaa accgggcgg ttccctgcgt    1620 ctgagctgcg cggcttccgg gttcaccttc tccaacgcgt ggatgagctg ggttcgccag    1680
gccccgggca aaggcctcga gtgggttggt cgtatcaagt ctaaaactga cggtggcacc    1740
acggattacg cggctccagt taaaggtcgt tttaccattt cccgcgacga tagcaaaaac    1800
actctgtatc tgcagatgaa ctctctgaaa actgaagaca ccgcagtcta ctactgtact    1860
accccgtggg aatggtcttg gtacgattat tggggccagg gcacgctggt tacggtgtct    1920
agcgctagta ccaagggccc cagcgtgttc cccctggcac ccagcagcaa gagcacatct    1980
ggcggaacag ccgctctggg ctgtctggtg aaagactact ccccgagcc cgtgaccgtg    2040 tcttggaact ctggcgccct gaccagcggc gtgcacacct ttccagccgt gctgcagagc    2100
agcggcctgt actccctgtc ctccgtggtc accgtgccct ctagctccct gggaacacag    2160
acatatatct gtaatgtcaa tcacaagcct tccaacacca aagtcgataa gaaagtcgag    2220
cccaagagct gcgacaaaac tcacacatgc ccaccgtgcc cagcacctga agctgcaggg    2280
ggaccgtcag tcttcctctt ccccccaaaa cccaaggaca ccctcatgat ctcccggacc    2340
cctgaggtca catgcgtggt ggtggacgtg agccacgaag accctgaggt caagttcaac    2400
tggtacgtgg acggcgtgga ggtgcataat gccaagacaa agccgcggga ggagcagtac    2460
aacagcacgt accgtgtggt cagcgtcctc accgtcctgc accaggactg gctgaatggc    2520
aaggagtaca agtgcaaggt ctccaacaaa gccctcggcg cccccatcga gaaaaccatc    2580
tccaaagcca aagggcagcc ccgagaacca caggtgtaca ccctgccccc atgccgggat    2640
gagctgacca agaaccaggt cagcctgtgg tgcctggtca aaggcttcta tcccagcgac    2700
atcgccgtgg agtgggagag caatgggcag ccggagaaca actacaagac cacgcctccc    2760
gtgctggact ccgacggctc cttcttcctc tacagcaagc tcaccgtgga caagagcagg    2820
tggcagcagg ggaacgtctt ctcatgctcc gtgatgcatg aggctctgca caaccactac    2880
acgcagaaga gcctctccct gtctccgggt aaatga                              2916

<210> SEQ ID NO 66
<211> LENGTH: 2916
<212> TYPE: DNA
<213> ORGANISM: Artificial Sequence
<220> FEATURE:
<223> OTHER INFORMATION: Synthetic Construct

<400> SEQUENCE: 66
caagtgcagc tgaaagagtc cggccctgga ctggtggccc ctagccagag cctgagcatc      60
acctgtaccg tgtccggctt cagcctgacc agctacggcg tgtcatgggt gcgccagcct     120
ccaggcaagt gtctggaatg gctgggcatc atctggggcg acggcagcac caattaccac     180
agcgccctga tcagcagact gagcatctcc aaggacaaca gcaagagcca ggtgttcctg     240
aagctgaaca gcctgcagac cgacgacacc gccacctact actgcgccaa gggcatcacc     300
accgtggtgg acgactacta cgctatggac tactggggcc agggcaccag cgtgacagtg     360
```

-continued

| | |
|---|---|
| tctagcggag gcggaggatc tggcggcgga ggaagtggcg gaggggggatc tgggggaggc | 420 |
| ggaagcgata tccagatgac ccagagccct gccagcctgt ctgcctctgt gggcgagaca | 480 |
| gtgaccatca catgccgggc cagcgagaac atcgacagct acctggcctg gtatcagcag | 540 |
| aagcagggca gagcccccca gctgctggtg tacgccgcca cctttctggc cgacgatgtg | 600 |
| cccagcagat tcagcggcag cggaagcggc acacagtaca gcctgaagat caactccctg | 660 |
| cagagcgagg acgtggcccg gtactactgc cagcactact acagcacccc ctacaccttc | 720 |
| ggctgcggca ccaagctgga aatcaaaggc gggggaggct ccggaggcgg cggaagtgga | 780 |
| ggcggcggaa gtggcggagg cggaggggggg gaagtgggg gcggaggcag tggggggggga | 840 |
| ggatccgagg tgcagctgct ggaatctggc ggcggactgg tgcagcctgg cggatctctg | 900 |
| agactgagct gtgccgccag cggcttcacc ttcagcacct acgccatgaa ctgggtgcgc | 960 |
| caggcccctg gcaaaggcct ggaatgggtg tcccggatca agcaagta caacaactac | 1020 |
| gccacctact acgccgacag cgtgaagggc cggttcacca tcagccggga cgacagcaag | 1080 |
| aacaccctgt acctgcagat gaacagcctg cgggccgagg acaccgccgt gtactattgt | 1140 |
| gtgcggcacg gcaacttcgg caacagctat gtgtcttggt ttgcctactg gggccagggc | 1200 |
| accctcgtga ccgtgtcaag cgctagcaca aagggcccta gcgtgttccc tctggccccc | 1260 |
| agcagcaaga gcacaagcgg cggaacagcc gccctgggct gcctcgtgaa ggactacttc | 1320 |
| cccgagcccg tgacagtgtc ttggaacagc ggagccctga agcggcgt gcacccttc | 1380 |
| cctgccgtgc tgcagagcag cggcctgtac tccctgagca gcgtggtcac cgtgcctagc | 1440 |
| agcagcctgg gcacccagac ctacatctgc aacgtgaacc acaagcccag caacaccaaa | 1500 |
| gtggacaaga aggtggagcc caagagctgt gatggcggag gagggtccgg aggcggaggc | 1560 |
| tccgaggtgc aattggttga atctggtggt ggtctggtaa accggggcgg ttccctgcgt | 1620 |
| ctgagctgcg cggcttccgg attcaccttc tccaacgcgt ggatgagctg ggttcgccag | 1680 |
| gccccgggca aaggcctcga gtgggttggt cgtatcaagt ctaaaactga cggtggcacc | 1740 |
| acggattacg cggctccagt taaaggtcgt tttaccattt cccgcgacga tagcaaaaac | 1800 |
| actctgtatc tgcagatgaa ctctctgaaa actgaagaca ccgcagtcta ctactgtact | 1860 |
| accccgtggg aatggtcttg gtacgattat tgggggccagg gcacgctggt tacggtgtct | 1920 |
| agcgctagta ccaagggccc cagcgtgttc cccctggcac ccagcagcaa gagcacatct | 1980 |
| ggcggaacag ccgctctggg ctgtctggtg aaagactact ccccgagcc cgtgaccgtg | 2040 |
| tcttggaact ctggcgccct gaccagcggc gtgcacacct ttccagccgt gctgcagagc | 2100 |
| agcggcctgt actccctgtc ctccgtggtc accgtgccct ctagctccct gggaacacag | 2160 |
| acatatatct gtaatgtcaa tcacaagcct tccaacacca aagtcgataa gaaagtcgag | 2220 |
| cccaagagct gcgacaaaac tcacacatgc ccaccgtgcc cagcacctga agctgcaggg | 2280 |
| ggaccgtcag tcttcctctt ccccccaaaa cccaaggaca ccctcatgat ctcccggacc | 2340 |
| cctgaggtca catgcgtggt ggtggacgtg agccacgaag accctgaggt caagttcaac | 2400 |
| tggtacgtgg acggcgtgga ggtgcataat gccaagacaa agccgcggga ggagcagtac | 2460 |
| aacagcacgt accgtgtggt cagcgtcctc accgtcctgc accaggactg gctgaatggc | 2520 |
| aaggagtaca agtgcaaggt ctccaacaaa gccctcggcg cccccatcga gaaaaccatc | 2580 |
| tccaaagcca agggcagccc cgagaaccca caggtgtaca ccctgccccc atgccgggat | 2640 |
| gagctgacca agaaccaggt cagcctgtgg tgcctggtca aaggcttcta tcccagcgac | 2700 |
| atcgccgtgg agtgggagag caatgggcag ccggagaaca actacaagac cacgcctccc | 2760 |

| | |
|---|---|
| gtgctggact ccgacggctc cttcttcctc tacagcaagc tcaccgtgga caagagcagg | 2820 |
| tggcagcagg ggaacgtctt ctcatgctcc gtgatgcatg aggctctgca caaccactac | 2880 |
| acgcagaaga gcctctccct gtctccgggt aaatga | 2916 |

<210> SEQ ID NO 67
<211> LENGTH: 2916
<212> TYPE: DNA
<213> ORGANISM: Artificial Sequence
<220> FEATURE:
<223> OTHER INFORMATION: Synthetic Construct

<400> SEQUENCE: 67

| | |
|---|---|
| cagatccagc tggtgcagag cggccctgag ctgaagaaac ccggcgagac agtgcggatc | 60 |
| agctgcaagg ccagcggcta caccttcacc gactacagca tccactgggt caagcaggcc | 120 |
| cctggcaagt gcctgaagtg gatgggctgg atcaacaccg agacaggcga gcccgcctac | 180 |
| gccgacgatt tcaagggcag attcgccttc agcctggaaa ccagcgccag caccgcctac | 240 |
| ctgcagatca acaacctgaa gaacgaggac accgccacct ttttctgcgc ccacccctac | 300 |
| gactacgacg tgctggatta ttggggccag ggcaccagcg tgaccgtgtc tagcggaggc | 360 |
| ggaggatctg gcggcggagg aagtggcgga gggggatctg ggggaggcgg atctgatacc | 420 |
| gtgctgacac agagccctgc cagcctggga gtgtccctgg acagagagc caccatcagc | 480 |
| tgtcgggcca gcaagagcgt gtccaccagc aactacagct atatccactg gtatcagcag | 540 |
| aagcccggcc agccccccaa gctgctgatc aaatacgtgt cctacctgga aagcggcgtg | 600 |
| cccgccagat tttctggctc tggcagcggc accgacttca ccctgaacat ccaccccgtg | 660 |
| gaagaggaag atgccgccac ctactactgc cagcacagca gagagttccc ttggaccttc | 720 |
| ggctgcggca ccaagctgga aatcaaaggc gggggaggct ccgaggcgg cggaagtgga | 780 |
| ggcggcggaa gtggcggagg cggaggggg gaagtgggg gcggaggcag tgggggggga | 840 |
| ggatccgagg tgcagctgct ggaatctggc ggcggactgg tgcagcctgg cggatctctg | 900 |
| agactgagct gtgccgccag cggcttcacc ttcagcacct acgccatgaa ctgggtgcgc | 960 |
| caggcccctg gcaaaggcct ggaatgggtg tcccggatca gaagcaagta caacaactac | 1020 |
| gccacctact acgccgacag cgtgaagggc cggttcacca tcagccggga cgacagcaag | 1080 |
| aacaccctgt acctgcagat gaacagcctg cgggccgagg acaccgccgt gtactattgt | 1140 |
| gtgcggcacg gcaacttcgg caacagctat gtgtcttggt ttgcctactg gggccagggc | 1200 |
| accctcgtga ccgtgtcaag cgctagcaca aagggcccta gcgtgttccc tctgccccc | 1260 |
| agcagcaaga gcacaagcgg cggaacagcc gccctgggct gcctcgtgaa ggactacttc | 1320 |
| cccgagcccg tgacagtgtc ttggaacagc ggagccctga agcggcgt gcacaccttc | 1380 |
| cctgccgtgc tgcagagcag cggcctgtac tccctgagca gcgtggtcac cgtgcctagc | 1440 |
| agcagcctgg gcacccagac ctacatctgc aacgtgaacc acaagcccag caacaccaaa | 1500 |
| gtggacaaga aggtggagcc caagagctgt gatggcggag agggtccgg aggcggaggc | 1560 |
| tccgaggtgc aattggttga atctggtggt ggtctggtaa accggggcgg ttccctgcgt | 1620 |
| ctgagctgcg cggcttccgg attcaccttc tccaacgcgt ggatgagctg ggttcgccag | 1680 |
| gccccgggca aaggcctcga gtgggttggt cgtatcaagt ctaaaactga cggtggcacc | 1740 |
| acggattacg cggctccagt taaaggtcgt tttaccattt cccgcgacga tagcaaaaac | 1800 |
| actctgtatc tgcagatgaa ctctctgaaa actgaagaca ccgcagtcta ctactgtact | 1860 |

| | |
|---|---|
| accccgtggg aatggtcttg gtacgattat tggggccagg gcacgctggt tacggtgtct | 1920 |
| agcgctagta ccaagggccc cagcgtgttc cccctggcac ccagcagcaa gagcacatct | 1980 |
| ggcggaacag ccgctctggg ctgtctggtg aaagactact tccccgagcc cgtgaccgtg | 2040 |
| tcttggaact ctggcgccct gaccagcggc gtgcacacct tccagccgt gctgcagagc | 2100 |
| agcggcctgt actccctgtc ctccgtggtc accgtgccct ctagctccct gggaacacag | 2160 |
| acatatatct gtaatgtcaa tcacaagcct tccaacacca aagtcgataa gaaagtcgag | 2220 |
| cccaagagct gcgacaaaac tcacacatgc ccaccgtgcc cagcacctga agctgcaggg | 2280 |
| ggaccgtcag tcttcctctt cccccccaaaa cccaaggaca ccctcatgat ctcccggacc | 2340 |
| cctgaggtca catgcgtggt ggtggacgtg agccacgaag accctgaggt caagttcaac | 2400 |
| tggtacgtgg acggcgtgga ggtgcataat gccaagacaa agccgcggga ggagcagtac | 2460 |
| aacagcacgt accgtgtggt cagcgtcctc accgtcctgc accaggactg gctgaatggc | 2520 |
| aaggagtaca agtgcaaggt ctccaacaaa gccctcggcg cccccatcga gaaaaccatc | 2580 |
| tccaaagcca aagggcagcc ccgagaacca caggtgtaca ccctgccccc atgccgggat | 2640 |
| gagctgacca agaaccaggt cagcctgtgg tgcctggtca aaggcttcta tcccagcgac | 2700 |
| atcgccgtgg agtgggagag caatgggcag ccggagaaca actacaagac cacgcctccc | 2760 |
| gtgctggact ccgacggctc cttcttcctc tacagcaagc tcaccgtgga caagagcagg | 2820 |
| tggcagcagg ggaacgtctt ctcatgctcc gtgatgcatg aggctctgca caaccactac | 2880 |
| acgcagaaga gcctctccct gtctccgggt aaatga | 2916 |

<210> SEQ ID NO 68
<211> LENGTH: 99
<212> TYPE: DNA
<213> ORGANISM: Artificial Sequence
<220> FEATURE:
<223> OTHER INFORMATION: Synthetic Construct

<400> SEQUENCE: 68

| | |
|---|---|
| ggcgggggag gctccggagg cggcggaagt agacaggcca gagtcgtgaa cggggggaggg | 60 |
| gggggaagtg ggggcggagg cagtgggggc ggaggatcc | 99 |

<210> SEQ ID NO 69
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 69

| | |
|---|---|
| caggtgcagc tggtccagag cggcgccgag gtgaagaaac ccgggtcctc tgtcaaggtg | 60 |
| tcatgcaagg ctagcggatt caccttaca gactacaaaa tccactgggt taggcaggca | 120 |
| cctggccaag gactcgaatg gatgggggtat ttcaacccaa attccggcta ctctacctat | 180 |
| gcccagaagt ttcagggaag agtgactatt acagctgata gagtaccag cactgcatac | 240 |
| atggagctgt cctctcttcg ctcagaggac accgccgtct actattgtgc tcggctgagc | 300 |
| cccggtggct actatgtgat ggatgcatgg gggcagggaa caaccgtaac agtgtcctct | 360 |
| gcgtcgacta agggcccttc agttttttcca ctcgccccca gtagcaagtc cacatctggg | 420 |
| ggtaccgctg ccctgggctg ccttgtgaaa gactatttcc ctgaaccagt cactgtgtca | 480 |
| tggaatagcg gagccctgac ctccggtgta cacacattcc ccgctgtgtt gcagtctagt | 540 |
| ggcctgtaca gcctctcctc tgttgtgacc gtcccttcaa gctccctggg gacacagacc | 600 |

| | |
|---|---|
| tatatctgta acgtgaatca taagccatct aacactaaag tagataaaaa agtggagccc | 660 |
| aagagttgcg acaaaacaca cacctgtccc ccttgcccag cccccgagct tctgggaggc | 720 |
| cctagcgtct ttctcttccc acccaagcct aaggatactc tgatgatatc caggacccca | 780 |
| gaagttacat gcgtggtcgt ggacgtctca cacgaggacc ccgaagtgaa atttaactgg | 840 |
| tacgttgatg gtgtggaagt ccataatgcc aagaccaagc tagagagga gcaatacaac | 900 |
| agtacatatc gcgtggtaag cgtgttgacc gttctccacc aggactggct caatgggaaa | 960 |
| gaatacaagt gtaaagtgtc caacaaagct ctgccagcac ccatcgagaa gactatttct | 1020 |
| aaggccaaag gccagccccg ggagcctcag gtctatacac ttccaccctc aagggatgaa | 1080 |
| ctgaccaaga accaagtgag cttgacttgc ctggtaaagg ggttctaccc ttccgacatc | 1140 |
| gctgtggagt gggagtctaa tggacaacca gaaaacaatt acaaaaccac acccctgtc | 1200 |
| ctcgacagtg atggcagctt tttcctgtat agcaaactta ccgttgacaa gtccagatgg | 1260 |
| cagcagggaa acgtgttctc atgtagcgtc atgcacgaag ctttgcataa ccactacaca | 1320 |
| cagaaaagcc tcagcctgag tccagggaag | 1350 |

<210> SEQ ID NO 70
<211> LENGTH: 639
<212> TYPE: DNA
<213> ORGANISM: Artificial Sequence
<220> FEATURE:
<223> OTHER INFORMATION: Synthetic Construct

<400> SEQUENCE: 70

| | |
|---|---|
| gacatccaaa tgacccagtc acctagtagc ctctccgcct ctgttggcga cagggtgaca | 60 |
| attacatgca gagcttcaca gggtatcaac aattacctga actggtatca gcagaaacca | 120 |
| gggaaggccc ccaagcgctt gatatataac accaataacc tgcaaactgg cgtccctagc | 180 |
| cggttctccg gatctggtag tggcaccgaa tttacactca ccatcagctc cctgcagcca | 240 |
| gaggatttcg ccacatacta ttgtcttcag cataattctt tccccacctt tgggcaagga | 300 |
| actaaactgg agattaagcg tactgtcgcc gctccctctg tgttcatttt tcctccaagt | 360 |
| gatgagcagc tcaaaagcgg taccgcatcc gttgtgtgcc tgcttaacaa cttctatccc | 420 |
| cgggaagcca aggtccaatg gaaggtggac aatgctctgc agtcaggaaa cagtcaggag | 480 |
| agcgtaaccg agcaggattc caaagactct acttactcat tgagctccac cctgacactc | 540 |
| tctaaggcag actatgaaaa gcataaagtg tacgcctgtg aggttaccca ccagggcctg | 600 |
| agtagccctg tgacaaagtc cttcaataggg ggagagtgc | 639 |

<210> SEQ ID NO 71
<211> LENGTH: 1476
<212> TYPE: DNA
<213> ORGANISM: Artificial Sequence
<220> FEATURE:
<223> OTHER INFORMATION: Synthetic Construct

<400> SEQUENCE: 71

| | |
|---|---|
| gaggttcagc tggagcagtc aggacctgtg ctggtgaagc ctgggacttc agtgaagatg | 60 |
| tcctgtaagg cttctggata cacattcact gactactata taaactggat aatacagagc | 120 |
| catggaaagt gtcttgagtg gattggagtt attaatcctg acagcggtgg tactgactac | 180 |
| aaccagaact tcaagggcaa ggccacattg actgttgaca gtcctccac cacagcctac | 240 |
| atggaactca ctagcctgac atctgaggac tctgcagtct attattgtgc aagaagggat | 300 |

```
tcttacggct tgactactg gggccaaggc accactctca cagtctcctc aggcggaggt    360
ggctcagggg gaggcggtag cggcggaggt ggctcagggg gaggcggtag cgacattgtg    420
ctgacccaga ctcccaaatt cctgcttgtg ccagcaggag acaggattac catgacctgc    480
aaggccagtc tgagtgtgac taatgatgta gcttggtatc aacagaaacc agggcagtct    540
cctaaactgc tgttatacta tgcatccaat cgcaacgctg gagtccctga tcgcttcact    600
ggcagtggat atgggacgga tttcactttc accatcacca ctttgcaggc tgaagacctg    660
gcagtttatt tctgtcagca ggattatacc tctcctccga cgttcggttg tggcaccaag    720
ctagaaatcc gtggtggcgg cggttctggc ggagggggtt ctggcccect ggggctatgg    780 agccagggtg gcggcggttc tggcggaggg ggttctggcg tggtggctc tggcggtgac    840 atccaaatga cccagtcacc tagtagcctc tccgcctctg ttggcgacag ggtgacaatt    900
acatgcagag cttcacaggg tatcaacaat tacctgaact ggtatcagca gaaaccaggg    960
aaggccccca gcgcttgat atataacacc aataacctgc aaactggcgt ccctagccgg   1020
ttctccggat ctggtagtgg caccgaattt acactcacca tcagctccct gcagccagag   1080
gatttcgcca catactattg tcttcagcat aattctttcc ccacctttgg caaggaact   1140 aaactggaga ttaagcgtac tgtcgccgct ccctctgtgt tcattttcc tccaagtgat   1200 gagcagctca aaagcggtac cgcatccgtt gtgtgcctgc ttaacaactt ctatccccgg   1260
gaagccaagg tccaatggaa ggtggacaat gctctgcagt caggaaacag tcaggagagc   1320
gtaaccgagc aggattccaa agactctact tactcattga gctccaccct gacactctct   1380
aaggcagact atgaaaagca taagtgtac gcctgtgagg ttacccacca gggcctgagt   1440
agccctgtga caaagtcctt caatagggga gagtgc                             1476
```

<210> SEQ ID NO 72
<211> LENGTH: 971
<212> TYPE: PRT
<213> ORGANISM: Artificial Sequence
<220> FEATURE:
<223> OTHER INFORMATION: Synthetic Construct

<400> SEQUENCE: 72

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Ser Gly Gly Gly Ser Gly Gly Gly Ser Asp Ile
    130                 135                 140

Gln Met Thr Gln Ser Pro Ala Ser Leu Ser Ala Ser Val Gly Glu Thr
145                 150                 155                 160
```

```
Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Val His
                245                 250                 255

Met Pro Leu Gly Phe Leu Gly Pro Arg Gln Ala Arg Val Val Asn Gly
                260                 265                 270

Gly Gly Gly Gly Ser Gly Gly Gly Ser Glu Val Gln Leu Leu Glu
            275                 280                 285

Ser Gly Gly Gly Leu Val Gln Pro Gly Gly Ser Leu Arg Leu Ser Cys
    290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Tyr Ala Asp Ser Val Lys Gly Arg Phe
                340                 345                 350

Thr Ile Ser Arg Asp Asp Ser Lys Asn Thr Leu Tyr Leu Gln Met Asn
            355                 360                 365

Ser Leu Arg Ala Glu Asp Thr Ala Val Tyr Tyr Cys Val Arg His Gly
    370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
                405                 410                 415

Pro Leu Ala Pro Ser Ser Lys Ser Thr Ser Gly Gly Thr Ala Ala Leu
                420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
    450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
                485                 490                 495

Ser Asn Thr Lys Val Asp Lys Lys Val Glu Pro Lys Ser Cys Asp Gly
                500                 505                 510

Gly Gly Gly Ser Gly Gly Gly Gly Ser Glu Val Gln Leu Val Glu Ser
            515                 520                 525

Gly Gly Gly Leu Val Lys Pro Gly Gly Ser Leu Arg Leu Ser Cys Ala
    530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
                565                 570                 575
```

-continued

Asp Gly Gly Thr Thr Asp Tyr Ala Ala Pro Val Lys Gly Arg Phe Thr
            580                 585                 590

Ile Ser Arg Asp Asp Ser Lys Asn Thr Leu Tyr Leu Gln Met Asn Ser
        595                 600                 605

Leu Lys Thr Glu Asp Thr Ala Val Tyr Tyr Cys Thr Thr Pro Trp Glu
    610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
                645                 650                 655

Lys Ser Thr Ser Gly Gly Thr Ala Ala Leu Gly Cys Leu Val Lys Asp
            660                 665                 670

Tyr Phe Pro Glu Pro Val Thr Val Ser Trp Asn Ser Gly Ala Leu Thr
        675                 680                 685

Ser Gly Val His Thr Phe Pro Ala Val Leu Gln Ser Ser Gly Leu Tyr
    690                 695                 700

Ser Leu Ser Ser Val Val Thr Val Pro Ser Ser Ser Leu Gly Thr Gln
705                 710                 715                 720

Thr Tyr Ile Cys Asn Val Asn His Lys Pro Ser Asn Thr Lys Val Asp
                725                 730                 735

Lys Lys Val Glu Pro Lys Ser Cys Asp Lys Thr His Thr Cys Pro Pro
            740                 745                 750

Cys Pro Ala Pro Glu Ala Ala Gly Gly Pro Ser Val Phe Leu Phe Pro
        755                 760                 765

Pro Lys Pro Lys Asp Thr Leu Met Ile Ser Arg Thr Pro Glu Val Thr
770                 775                 780

Cys Val Val Val Asp Val Ser His Glu Asp Pro Glu Val Lys Phe Asn
785                 790                 795                 800

Trp Tyr Val Asp Gly Val Glu Val His Asn Ala Lys Thr Lys Pro Arg
                805                 810                 815

Glu Glu Gln Tyr Asn Ser Thr Tyr Arg Val Val Ser Val Leu Thr Val
            820                 825                 830

Leu His Gln Asp Trp Leu Asn Gly Lys Glu Tyr Lys Cys Lys Val Ser
        835                 840                 845

Asn Lys Ala Leu Gly Ala Pro Ile Glu Lys Thr Ile Ser Lys Ala Lys
    850                 855                 860

Gly Gln Pro Arg Glu Pro Gln Val Tyr Thr Leu Pro Pro Cys Arg Asp
865                 870                 875                 880

Glu Leu Thr Lys Asn Gln Val Ser Leu Trp Cys Leu Val Lys Gly Phe
                885                 890                 895

Tyr Pro Ser Asp Ile Ala Val Glu Trp Glu Ser Asn Gly Gln Pro Glu
            900                 905                 910

Asn Asn Tyr Lys Thr Thr Pro Pro Val Leu Asp Ser Asp Gly Ser Phe
        915                 920                 925

Phe Leu Tyr Ser Lys Leu Thr Val Asp Lys Ser Arg Trp Gln Gln Gly
    930                 935                 940

Asn Val Phe Ser Cys Ser Val Met His Glu Ala Leu His Asn His Tyr
945                 950                 955                 960

Thr Gln Lys Ser Leu Ser Leu Ser Pro Gly Lys
                965                 970

<210> SEQ ID NO 73
<211> LENGTH: 689
<212> TYPE: PRT

<213> ORGANISM: Artificial Sequence
<220> FEATURE:
<223> OTHER INFORMATION: Synthetic Construct

<400> SEQUENCE: 73

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe
    290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Asn Ser Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
```

```
            385                 390                 395                 400
Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
                420                 425                 430

Ser Ser Leu Gly Thr Gln Thr Tyr Ile Cys Asn Val Asn His Lys Pro
                435                 440                 445

Ser Asn Thr Lys Val Asp Lys Lys Val Glu Pro Lys Ser Cys Asp Lys
                450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
                500                 505                 510

Pro Glu Val Lys Phe Asn Trp Tyr Val Asp Gly Val Glu Val His Asn
                515                 520                 525

Ala Lys Thr Lys Pro Arg Glu Glu Gln Tyr Asn Ser Thr Tyr Arg Val
                530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
                580                 585                 590

Leu Pro Pro Cys Arg Asp Glu Leu Thr Lys Asn Gln Val Ser Leu Trp
                595                 600                 605

Cys Leu Val Lys Gly Phe Tyr Pro Ser Asp Ile Ala Val Glu Trp Glu
                610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
                660                 665                 670

Ala Leu His Asn His Tyr Thr Gln Lys Ser Leu Ser Leu Ser Pro Gly
                675                 680                 685

Lys

<210> SEQ ID NO 74
<211> LENGTH: 497
<212> TYPE: PRT
<213> ORGANISM: Artificial Sequence
<220> FEATURE:
<223> OTHER INFORMATION: Synthetic Construct

<400> SEQUENCE: 74

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val Ser Trp Val Arg Gln Pro Pro Gly Lys Cys Leu Glu Trp Leu
                35                  40                  45

Gly Ile Ile Trp Gly Asp Gly Ser Thr Asn Tyr His Ser Ala Leu Ile
            50                  55                  60
```

```
Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Gly Ile Thr Thr Val Val Asp Tyr Tyr Ala Met Asp Tyr Trp
            100                 105                 110

Gly Gln Gly Thr Ser Val Thr Val Ser Ser Gly Gly Gly Ser Gly
        115                 120                 125

Gly Gly Gly Ser Gly Gly Gly Ser Gly Gly Gly Ser Asp Ile
        130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
                180                 185                 190

Ala Thr Phe Leu Ala Asp Asp Val Pro Ser Arg Phe Ser Gly Ser Gly
            195                 200                 205

Ser Gly Thr Gln Tyr Ser Leu Lys Ile Asn Ser Leu Gln Ser Glu Asp
210                 215                 220

Val Ala Arg Tyr Tyr Cys Gln His Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Arg Gln Ala Arg Val Val Asn Gly Gly Gly Gly Ser
            260                 265                 270

Gly Gly Gly Gly Ser Gly Gly Gly Ser Gln Ala Val Val Thr Gln
        275                 280                 285

Glu Pro Ser Leu Thr Val Ser Pro Gly Gly Thr Val Thr Leu Thr Cys
290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
                325                 330                 335

Lys Arg Ala Pro Gly Thr Pro Ala Arg Phe Ser Gly Ser Leu Leu Gly
                340                 345                 350

Gly Lys Ala Ala Leu Thr Leu Ser Gly Ala Gln Pro Glu Asp Glu Ala
        355                 360                 365

Glu Tyr Tyr Cys Ala Leu Trp Tyr Ser Asn Leu Trp Val Phe Gly Gly
        370                 375                 380

Gly Thr Lys Leu Thr Val Leu Gly Gln Pro Lys Ala Ala Pro Ser Val
385                 390                 395                 400

Thr Leu Phe Pro Pro Ser Ser Glu Glu Leu Gln Ala Asn Lys Ala Thr
                405                 410                 415

Leu Val Cys Leu Ile Ser Asp Phe Tyr Pro Gly Ala Val Thr Val Ala
                420                 425                 430

Trp Lys Ala Asp Ser Ser Pro Val Lys Ala Gly Val Glu Thr Thr Thr
            435                 440                 445

Pro Ser Lys Gln Ser Asn Asn Lys Tyr Ala Ala Ser Ser Tyr Leu Ser
        450                 455                 460

Leu Thr Pro Glu Gln Trp Lys Ser His Arg Ser Tyr Ser Cys Gln Val
465                 470                 475                 480
```

Thr His Glu Gly Ser Thr Val Glu Lys Thr Val Ala Pro Thr Glu Cys
            485                 490                 495

Ser

<210> SEQ ID NO 75
<211> LENGTH: 497
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Gly Gly Gly Gly Ser Gly Gly Gly Gly Gly Gly Ser
            260                 265                 270

Gly Gly Gly Gly Ser Gly Gly Gly Ser Gln Ala Val Val Thr Gln
        275                 280                 285

Glu Pro Ser Leu Thr Val Ser Pro Gly Gly Thr Val Thr Leu Thr Cys
    290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
                325                 330                 335

Lys Arg Ala Pro Gly Thr Pro Ala Arg Phe Ser Gly Ser Leu Leu Gly

```
                  340                 345                 350
Gly Lys Ala Ala Leu Thr Leu Ser Gly Ala Gln Pro Glu Asp Glu Ala
            355                 360                 365
Glu Tyr Tyr Cys Ala Leu Trp Tyr Ser Asn Leu Trp Val Phe Gly Gly
        370                 375                 380
Gly Thr Lys Leu Thr Val Leu Gly Gln Pro Lys Ala Ala Pro Ser Val
385                 390                 395                 400
Thr Leu Phe Pro Pro Ser Ser Glu Glu Leu Gln Ala Asn Lys Ala Thr
                405                 410                 415
Leu Val Cys Leu Ile Ser Asp Phe Tyr Pro Gly Ala Val Thr Val Ala
            420                 425                 430
Trp Lys Ala Asp Ser Ser Pro Val Lys Ala Gly Val Glu Thr Thr Thr
        435                 440                 445
Pro Ser Lys Gln Ser Asn Asn Lys Tyr Ala Ala Ser Ser Tyr Leu Ser
450                 455                 460
Leu Thr Pro Glu Gln Trp Lys Ser His Arg Ser Tyr Ser Cys Gln Val
                470                 475                 480
Thr His Glu Gly Ser Thr Val Glu Lys Thr Val Ala Pro Thr Glu Cys
            485                 490                 495
Ser
```

<210> SEQ ID NO 76
<211> LENGTH: 674
<212> TYPE: PRT
<213> ORGANISM: Artificial Sequence
<220> FEATURE:
<223> OTHER INFORMATION: Synthetic Construct

<400> SEQUENCE: 76

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Gly Tyr
            20                  25                  30
Thr Met Asn Trp Val Arg Gln Ala Pro Gly Gln Gly Leu Glu Trp Met
        35                  40                  45
Gly Leu Ile Thr Pro Tyr Asn Gly Ala Ser Ser Tyr Asn Gln Lys Phe
    50                  55                  60
Arg Gly Lys Ala Thr Met Thr Val Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Gly Tyr Asp Gly Arg Gly Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Glu Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
```

-continued

Ser Asn Thr Lys Val Asp Glu Lys Val Glu Pro Lys Ser Cys Asp Gly
    210                 215                 220

Gly Gly Gly Ser Gly Gly Gly Ser Gln Ala Val Val Thr Gln Glu
225             230             235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
        275                 280                 285

Arg Ala Pro Gly Thr Pro Ala Arg Phe Ser Gly Ser Leu Leu Gly Gly
290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Thr Ala Ala
        355                 360                 365

Leu Gly Cys Leu Val Lys Asp Tyr Phe Pro Glu Pro Val Thr Val Ser
370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
        435                 440                 445

Lys Thr His Thr Cys Pro Pro Cys Pro Ala Pro Glu Ala Ala Gly Gly
450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
610                 615                 620

-continued

```
Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
            645                 650                 655

Glu Ala Leu His Asn His Tyr Thr Gln Lys Ser Leu Ser Leu Ser Pro
            660                 665                 670

Gly Lys

<210> SEQ ID NO 77
<211> LENGTH: 449
<212> TYPE: PRT
<213> ORGANISM: Artificial Sequence
<220> FEATURE:
<223> OTHER INFORMATION: Synthetic Construct

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Thr Pro Tyr Asn Gly Ala Ser Ser Tyr Asn Gln Lys Phe
    50                  55                  60

Arg Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Arg Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
                    305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 78
<211> LENGTH: 213
<212> TYPE: PRT
<213> ORGANISM: Artificial Sequence
<220> FEATURE:
<223> OTHER INFORMATION: Synthetic Construct

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
                20                  25                  30

His Trp Tyr Gln Gln Lys Ser Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Lys His Pro Leu Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Arg Lys Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 79
<211> LENGTH: 514
<212> TYPE: PRT
<213> ORGANISM: Artificial Sequence
<220> FEATURE:
<223> OTHER INFORMATION: Synthetic Construct

<400> SEQUENCE: 79

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Val His
                245                 250                 255

Met Pro Leu Gly Phe Leu Gly Pro Arg Gln Ala Arg Val Val Asn Gly
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Tyr Ala Asp Ser Val Lys Gly Arg Phe
            340                 345                 350

Thr Ile Ser Arg Asp Asp Ser Lys Asn Thr Leu Tyr Leu Gln Met Asn
        355                 360                 365
```

-continued

```
Ser Leu Arg Ala Glu Asp Thr Ala Val Tyr Tyr Cys Val Arg His Gly
    370                 375                 380
Asn Phe Gly Asn Ser Tyr Val Ser Trp Phe Ala Tyr Trp Gly Gln Gly
385                 390                 395                 400
Thr Leu Val Thr Val Ser Ser Ala Ser Val Ala Ala Pro Ser Val Phe
                405                 410                 415
Ile Phe Pro Pro Ser Asp Glu Gln Leu Lys Ser Gly Thr Ala Ser Val
            420                 425                 430
Val Cys Leu Leu Asn Asn Phe Tyr Pro Arg Glu Ala Lys Val Gln Trp
        435                 440                 445
Lys Val Asp Asn Ala Leu Gln Ser Gly Asn Ser Gln Glu Ser Val Thr
450                 455                 460
Glu Gln Asp Ser Lys Asp Ser Thr Tyr Ser Leu Ser Ser Thr Leu Thr
465                 470                 475                 480
Leu Ser Lys Ala Asp Tyr Glu Lys His Lys Val Tyr Ala Cys Glu Val
                485                 490                 495
Thr His Gln Gly Leu Ser Ser Pro Val Thr Lys Ser Phe Asn Arg Gly
            500                 505                 510
Glu Cys

<210> SEQ ID NO 80
<211> LENGTH: 514
<212> TYPE: PRT
<213> ORGANISM: Artificial Sequence
<220> FEATURE:
<223> OTHER INFORMATION: Synthetic Construct

<400> SEQUENCE: 80

Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Thr Ser Tyr
                20                  25                  30
Gly Val Ser Trp Val Arg Gln Pro Pro Gly Lys Cys Leu Glu Trp Leu
            35                  40                  45
Gly Ile Ile Trp Gly Asp Gly Ser Thr Asn Tyr His Ser Ala Leu Ile
        50                  55                  60
Ser Arg Leu Ser Ile Ser Lys Asp Asn Ser Lys Ser Gln Val Phe Leu
65                  70                  75                  80
Lys Leu Asn Ser Leu Gln Thr Asp Asp Thr Ala Thr Tyr Tyr Cys Ala
                85                  90                  95
Lys Gly Ile Thr Thr Val Val Asp Asp Tyr Tyr Ala Met Asp Tyr Trp
            100                 105                 110
Gly Gln Gly Thr Ser Val Thr Val Ser Ser Gly Gly Gly Gly Ser Gly
        115                 120                 125
Gly Gly Gly Ser Gly Gly Gly Gly Ser Gly Gly Gly Gly Ser Asp Ile
    130                 135                 140
Gln Met Thr Gln Ser Pro Ala Ser Leu Ser Ala Ser Val Gly Glu Thr
145                 150                 155                 160
Val Thr Ile Thr Cys Arg Ala Ser Glu Asn Ile Asp Ser Tyr Leu Ala
                165                 170                 175
Trp Tyr Gln Gln Lys Gln Gly Lys Ser Pro Gln Leu Leu Val Tyr Ala
            180                 185                 190
Ala Thr Phe Leu Ala Asp Asp Val Pro Ser Arg Phe Ser Gly Ser Gly
        195                 200                 205
```

Ser Gly Thr Gln Tyr Ser Leu Lys Ile Asn Ser Leu Gln Ser Glu Asp
         210                 215                 220

Val Ala Arg Tyr Tyr Cys Gln His Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Gly Gly Gly Ser Gly Gly Gly Gly Gly Ser
            260                 265                 270

Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Tyr Ala Asp Ser Val Lys Gly Arg Phe
            340                 345                 350

Thr Ile Ser Arg Asp Asp Ser Lys Asn Thr Leu Tyr Leu Gln Met Asn
        355                 360                 365

Ser Leu Arg Ala Glu Asp Thr Ala Val Tyr Tyr Cys Val Arg His Gly
370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Val Ala Ala Pro Ser Val Phe
                405                 410                 415

Ile Phe Pro Pro Ser Asp Glu Gln Leu Lys Ser Gly Thr Ala Ser Val
            420                 425                 430

Val Cys Leu Leu Asn Asn Phe Tyr Pro Arg Glu Ala Lys Val Gln Trp
        435                 440                 445

Lys Val Asp Asn Ala Leu Gln Ser Gly Asn Ser Gln Glu Ser Val Thr
450                 455                 460

Glu Gln Asp Ser Lys Asp Ser Thr Tyr Ser Leu Ser Ser Thr Leu Thr
465                 470                 475                 480

Leu Ser Lys Ala Asp Tyr Glu Lys His Lys Val Tyr Ala Cys Glu Val
                485                 490                 495

Thr His Gln Gly Leu Ser Ser Pro Val Thr Lys Ser Phe Asn Arg Gly
            500                 505                 510

Glu Cys

<210> SEQ ID NO 81
<211> LENGTH: 232
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp

```
                 50                  55                  60
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Val Arg His Gly Asn Phe Gly Asn Ser Tyr Val Ser Trp Phe
                    100                 105                 110

Ala Tyr Trp Gly Gln Gly Thr Leu Val Thr Val Ser Ser Ala Ser Val
                115                 120                 125

Ala Ala Pro Ser Val Phe Ile Phe Pro Pro Ser Asp Glu Gln Leu Lys
            130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230

<210> SEQ ID NO 82
<211> LENGTH: 956
<212> TYPE: PRT
<213> ORGANISM: Artificial Sequence
<220> FEATURE:
<223> OTHER INFORMATION: Synthetic Construct

<400> SEQUENCE: 82

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ser Tyr
                20                  25                  30

Gly Val Ser Trp Val Arg Gln Pro Pro Gly Lys Cys Leu Glu Trp Leu
            35                  40                  45

Gly Ile Ile Trp Gly Asp Gly Ser Thr Asn Tyr His Ser Ala Leu Ile
        50                  55                  60

Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Gly Ile Thr Thr Val Val Asp Asp Tyr Tyr Ala Met Asp Tyr Trp
                100                 105                 110

Gly Gln Gly Thr Ser Val Thr Val Ser Ser Gly Gly Gly Gly Ser Gly
            115                 120                 125

Gly Gly Gly Ser Gly Gly Gly Ser Gly Gly Gly Gly Ser Asp Ile
        130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
```

-continued

```
                180                 185                 190
Ala Thr Phe Leu Ala Asp Asp Val Pro Ser Arg Phe Ser Gly Ser Gly
            195                 200                 205

Ser Gly Thr Gln Tyr Ser Leu Lys Ile Asn Ser Leu Gln Ser Glu Asp
            210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Val His
                245                 250                 255

Met Pro Leu Gly Phe Leu Gly Pro Arg Gln Ala Arg Val Val Asn Gly
                260                 265                 270

Gly Gly Gly Gly Ser Gly Gly Gly Ser Gln Ala Val Val Thr Gln
            275                 280                 285

Glu Pro Ser Leu Thr Val Ser Pro Gly Gly Thr Val Thr Leu Thr Cys
            290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
                325                 330                 335

Lys Arg Ala Pro Gly Thr Pro Ala Arg Phe Ser Gly Ser Leu Leu Gly
                340                 345                 350

Gly Lys Ala Ala Leu Thr Leu Ser Gly Ala Gln Pro Glu Asp Glu Ala
            355                 360                 365

Glu Tyr Tyr Cys Ala Leu Trp Tyr Ser Asn Leu Trp Val Phe Gly Gly
            370                 375                 380

Gly Thr Lys Leu Thr Val Leu Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415

Ala Leu Gly Cys Leu Val Lys Asp Tyr Phe Pro Glu Pro Val Thr Val
                420                 425                 430

Ser Trp Asn Ser Gly Ala Leu Thr Ser Gly Val His Thr Phe Pro Ala
            435                 440                 445

Val Leu Gln Ser Ser Gly Leu Tyr Ser Leu Ser Ser Val Val Thr Val
            450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Gly Gly Gly Gly Ser Gly Gly Gly Ser Gln Val Gln Leu Val
            500                 505                 510

Gln Ser Gly Ala Glu Val Lys Lys Pro Gly Ala Ser Val Lys Val Ser
            515                 520                 525

Cys Lys Ala Ser Gly Tyr Ser Phe Thr Gly Tyr Thr Met Asn Trp Val
            530                 535                 540

Arg Gln Ala Pro Gly Gln Gly Leu Glu Trp Met Gly Leu Ile Thr Pro
545                 550                 555                 560

Tyr Asn Gly Ala Ser Ser Tyr Asn Gln Lys Phe Arg Gly Lys Ala Thr
                565                 570                 575

Met Thr Val Asp Thr Ser Thr Ser Thr Val Tyr Met Glu Leu Ser Ser
                580                 585                 590

Leu Arg Ser Glu Asp Thr Ala Val Tyr Tyr Cys Ala Arg Gly Gly Tyr
            595                 600                 605
```

```
Asp Gly Arg Gly Phe Asp Tyr Trp Gly Gln Gly Thr Leu Val Thr Val
            610                 615                 620

Ser Ser Ala Ser Thr Lys Gly Pro Ser Val Phe Pro Leu Ala Pro Ser
625                 630                 635                 640

Ser Lys Ser Thr Ser Gly Gly Thr Ala Ala Leu Gly Cys Leu Val Glu
                645                 650                 655

Asp Tyr Phe Pro Glu Pro Val Thr Val Ser Trp Asn Ser Gly Ala Leu
            660                 665                 670

Thr Ser Gly Val His Thr Phe Pro Ala Val Leu Gln Ser Ser Gly Leu
        675                 680                 685

Tyr Ser Leu Ser Ser Val Val Thr Val Pro Ser Ser Ser Leu Gly Thr
690                 695                 700

Gln Thr Tyr Ile Cys Asn Val Asn His Lys Pro Ser Asn Thr Lys Val
705                 710                 715                 720

Asp Glu Lys Val Glu Pro Lys Ser Cys Asp Lys Thr His Thr Cys Pro
                725                 730                 735

Pro Cys Pro Ala Pro Glu Ala Ala Gly Gly Pro Ser Val Phe Leu Phe
            740                 745                 750

Pro Pro Lys Pro Lys Asp Thr Leu Met Ile Ser Arg Thr Pro Glu Val
        755                 760                 765

Thr Cys Val Val Val Asp Val Ser His Glu Asp Pro Glu Val Lys Phe
770                 775                 780

Asn Trp Tyr Val Asp Gly Val Glu Val His Asn Ala Lys Thr Lys Pro
785                 790                 795                 800

Arg Glu Glu Gln Tyr Asn Ser Thr Tyr Arg Val Val Ser Val Leu Thr
                805                 810                 815

Val Leu His Gln Asp Trp Leu Asn Gly Lys Glu Tyr Lys Cys Lys Val
            820                 825                 830

Ser Asn Lys Ala Leu Gly Ala Pro Ile Glu Lys Thr Ile Ser Lys Ala
        835                 840                 845

Lys Gly Gln Pro Arg Glu Pro Gln Val Tyr Thr Leu Pro Pro Cys Arg
850                 855                 860

Asp Glu Leu Thr Lys Asn Gln Val Ser Leu Trp Cys Leu Val Lys Gly
865                 870                 875                 880

Phe Tyr Pro Ser Asp Ile Ala Val Glu Trp Glu Ser Asn Gly Gln Pro
                885                 890                 895

Glu Asn Asn Tyr Lys Thr Thr Pro Pro Val Leu Asp Ser Asp Gly Ser
            900                 905                 910

Phe Phe Leu Tyr Ser Lys Leu Thr Val Asp Lys Ser Arg Trp Gln Gln
        915                 920                 925

Gly Asn Val Phe Ser Cys Ser Val Met His Glu Ala Leu His Asn His
930                 935                 940

Tyr Thr Gln Lys Ser Leu Ser Leu Ser Pro Gly Lys
945                 950                 955

<210> SEQ ID NO 83
<211> LENGTH: 956
<212> TYPE: PRT
<213> ORGANISM: Artificial Sequence
<220> FEATURE:
<223> OTHER INFORMATION: Synthetic Construct

<400> SEQUENCE: 83

Gln Val Gln Leu Lys Glu Ser Gly Pro Gly Leu Val Ala Pro Ser Gln
1               5                   10                  15
```

```
Ser Leu Ser Ile Thr Cys Thr Val Ser Gly Phe Ser Leu Thr Ser Tyr
            20                  25                  30

Gly Val Ser Trp Val Arg Gln Pro Gly Lys Cys Leu Glu Trp Leu
        35                  40                  45

Gly Ile Ile Trp Gly Asp Gly Ser Thr Asn Tyr His Ser Ala Leu Ile
 50                  55                  60

Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Ser Gly
        115                 120                 125

Gly Gly Gly Ser Gly Gly Gly Ser Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
                180                 185                 190

Ala Thr Phe Leu Ala Asp Asp Val Pro Ser Arg Phe Ser Gly Ser Gly
            195                 200                 205

Ser Gly Thr Gln Tyr Ser Leu Lys Ile Asn Ser Leu Gln Ser Glu Asp
        210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Gly Gly Gly Ser Gly Gly Gly Gly Gly Ser
        260                 265                 270

Gly Gly Gly Gly Ser Gly Gly Gly Ser Gln Ala Val Val Thr Gln
        275                 280                 285

Glu Pro Ser Leu Thr Val Ser Pro Gly Gly Thr Val Thr Leu Thr Cys
290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
                325                 330                 335

Lys Arg Ala Pro Gly Thr Pro Ala Arg Phe Ser Gly Ser Leu Leu Gly
                340                 345                 350

Gly Lys Ala Ala Leu Thr Leu Ser Gly Ala Gln Pro Glu Asp Glu Ala
            355                 360                 365

Glu Tyr Tyr Cys Ala Leu Trp Tyr Ser Asn Leu Trp Val Phe Gly Gly
        370                 375                 380

Gly Thr Lys Leu Thr Val Leu Ser Ser Ala Ser Thr Lys Gly Pro Ser
385                 390                 395                 400

Val Phe Pro Leu Ala Pro Ser Ser Lys Ser Thr Ser Gly Gly Thr Ala
            405                 410                 415

Ala Leu Gly Cys Leu Val Lys Asp Tyr Phe Pro Glu Pro Val Thr Val
            420                 425                 430
```

```
Ser Trp Asn Ser Gly Ala Leu Thr Ser Gly Val His Thr Phe Pro Ala
            435                 440                 445

Val Leu Gln Ser Ser Gly Leu Tyr Ser Leu Ser Val Val Thr Val
450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Gly Gly Gly Gly Ser Gly Gly Gly Ser Gln Val Gln Leu Val
            500                 505                 510

Gln Ser Gly Ala Glu Val Lys Lys Pro Gly Ala Ser Val Lys Val Ser
            515                 520                 525

Cys Lys Ala Ser Gly Tyr Ser Phe Thr Gly Tyr Thr Met Asn Trp Val
530                 535                 540

Arg Gln Ala Pro Gly Gln Gly Leu Glu Trp Met Gly Leu Ile Thr Pro
545                 550                 555                 560

Tyr Asn Gly Ala Ser Ser Tyr Asn Gln Lys Phe Arg Gly Lys Ala Thr
                565                 570                 575

Met Thr Val Asp Thr Ser Thr Ser Thr Val Tyr Met Glu Leu Ser Ser
            580                 585                 590

Leu Arg Ser Glu Asp Thr Ala Val Tyr Tyr Cys Ala Arg Gly Gly Tyr
        595                 600                 605

Asp Gly Arg Gly Phe Asp Tyr Trp Gly Gln Gly Thr Leu Val Thr Val
            610                 615                 620

Ser Ser Ala Ser Thr Lys Gly Pro Ser Val Phe Pro Leu Ala Pro Ser
625                 630                 635                 640

Ser Lys Ser Thr Ser Gly Gly Thr Ala Ala Leu Gly Cys Leu Val Glu
                645                 650                 655

Asp Tyr Phe Pro Glu Pro Val Thr Val Ser Trp Asn Ser Gly Ala Leu
            660                 665                 670

Thr Ser Gly Val His Thr Phe Pro Ala Val Leu Gln Ser Ser Gly Leu
        675                 680                 685

Tyr Ser Leu Ser Ser Val Val Thr Val Pro Ser Ser Ser Leu Gly Thr
    690                 695                 700

Gln Thr Tyr Ile Cys Asn Val Asn His Lys Pro Ser Asn Thr Lys Val
705                 710                 715                 720

Asp Glu Lys Val Glu Pro Lys Ser Cys Asp Lys Thr His Thr Cys Pro
                725                 730                 735

Pro Cys Pro Ala Pro Glu Ala Ala Gly Gly Pro Ser Val Phe Leu Phe
            740                 745                 750

Pro Pro Lys Pro Lys Asp Thr Leu Met Ile Ser Arg Thr Pro Glu Val
        755                 760                 765

Thr Cys Val Val Val Asp Val Ser His Glu Asp Pro Glu Val Lys Phe
    770                 775                 780

Asn Trp Tyr Val Asp Gly Val Glu Val His Asn Ala Lys Thr Lys Pro
785                 790                 795                 800

Arg Glu Glu Gln Tyr Asn Ser Thr Tyr Arg Val Val Ser Val Leu Thr
                805                 810                 815

Val Leu His Gln Asp Trp Leu Asn Gly Lys Glu Tyr Lys Cys Lys Val
            820                 825                 830

Ser Asn Lys Ala Leu Gly Ala Pro Ile Glu Lys Thr Ile Ser Lys Ala
        835                 840                 845

Lys Gly Gln Pro Arg Glu Pro Gln Val Tyr Thr Leu Pro Pro Cys Arg
```

```
                850                 855                 860
Asp Glu Leu Thr Lys Asn Gln Val Ser Leu Trp Cys Leu Val Lys Gly
865                 870                 875                 880

Phe Tyr Pro Ser Asp Ile Ala Val Glu Trp Glu Ser Asn Gly Gln Pro
                885                 890                 895

Glu Asn Asn Tyr Lys Thr Thr Pro Pro Val Leu Asp Ser Asp Gly Ser
                900                 905                 910

Phe Phe Leu Tyr Ser Lys Leu Thr Val Asp Lys Ser Arg Trp Gln Gln
                915                 920                 925

Gly Asn Val Phe Ser Cys Ser Val Met His Glu Ala Leu His Asn His
                930                 935                 940

Tyr Thr Gln Lys Ser Leu Ser Leu Ser Pro Gly Lys
945                 950                 955

<210> SEQ ID NO 84
<211> LENGTH: 674
<212> TYPE: PRT
<213> ORGANISM: Artificial Sequence
<220> FEATURE:
<223> OTHER INFORMATION: Synthetic Construct

<400> SEQUENCE: 84

Gln Ala Val Val Thr Gln Glu Pro Ser Leu Thr Val Ser Pro Gly Gly
1                   5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
            50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
                100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
                180                 185                 190

Ile Cys Asn Val Asn His Lys Pro Ser Asn Thr Lys Val Asp Lys Lys
            195                 200                 205

Val Glu Pro Lys Ser Cys Asp Gly Gly Gly Ser Gly Gly Gly Gly
            210                 215                 220

Ser Gln Val Gln Leu Val Gln Ser Gly Ala Glu Val Lys Lys Pro Gly
225                 230                 235                 240

Ala Ser Val Lys Val Ser Cys Lys Ala Ser Gly Tyr Ser Phe Thr Gly
                245                 250                 255

Tyr Thr Met Asn Trp Val Arg Gln Ala Pro Gly Gln Gly Leu Glu Trp
```

```
            260                 265                 270
Met Gly Leu Ile Thr Pro Tyr Asn Gly Ala Ser Ser Tyr Asn Gln Lys
            275                 280                 285

Phe Arg Gly Lys Ala Thr Met Thr Val Asp Thr Ser Thr Ser Thr Val
290                 295                 300

Tyr Met Glu Leu Ser Ser Leu Arg Ser Glu Asp Thr Ala Val Tyr Tyr
305                 310                 315                 320

Cys Ala Arg Gly Gly Tyr Asp Gly Arg Gly Phe Asp Tyr Trp Gly Gln
                325                 330                 335

Gly Thr Leu Val Thr Val Ser Ser Ala Ser Thr Lys Gly Pro Ser Val
            340                 345                 350

Phe Pro Leu Ala Pro Ser Ser Lys Ser Thr Ser Gly Gly Thr Ala Ala
                355                 360                 365

Leu Gly Cys Leu Val Glu Asp Tyr Phe Pro Glu Pro Val Thr Val Ser
            370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Glu Lys Val Glu Pro Lys Ser Cys Asp
            435                 440                 445

Lys Thr His Thr Cys Pro Pro Cys Pro Ala Pro Glu Ala Ala Gly Gly
        450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
            530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
            595                 600                 605

Glu Ser Asn Gly Gln Pro Glu Asn Asn Tyr Lys Thr Thr Pro Pro Val
        610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys
```

-continued

```
<210> SEQ ID NO 85
<211> LENGTH: 971
<212> TYPE: PRT
<213> ORGANISM: Artificial Sequence
<220> FEATURE:
<223> OTHER INFORMATION: Synthetic Construct

<400> SEQUENCE: 85

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Ser Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Gly Gly Gly Ser Phe Val Gly Gly Thr Gly Gly
            260                 265                 270

Gly Ser Gly Gly Gly Ser Gly Gly Ser Glu Val Gln Leu Leu Glu
        275                 280                 285

Ser Gly Gly Gly Leu Val Gln Pro Gly Gly Ser Leu Arg Leu Ser Cys
290                 295                 300

Ala Ala Ser Gly Phe Thr Phe Ser Thr Tyr Ala Met Asn Trp Val Arg
305                 310                 315                 320

Gln Ala Pro Gly Lys Gly Leu Glu Trp Val Ser Arg Ile Arg Ser Lys
                325                 330                 335

Tyr Asn Asn Tyr Ala Thr Tyr Tyr Ala Asp Ser Val Lys Gly Arg Phe
            340                 345                 350

Thr Ile Ser Arg Asp Asp Ser Lys Asn Thr Leu Tyr Leu Gln Met Asn
        355                 360                 365
```

-continued

```
Ser Leu Arg Ala Glu Asp Thr Ala Val Tyr Tyr Cys Val Arg His Gly
    370                 375                 380

Asn Phe Gly Asn Ser Tyr Val Ser Trp Phe Ala Tyr Trp Gly Gln Gly
385                 390                 395                 400

Thr Leu Val Thr Val Ser Ser Ala Ser Thr Lys Gly Pro Ser Val Phe
            405                 410                 415

Pro Leu Ala Pro Ser Ser Lys Ser Thr Ser Gly Gly Thr Ala Ala Leu
                420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
                485                 490                 495

Ser Asn Thr Lys Val Asp Lys Lys Val Glu Pro Lys Ser Cys Asp Gly
                500                 505                 510

Gly Gly Gly Ser Gly Gly Gly Ser Glu Val Gln Leu Val Glu Ser
            515                 520                 525

Gly Gly Gly Leu Val Lys Pro Gly Gly Ser Leu Arg Leu Ser Cys Ala
530                 535                 540

Ala Ser Gly Phe Thr Phe Ser Asn Ala Trp Met Ser Trp Val Arg Gln
545                 550                 555                 560

Ala Pro Gly Lys Gly Leu Glu Trp Val Gly Arg Ile Lys Ser Lys Thr
                565                 570                 575

Asp Gly Gly Thr Thr Asp Tyr Ala Ala Pro Val Lys Gly Arg Phe Thr
                580                 585                 590

Ile Ser Arg Asp Asp Ser Lys Asn Thr Leu Tyr Leu Gln Met Asn Ser
            595                 600                 605

Leu Lys Thr Glu Asp Thr Ala Val Tyr Tyr Cys Thr Thr Pro Trp Glu
    610                 615                 620

Trp Ser Trp Tyr Asp Tyr Trp Gly Gln Gly Thr Leu Val Thr Val Ser
625                 630                 635                 640

Ser Ala Ser Thr Lys Gly Pro Ser Val Phe Pro Leu Ala Pro Ser Ser
            645                 650                 655

Lys Ser Thr Ser Gly Gly Thr Ala Ala Leu Gly Cys Leu Val Lys Asp
                660                 665                 670

Tyr Phe Pro Glu Pro Val Thr Val Ser Trp Asn Ser Gly Ala Leu Thr
            675                 680                 685

Ser Gly Val His Thr Phe Pro Ala Val Leu Gln Ser Ser Gly Leu Tyr
    690                 695                 700

Ser Leu Ser Ser Val Val Thr Val Pro Ser Ser Ser Leu Gly Thr Gln
705                 710                 715                 720

Thr Tyr Ile Cys Asn Val Asn His Lys Pro Ser Asn Thr Lys Val Asp
                725                 730                 735

Lys Lys Val Glu Pro Lys Ser Cys Asp Lys Thr His Thr Cys Pro Pro
            740                 745                 750

Cys Pro Ala Pro Glu Ala Ala Gly Gly Pro Ser Val Phe Leu Phe Pro
            755                 760                 765

Pro Lys Pro Lys Asp Thr Leu Met Ile Ser Arg Thr Pro Glu Val Thr
    770                 775                 780

Cys Val Val Val Asp Val Ser His Glu Asp Pro Glu Val Lys Phe Asn
```

```
                785                 790                 795                 800
Trp Tyr Val Asp Gly Val Glu Val His Asn Ala Lys Thr Lys Pro Arg
                805                 810                 815
Glu Glu Gln Tyr Asn Ser Thr Tyr Arg Val Val Ser Val Leu Thr Val
            820                 825                 830
Leu His Gln Asp Trp Leu Asn Gly Lys Glu Tyr Lys Cys Lys Val Ser
        835                 840                 845
Asn Lys Ala Leu Gly Ala Pro Ile Glu Lys Thr Ile Ser Lys Ala Lys
    850                 855                 860
Gly Gln Pro Arg Glu Pro Gln Val Tyr Thr Leu Pro Pro Cys Arg Asp
865                 870                 875                 880
Glu Leu Thr Lys Asn Gln Val Ser Leu Trp Cys Leu Val Lys Gly Phe
                885                 890                 895
Tyr Pro Ser Asp Ile Ala Val Glu Trp Glu Ser Asn Gly Gln Pro Glu
            900                 905                 910
Asn Asn Tyr Lys Thr Thr Pro Pro Val Leu Asp Ser Asp Gly Ser Phe
        915                 920                 925
Phe Leu Tyr Ser Lys Leu Thr Val Asp Lys Ser Arg Trp Gln Gln Gly
    930                 935                 940
Asn Val Phe Ser Cys Ser Val Met His Glu Ala Leu His Asn His Tyr
945                 950                 955                 960
Thr Gln Lys Ser Leu Ser Leu Ser Pro Gly Lys
                965                 970

<210> SEQ ID NO 86
<211> LENGTH: 33
<212> TYPE: PRT
<213> ORGANISM: Artificial Sequence
<220> FEATURE:
<223> OTHER INFORMATION: Synthetic Construct

<400> SEQUENCE: 86

Gly Gly Gly Gly Ser Val His Met Pro Leu Gly Phe Leu Gly Pro Arg
1               5                   10                  15
Gln Ala Arg Val Val Asn Gly Gly Gly Gly Ser Gly Gly Gly Gly
            20                  25                  30
Ser

<210> SEQ ID NO 87
<211> LENGTH: 35
<212> TYPE: PRT
<213> ORGANISM: Artificial Sequence
<220> FEATURE:
<223> OTHER INFORMATION: Synthetic Construct

<400> SEQUENCE: 87

Gly Gly Gly Gly Ser Val His Met Pro Leu Gly Phe Leu Gly Pro Arg
1               5                   10                  15
Gln Ala Arg Val Val Asn Gly Gly Gly Gly Ser Gly Gly Gly Gly
            20                  25                  30
Ser Gly Gly
        35

<210> SEQ ID NO 88
<211> LENGTH: 33
<212> TYPE: PRT
<213> ORGANISM: Artificial Sequence
<220> FEATURE:
<223> OTHER INFORMATION: Synthetic Construct
```

<400> SEQUENCE: 88

Gly Gly Gly Gly Ser Gly Gly Gly Gly Ser Gly Gly Gly Gly Ser Phe
1               5                   10                  15

Val Gly Gly Thr Gly Gly Gly Ser Gly Gly Gly Ser Gly Gly
            20                  25                  30

Ser

<210> SEQ ID NO 89
<211> LENGTH: 33
<212> TYPE: PRT
<213> ORGANISM: Artificial Sequence
<220> FEATURE:
<223> OTHER INFORMATION: Synthetic Construct

<400> SEQUENCE: 89

Gly Gly Gly Gly Ser Gly Gly Gly Ser Lys Lys Ala Ala Pro Val
1               5                   10                  15

Asn Gly Gly Gly Gly Ser Gly Gly Gly Ser Gly Gly Gly Gly
            20                  25                  30

Ser

<210> SEQ ID NO 90
<211> LENGTH: 33
<212> TYPE: PRT
<213> ORGANISM: Artificial Sequence
<220> FEATURE:
<223> OTHER INFORMATION: Synthetic Construct

<400> SEQUENCE: 90

Gly Gly Gly Gly Ser Gly Gly Gly Gly Ser Pro Met Ala Lys Lys Val
1               5                   10                  15

Asn Gly Gly Gly Gly Ser Gly Gly Gly Ser Gly Gly Gly Gly
            20                  25                  30

Ser

<210> SEQ ID NO 91
<211> LENGTH: 33
<212> TYPE: PRT
<213> ORGANISM: Artificial Sequence
<220> FEATURE:
<223> OTHER INFORMATION: Synthetic Construct

<400> SEQUENCE: 91

Gly Gly Gly Gly Ser Gly Gly Gly Gly Ser Gln Ala Arg Ala Lys Val
1               5                   10                  15

Asn Gly Gly Gly Gly Ser Gly Gly Gly Ser Gly Gly Gly Gly
            20                  25                  30

Ser

<210> SEQ ID NO 92
<211> LENGTH: 33
<212> TYPE: PRT
<213> ORGANISM: Artificial Sequence
<220> FEATURE:
<223> OTHER INFORMATION: Synthetic Construct

<400> SEQUENCE: 92

Gly Gly Gly Gly Ser Gly Gly Gly Gly Ser Val His Met Pro Leu Gly
1               5                   10                  15

Phe Leu Gly Pro Gly Gly Gly Gly Ser Gly Gly Gly Gly Ser Gly Gly

-continued

```
                20                  25                  30

Ser

<210> SEQ ID NO 93
<211> LENGTH: 33
<212> TYPE: PRT
<213> ORGANISM: Artificial Sequence
<220> FEATURE:
<223> OTHER INFORMATION: Synthetic Construct

<400> SEQUENCE: 93

Gly Gly Gly Gly Ser Gly Gly Gly Ser Gln Ala Arg Ala Lys Gly
1               5                   10                  15

Gly Gly Gly Ser Gly Gly Gly Gly Ser Gly Gly Gly Ser Gly Gly
                20                  25                  30

Ser

<210> SEQ ID NO 94
<211> LENGTH: 33
<212> TYPE: PRT
<213> ORGANISM: Artificial Sequence
<220> FEATURE:
<223> OTHER INFORMATION: Synthetic Construct

<400> SEQUENCE: 94

Gly Gly Gly Gly Ser Val His Met Pro Leu Gly Phe Leu Gly Pro
1               5                   10                  15

Met Ala Lys Lys Gly Gly Gly Gly Ser Gly Gly Gly Ser Gly Gly
                20                  25                  30

Ser

<210> SEQ ID NO 95
<211> LENGTH: 33
<212> TYPE: PRT
<213> ORGANISM: Artificial Sequence
<220> FEATURE:
<223> OTHER INFORMATION: Synthetic Construct

<400> SEQUENCE: 95

Gly Gly Gly Gly Ser Gly Gly Gly Ser Lys Lys Ala Ala Pro Gly
1               5                   10                  15

Gly Gly Ser Gly Gly Gly Gly Ser Gly Gly Gly Ser Gly Gly
                20                  25                  30

Ser

<210> SEQ ID NO 96
<211> LENGTH: 33
<212> TYPE: PRT
<213> ORGANISM: Artificial Sequence
<220> FEATURE:
<223> OTHER INFORMATION: Synthetic Construct

<400> SEQUENCE: 96

Gly Gly Gly Gly Ser Gly Gly Gly Ser Pro Met Ala Lys Lys Gly
1               5                   10                  15

Gly Gly Ser Gly Gly Gly Gly Ser Gly Gly Gly Ser Gly Gly
                20                  25                  30

Ser

<210> SEQ ID NO 97
<211> LENGTH: 18
```

```
<212> TYPE: PRT
<213> ORGANISM: Artificial Sequence
<220> FEATURE:
<223> OTHER INFORMATION: Synthetic Construct

<400> SEQUENCE: 97

Val His Met Pro Leu Gly Phe Leu Gly Pro Arg Gln Ala Arg Val Val
1               5                   10                  15

Asn Gly

<210> SEQ ID NO 98
<211> LENGTH: 6
<212> TYPE: PRT
<213> ORGANISM: Artificial Sequence
<220> FEATURE:
<223> OTHER INFORMATION: Synthetic Construct

<400> SEQUENCE: 98

Phe Val Gly Gly Thr Gly
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

Lys Lys Ala Ala Pro Val Asn Gly
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 100

Pro Met Ala Lys Lys Val Asn Gly
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 101

Gln Ala Arg Ala Lys Val Asn Gly
1               5

<210> SEQ ID NO 102
<211> LENGTH: 10
<212> TYPE: PRT
<213> ORGANISM: Artificial Sequence
<220> FEATURE:
<223> OTHER INFORMATION: Synthetic Construct

<400> SEQUENCE: 102

Val His Met Pro Leu Gly Phe Leu Gly Pro
1               5                   10

<210> SEQ ID NO 103
```

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 103

Gln Ala Arg Ala Lys
1               5

<210> SEQ ID NO 104
<211> LENGTH: 15
<212> TYPE: PRT
<213> ORGANISM: Artificial Sequence
<220> FEATURE:
<223> OTHER INFORMATION: Synthetic Construct

<400> SEQUENCE: 104

Val His Met Pro Leu Gly Phe Leu Gly Pro Pro Met Ala Lys Lys
1               5                   10                  15

<210> SEQ ID NO 105
<211> LENGTH: 5
<212> TYPE: PRT
<213> ORGANISM: Artificial Sequence
<220> FEATURE:
<223> OTHER INFORMATION: Synthetic Construct

<400> SEQUENCE: 105

Lys Lys Ala Ala Pro
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic Construct

<400> SEQUENCE: 106

Pro Met Ala Lys Lys
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic Construct

<400> SEQUENCE: 107

Gly Tyr Thr Met Asn
1               5

<210> SEQ ID NO 108
<211> LENGTH: 17
<212> TYPE: PRT
<213> ORGANISM: Artificial Sequence
<220> FEATURE:
<223> OTHER INFORMATION: Synthetic Construct

<400> SEQUENCE: 108

Leu Ile Thr Pro Tyr Asn Gly Ala Ser Ser Tyr Asn Gln Lys Phe Arg
1               5                   10                  15

Gly
```

```
<210> SEQ ID NO 109
<211> LENGTH: 10
<212> TYPE: PRT
<213> ORGANISM: Artificial Sequence
<220> FEATURE:
<223> OTHER INFORMATION: Synthetic Construct

<400> SEQUENCE: 109

Gly Gly Tyr Asp Gly Arg Gly Phe Asp Tyr
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Ser Ala Ser Ser Ser Val Ser Tyr Met His
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Synthetic Construct

<400> SEQUENCE: 111

Asp Thr Ser Lys Leu Ala Ser
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic Construct

<400> SEQUENCE: 112

Gln Gln Trp Ser Lys His Pro Leu Thr
1               5

<210> SEQ ID NO 113
<211> LENGTH: 119
<212> TYPE: PRT
<213> ORGANISM: Artificial Sequence
<220> FEATURE:
<223> OTHER INFORMATION: Synthetic Construct

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Thr Pro Tyr Asn Gly Ala Ser Ser Tyr Asn Gln Lys Phe
    50                  55                  60

Arg Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Gly Gly Tyr Asp Gly Arg Gly Phe Asp Tyr Trp Gly Gln Gly
            100                 105                 110

Thr Leu Val Thr Val Ser Ser
        115

<210> SEQ ID NO 114
<211> LENGTH: 106
<212> TYPE: PRT
<213> ORGANISM: Artificial Sequence
<220> FEATURE:
<223> OTHER INFORMATION: Synthetic Construct

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Ser Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Lys His Pro Leu Thr
                85                  90                  95

Phe Gly Gln Gly Thr Lys Leu Glu Ile Lys
            100                 105

<210> SEQ ID NO 115
<211> LENGTH: 120
<212> TYPE: PRT
<213> ORGANISM: Artificial Sequence
<220> FEATURE:
<223> OTHER INFORMATION: Synthetic Construct

<400> SEQUENCE: 115

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 116
<211> LENGTH: 106
<212> TYPE: PRT
<213> ORGANISM: Artificial Sequence
<220> FEATURE:
<223> OTHER INFORMATION: Synthetic Construct -continued

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys
            100                 105

<210> SEQ ID NO 117
<211> LENGTH: 648
<212> TYPE: DNA
<213> ORGANISM: Artificial Sequence
<220> FEATURE:
<223> OTHER INFORMATION: Synthetic Construct

<400> SEQUENCE: 117
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca acaagagagc ccctggcacc     180
cctgccagat tcagcggatc tctgctggga ggaaaggccg ccctgacact gtctggcgcc     240
cagccagaag atgaggccga gtactactgc gccctgtggt acagcaacct gtgggtgttc     300
ggcggaggca ccaagctgac agtcctaggt caacccaagg ctgccccccag cgtgaccctg   360
ttccccccca gcagcgagga actgcaggcc aacaaggcca ccctggtctg cctgatcagc     420
gacttctacc caggcgccgt gaccgtggcc tggaaggccg acagcagccc cgtgaaggcc     480
ggcgtggaga ccaccacccc cagcaagcag agcaacaaca gtacgccgc cagcagctac      540
ctgagcctga cccccgagca gtggaagagc acaggtcct acagctgcca ggtgacccac      600
gagggcagca ccgtggagaa aaccgtggcc cccaccgagt gcagctga                  648

<210> SEQ ID NO 118
<211> LENGTH: 2916
<212> TYPE: DNA
<213> ORGANISM: Artificial Sequence
<220> FEATURE:
<223> OTHER INFORMATION: Synthetic Construct

<400> SEQUENCE: 118
caagtgcagc tgaaagagtc cggccctgga ctggtggccc ctagccagag cctgagcatc      60
acctgtaccg tgtccggctt cagcctgacc agctacggcg tgcatgggt gcgccagcct     120
ccaggcaagt gtctggaatg gctgggcatc atctggggcg acggcagcac caattaccac     180
agcgccctga tcagcagact gagcatctcc aaggacaaca gcaagagcca ggtgttcctg     240
aagctgaaca gcctgcagac cgacgacacc gccacctact actgcgccaa gggcatcacc     300
accgtggtgg acgactacta cgctatggac tactggggcc agggcaccag cgtgacagtg     360
tctagcggag gcggaggatc tggcggcgga ggaagtggcg gaggggatc tggggaggc      420

```
ggaagcgata tccagatgac ccagagccct gccagcctgt ctgcctctgt gggcgagaca    480
gtgaccatca catgccgggc cagcgagaac atcgacagct acctggcctg gtatcagcag    540
aagcagggca agagccccca gctgctggtg tacgccgcca cctttctggc cgacgatgtg    600
cccagcagat tcagcggcag cggaagcggc acacagtaca gcctgaagat caactccctg    660
cagagcgagg acgtggcccg gtactactgc agcactact acagcacccc ctacaccttc    720
ggctgcggca ccaagctgga aatcaaagga ggcggcggaa gtgtgcacat gcccctgggc    780
ttcctgggcc ccagacaggc cagagtcgtg aacggggggg gcggaggcag tgggggggga    840
ggatccgagg tgcagctgct ggaatctggc ggcggactgg tgcagcctgg cggatctctg    900
agactgagct gtgccgccag cggcttcacc ttcagcacct acgccatgaa ctgggtgcgc    960
caggcccctg gcaaaggcct ggaatgggtg tccggatca gaagcaagta caacaactac   1020
gccacctact acgccgacag cgtgaaggc cggttcacca tcagccggga cgacagcaag   1080
aacaccctgt acctgcagat gaacagcctg cgggccgagg acaccgccgt gtactattgt   1140
gtgcggcacg gcaacttcgg caacagctat gtgtcttggt ttgcctactg gggccagggc   1200
accctcgtga ccgtgtcaag cgctagcaca aagggcccta gcgtgttccc tctggccccc   1260
agcagcaaga gcacaagcgg cggaacagcc gccctgggct gcctcgtgaa ggactacttc   1320
cccgagcccg tgacagtgtc ttggaacagc ggagccctga caagcggcgt gcacaccttc   1380
cctgccgtgc tgcagagcag cggcctgtac tccctgagca gcgtggtcac cgtgcctagc   1440
agcagcctgg gcacccagac ctacatctgc aacgtgaacc acaagcccag caacaccaaa   1500
gtggacaaga aggtggagcc caagagctgt gatggcggag agggtccgg gggcggagga   1560 tccgaggtgc aattggttga atctggtggt ggtctggtaa accgggcgg ttccctgcgt   1620 ctgagctgcg cggcttccgg gttcaccttc tccaacgcgt ggatgagctg ggttcgccag   1680
gccccgggca aaggcctcga gtgggttggt cgtatcaagt ctaaaactga cggtggcacc   1740
acggattacg cggctccagt taaaggtcgt tttaccattt cccgcgacga tagcaaaaac   1800
actctgtatc tgcagatgaa ctctctgaaa actgaagaca ccgcagtcta ctactgtact   1860
accccgtggg aatggtcttg gtacgattat tggggccagg gcacgctggt tacggtgtct   1920
agcgctagta ccaagggccc cagcgtgttc cccctggcac ccagcagcaa gagcacatct   1980
ggcggaacag ccgctctggg ctgtctggtg aaagactact cccccgagcc cgtgaccgtg   2040
tcttggaact ctggcgccct gaccagcggc gtgcacacct tccagccgt gctgcagagc   2100 agcggcctgt actccctgtc ctccgtggtc accgtgccct agctcccct gggaacacag   2160 acatatatct gtaatgtcaa tcacaagcct tccaacacca agtcgataa gaaagtcgag   2220 cccaagagct cgacaaaac tcacacatgc ccaccgtgcc cagcacctga gctgcaggg   2280 ggaccgtcag tcttcctctt ccccccaaaa cccaaggaca cctcatgat ctcccggacc   2340 cctgaggtca catgcgtggt ggtggacgtg agccacgaag accctgaggt caagttcaac   2400
tggtacgtgg acggcgtgga ggtgcataat gccaagacaa agccgcggga ggagcagtac   2460
aacagcacgt accgtgtggt cagcgtcctc accgtcctgc accaggactg gctgaatggc   2520
aaggagtaca agtgcaaggt ctccaacaaa gccctcggcg cccccatcga gaaaaccatc   2580
tccaaagcca agggcagccc cgagaaccca caggtgtaca ccctgccccc atgccgggat   2640
gagctgacca agaaccaggt cagcctgtgg tgcctggtca aaggcttcta tcccagcgac   2700
atcgccgtga gtgggagag caatgggcag ccggagaaca actacaagac cacgcctccc   2760
gtgctggact ccgacggctc cttcttcctc tacagcaagc tcaccgtgga caagagcagg   2820
```

| | | |
|---|---|---|
| tggcagcagg ggaacgtctt ctcatgctcc gtgatgcatg aggctctgca caaccactac | 2880 |
| acgcagaaga gcctctccct gtctccgggt aaatga | 2916 |

<210> SEQ ID NO 119
<211> LENGTH: 2070
<212> TYPE: DNA
<213> ORGANISM: Artificial Sequence
<220> FEATURE:
<223> OTHER INFORMATION: Synthetic Construct

<400> SEQUENCE: 119

| | |
|---|---|
| gaggtgcaat tggttgaatc tggtggtggt ctggtaaaac cgggcggttc cctgcgtctg | 60 |
| agctgcgcgg cttccggatt caccttctcc aacgcgtgga tgagctgggt tcgccaggcc | 120 |
| ccgggcaaag gcctcgagtg ggttggtcgt atcaagtcta aaactgacgg tgcaccacg | 180 |
| gattacgcgg ctccagttaa aggtcgtttt accatttccc gcgacgatag caaaaacact | 240 |
| ctgtatctgc agatgaactc tctgaaaact gaagacaccg cagtctacta ctgtactacc | 300 |
| ccgtgggaat ggtcttggta cgattattgg ggccagggca cgctggttac ggtgtcttcc | 360 |
| gctagcacaa agggcccta gcgtgttcct ctggccccca gcagcaagag cacaagcggc | 420 |
| ggaacagccg ccctgggctg cctcgtgaag gactacttcc ccgagcccgt gacagtgtct | 480 |
| tggaacagcg gagccctgac aagcggcgtg cacacttcc ctgccgtgct gcagagcagc | 540 |
| ggcctgtact ccctgagcag cgtggtcacc gtgcctagca gcagcctggg cacccagacc | 600 |
| tacatctgca acgtgaacca caagcccagc aacaccaaag tggacaagaa ggtggagccc | 660 |
| aagagctgtg atggcggagg agggtccgga ggcggaggat ccgaggtgca gctgctggaa | 720 |
| tctggcggcg gactggtgca gcctggcgga tctctgagac tgagctgtgc cgccagcggc | 780 |
| ttcaccttca gcacctacgc catgaactgg gtgcgccagg ccctggcaa aggcctggaa | 840 |
| tgggtgtccc ggatcagaag caagtacaac aactacgcca ctactacgc cgacagcgtg | 900 |
| aagggccggt tcaccatcag ccgggacgac agcaagaaca ccctgtacct gcagatgaac | 960 |
| agcctgcggg ccgaggacac cgccgtgtac tattgtgtgc ggcacggcaa cttcggcaac | 1020 |
| agctatgtgt cttggtttgc ctactggggc cagggcaccc tcgtgaccgt gtcaagcgct | 1080 |
| agtaccaagg gcccagcgt gttccccctg gcacccagca gcaagagcac atctggcgga | 1140 |
| acagccgctc tgggctgtct ggtgaaagac tacttccccg agcccgtgac cgtgtcttgg | 1200 |
| aactctggcg ccctgaccag cggcgtgcac acctttccag ccgtgctgca gagcagcggc | 1260 |
| ctgtactccc tgtcctccgt ggtcaccgtg ccctctagct ccctgggaac acagacatat | 1320 |
| atctgtaatg tcaatcacaa gccttccaac accaaagtcg ataagaaagt cgagcccaag | 1380 |
| agctgcgaca aaactcacac atgcccaccg tgcccagcac ctgaagctgc aggggaccg | 1440 |
| tcagtcttcc tcttcccccc aaaacccaag gacacctca tgatctcccg gacccctgag | 1500 |
| gtcacatgcg tggtggtgga cgtgagccac gaagaccctg aggtcaagtt caactggtac | 1560 |
| gtggacggcg tggaggtgca taatgccaag acaaagccgc gggaggagca gtacaacagc | 1620 |
| acgtaccgtg tggtcagcgt cctcaccgtc ctgcaccagg actggctgaa tggcaaggag | 1680 |
| tacaagtgca aggtctccaa caaagccctc ggcgccccca tcgagaaaac catctccaaa | 1740 |
| gccaaagggc agccccgaga accacaggtg tacaccctgc ccccatgccg ggatgagctg | 1800 |
| accaagaacc aggtcagcct gtggtgcctg gtcaaaggct tctatcccag cgacatcgcc | 1860 |
| gtggagtggg agagcaatgg gcagccggag aacaactaca agaccacgcc tcccgtgctg | 1920 |

| | |
|---|---|
| gactccgacg gctccttctt cctctacagc aagctcaccg tggacaagag caggtggcag | 1980 |
| caggggaacg tcttctcatg ctccgtgatg catgaggctc tgcacaacca ctacacgcag | 2040 |
| aagagcctct ccctgtctcc gggtaaatga | 2070 |

<210> SEQ ID NO 120
<211> LENGTH: 1494
<212> TYPE: DNA
<213> ORGANISM: Artificial Sequence
<220> FEATURE:
<223> OTHER INFORMATION: Synthetic Construct

<400> SEQUENCE: 120

| | |
|---|---|
| caagtgcagc tgaaagagtc cggccctgga ctggtggccc ctagccagag cctgagcatc | 60 |
| acctgtaccg tgtccggctt cagcctgacc agctacggcg tgtcatgggt gcgccagcct | 120 |
| ccaggcaagt gtctggaatg gctgggcatc atctggggcg acggcagcac caattaccac | 180 |
| agcgccctga tcagcagact gagcatctcc aaggacaaca gcaagagcca ggtgttcctg | 240 |
| aagctgaaca gcctgcagac cgacgacacc gccacctact actgcgccaa gggcatcacc | 300 |
| accgtggtgg acgactacta cgctatggac tactggggcc agggcaccag cgtgacagtg | 360 |
| tctagcggag cgcgaggatc tggcggcgga ggaagtggcg gaggggggatc tggggggaggc | 420 |
| ggaagcgata tccagatgac ccagagcccc gccagcctgt ctgcctctgt gggcgagaca | 480 |
| gtgaccatca catgccgggc cagcgagaac atcgacagct acctggcctg tatcagcag | 540 |
| aagcagggca agagccccca gctgctggtg tacgccgcca cctttctggc cgacgatgtg | 600 |
| cccagcagat tcagcggcag cggaagcggc acacagtaca gcctgaagat caactccctg | 660 |
| cagagcgagg acgtggcccg gtactactgc cagcactact acagcacccc ctacaccttc | 720 |
| ggctgcggca ccaagctgga aatcaaaggc gggggaggct ccggaggcgg cggaagtaga | 780 |
| caggccagag tcgtgaacgg ggggaggggggg ggaagtgggg gcggaggcag tggggggcgga | 840 |
| ggatcccagg ccgtcgtgac ccaggaaccc agcctgacag tgtctcctgg cggcaccgtg | 900 |
| accctgacat gtggcagttc tacaggcgcc gtgaccacca gcaactacgc caactgggtg | 960 |
| caggaaaagc ccggccaggc cttcagagga ctgatcggcg gcaccaacaa gagagcccct | 1020 |
| ggcaccccctg ccagattcag cggatctctg ctgggaggaa aggccgccct gacactgtct | 1080 |
| ggcgcccagc cagaagatga ggccgagtac tactgcgccc tgtggtacag caacctgtgg | 1140 |
| gtgttcggcg gaggcaccaa gctgacagtc ctaggtcaac ccaaggctgc ccccagcgtg | 1200 |
| accctgttcc cccccagcag cgaggaactg caggccaaca aggccaccct ggtctgcctg | 1260 |
| atcagcgact tctacccagg cgccgtgacc gtggcctgga aggccgacag cagcccgtg | 1320 |
| aaggccggcg tggagaccac cacccccagc aagcagagca caacaagta cgccgccagc | 1380 |
| agctacctga gcctgacccc cgagcagtgg aagagccaca ggtcctacag ctgccaggtg | 1440 |
| acccacgagg gcagcaccgt ggagaaaacc gtggccccca ccgagtgcag ctga | 1494 |

<210> SEQ ID NO 121
<211> LENGTH: 1494
<212> TYPE: DNA
<213> ORGANISM: Artificial Sequence
<220> FEATURE:
<223> OTHER INFORMATION: Synthetic Construct

<400> SEQUENCE: 121

| | |
|---|---|
| caagtgcagc tgaaagagtc cggccctgga ctggtggccc ctagccagag cctgagcatc | 60 |
| acctgtaccg tgtccggctt cagcctgacc agctacggcg tgtcatgggt gcgccagcct | 120 |

-continued

```
ccaggcaagt gtctggaatg gctgggcatc atctggggcg acggcagcac caattaccac      180
agcgccctga tcagcagact gagcatctcc aaggacaaca gcaagagcca ggtgttcctg      240
aagctgaaca gcctgcagac cgacgacacc gccacctact actgcgccaa gggcatcacc      300
accgtggtgg acgactacta cgctatggac tactggggcc agggcaccag cgtgacagtg      360
tctagcggag gcggaggatc tggcggcgga ggaagtggcg agggggatc tggggggaggc      420 ggaagcgata tccagatgac ccagagccct gccagcctgt ctgcctctgt gggcgagaca      480
gtgaccatca catgccgggc cagcgagaac atcgacagct acctggcctg tatcagcag       540 aagcagggca agagccccca gctgctggtg tacgccgcca cctttctggc cgacgatgtg      600
cccagcagat tcagcggcag cggaagcggc acacagtaca gcctgaagat caactccctg      660
cagagcgagg acgtggcccg gtactactgc cagcactact acagcacccc ctacaccttc      720
ggctgcggca ccaagctgga aatcaaaggc gggggaggct ccggaggcgg cggaagtgga      780
ggcggcggaa gtggcggagg cggaggggg gaagtgggg gcggaggcag tggggggga       840 ggatcccagg ccgtcgtgac ccaggaaccc agcctgacag tgtctcctgg cggcaccgtg      900
accctgacat gtggcagttc tacaggcgcc gtgaccacca gcaactacgc caactgggtg      960
caggaaaagc ccggccaggc cttcagagga ctgatcggcg gcaccaacaa gagagcccct     1020
ggcacccctg ccagattcag cggatctctg ctgggaggaa aggccgccct gacactgtct     1080 ggcgccagc cagaagatga ggccgagtac tactgcgccc tgtggtacag caacctgtgg     1140
gtgttcggcg gaggcaccaa gctgacagtc ctaggtcaac ccaaggctgc ccccagcgtg     1200
accctgttcc cccccagcag cgaggaactg caggccaaca aggccaccct ggtctgcctg     1260
atcagcgact cctacccagg cgccgtgacc gtggcctgga aggccgacag cagcccgtg      1320 aaggccggcg tggagaccac caccccagc aagcagagca caacaagta cgccgccagc      1380 agctacctga gcctgacccc cgagcagtgg aagagccaca ggtcctacag ctgccaggtg     1440
acccacgagg gcagcaccgt ggagaaaacc gtggccccca ccgagtgcag ctga            1494
```

<210> SEQ ID NO 122
<211> LENGTH: 2025
<212> TYPE: DNA
<213> ORGANISM: Artificial Sequence
<220> FEATURE:
<223> OTHER INFORMATION: Synthetic Construct

<400> SEQUENCE: 122

```
caggtgcagc tggtgcagtc tggcgccgaa gtgaagaaac caggcgccag cgtgaaggtg       60
tcctgcaagg ccagcggcta cagcttcacc ggctacacca tgaactgggt gcgccaggct      120
cctggacagg gcctggaatg gatgggcctg atcacccct acaacggcgc cagcagctac      180
aaccagaagt tccggggcaa ggccaccatg accgtggaca ccagcacctc caccgtgtat      240
atggaactga gcagcctgcg gagcgaggac accgccgtgt actattgtgc cagaggcggc      300
tacgacggca gaggcttcga ttattggggc cagggcaccc tcgtgaccgt gtcctctgct      360
agcaccaagg cccctccgt gtttcctctg gccccttcca gcaagtccac ctctggcgga      420
actgccgctc tgggctgcct ggtggaagat tacttccccg agcccgtgac cgtgtcctgg      480
aattctggcg ctctgacctc cggcgtgcac acctttccag ctgtgctgca gtcctccggc      540
ctgtactccc tgtcctccgt cgtgacagtg ccctccagct ctctgggcac ccagacctac      600
atctgcaacg tgaaccacaa gccctccaac accaaggtgg acgagaaggt ggaacccaag      660
```

```
tcctgcgacg gtggcggagg ttccggaggc ggaggatccc aggctgtcgt gacccaggaa      720
ccctccctga cagtgtctcc tggcggcacc gtgaccctga cctgtggatc ttctaccggc      780
gctgtgacca cctccaacta cgccaattgg gtgcaggaaa agcccggcca ggccttcaga      840
ggactgatcg gcggcaccaa caagagagcc cctggcaccc ctgccagatt ctccggttct      900
ctgctgggcg gcaaggctgc cctgactctg tctggtgctc agcctgagga cgaggccgag      960
tactactgcg ccctgtggta ctccaacctg tgggtgttcg gcggaggcac caagctgacc     1020
gtgctgtcca gcgcttccac caagggaccc agtgtgttcc ccctggcccc cagctccaag     1080
tctacatccg gtggcacagc tgccctggga tgtctcgtga aggactactt tcctgagcct     1140
gtgacagtgt cttggaacag cggagccctg accagcggag tgcacacatt ccctgcagtg     1200
ctgcagagca gcggcctgta tagcctgagc agcgtcgtga ccgtgccttc ctctagcctg     1260
ggaacacaga catatatctg taatgtgaat cataagccca gtaataccaa agtggataag     1320
aaagtggaac taagagctga cgataagacc cacacctgtc cccctgccc tgctcctgaa     1380 gctgctggtg gccctagcgt gttcctgttc cccccaaagc caaggacac cctgatgatc     1440 tcccggaccc ccgaagtgac ctgcgtggtg gtggatgtgt cccacgagga ccctgaagtg     1500
aagttcaatt ggtacgtgga cggcgtggaa gtgcacaacg ccaagaccaa gcctagagag     1560
gaacagtaca actccaccta ccgggtggtg tccgtgctga cagtgctgca ccaggactgg     1620
ctgaacggca agagtacaa gtgcaaggtg tccaacaagg ccctgggcgc tcccatcgaa     1680
aagaccatct ccaaggccaa gggccagccc cgggaacccc aggtgtacac cctgcccca     1740 tgccgggatg agctgaccaa gaaccaggtc agcctgtggt gcctggtcaa aggcttctat     1800
cccagcgaca tcgccgtgga gtgggagagc aatgggcagc cggagaacaa ctacaagacc     1860
acgcctcccg tgctggactc cgacggctcc ttcttcctct acagcaagct caccgtggac     1920
aagagcaggt ggcagcaggg gaacgtcttc tcatgctccg tgatgcatga ggctctgcac     1980
aaccactaca cgcagaagag cctctccctg tctccgggta aatga                    2025

<210> SEQ ID NO 123
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 123
caggtgcagc tggtgcagtc tggcgccgaa gtgaagaaac caggcgccag cgtgaaggtg       60
tcctgcaagg ccagcggcta cagcttcacc ggctacacca tgaactgggt gcgccaggct      120
cctggacagg gctggaatg gatgggcctg atcaccccct acaacggcgc cagcagctac      180
aaccagaagt tccggggcaa ggccaccatg accgtggaca ccagcacctc caccgtgtat      240
atggaactga gcagcctgcg gagcgaggac accgccgtgt actattgtgc cagaggcggc      300
tacgacggca gaggcttcga ttattgggc cagggcaccc tcgtgaccgt gtcctctgct      360
agcaccaagg gccctccgt gttccccctg gccccagca gcaagagcac cagcggcggc      420
acagccgctc tgggctgcct ggtcgaggac tacttccccg agcccgtgac cgtgtcctgg      480
aacagcggag ccctgacctc cggcgtgcac accttccccg ccgtgctgca gagttctggc      540
ctgtatagcc tgagcagcgt ggtcaccgtg ccttctagca gcctgggcac ccagacctac      600
atctgcaacg tgaaccacaa gcccagcaac accaaggtgg acgagaaggt ggagcccaag      660
agctgcgaca aaaactcaca catgcccaccg tgcccagcac ctgaagctgc agggggaccg      720
```

```
tcagtcttcc tcttcccccc aaaacccaag acaccctca tgatctcccg gaccctgag      780 gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ggcgccccca tcgagaaaac catctccaaa     1020
gccaaagggc agccccgaga accacaggtg tgcaccctgc ccccatcccg ggatgagctg     1080
accaagaacc aggtcagcct ctcgtgcgca gtcaaaggct tctatcccag cgacatcgcc     1140
gtggagtggg agagcaatgg gcagccggag aacaactaca agaccacgcc tcccgtgctg     1200
gactccgacg gctccttctt cctcgtgagc aagctcaccg tggacaagag caggtggcag     1260
caggggaacg tcttctcatg ctccgtgatg catgaggctc tgcacaacca ctacacgcag     1320
aagagcctct ccctgtctcc gggtaaatga                                     1350
```

<210> SEQ ID NO 124
<211> LENGTH: 642
<212> TYPE: DNA
<213> ORGANISM: Artificial Sequence
<220> FEATURE:
<223> OTHER INFORMATION: Synthetic Construct

<400> SEQUENCE: 124

```
gacatccaga tgacccagag ccccagcagc ctgtctgcca gcgtgggcga cagagtgacc       60
atcacctgta gcgccagcag cagcgtgtcc tacatgcact ggtatcagca gaagtccggc      120
aaggccccca agctgctgat ctacgacacc agcaagctgg cctccggcgt gcccagcaga      180
ttttctggca gcggctccgg caccgacttc accctgacaa tcagctccct ccagcccgag      240
gacttcgcca cctactactg ccagcagtgg tccaagcacc ccctgacctt tggccagggc      300
accaagctgg aaatcaagcg tacggtggct gcaccatctg tcttcatctt cccgccatct      360
gatcggaagt tgaaatctgg aactgcctct gttgtgtgcc tgctgaataa cttctatccc      420
agagaggcca agtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                        642
```

<210> SEQ ID NO 125
<211> LENGTH: 1545
<212> TYPE: DNA
<213> ORGANISM: Artificial Sequence
<220> FEATURE:
<223> OTHER INFORMATION: Synthetic Construct

<400> SEQUENCE: 125

```
caagtgcagc tgaaagagtc cggccctgga ctggtggccc ctagccagag cctgagcatc       60
acctgtaccg tgtccggctt cagcctgacc agctacggcg tgtcatgggt gcgccagcct      120
ccaggcaagt gtctggaatg gctgggcatc atctgggggcg acggcagcac caattaccac      180
agcgccctga tcagcagact gagcatctcc aaggacaaca gcaagagcca ggtgttcctg      240
aagctgaaca gcctgcagac cgacgacacc gccacctact actgcgccaa gggcatcacc      300
accgtggtgg acgactacta cgctatggac tactggggcc agggcaccag cgtgacagtg      360
tctagcggag gcggaggatc tggcggcgga ggaagtggcg gagggggatc tggggggaggc     420
```

```
ggaagcgata tccagatgac ccagagccct gccagcctgt ctgcctctgt gggcgagaca    480
gtgaccatca catgccgggc cagcgagaac atcgacagct acctggcctg gtatcagcag    540
aagcagggca agagccccca gctgctggtg tacgccgcca cctttctggc cgacgatgtg    600
cccagcagat tcagcggcag cggaagcggc acacagtaca gcctgaagat caactccctg    660
cagagcgagg acgtggcccg gtactactgc cagcactact acagcacccc ctacaccttc    720
ggctgcggca ccaagctgga aatcaaagga ggcggcggaa gtgtgcacat gcccctgggc    780
ttcctgggcc ccagacaggc cagagtcgtg aacggggggg gcggaggcag tggggggga    840
ggatccgagg tgcagctgct ggaatctggc ggcggactgg tgcagcctgg cggatctctg    900
agactgagct gtgccgccag cggcttcacc ttcagcacct acgccatgaa ctgggtgcgc    960
caggcccctg gcaaaggcct ggaatgggtg tcccggatca gaagcaagta caacaactac   1020
gccacctact acgccgacag cgtgaagggc cggttcacca tcagccggga cgacagcaag   1080
aacaccctgt acctgcagat gaacagcctg cgggccgagg acaccgccgt gtactattgt   1140
gtgcggcacg gcaacttcgg caacagctat gtgtcttggt ttgcctactg gggccagggc   1200
accctcgtga ccgtgtcaag cgctagcgtg gccgctccct ccgtgttcat cttcccacct   1260
tccgacgagc agctgaagtc cggcaccgct tctgtcgtgt gcctgctgaa caacttctac   1320
cccgcgagg ccaaggtgca gtggaaggtg gacaacgccc tgcagtccgg caacagccag   1380
gaatccgtga ccgagcagga ctccaaggac agcacctact ccctgtcctc caccctgacc   1440
ctgtccaagg ccgactacga gaagcacaag gtgtacgcct gcgaagtgac ccaccagggc   1500
ctgtctagcc ccgtgaccaa gtctttcaac cggggcgagt gctga                   1545
```

<210> SEQ ID NO 126
<211> LENGTH: 1545
<212> TYPE: DNA
<213> ORGANISM: Artificial Sequence
<220> FEATURE:
<223> OTHER INFORMATION: Synthetic Construct

<400> SEQUENCE: 126

```
caagtgcagc tgaaagagtc cggccctgga ctggtggccc ctagccagag cctgagcatc     60
acctgtaccg tgtccggctt cagcctgacc agctacggcg tgtcatgggt gcgccagcct    120
ccaggcaagt gtctggaatg gctgggcatc atctggggcg acggcagcac caattaccac    180
agcgccctga tcagcagact gagcatctcc aaggacaaca gcaagagcca ggtgttcctg    240
aagctgaaca gcctgcagac cgacgacacc gccacctact actgcgccaa gggcatcacc    300
accgtggtgg acgactacta cgctatggac tactggggcc agggcaccag cgtgacagtg    360
tctagcggag gcggaggatc tggcggcgga ggaagtggcg gagggggatc tgggggaggc    420
ggaagcgata tccagatgac ccagagccct gccagcctgt ctgcctctgt gggcgagaca    480
gtgaccatca catgccgggc cagcgagaac atcgacagct acctggcctg gtatcagcag    540
aagcagggca agagccccca gctgctggtg tacgccgcca cctttctggc cgacgatgtg    600
cccagcagat tcagcggcag cggaagcggc acacagtaca gcctgaagat caactccctg    660
cagagcgagg acgtggcccg gtactactgc cagcactact acagcacccc ctacaccttc    720
ggctgcggca ccaagctgga aatcaaaggc gggggaggct ccggaggcgg cggaagtgga    780
ggcggcggaa gtggcggagg cggagggggg ggaagtgggg gcggaggcag tggggggga    840
ggatccgagg tgcagctgct ggaatctggc ggcggactgg tgcagcctgg cggatctctg    900
agactgagct gtgccgccag cggcttcacc ttcagcacct acgccatgaa ctgggtgcgc    960
```

| | |
|---|---|
| caggcccctg gcaaaggcct ggaatgggtg tcccggatca gaagcaagta caacaactac | 1020 |
| gccacctact acgccgacag cgtgaagggc cggttcacca tcagccggga cgacagcaag | 1080 |
| aacaccctgt acctgcagat gaacagcctg cgggccgagg acaccgccgt gtactattgt | 1140 |
| gtgcggcacg gcaacttcgg caacagctat gtgtcttggt ttgcctactg gggccagggc | 1200 |
| accctcgtga ccgtgtcaag cgctagcgtg gccgctccct ccgtgttcat cttcccacct | 1260 |
| tccgacgagc agctgaagtc cggcaccgct tctgtcgtgt gcctgctgaa caacttctac | 1320 |
| ccccgcgagg ccaaggtgca gtggaaggtg gacaacgccc tgcagtccgg caacagccag | 1380 |
| gaatccgtga ccgagcagga ctccaaggac agcacctact ccctgtcctc caccctgacc | 1440 |
| ctgtccaagg ccgactacga gaagcacaag gtgtacgcct gcgaagtgac ccaccagggc | 1500 |
| ctgtctagcc ccgtgaccaa gtctttcaac cggggcgagt gctga | 1545 |

<210> SEQ ID NO 127
<211> LENGTH: 699
<212> TYPE: DNA
<213> ORGANISM: Artificial Sequence
<220> FEATURE:
<223> OTHER INFORMATION: Synthetic Construct

<400> SEQUENCE: 127

| | |
|---|---|
| gaagtgcagc tgctggaatc cggcggagga ctggtgcagc ctggcggatc tctgagactg | 60 |
| tcttgtgccg cctccggctt caccttctcc acctacgcca tgaactgggt gcgacaggct | 120 |
| cctggcaagg gcctggaatg ggtgtcccgg atcagatcca gtacaacaa ctacgccacc | 180 |
| tactacgccg actccgtgaa gggccggttc accatctctc gggacgactc caagaacacc | 240 |
| ctgtacctgc agatgaactc cctgcgggcc gaggacaccg ccgtgtacta ttgtgtgcgg | 300 |
| cacggcaact tcggcaactc ctatgtgtct tggtttgcct actggggcca gggcacgcctc | 360 |
| gtgaccgtgt catctgctag cgtggccgct ccctccgtgt tcatcttccc accttccgac | 420 |
| gagcagctga agtccggcac cgcttctgtc gtgtgcctgc tgaacaactt ctaccccgc | 480 |
| gaggccaagg tgcagtggaa ggtggacaac gccctgcagt ccggcaacag ccaggaatcc | 540 |
| gtgaccgagc aggactccaa ggacagcacc tactccctgt cctccaccct gaccctgtcc | 600 |
| aaggccgact acgagaagca caaggtgtac gcctgcgaag tgacccacca gggcctgtct | 660 |
| agccccgtga ccaagtcttt caaccggggc gagtgctga | 699 |

<210> SEQ ID NO 128
<211> LENGTH: 2871
<212> TYPE: DNA
<213> ORGANISM: Artificial Sequence
<220> FEATURE:
<223> OTHER INFORMATION: Synthetic Construct

<400> SEQUENCE: 128

| | |
|---|---|
| caagtgcagc tgaaagagtc cggccctgga ctggtggccc ctagccagag cctgagcatc | 60 |
| acctgtaccg tgtccggctt cagcctgacc agctacggcg tgcatgggt gcgccagcct | 120 |
| ccaggcaagt gtctggaatg gctgggcatc atctggggcg acggcagcac caattaccac | 180 |
| agcgccctga tcagcagact gagcatctcc aaggacaaca gcaagagcca ggtgttcctg | 240 |
| aagctgaaca gcctgcagac cgacgacacc gccacctact actgcgccaa gggcatcacc | 300 |
| accgtggtgg acgactacta cgctatggac tactggggcc agggcaccag cgtgacagtg | 360 |
| tctagcggag gcggaggatc tggcggcgga ggaagtggcg gaggggggatc tgggggaggc | 420 |

```
ggaagcgata tccagatgac ccagagccct gccagcctgt ctgcctctgt gggcgagaca   480
gtgaccatca catgccgggc cagcgagaac atcgacagct acctggcctg gtatcagcag   540
aagcagggca agagccccca gctgctggtg tacgccgcca cctttctggc cgacgatgtg   600
cccagcagat tcagcggcag cggaagcggc acacagtaca gcctgaagat caactccctg   660
cagagcgagg acgtggcccg gtactactgc cagcactact acagcacccc ctacaccttc   720
ggctgcggca ccaagctgga aatcaaagga ggcggcggaa gtgtgcacat gcccctgggc   780
ttcctgggcc ccagacaggc cagagtcgtg aacggggggg cggaggcag tgggggggga   840
ggatcccagg ccgtcgtgac ccaggaaccc agcctgacag tgtctcctgg cggcaccgtg   900
accctgacat gtggcagttc tacaggcgcc gtgaccacca gcaactacgc caactgggtg   960
caggaaaagc ccggccaggc cttcagagga ctgatcggcg gcaccaacaa gagagcccct  1020
ggcacccctg ccagattcag cggatctctg ctgggaggaa aggccgccct gacactgtct  1080
ggcgcccagc cagaagatga ggccgagtac tactgcgccc tgtggtacag caacctgtgg  1140
gtgttcggcg gaggcaccaa gctgacagtg ctgagcagcc ttccaccaa gggacccagt  1200
gtgttccccc tggcccccag ctccaagtct catccggtg gcacagctgc cctgggatgt  1260
ctcgtgaagg actactttcc tgagcctgtg acagtgtctt ggaacagcgg agccctgacc  1320
agcggagtgc acacattccc tgcagtgctg cagagcagcg gcctgtatag cctgagcagc  1380
gtcgtgaccg tgccttcctc tagcctggga acacagacat atatctgtaa tgtgaatcat  1440
aagcccagta ataccaaagt ggataagaaa gtggaaccta gagctgcga tggcggagga  1500
gggtccggag cgagggtc ccaggtgcag ctggtgcagt ctggcgccga agtgaagaaa  1560
ccaggcgcca gcgtgaaggt gtcctgcaag gccagcggct acagcttcac cggctacacc  1620
atgaactggg tgcgccaggc tcctggacag ggcctggaat ggatgggcct gatcacccc  1680
tacaacggcg ccagcagcta caaccagaag ttccggggca aggccaccat gaccgtggac  1740
accagcacct ccaccgtgta tatggaactg agcagcctgc ggagcgagga caccgccgtg  1800
tactattgtg ccagaggcgg ctacgacggc agaggcttcg attattgggg ccagggcacc  1860
ctcgtgaccg tgtcctctgc tagcaccaag ggccctccg tgttccccct ggccccccag  1920
agcaagagca ccagcggcgg cacagccgct ctgggctgcc tggtcgagga ctacttcccc  1980
gagcccgtga ccgtgtcctg gaacagcgga gccctgacct ccggcgtgca caccttcccc  2040
gccgtgctgc agagttctgg cctgtatagc ctgagcagcg tggtcaccgt gccttctagc  2100
agcctgggca cccagaccta catctgcaac gtgaaccaca agcccagcaa caccaaggtg  2160
gacgagaagg tggagcccaa gagctgcgac aaaaactcac acatgcccac cgtgcccagca 2220
cctgaagctg caggggggacc gtcagtcttc ctcttccccc caaaacccaa ggacaccctc  2280
atgatctccc ggacccctga ggtcacatgc gtggtggtgg acgtgagcca cgaagaccct  2340
gaggtcaagt tcaactggta cgtggacggc gtggaggtgc ataatgccaa gacaaagccg  2400
cgggaggagc agtacaacag cacgtaccgt gtggtcagcg tcctcaccgt cctgcaccag  2460
gactggctga atggcaagga gtacaagtgc aaggtctcca acaaagccct cggcgccccc  2520
atcgagaaaa ccatctccaa agccaaaggg cagccccgag aaccacaggt gtacaccctg  2580
cccccatgcc gggatgagct gaccaagaac caggtcagcc tgtggtgcct ggtcaaaggc  2640
ttctatccca gcgacatcgc cgtggagtgg gagagcaatg ggcagccgga gaacaactac  2700
aagaccacgc ctcccgtgct ggactccgac ggctccttct tcctctacag caagctcacc  2760
gtggacaaga gcaggtggca gcaggggaac gtcttctcat gctccgtgat gcatgaggct  2820
```
ctgcacaacc actacacgca gaagagcctc tccctgtctc cgggtaaatg a        2871

<210> SEQ ID NO 129
<211> LENGTH: 2871
<212> TYPE: DNA
<213> ORGANISM: Artificial Sequence
<220> FEATURE:
<223> OTHER INFORMATION: Synthetic Construct

<400> SEQUENCE: 129

| | |
|---|---:|
| caagtgcagc tgaaagagtc cggccctgga ctggtggccc tagccagag cctgagcatc | 60 |
| acctgtaccg tgtccggctt cagcctgacc agctacggcg tgtcatgggt gcgccagcct | 120 |
| ccaggcaagt gtctggaatg gctgggcatc atctggggcg acggcagcac caattaccac | 180 |
| agcgccctga tcagcagact gagcatctcc aaggacaaca gcaagagcca ggtgttcctg | 240 |
| aagctgaaca gcctgcagac cgacgacacc gccacctact actgcgccaa gggcatcacc | 300 |
| accgtggtgg acgactacta cgctatggac tactggggcc agggcaccag cgtgacagtg | 360 |
| tctagcggag gcggaggatc tggcggcgga ggaagtggcg gaggggatc tggggaggc | 420 |
| ggaagcgata tccagatgac ccagagccct gccagcctgt ctgcctctgt gggcgagaca | 480 |
| gtgaccatca catgccgggc cagcgagaac atcgacagct acctggcctg gtatcagcag | 540 |
| aagcagggca agagccccca gctgctggtg tacgccgcca cctttctggc cgacgatgtg | 600 |
| cccagcagat tcagcggcag cggaagcggc acacagtaca gcctgaagat caactccctg | 660 |
| cagagcgagg acgtggcccg gtactactgc cagcactact acagcacccc ctacaccttc | 720 |
| ggctgcggca ccaagctgga aatcaaaggc gggggaggct ccggaggcgg cggaagtgga | 780 |
| ggcggcggaa gtggcggagg cggagggggg gaagtgggg gcggaggcag tggggggga | 840 |
| ggatcccagg ccgtcgtgac ccaggaaccc agcctgacag tgtctcctgg cggcaccgtg | 900 |
| accctgacat gtggcagttc tacaggcgcc gtgaccacca gcaactacgc caactgggtg | 960 |
| caggaaaagc ccggccaggc cttcagagga ctgatcggcg gcaccaacaa gagagcccct | 1020 |
| ggcaccctg ccagattcag cggatctctg ctgggaggaa aggccgccct gacactgtct | 1080 |
| ggcgcccagc cagaagatga ggccgagtac tactgcgccc tgtggtacag caacctgtgg | 1140 |
| gtgttcggcg gaggcaccaa gctgacagtg ctgagcagcg cttccaccaa gggacccagt | 1200 |
| gtgttccccc tggcccccag ctccaagtct acatccggtg gcacagctgc cctgggatgt | 1260 |
| ctcgtgaagg actactttcc tgagcctgtg acagtgtctt ggaacagcgg agccctgacc | 1320 |
| agcggagtgc acacattccc tgcagtgctg cagagcagcg gcctgtatag cctgagcagc | 1380 |
| gtcgtgaccg tgccttcctc tagcctggga acacagacat atatctgtaa tgtgaatcat | 1440 |
| aagcccagta ataccaaagt ggataagaaa gtgaaccta agagctgcga tggcggagga | 1500 |
| gggtccggag gcggagggtc ccaggtgcag ctggtgcagt ctggcgccga agtgaagaaa | 1560 |
| ccaggcgcca gcgtgaaggt gtcctgcaag gccagcggct acagcttcac cggctacacc | 1620 |
| atgaactggg tgcgccaggc tcctggacag ggcctggaat ggatgggcct gatcaccccc | 1680 |
| tacaacggcg ccagcagcta caaccagaag ttcggggca aggccaccat gaccgtggac | 1740 |
| accagcacct ccaccgtgta tatggaactg agcagcctgc ggagcgagga caccgccgtg | 1800 |
| tactattgtg ccagaggcgg ctacgacggc agaggcttcg attattgggg ccagggcacc | 1860 |
| ctcgtgaccg tgtcctctgc tagcaccaag ggcccctccg tgttcccct ggcccccagc | 1920 |
| agcaagagca ccagcggcgg cacagccgct ctgggctgcc tggtcgagga ctacttcccc | 1980 |

```
gagcccgtga ccgtgtcctg aacagcgga gccctgacct ccggcgtgca ccttccc     2040
gccgtgctgc agagttctgg cctgtatagc ctgagcagcg tggtcaccgt gccttctagc  2100
agcctgggca cccagaccta catctgcaac gtgaaccaca agcccagcaa caccaaggtg  2160
gacgagaagg tggagcccaa agctgcgac aaaactcaca catgcccacc gtgcccagca  2220
cctgaagctg caggggggacc gtcagtcttc ctcttccccc caaaacccaa ggacaccctc  2280
atgatctccc ggacccctga ggtcacatgc gtggtggtgg acgtgagcca cgaagaccct  2340
gaggtcaagt tcaactggta cgtggacggc gtggaggtgc ataatgccaa gacaaagccg  2400
cgggaggagc agtacaacag cacgtaccgt gtggtcagcg tcctcaccgt cctgcaccag  2460
gactggctga atggcaagga gtacaagtgc aaggtctcca acaaagccct cggcgccccc  2520
atcgagaaaa ccatctccaa agccaaaggg cagccccgag aaccacaggt gtacaccctg  2580
cccccatgcc gggatgagct gaccaagaac caggtcagcc tgtggtgcct ggtcaaaggc  2640
ttctatccca gcgacatcgc cgtggagtgg gagagcaatg ggcagccgga gaacaactac  2700
aagaccacgc ctcccgtgct ggactccgac ggctccttct tcctctacag caagctcacc  2760
gtggacaaga gcaggtggca gcaggggaac gtcttctcat gctccgtgat gcatgaggct  2820
ctgcacaacc actacacgca gaagagcctc tccctgtctc cgggtaaatg a           2871
```

<210> SEQ ID NO 130
<211> LENGTH: 2025
<212> TYPE: DNA
<213> ORGANISM: Artificial Sequence
<220> FEATURE:
<223> OTHER INFORMATION: Synthetic Construct

<400> SEQUENCE: 130

```
caggccgtcg tgacccagga acccagcctg acagtgtctc ctggcggcac cgtgaccctg    60
acatgtggca gttctacagg cgccgtgacc accagcaact acgccaactg ggtgcaggaa   120
aagcccggcc aggccttcag aggactgatc ggcggcacca caagagagc ccctggcacc   180
cctgccagat tctccggttc tctgctgggc ggcaaggctg ccctgactct gtctggtgct   240
cagcctgagg acgaggccga gtactactgc gccctgtggt actccaacct gtgggtgttc   300
ggcggaggca ccaagctgac cgtgctgtcc agcgcttcca ccaagggacc cagtgtgttc   360
cccctggccc ccagctccaa gtctacatcc ggtggcacag ctgccctggg atgtctcgtg   420
aaggactact ttcctgagcc tgtgacagtg tcttggaaca gcggagccct gaccagcgga   480
gtgcacacat tccctgcagt gctgcagagc agcggcctgt atagcctgag cagcgtcgtg   540
accgtgcctt cctctagcct gggaacacag acatatatct gtaatgtgaa tcataagccc   600
agtaatacca aagtggataa gaaagtggaa cctaagagct cgatggcgg aggagggtcc   660
ggaggcggag ggtcccaggt gcagctggtg cagtctggcg ccgaagtgaa gaaaccaggc   720
gccagcgtga aggtgtcctg caaggccagc ggctacagct tcaccggcta caccatgaac   780
tgggtgcgcc aggctcctgg acagggcctg gaatggatgg gcctgatcac cccctacaac   840
ggcgccagca gctacaacca gaagttccgg ggcaaggcca ccatgaccgt ggacaccagc   900
acctccaccg tgtatatgga actgagcagc ctgcggagcg aggacaccgc cgtgtactat   960
tgtgccagag gcggctacga cggcagaggc ttcgattatt ggggccaggg caccctcgtg  1020
accgtgtcct ctgctagcac caagggcccc tccgtgttcc ccctggcccc cagcagcaag  1080
agcaccagcg gcgcacagc cgctctgggc tgcctggtcg aggactactt ccccgagccc  1140
gtgaccgtgt cctggaacag cggagccctg acctccggcg tgcacacctt ccccgccgtg  1200
```

-continued

```
ctgcagagtt ctggcctgta tagcctgagc agcgtggtca ccgtgccttc tagcagcctg    1260
ggcacccaga cctacatctg caacgtgaac cacaagccca gcaacaccaa ggtggacgag    1320
aaggtggagc ccaagagctg cgacaaaact cacacatgcc caccgtgccc agcacctgaa    1380
gctgcagggg gaccgtcagt cttcctcttc cccccaaaac ccaaggacac cctcatgatc    1440
tcccggaccc ctgaggtcac atgcgtggtg gtggacgtga gccacgaaga ccctgaggtc    1500
aagttcaact ggtacgtgga cggcgtggag gtgcataatg ccaagacaaa gccgcgggag    1560
gagcagtaca acagcacgta ccgtgtggtc agcgtcctca ccgtcctgca ccaggactgg    1620
ctgaatggca aggagtacaa gtgcaaggtc tccaacaaag ccctcggcgc ccccatcgag    1680
aaaaccatct ccaaagccaa agggcagccc cgagaaccac aggtgtacac cctgccccca    1740
tgccgggatg agctgaccaa gaaccaggtc agcctgtggt gcctggtcaa aggcttctat    1800
cccagcgaca tcgccgtgga gtgggagagc aatgggcagc cggagaacaa ctacaagacc    1860
acgcctcccg tgctggactc cgacggctcc ttcttcctct acagcaagct caccgtggac    1920
aagagcaggt ggcagcaggg gaacgtcttc tcatgctccg tgatgcatga ggctctgcac    1980
aaccactaca cgcagaagag cctctccctg tctccgggta aatga    2025
```

<210> SEQ ID NO 131
<211> LENGTH: 2916
<212> TYPE: DNA
<213> ORGANISM: Artificial Sequence
<220> FEATURE:
<223> OTHER INFORMATION: Synthetic Construct

<400> SEQUENCE: 131

```
caagtgcagc tgaaagagtc cggccctgga ctggtggccc ctagccagag cctgagcatc      60
acctgtaccg tgtccggctt cagcctgacc agctacggcg tgtcatgggt gcgccagcct     120
ccaggcaagt gtctggaatg ctgggcatc atctgggcg acggcagcac caattaccac      180
agcgccctga tcagcagact gagcatctcc aaggacaaca gcaagagcca ggtgttcctg     240
aagctgaaca gcctgcagac cgacgacacc gccacctact actgcgccaa gggcatcacc     300
accgtggtgg acgactacta cgctatggac tactggggcc agggcaccag cgtgacagtg     360
tctagcggag gcggaggatc tggcggcgga ggaagtggcg aggggggatc tggggaggc     420 ggaagcgata tccagatgac ccagagccct gccagcctgt ctgcctctgt gggcgagaca     480
gtgaccatca catgccgggc cagcgagaac atcgacagct acctggcctg gtatcagcag     540
aagcagggca gagcccccca gctgctggtg tacgccgcca cctttctggc cgacgatgtg     600
cccagcagat tcagcggcag cggaagcggc acacagtaca gcctgaagat caactccctg     660
cagagcgagg acgtggcccg gtactactgc cagcactact acagcacccc ctacaccttc     720
ggctgcggca ccaagctgga aatcaaaggc gggggaggct ccggaggcgg cggaagtgga     780
ggcggcggaa gtttcgtggg gggaccgggg ggcgaggca gtggggggg aggatccggg     840 ggatccgagg tgcagctgct ggaatctggc ggcggactgg tgcagcctgg cggatctctg     900
agactgagct gtgccgccag cggcttcacc ttcagcacct acgccatgaa ctgggtgcgc     960
caggcccctg gcaaaggcct ggaatgggtg tcccggatca gaagcaagta caacaactac    1020
gccacctact acgccgacag cgtgaagggc cggttcacca tcagccggga cgacagcaag    1080
aacaccctgt acctgcagat gaacagcctg cgggccgagg acaccgccgt gtactattgt    1140
gtgcggcacg gcaacttcgg caacagctat gtgtcttggt ttgcctactg gggccagggc    1200
```

-continued

```
accctcgtga ccgtgtcaag cgctagcaca aagggcccta gcgtgttccc tctggccccc    1260
agcagcaaga gcacaagcgg cggaacagcc gccctgggct gcctcgtgaa ggactacttc    1320
cccgagcccg tgacagtgtc ttggaacagc ggagccctga caagcggcgt gcacaccttc    1380
cctgccgtgc tgcagagcag cggcctgtac tccctgagca gcgtggtcac cgtgcctagc    1440
agcagcctgg gcacccagac ctacatctgc aacgtgaacc acaagcccag caacaccaaa    1500
gtggacaaga aggtggagcc caagagctgt gatggcggag agggtccggg ggcggagga    1560 tccgaggtgc aattggttga atctggtggt ggtctggtaa accgggcgg ttccctgcgt     1620 ctgagctgcg cggcttccgg gttcaccttc tccaacgcgt ggatgagctg ggttcgccag    1680
gccccgggca aaggcctcga gtgggttggt cgtatcaagt ctaaaactga cggtggcacc    1740
acggattacg cggctccagt taaaggtcgt tttaccattt cccgcgacga tagcaaaaac    1800
actctgtatc tgcagatgaa ctctctgaaa actgaagaca ccgcagtcta ctactgtact    1860
accccgtggg aatggtcttg gtacgattat tggggccagg gcacgctggt tacggtgtct    1920
agcgctagta ccaagggccc cagcgtgttc ccctggcac ccagcagcaa gagcacatct      1980
ggcggaacag ccgctctggg ctgtctggtg aaagactact ccccgagcc cgtgaccgtg    2040 tcttggaact ctggcgccct gaccagcggc gtgcacacct tccagcgt gctgcagagc      2100 agcggcctgt actccctgtc ctccgtggtc accgtgccct agctccct gggaacacag       2160 acatatatct gtaatgtcaa tcacaagcct tccaacacca aagtcgataa gaaagtcgag    2220
cccaagagct gcgacaaaac tcacacatgc ccaccgtgcc cagcacctga gctgcaggg     2280 ggaccgtcag tcttcctctt ccccccaaaa cccaaggaca ccctcatgat ctcccggacc    2340
cctgaggtca catgcgtggt ggtggacgtg agccacgaag accctgaggt caagttcaac    2400
tggtacgtgg acggcgtgga ggtgcataat gccaagacaa agccgcggga ggagcagtac    2460
aacagcacgt accgtgtggt cagcgtcctc accgtcctgc accaggactg gctgaatggc    2520
aaggagtaca agtgcaaggt ctccaacaaa gccctcggcg cccccatcga gaaaaccatc    2580
tccaaagcca aagggcagcc ccgagaacca caggtgtaca ccctgccccc atgccgggat    2640
gagctgacca gaaccaggt cagcctgtgg tgcctggtca aaggcttcta tcccagcgac    2700
atcgccgtgg agtgggagag caatgggcag ccggagaaca actacaagac cacgcctccc    2760
gtgctggact ccgacggctc cttcttcctc tacagcaagc tcaccgtgga caagagcagg    2820
tggcagcagg ggaacgtctt ctcatgctcc gtgatgcatg aggctctgca caaccactac    2880
acgcagaaga gcctctccct gtctccgggt aaatga                              2916
```

<210> SEQ ID NO 132
<211> LENGTH: 449
<212> TYPE: PRT
<213> ORGANISM: Artificial Sequence
<220> FEATURE:
<223> OTHER INFORMATION: Synthetic Construct

<400> SEQUENCE: 132

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60
```

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asn Leu Gly Pro Phe Phe Tyr Phe Asp Tyr Trp Gly Gln Gly
        100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 133
<211> LENGTH: 214
<212> TYPE: PRT

<213> ORGANISM: Artificial Sequence
<220> FEATURE:
<223> OTHER INFORMATION: Synthetic Construct

<400> SEQUENCE: 133

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Arg Tyr Thr Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Arg Lys Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 134
<211> LENGTH: 675
<212> TYPE: PRT
<213> ORGANISM: Artificial Sequence
<220> FEATURE:
<223> OTHER INFORMATION: Synthetic Construct

<400> SEQUENCE: 134

```
Gln Ala Val Val Thr Gln Glu Pro Ser Leu Thr Val Ser Pro Gly Gly
1               5                   10                  15
Thr Val Thr Leu Thr Cys Gly Ser Ser Thr Gly Ala Val Thr Thr Ser
            20                  25                  30
Asn Tyr Ala Asn Trp Val Gln Glu Lys Pro Gly Gln Ala Phe Arg Gly
        35                  40                  45
Leu Ile Gly Gly Thr Asn Lys Arg Ala Pro Gly Thr Pro Ala Arg Phe
    50                  55                  60
Ser Gly Ser Leu Leu Gly Gly Lys Ala Ala Leu Thr Leu Ser Gly Ala
65                  70                  75                  80
Gln Pro Glu Asp Glu Ala Glu Tyr Tyr Cys Ala Leu Trp Tyr Ser Asn
                85                  90                  95
Leu Trp Val Phe Gly Gly Gly Thr Lys Leu Thr Val Leu Ser Ser Ala
            100                 105                 110
```

```
Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
        130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Gly Gly Gly Ser Gly Gly Gly Gly
210                 215                 220

Ser Glu Val Gln Leu Val Glu Ser Gly Gly Gly Leu Val Gln Pro Gly
225                 230                 235                 240

Gly Ser Leu Arg Leu Ser Cys Ala Ala Ser Gly Phe Asn Ile Lys Asp
                245                 250                 255

Thr Tyr Ile His Trp Val Arg Gln Ala Pro Gly Lys Gly Leu Glu Trp
            260                 265                 270

Val Ala Arg Ile Tyr Pro Thr Asn Gly Tyr Thr Arg Tyr Ala Asp Ser
        275                 280                 285

Val Lys Gly Arg Phe Thr Ile Ser Ala Asp Thr Ser Lys Asn Thr Ala
290                 295                 300

Tyr Leu Gln Met Asn Ser Leu Arg Ala Glu Asp Thr Ala Val Tyr Tyr
305                 310                 315                 320

Cys Ser Arg Trp Gly Gly Glu Gly Phe Tyr Ala Met Asp Tyr Trp Gly
                325                 330                 335

Gln Gly Thr Leu Val Thr Val Ser Ser Ala Ser Thr Lys Gly Pro Ser
            340                 345                 350

Val Phe Pro Leu Ala Pro Ser Ser Lys Ser Thr Ser Gly Gly Thr Ala
        355                 360                 365

Ala Leu Gly Cys Leu Val Glu Asp Tyr Phe Pro Glu Pro Val Thr Val
370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Glu Lys Val Glu Pro Lys Ser Cys
        435                 440                 445

Asp Lys Thr His Thr Cys Pro Pro Cys Pro Ala Pro Glu Ala Ala Gly
450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
        515                 520                 525

Arg Val Val Ser Val Leu Thr Val Leu His Gln Asp Trp Leu Asn Gly
```

```
                530                 535                 540
Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Cys Arg Asp Glu Leu Thr Lys Asn Gln Val Ser
                580                 585                 590

Leu Trp Cys Leu Val Lys Gly Phe Tyr Pro Ser Asp Ile Ala Val Glu
            595                 600                 605

Trp Glu Ser Asn Gly Gln Pro Glu Asn Asn Tyr Lys Thr Thr Pro Pro
        610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
                660                 665                 670

Pro Gly Lys
        675

<210> SEQ ID NO 135
<211> LENGTH: 957
<212> TYPE: PRT
<213> ORGANISM: Artificial Sequence
<220> FEATURE:
<223> OTHER INFORMATION: Synthetic Construct

<400> SEQUENCE: 135

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val Ser Trp Val Arg Gln Pro Pro Gly Lys Cys Leu Glu Trp Leu
            35                  40                  45

Gly Ile Ile Trp Gly Asp Gly Ser Thr Asn Tyr His Ser Ala Leu Ile
        50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Tyr Tyr Ala Met Asp Tyr Trp
                100                 105                 110

Gly Gln Gly Thr Ser Val Thr Val Ser Ser Gly Gly Gly Ser Gly
            115                 120                 125

Gly Gly Gly Ser Gly Gly Gly Ser Gly Gly Gly Ser Asp Ile
        130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
                180                 185                 190

Ala Thr Phe Leu Ala Asp Asp Val Pro Ser Arg Phe Ser Gly Ser Gly
            195                 200                 205

Ser Gly Thr Gln Tyr Ser Leu Lys Ile Asn Ser Leu Gln Ser Glu Asp
```

```
            210                 215                 220
Val Ala Arg Tyr Tyr Cys Gln His Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Gly Gly Gly Ser Gly Gly Gly Gly Gly Gly Gly Ser
            260                 265                 270

Gly Gly Gly Gly Ser Gly Gly Gly Ser Gln Ala Val Val Thr Gln
            275                 280                 285

Glu Pro Ser Leu Thr Val Ser Pro Gly Gly Thr Val Thr Leu Thr Cys
290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
                325                 330                 335

Lys Arg Ala Pro Gly Thr Pro Ala Arg Phe Ser Gly Ser Leu Leu Gly
                340                 345                 350

Gly Lys Ala Ala Leu Thr Leu Ser Gly Ala Gln Pro Glu Asp Glu Ala
                355                 360                 365

Glu Tyr Tyr Cys Ala Leu Trp Tyr Ser Asn Leu Trp Val Phe Gly Gly
370                 375                 380

Gly Thr Lys Leu Thr Val Leu Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415

Ala Leu Gly Cys Leu Val Lys Asp Tyr Phe Pro Glu Pro Val Thr Val
                420                 425                 430

Ser Trp Asn Ser Gly Ala Leu Thr Ser Gly Val His Thr Phe Pro Ala
                435                 440                 445

Val Leu Gln Ser Ser Gly Leu Tyr Ser Leu Ser Ser Val Val Thr Val
                450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Gly Gly Gly Ser Gly Gly Gly Gly Ser Glu Val Gln Leu Val
                500                 505                 510

Glu Ser Gly Gly Gly Leu Val Gln Pro Gly Gly Ser Leu Arg Leu Ser
                515                 520                 525

Cys Ala Ala Ser Gly Phe Asn Ile Lys Asp Thr Tyr Ile His Trp Val
530                 535                 540

Arg Gln Ala Pro Gly Lys Gly Leu Glu Trp Val Ala Arg Ile Tyr Pro
545                 550                 555                 560

Thr Asn Gly Tyr Thr Arg Tyr Ala Asp Ser Val Lys Gly Arg Phe Thr
                565                 570                 575

Ile Ser Ala Asp Thr Ser Lys Asn Thr Ala Tyr Leu Gln Met Asn Ser
                580                 585                 590

Leu Arg Ala Glu Asp Thr Ala Val Tyr Tyr Cys Ser Arg Trp Gly Gly
                595                 600                 605

Glu Gly Phe Tyr Ala Met Asp Tyr Trp Gly Gln Gly Thr Leu Val Thr
                610                 615                 620

Val Ser Ser Ala Ser Thr Lys Gly Pro Ser Val Phe Pro Leu Ala Pro
625                 630                 635                 640
```

```
Ser Ser Lys Ser Thr Ser Gly Gly Thr Ala Ala Leu Gly Cys Leu Val
            645                 650                 655

Glu Asp Tyr Phe Pro Glu Pro Val Thr Val Ser Trp Asn Ser Gly Ala
        660                 665                 670

Leu Thr Ser Gly Val His Thr Phe Pro Ala Val Leu Gln Ser Ser Gly
    675                 680                 685

Leu Tyr Ser Leu Ser Ser Val Val Thr Val Pro Ser Ser Ser Leu Gly
690                 695                 700

Thr Gln Thr Tyr Ile Cys Asn Val Asn His Lys Pro Ser Asn Thr Lys
705                 710                 715                 720

Val Asp Glu Lys Val Glu Pro Lys Ser Cys Asp Lys Thr His Thr Cys
                725                 730                 735

Pro Pro Cys Pro Ala Pro Glu Ala Ala Gly Gly Pro Ser Val Phe Leu
            740                 745                 750

Phe Pro Pro Lys Pro Lys Asp Thr Leu Met Ile Ser Arg Thr Pro Glu
        755                 760                 765

Val Thr Cys Val Val Val Asp Val Ser His Glu Asp Pro Glu Val Lys
    770                 775                 780

Phe Asn Trp Tyr Val Asp Gly Val Glu Val His Asn Ala Lys Thr Lys
785                 790                 795                 800

Pro Arg Glu Glu Gln Tyr Asn Ser Thr Tyr Arg Val Val Ser Val Leu
                805                 810                 815

Thr Val Leu His Gln Asp Trp Leu Asn Gly Lys Glu Tyr Lys Cys Lys
            820                 825                 830

Val Ser Asn Lys Ala Leu Gly Ala Pro Ile Glu Lys Thr Ile Ser Lys
        835                 840                 845

Ala Lys Gly Gln Pro Arg Glu Pro Gln Val Tyr Thr Leu Pro Pro Cys
    850                 855                 860

Arg Asp Glu Leu Thr Lys Asn Gln Val Ser Leu Trp Cys Leu Val Lys
865                 870                 875                 880

Gly Phe Tyr Pro Ser Asp Ile Ala Val Glu Trp Glu Ser Asn Gly Gln
                885                 890                 895

Pro Glu Asn Asn Tyr Lys Thr Thr Pro Pro Val Leu Asp Ser Asp Gly
            900                 905                 910

Ser Phe Phe Leu Tyr Ser Lys Leu Thr Val Asp Lys Ser Arg Trp Gln
        915                 920                 925

Gln Gly Asn Val Phe Ser Cys Ser Val Met His Glu Ala Leu His Asn
    930                 935                 940

His Tyr Thr Gln Lys Ser Leu Ser Leu Ser Pro Gly Lys
945                 950                 955

<210> SEQ ID NO 136
<211> LENGTH: 957
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45
```

-continued

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
 65                  70                  75                  80

Lys Leu Asn Ser Leu Gln Thr Asp Asp Thr Ala Thr Tyr Tyr Cys Ala
                 85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Gly Ser Val His
                245                 250                 255

Met Pro Leu Gly Phe Leu Gly Pro Arg Gln Ala Arg Val Val Asn Gly
            260                 265                 270

Gly Gly Gly Gly Ser Gly Gly Gly Ser Gln Ala Val Val Thr Gln
        275                 280                 285

Glu Pro Ser Leu Thr Val Ser Pro Gly Gly Thr Val Thr Leu Thr Cys
290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
            325                 330                 335

Lys Arg Ala Pro Gly Thr Pro Ala Arg Phe Ser Gly Ser Leu Leu Gly
            340                 345                 350

Gly Lys Ala Ala Leu Thr Leu Ser Gly Ala Gln Pro Glu Asp Glu Ala
        355                 360                 365

Glu Tyr Tyr Cys Ala Leu Trp Tyr Ser Asn Leu Trp Val Phe Gly Gly
    370                 375                 380

Gly Thr Lys Leu Thr Val Leu Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415

Ala Leu Gly Cys Leu Val Lys Asp Tyr Phe Pro Glu Pro Val Thr Val
            420                 425                 430

Ser Trp Asn Ser Gly Ala Leu Thr Ser Gly Val His Thr Phe Pro Ala
        435                 440                 445

Val Leu Gln Ser Ser Gly Leu Tyr Ser Leu Ser Ser Val Val Thr Val
    450                 455                 460

```
Pro Ser Ser Ser Leu Gly Thr Gln Thr Tyr Ile Cys Asn Val Asn His
465                 470                 475                 480

Lys Pro Ser Asn Thr Lys Val Asp Lys Val Glu Pro Lys Ser Cys
                485                 490                 495

Asp Gly Gly Gly Ser Gly Gly Gly Ser Glu Val Gln Leu Val
        500                 505                 510

Glu Ser Gly Gly Gly Leu Val Gln Pro Gly Gly Ser Leu Arg Leu Ser
    515                 520                 525

Cys Ala Ala Ser Gly Phe Asn Ile Lys Asp Thr Tyr Ile His Trp Val
    530                 535                 540

Arg Gln Ala Pro Gly Lys Gly Leu Glu Trp Val Ala Arg Ile Tyr Pro
545                 550                 555                 560

Thr Asn Gly Tyr Thr Arg Tyr Ala Asp Ser Val Lys Gly Arg Phe Thr
                565                 570                 575

Ile Ser Ala Asp Thr Ser Lys Asn Thr Ala Tyr Leu Gln Met Asn Ser
                580                 585                 590

Leu Arg Ala Glu Asp Thr Ala Val Tyr Tyr Cys Ser Arg Trp Gly Gly
    595                 600                 605

Glu Gly Phe Tyr Ala Met Asp Tyr Trp Gly Gln Gly Thr Leu Val Thr
    610                 615                 620

Val Ser Ser Ala Ser Thr Lys Gly Pro Ser Val Phe Pro Leu Ala Pro
625                 630                 635                 640

Ser Ser Lys Ser Thr Ser Gly Gly Thr Ala Ala Leu Gly Cys Leu Val
                645                 650                 655

Glu Asp Tyr Phe Pro Glu Pro Val Thr Val Ser Trp Asn Ser Gly Ala
                660                 665                 670

Leu Thr Ser Gly Val His Thr Phe Pro Ala Val Leu Gln Ser Ser Gly
                675                 680                 685

Leu Tyr Ser Leu Ser Ser Val Val Thr Val Pro Ser Ser Ser Leu Gly
    690                 695                 700

Thr Gln Thr Tyr Ile Cys Asn Val Asn His Lys Pro Ser Asn Thr Lys
705                 710                 715                 720

Val Asp Glu Lys Val Glu Pro Lys Ser Cys Asp Lys Thr His Thr Cys
                725                 730                 735

Pro Pro Cys Pro Ala Pro Glu Ala Ala Gly Gly Pro Ser Val Phe Leu
                740                 745                 750

Phe Pro Pro Lys Pro Lys Asp Thr Leu Met Ile Ser Arg Thr Pro Glu
                755                 760                 765

Val Thr Cys Val Val Val Asp Val Ser His Glu Asp Pro Glu Val Lys
                770                 775                 780

Phe Asn Trp Tyr Val Asp Gly Val Glu Val His Asn Ala Lys Thr Lys
785                 790                 795                 800

Pro Arg Glu Glu Gln Tyr Asn Ser Thr Tyr Arg Val Val Ser Val Leu
                805                 810                 815

Thr Val Leu His Gln Asp Trp Leu Asn Gly Lys Glu Tyr Lys Cys Lys
                820                 825                 830

Val Ser Asn Lys Ala Leu Gly Ala Pro Ile Glu Lys Thr Ile Ser Lys
                835                 840                 845

Ala Lys Gly Gln Pro Arg Glu Pro Gln Val Tyr Thr Leu Pro Pro Cys
                850                 855                 860

Arg Asp Glu Leu Thr Lys Asn Gln Val Ser Leu Trp Cys Leu Val Lys
865                 870                 875                 880

Gly Phe Tyr Pro Ser Asp Ile Ala Val Glu Trp Glu Ser Asn Gly Gln
```

```
                    885                 890                 895
Pro Glu Asn Asn Tyr Lys Thr Thr Pro Pro Val Leu Asp Ser Asp Gly
                900                 905                 910

Ser Phe Phe Leu Tyr Ser Lys Leu Thr Val Asp Lys Ser Arg Trp Gln
                915                 920                 925

Gln Gly Asn Val Phe Ser Cys Ser Val Met His Glu Ala Leu His Asn
            930                 935                 940

His Tyr Thr Gln Lys Ser Leu Ser Leu Ser Pro Gly Lys
945                 950                 955
```

<210> SEQ ID NO 137
<211> LENGTH: 449
<212> TYPE: PRT
<213> ORGANISM: Artificial Sequence
<220> FEATURE:
<223> OTHER INFORMATION: Synthetic Construct

<400> SEQUENCE: 137

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr His Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
                    290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 138
<211> LENGTH: 216
<212> TYPE: PRT
<213> ORGANISM: Artificial Sequence
<220> FEATURE:
<223> OTHER INFORMATION: Synthetic Construct

<400> SEQUENCE: 138

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Thr Asn Glu His
                85                  90                  95

Tyr Tyr Thr Phe Gly Gln Gly Thr Lys Val Glu Ile Lys Arg Thr Val
                100                 105                 110

Ala Ala Pro Ser Val Phe Ile Phe Pro Pro Ser Asp Arg Lys Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205
```

```
Lys Ser Phe Asn Arg Gly Glu Cys
        210                 215

<210> SEQ ID NO 139
<211> LENGTH: 956
<212> TYPE: PRT
<213> ORGANISM: Artificial Sequence
<220> FEATURE:
<223> OTHER INFORMATION: Synthetic Construct

<400> SEQUENCE: 139

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Cys Leu Glu Trp Leu
        35                  40                  45

Gly Ile Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Ile Thr Thr Val Val Asp Asp Tyr Tyr Ala Met Asp Tyr Trp
            100                 105                 110

Gly Gln Gly Thr Ser Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ala Ser Leu Ser Ala Ser Val Gly Glu Thr
145                 150                 155                 160

Val Thr Ile Thr Cys Arg Ala Ser Glu Asn Ile Asp Ser Tyr Leu Ala
                165                 170                 175

Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
    210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Val His
                245                 250                 255

Met Pro Leu Gly Phe Leu Gly Pro Arg Gln Ala Arg Val Val Asn Gly
            260                 265                 270

Gly Gly Gly Gly Ser Gly Gly Gly Ser Gln Ala Val Val Thr Gln
        275                 280                 285

Glu Pro Ser Leu Thr Val Ser Pro Gly Gly Thr Val Thr Leu Thr Cys
    290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
                325                 330                 335

Lys Arg Ala Pro Gly Thr Pro Ala Arg Phe Ser Gly Ser Leu Leu Gly
            340                 345                 350
```

-continued

Gly Lys Ala Ala Leu Thr Leu Ser Gly Ala Gln Pro Glu Asp Glu Ala
            355                 360                 365

Glu Tyr Tyr Cys Ala Leu Trp Tyr Ser Asn Leu Trp Val Phe Gly Gly
        370                 375                 380

Gly Thr Lys Leu Thr Val Leu Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415

Ala Leu Gly Cys Leu Val Lys Asp Tyr Phe Pro Glu Pro Val Thr Val
                420                 425                 430

Ser Trp Asn Ser Gly Ala Leu Thr Ser Gly Val His Thr Phe Pro Ala
            435                 440                 445

Val Leu Gln Ser Ser Gly Leu Tyr Ser Leu Ser Ser Val Val Thr Val
            450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Gly Gly Gly Ser Gly Gly Gly Ser Gln Val Gln Leu Val
                500                 505                 510

Gln Ser Gly Ala Glu Val Lys Lys Pro Gly Ala Ser Val Lys Val Ser
            515                 520                 525

Cys Lys Ala Ser Gly Tyr Thr Phe Thr Ser Tyr Tyr Met His Trp Val
            530                 535                 540

Arg Gln Ala Pro Gly Gln Gly Leu Glu Trp Met Gly Ile Ile Asn Pro
545                 550                 555                 560

Ser Gly Gly Ser Thr Ser Tyr Ala Gln Lys Phe Gln Gly Arg Val Thr
                565                 570                 575

Met Thr His Asp Thr Ser Thr Ser Thr Val Tyr Met Glu Leu Ser Ser
                580                 585                 590

Leu Arg Ser Glu Asp Thr Ala Val Tyr Tyr Cys Ala Arg Ser Phe Phe
            595                 600                 605

Thr Gly Phe His Leu Asp Tyr Trp Gly Gln Gly Thr Leu Val Thr Val
            610                 615                 620

Ser Ser Ala Ser Thr Lys Gly Pro Ser Val Phe Pro Leu Ala Pro Ser
625                 630                 635                 640

Ser Lys Ser Thr Ser Gly Gly Thr Ala Ala Leu Gly Cys Leu Val Glu
                645                 650                 655

Asp Tyr Phe Pro Glu Pro Val Thr Val Ser Trp Asn Ser Gly Ala Leu
                660                 665                 670

Thr Ser Gly Val His Thr Phe Pro Ala Val Leu Gln Ser Ser Gly Leu
            675                 680                 685

Tyr Ser Leu Ser Ser Val Val Thr Val Pro Ser Ser Ser Leu Gly Thr
            690                 695                 700

Gln Thr Tyr Ile Cys Asn Val Asn His Lys Pro Ser Asn Thr Lys Val
705                 710                 715                 720

Asp Glu Lys Val Glu Pro Lys Ser Cys Asp Lys Thr His Thr Cys Pro
                725                 730                 735

Pro Cys Pro Ala Pro Glu Ala Ala Gly Gly Pro Ser Val Phe Leu Phe
                740                 745                 750

Pro Pro Lys Pro Lys Asp Thr Leu Met Ile Ser Arg Thr Pro Glu Val
            755                 760                 765

```
Thr Cys Val Val Val Asp Val Ser His Glu Asp Pro Glu Val Lys Phe
    770                 775                 780
Asn Trp Tyr Val Asp Gly Val Glu Val His Asn Ala Lys Thr Lys Pro
785                 790                 795                 800
Arg Glu Glu Gln Tyr Asn Ser Thr Tyr Arg Val Val Ser Val Leu Thr
                805                 810                 815
Val Leu His Gln Asp Trp Leu Asn Gly Lys Glu Tyr Lys Cys Lys Val
            820                 825                 830
Ser Asn Lys Ala Leu Gly Ala Pro Ile Glu Lys Thr Ile Ser Lys Ala
        835                 840                 845
Lys Gly Gln Pro Arg Glu Pro Gln Val Tyr Thr Leu Pro Pro Cys Arg
850                 855                 860
Asp Glu Leu Thr Lys Asn Gln Val Ser Leu Trp Cys Leu Val Lys Gly
865                 870                 875                 880
Phe Tyr Pro Ser Asp Ile Ala Val Glu Trp Glu Ser Asn Gly Gln Pro
                885                 890                 895
Glu Asn Asn Tyr Lys Thr Thr Pro Pro Val Leu Asp Ser Asp Gly Ser
            900                 905                 910
Phe Phe Leu Tyr Ser Lys Leu Thr Val Asp Lys Ser Arg Trp Gln Gln
        915                 920                 925
Gly Asn Val Phe Ser Cys Ser Val Met His Glu Ala Leu His Asn His
930                 935                 940
Tyr Thr Gln Lys Ser Leu Ser Leu Ser Pro Gly Lys
945                 950                 955
```

<210> SEQ ID NO 140
<211> LENGTH: 956
<212> TYPE: PRT
<213> ORGANISM: Artificial Sequence
<220> FEATURE:
<223> OTHER INFORMATION: Synthetic Construct

<400> SEQUENCE: 140

```
Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Thr Ser Tyr
            20                  25                  30
Gly Val Ser Trp Val Arg Gln Pro Pro Gly Lys Cys Leu Glu Trp Leu
        35                  40                  45
Gly Ile Ile Trp Gly Asp Gly Ser Thr Asn Tyr His Ser Ala Leu Ile
    50                  55                  60
Ser Arg Leu Ser Ile Ser Lys Asp Asn Ser Lys Ser Gln Val Phe Leu
65                  70                  75                  80
Lys Leu Asn Ser Leu Gln Thr Asp Asp Thr Ala Thr Tyr Tyr Cys Ala
                85                  90                  95
Lys Gly Ile Thr Thr Val Val Asp Asp Tyr Tyr Ala Met Asp Tyr Trp
            100                 105                 110
Gly Gln Gly Thr Ser Val Thr Val Ser Ser Gly Gly Gly Gly Ser Gly
        115                 120                 125
Gly Gly Gly Ser Gly Gly Gly Ser Gly Gly Gly Ser Asp Ile
    130                 135                 140
Gln Met Thr Gln Ser Pro Ala Ser Leu Ser Ala Ser Val Gly Glu Thr
145                 150                 155                 160
Val Thr Ile Thr Cys Arg Ala Ser Glu Asn Ile Asp Ser Tyr Leu Ala
                165                 170                 175
```

```
Trp Tyr Gln Gln Lys Gln Gly Lys Ser Pro Gln Leu Leu Val Tyr Ala
            180                 185                 190

Ala Thr Phe Leu Ala Asp Asp Val Pro Ser Arg Phe Ser Gly Ser Gly
        195                 200                 205

Ser Gly Thr Gln Tyr Ser Leu Lys Ile Asn Ser Leu Gln Ser Glu Asp
        210                 215                 220

Val Ala Arg Tyr Tyr Cys Gln His Tyr Tyr Ser Thr Pro Tyr Thr Phe
225                 230                 235                 240

Gly Cys Gly Thr Lys Leu Glu Ile Lys Gly Gly Gly Ser Gly Gly
                245                 250                 255

Gly Gly Ser Gly Gly Gly Gly Ser Gly Gly Gly Gly Gly Gly Gly Ser
        260                 265                 270

Gly Gly Gly Gly Ser Gly Gly Gly Ser Gln Ala Val Val Thr Gln
        275                 280                 285

Glu Pro Ser Leu Thr Val Ser Pro Gly Gly Thr Val Thr Leu Thr Cys
        290                 295                 300

Gly Ser Ser Thr Gly Ala Val Thr Thr Ser Asn Tyr Ala Asn Trp Val
305                 310                 315                 320

Gln Glu Lys Pro Gly Gln Ala Phe Arg Gly Leu Ile Gly Gly Thr Asn
                325                 330                 335

Lys Arg Ala Pro Gly Thr Pro Ala Arg Phe Ser Gly Ser Leu Leu Gly
                340                 345                 350

Gly Lys Ala Ala Leu Thr Leu Ser Gly Ala Gln Pro Glu Asp Glu Ala
            355                 360                 365

Glu Tyr Tyr Cys Ala Leu Trp Tyr Ser Asn Leu Trp Val Phe Gly Gly
        370                 375                 380

Gly Thr Lys Leu Thr Val Leu Ser Ser Ala Ser Thr Lys Gly Pro Ser
385                 390                 395                 400

Val Phe Pro Leu Ala Pro Ser Ser Lys Ser Thr Ser Gly Gly Thr Ala
                405                 410                 415

Ala Leu Gly Cys Leu Val Lys Asp Tyr Phe Pro Glu Pro Val Thr Val
            420                 425                 430

Ser Trp Asn Ser Gly Ala Leu Thr Ser Gly Val His Thr Phe Pro Ala
        435                 440                 445

Val Leu Gln Ser Ser Gly Leu Tyr Ser Leu Ser Ser Val Val Thr Val
450                 455                 460

Pro Ser Ser Ser Leu Gly Thr Gln Thr Tyr Ile Cys Asn Val Asn His
465                 470                 475                 480

Lys Pro Ser Asn Thr Lys Val Asp Lys Lys Val Glu Pro Lys Ser Cys
                485                 490                 495

Asp Gly Gly Gly Gly Ser Gly Gly Gly Gly Ser Gln Val Gln Leu Val
            500                 505                 510

Gln Ser Gly Ala Glu Val Lys Lys Pro Gly Ala Ser Val Lys Val Ser
        515                 520                 525

Cys Lys Ala Ser Gly Tyr Thr Phe Thr Ser Tyr Tyr Met His Trp Val
        530                 535                 540

Arg Gln Ala Pro Gly Gln Gly Leu Glu Trp Met Gly Ile Ile Asn Pro
545                 550                 555                 560

Ser Gly Gly Ser Thr Ser Tyr Ala Gln Lys Phe Gln Gly Arg Val Thr
                565                 570                 575

Met Thr His Asp Thr Ser Thr Ser Thr Val Tyr Met Glu Leu Ser Ser
                580                 585                 590

Leu Arg Ser Glu Asp Thr Ala Val Tyr Tyr Cys Ala Arg Ser Phe Phe
```

```
                     595                 600                 605

Thr Gly Phe His Leu Asp Tyr Trp Gly Gln Gly Thr Leu Val Thr Val
            610                 615                 620

Ser Ser Ala Ser Thr Lys Gly Pro Ser Val Phe Pro Leu Ala Pro Ser
625                 630                 635                 640

Ser Lys Ser Thr Ser Gly Gly Thr Ala Ala Leu Gly Cys Leu Val Glu
                645                 650                 655

Asp Tyr Phe Pro Glu Pro Val Thr Val Ser Trp Asn Ser Gly Ala Leu
            660                 665                 670

Thr Ser Gly Val His Thr Phe Pro Ala Val Leu Gln Ser Ser Gly Leu
            675                 680                 685

Tyr Ser Leu Ser Ser Val Val Thr Val Pro Ser Ser Ser Leu Gly Thr
            690                 695                 700

Gln Thr Tyr Ile Cys Asn Val Asn His Lys Pro Ser Asn Thr Lys Val
705                 710                 715                 720

Asp Glu Lys Val Glu Pro Lys Ser Cys Asp Lys Thr His Thr Cys Pro
                725                 730                 735

Pro Cys Pro Ala Pro Glu Ala Ala Gly Gly Pro Ser Val Phe Leu Phe
            740                 745                 750

Pro Pro Lys Pro Lys Asp Thr Leu Met Ile Ser Arg Thr Pro Glu Val
            755                 760                 765

Thr Cys Val Val Val Asp Val Ser His Glu Asp Pro Glu Val Lys Phe
770                 775                 780

Asn Trp Tyr Val Asp Gly Val Glu Val His Asn Ala Lys Thr Lys Pro
785                 790                 795                 800

Arg Glu Glu Gln Tyr Asn Ser Thr Tyr Arg Val Val Ser Val Leu Thr
                805                 810                 815

Val Leu His Gln Asp Trp Leu Asn Gly Lys Glu Tyr Lys Cys Lys Val
            820                 825                 830

Ser Asn Lys Ala Leu Gly Ala Pro Ile Glu Lys Thr Ile Ser Lys Ala
            835                 840                 845

Lys Gly Gln Pro Arg Glu Pro Gln Val Tyr Thr Leu Pro Pro Cys Arg
850                 855                 860

Asp Glu Leu Thr Lys Asn Gln Val Ser Leu Trp Cys Leu Val Lys Gly
865                 870                 875                 880

Phe Tyr Pro Ser Asp Ile Ala Val Glu Trp Glu Ser Asn Gly Gln Pro
                885                 890                 895

Glu Asn Asn Tyr Lys Thr Thr Pro Pro Val Leu Asp Ser Asp Gly Ser
            900                 905                 910

Phe Phe Leu Tyr Ser Lys Leu Thr Val Asp Lys Ser Arg Trp Gln Gln
            915                 920                 925

Gly Asn Val Phe Ser Cys Ser Val Met His Glu Ala Leu His Asn His
930                 935                 940

Tyr Thr Gln Lys Ser Leu Ser Leu Ser Pro Gly Lys
945                 950                 955

<210> SEQ ID NO 141
<211> LENGTH: 674
<212> TYPE: PRT
<213> ORGANISM: Artificial Sequence
<220> FEATURE:
<223> OTHER INFORMATION: Synthetic Construct

<400> SEQUENCE: 141

Gln Ala Val Val Thr Gln Glu Pro Ser Leu Thr Val Ser Pro Gly Gly
```

-continued

```
1               5                   10                  15
Thr Val Thr Leu Thr Cys Gly Ser Ser Thr Gly Ala Val Thr Thr Ser
                20                  25                  30
Asn Tyr Ala Asn Trp Val Gln Glu Lys Pro Gly Gln Ala Phe Arg Gly
                35                  40                  45
Leu Ile Gly Gly Thr Asn Lys Arg Ala Pro Gly Thr Pro Ala Arg Phe
                50                  55                  60
Ser Gly Ser Leu Leu Gly Gly Lys Ala Ala Leu Thr Leu Ser Gly Ala
65                  70                  75                  80
Gln Pro Glu Asp Glu Ala Glu Tyr Tyr Cys Ala Leu Trp Tyr Ser Asn
                85                  90                  95
Leu Trp Val Phe Gly Gly Gly Thr Lys Leu Thr Val Leu Ser Ser Ala
                100                 105                 110
Ser Thr Lys Gly Pro Ser Val Phe Pro Leu Ala Pro Ser Ser Lys Ser
            115                 120                 125
Thr Ser Gly Gly Thr Ala Ala Leu Gly Cys Leu Val Lys Asp Tyr Phe
            130                 135                 140
Pro Glu Pro Val Thr Val Ser Trp Asn Ser Gly Ala Leu Thr Ser Gly
145                 150                 155                 160
Val His Thr Phe Pro Ala Val Leu Gln Ser Ser Gly Leu Tyr Ser Leu
                165                 170                 175
Ser Ser Val Val Thr Val Pro Ser Ser Ser Leu Gly Thr Gln Thr Tyr
            180                 185                 190
Ile Cys Asn Val Asn His Lys Pro Ser Asn Thr Lys Val Asp Lys Lys
            195                 200                 205
Val Glu Pro Lys Ser Cys Asp Gly Gly Gly Ser Gly Gly Gly Gly Gly
210                 215                 220
Ser Gln Val Gln Leu Val Gln Ser Gly Ala Glu Val Lys Lys Pro Gly
225                 230                 235                 240
Ala Ser Val Lys Val Ser Cys Lys Ala Ser Gly Tyr Thr Phe Thr Ser
                245                 250                 255
Tyr Tyr Met His Trp Val Arg Gln Ala Pro Gly Gln Gly Leu Glu Trp
            260                 265                 270
Met Gly Ile Ile Asn Pro Ser Gly Gly Ser Thr Ser Tyr Ala Gln Lys
            275                 280                 285
Phe Gln Gly Arg Val Thr Met Thr His Asp Thr Ser Thr Ser Thr Val
            290                 295                 300
Tyr Met Glu Leu Ser Ser Leu Arg Ser Glu Asp Thr Ala Val Tyr Tyr
305                 310                 315                 320
Cys Ala Arg Ser Phe Phe Thr Gly Phe His Leu Asp Tyr Trp Gly Gln
                325                 330                 335
Gly Thr Leu Val Thr Val Ser Ser Ala Ser Thr Lys Gly Pro Ser Val
            340                 345                 350
Phe Pro Leu Ala Pro Ser Ser Lys Ser Thr Ser Gly Gly Thr Ala Ala
            355                 360                 365
Leu Gly Cys Leu Val Glu Asp Tyr Phe Pro Glu Pro Val Thr Val Ser
            370                 375                 380
Trp Asn Ser Gly Ala Leu Thr Ser Gly Val His Thr Phe Pro Ala Val
385                 390                 395                 400
Leu Gln Ser Ser Gly Leu Tyr Ser Leu Ser Ser Val Val Thr Val Pro
                405                 410                 415
Ser Ser Ser Leu Gly Thr Gln Thr Tyr Ile Cys Asn Val Asn His Lys
            420                 425                 430
```

-continued

```
Pro Ser Asn Thr Lys Val Asp Glu Lys Val Glu Pro Lys Ser Cys Asp
        435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys

<210> SEQ ID NO 142
<211> LENGTH: 5
<212> TYPE: PRT
<213> ORGANISM: Artificial Sequence
<220> FEATURE:
<223> OTHER INFORMATION: Synthetic Construct

<400> SEQUENCE: 142

Asp Tyr Thr Met Asp
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Asp Val Asn Pro Asn Ser Gly Gly Ser Ile Val Asn Arg Arg Phe Lys
1               5                   10                  15

Gly

<210> SEQ ID NO 144
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 144

Asn Leu Gly Pro Phe Phe Tyr Phe Asp Tyr
1               5                   10

<210> SEQ ID NO 145
<211> LENGTH: 7
<212> TYPE: PRT
<213> ORGANISM: Artificial Sequence
<220> FEATURE:
<223> OTHER INFORMATION: Synthetic Construct

<400> SEQUENCE: 145

Thr Ser Asn Tyr Ala Asn Trp
1               5

<210> SEQ ID NO 146
<211> LENGTH: 20
<212> TYPE: PRT
<213> ORGANISM: Artificial Sequence
<220> FEATURE:
<223> OTHER INFORMATION: Synthetic Construct

<400> SEQUENCE: 146

Gly Thr Asn Lys Arg Ala Pro Gly Thr Pro Ala Arg Phe Ser Gly Ser
1               5                   10                  15

Leu Leu Gly Gly
            20

<210> SEQ ID NO 147
<211> LENGTH: 5
<212> TYPE: PRT
<213> ORGANISM: Artificial Sequence
<220> FEATURE:
<223> OTHER INFORMATION: Synthetic Construct

<400> SEQUENCE: 147

Thr Lys Leu Thr Val
1               5

<210> SEQ ID NO 148
<211> LENGTH: 11
<212> TYPE: PRT
<213> ORGANISM: Artificial Sequence
<220> FEATURE:
<223> OTHER INFORMATION: Synthetic Construct

<400> SEQUENCE: 148

Lys Ala Ser Gln Asp Val Ser Thr Ala Val Ala
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Synthetic Construct

<400> SEQUENCE: 149

Ser Ala Ser Phe Arg Tyr Thr
1               5
```

```
<210> SEQ ID NO 150
<211> LENGTH: 9
<212> TYPE: PRT
<213> ORGANISM: Artificial Sequence
<220> FEATURE:
<223> OTHER INFORMATION: Synthetic Construct

<400> SEQUENCE: 150

Gln Gln His Tyr Thr Thr Pro Pro Thr
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic Construct

<400> SEQUENCE: 151

Ser Tyr Tyr Met His
1               5

<210> SEQ ID NO 152
<211> LENGTH: 17
<212> TYPE: PRT
<213> ORGANISM: Artificial Sequence
<220> FEATURE:
<223> OTHER INFORMATION: Synthetic Construct

<400> SEQUENCE: 152

Ile Ile Asn Pro Ser Gly Gly Ser Thr Ser Tyr Ala Gln Lys Phe Gln
1               5                   10                  15

Gly

<210> SEQ ID NO 153
<211> LENGTH: 10
<212> TYPE: PRT
<213> ORGANISM: Artificial Sequence
<220> FEATURE:
<223> OTHER INFORMATION: Synthetic Construct

<400> SEQUENCE: 153

Ser Phe Phe Thr Gly Phe His Leu Asp Tyr
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct

<400> SEQUENCE: 154

Arg Ala Ser Gln Ser Val Ser Ser Ser Tyr Leu Ala
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Synthetic Construct

<400> SEQUENCE: 155

Gly Ala Ser Ser Arg Ala Thr
1               5
```

<210> SEQ ID NO 156
<211> LENGTH: 10
<212> TYPE: PRT
<213> ORGANISM: Artificial Sequence
<220> FEATURE:
<223> OTHER INFORMATION: Synthetic Construct

<400> SEQUENCE: 156

Gln Gln Tyr Thr Asn Glu His Tyr Tyr Thr
1               5                   10

<210> SEQ ID NO 157
<211> LENGTH: 119
<212> TYPE: PRT
<213> ORGANISM: Artificial Sequence
<220> FEATURE:
<223> OTHER INFORMATION: Synthetic Construct

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr His Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Gly Phe His Leu Asp Tyr Trp Gly Gln Gly
            100                 105                 110

Thr Leu Val Thr Val Ser Ser
        115

<210> SEQ ID NO 158
<211> LENGTH: 109
<212> TYPE: PRT
<213> ORGANISM: Artificial Sequence
<220> FEATURE:
<223> OTHER INFORMATION: Synthetic Construct

<400> SEQUENCE: 158

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Thr Asn Glu His
                85                  90                  95

Tyr Tyr Thr Phe Gly Gln Gly Thr Lys Val Glu Ile Lys
            100                 105

```
<210> SEQ ID NO 159
<211> LENGTH: 119
<212> TYPE: PRT
<213> ORGANISM: Artificial Sequence
<220> FEATURE:
<223> OTHER INFORMATION: Synthetic Construct

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser
        115

<210> SEQ ID NO 160
<211> LENGTH: 120
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser
        115                 120

<210> SEQ ID NO 161
<211> LENGTH: 107
<212> TYPE: PRT
<213> ORGANISM: Artificial Sequence
<220> FEATURE:
<223> OTHER INFORMATION: Synthetic Construct

<400> SEQUENCE: 161

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Arg Tyr Thr Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 162
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 162
gaagttcagc tggttgaaag cggtggtggt ctggttcagc ctggtggtag cctgcgtctg      60
agctgtgcag caagcggttt tacctttaac gattatacca tggattgggt tcgtcaggca     120
ccgggtaaag gtctggaatg ggttgcagat gttaatccga atagcggtgg tagcattgtt     180
aaccgtcgtt ttaaaggtcg ttttacccct gagcgttgatc gtagcaaaaa taccctgtat     240
ctgcaaatga atagtctgcg tgcagaggat accgcagtgt attattgtgc acgtaacctg     300
ggtccgttct tctactttga ttattggggt cagggcaccc tggttaccgt tagcagcgct     360
agcaccaagg gcccctccgt gttccccctg gccccagca gcaagagcac cagcggcggc     420
acagccgctc tgggctgcct ggtcgaggac tacttccccg agcccgtgac cgtgtcctgg     480
aacagcggag ccctgacctc cggcgtgcac accttccccg ccgtgctgca gagttctggc     540
ctgtatagcc tgagcagcgt ggtcaccgtg ccttctagca gcctgggcac ccagacctac     600
atctgcaacg tgaaccacaa gcccagcaac accaaggtgg acgagaaggt ggagcccaag     660
agctgcgaca aaactcacac atgcccaccg tgcccagcac ctgaagctgc aggggaccg     720 tcagtcttcc tcttccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ggcgccccca tcgagaaaac catctccaaa    1020
gccaaagggc agccccgaga accacaggtg tgcaccctgc cccatcccg ggatgagctg    1080 accaagaacc aggtcagcct ctcgtgcgca gtcaaaggct tctatcccag cgacatcgcc    1140
gtggagtggg agagcaatgg gcagccggag aacaactaca agaccacgcc tcccgtgctg    1200
gactccgacg gctccttctt cctcgtgagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                    1350

<210> SEQ ID NO 163
<211> LENGTH: 645
<212> TYPE: DNA

<213> ORGANISM: Artificial Sequence
<220> FEATURE:
<223> OTHER INFORMATION: Synthetic Construct

<400> SEQUENCE: 163

| | | | | | |
|---|---|---|---|---|---|
| gacatccaga | tgacccagag | ccccagcagc | ctgtctgcca | gcgtgggcga | cagagtgacc | 60 |
| atcacatgca | aggccagcca | ggacgtgtcc | acagccgtgg | cctggtatca | gcagaagcct | 120 |
| ggcaaggccc | ccaagctgct | gatctacagc | gccagcttcc | ggtacaccgg | cgtgcccagc | 180 |
| agattcagcg | gcagcagatc | cggcaccgac | ttcaccctga | ccatcagctc | cctgcagccc | 240 |
| gaggacttcg | ccacctacta | ctgccagcag | cactacacca | cccccccac | atttggccag | 300 |
| ggcaccaagg | tggaaatcaa | gcgtacggtg | gctgcaccat | ctgtcttcat | cttcccgcca | 360 |
| tctgatcgga | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaaacacaaa | gtctacgcct | gcgaagtcac | ccatcagggc | 600 |
| ctgagctcgc | ccgtcacaaa | gagcttcaac | aggggagagt | gttag | | 645 |

<210> SEQ ID NO 164
<211> LENGTH: 2874
<212> TYPE: DNA
<213> ORGANISM: Artificial Sequence
<220> FEATURE:
<223> OTHER INFORMATION: Synthetic Construct

<400> SEQUENCE: 164

| | | | | | |
|---|---|---|---|---|---|
| caagtgcagc | tgaaagagtc | cggccctgga | ctggtggccc | ctagccagag | cctgagcatc | 60 |
| acctgtaccg | tgtccggctt | cagcctgacc | agctacggcg | tgtcatgggt | gcgccagcct | 120 |
| ccaggcaagt | gtctggaatg | gctgggcatc | atctggggcg | acggcagcac | caattaccac | 180 |
| agcgccctga | tcagcagact | gagcatctcc | aaggacaaca | gcaagagcca | ggtgttcctg | 240 |
| aagctgaaca | gcctgcagac | cgacgacacc | gccacctact | actgcgccaa | gggcatcacc | 300 |
| accgtggtgg | acgactacta | cgctatggac | tactggggcc | agggcaccag | cgtgacagtg | 360 |
| tctagcggag | gcggaggatc | tggcggcgga | ggaagtggcg | gagggggatc | tggggaggc | 420 |
| ggaagcgata | tccagatgac | ccagagccct | gccagcctgt | ctgcctctgt | gggcgagaca | 480 |
| gtgaccatca | catgccgggc | cagcgagaac | atcgacagct | acctggcctg | gtatcagcag | 540 |
| aagcagggca | agagccccca | gctgctggtg | tacgccgcca | cctttctggc | cgacgatgtg | 600 |
| cccagcagat | tcagcggcag | cggaagcggc | acacagtaca | gcctgaagat | caactccctg | 660 |
| cagagcgagg | acgtggcccg | gtactactgc | cagcactact | acagcacccc | ctacaccttc | 720 |
| ggctgcggca | ccaagctgga | aatcaaaggc | gggggaggct | ccggaggcgg | cggaagtgga | 780 |
| ggcggcggaa | gtggcggagg | cggaggggg | ggaagtgggg | gcggaggcag | tggggggga | 840 |
| ggatcccagg | ccgtcgtgac | ccaggaaccc | agcctgacag | tgtctcctgg | cggcaccgtg | 900 |
| accctgacat | gtggcagttc | tacaggcgcc | gtgaccacca | gcaactacgc | caactgggtg | 960 |
| caggaaaagc | ccggccaggc | cttcaggaga | ctgatcggcg | gcaccaacaa | gagagcccct | 1020 |
| ggcacccctg | ccagattcag | cggatctctg | ctgggaggaa | aggccgccct | gacactgtct | 1080 |
| ggcgcccagc | cagaagatga | ggccgagtac | tactgcgccc | tgtggtacag | caacctgtgg | 1140 |
| gtgttcggcg | gaggcaccaa | gctgacagtg | ctgagcagcg | cttccaccaa | gggacccagt | 1200 |
| gtgttccccc | tggcccccag | ctccaagtct | acatccggtg | gcacagctgc | cctgggatgt | 1260 |

```
ctcgtgaagg actactttcc tgagcctgtg acagtgtctt ggaacagcgg agccctgacc    1320
agcggagtgc acacattccc tgcagtgctg cagagcagcg gcctgtatag cctgagcagc    1380
gtcgtgaccg tgccttcctc tagcctggga acacagacat atatctgtaa tgtgaatcat    1440
aagcccagta ataccaaagt ggataagaaa gtggaaccta agagctgcga tggcggagga    1500
gggtccggag gcggagggtc cgaggtccag ctggtcgagt ctggaggagg actggtgcag    1560
ccaggcggat ctctgagact gagctgcgcc gccagcggat tcaacatcaa ggacacctac    1620
atccactggg tgaggcaggc ccctggaaag ggactggagt gggtggccag aatctacccc    1680
accaacggct acacaagata cgccgacagc gtgaagggca gattcaccat cagcgccgac    1740
accagcaaga acaccgccta cctgcagatg aacagcctga gagccgagga cacagccgtg    1800
tactactgct ctagatgggg aggcgagggc ttctacgcca tggactactg gggacagggc    1860
acactggtga ccgtgtccag cgctagcacc aagggcccct ccgtgttccc cctggccccc    1920
agcagcaaga gcaccagcgg cggcacagcc gctctgggct gcctggtcga ggactacttc    1980
cccgagcccg tgaccgtgtc ctggaacagc ggagccctga cctccggcgt gcacaccttc    2040
cccgccgtgc tgcagagttc tggcctgtat agcctgagca gcgtggtcac cgtgccttct    2100
agcagcctgg gcacccagac ctacatctgc aacgtgaacc acaagcccag caacaccaag    2160
gtggacgaga aggtggagcc caagagctgc gacaaaactc acacatgccc accgtgccca    2220
gcacctgaag ctgcaggggg accgtcagtc ttcctcttcc ccccaaaacc caaggacacc    2280
ctcatgatct cccggacccc tgaggtcaca tgcgtggtgg tggacgtgag ccacgaagac    2340
cctgaggtca agttcaactg gtacgtggac ggcgtggagg tgcataatgc caagacaaag    2400
ccgcgggagg agcagtacaa cagcacgtac cgtgtggtca gcgtcctcac cgtcctgcac    2460
caggactggc tgaatggcaa ggagtacaag tgcaaggtct ccaacaaagc cctcggcgcc    2520
cccatcgaga aaaccatctc caaagccaaa gggcagcccc gagaaccaca ggtgtacacc    2580
ctgcccccat gccgggatga gctgaccaag aaccaggtca gcctgtggtg cctggtcaaa    2640
ggcttctatc ccagcgacat cgccgtggag tgggagagca atgggcagcc ggagaacaac    2700
tacaagacca cgcctcccgt gctggactcc gacggctcct tcttcctcta cagcaagctc    2760
accgtggaca gagcaggtg gcagcagggg aacgtcttct catgctccgt gatgcatgag    2820
gctctgcaca accactacac gcagaagagc ctctccctgt ctccgggtaa atga    2874
```

<210> SEQ ID NO 165
<211> LENGTH: 2874
<212> TYPE: DNA
<213> ORGANISM: Artificial Sequence
<220> FEATURE:
<223> OTHER INFORMATION: Synthetic Construct

<400> SEQUENCE: 165

```
caagtgcagc tgaaagagtc cggccctgga ctggtggccc ctagccagag cctgagcatc      60
acctgtaccg tgtccggctt cagcctgacc agctacggcg tgtcatgggt gcgccagcct     120
ccaggcaagt gtctggaatg gctgggcatc atctggggcg acggcagcac caattaccac     180
agcgccctga tcagcagact gagcatctcc aaggacaaca gcaagagcca ggtgttcctg     240
aagctgaaca gcctgcagac cgacgacacc gccaccctact actgcgccaa gggcatcacc     300
accgtggtgg acgactacta cgctatggac tactggggcc agggcaccag cgtgacagtg     360
tctagcggag gcggaggatc tggcggcgga ggaagtggcg gagggggatc tgggggaggc     420
```

```
ggaagcgata tccagatgac ccagagccct gccagcctgt ctgcctctgt gggcgagaca    480
gtgaccatca catgccgggc cagcgagaac atcgacagct acctggcctg gtatcagcag    540
aagcagggca agagccccca gctgctggtg tacgccgcca cctttctggc cgacgatgtg    600
cccagcagat tcagcggcag cggaagcggc acacagtaca gcctgaagat caactccctg    660
cagagcgagg acgtggcccg gtactactgc cagcactact acagcacccc ctacaccttc    720
ggctgcggca ccaagctgga aatcaaagga ggcggcggaa gtgtgcacat gcccctgggc    780
ttcctgggcc ccagacaggc cagagtcgtg aacggggggg gcggaggcag tgggggggga    840
ggatcccagg ccgtcgtgac ccaggaaccc agcctgacag tgtctcctgg cggcaccgtg    900
accctgacat gtggcagttc tacaggcgcc gtgaccacca gcaactacgc caactgggtg    960
caggaaaagc ccggccaggc cttcagagga ctgatcggcg gcaccaacaa gagagcccct   1020
ggcacccctg ccagattcag cggatctctg ctgggaggaa aggccgccct gacactgtct   1080
ggcgcccagc cagaagatga ggccgagtac tactgcgccc tgtggtacag caacctgtgg   1140
gtgttcggcg gaggcaccaa gctgacagtg ctgagcagcc cttccaccaa gggacccagt   1200
gtgttccccc tggcccccag ctccaagtct acatccggtg gcacagctgc cctgggatgt   1260
ctcgtgaagg actactttcc tgagcctgtg acagtgtctt ggaacagcgg agccctgacc   1320
agcggagtgc acacattccc tgcagtgctg cagagcagcg gcctgtatag cctgagcagc   1380
gtcgtgaccg tgccttcctc tagcctggga acacagacat atatctgtaa tgtgaatcat   1440
aagcccagta ataccaaagt ggataagaaa gtggaaccta gagctgcga tggcggagga   1500 gggtccggag gcgagggtc cgaggtccag ctggtcgagt ctggaggagg actggtgcag   1560
ccaggcggat ctctgagact gagctgcgcc gccagcggat tcaacatcaa ggacacctac   1620
atccactggg tgaggcaggc ccctggaaag ggactggagt gggtggccag aatctacccc   1680
accaacggct acacaagata cgccgacagc gtgaagggca gattcaccat cagcgccgac   1740
accagcaaga caccgccta cctgcagatg aacagcctga gagccgagga cacagccgtg   1800
tactactgct ctagatgggg aggcgagggc ttctacgcca tggactactg gggacagggc   1860
acactggtga ccgtgtccag cgctagcacc aagggcccct ccgtgttccc cctggccccc   1920
agcagcaaga gcaccagcgg cggcacagcc gctctgggct gcctggtcga ggactacttc   1980
cccgagcccg tgaccgtgtc ctggaacagc ggagccctga cctccggcgt gcacaccttc   2040
cccgccgtgc tgcagagttc tggcctgtat agcctgagca gcgtggtcac cgtgccttct   2100
agcagcctgg gcacccagac ctacatctgc aacgtgaacc acaagcccag caacaccaag   2160
gtggacgaga aggtggagcc caagagctgc gacaaaactc acacatgccc accgtgccca   2220
gcacctgaag ctgcaggggg accgtcagtc ttcctcttcc ccccaaaacc caaggacacc   2280
ctcatgatct cccggacccc tgaggtcaca tgcgtggtgg tggacgtgag ccacgaagac   2340
cctgaggtca agttcaactg gtacgtggac ggcgtggagg tgcataatgc caagacaaag   2400
ccgcgggagg agcagtacaa cagcacgtac cgtgtggtca gcgtcctcac cgtcctgcac   2460
caggactggc tgaatggcaa ggagtacaag tgcaaggtct ccaacaaagc cctcggcgcc   2520
cccatcgaga aaaccatctc caaagccaaa gggcagcccc gagaaccaca ggtgtacacc   2580
ctgcccccat gccgggatga gctgaccaag aaccaggtca gcctgtggtg cctggtcaaa   2640
ggcttctatc ccagcgacat cgccgtggag tgggagagca atgggcagcc ggagaacaac   2700
tacaagacca cgcctcccgt gctggactcc gacggctcct tcttcctcta cagcaagctc   2760
accgtggaca agagcaggtg gcagcagggg aacgtcttct catgctccgt gatgcatgag   2820
```

```
gctctgcaca accactacac gcagaagagc ctctccctgt ctccgggtaa atga        2874
```

<210> SEQ ID NO 166
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 166

```
caggtgcaat tggttcaatc tggtgctgaa gtaaaaaaac cgggcgcttc cgttaaagtg   60
agctgcaaag catccggata caccttcact tcctattaca tgcactgggt tcgtcaagcc  120
ccgggccagg gtctggaatg gatgggcatc attaacccaa gcggtggctc tacctcctac  180
gcgcagaaat tccagggtcg cgtcacgatg acccatgaca ctagcacctc taccgtttat  240
atggagctgt ccagcctgcg ttctgaagat actgcagtgt actactgtgc acgctctttc  300
ttcactggtt tccatctgga ctattggggt caaggcaccc tcgtaacggt tcttctgct   360
agcaccaagg gcccctccgt gttccccctg gccccagca gcaagagcac cagcggcggc   420
acagccgctc tgggctgcct ggtcgaggac tacttcccg agcccgtgac cgtgtcctgg   480
aacagcggag ccctgaccct cggcgtgcac accttccccg ccgtgctgca gagttctggc  540
ctgtatagcc tgagcagcgt ggtcaccgtg ccttctagca gcctgggcac ccagacctac  600
atctgcaacg tgaaccacaa gcccagcaac accaaggtgg acgagaaggt ggagcccaag  660
agctgcgaca aaactcacac atgcccaccg tgcccagcac ctgaagctgc aggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ggcgccccca tcgagaaaac catctccaaa 1020
gccaaagggc agccccgaga accacaggtg tgcaccctgc ccccatcccg ggatgagctg 1080
accaagaacc aggtcagcct ctcgtgcgca gtcaaaggct tctatcccag cgacatcgcc 1140
gtggagtggg agagcaatgg gcagccggag aacaactaca agaccacgcc tcccgtgctg 1200
gactccgacg gctccttctt cctcgtgagc aagctcaccg tggacaagag caggtggcag 1260
caggggaacg tcttctcatg ctccgtgatg catgaggctc tgcacaacca ctacacgcag 1320
aagagcctct ccctgtctcc gggtaaatga                                  1350
```

<210> SEQ ID NO 167
<211> LENGTH: 651
<212> TYPE: DNA
<213> ORGANISM: Artificial Sequence
<220> FEATURE:
<223> OTHER INFORMATION: Synthetic Construct

<400> SEQUENCE: 167

```
gaaatcgtgt taacgcagtc tccaggcacc ctgtctttgt ctccagggga aagagccacc   60
ctctcttgca gggccagtca gagtgttagc agcagctact tagcctggta ccagcagaaa  120
cctggccagg ctcccaggct cctcatctat ggagcatcca gcagggccac tggcatccca  180
gacaggttca gtggcagtgg atccgggaca gacttcactc tcaccatcag cagactggag  240
cctgaagatt ttgcagtgta ttactgtcag cagtatacca cgaacatta ttatacgttc   300
```

| | |
|---|---|
| ggccagggga ccaaagtgga atcaaacgt acggtggctg caccatctgt cttcatcttc | 360 |
| ccgccatctg atcggaagtt gaaatctgga actgcctctg ttgtgtgcct gctgaataac | 420 |
| ttctatccca gagaggccaa agtacagtgg aaggtggata cgccctcca atcgggtaac | 480 |
| tcccaggaga gtgtcacaga gcaggacagc aaggacagca cctacagcct cagcagcacc | 540 |
| ctgacgctga gcaaagcaga ctacgagaaa cacaaagtct acgcctgcga agtcacccat | 600 |
| cagggcctga gctcgcccgt cacaaagagc ttcaacaggg gagagtgtta g | 651 |

<210> SEQ ID NO 168
<211> LENGTH: 2871
<212> TYPE: DNA
<213> ORGANISM: Artificial Sequence
<220> FEATURE:
<223> OTHER INFORMATION: Synthetic Construct

<400> SEQUENCE: 168

| | |
|---|---|
| caagtgcagc tgaaagagtc cggccctgga ctggtggccc ctagccagag cctgagcatc | 60 |
| acctgtaccg tgtccggctt cagcctgacc agctacggcg tgtcatgggt gcgccagcct | 120 |
| ccaggcaagt gtctggaatg ctgggcatc atctggggcg acggcagcac caattaccac | 180 |
| agcgccctga tcagcagact gagcatctcc aaggacaaca gcaagagcca ggtgttcctg | 240 |
| aagctgaaca gcctgcagac cgacgacacc gccacctact actgcgccaa gggcatcacc | 300 |
| accgtggtgg acgactacta cgctatggac tactggggcc agggcaccag cgtgacagtg | 360 |
| tctagcggag gcggaggatc tggcggcgga ggaagtggcg aggggatc tggggaggc | 420 |
| ggaagcgata tccagatgac ccagagccct gccagcctgt ctgcctctgt gggcgagaca | 480 |
| gtgaccatca catgccgggc cagcgagaac atcgacagct acctggcctg gtatcagcag | 540 |
| aagcagggca gagccccca gctgctggtg tacgccgcca cctttctggc cgacgatgtg | 600 |
| cccagcagat tcagcggcag cggaagcggc acacagtaca gcctgaagat caactccctg | 660 |
| cagagcgagg acgtggcccg gtactactgc cagcactact acagcacccc ctacaccttc | 720 |
| ggctgcggca ccaagctgga aatcaaagga ggcggcggaa gtgtgcacat gccctggc | 780 |
| ttcctgggcc ccagacaggc cagagtcgtg aacggggggg gcggaggcag tggggggga | 840 |
| ggatcccagg ccgtcgtgac ccaggaaccc agcctgacag tgtctcctgg cggcaccgtg | 900 |
| accctgacat gtggcagttc tacaggcgcc gtgaccacca gcaactacgc caactgggtg | 960 |
| caggaaaagc ccggccaggc cttcagagga ctgatcggcg gcaccaacaa gagagcccct | 1020 |
| ggcacccctg ccagattcag cggatctctg ctgggaggaa aggccgccct gacactgtct | 1080 |
| ggcgcccagc cagaagatga ggccgagtac tactgcgccc tgtggtacag caacctgtgg | 1140 |
| gtgttcggcg gaggcaccaa gctgacagtc ctgagcagcg cttccaccaa gggacccagt | 1200 |
| gtgttccccc tggcccccag ctccaagtct acatccggtg gcacagctgc cctgggatgt | 1260 |
| ctcgtgaagg actactttcc tgagcctgtg acagtgtctt ggaacagcgg agccctgacc | 1320 |
| agcggagtgc acacattccc tgcagtgctg cagagcagcg gcctgtatag cctgagcagc | 1380 |
| gtcgtgaccg tgccttcctc tagcctggga acacagacat atatctgtaa tgtgaatcat | 1440 |
| aagcccagta ataccaaagt ggataagaaa gtggaaccta gagctgcga tggcggagga | 1500 |
| gggtccggag gcggagggtc ccaggtgcaa ttggttcaat ctggtgctga agtaaaaaaa | 1560 |
| ccgggcgctt ccgttaaagt gagctgcaaa gcatccggat acaccttcac ttcctattac | 1620 |
| atgcactggg ttcgtcaagc cccgggccag ggtctggaat ggatgggcat cattaaccca | 1680 |
| agcggtggct ctacctccta cgcgcagaaa ttccagggtc gcgtcacgat gacccatgac | 1740 |

```
actagcacct ctaccgttta tatggagctg tccagcctgc gttctgaaga tactgcagtg    1800
tactactgtg cacgctcttt cttcactggt ttccatctgg actattgggg tcaaggcacc    1860
ctcgtaacgg tttcttctgc tagcaccaag ggcccctccg tgttcccct ggccccagc     1920 agcaagagca ccagcggcgg cacagccgct ctgggctgcc tggtcgagga ctacttcccc    1980
gagcccgtga ccgtgtcctg aacagcgga gccctgacct ccggcgtgca ccttcccc       2040 gccgtgctgc agagttctgg cctgtatagc ctgagcagcg tggtcaccgt gccttctagc    2100
agcctgggca cccagaccta catctgcaac gtgaaccaca agcccagcaa caccaaggtg    2160
gacgagaagg tggagcccaa gagctgcgac aaaactcaca catgcccacc gtgcccagca    2220
cctgaagctg caggggggacc gtcagtcttc ctcttccccc caaaacccaa ggacaccctc    2280
atgatctccc ggacccctga ggtcacatgc gtggtggtgg acgtgagcca cgaagaccct    2340
gaggtcaagt tcaactggta cgtggacggc gtggaggtgc ataatgccaa gacaaagccg    2400
cgggaggagc agtacaacag cacgtaccgt gtggtcagcg tcctcaccgt cctgcaccag    2460
gactggctga atggcaagga gtacaagtgc aaggtctcca acaaagccct cggcgccccc    2520
atcgagaaaa ccatctccaa agccaaaggg cagccccgag aaccacaggt gtacaccctg    2580
cccccatgcc gggatgagct gaccaagaac caggtcagcc tgtggtgcct ggtcaaaggc    2640
ttctatccca gcgacatcgc cgtggagtgg gagagcaatg ggcagccgga gaacaactac    2700
aagaccacgc ctcccgtgct ggactccgac ggctccttct tcctctacag caagctcacc    2760
gtggacaaga gcaggtggca gcaggggaac gtcttctcat gctccgtgat gcatgaggct    2820
ctgcacaacc actacacgca gaagagcctc tccctgtctc cgggtaaatg a             2871
```

<210> SEQ ID NO 169
<211> LENGTH: 2857
<212> TYPE: DNA
<213> ORGANISM: Artificial Sequence
<220> FEATURE:
<223> OTHER INFORMATION: Synthetic Construct

<400> SEQUENCE: 169

```
agagtccggc cctggactgg tggcccctag ccagagcctg agcatcacct gtaccgtgtc     60
cggcttcagc ctgaccagct acggcgtgtc atgggtgcgc cagcctccag gcaagtgtct    120
ggaatggctg gcatcatct ggggcgacgg cagcaccaat taccacagcg ccctgatcag    180
cagactgagc atctccaagg acaacagcaa gagccaggtg ttcctgaagc tgaacagcct    240
gcagaccgac gacaccgcca cctactactg cgccaagggc atcaccaccg tggtggacga    300
ctactacgct atggactact ggggccaggg caccagcgtg acagtgtcta gcggaggcgg    360
aggatctggc ggcggaggaa gtggcggagg ggatctggg ggaggcggaa gcgatatcca    420
gatgacccag agccctgcca gcctgtctgc ctctgtgggc gagacagtga ccatcacatg    480
ccgggccagc gagaacatcg acagctacct ggcctggtat cagcagaagc agggcaagag    540 ccccagctg ctggtgtacg ccgccacctt tctggccgac gatgtgccca gcagattcag    600
cggcagcgga agcggcacac agtacagcct gaagatcaac tccctgcaga gcgaggacgt    660
ggcccggtac tactgccagc actactacag caccccctac accttcggct gcggcaccaa    720
gctggaaatc aaaggcgggg gaggctccgg aggcggcgga agtggaggcg gcggaagtgg    780
cggaggcgga gggggggaa gtgggggcgg aggcagtggg gggggaggat cccaggccgt    840
cgtgacccag gaaccagcc tgacagtgtc tcctggcggc accgtgaccc tgacatgtgg    900
```

-continued

```
cagttctaca ggcgccgtga ccaccagcaa ctacgccaac tgggtgcagg aaaagcccgg      960
ccaggccttc agaggactga tcggcggcac caacaagaga gcccctggca cccctgccag     1020
attcagcgga tctctgctgg aggaaaggc cgccctgaca ctgtctggcg cccagccaga     1080
agatgaggcc gagtactact gcgccctgtg gtacagcaac ctgtgggtgt tcggcggagg     1140
caccaagctg acagtgctga gcagcgcttc caccaaggga cccagtgtgt tcccctggc     1200
ccccagctcc aagtctacat ccggtggcac agctgccctg gatgtctcg tgaaggacta     1260
ctttcctgag cctgtgacag tgtcttggaa cagcggagcc ctgaccagcg gagtgcacac     1320
attccctgca gtgctgcaga gcagcggcct gtatagcctg agcagcgtcg tgaccgtgcc     1380
ttcctctagc ctgggaacac agacatatat ctgtaatgtg aatcataagc ccagtaatac     1440
caaagtggat aagaaagtgg aacctaagag ctgcgatggc ggaggagggt ctggaggcgg     1500
agggtcccag gtgcaattgg ttcaatctgg tgctgaagta aaaaaaccgg gcgcttccgt     1560
taaagtgagc tgcaaagcat ccggatacac cttcacttcc tattacatgc actgggttcg     1620
tcaagccccg ggccagggtc tggaatggat gggcatcatt aacccaagcg gtggctctac     1680
ctcctacgcg cagaaattcc agggtcgcgt cacgatgacc catgacacta gcacctctac     1740
cgtttatatg gagctgtcca gcctgcgttc tgaagatact gcagtgtact actgtgcacg     1800
ctctttcttc actggtttcc atctggacta ttggggtcaa ggcaccctcg taacggtttc     1860
ttctgctagc accaagggcc cctccgtgtt ccccctggcc cccagcagca gagcaccag     1920
cggcggcaca gccgctctgg gctgcctggt cgaggactac ttccccgagc ccgtgaccgt     1980
gtcctggaac agcggagccc tgacctccgg cgtgcacacc ttccccgccg tgctgcagag     2040
ttctggcctg tatagcctga gcagcgtggt caccgtgcct tctagcagcc tgggcaccca     2100
gacctacatc tgcaacgtga accacaagcc cagcaacacc aaggtggacg agaaggtgga     2160
gcccaagagc tgcgacaaaa ctcacacatg cccaccgtgc ccagcacctg aagctgcagg     2220
gggaccgtca gtcttcctct tccccccaaa acccaaggac accctcatga tctcccggac     2280
ccctgaggtc acatgcgtgg tggtggacgt gagccacgaa gaccctgagg tcaagttcaa     2340
ctggtacgtg gacggcgtgg aggtgcataa tgccaagaca aagccgcggg aggagcagta     2400
caacagcacg taccgtgtgg tcagcgtcct caccgtcctg caccaggact ggctgaatgg     2460
caaggagtac aagtgcaagg tctccaacaa agccctcggc gcccccatcg agaaaaccat     2520
ctccaaagcc aaagggcagc cccgagaacc acaggtgtac accctgcccc catgccggga     2580
tgagctgacc aagaaccagg tcagcctgtg tgcctggtc aaaggcttct atcccagcga     2640
catcgccgtg gagtgggaga gcaatgggca gccggagaac aactacaaga ccacgcctcc     2700
cgtgctggac tccgacggct ccttcttcct ctacagcaag ctcaccgtgg acaagagcag     2760
gtggcagcag gggaacgtct tctcatgctc cgtgatgcat gaggctctgc acaaccacta     2820
cacgcagaag agcctctccc tgtctccggg taaatga                            2857
```

<210> SEQ ID NO 170
<211> LENGTH: 2025
<212> TYPE: DNA
<213> ORGANISM: Artificial Sequence
<220> FEATURE:
<223> OTHER INFORMATION: Synthetic Construct

<400> SEQUENCE: 170

```
caggccgtcg tgacccagga acccagcctg acagtgtctc ctggcggcac cgtgaccctg       60
acatgtggca gttctacagg cgccgtgacc accagcaact acgccaactg ggtgcaggaa      120
```

```
aagcccggcc aggccttcag aggactgatc ggcggcacca acaagagagc ccctggcacc    180
cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtgctgagc agcgcttcca ccaagggacc cagtgtgttc    360
cccctggccc ccagctccaa gtctacatcc ggtggcacag ctgccctggg atgtctcgtg    420
aaggactact ttcctgagcc tgtgacagtg tcttggaaca gcggagccct gaccagcgga    480
gtgcacacat tccctgcagt gctgcagagc agcggcctgt atagcctgag cagcgtcgtg    540
accgtgcctt cctctagcct gggaacacag acatatatct gtaatgtgaa tcataagccc    600
agtaatacca aagtggataa gaaagtggaa cctaagagct gcgatggcgg aggagggtct    660
ggaggcggag ggtcccaggt gcaattggtt caatctggtg ctgaagtaaa aaaaccgggc    720
gcttccgtta aagtgagctg caaagcatcc ggatacacct tcacttccta ttacatgcac    780
tgggttcgtc aagccccggg ccagggtctg aatggatgg gcatcattaa cccaagcggt     840
ggctctacct cctacgcgca gaaattccag ggtcgcgtca cgatgaccca tgacactagc    900
acctctaccg tttatatgga gctgtccagc ctgcgttctg aagatactgc agtgtactac    960
tgtgcacgct ctttcttcac tggtttccat ctggactatt ggggtcaagg caccctcgta   1020
acggtttctt ctgctagcac caagggcccc tccgtgttcc cctggcccc cagcagcaag    1080
agcaccagcg gcggcacagc cgctctgggc tgcctggtcg aggactactt ccccgagccc   1140
gtgaccgtgt cctggaacag cggagccctg acctccggcg tgcacacctt ccccgccgtg   1200
ctgcagagtt ctggcctgta tagcctgagc agcgtggtca ccgtgccttc tagcagcctg   1260
ggcacccaga cctacatctg caacgtgaac cacaagccca gcaacaccaa ggtggacgag   1320
aaggtggagc ccaagagctg cgacaaaact cacacatgcc caccgtgccc agcacctgaa   1380
gctgcagggg gaccgtcagt cttcctcttc cccccaaaac ccaaggacac cctcatgatc   1440
tcccggaccc ctgaggtcac atgcgtggtg gtggacgtga gccacgaaga ccctgaggtc   1500
aagttcaact ggtacgtgga cggcgtggag gtgcataatg ccaagacaaa gccgcgggag   1560
gagcagtaca acagcacgta ccgtgtggtc agcgtcctca ccgtcctgca ccaggactgg   1620
ctgaatggca aggagtacaa gtgcaaggtc tccaacaaag ccctcggcgc ccccatcgag   1680
aaaaccatct ccaaagccaa agggcagccc cgagaaccac aggtgtacac cctgccccca   1740
tgccgggatg agctgaccaa gaaccaggtc agcctgtggt gcctggtcaa aggcttctat   1800
cccagcgaca tcgccgtgga gtgggagagc aatgggcagc cggagaacaa ctacaagacc   1860
acgcctcccg tgctggactc cgacggctcc ttcttcctct acagcaagct caccgtggac   1920
aagagcaggt ggcagcaggg gaacgtcttc tcatgctccg tgatgcatga ggctctgcac   1980
aaccactaca cgcagaagag cctctccctg tctccgggta aatga                   2025
```

PROTEASE-ACTIVATED T CELL BISPECIFIC MOLECULES

CROSS REFERENCE TO RELATED APPLICATIONS

This application is a continuation of International Patent Application No. PCT/EP2017/056556, filed on Mar. 20, 2017, which claims priority to European Patent Application No. 16161740.2, filed on Mar. 22, 2016, and to U.S. Patent Application No. 62/433,327, filed on Dec. 13, 2016, the disclosures of which are incorporated herein by reference in their entirety.

SEQUENCE LISTING

The instant application contains a Sequence listing which has been submitted electronically in ASCII format and is hereby incorporated by reference in its entirety. Said ASCII copy, created on Jan. 2, 2019, is named 51177-025001_Sequence_Listing_1.2.19_ST25 and is 309,162 bytes in size.

FIELD OF THE INVENTION

The present invention generally relates to novel protease-activatable antigen-binding molecules that comprise an anti-idiotype-binding moiety which reversibly masks antigen binding of the molecule.

Specifically, the invention relates to T cell binding molecules having an anti-idiotype-binding moiety that masks the CD3-binding moiety until cleaved by a protease. This allows the CD3-binding moiety to be inaccessible or "masked" until it is in proximity to a target tissue, such as a tumor, e.g., tumor-infiltrating T cells. In addition, the present invention relates to polynucleotides encoding such protease-activated T cell binding molecules and idiotype-specific polypeptides, and vectors and host cells comprising such polynucleotides. The invention further relates to methods for producing the protease-activated T cell binding molecules of the invention, and to methods of using the same, e.g., in the treatment of disease.

BACKGROUND

The selective destruction of an individual target cell or a specific target cell type is often desirable in a variety of clinical settings. For example, it is a primary goal of cancer therapy to specifically destroy tumor cells, while leaving healthy cells and tissues intact and undamaged. An attractive way of achieving this is by inducing an immune response against the tumor, to make immune effector cells such as natural killer (NK) cells or cytotoxic T lymphocytes (CTLs) attack and destroy tumor cells. In this regard, bispecific antibodies designed to bind with one "arm" to a surface antigen on target cells, and with the second "arm" to an activating, invariant component of the T cell receptor (TCR) complex, have become of interest in recent years. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs.

In this context it is crucial that CTLs are activated only when in close proximity to a target cell, i.e., the immunological synapse is mimicked. Particularly desirable are T cell activating bispecific molecules that do not require lymphocyte preconditioning or co-stimulation in order to elicit efficient lysis of target cells. Several bispecific antibody formats have been developed and their suitability for T cell mediated immunotherapy investigated. These include BiTE (bispecific T cell engager) molecules (Nagorsen and Bäuerle, Exp Cell Res 317, 1255-1260 (2011)), diabodies (Holliger et al., Prot Eng 9, 299-305 (19%)) and derivatives thereof, such as tandem diabodies (Kipriyanov et al., J Mol Biol 293, 41-66 (1999)), DART (dual affinity retargeting) molecules, (Moore et al., Blood 117, 4542-51 (2011)), and triomabs (Seimetz et al., Cancer Treat Rev 36, 458-467 (2010)).

The task of generating bispecific molecules suitable for treatment provides several technical challenges related to efficacy, toxicity, applicability and producibility that have to be met. In instances where the bispecific molecule targets an antigen on a target cell, e.g., a cancer cell, that is also expressed in non-target tissue, toxicity can occur. There is thus a need for efficacious T cell activating bispecific molecules that unleash full T cell activation in the presence of target cells but not in the presence of normal cells or tissue.

SUMMARY OF THE INVENTION

The invention generally relates to T cell activating bispecific molecules that are activated selectively in the presence of a target cell.

In one aspect, the invention relates to a protease-activatable T cell activating bispecific molecule comprising
(a) a first antigen binding moiety capable of specific binding to CD3;
(b) a second antigen binding moiety capable of specific binding to a target cell antigen; and
(c) a masking moiety covalently attached to the T cell bispecific binding molecule through a protease-cleavable linker, wherein the masking moiety is capable of specific binding to the idiotype of the first or the second antigen binding moiety thereby reversibly concealing the first or second antigen binding moiety.

In one embodiment, the masking moiety of the protease-activatable T cell activating bispecific molecule is covalently attached to the first antigen binding moiety. In one embodiment the masking moiety is covalently attached to the heavy chain variable region of the first antigen binding moiety. In one embodiment the masking moiety is covalently attached to the light chain variable region of the first antigen binding moiety. In one embodiment the masking moiety is an anti-idiotype scFv. In one embodiment the protease-activatable T cell activating bispecific molecule comprises a second masking moiety reversibly concealing the second antigen binding moiety.

In one embodiment the protease capable of cleaving the protease-cleavable linker is expressed by the target cell. In one embodiment the second antigen binding moiety is a crossover Fab molecule wherein either the variable or the constant regions of the Fab light chain and the Fab heavy chain are exchanged. In one embodiment the second antigen binding moiety is a crossover Fab molecule wherein the constant regions of the Fab light chain and the Fab heavy chain are exchanged. In one embodiment the first antigen binding moiety is a conventional Fab molecule. In one embodiment the protease-activatable T cell activating bispecific molecule comprises not more than one antigen binding moiety capable of specific binding to CD3. In one embodiment the protease-activatable T cell activating bispecific molecule comprises a third antigen binding moiety which is a Fab molecule capable of specific binding to a target cell antigen. In one particular embodiment the third antigen binding moiety is identical to the second antigen binding moiety. In one particular embodiment the third antigen binding moiety is not identical to the second antigen binding moiety. In one embodiment the second antigen binding moiety is capable of specific binding to FolR1 or HER1. In one embodiment the second antigen binding moiety is capable of specific binding to FolR1, HER1 or Mesothelin. In one embodiment the second antigen binding moiety is capable of specific binding to FolR1, HER1, HER2 or Mesothelin.

In one embodiment the first and the second antigen binding moiety are fused to each other, optionally via a peptide linker. In one particular embodiment the second antigen binding moiety is fused at the C-terminus of the Fab heavy chain to the N-terminus of the Fab heavy chain of the first antigen binding moiety. In one particular embodiment the first antigen binding moiety is fused at the C-terminus of the Fab heavy chain to the N-terminus of the Fab heavy chain of the second antigen binding moiety. In one particular embodiment the Fab light chain of the first antigen binding moiety and the Fab light chain of the second antigen binding moiety are fused to each other, optionally via a peptide linker.

In one embodiment the protease-activatable T cell activating bispecific molecule additionally comprises an Fc domain composed of a first and a second subunit capable of stable association. In one embodiment the Fc domain is an IgG, specifically an IgG$_1$ or IgG$_4$, Fc domain. In one embodiment the Fc domain is a human Fc domain. In one embodiment the Fc domain exhibits reduced binding affinity to an Fc receptor and/or reduced effector function, as compared to a native IgG$_1$ Fc domain. In one embodiment the Fc domain comprises one or more amino acid substitution that reduces binding to an Fc receptor and/or effector function. In one particular embodiment the one or more amino acid substitution is at one or more position selected from the group of L234, L235, and P329 (Kabat numbering). In one particular embodiment each subunit of the Fc domain comprises three amino acid substitutions that reduce binding to an activating Fc receptor and/or effector function wherein said amino acid substitutions are L234A, L235A and P329G. In one particular embodiment the Fc receptor is an Fcγ receptor. In one embodiment the effector function is antibody-dependent cell-mediated cytotoxicity (ADCC). In one embodiment, the target cell is a human cell.

In one embodiment the masking moiety comprises a heavy chain variable region comprising at least one of:
(a) a heavy chain complementarity determining region (CDR H) 1 amino acid sequence of DYSIH (SEQ ID NO:20);
(b) a CDR H2 amino acid sequence of WINTETGEPAY-ADDFKG (SEQ ID NO:21); and
(c) a CDR H3 amino acid sequence of PYDYDVLDY (SEQ ID NO:22).

In one embodiment the masking moiety comprises a light chain variable region comprising at least one of:
(a) a light chain (CDR L)1 amino acid sequence of RASKSVSTSNYSYIH (SEQ ID NO:23);
(b) a CDR L2 amino acid sequence of YVSYLES (SEQ ID NO:24); and
(c) a CDR L3 amino acid sequence of QHSREFPWT (SEQ ID NO:25).

In one embodiment the masking moiety comprises a heavy chain variable region comprising:
(a) a heavy chain complementarity determining region (CDR H) 1 amino acid sequence of DYSIH (SEQ ID NO:20);
(b) a CDR H2 amino acid sequence of WINTETGEPAY-ADDFKG (SEQ ID NO:21);
(c) a CDR H3 amino acid sequence of PYDYDVLDY (SEQ ID NO:22); and a light chain variable region comprising:
(d) a light chain (CDR L)1 amino acid sequence of RASKSVSTSNYSYIH (SEQ ID NO:23);
(e) a CDR L2 amino acid sequence of YVSYLES (SEQ ID NO:24); and
(f) a CDR L3 amino acid sequence of QHSREFPWT (SEQ ID NO:25).

In one embodiment the masking moiety comprises a heavy chain variable region comprising at least one of:
(a) a heavy chain complementarity determining region (CDR H) 1 amino acid sequence of SYGVS (SEQ ID NO:26);
(b) a CDR H2 amino acid sequence of IIWGDGSTNYH-SALIS (SEQ ID NO:27); and
(c) a CDR H3 amino acid sequence of GITIVVD-DYYAMDY (SEQ ID NO:28).

In one embodiment the masking moiety comprises a light chain variable region comprising at least one of:
(a) a light chain (CDR L)1 amino acid sequence of RASENIDSYLA (SEQ ID NO:29);
(b) a CDR L2 amino acid sequence of AATFLAD (SEQ ID NO:30); and
(c) a CDR L3 amino acid sequence of QHYYSTPYT (SEQ ID NO:31).

In one embodiment the masking moiety comprises a heavy chain variable region comprising:
(a) a heavy chain complementarity determining region (CDR H) 1 amino acid sequence of SYGVS (SEQ ID NO:26);
(b) a CDR H2 amino acid sequence of IWGDGSTNYH-SALIS (SEQ ID NO:27);
(c) a CDR H3 amino acid sequence of GTITVVD-DYYAMDY (SEQ ID NO:28); and a light chain variable region comprising:
(d) a light chain (CDR L)1 amino acid sequence of RASENIDSYLA (SEQ ID NO:29);
(e) a CDR L2 amino acid sequence of AATFLAD (SEQ ID NO:30); and
(f) a CDR L3 amino acid sequence of QHYYSTPYT (SEQ ID NO:31).

In one embodiment the protease cleavable linker comprises at least one protease recognition sequence. In one embodiment the protease cleavable linker comprises a protease recognition sequence. In one embodiment the protease recognition sequence is selected from the group consisting of:

```
                                          (SEQ ID NO: 36)
    (a) RQARVVNG;

(SEQ ID NO: 37)
    (b) VHMPLGFLGPGRSRGSFP;

(SEQ ID NO: 38)
    (c) RQARVVNGXXXXXVPLSLYSG;
    and
```

-continued

```
                                          (SEQ ID NO: 39)
(d) RQARVVNGVPLSLYSG (SEQ ID NO: 40)
(e) PLGLWSQ, wherein X is any amino acid.
```

In one embodiment the protease cleavable linker comprises a protease recognition sequence. In one embodiment the protease recognition sequence is selected from the group consisting of:

```
                                          (SEQ ID NO: 36)
(a) RQARVVNG;

(SEQ ID NO: 37)
(b) VHMPLGFLGPGRSRGSFP;

(SEQ ID NO: 38)
(c) RQARVVNGXXXXXVPLSLYSG;

(SEQ ID NO: 39)
(d) RQARVVNGVPLSLYSG;

(SEQ ID NO: 40)
(e) PLGLWSQ;

(SEQ ID NO: 97)
(f) VHMPLGFLGPRQARVVNG;

(SEQ ID NO: 98)
(g) FVGGTG;

(SEQ ID NO: 99)
(h) KKAAPVNG;

(SEQ ID NO: 100)
(i) PMAKKVNG;

(SEQ ID NO: 101)
(j) QARAKVNG;

(SEQ ID NO: 102)
(k) VHMPLGFLGP;

(SEQ ID NO: 103)
(l) QARAK;

(SEQ ID NO: 104)
(m) VHMPLGFLGPPMAKK;

(SEQ ID NO: 105)
(n) KKAAP;
and (SEQ ID NO: 106)
(o) PMAKK, wherein X is any amino acid.
```

In one embodiment the protease capable of cleaving the protease-cleavable linker is selected from the group consisting of metalloproteinase, e.g., matrix metalloproteinase (MMP) 1-28 and A Disintegrin And Metalloproteinase (ADAM) 2, 7-12, 15, 17-23, 28-30 and 33, serine protease, e.g., urokinase-type plasminogen activator and Matriptase, cysteine protease, aspartic protease, and cathepsin protease. In one specific embodiment the protease is MMP9 or MMP2. In a further specific embodiment, the protease is Matriptase. In one embodiment the protease cleavable linker comprises the protease recognition sequence RQARVVNG (SEQ ID NO:36).

In one embodiment of the protease-activatable T cell activating bispecific molecule described herein the first antigen binding moiety comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO: 44, SEQ ID NO: 45 and SEQ ID NO: 46 and at least one light chain CDR selected from the group of SEQ ID NO: 17. SEQ ID NO: 18 and SEQ ID NO: 19.

In one embodiment of the protease-activatable T cell activating bispecific molecule described herein the first antigen binding moiety comprises the heavy chain complementarity determining region (CDRs) of SEQ ID NO: 44, SEQ ID NO: 45 and SEQ ID NO: 46 and the light chain CDRs of SEQ ID NO: 17, SEQ ID NO: 18 and SEQ ID NO: 19.

In one embodiment of the protease-activatable T cell activating bispecific molecule described herein the first antigen binding moiety comprises a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55.

In one embodiment of the protease-activatable T cell activating bispecific molecule described herein the first antigen binding moiety comprises a heavy chain variable region comprising the amino acid sequence of SEQ ID NO: 43 and a light chain variable region comprising the amino acid sequence of SEQ ID NO: 55.

In one embodiment of the protease-activatable T cell activating bispecific molecule described herein the second antigen binding moiety is capable of specific binding to FolR1 and comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO: 14, SEQ ID NO: 15 and SEQ ID NO: 16 and at least one light chain CDR comprising an amino acid sequence that is at least about 95%, 96%, 97%, 98%, 99% or 100% identical to an amino acid sequence selected from the group consisting of SEQ ID NO: 17, SEQ ID NO: 18 and SEQ ID NO: 19.

In one embodiment of the protease-activatable T cell activating bispecific molecule described herein the second antigen binding moiety is capable of specific binding to FolR1 and comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO: 151, SEQ ID NO: 152 and SEQ ID NO: 153 and at least one light chain CDR comprising an amino acid sequence that is at least about 95%. 96%, 97%, 98%, 99% or 100% identical to an amino acid sequence selected from the group consisting of SEQ ID NO: 154, SEQ ID NO: 155 and SEQ ID NO: 156.

In one embodiment of the protease-activatable T cell activating bispecific molecule described herein the second antigen binding moiety is capable of specific binding to FolR1 and comprises at least one heavy chain complementarity determining region (CDR) comprising an amino acid sequence selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In one embodiment of the protease-activatable T cell activating bispecific molecule described herein the second antigen binding moiety is capable of specific binding to FolR1 and comprises at least one heavy chain complementarity determining region (CDR) comprising an amino acid sequence selected from the group consisting of SEQ ID NO: 151, SEQ ID NO: 152 and SEQ ID NO: 153 and at least one light chain CDR selected from the group of SEQ ID NO: 154, SEQ ID NO: 155 and SEQ ID NO: 156.

In one embodiment of the protease-activatable T cell activating bispecific molecule described herein the second antigen binding moiety comprises a heavy chain variable region comprising an amino acid sequence that is at least about 95%. 96%, 97%, 98%, 99% or 100% identical to the amino acid sequence of SEQ ID NO: 47 and a light chain variable region comprising an amino acid sequence that is at least about 95%, 96%, 97%, 98%, 99% or 100% identical to the amino acid sequence of SEQ ID NO: 55.

In one embodiment of the protease-activatable T cell activating bispecific molecule described herein the second antigen binding moiety comprises a heavy chain variable region comprising an amino acid sequence that is at least about 95%, 96%, 97%, 98%, 99% or 100% identical to the amino acid sequence of SEQ ID NO: 157 and a light chain variable region comprising an amino acid sequence that is at least about 95%, 96%, 97%, 98%, 99% or 100% identical to the amino acid sequence of SEQ ID NO: 158.

In one embodiment of the protease-activatable T cell activating bispecific molecule described herein the second antigen binding moiety comprises a heavy chain variable region comprising the amino acid sequence of SEQ ID NO: 47 and a light chain variable region comprising the amino acid sequence of SEQ ID NO: 55.

In one embodiment of the protease-activatable T cell activating bispecific molecule described herein the second antigen binding moiety comprises a heavy chain variable region comprising the amino acid sequence of SEQ ID NO: 157 and a light chain variable region comprising the amino acid sequence of SEQ ID NO: 158.

In one embodiment of the protease-activatable T cell activating bispecific molecule described herein the second antigen binding moiety is capable of specific binding to Mesothelin and comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO: 107, SEQ ID NO: 108 and SEQ ID NO: 109 and at least one light chain CDR comprising an amino acid sequence that is at least about 95%, 96%, 97%, 98%, 99% or 100% identical to an amino acid sequence selected from the group consisting of SEQ ID NO: 110, SEQ ID NO: 111 and SEQ ID NO: 112.

In one embodiment of the protease-activatable T cell activating bispecific molecule described herein the second antigen binding moiety is capable of specific binding to Mesothelin and comprises at least one heavy chain complementarity determining region (CDR) comprising an amino acid sequence selected from the group consisting of SEQ ID NO: 107, SEQ ID NO: 108 and SEQ ID NO: 109 and at least one light chain CDR selected from the group of SEQ ID NO: 110, SEQ ID NO: 111 and SEQ ID NO: 112.

In one embodiment of the protease-activatable T cell activating bispecific molecule described herein the second antigen binding moiety comprises a heavy chain variable region comprising an amino acid sequence that is at least about 95%, 96%. 97%, 98%, 99% or 100% identical to the amino acid sequence of SEQ ID NO: 113 and a light chain variable region comprising an amino acid sequence that is at least about 95%, 96%, 97%, 98%, 99% or 100% identical to the amino acid sequence of SEQ ID NO: 114.

In one embodiment of the protease-activatable T cell activating bispecific molecule described herein the second antigen binding moiety comprises a heavy chain variable region comprising the amino acid sequence of SEQ ID NO: 113 and a light chain variable region comprising the amino acid sequence of SEQ ID NO: 114.

In one embodiment of the protease-activatable T cell activating bispecific molecule described herein the second antigen binding moiety is capable of specific binding to HER1 and comprises at least one heavy chain complementarity determining region (CDR) of any one of the antibodies disclosed in WO/2006/082515 incorporated herein by reference in its entirety.

In one embodiment of the protease-activatable T cell activating bispecific molecule described herein the second antigen binding moiety is capable of specific binding to HER1 and comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO: 56, SEQ ID NO: 57 and SEQ ID NO: 58 and at least one light chain CDR comprising an amino acid sequence that is at least about 95%. %%, 97%, 98%, 99% or 100% identical to an amino acid sequence selected from the group consisting of SEQ ID NO: 59, SEQ ID NO: 60 and SEQ ID NO: 61.

In one embodiment of the protease-activatable T cell activating bispecific molecule described herein the second antigen binding moiety is capable of specific binding to HER1 and comprises at least one heavy chain complementarity determining region (CDR) selected from the group consisting of SEQ ID NO: 56. SEQ ID NO: 57 and SEQ ID NO: 58 and at least one light chain CDR selected from the group of SEQ ID NO: 59, SEQ ID NO: 60 and SEQ ID NO: 61.

In one embodiment of the protease-activatable T cell activating bispecific molecule described herein the second antigen binding moiety comprises a heavy chain comprising an amino acid sequence that is at least about 95%, %%, 97%, 98%, 99% or 100% identical to the amino acid sequence of SEQ ID NO: 32 and a light chain comprising an amino acid sequence that is at least about 95%, %%, 97%, 98%, 99% or 100% identical to the amino acid sequence of SEQ ID NO: 33. In one embodiment of the protease-activatable T cell activating bispecific molecule described herein the second antigen binding moiety comprises a heavy chain comprising the amino acid sequence of SEQ ID NO: 32 and a light chain comprising the amino acid sequence of SEQ ID NO: 33.

In one embodiment, the first antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, and the second and third antigen binding moieties are capable of specific binding to HER2, wherein the second antigen binding moiety comprises a heavy chain variable region comprising an amino acid sequence that is at least about 95%, 96%, 97%, 98%, 99% or 100% identical to the amino acid sequence of SEQ ID NO: 160 and a light chain variable region comprising an amino acid sequence that is at least about 95%, 96%, 97%, 98%, 99% or 100% identical to the amino acid sequence of SEQ ID NO: 161, wherein the third antigen binding moiety comprises a heavy chain variable region comprising an amino acid sequence that is at least about 95%, 96%, 97%, 98%, 99% or 100% identical to the amino acid sequence of SEQ ID NO: 159 and a light chain variable region comprising an amino acid sequence that is at least about 95%, 96%, 97%, 98%, 99% or 100% identical to the amino acid sequence of SEQ ID NO: 161.

In one particular embodiment the protease-activatable T cell activating bispecific molecule described herein comprises
  (a) a rust heavy chain comprising the amino acid sequence of SEQ ID NO:2;
  (b) a second heavy chain comprising the amino acid sequence of SEQ ID NO:3; and
  (c) a light chain comprising the amino acid sequence of SEQ ID NO:1.

In one particular embodiment the protease-activatable T cell activating bispecific molecule described herein comprises
  (a) a first heavy chain comprising the amino acid sequence of SEQ ID NO:4;
  (b) a second heavy chain comprising the amino acid sequence of SEQ ID NO:3; and
  (c) a light chain comprising the amino acid sequence of SEQ ID NO:1.

In one particular embodiment the protease-activatable T cell activating bispecific molecule described herein comprises
  (a) at least one heavy chain comprising the amino acid sequence of SEQ ID NO:32;
  (b) at least one light chain comprising the amino acid sequence of SEQ ID NO:34.

In one particular embodiment the protease-activatable T cell activating bispecific molecule described herein comprises
  (a) a first heavy chain comprising the amino acid sequence of SEQ ID NO:72;
  (b) a second heavy chain comprising the amino acid sequence of SEQ ID NO:3; and
  (c) a light chain comprising an amino acid sequence of SEQ ID NO:1.

In one particular embodiment the protease-activatable T cell activating bispecific molecule described herein comprises
  (a) a first heavy chain comprising the amino acid sequence of SEQ ID NO:85;
  (b) a second heavy chain comprising the amino acid sequence of SEQ ID NO:3; and
  (c) a light chain comprising an amino acid sequence of SEQ ID NO:1.

In one particular embodiment the protease-activatable T cell activating bispecific molecule described herein comprises
  (a) a first heavy chain comprising the amino acid sequence of SEQ ID NO:73;
  (b) a second heavy chain comprising the amino acid sequence of SEQ ID NO:3;
  (c) a first light chain comprising an amino acid sequence of SEQ ID NO:1; and
  (d) a second light chain comprising an amino acid sequence of SEQ ID NO: 74.

In one particular embodiment the protease-activatable T cell activating bispecific molecule described herein comprises
  (a) a first heavy chain comprising the amino acid sequence of SEQ ID NO:77;
  (b) a second heavy chain comprising the amino acid sequence of SEQ ID NO:82;
  (c) a first light chain comprising an amino acid sequence of SEQ ID NO:78; and
  (d) a second light chain comprising an amino acid sequence of SEQ ID NO:81.

In one particular embodiment the protease-activatable T cell activating bispecific molecule described herein comprises
  (a) a first heavy chain comprising the amino acid sequence of SEQ ID NO:76;
  (b) a second heavy chain comprising the amino acid sequence of SEQ ID NO:77;
  (c) a first light chain comprising an amino acid sequence of SEQ ID NO:78; and
  (d) a second light chain comprising an amino acid sequence of SEQ ID NO:79.

In one particular embodiment the protease-activatable T cell activating bispecific molecule described herein comprises
  (a) a first heavy chain comprising the amino acid sequence of SEQ ID NO:132;
  (b) a second heavy chain comprising the amino acid sequence of SEQ ID NO:136;
  (c) a first light chain comprising an amino acid sequence of SEQ ID NO:81; and
  (d) a second light chain comprising an amino acid sequence of SEQ ID NO:133.

In one particular embodiment the protease-activatable T cell activating bispecific molecule described herein comprises
  (a) a first heavy chain comprising the amino acid sequence of SEQ ID NO:137;
  (b) a second heavy chain comprising the amino acid sequence of SEQ ID NO:139;
  (c) a first light chain comprising an amino acid sequence of SEQ ID NO:81; and
  (d) a second light chain comprising an amino acid sequence of SEQ ID NO:138.

In one aspect, the invention relates to an idiotype-specific polypeptide for reversibly concealing an anti-CD3 antigen binding site of a molecule. In one embodiment the idiotype-specific polypeptide is an anti-idiotype scFv. In one embodiment the idiotype-specific polypeptide is covalently attached to the molecule through a linker. In one embodiment the linker is a peptide linker. In one embodiment the linker is a protease-cleavable linker. In one embodiment the peptide linker comprises at least one protease recognition site. In one embodiment the protease is selected from the group consisting of metalloproteinase, e.g., matrix metalloproteinase (MMP) 1-28 and A Disintegrin And Metalloproteinase (ADAM) 2, 7-12, 15, 17-23, 28-30 and 33, serine protease, e.g., urokinase-type plasminogen activator and Matriptase, cysteine protease, aspartic protease, and cathepsin protease. In one specific embodiment the protease is MMP9 or MMP2. In a further specific embodiment, the protease is Matriptase. In one embodiment the idiotype-specific polypeptide is covalently attached to the molecule through more than one linker. In one embodiment the idiotype-specific polypeptide is covalently attached to the molecule through two linkers.

In one embodiment the molecule which comprises the anti-CD3 antigen binding site is a T-cell activating bispecific molecule. In one particular embodiment the idiotype-specific polypeptide comprises a heavy chain variable region comprising at least one of:

(a) a heavy chain complementarity determining region (CDR H) 1 amino acid sequence of DYSIH (SEQ ID NO:20);
(b) a CDR H2 amino acid sequence of WINTETGEPAY-ADDFKG (SEQ ID NO:21); and
(c) a CDR H3 amino acid sequence of PYDYDVLDY (SEQ ID NO:22).

In one particular embodiment the idiotype-specific polypeptide comprises a light chain variable region comprising at least one of:
(a) a light chain (CDR L)1 amino acid sequence of RASKSVSTSNYSYIH (SEQ ID NO:23);
(b) a CDR L2 amino acid sequence of YVSYLES (SEQ ID NO:24); and
(c) a CDR L3 amino acid sequence of QHSREFPWT (SEQ ID NO:25).

In one particular embodiment the idiotype-specific polypeptide comprises:
(a) a heavy chain complementarity determining region (CDR H) 1 amino acid sequence of DYSIH (SEQ ID NO:20);
(b) a CDR H2 amino acid sequence of WINTETGEPAY-ADDFKG (SEQ ID NO:21);
(c) a CDR H3 amino acid sequence of PYDYDVLDY (SEQ ID NO:22); and a light chain variable region comprising:
(d) a light chain (CDR L)1 amino acid sequence of RASKSVSTSNYSYIH (SEQ ID NO:23);
(e) a CDR L2 amino acid sequence of YVSYLES (SEQ ID NO:24); and
(f) a CDR L3 amino acid sequence of QHSREFPWT (SEQ ID NO:25).

In one particular embodiment the idiotype-specific polypeptide comprises a heavy chain variable region comprising at least one of:
(a) a heavy chain complementarity determining region (CDR H) 1 amino acid sequence of SYGVS (SEQ ID NO:26);
(b) a CDR H2 amino acid sequence of IWGDGSTNYH-SALIS (SEQ ID NO:27); and
(c) a CDR H3 amino acid sequence of GITVVD-DYYAMDY (SEQ ID NO:28).

In one particular embodiment the idiotype-specific polypeptide comprises a light chain variable region comprising at least one of:
(a) a light chain (CDR L)1 amino acid sequence of RASENIDSYLA (SEQ ID NO:29);
(b) a CDR L2 amino acid sequence of AATFLAD (SEQ ID NO:30); and
(c) a CDR L3 amino acid sequence of QHYYSTPYT (SEQ ID NO:31).

In one particular embodiment the idiotype-specific polypeptide comprises a heavy chain variable region comprising:
(a) a heavy chain complementarity determining region (CDR H) 1 amino acid sequence of SYGVS (SEQ ID NO:26);
(b) a CDR H2 amino acid sequence of IWGDGSTNYH-SALIS (SEQ ID NO:27);
(c) a CDR H3 amino acid sequence of GITVVD-DYYAMDY (SEQ ID NO:28); and a light chain variable region comprising:
(d) a light chain (CDR L)1 amino acid sequence of RASENIDSYLA (SEQ ID NO:29);
(e) a CDR L2 amino acid sequence of AATFLAD (SEQ ID NO:30); and
(f) a CDR L3 amino acid sequence of QHYYSTPYT (SEQ ID NO:31).

According to another aspect of the invention, an isolated polynucleotide encoding a protease-activatable T cell activating bispecific molecule of the invention or a fragment thereof is provided.

The invention also encompasses polypeptides encoded by the polynucleotides of the invention. The invention further provides an expression vector comprising the isolated polynucleotide of the invention, and a host cell comprising the isolated polynucleotide or the expression vector of the invention. In some embodiments the host cell is a eukaryotic cell, particularly a mammalian cell.

In another aspect is provided a method of producing the protease-activated T cell molecule of the invention, comprising the steps of a) culturing the host cell of the invention under conditions suitable for the expression of the protease-activated T cell molecule and b) recovering the protease-activated T cell molecule. The invention also encompasses a protease-activated T cell molecule produced by the method of the invention.

In another aspect is provided a method of producing the idiotype-specific polypeptide of the invention, comprising the steps of a) culturing the host cell of the invention under conditions suitable for the expression of the protease-activated T cell molecule and b) recovering the idiotype-specific polypeptide. The invention also encompasses a idiotype-specific polypeptide produced by the method of the invention.

The invention further provides a pharmaceutical composition comprising the protease-activatable T cell activating bispecific molecule of the invention and a pharmaceutically acceptable carrier.

Also encompassed by the invention are methods of using the protease-activated T cell molecule and pharmaceutical composition of the invention. In one aspect the invention provides a protease-activated T cell molecule or a pharmaceutical composition of the invention for use as a medicament. In one aspect is provided a protease-activated T cell molecule or a pharmaceutical composition according to the invention for use in the treatment of a disease in an individual in need thereof. In a specific embodiment the disease is cancer.

Also provided is the use of a protease-activated T cell molecule of the invention for the manufacture of a medicament for the treatment of a disease in an individual in need thereof; as well as a method of treating a disease in an individual, comprising administering to said individual a therapeutically effective amount of a composition comprising the protease-activated T cell molecule according to the invention in a pharmaceutically acceptable form. In a specific embodiment the disease is cancer. In any of the above embodiments the individual preferably is a mammal, particularly a human.

The invention also provides a method for inducing lysis of a target cell, particularly a tumor cell, comprising contacting a target cell with a protease-activated T cell molecule of the invention in the presence of a T cell, particularly a cytotoxic T cell.

In another aspect the invention also provides a composition comprising a protease-activatable T cell activating bispecific molecule described herein and a pharmaceutically acceptable carrier.

In another aspect the invention also provides a composition comprising an idiotype-specific polypeptide as described herein and a pharmaceutically acceptable carrier.

In another aspect the invention also provides a protease-activatable T cell activating bispecific molecule or an idiotype-specific polypeptide as described herein, or the composition described herein, for use as a medicament. In one embodiment the medicament is for treating or delaying progression of cancer, treating or delaying progression of an immune related disease, and/or enhancing or stimulating an immune response or function in an individual.

In another aspect the invention also provides a protease-activatable T cell activating bispecific molecule or idiotype-specific polypeptide as described herein for use in the treatment of a disease in an individual in need thereof. In one embodiment, the disease is a proliferative disorder, particularly cancer.

In another aspect the invention also provides a method of treating a disease in an individual, comprising administering to said individual a therapeutically effective amount of a composition comprising the protease-activatable T cell activating bispecific molecule or composition as described herein.

In another aspect the invention also provides a method for inducing lysis of a target cell, comprising contacting a target cell with the protease-activatable T cell activating bispecific molecule or composition as described herein in the presence of a T cell. In one embodiment the method for inducing lysis of a target cell is an in vitro method. In one embodiment the target cell is a cancer cell. In one embodiment the target cell expresses a protease capable of activating the protease-activatable T cell activating bispecific molecule.

In another aspect the invention also provides an anti-idiotype CD3 antibody or antigen-binding fragment thereof specific for an idiotype of an anti-CD3 antigen-binding molecule, wherein the anti-idiotype CD3 antibody or fragment thereof when bound to the anti-CD3 antigen-binding molecule specifically blocks binding of the anti-CD3 antigen-binding molecule to CD3.

In one embodiment, the anti-idiotype CD3 antibody or antigen-binding fragment thereof is reversibly associated with the anti-CD3 antigen-binding molecule through a peptide linker comprising a protease recognition site. In one embodiment, the CD3 is a mouse, monkey or human CD3.

In another aspect the invention provides a method of reducing in vivo toxicity of a T cell activating bispecific molecule comprising attaching an idiotype-specific polypeptide as described herein to the T cell activating bispecific molecule with a protease-cleavable linker to form a protease-activatable T cell activating bispecific molecule, wherein the protease-activatable T cell activating bispecific molecule has reduced in vivo toxicity compared to the T cell activating bispecific molecule.

SHORT DESCRIPTION OF THE FIGURES

FIGS. 1A-1E depict schematics of different CD3 binders with masking moieties. FIG. 1A: 7859 anti-ID CH2527 scFv 4.15.64 MK062 Matriptase site CD3 Fc. FIG. 1B: 7860 anti-ID CH2527 scFv 4.32.63 MK062 Matriptase site CD3 Fc. FIG. 1C: 7857 anti-ID CH2527 scFv 4.15.64 non-cleavable linker CD3 Fc. FIG. 1D: ID 7858 anti-ID CH2527 scFv 4.32.63 non-cleavable linker CD3 Fc. FIG. 1E: 7861 monovalent CD3 Fc.

FIG. 2 shows a table summarizing the affinities of the anti-idiotypic masking moieties to the CD3 binder (CH2527).

FIGS. 3A-3D shows Capillary Electrophoresis-SDS analysis of the molecules depicted in FIGS. 1A and 1B. FIGS. 3A and 3B: Capillary Electrophoresis-SDS analysis of the molecule depicted in FIG. 1A under non reducing (FIG. 3A) and reducing conditions (FIG. 3B). Comparison of the untreated (I) and treated molecule (III) shows complete cleavage of the anti-ID scFv after rhMatriptase/ST14 treatment for 48 h at 37° C. One sample (H) was untreated but incubated at 37° C. for 48 h. FIGS. 3C and 3D: Capillary Electrophoresis-SDS analysis of the molecule depicted in FIG. 1B under non-reducing (FIG. 3C) and reducing conditions (FIG. 3D). Comparison of the untreated (I) and treated molecule (III) shows complete cleavage of the anti-ID scFv after rhMatriptase/ST14 treatment for 48 h at 37° C. One sample (II) was untreated but incubated at 37° C. for 48 h.

FIGS. 4A-4C show the effect of anti-idiotypic masking of CD3 binding. FIGS. 4A and 4B depict results of Jurkat NFAT reporter assays to show the masking effect of anti-idiotypic CD3 scFv 4.15.64 (FIG. 4A) or anti-idiotypic CD3 scFv 4.32.63 (FIG. 4B). Monovalent CD3 IgGs were cross-linked via an anti-human Fc antibody (coated on assay plate) before Jurkat NFAT (acute lymphatic leukemia reporter cell line with a NFAT promoter, expressing human CD3ε) were added. The Jurkat-NFAT reporter cell line (Promega) is a human acute lymphatic leukemia reporter cell line with a NFAT promoter, expressing human CD3ε. If CD3 binder binds CD3ε Luciferase is expressed and this can be measured in Luminescence after addition of One-Glo substrate (Promega). FIG. 4C shows a comparison of EC50 values of CD3ε binding for masked and unmasked monovalent CD3 binder.

FIGS. 5A-5H depict schematics of different T cell bispecific molecules with masking moieties. FIG. 5A: 7344 anti-ID CH2527 scFv 4.15.64 MK062 Matriptase site CD3 16D5 Fc. FIG. 5B: 7676 anti-ID CH2527 scFv 4.15.64 non-cleavable linker CD3 16D5 Fc. FIG. 5C: 7496 anti-ID CH2527 scFv 4.32.63 MK062 Matriptase site CD3 16D5 Fc. FIG. 5D: 7611 anti-ID CH2527 scFv 4.32.63 non-cleavable linker CD3 16D5 Fc. FIG. 5E: 6298 GA916-D-16D5-02 sf W(1). FolR1 16D5 classic 2+1 TCB with common light chain. FIG. 5F: 6100 GA916-D-16D5 sf W(3a). FolR1 16D5 inverted 2+1 TCB with common light chain. FIG. 5G: ID 6182 DP47GS TCB sf CHO W(9a). DP47 inverted 2+1 TCB. FIG. 5H: 7494 anti-ID CH2527 Fab 4.15.64 MK062 Matriptase site CD3 16D5 Fc.

Figure 5A:
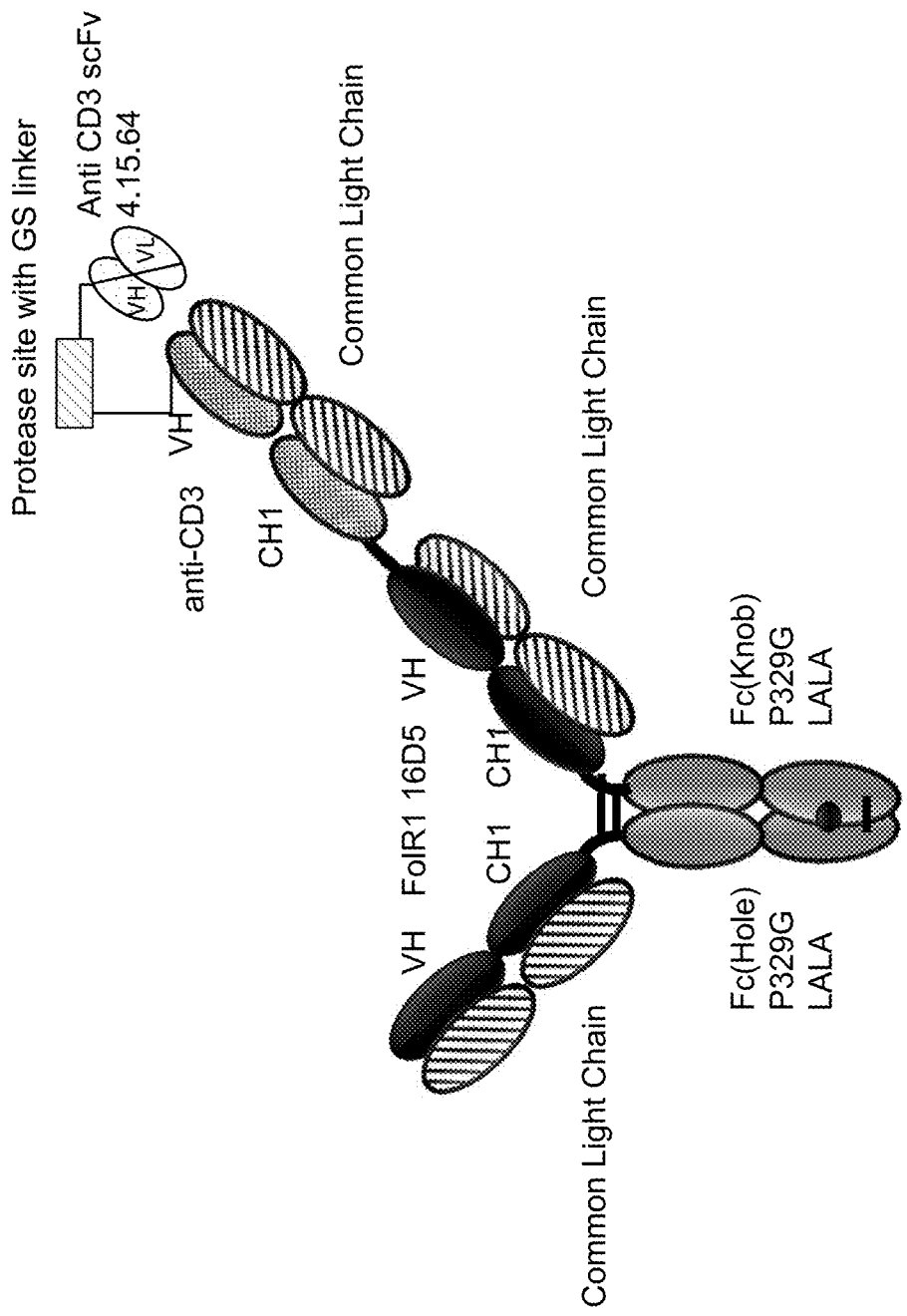
Figure 5B:
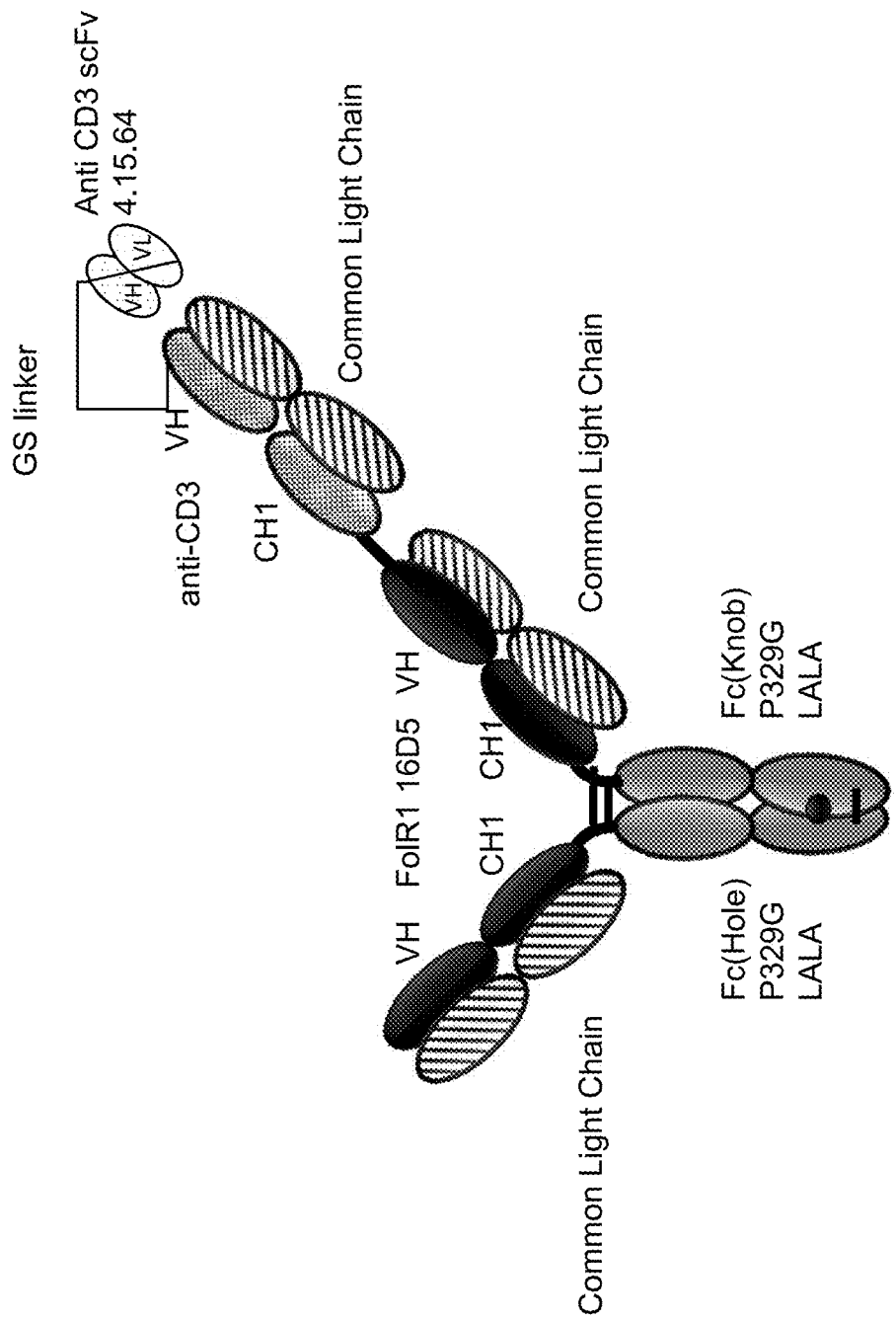
Figure 5C:
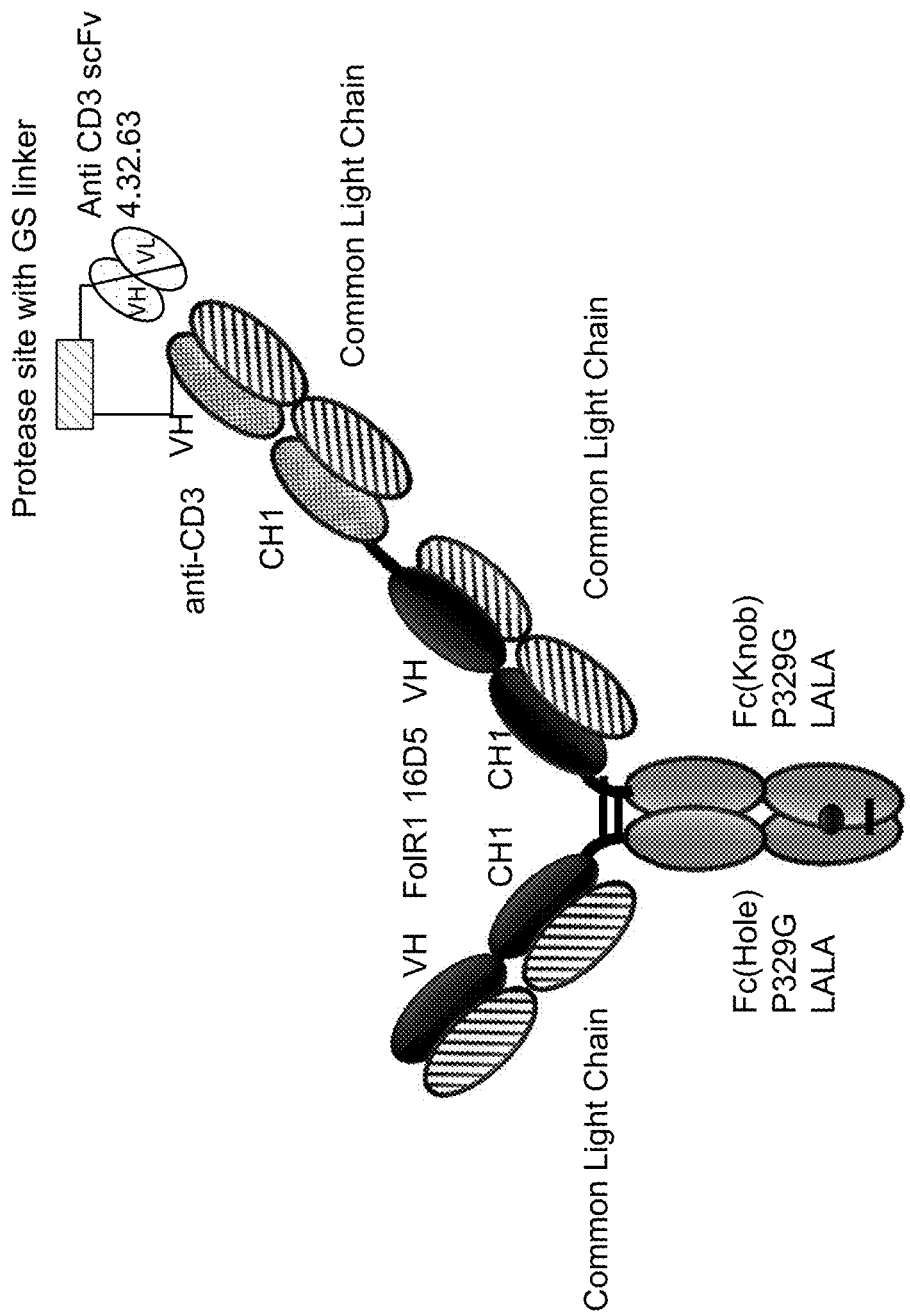
Figure 12A:
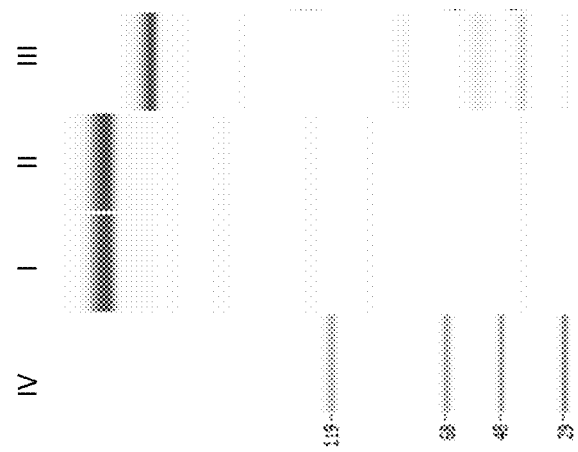
Figure 12B:
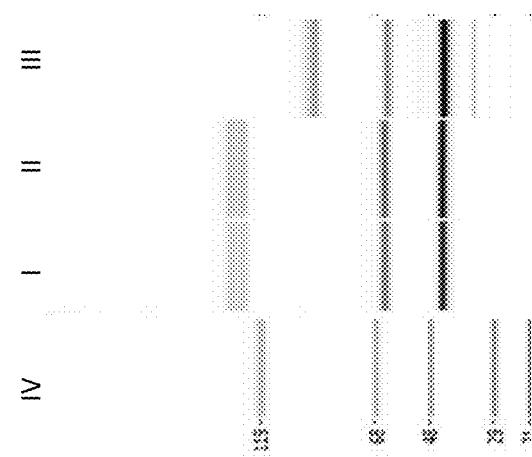
Figure 12C:
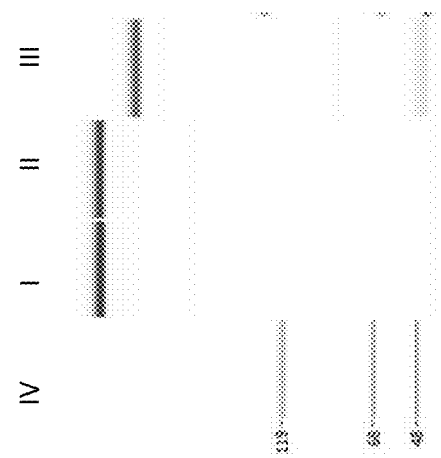
Figure 12D:
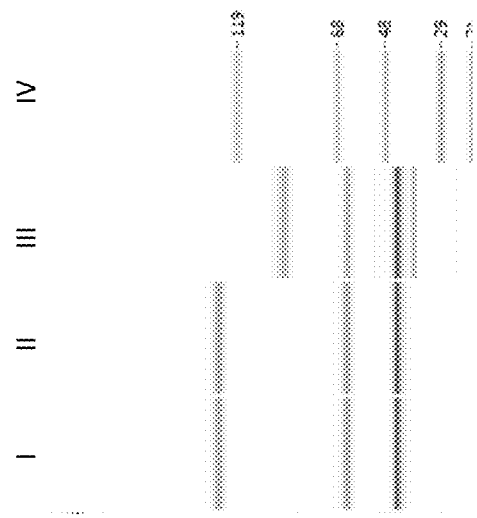

FIG. 12A-12D show shows Capillary Electrophoresis-SDS analysis of the molecules depicted in FIGS. 5A and 5C. FIGS. 12A and 12B show Capillary Electrophoresis-SDS analysis of the molecules depicted in FIG. 5A (ID 7344) anti-ID CH2527 scFv 4.15.64 MK062 CD3 16D6 Fc under non reducing (FIG. 12A) and reducing conditions (FIG. 12B). Comparison of the untreated (I) and treated molecule (III) shows complete cleavage of the anti-ID scFv after rhMatriptase/ST14 treatment for 48 h at 37° C. One sample (II) was untreated but incubated at 37° C. for 48 h. Pre-stained protein Marker (IV) Mark 12 (Invitrogen) was used for estimation of correct molecule weight. FIGS. 12C and 12D shows Capillary Electrophoresis of the molecule depicted in FIG. 5C (ID 7496) anti-ID CH2527 scFv 4.32.63 MK062 CD3 16D6 Fc under non reducing (FIG. 12C) and reducing conditions (FIG. 12D). Comparison of the untreated (I) and treated molecule (III) shows complete cleavage of the anti-ID scFv after rhMatriptase/ST14 treatment for 48 h at 37° C. One sample (II) was untreated but incubated at 37° C. for 48 h. Pre-stained protein Marker (IV) Mark 12 (Invitrogen) was used for estimation of correct molecule weight.

FIG. 13 shows FolR1 expression level quantification done by Qifikit (Dako). Antibody for FolR1: #LS-C125620-100 (LifeSpan BioSciences Inc); used at 20 µg/ml; mouse IgG1 isotype: #554121 (BD).

Figure 14A:
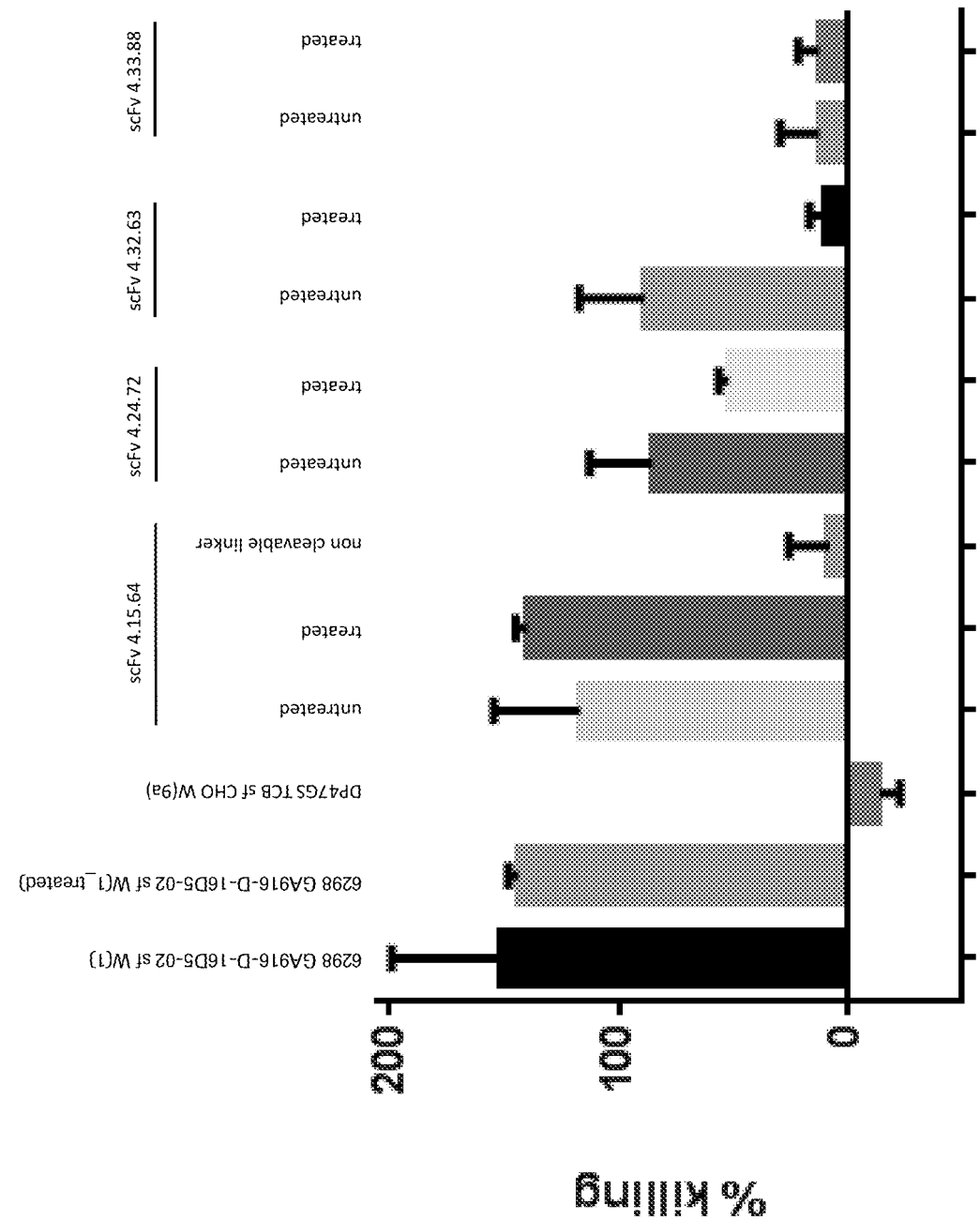
Figure 14B:
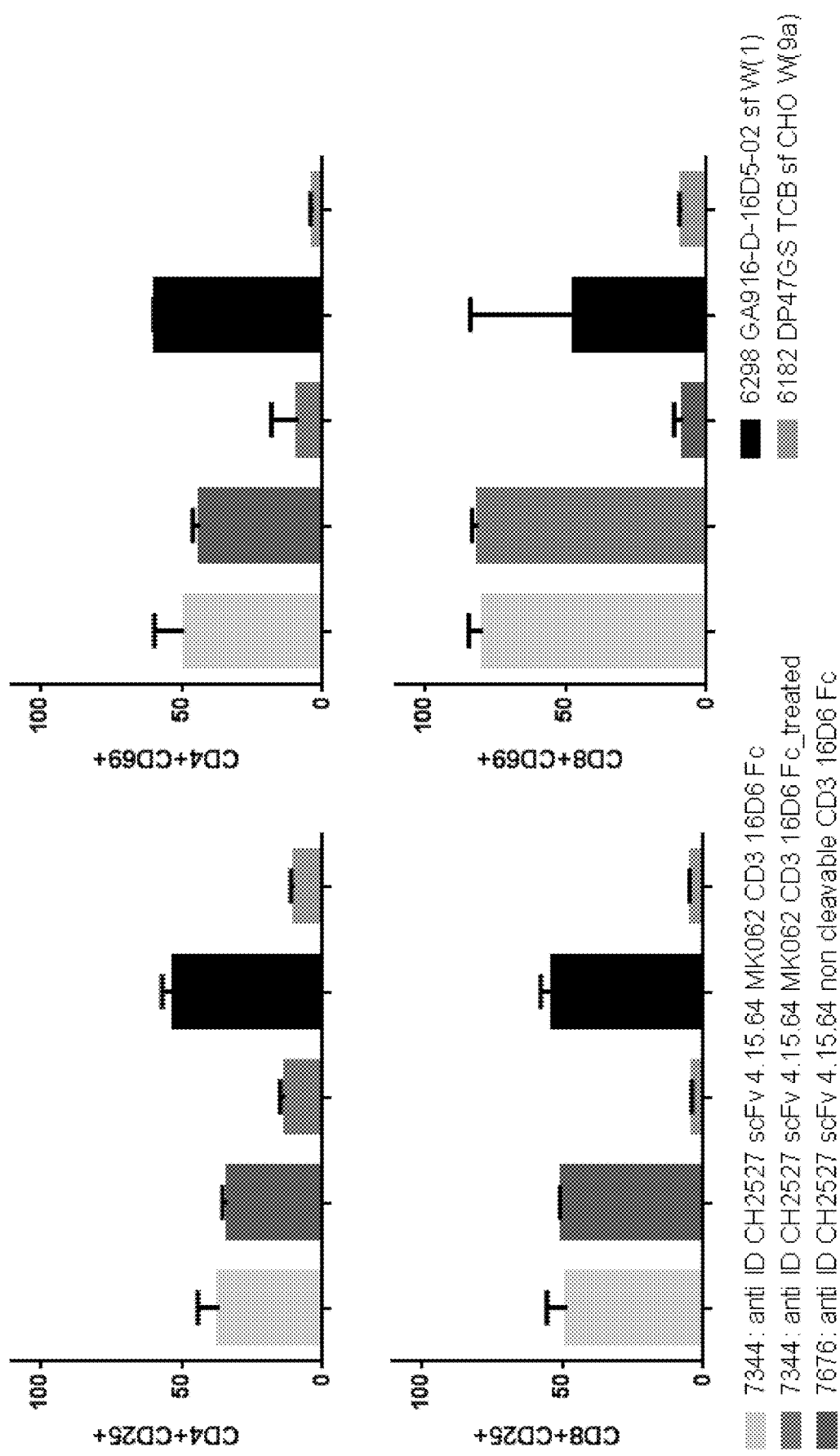

FIGS. 14A and 14B show T cell activation by protease activated TCBs. FIG. 14A shows killing of Skov3 cells induced by protease-activated TCB molecules at a concentration of 10 nM (TCBs with different anti-idiotypic CD3 masks, cleavable and non-cleavable linker, molecules pre-treated with purified rhMatriptase/ST14) and human PBMCs after 48 h of incubation (E:T=7:1, effectors are human PBMCs). Pre-treatment with rhMatriptase/ST14 (R&D Systems) was done for 24 h at 37° C. FIG. 14B shows T cell activation of human PBMCs induced by protease activated TCB binding of 10 nM (TCBs with different anti-idiotypic CD3 masks, cleavable and non-cleavable linker, treated molecules) on Skov3 cells after 48 h of incubation (E:T=7:1, effectors are human PBMCs). T cell activation markers CD25 (left panels) and CD69 (right panels). CD4+ and CD8+ T cells as indicated.

Figure 15A:
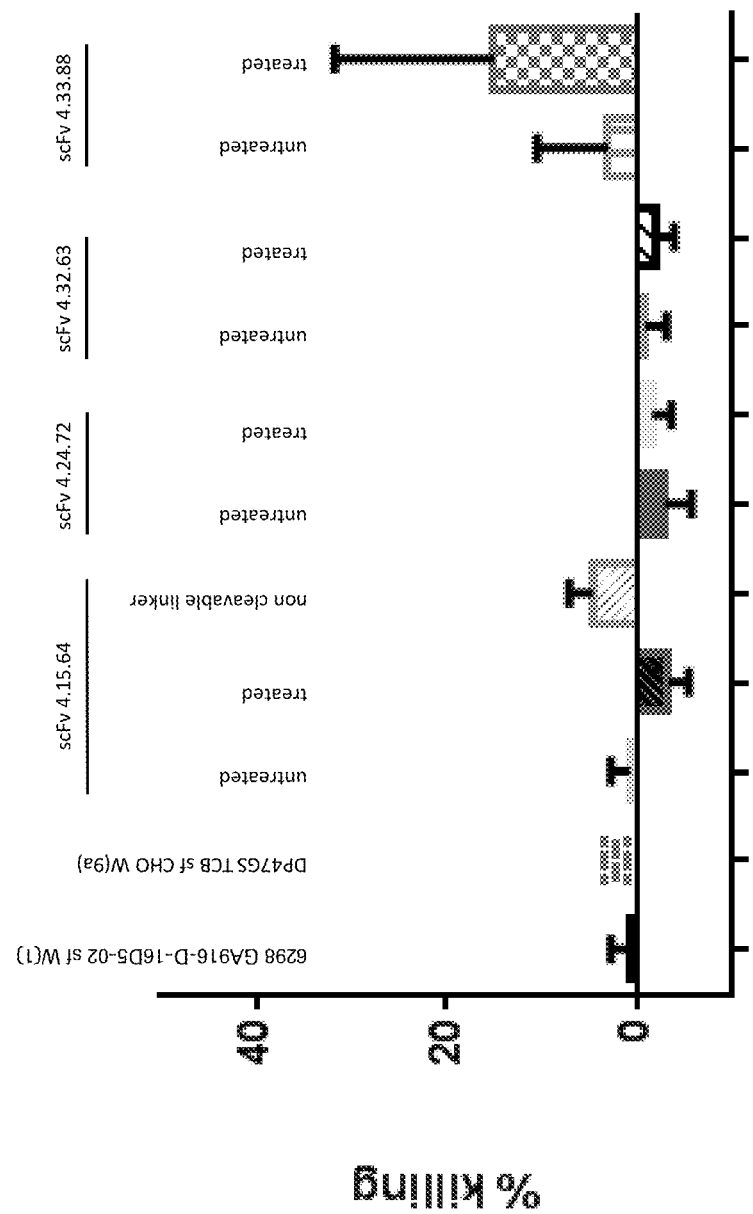

FIGS. 15A and 15B show T cell activation by protease activated TCBs. FIG. 15A shows killing of Mkn-45 cells induced by protease activated TCB molecules at a concentration of 100 nM (TCBs with different anti-idiotypic CD3 masks, cleavable and non-cleavable linker, treated molecules) and human PBMCs after 48 h of incubation (E:T=7:1, effectors are human PBMCs). Pre-treatment with rhMatriptase/ST14 (R&D Systems) was done for 24 h at 37° C. FIG. 15B shows T cell activation of human PBMCs induced by protease activated TCB binding of 100 nM (TCBs with different anti-idiotypic CD3 masks, cleavable and non-cleavable linker, treated molecules) on Mkn-45 cells after 48 h of incubation (E:T=7:1, effectors are human PBMCs). T cell activation markers CD25 (left panels) and CD69 (right panels). CD4+ and CD8+ T cells as indicated.

Figure 16:
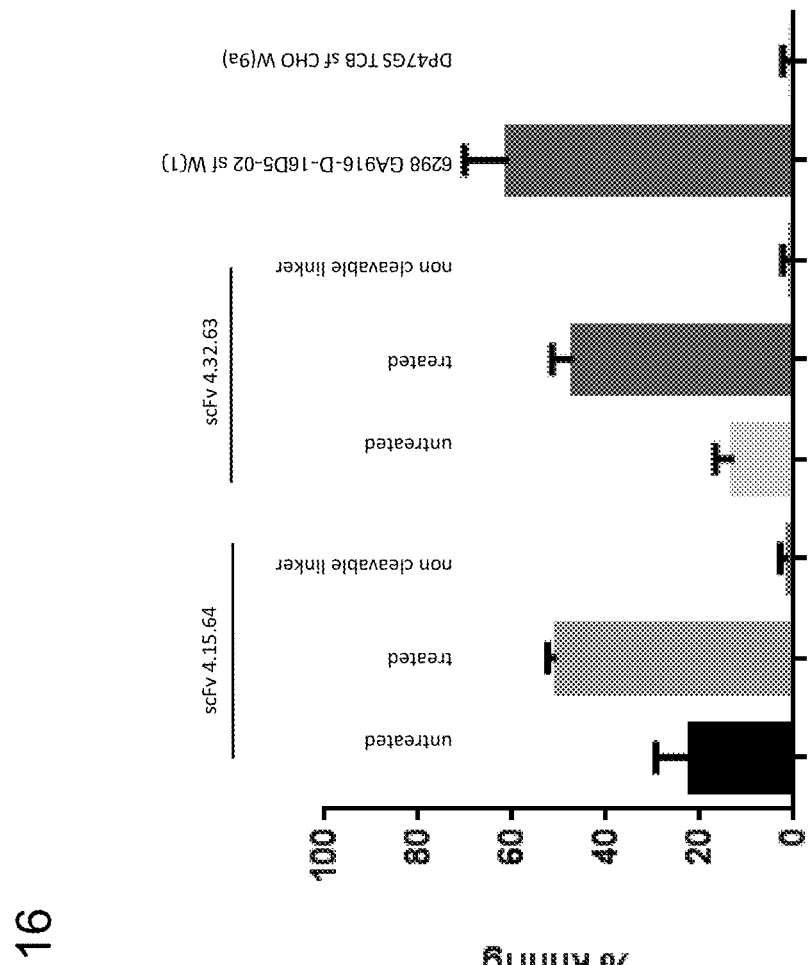

FIG. 16 shows killing of HT29 cells induced by protease activated TCB molecules at a concentration of 10 nM (TCBs with different anti-idiotypic CD3 masks, cleavable and non-cleavable linker, treated molecules) and human PBMCs after 48 h of incubation (E:T=10:1, effectors are human PBMCs). Pre-treatment with rhMatriptase/ST14 (R&D Systems) was done for 24 h at 37° C. Bars from left to right are 7344: anti-ID CH2527 scFv 4.15.64 MK062 CD3 16D6Fc; 7344: anti-ID CH2527 scFv 4.15.64 MK062 CD3 16D6Fc_treated; 7676: anti-ID CH2527 scFv 4.15.64 non-cleavable CD3 16D6Fc; 74% anti-ID CH2527 scFv 4.32.63 MK062 CD3 16D6 Fc; 7496 anti-ID CH2527 scFv 4.32.63 MK062 CD3 16D6 Fc_treated; 7611: ID anti CH2527 scFv 4.32.63 non-cleavable linker CD3 16D6 Fc; 6298 GA916-D-16D5-02 sf W(1); 6182 DP47GS TCB sf CHO W(9a).

Figure 17:
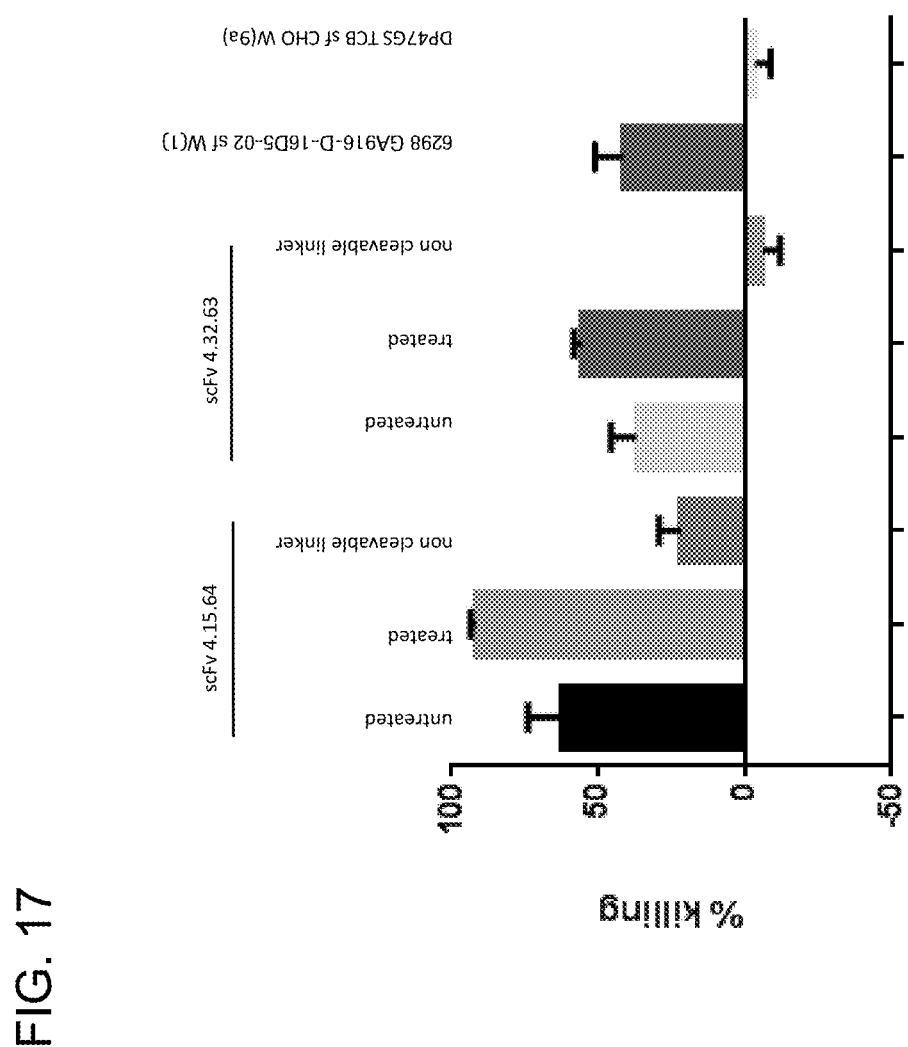

FIG. 17 shows killing of Skov3 cells induced by protease activated TCB molecules at a concentration of 10 nM (TCBs with different anti-idiotypic CD3 masks, cleavable and non-cleavable linker, treated molecules) and human PBMCs (from a different donor than PBMCs used for FIG. 14A) after 48 h of incubation (E:T=10:1, effectors are human PBMCs). Pre-treatment with rhMatriptase/ST14 (R&D Systems) was done for 24 h at 37° C. Bars from left to right are 7344: anti-ID CH2527 scFv 4.15.64 MK062 CD3 16D6Fc; 7344: anti-ID CH2527 scFv 4.15.64 MK062 CD3 16D6Fc_treated; 7676: anti-ID CH2527 scFv 4.15.64 non-cleavable CD3 16D6Fc; 7496 anti-ID CH2527 scFv 4.32.63 MK062 CD3 16D6 Fc; 74% anti-ID CH2527 scFv 4.32.63 MK062 CD3 16D6 Fc_treated; 7611: ID anti CH2527 scFv 4.32.63 non-cleavable linker CD3 16D6 Fc; 6298 GA916-D-16D5-02 sf W(1); 6182 DP47GS TCB sf CHO W(9a).

Figure 18A:
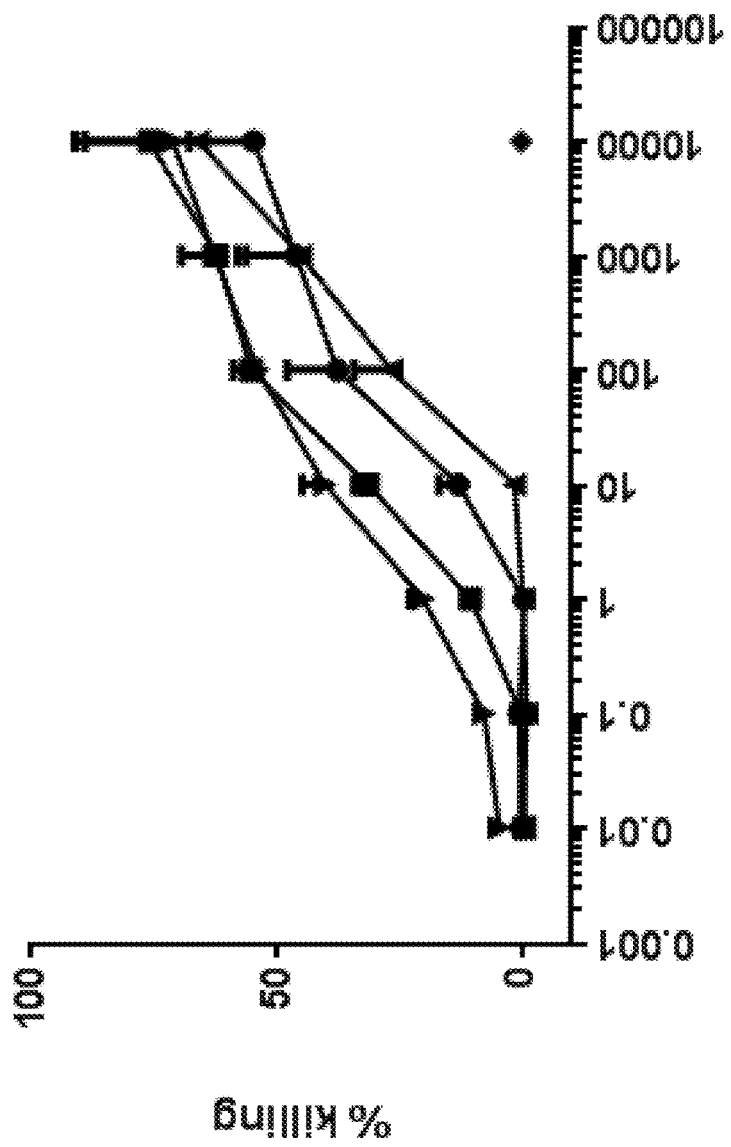
Figure 18B:
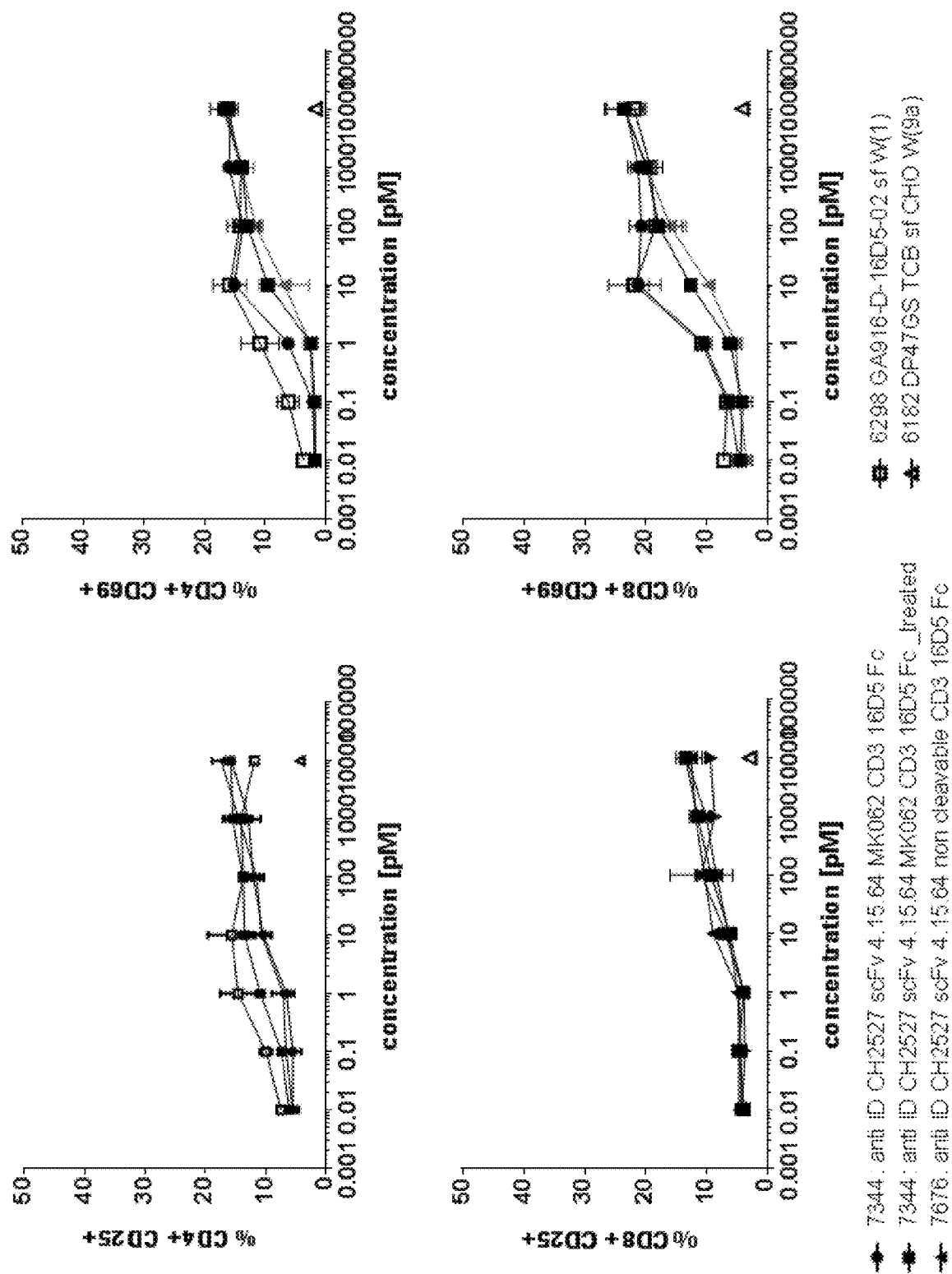

FIGS. 18A and 18B show T cell activation by protease activated TCBs. FIG. 18A shows dose-dependent killing of HeLa cells induced by protease activated TCB molecules (TCB with anti-idiotypic CD3 4.15.64 mask, cleavable and non-cleavable linker, treated molecule) and human PBMCs (isolated from buffy coat) after 48 h of incubation (E:T=10:1, effectors are human PBMCs). Pre-treatment with rhMatriptase/ST14 (R&D Systems) was done for 24 h at 37° C. FIG. 18B shows dose-dependent T cell activation of human PBMCs induced by protease activated TCB binding (TCB with anti-idiotypic CD3 4.15.64 mask, cleavable and non-cleavable linker, treated molecule) on HeLa cells after 48 h of incubation (E:T=10:1, effectors are human PBMCs). T cell activation markers CD25 (left panels) and CD69 (right panels). CD4+ and CD8+ T cells as indicated.

Figure 19A:
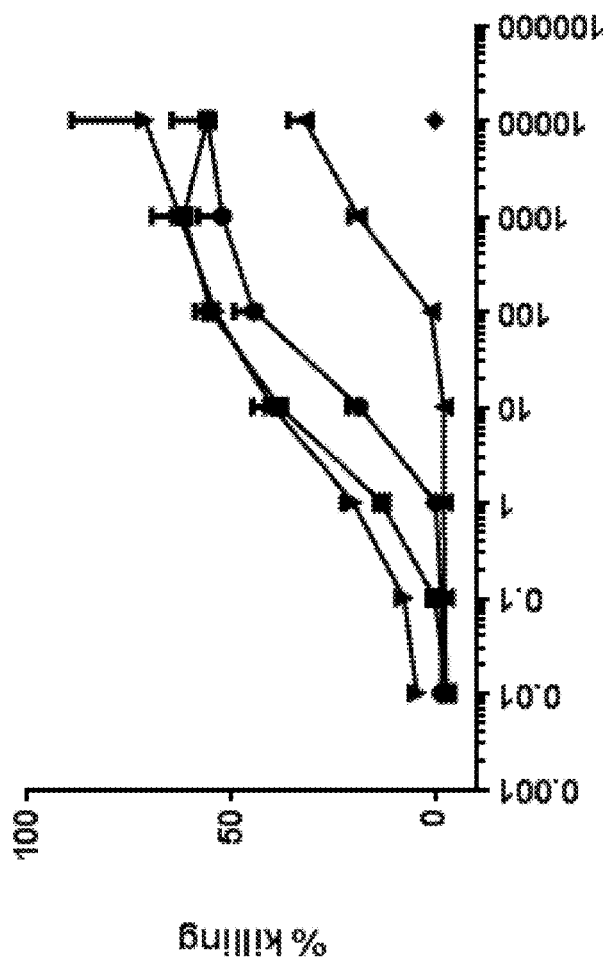
Figure 19B:
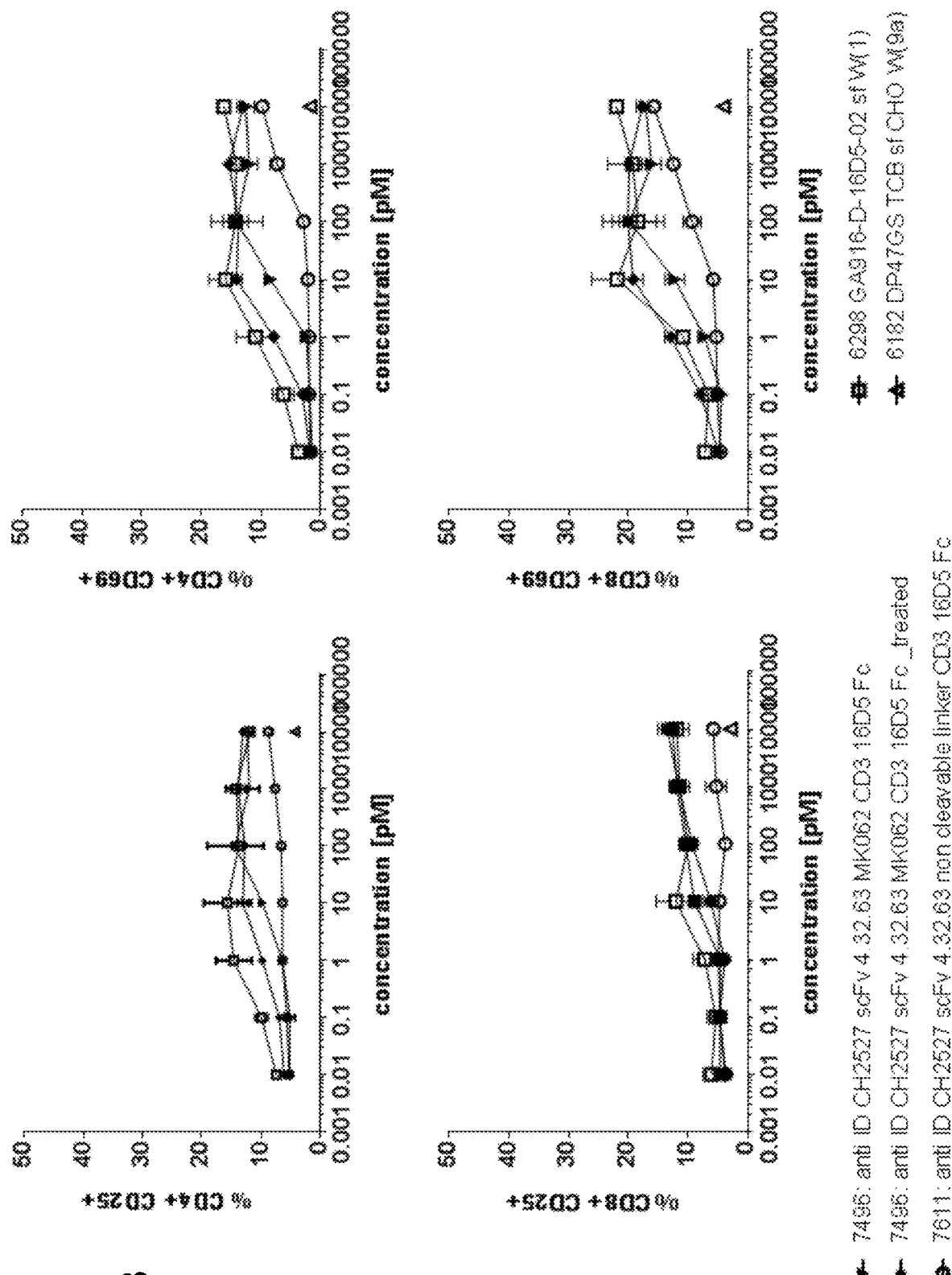

FIGS. 19A and 19B show T cell activation by protease activated TCBs. FIG. 19A shows dose-dependent killing of HeLa cells induced by protease activated TCB molecules (TCB with anti-idiotypic CD3 4.32.63 mask, cleavable and non-cleavable linker, treated molecule) and human PBMCs (isolated from buffy coat) after 48 h of incubation (E:T=10:1, effectors are human PBMCs). Pre-treatment with rhMatriptase/ST14 (R&D Systems) was done for 24 h at 37° C. FIG. 19B shows dose-dependent T cell activation of human PBMCs induced by protease activated TCB binding (TCB with anti-idiotypic CD3 4.32.63 mask. cleavable and non-cleavable linker, treated molecule) on HeLa cells after 48 h of incubation (E:T=10:1, effectors are human PBMCs). T cell activation markers CD25 (left panels) and CD69 (right panels). CD4+ and CD8+ T cells as indicated.

Figure 20A:
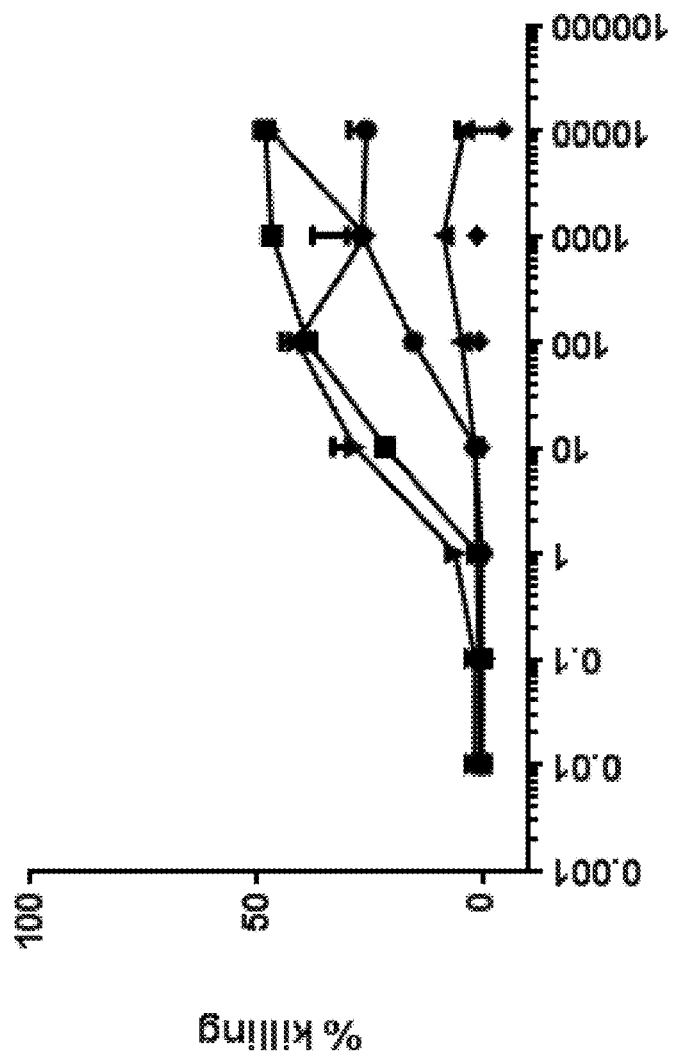
Figure 20B:
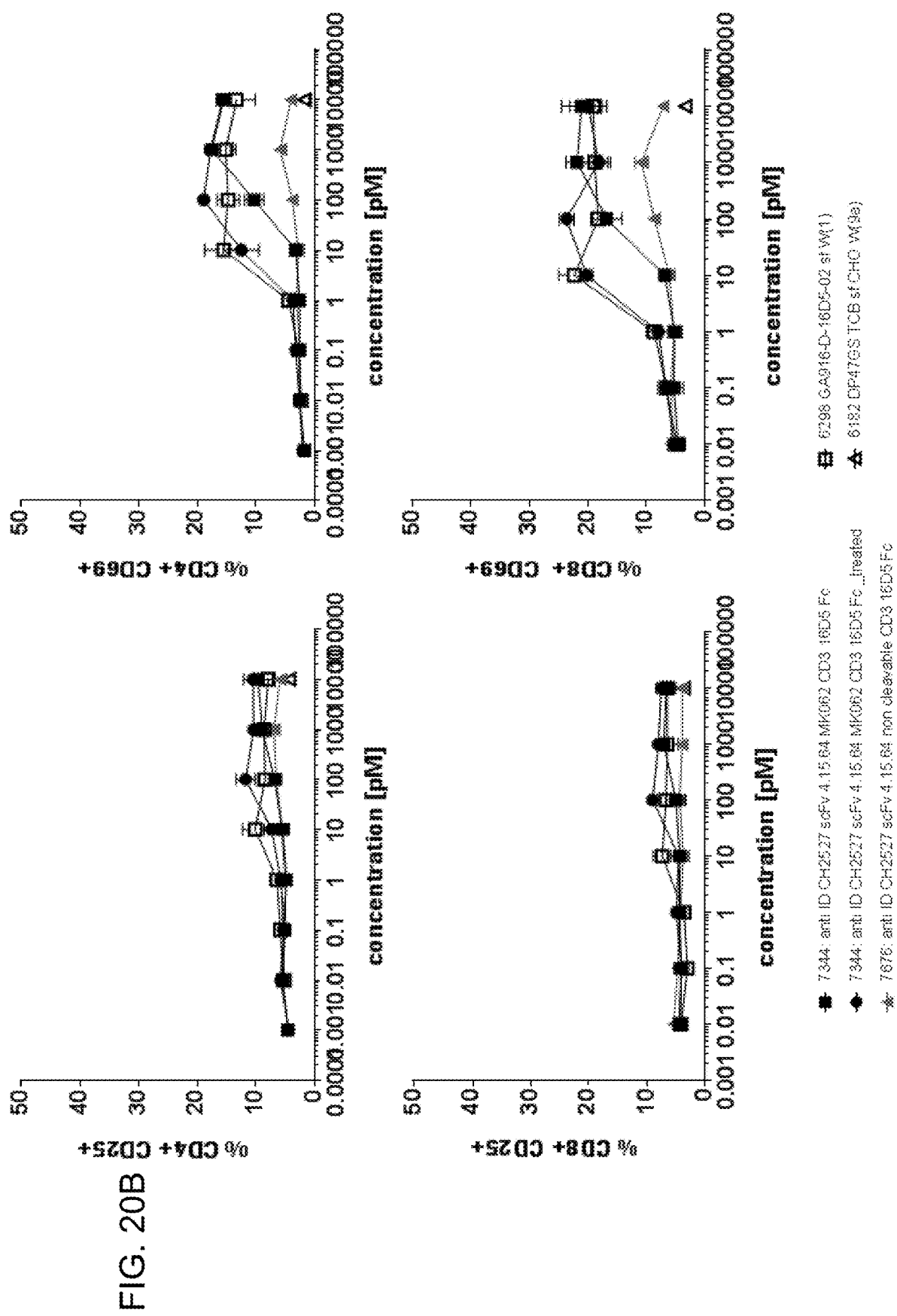

FIGS. 20A and 20B show T cell activation by protease activated TCBs. FIG. 20A shows dose-dependent killing of Skov3 cells induced by protease activated TCB molecules (TCB with anti-idiotypic CD3 4.15.64 mask. cleavable and non-cleavable linker, treated molecule) and human PBMCs (isolated from buffy coat) after 48 h of incubation (E:T=10:1, effectors are human PBMCs). Pre-treatment with rhMatriptase/ST14 (R&D Systems) was done for 24 h at 37° C. FIG. 20B shows dose-dependent T cell activation of human PBMCs induced by protease activated TCB binding (TCB with anti-idiotypic CD3 4.15.64 mask, cleavable and non-cleavable linker, treated molecule) on Skov3 cells after 48 h of incubation (E:T=10:1, effectors are human PBMCs). T cell activation markers CD25 (left panels) and CD69 (right panels). CD4+ and CD8+ T cells as indicated.

Figure 21B:
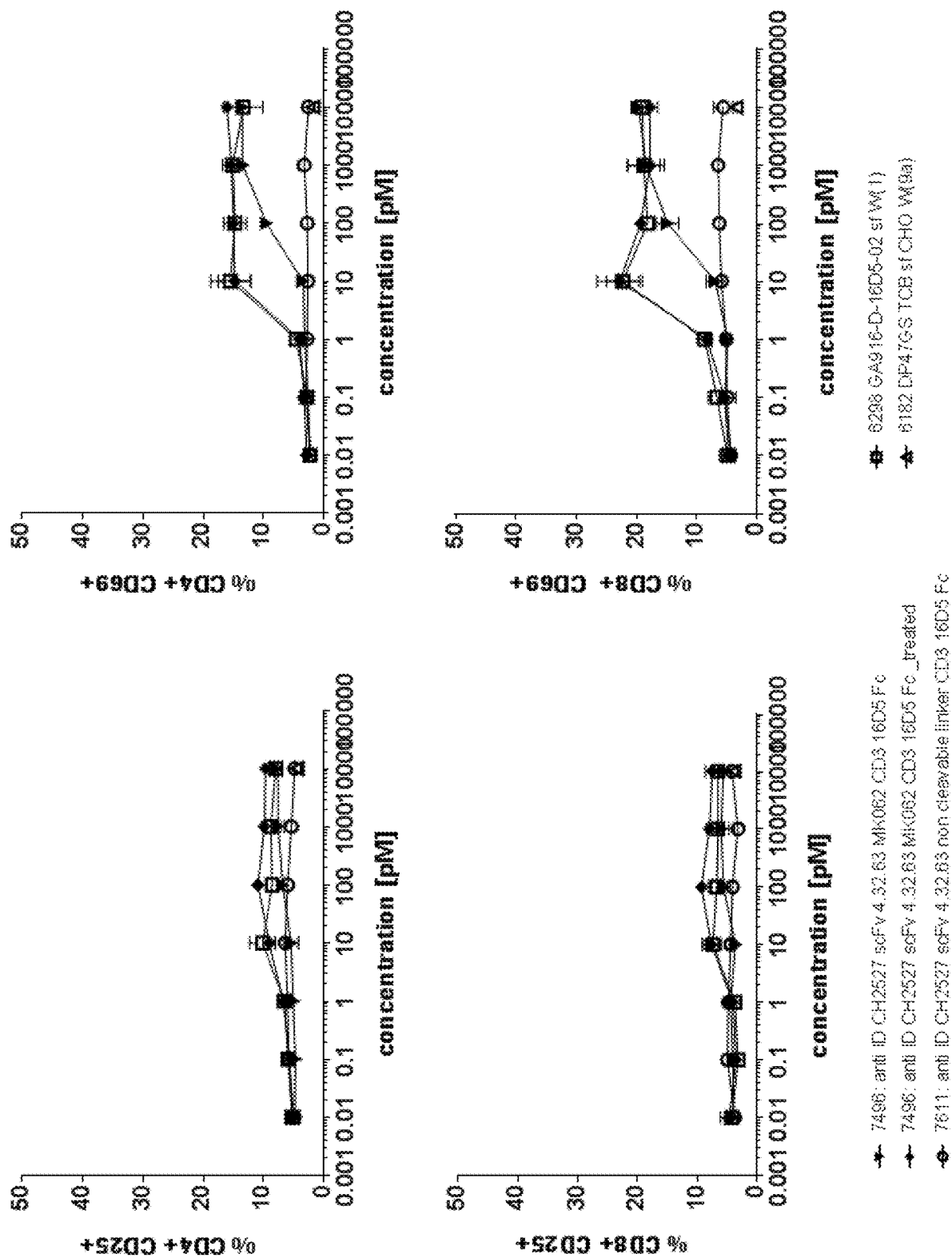

FIGS. 21A and 21B show T cell activation by protease activated TCBs. FIG. 21A shows dose-dependent killing of Skov3 cells induced by protease activated TCB molecules (TCB with anti-idiotypic CD3 4.32.63 mask, cleavable and non-cleavable linker, treated molecule) and human PBMCs (isolated from buffy coat) after 48 h of incubation (E:T=10:1, effectors are human PBMCs). Pre-treatment with rhMatriptase/ST14 (R&D Systems) was done for 24 h at 37°

C. FIG. 21B shows dose-dependent T cell activation of human PBMCs induced by protease activated TCB binding (TCB with anti-idiotypic CD3 4.32.63 mask. cleavable and non-cleavable linker, treated molecule) on Skov3 cells after 48 h of incubation (E:T=10:1, effectors are human PBMCs). T cell activation markers CD25 (left panels) and CD69 (right panels). CD4+ and CD8+ T cells as indicated.

Figure 22A:
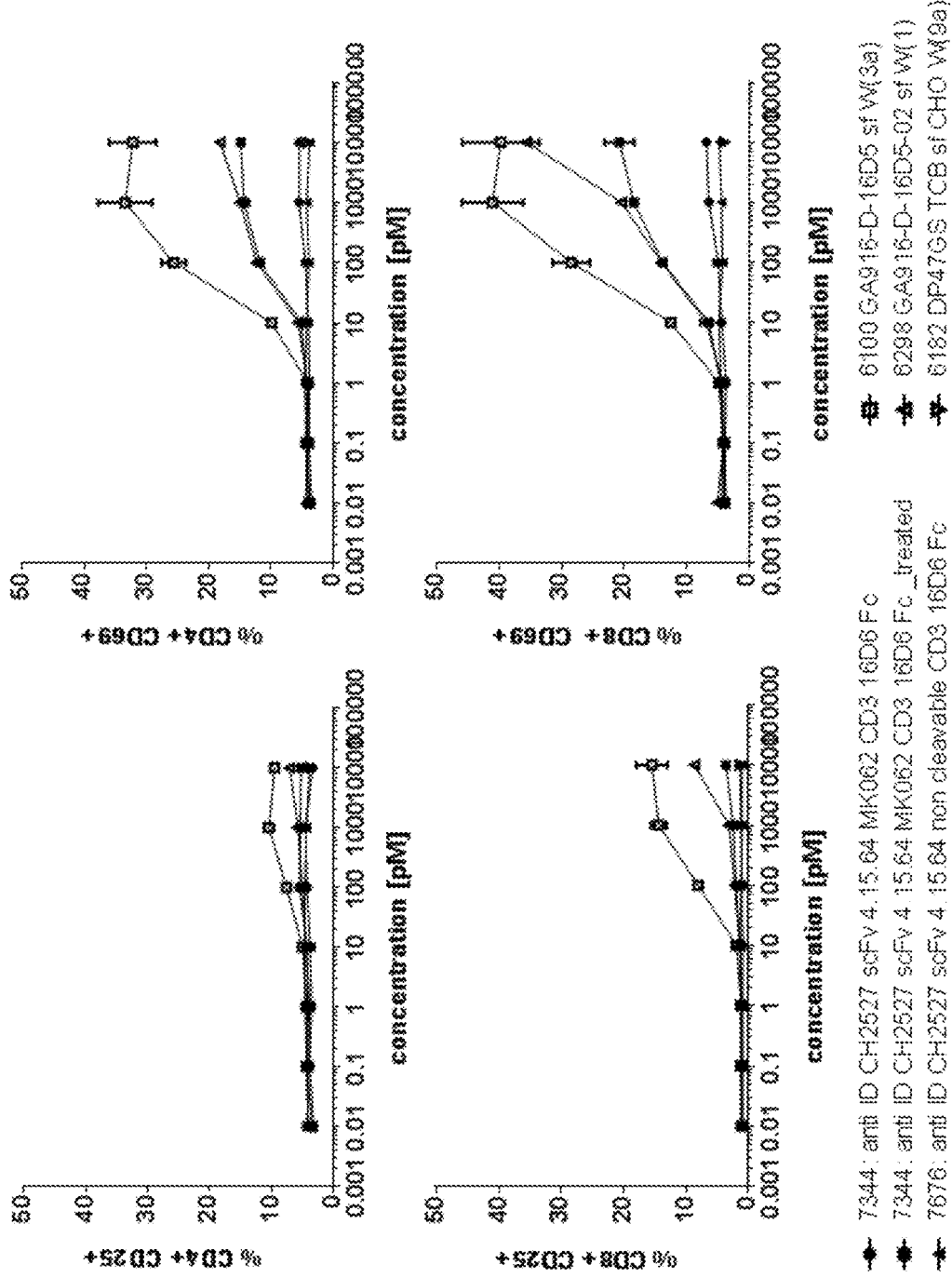
Figure 22B:
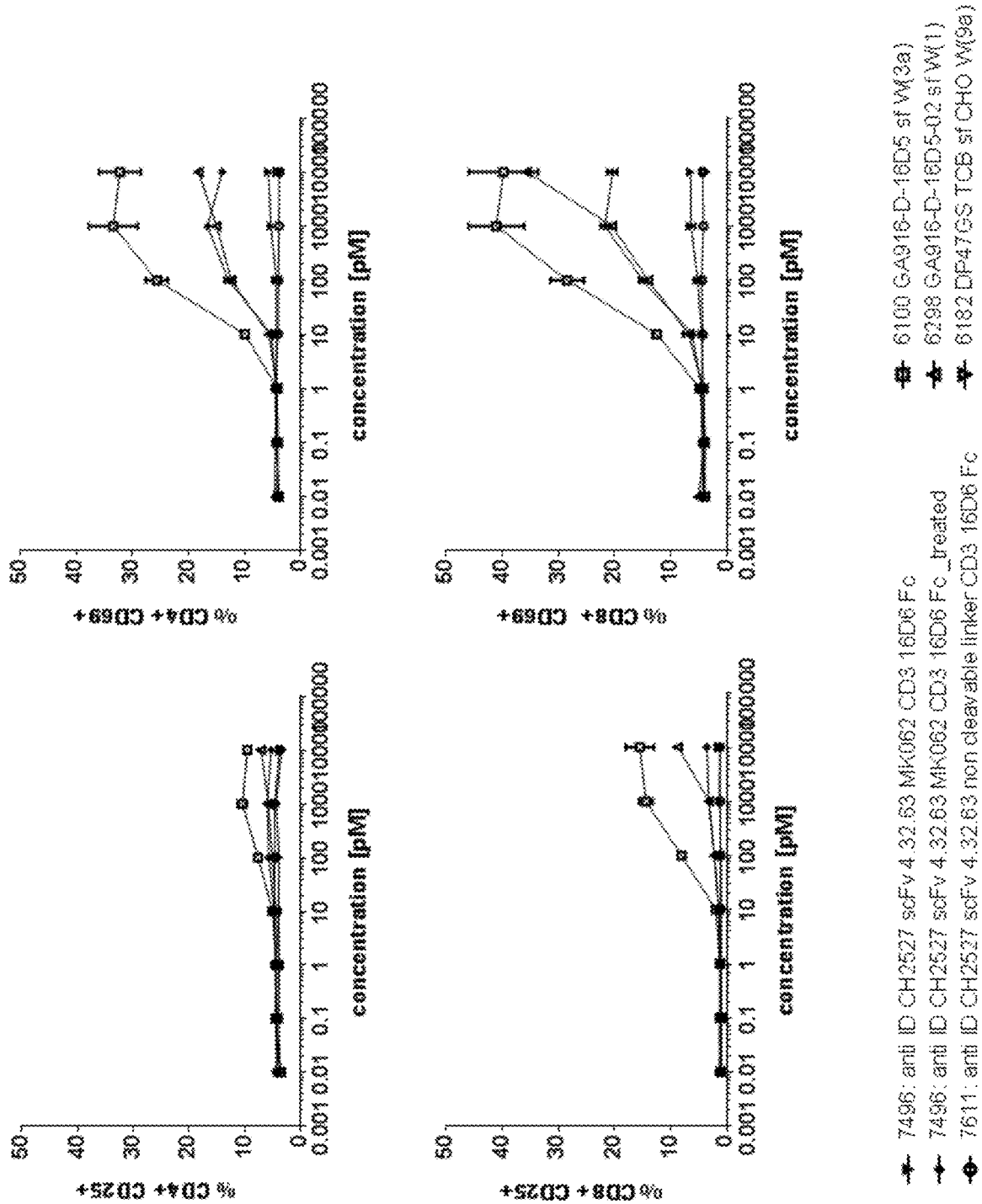

FIGS. 22A and 22B show T cell activation by protease activated TCBs. FIG. 22A shows dose-dependent T cell activation of human PBMCs (different donor than in experiments described above) induced by protease activated TCB binding (TCB with anti-idiotypic CD3 4.15.64 mask, cleavable and non-cleavable linker, treated molecule) on HT29 cells after 48 h of incubation (E:T=10:1, effectors are human PBMCs). T cell activation markers CD25 (left panels) and CD69 (right panels). CD4+ and CD8+ T cells as indicated. FIG. 22B shows dose-dependent T cell activation of human PBMCs (different donor than in FIG. 16) induced by protease activated TCB binding (TCB with anti-idiotypic CD3 4.32.63 mask. cleavable and non-cleavable linker, treated molecule) on HT29 cells after 48 h of incubation (E:T=10:1, effectors are human PBMCs). T cell activation markers CD25 (left panels) and CD69 (right panels). CD4+ and CD8+ T cells as indicated.

Figure 23:
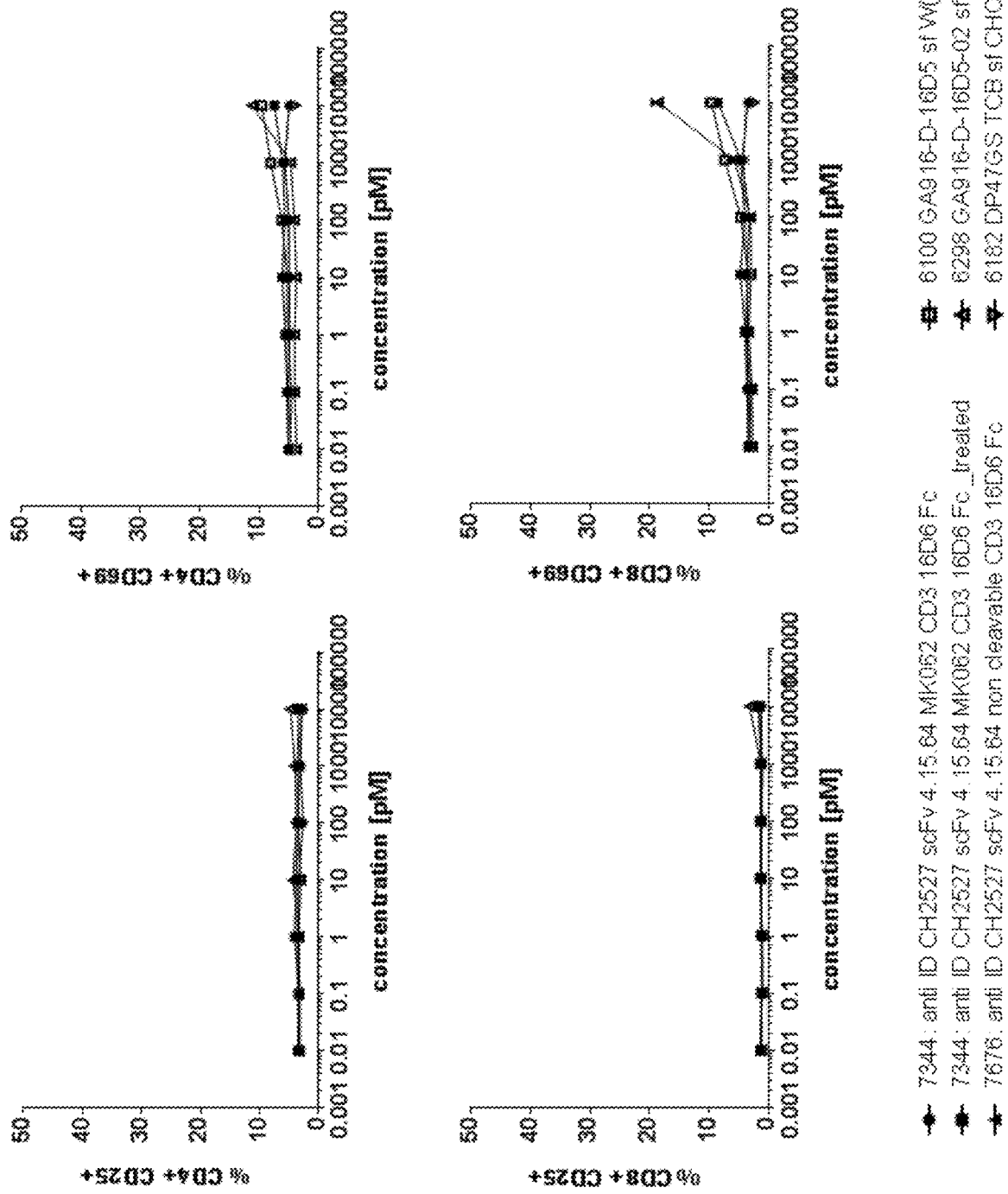

FIG. 23 shows dose-dependent T cell activation of human PBMCs (different donor than in experiments described above) induced by protease activated TCB binding (TCB with anti-idiotypic CD3 4.15.64 mask, cleavable and non-cleavable linker, treated molecule) on HRCEpiC cells after 48 h of incubation (E:T=10:1, effectors are human PBMCs). T cell activation markers CD25 (left panels) and CD69 (right panels). CD4+ and CD8+ T cells as indicated.

Figure 24:
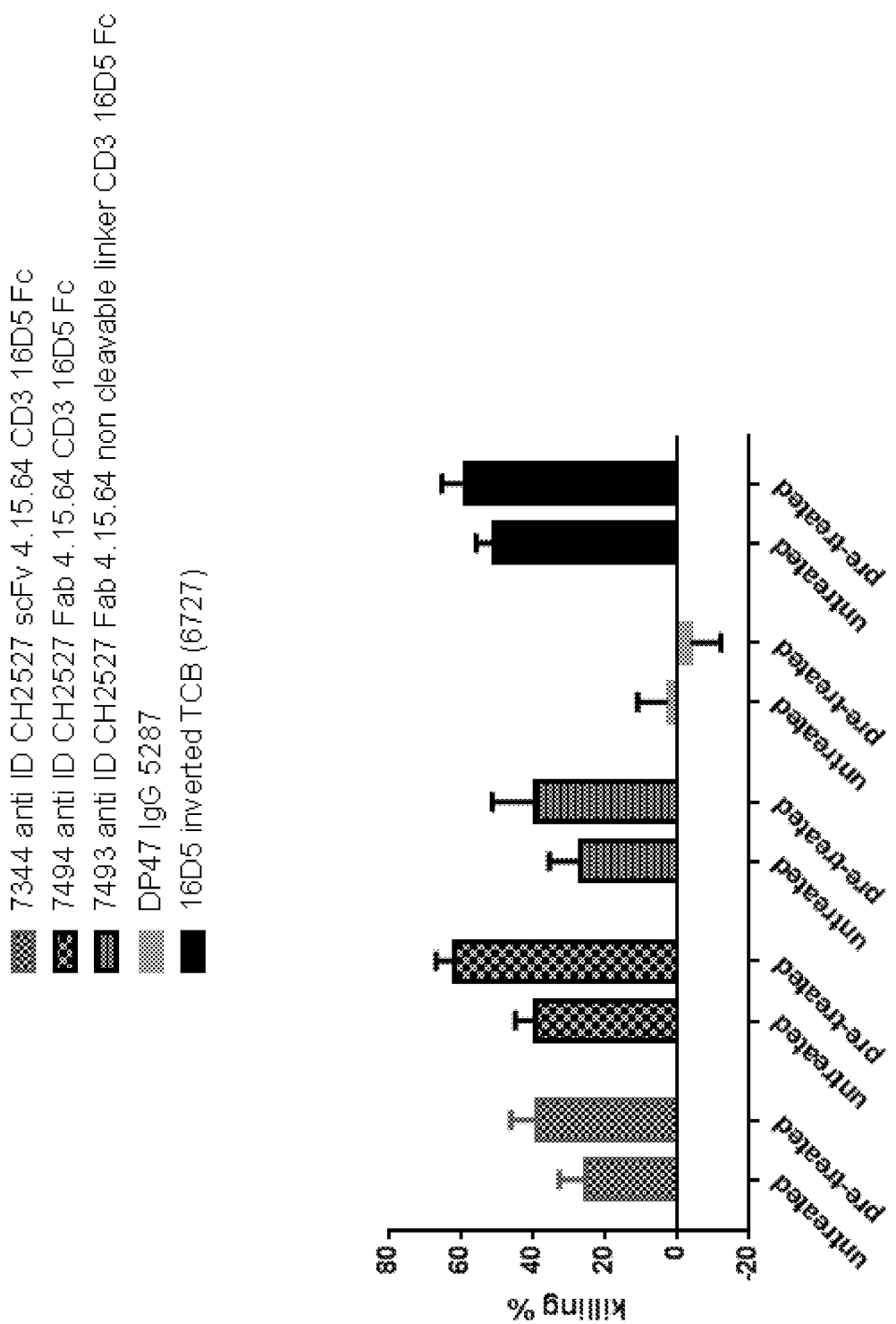

FIG. 24 shows killing of Ovcar3 cells induced by protease activated TCB molecules at a concentration of 50 nM (TCBs with different anti-idiotypic CD3 masks, cleavable and non-cleavable linker, treated molecules) and human PBMCs after 48 h of incubation (E:T=10:1, effectors are human PBMCs). Pre-treatment with rhMatriptase/ST14 (R&D Systems) was done for 10 min at 37° C. (not fully cleaved).

Figure 25:
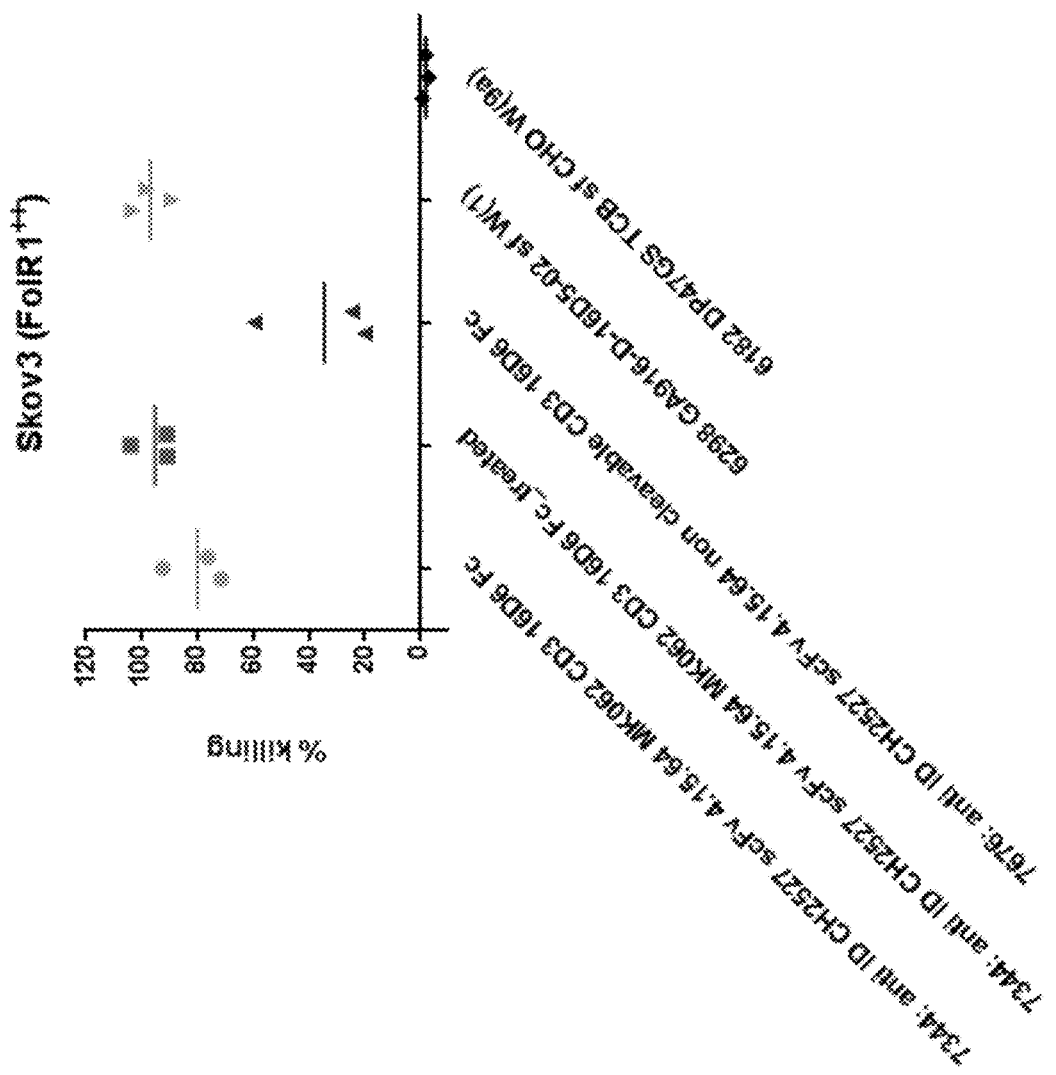

FIG. 25 shows killing of Skov3 cells induced by 10 nM of protease activated TCB molecules (TCB with anti-idiotypic CD3 4.15.64 mask, cleavable and non-cleavable linker, treated molecule) and human PBMCs (isolated from buffy coat) after 48 h of incubation (E:T=10:1. effectors are three different Donors for human PBMCs). Pre-treatment with rhMatriptase/ST14 (R&D Systems) was done for 24 h at 37° C.

Figure 26:
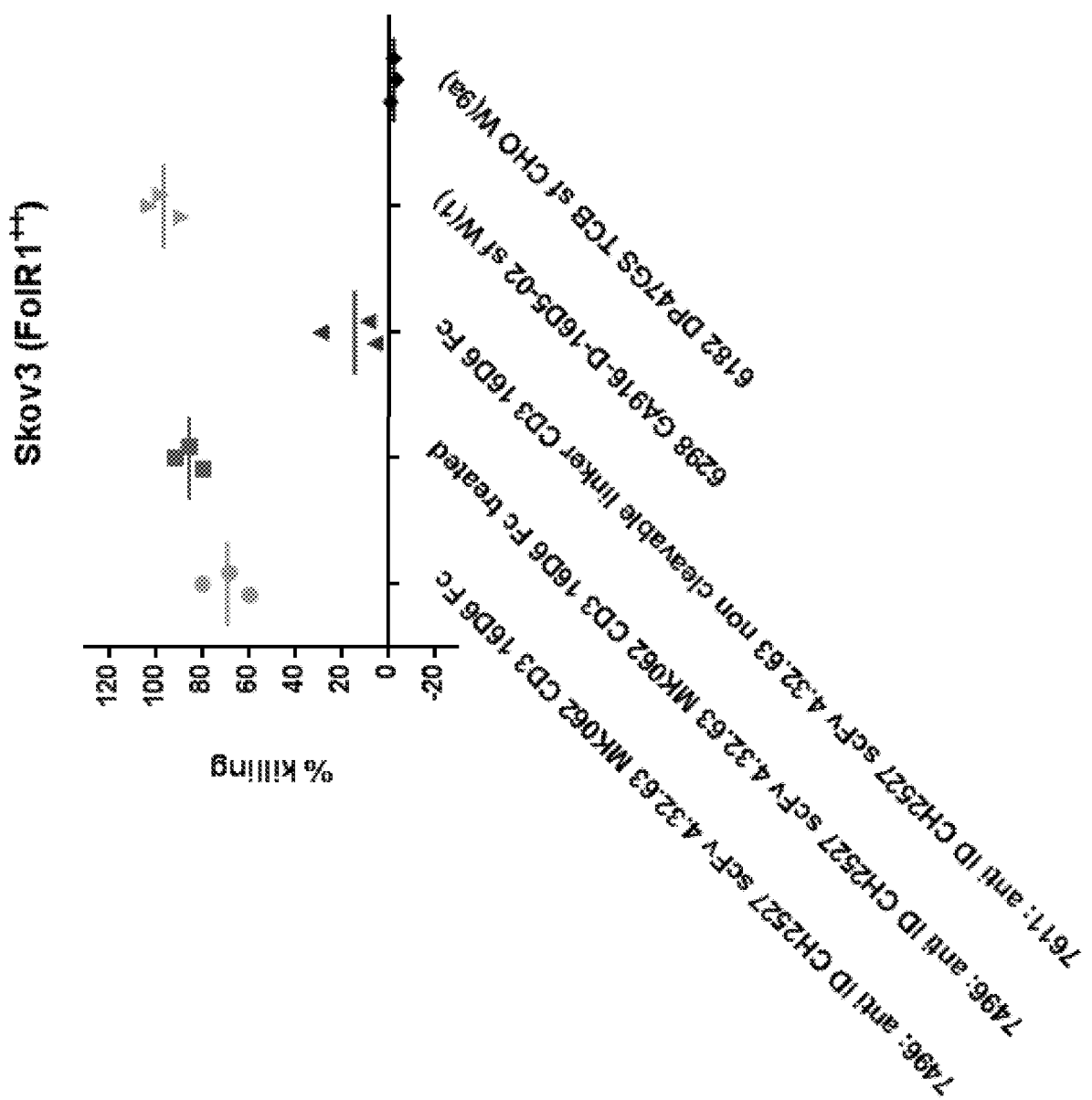

FIG. 26 shows killing of Skov3 cells induced by 10 nM of protease activated TCB molecules (TCB with anti-idiotypic CD3 4.32.63 mask, cleavable and non-cleavable linker, treated molecule) and human PBMCs (isolated from buffy coat) after 48 h of incubation (E:T=10:1. effectors are three different Donors for human PBMCs). Pre-treatment with rhMatriptase/ST14 (R&D Systems) was done for 24 h at 37° C.

Figure 27:
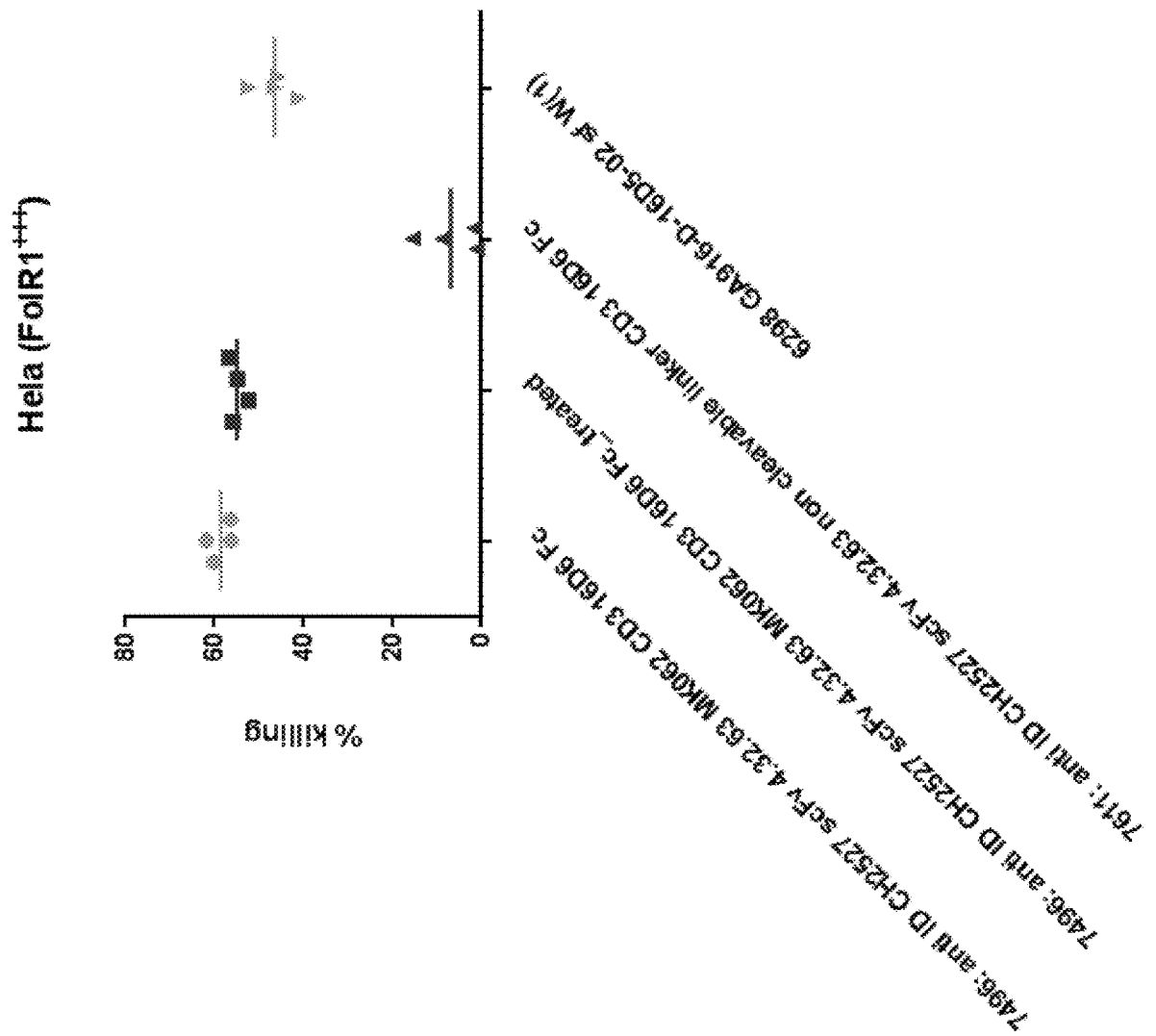

FIG. 27 shows killing of HeLa cells induced by 100 pM of protease activated TCB molecules (TCB with anti-idiotypic CD3 4.32.63 mask, cleavable and non-cleavable linker, treated molecule) and human PBMCs (isolated from buffy coat) after 48 h of incubation (E:T=10:1, effectors are three different Donors for human PBMCs). Pre-treatment with rhMatriptase/ST14 (R&D Systems) was done for 24 h at 37° C.

Figure 28:
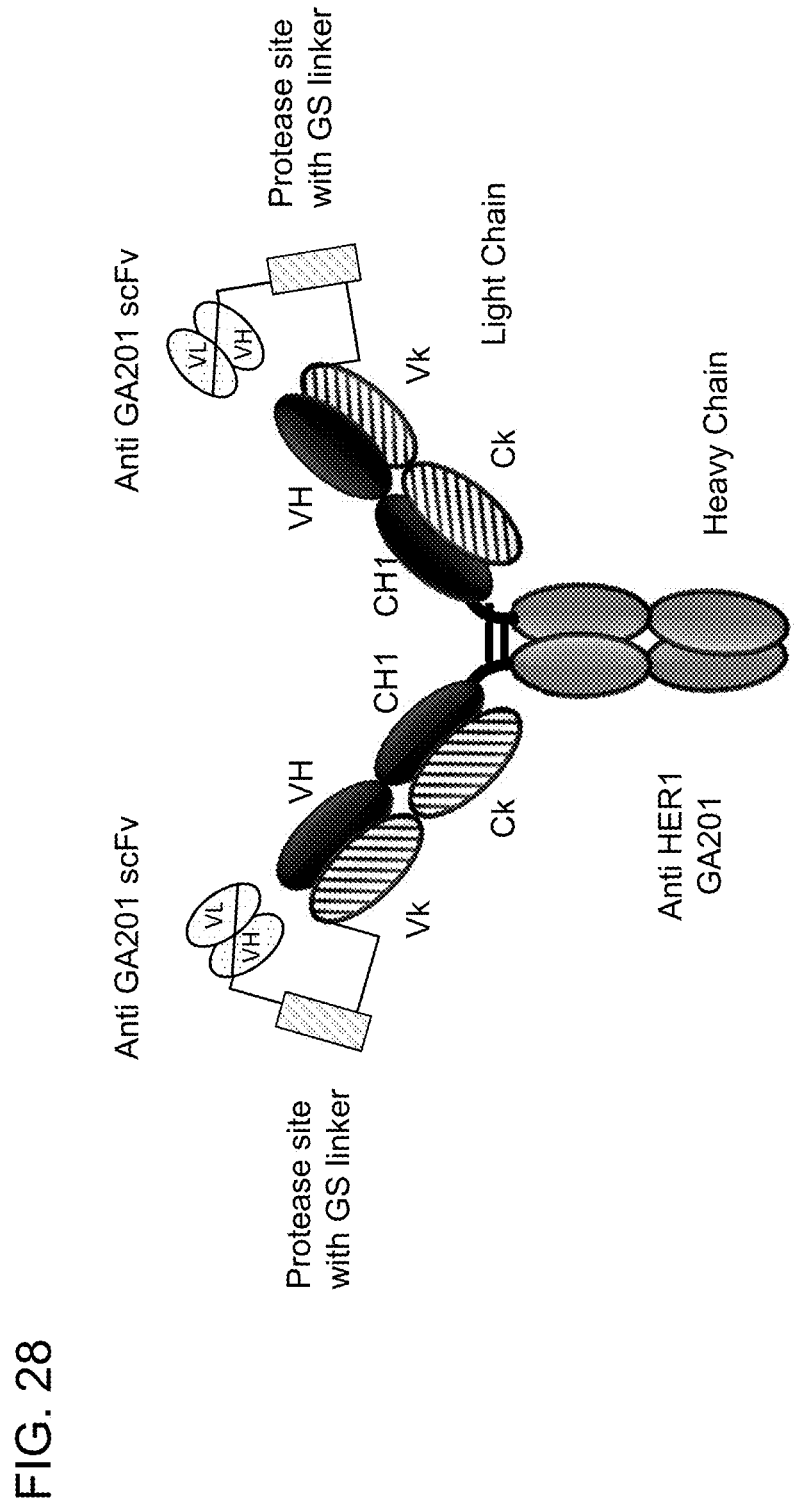

FIG. 28 depicts a schematic of anti-ID GA201 scFv Matrix Metalloprotease site GA201 Fc (GA201-anti-GA201-scFv).

Figure 29:
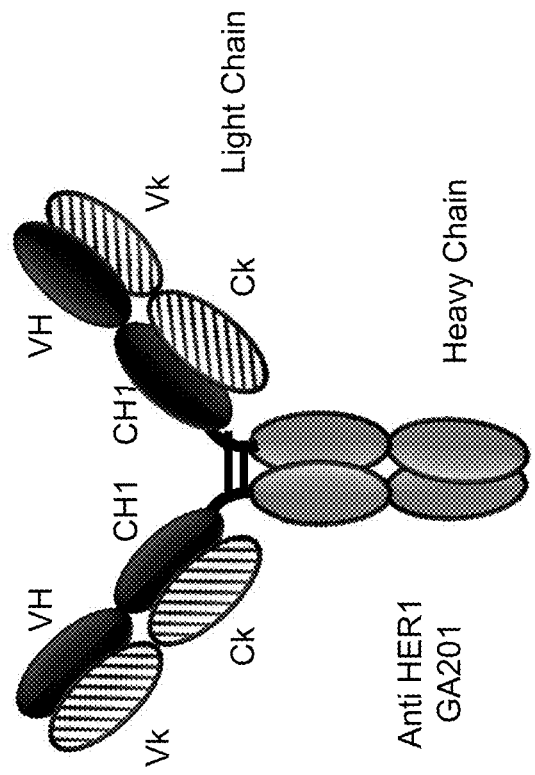

FIG. 29 depicts a schematics of the anti HER1 antibody GA201.

Figure 30B:
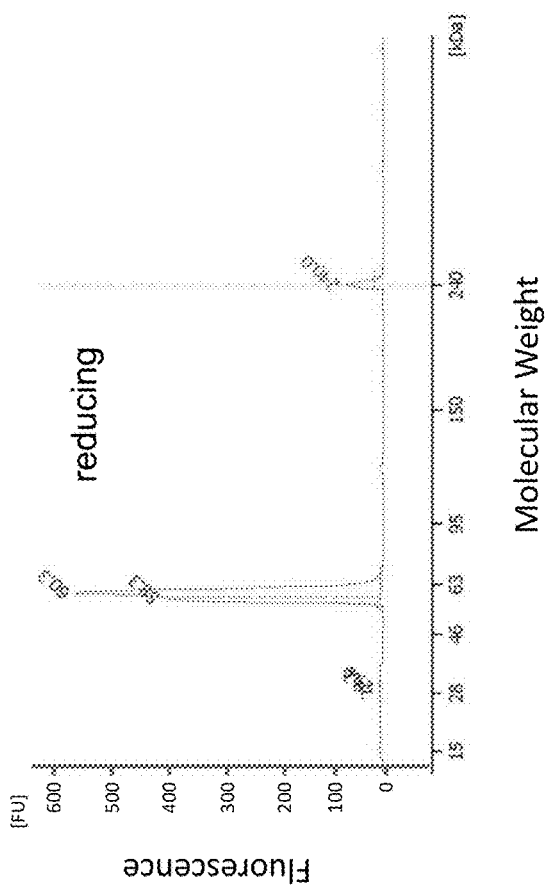
Figure 30A:
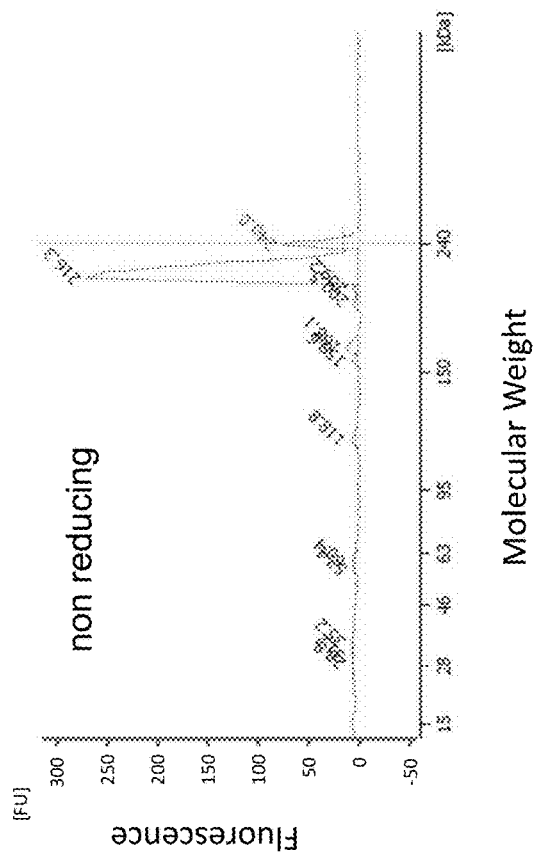

FIGS. 30A and 30B show capillary Electrophoresis-SDS analysis of the molecule depicted in FIG. 28 under non-reducing (FIG. 30A) and reducing conditions (FIG. 30B). The molecule depicted in FIG. 28 was purified to homogeneity by Protein A and Size Exclusion chromatography and subjected to Capillary electrophoresis-SDS analysis.

Figure 31:
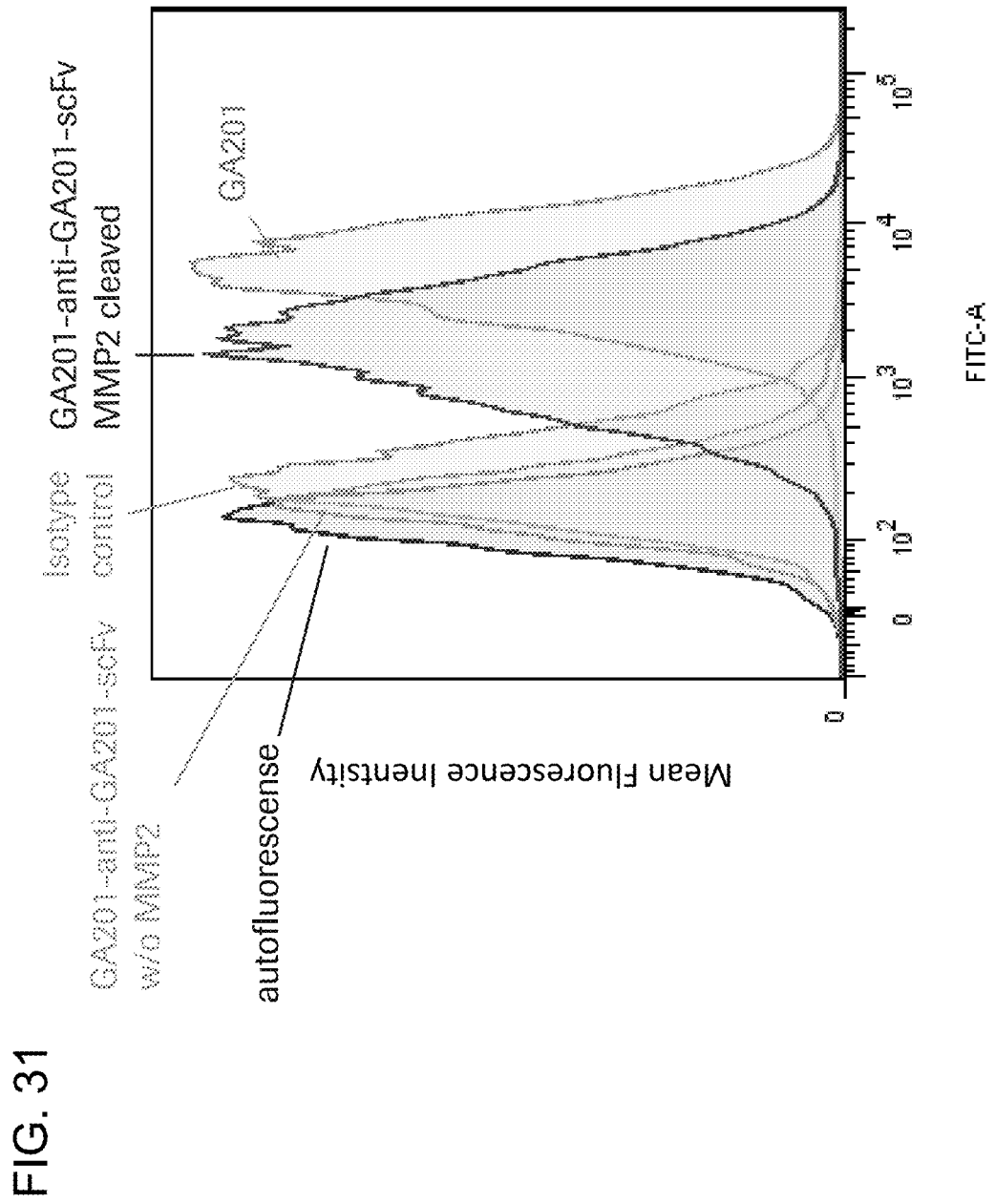

FIG. 31 shows FACS analysis of GA201-anti-GA201-scFv and GA201 binding to HER1 expressed on H322M cells to confirm masking effect of anti-idiotypic GA201 scFv. GA201-anti-GA201-scFv was incubated overnight with the Matrix Metalloprotease MMP-2 and binding to H322M cells was compared to uncleaved GA201-anti-GA201-scFv, GA201 and an isotype IgG1 control antibody. Binding to HER1 on H322M cells was detected with a F(ab')2-goat anti-human IgG Fc secondary antibody FITC conjugate and analyzed by FACS using the BD FACS Canto II. The median fluorescence intensity (MFI) was used for analysis.

FIG. 32 shows surface plasmon resonance analysis of HER1 binding of masked and unmasked GA201, before and after MMP2 cleavage.

Figure 33A:
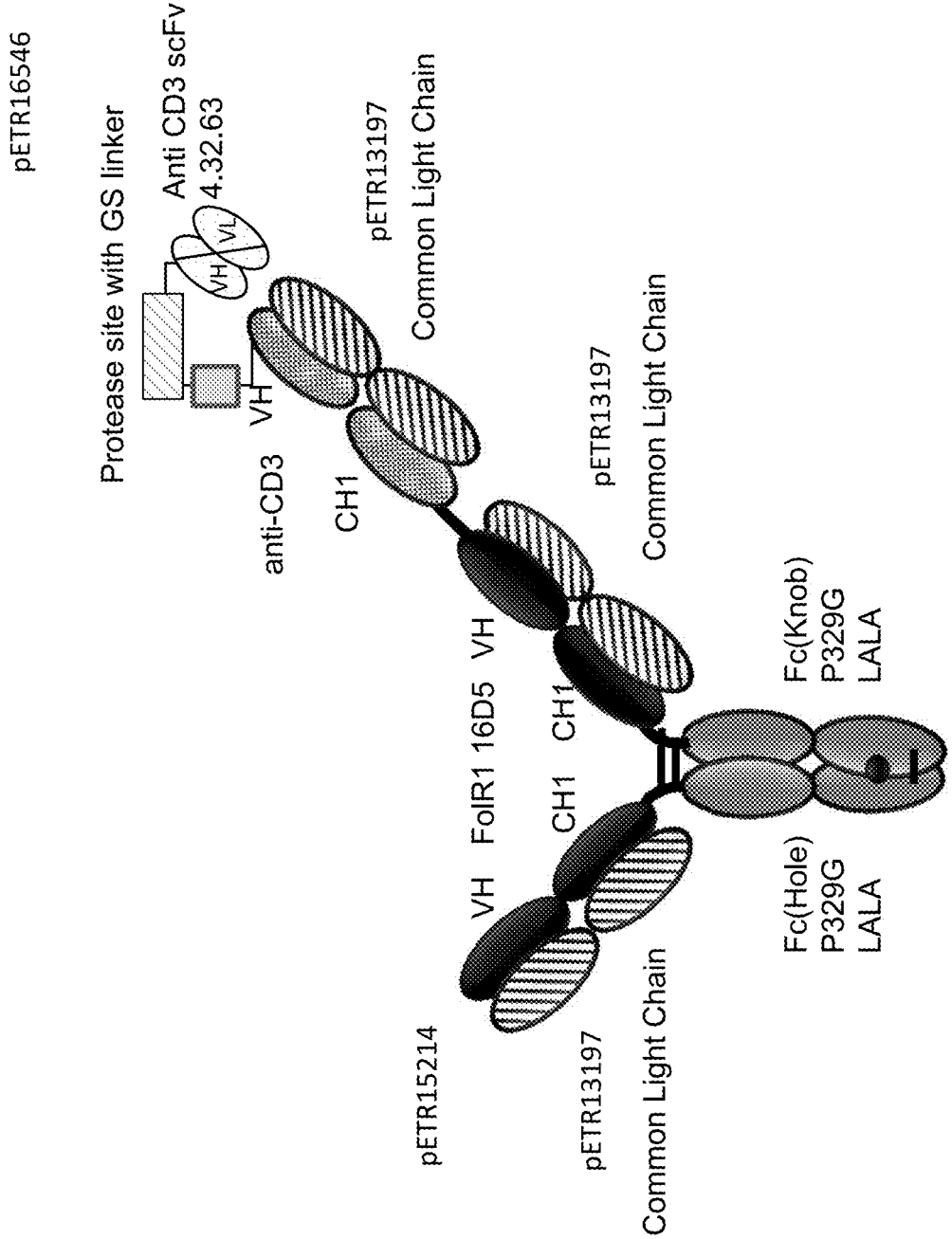
Figure 33B:
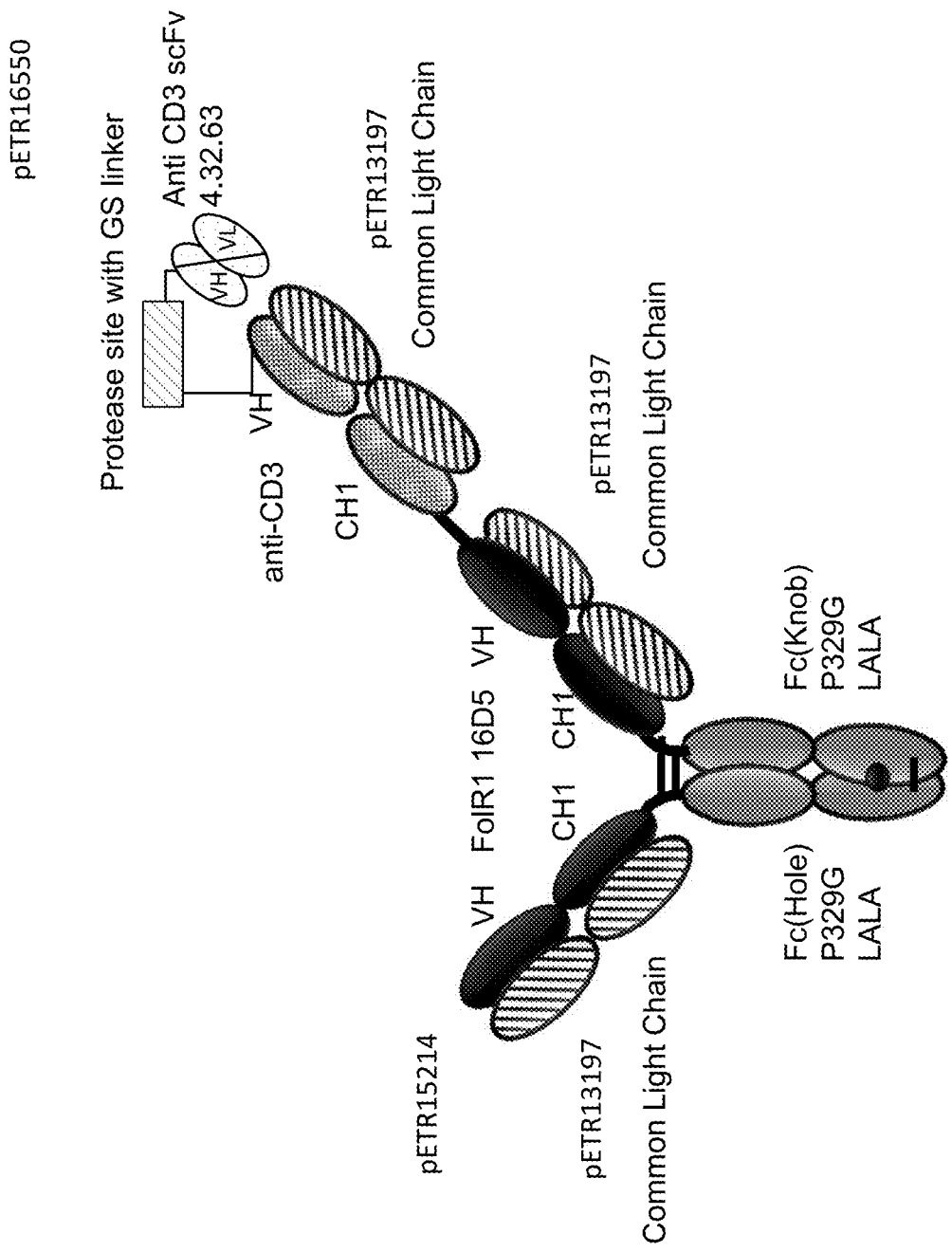
Figure 33C:
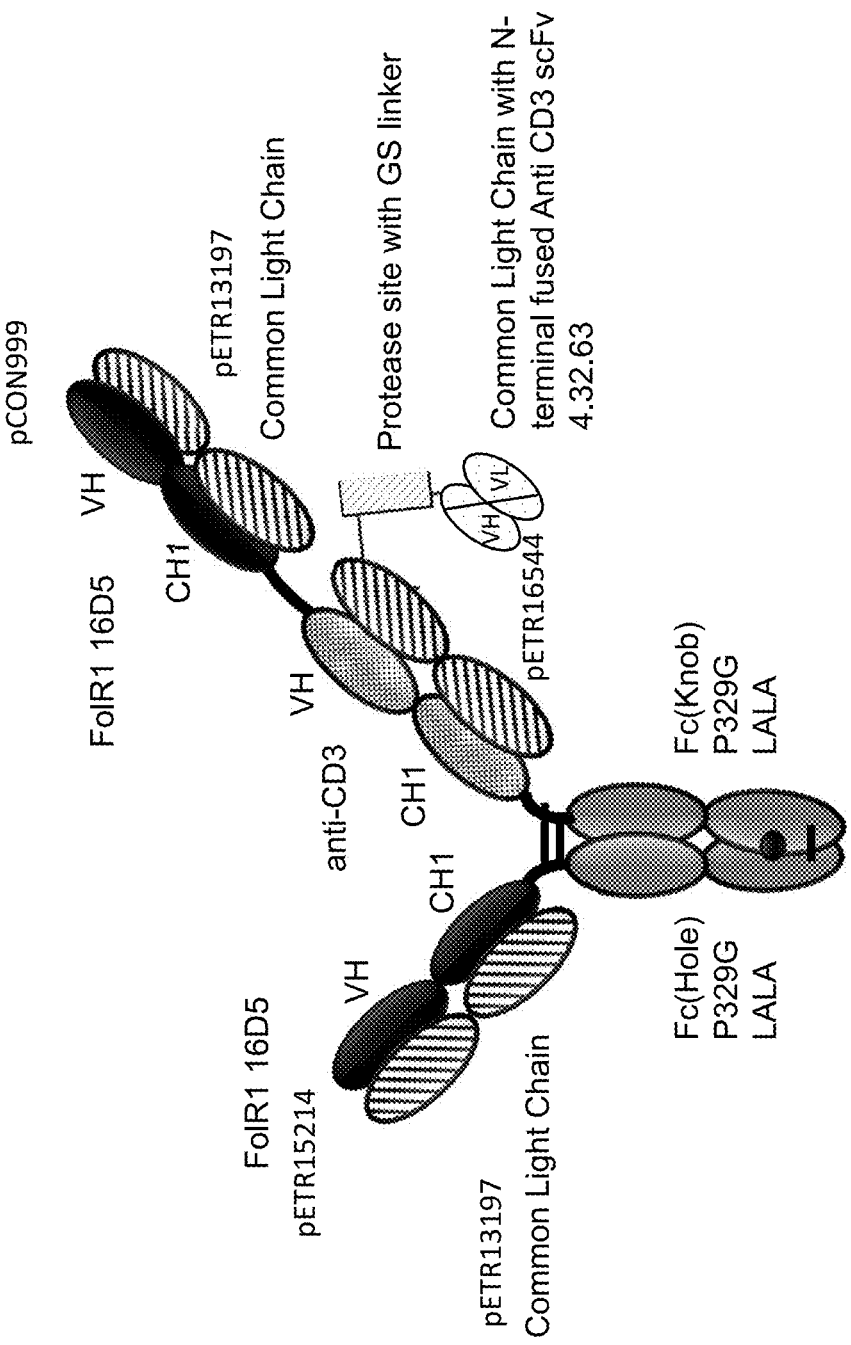
Figure 33D:
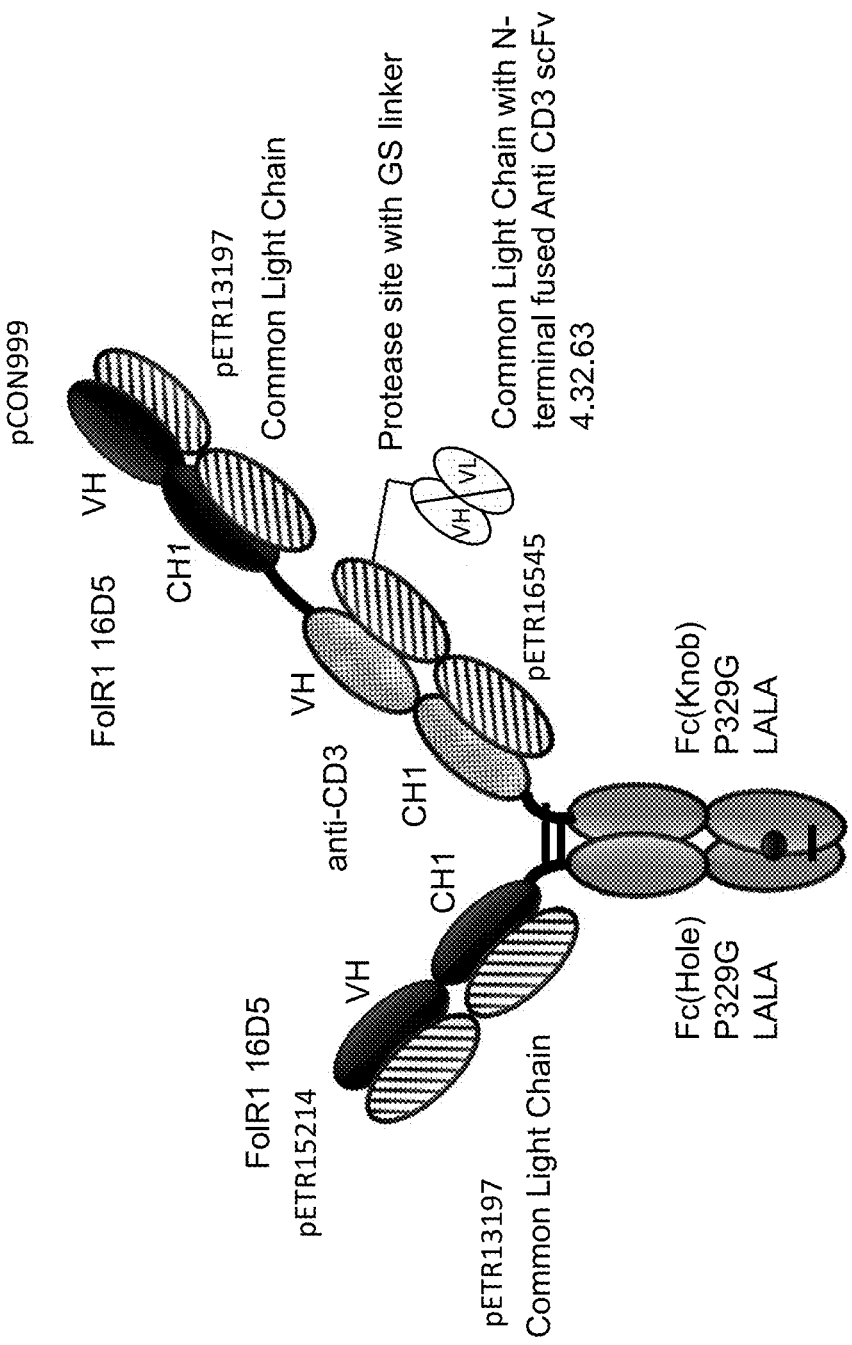
Figure 33E:
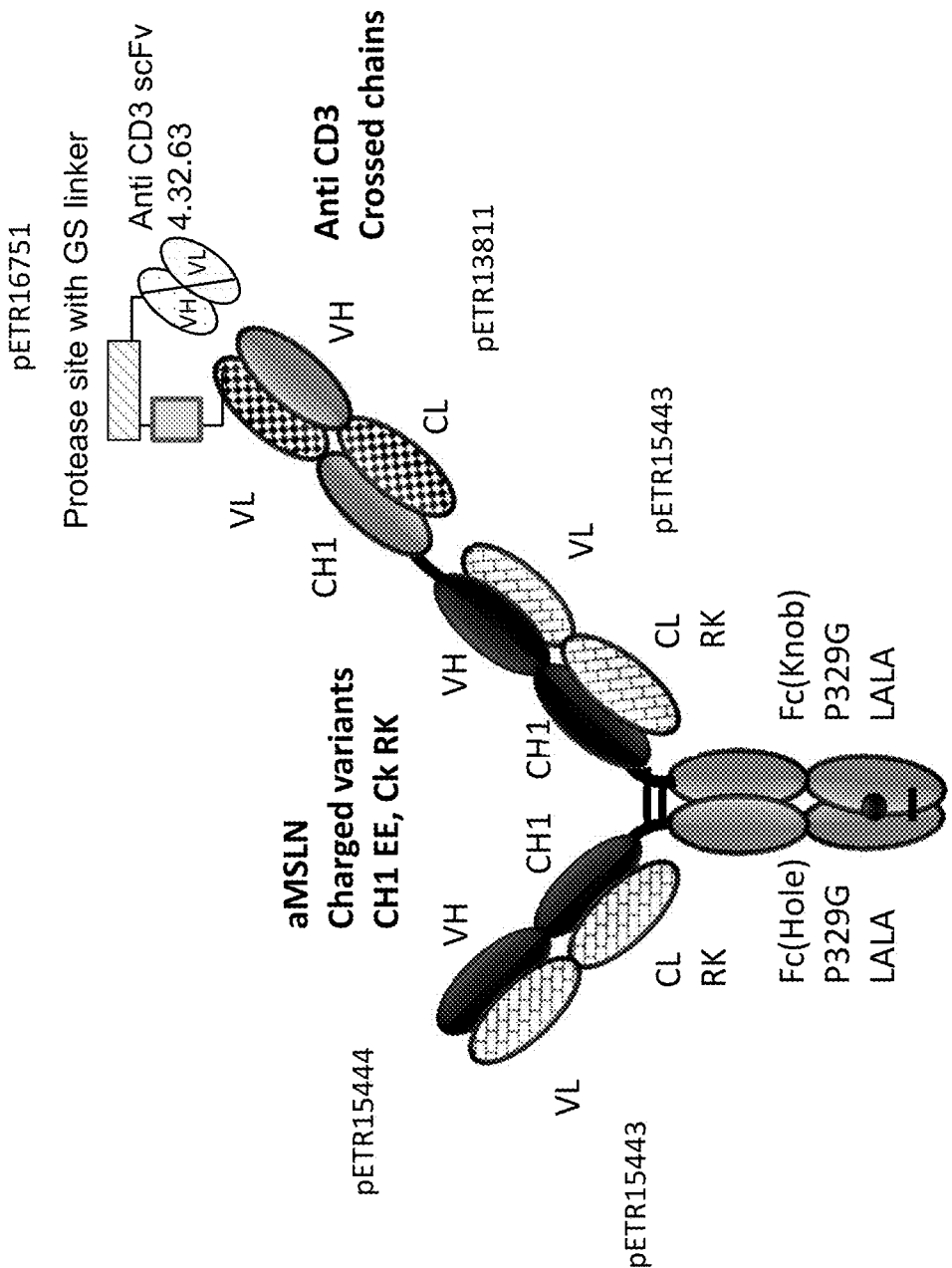
Figure 33F:
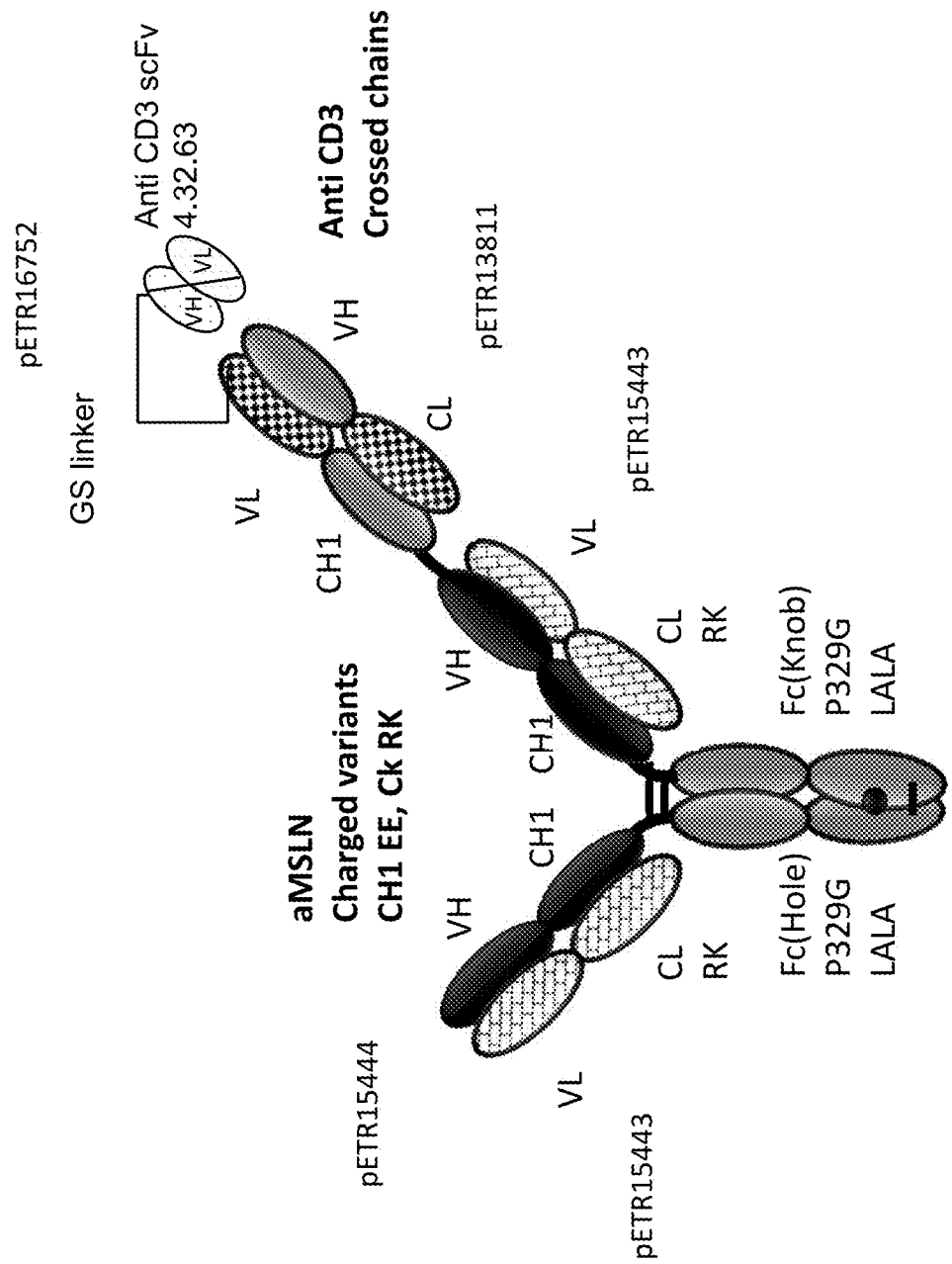
Figure 33G:
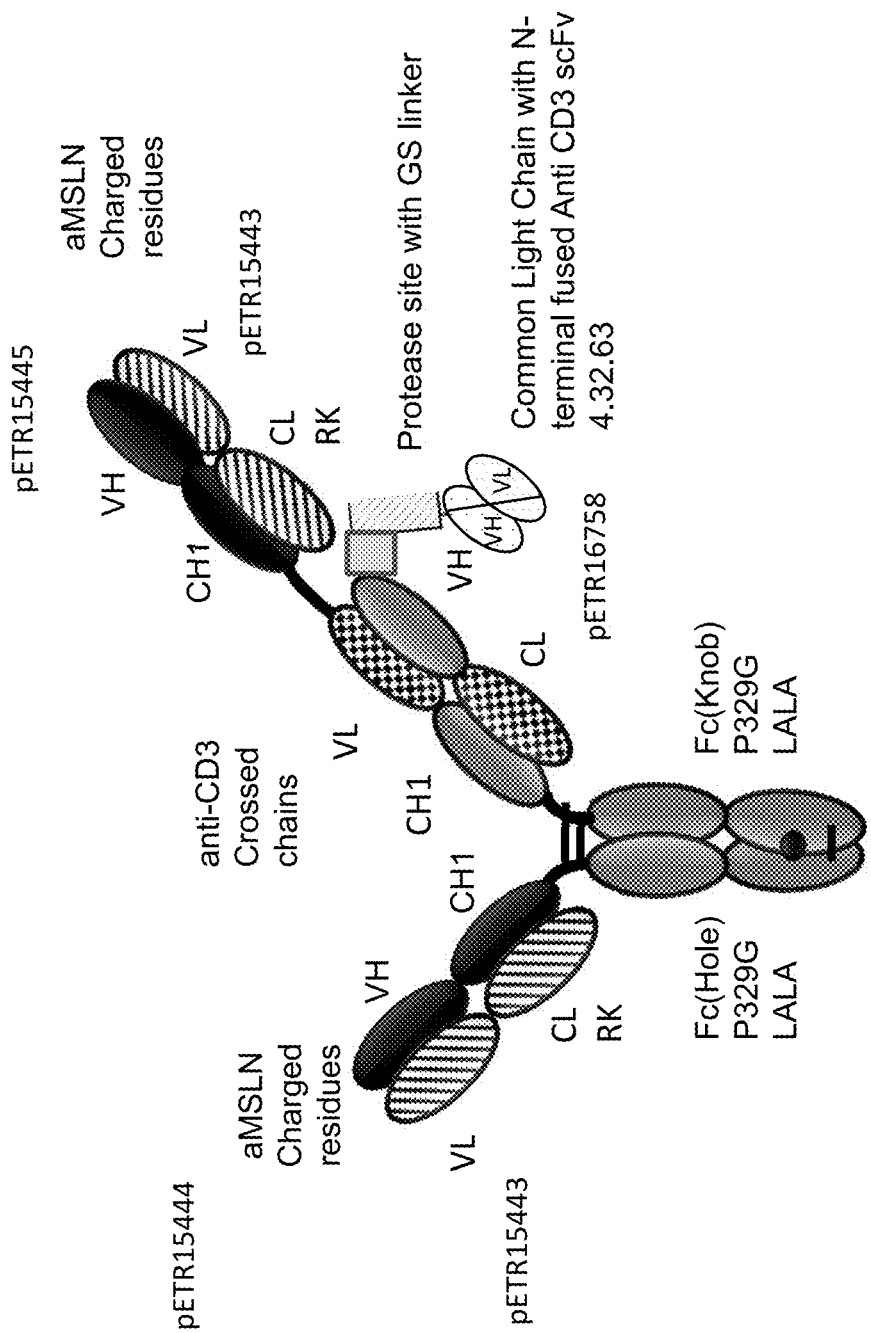
Figure 33H:
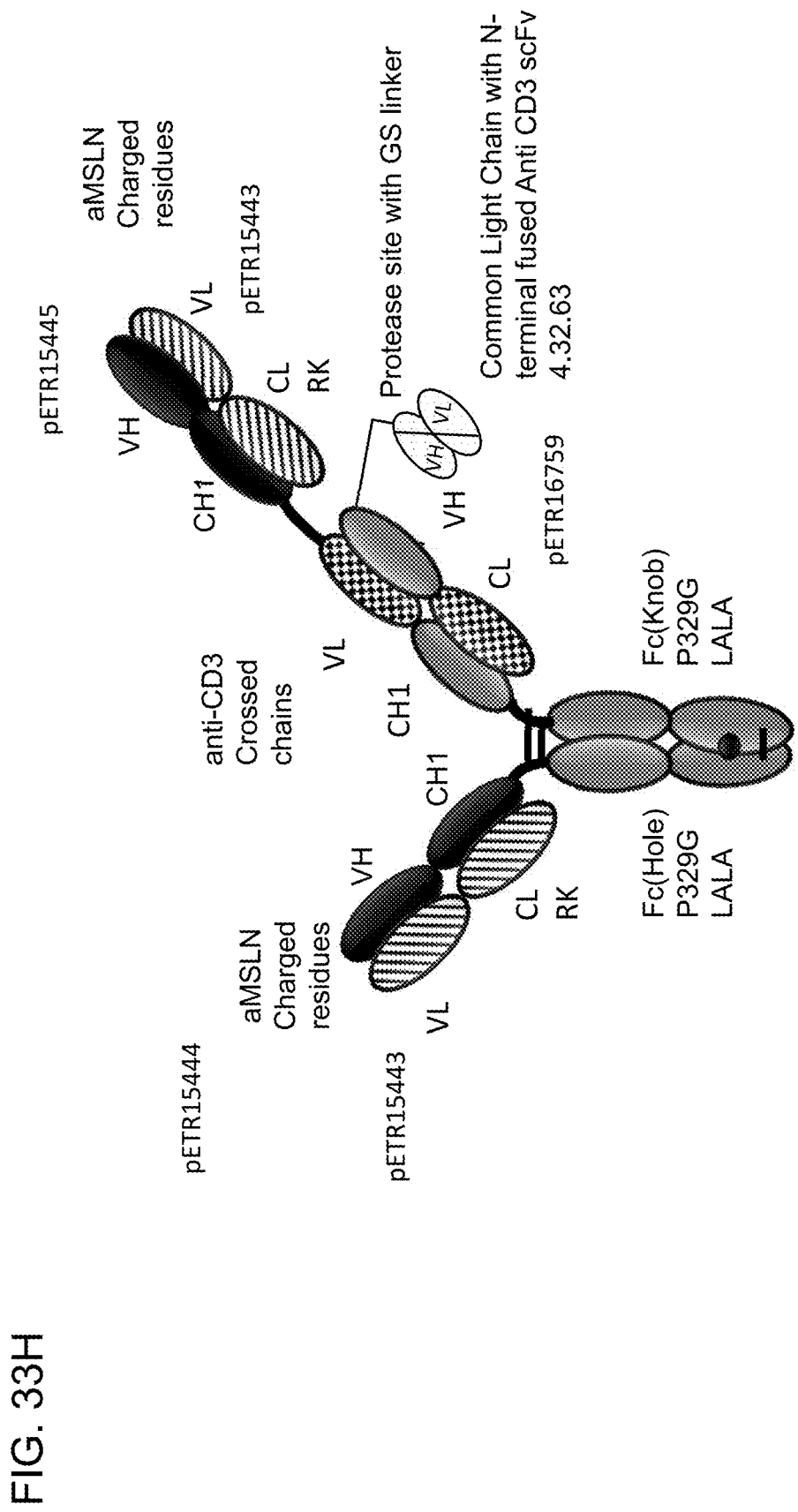
Figure 33I:
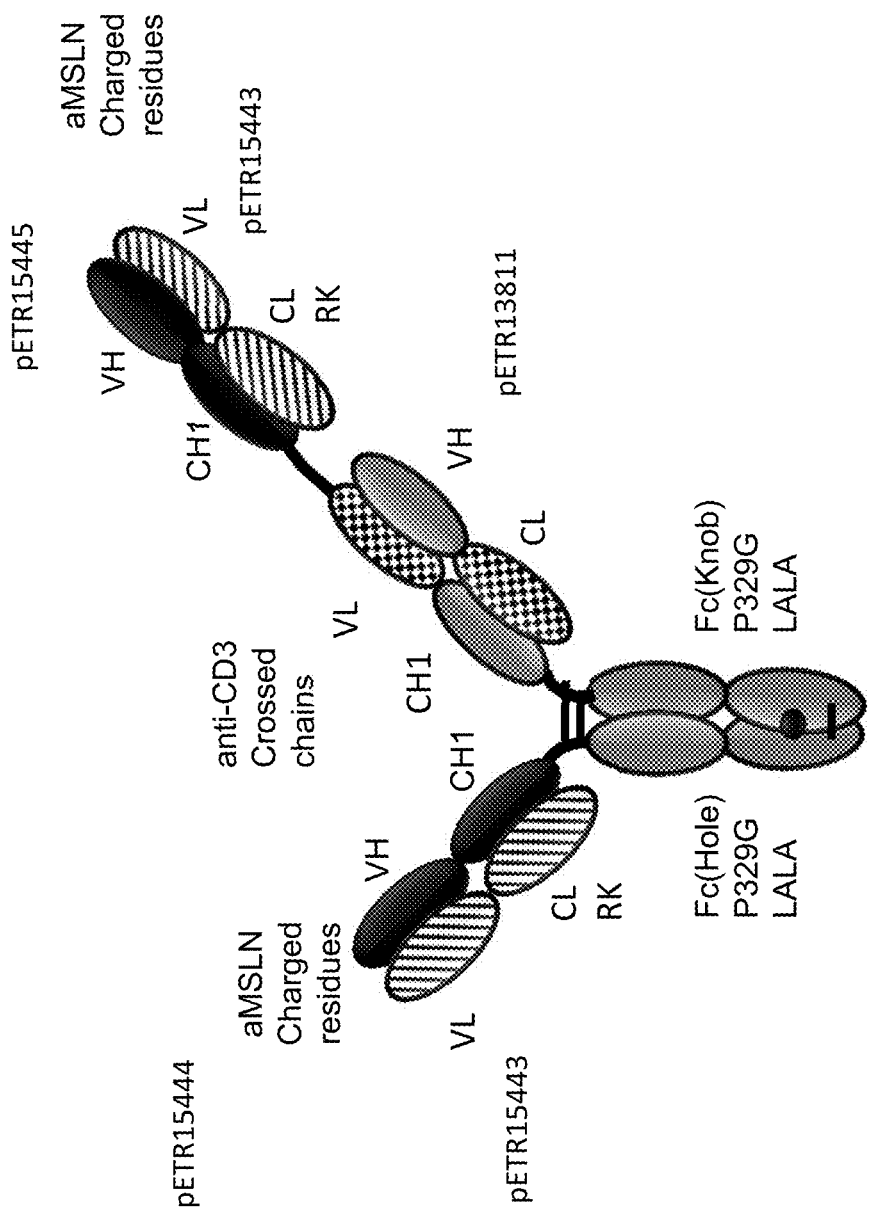
Figure 33J:
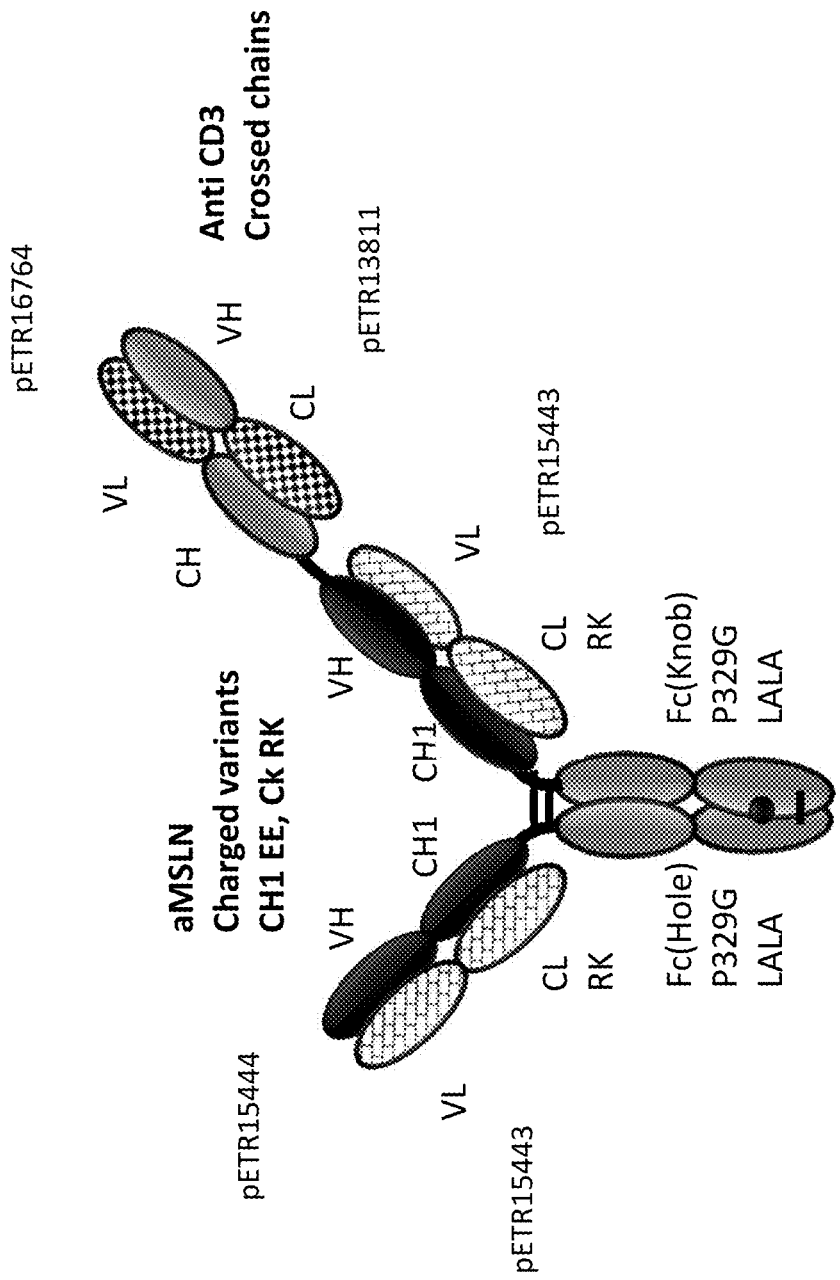

FIGS. 33A-33J depict schematics of different T cell bispecific molecules with masking moieties. FIG. 33A: ID 8364. 16D5 TCB, classic format, anti ID CH2527 scFv 4.32.63 MMP9-MK062 Matriptase site N-terminally fused to CD3. FIG. 33B: ID 8363. 16D5 TCB, classic format, anti ID CH2527 scFv 4.32.63 Cathepsin S/B site N-terminally fused to CD3. FIG. 33C: ID 8365. 16D5 TCB, inverted format, anti ID CH2527 scFv 4.32.63 MK062 Matriptase site N-terminally fused to common light chain. FIG. 33D: ID 8366. 16D5 TCB, inverted format, anti ID CH2527 scFv 4.32.63 non-cleavable linker N-terminally fused to common light chain. FIG. 33E: ID 8672. aMesothelin RG7787 charged residues TCB, classic format, anti ID CH2527 scFv 4.32.63 MMP9-MK062 Matriptase site N-terminally fused to CD3 X Fab. FIG. 33F: ID 8673. aMesothelin RG7787 charged residues TCB, classic format, anti ID CH2527 scFv 4.32.63 non-cleavable linker N-terminally fused to CD3 X Fab. FIG. 33G: ID 8674. aMesothelin RG7787 charged residues TCB, inverted format, anti ID CH2527 scFv 4.32.63 MMP9-MK062 Matriptase site N-terminally fused to CD3 XFab. FIG. 33H: 8675. aMesothelin RG7787 charged residues TCB, inverted format, anti ID CH2527 scFv 4.32.63 non-cleavable linker N-terminally fused to CD3 XFab. FIG. 33I: ID 8505. aMesothelin RG7787 charged residues CD3 XFab TCB, inverted format. FIG. 33J: ID 8676. CD3 XFab aMesothelin RG7787 charged residues TCB, classic format.

Figure 34:
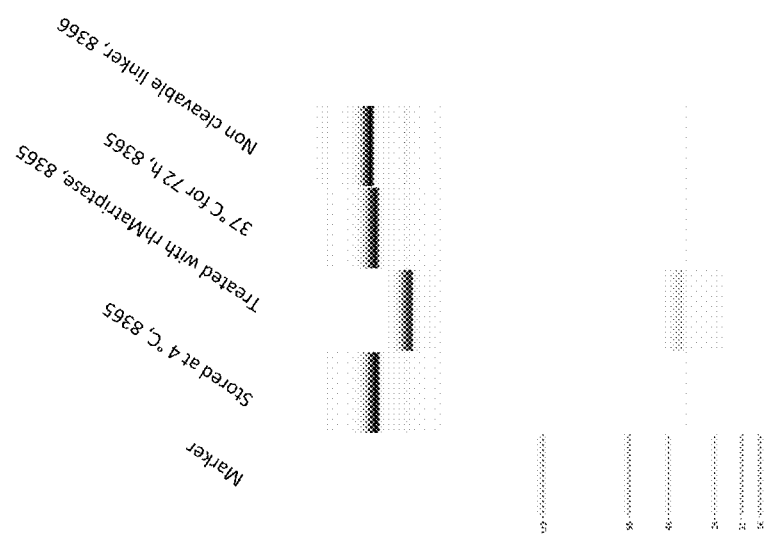

FIG. 34 depicts CE-SDS analysis of the TCB ID 8365 and TCB ID 8366 (final purified preparation): Lane A=Protein standard, lane B=protein stored at 4° C., lane C=protein pretreated with rhMatriptase/ST14 (R&D Systems), lane D=protein incubated for 72 h at 37° C. and lane E=molecule 3.

Figure 35A:
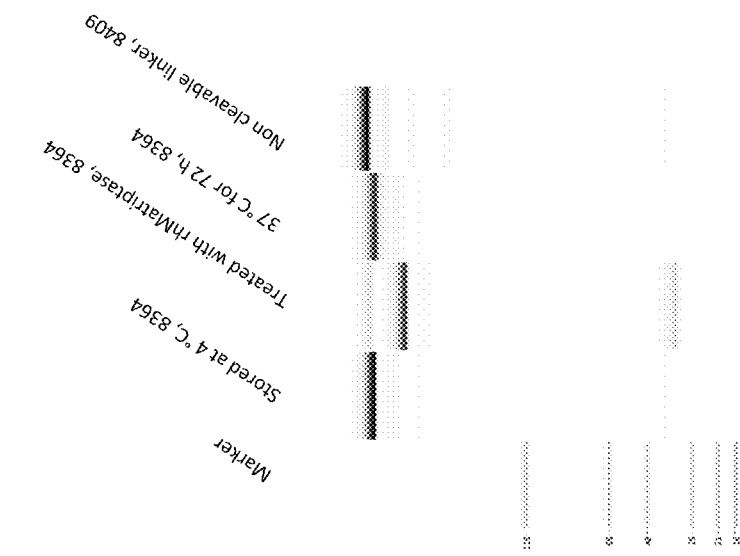
Figure 35B:
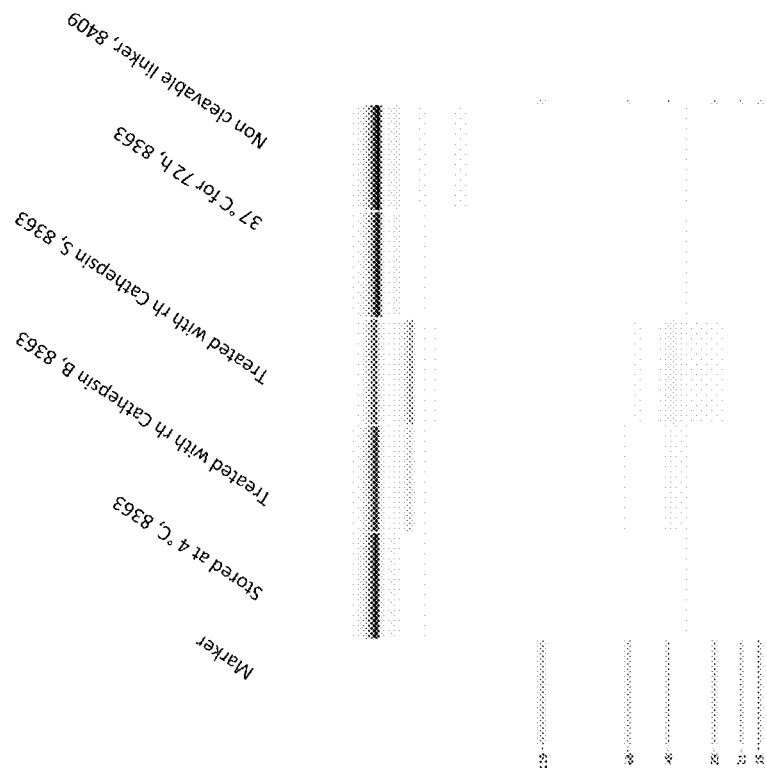

FIGS. 35A and 35B. depicts CE-SDS analysis of the TCB depicted in FIG. 33A (ID 8364) and the TCB depicted in FIG. 33B (ID 8363). FIG. 35A: CE-SDS analysis of the TCB 8364 (final purified preparation): Lane A=Protein standard, lane B=protein stored at 4° C., lane C=protein pretreated with rhMatriptase/ST14 (R&D Systems), lane D=protein incubated for 72 h at 37° C. and lane E=non-cleavable linker construct. FIG. 35B: CE-SDS analysis of the TCB 8363 (final purified preparation): Lane A=Protein standard, lane B=protein stored at 4° C., lane C=protein pretreated with rhCathepsin B (R&D Systems), lane D=protein pretreated with rhCathepsin S (R&D Systems), lane E=protein incubated for 72 h at 37° C. and lane F=non-cleavable linker construct.

Figure 36A:
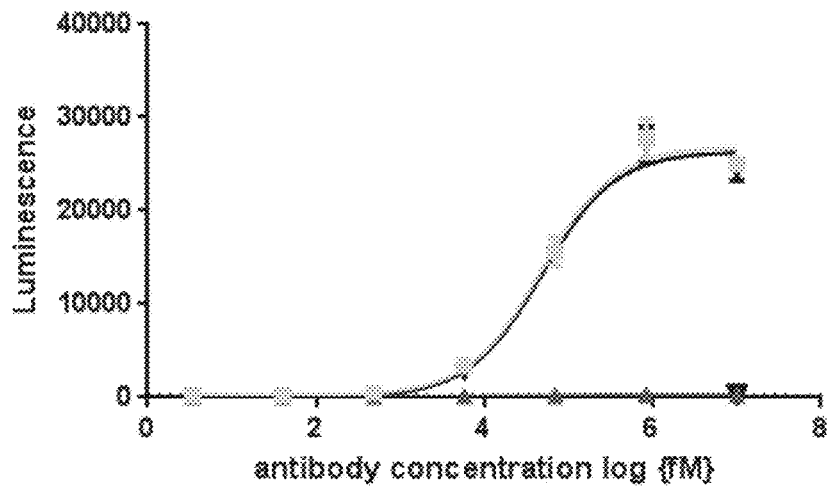
Figure 36A:
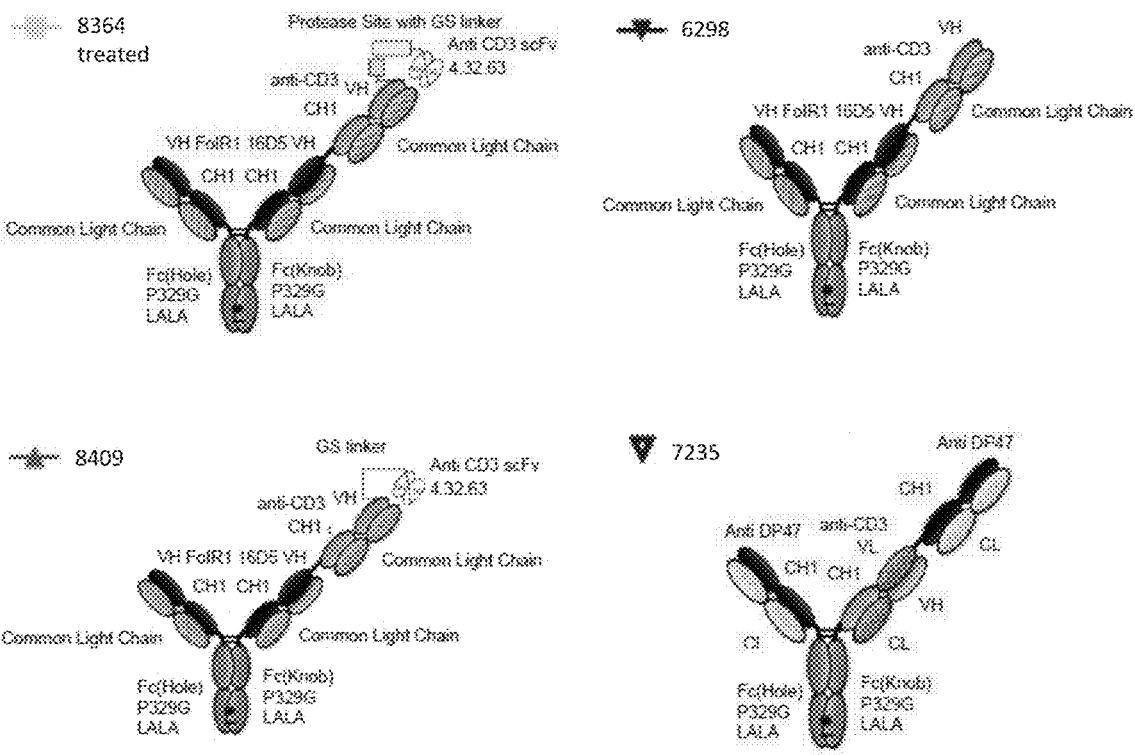
Figure 36B:
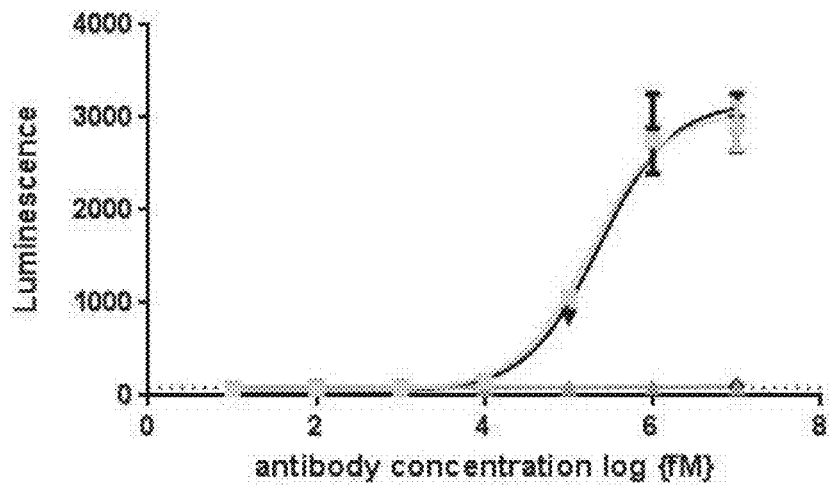
Figure 36B:
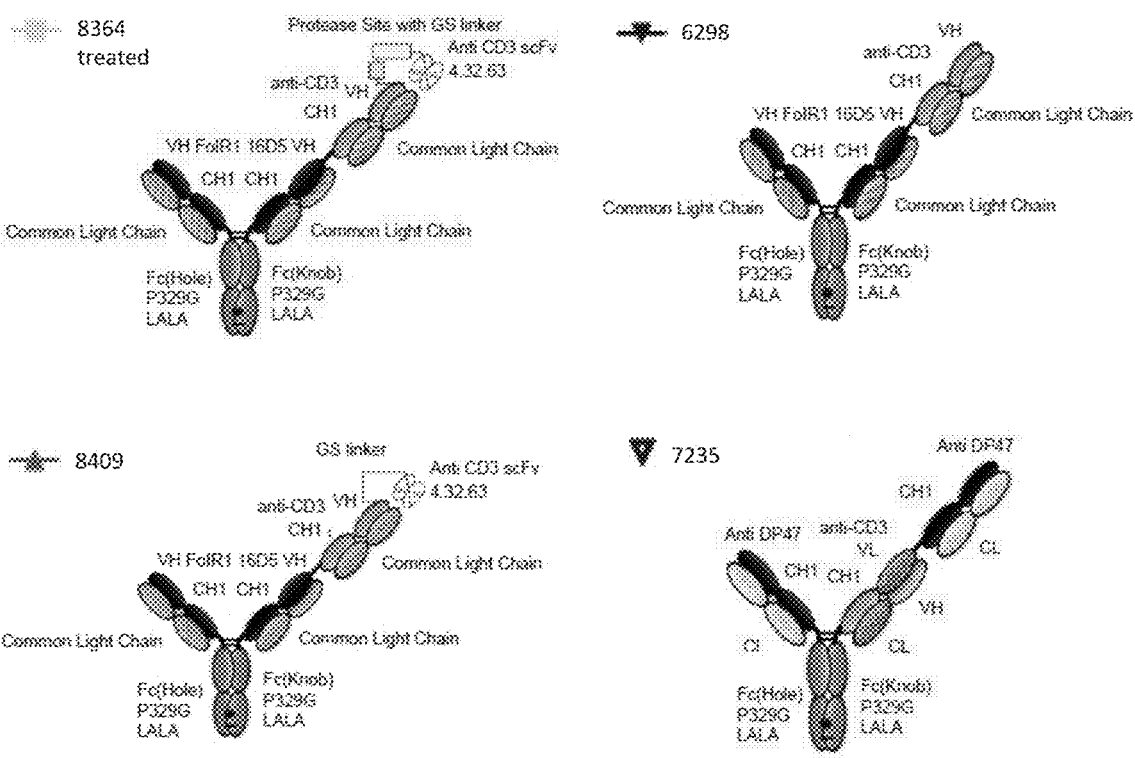

FIGS. 36A and 36B. depicts Jurkat NFAT activation assay using HeLa and Skov-3 cells as target cells. Each point represents the mean value of triplicates. Standard deviation is indicated by error bars. Jurkat-NFAT reporter cell line (Promega) is a human acute lymphatic leukemia reporter cell line with a NFAT promoter, expressing human CD3e. If the CD3 binder of the TCB binds the tumor target and the CD3 (cross-linkage is necessary) binds CD3ε the Luciferase expression can be measured in Luminescence after addition of One-Glo substrate (Promega). The FolR1 TCB (black triangles pointing down) and the pretreated protease activated TCB (8364, grey filled squares) with N-terminally fused anti ID CD3 4.32.63 scFv and MMP9-Matriptase MK062 site were compared. The molecule was treated with rhMatriptase/ST14 (R&D Systems) for about 20 h at 37° C. The masked TCB (containing a GS non-cleavable linker, grey triangles pointing up) and the non-targeted TCB control (empty triangle pointing down) are shown as well. The dotted line shows the Luminescence of target cells and effector cells without any TCB.

FIG. 36A shows a Jurkat NFAT activation assay using HeLa cells as target cells.

FIG. 36B shows a Jurkat NFAT activation assay using Skov-3 cells as target cells.

Figure 37A:
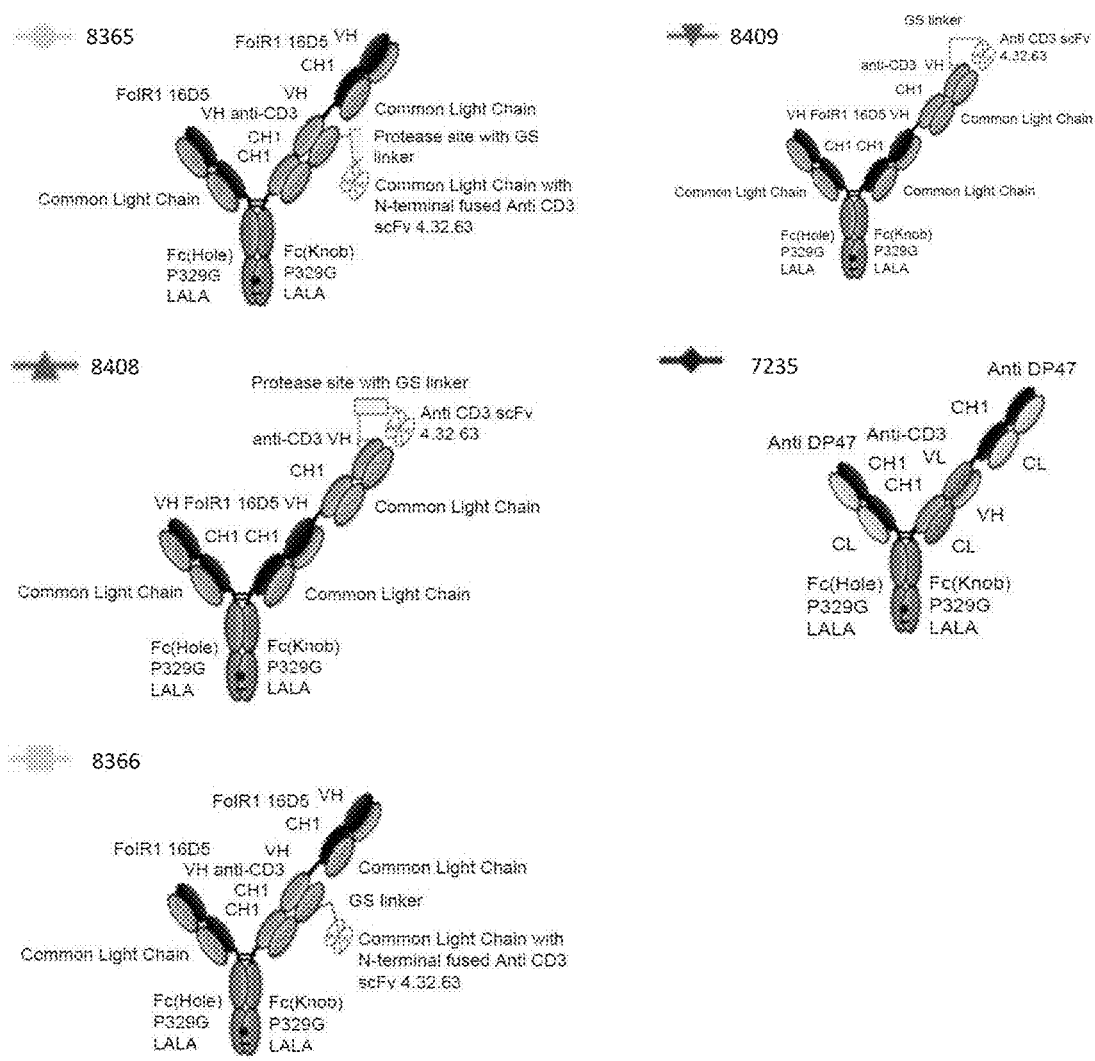
Figure 37B:
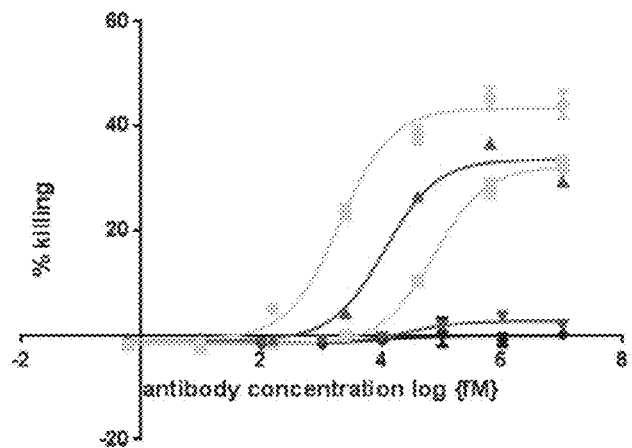
Figure 37B:
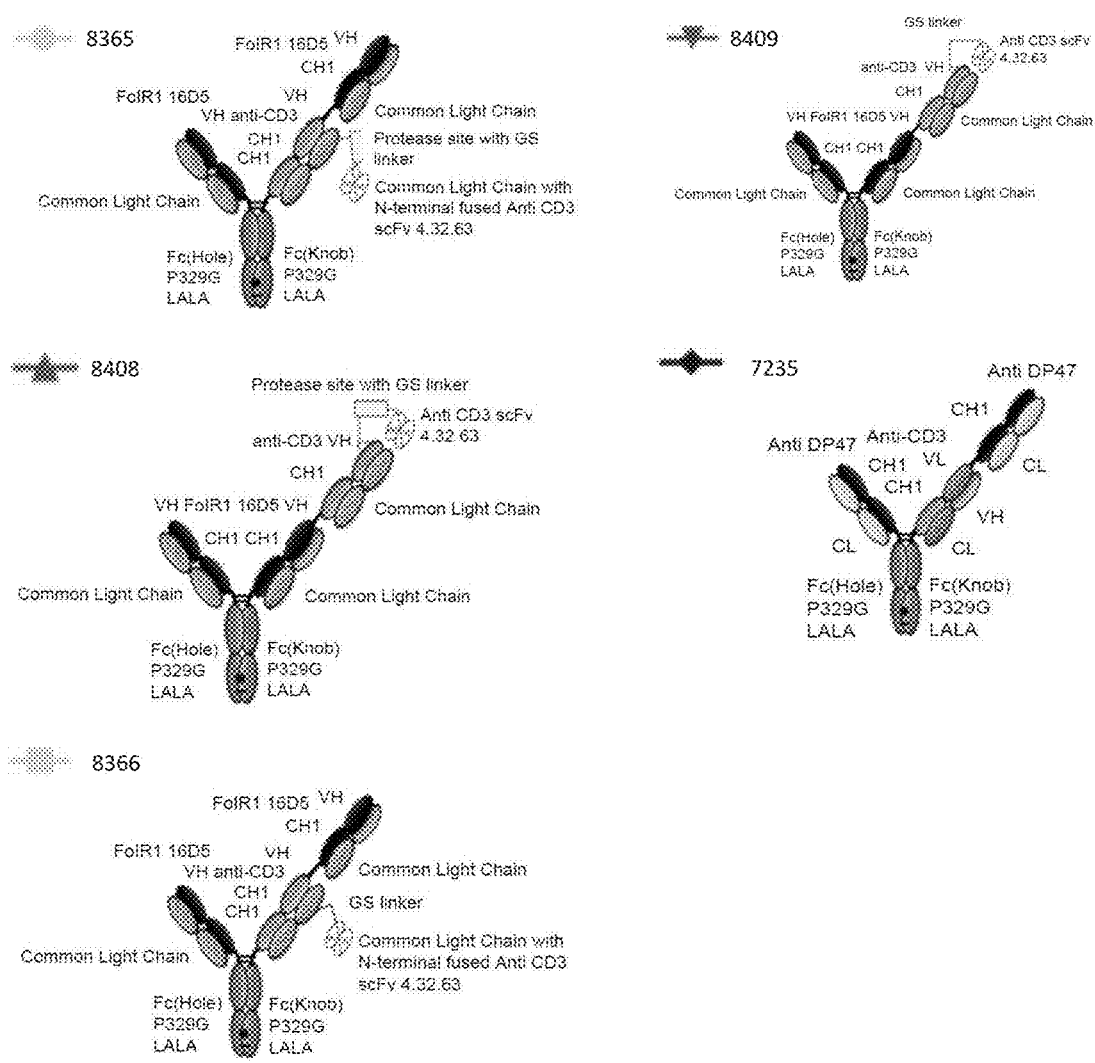
Figure 37C:
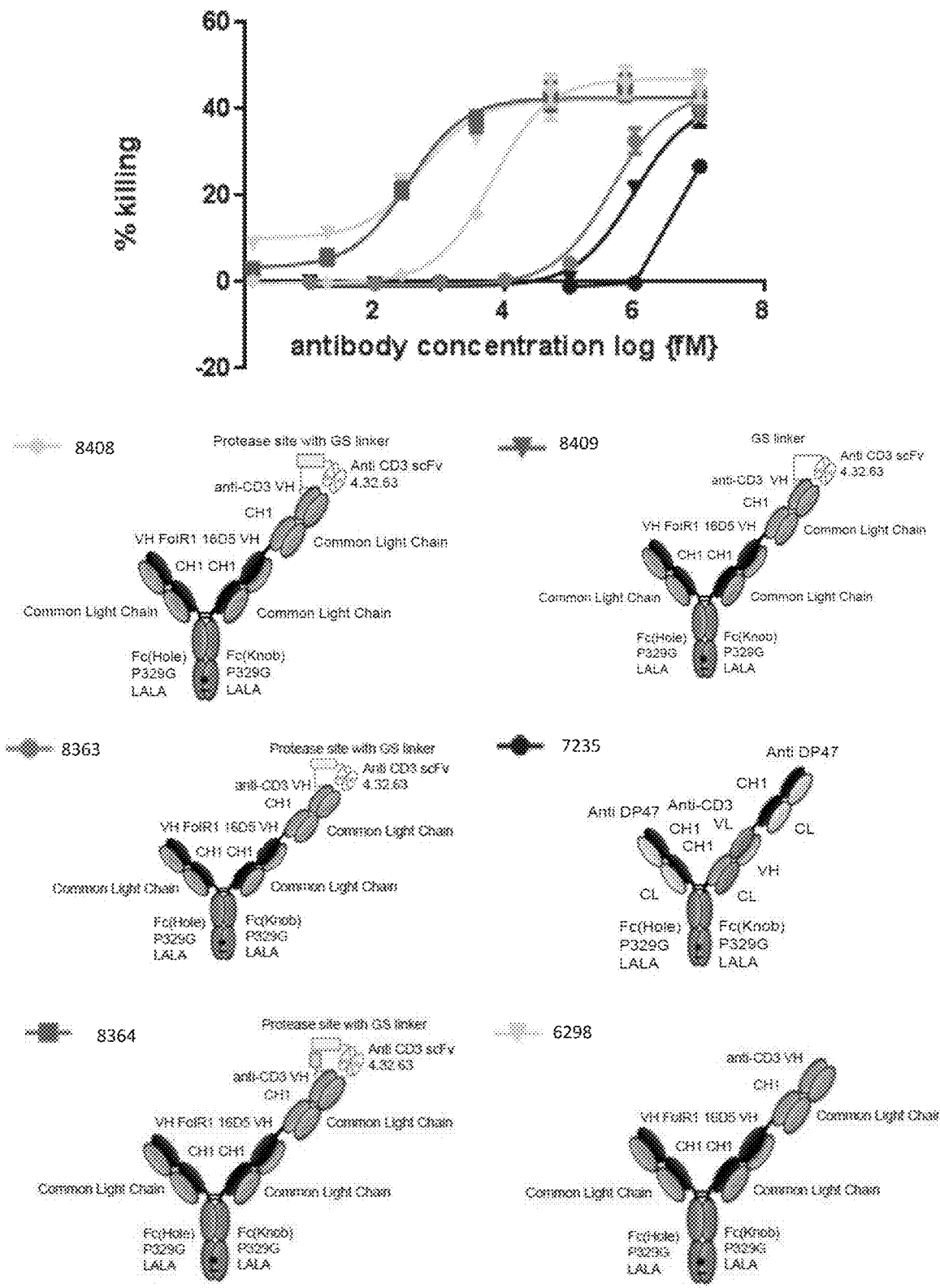
Figure 37D:
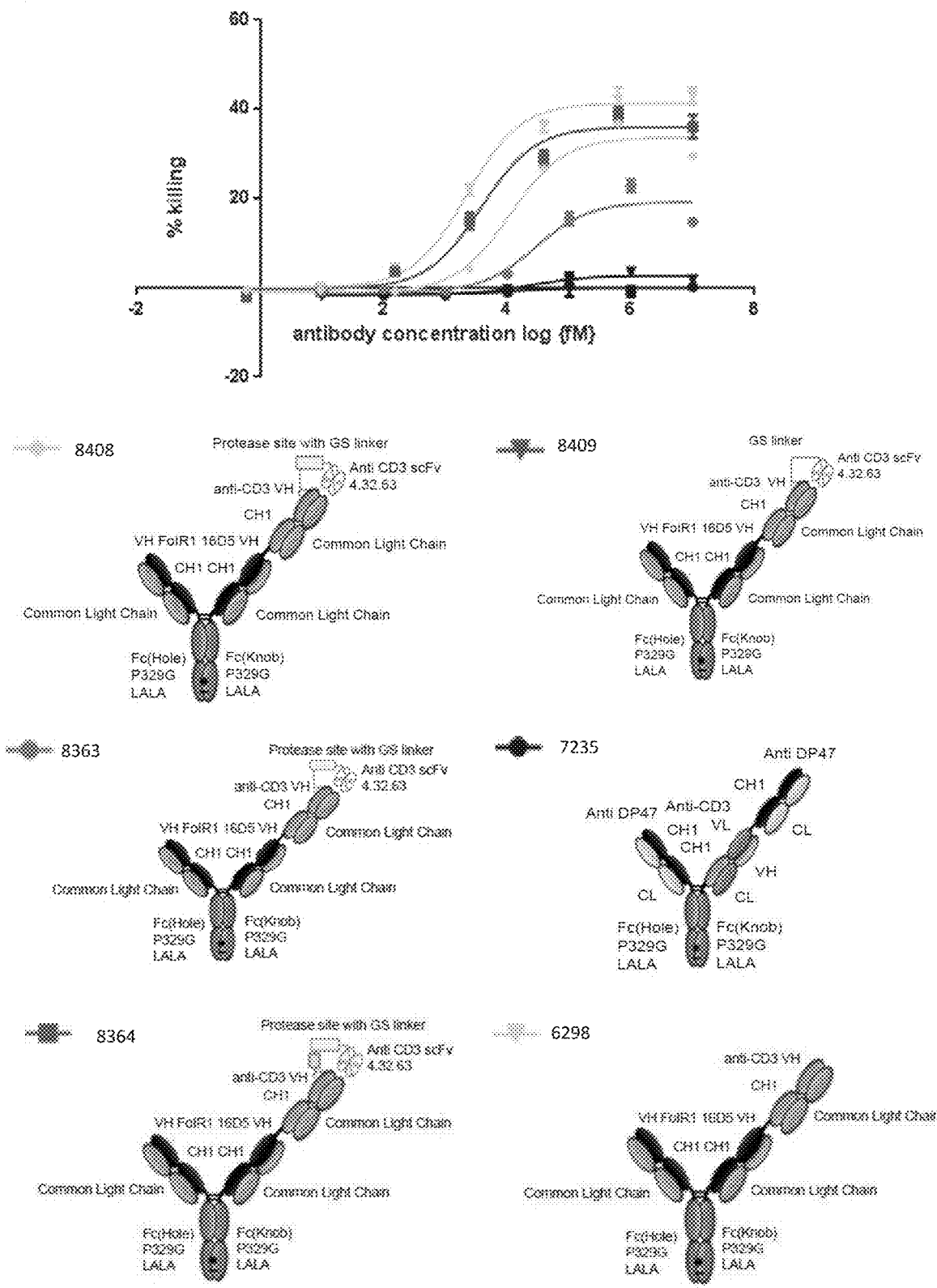

FIGS. 37A-37D depict tumor cell cytotoxicity mediated by FolR1 TCBs and human PBMCs (Effector:Target=10:1). Each point represents the mean value of triplicates. Standard deviation is indicated by error bars. FIG. 37A: HeLa target cell cytotoxicity. Comparison of two different formats of the Protease activated TCBs both containing an anti idiotypic CD3 scFv linked with a MK062 Matriptase linker. FIG. 37B: Skov-3 target cell cytotoxicity. Comparison of two different formats of the Protease activated TCBs both containing an anti idiotypic CD3 scFv linked with a MK062 Matriptase linker. FIG. 37C: HeLa target cell cytotoxicity. Comparison of classic Protease activated TCB containing an anti idiotypic CD3 scFv and GS linkers with different protease sites. Protease activated TCB containing the MMP9-Matriptase MK062 linker (8364, grey squares), FolR1 TCB (light grey triangles pointing down), protease activated TCB containing only Matriptase MK062 (light grey rhomb)/Cathepsin site (grey circles) or non-cleavable linker (black triangles pointing down). FIG. 37D: Skov-3 target cell cytotoxicity. Comparison of classic Protease activated TCB containing an anti idiotypic CD3 scFv and GS linkers with different protease sites. Protease activated TCB containing the MMP9-Matriptase MK062 linker (8364, grey squares), FolR1 TCB (light grey triangles pointing down), protease activated TCB containing only Matriptase MK062 (light grey rhomb)/Cathepsin site (grey circles) or non-cleavable linker (black triangles pointing down).

Figure 38A:
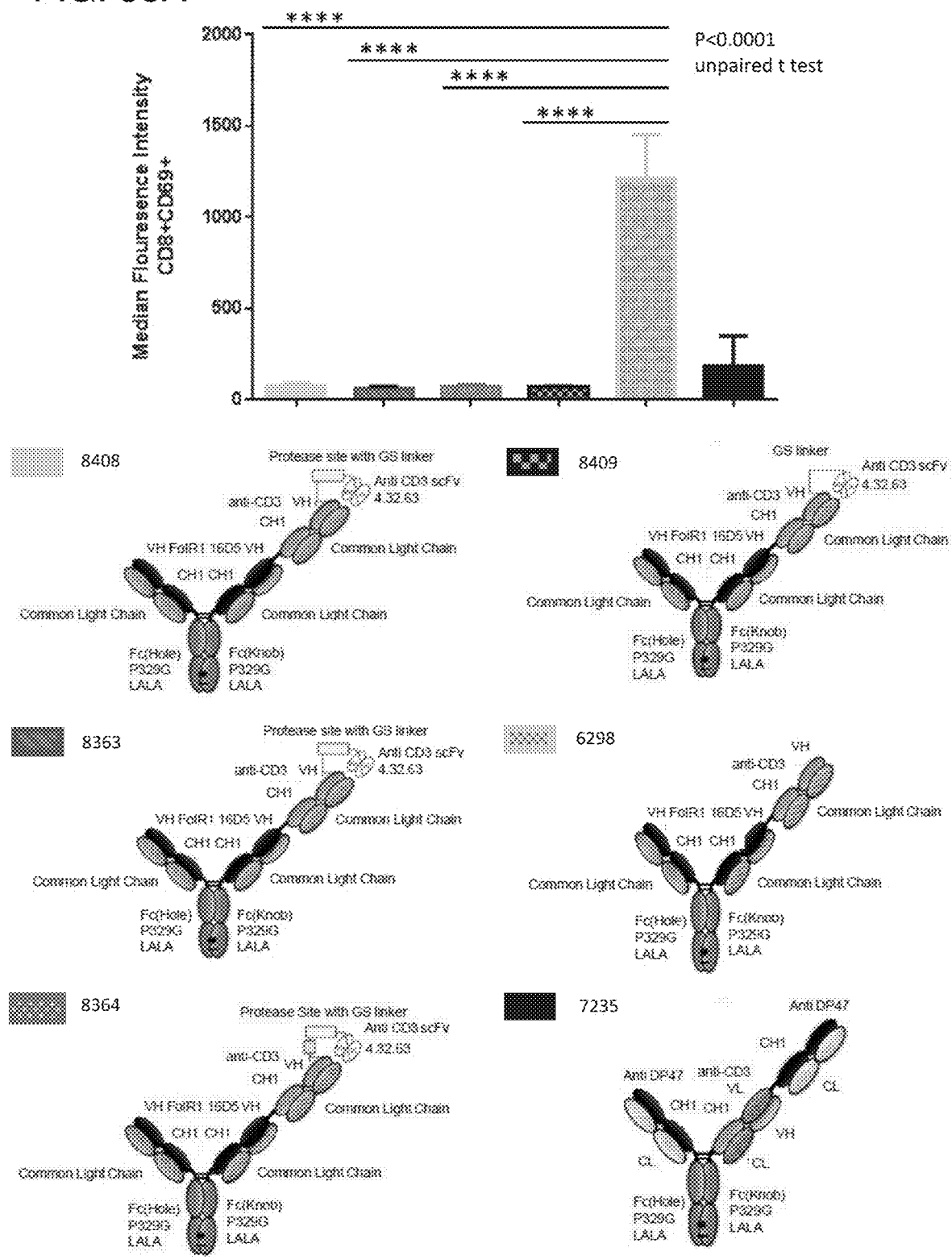
Figure 38B:
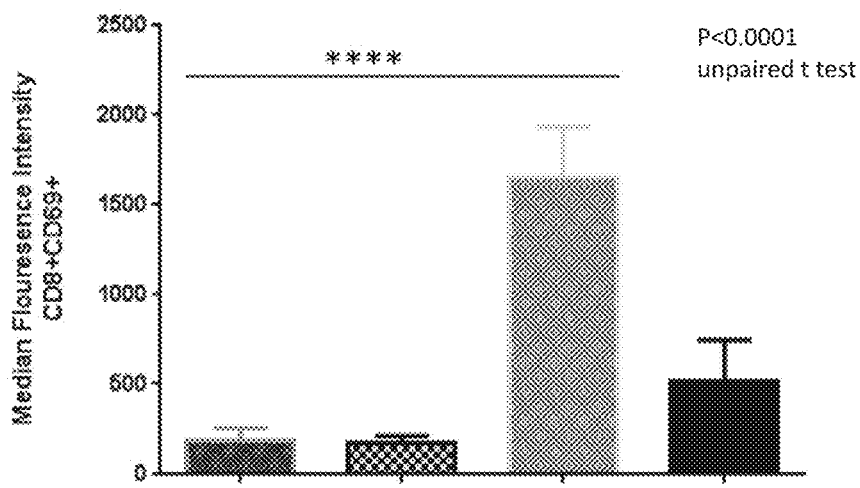
Figure 38B:
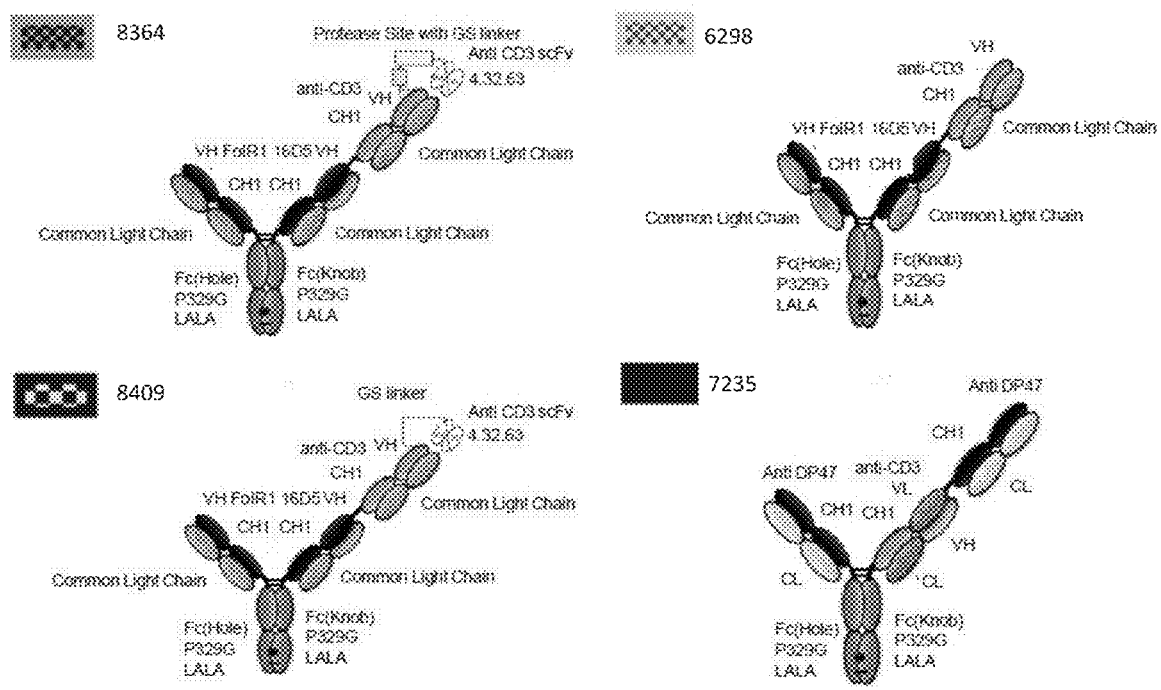

FIGS. 38A and 38B depict quantification of CD69 of CD8 positive cells after co-incubation of primary human renal epithelial cortical cells (FIG. 38A) or human bronchial epithelial cells (FIG. 38B) with 200 nM of the different TCBs and three different donors of human PBMCs. T cells were stained after 48 h of incubation. (E:T=10:1, effectors are human PBMCs). Median fluorescence intensity of T cell activation marker CD69 for CD8' T cells is shown. Each point represents the mean value of triplicates of three different human PBMC donors. Standard deviation is indicated in error bars. Unpaired t test was used for statistical analysis.

Figure 39A:
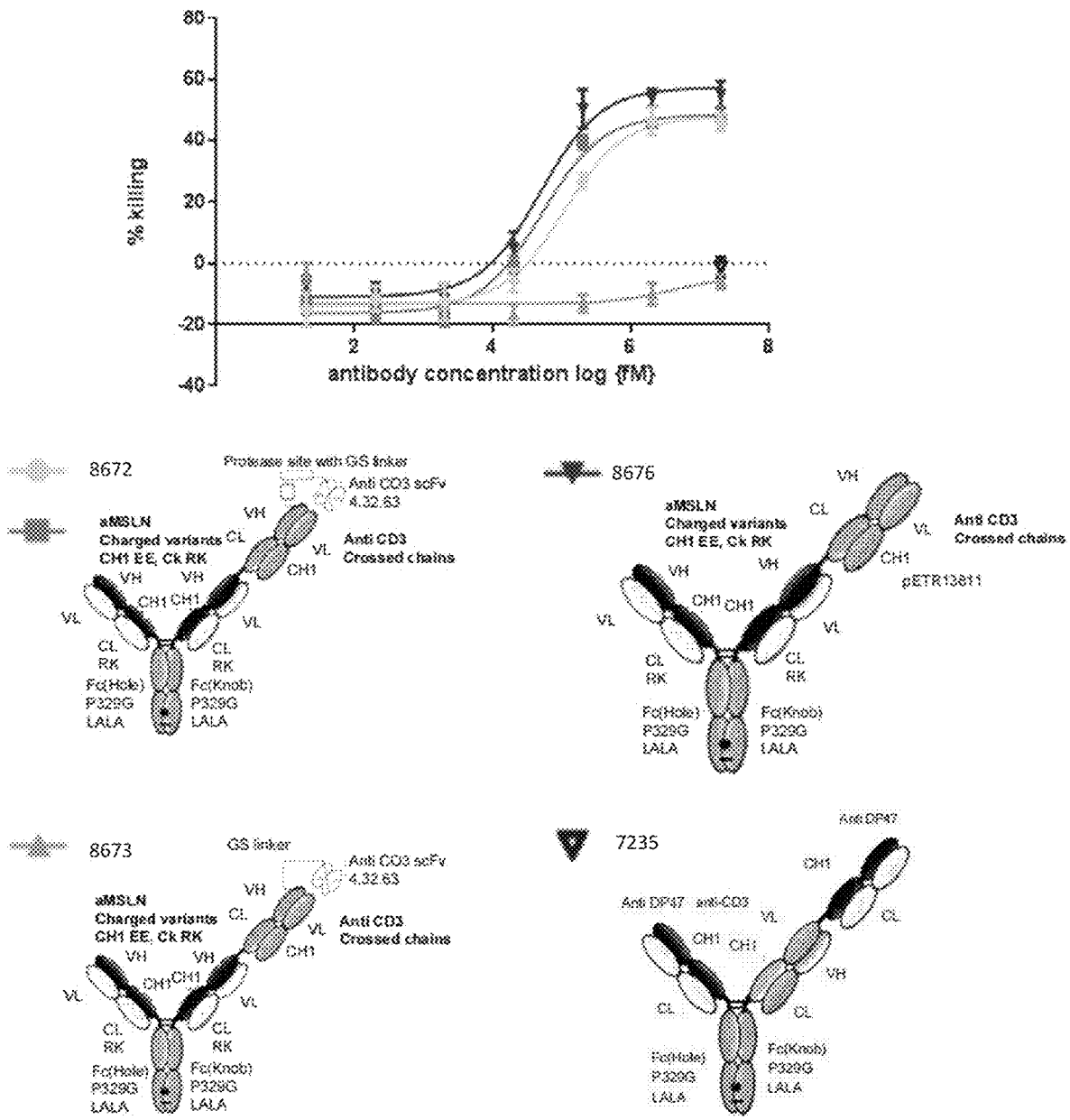
Figure 39B:
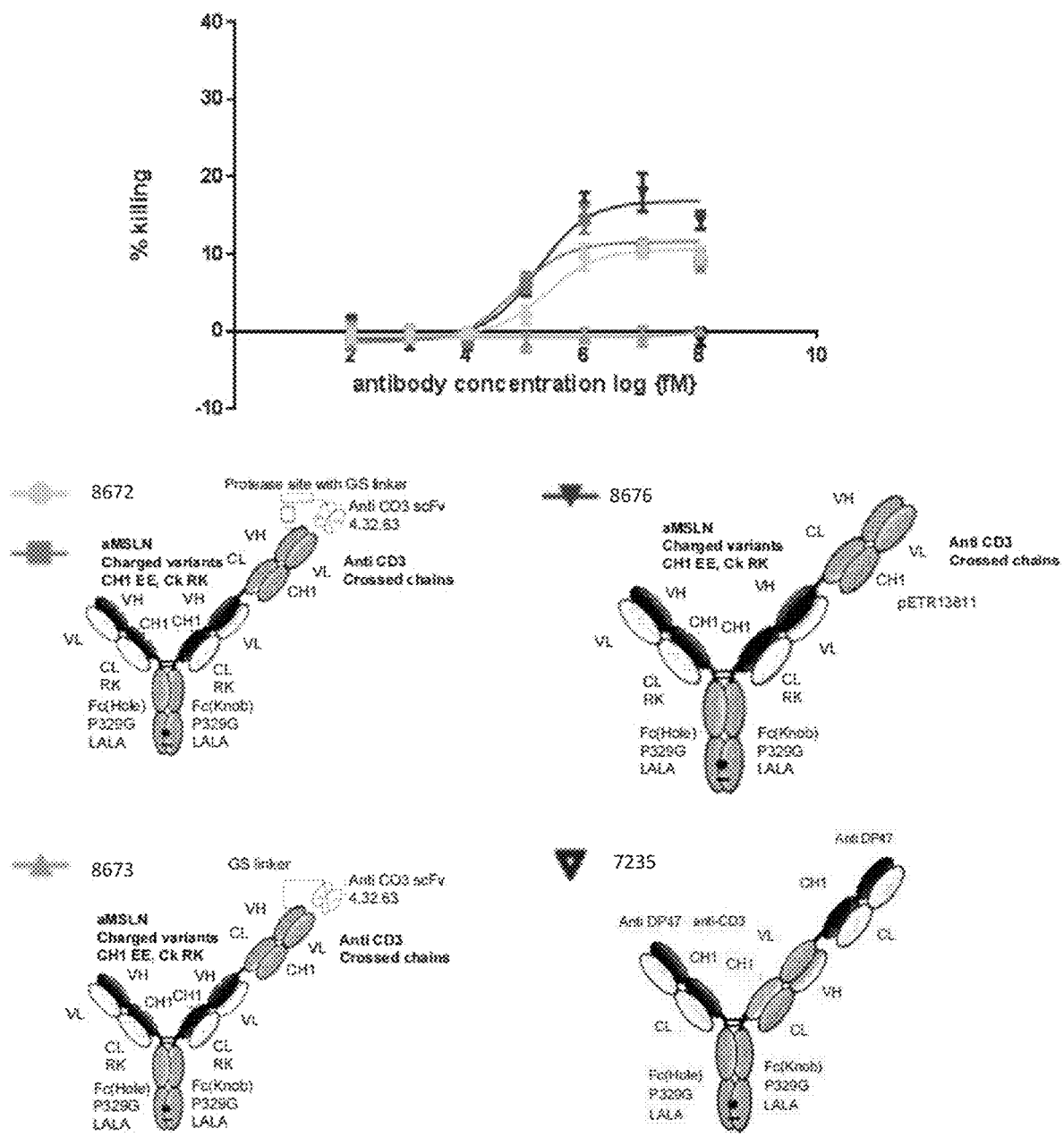

FIGS. 39A and 39B depict tumor cell cytotoxicity mediated by MSLN TCBs and human PBMCs (Effector:Target=10:1). Maximal lysis of the target cells (=100%) was achieved by incubation of target cells with 1% Triton X-100 20 h before LDH readout. Minimal lysis (=0%) refers to target cells co-incubated with effector cells without any TCB. Each point represents the mean value of triplicates. Standard deviation is indicated by error bars. FIG. 39A: NCI H5% target cell cytotoxicity. Protease activated MSLN TCB containing an anti idiotypic CD3 scFv linked with a MMP9-MK062 Matriptase linker. The protease activated TCB (8672, light grey circles), the MSLN TCB (dark grey triangles pointing down) and the protease activated TCB containing a non-cleavable linker (8673, grey triangles pointing up) are compared. FIG. 39B: AsPC-1 target cell cytotoxicity. Protease activated MSLN TCB containing an anti idiotypic CD3 scFv linked with a MMP9-MK062 Matriptase linker. The protease activated TCB (8672, light grey circles), the MSLN TCB (dark grey triangles pointing down) and the protease activated TCB containing a non-cleavable linker (8673, grey triangles pointing up) are compared.

Figure 40:
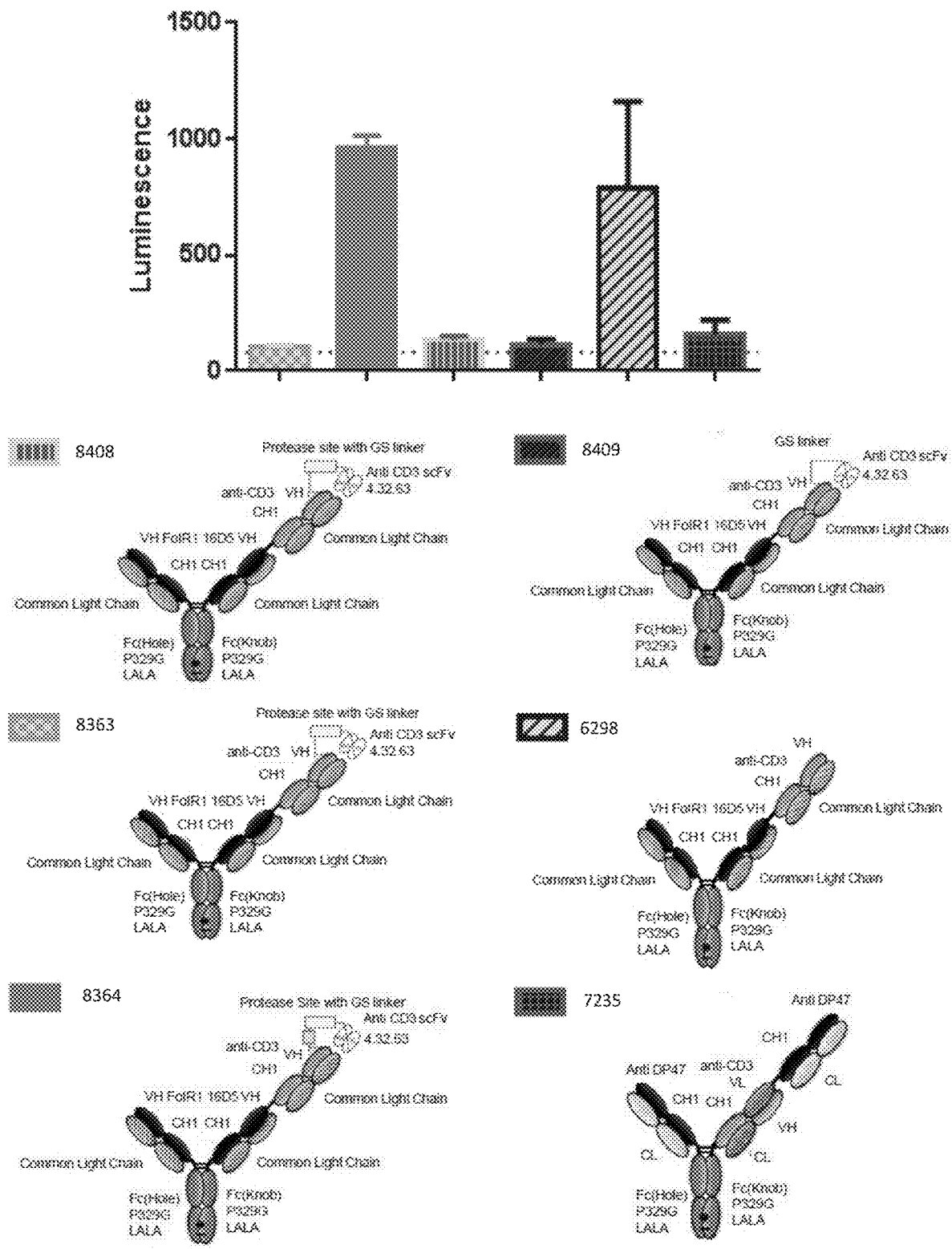

FIG. 40 depicts a Jurkat-NFAT activation assay with primary tumor samples and Protease activated FolR1 TCBs. Jurkat NFAT reporter cells are activated after co-incubation with FolR1 TCB (6298) and Protease activated FolR1 TCB containing MMP9-Matriptase cleavage site (8364). Protease activated FolR1 TCBs (8363, 8408) and control TCBs (8409, 7235) do not induce Luciferase expression. The dotted line indicates the baseline Luminescence for Jurkat NFAT cells co-incubated with tumor.

Figure 41A:
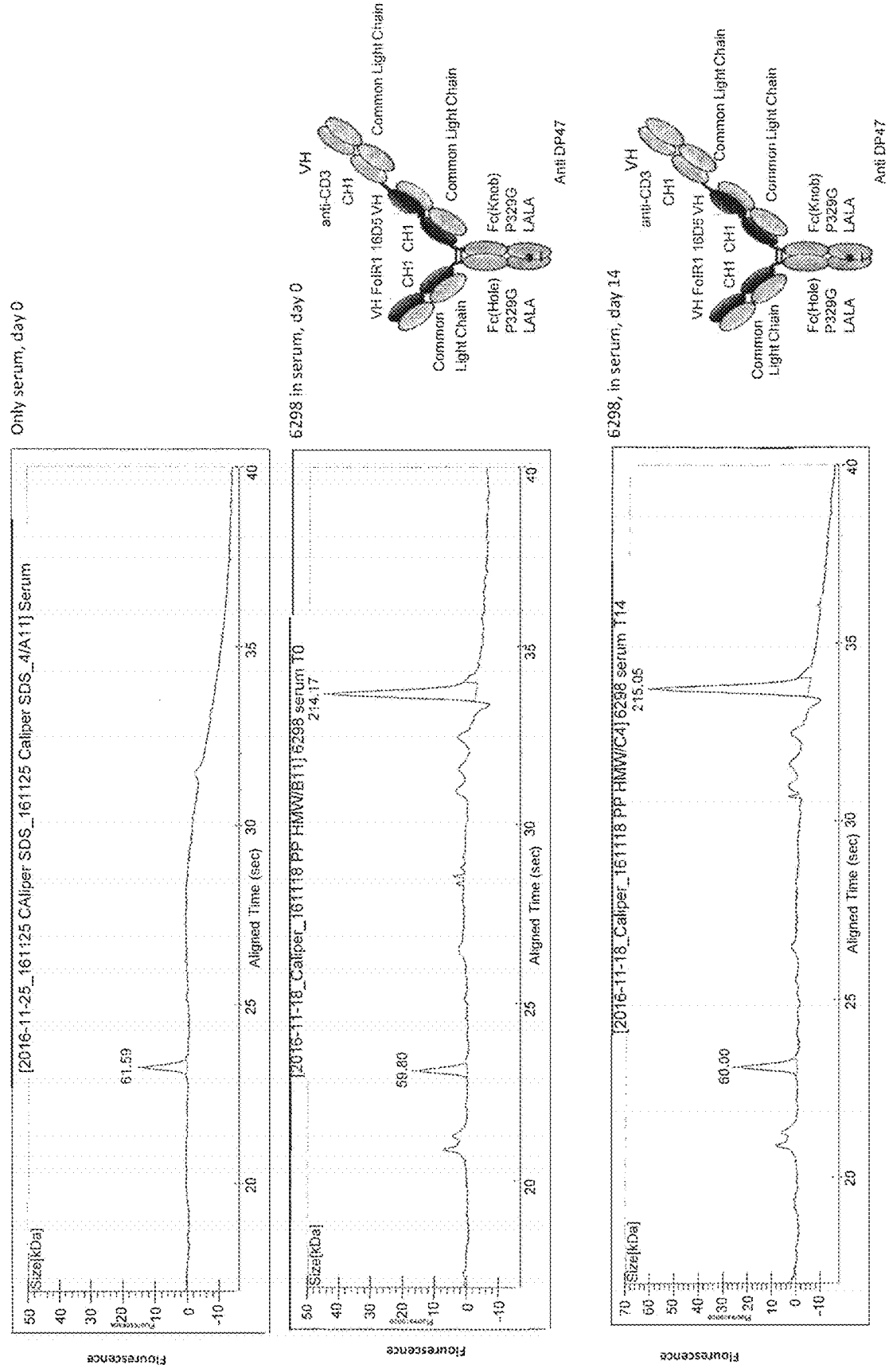
Figure 41B:
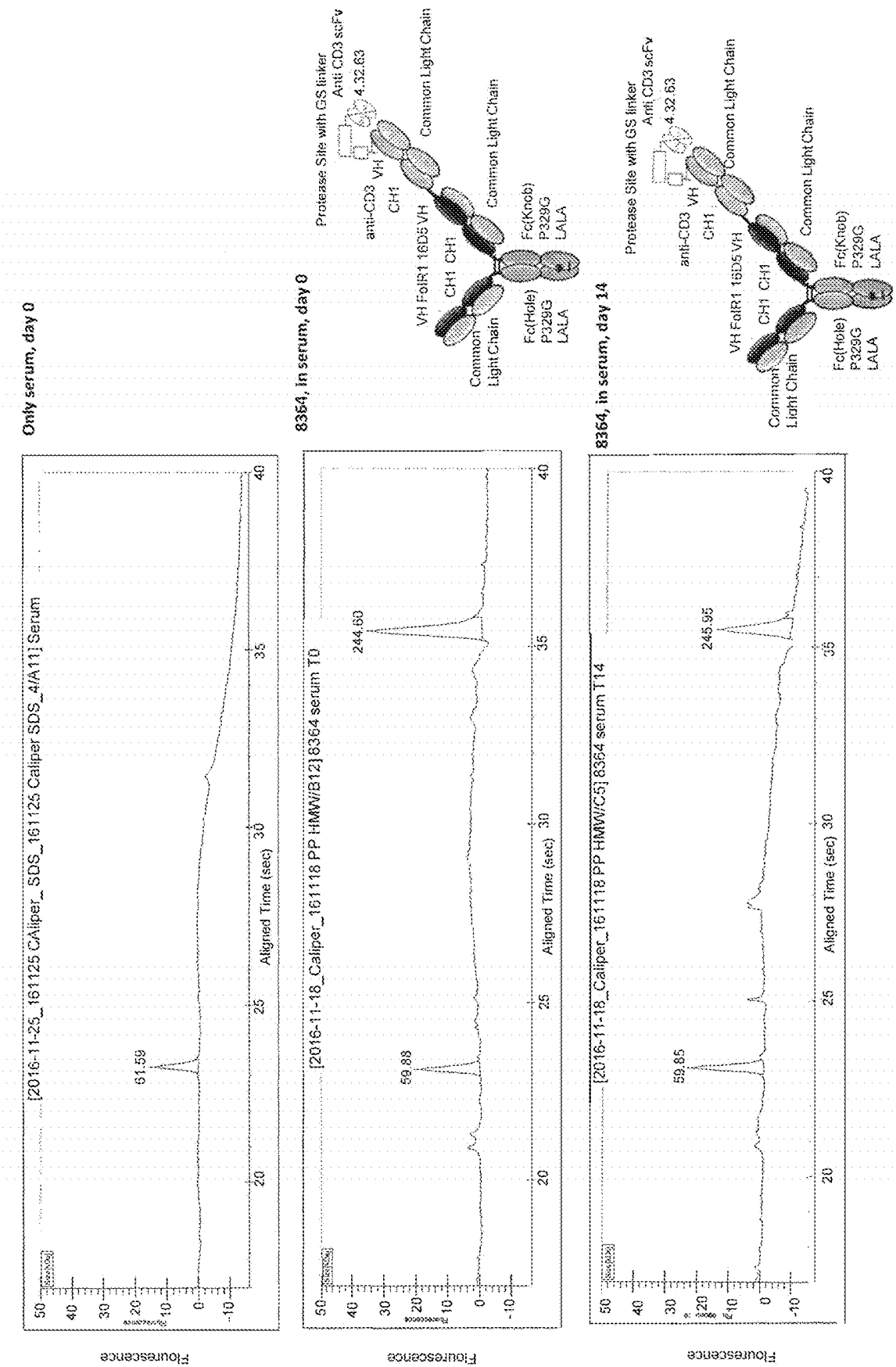
Figure 41C:
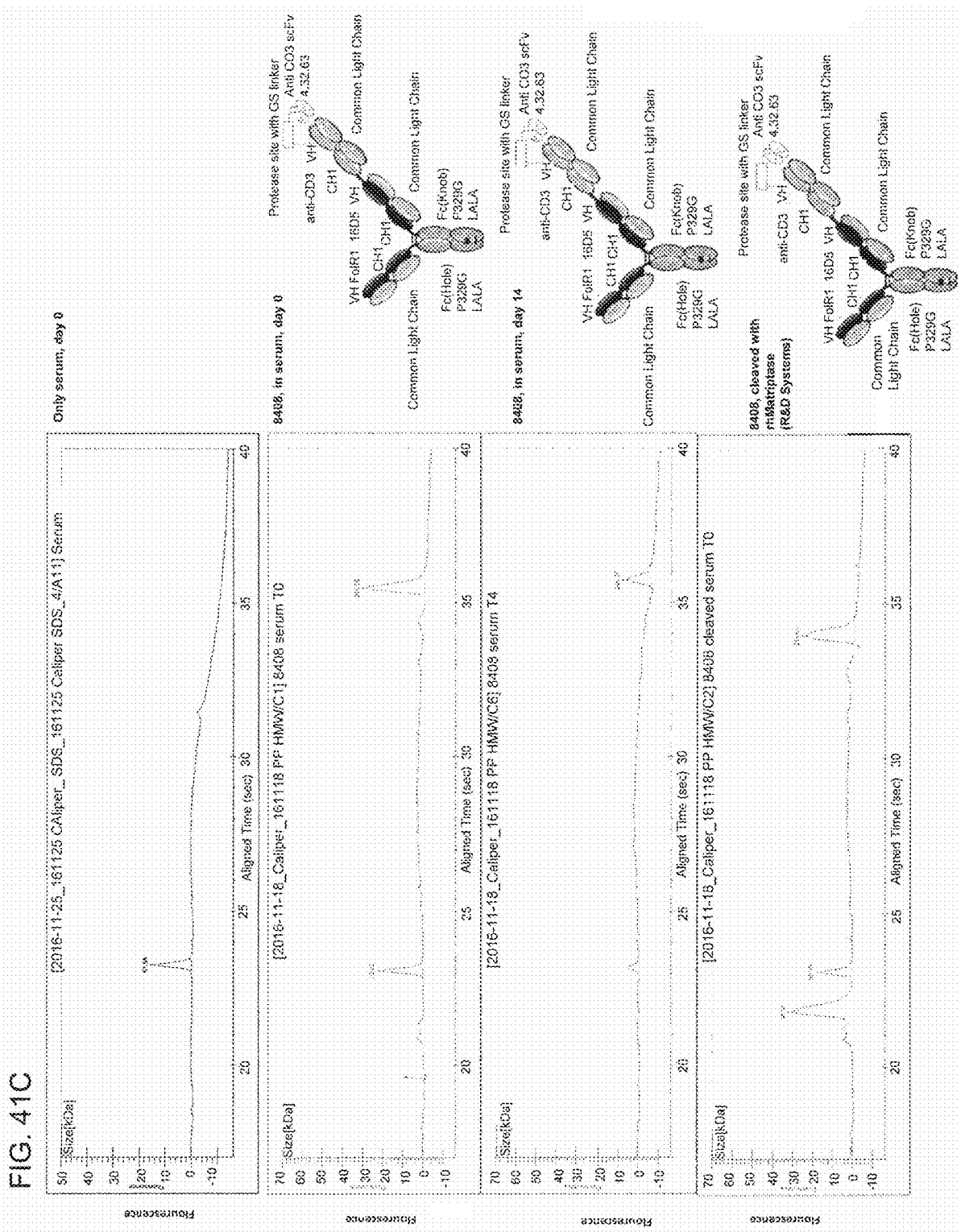

FIGS. 41A-41C: Capillary electrophoresis of protease activated TCBs after incubation in human serum. Molecules were incubated for 0 or 14 days in human IgG depleted serum at 37° C. in a humidified incubator (5% $CO_2$). All molecules were purified by affinity chromatography (ProteinA) and then analyzed by Capillary electrophoresis. FIG. 41A: CE-SDS analysis of serum, FolR1 TCB (6298) in serum at day 0 and day 14. FIG. 41B: CE-SDS analysis of serum, Protease activated FolR1 TCB with MMP9-Matriptase linker (8364) in serum at day 0 and day 14. FIG. 41C: CE-SDS analysis of serum, Protease activated FolR1 TCB with Matriptase linker (8408) in serum at day 0 and day 14 and the precleaved molecule in serum.

Figure 42A:
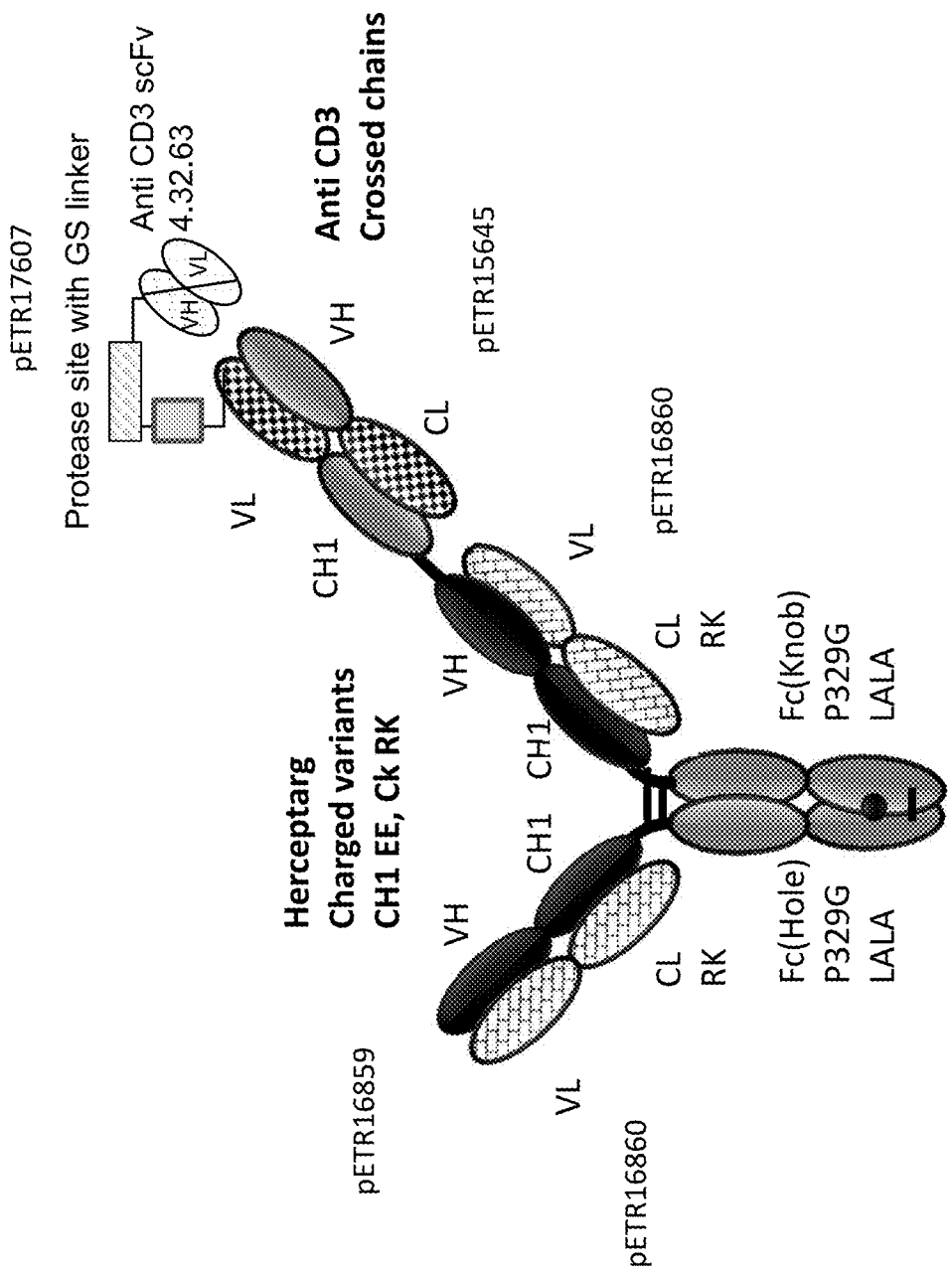
Figure 42B:
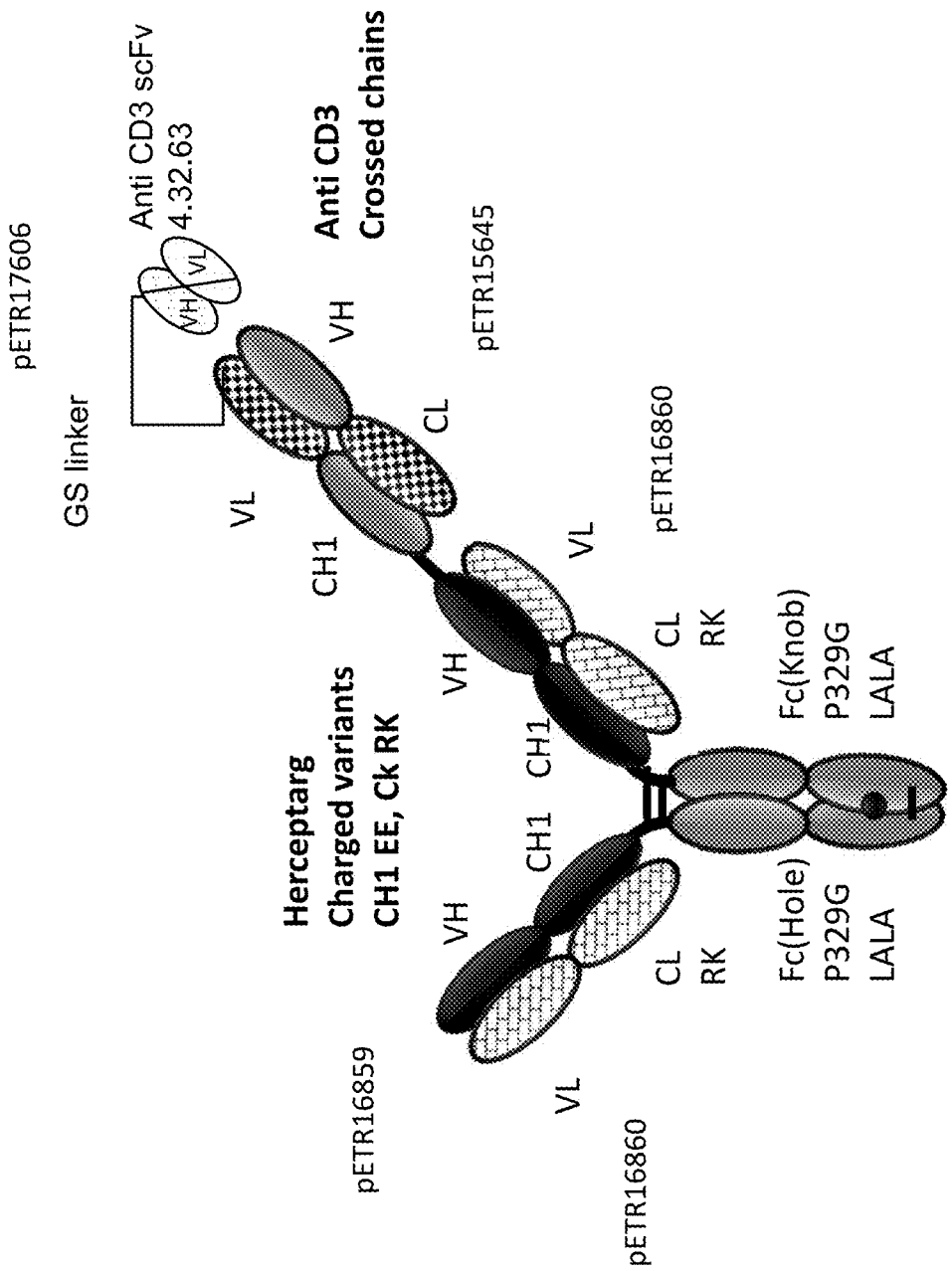
Figure 42C:
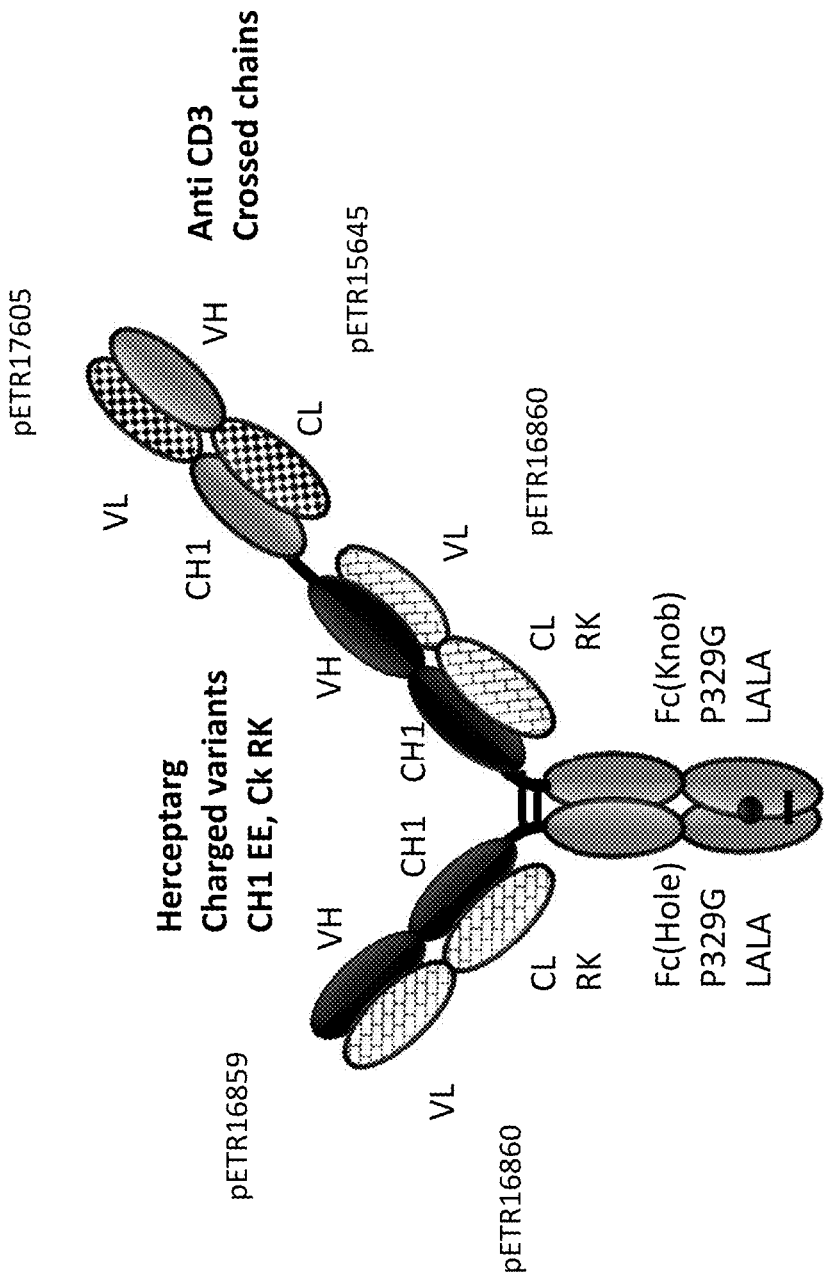
Figure 42D:
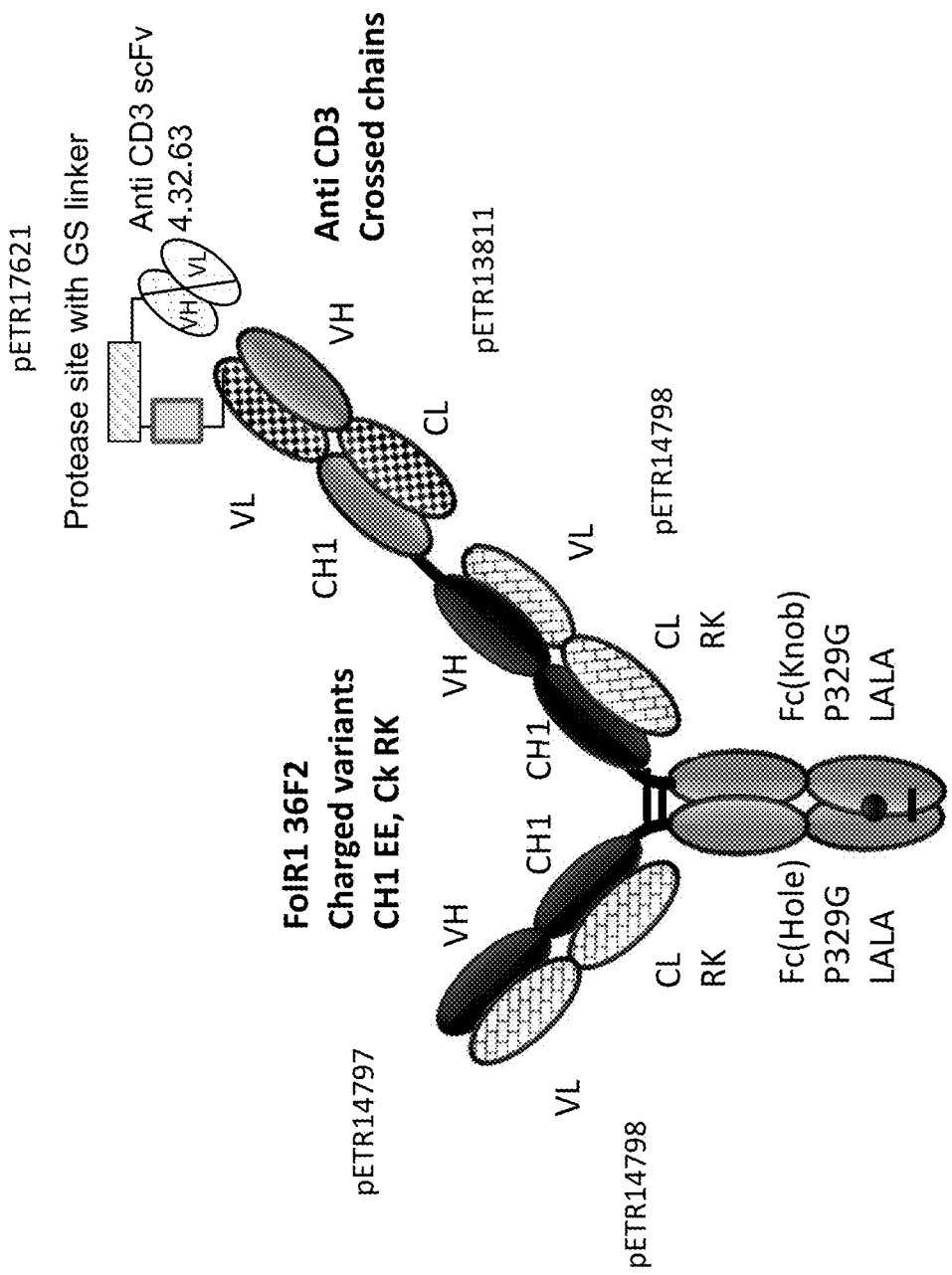
Figure 42E:
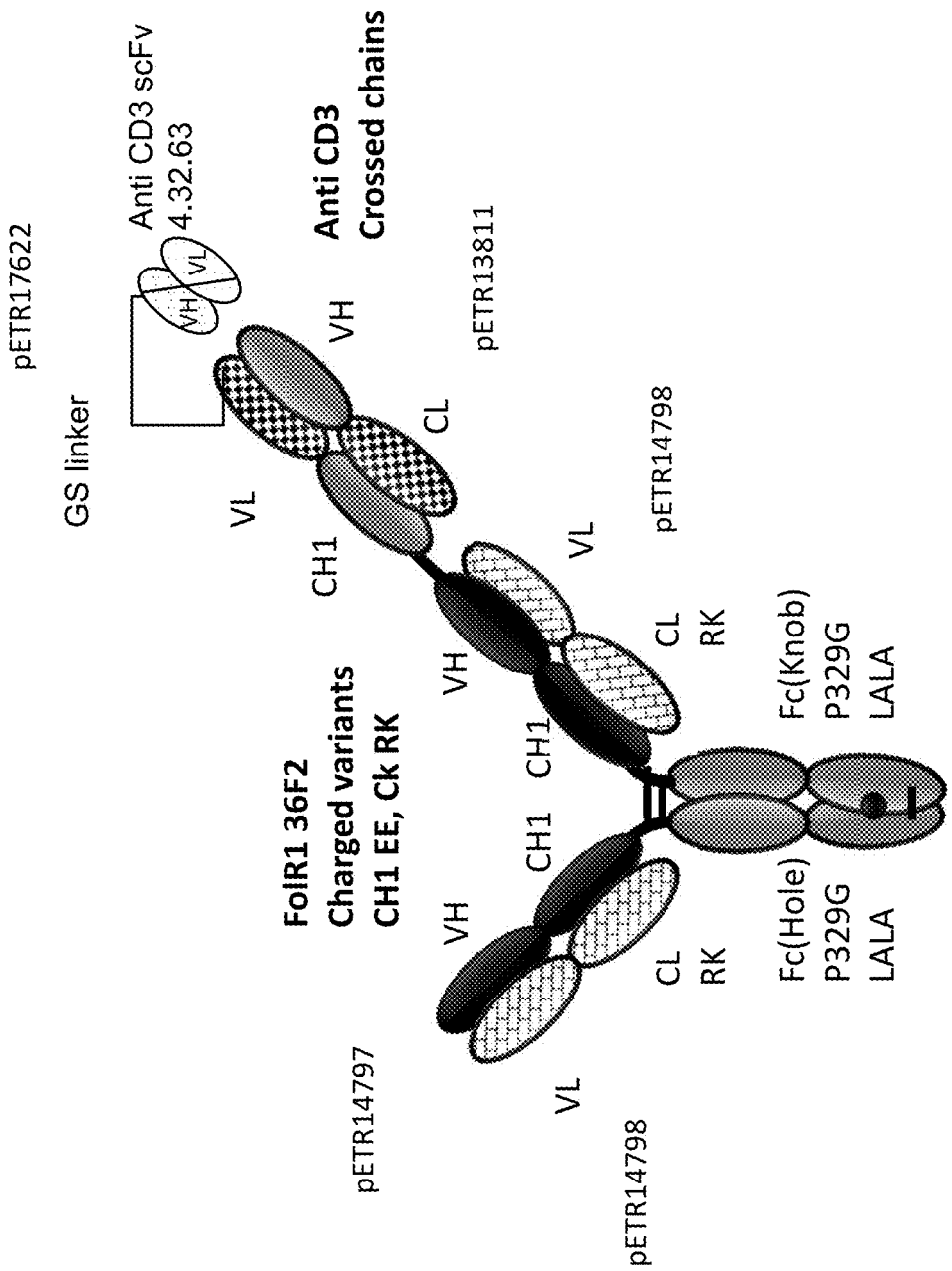
Figure 42F:
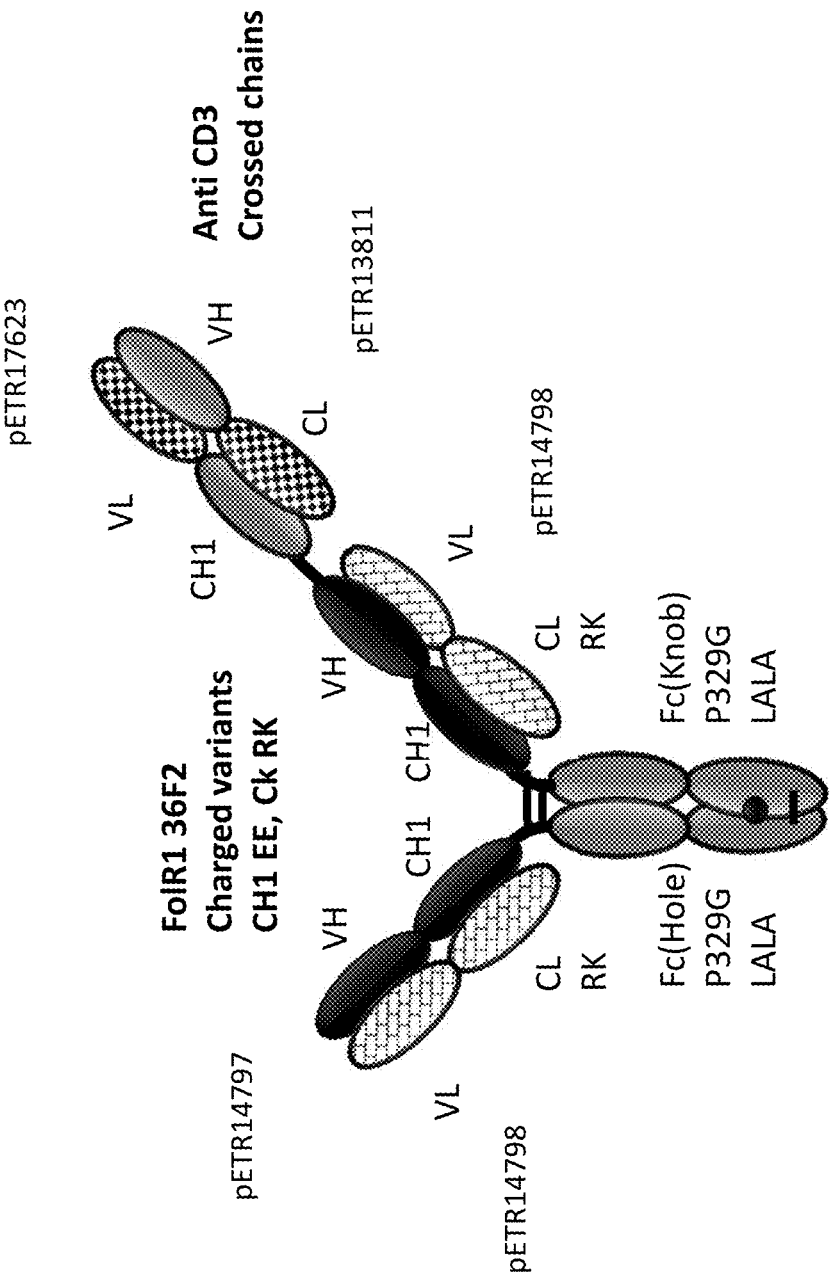

FIGS. 42A-42F depict schematics of different T cell bispecific molecules with masking moieties. FIG. 42A: ID 8955. Herceptarg TCB, classic format, anti ID CH2527 scFv 4.32.63 MK062 MMP9 linker N-terminally fused to VH. FIG. 42B: ID 8957. Herceptarg TCB, classic format, anti ID CH2527 scFv 4.32.63 non cleavable linker N-terminally fused to VH. FIG. 42C: ID 8959. Herceptarg TCB, classic format. FIG. 42D: ID 8997. FolR1 36F2 TCB, classic format, anti ID CH2527 scFv 4.32.63 MK062 MMP9 linker N-terminally fused to VH. FIG. 42E: ID 8998. FolR1 36F2 TCB, classic format, anti ID CH2527 scFv 4.32.63 non cleavable linker N-terminally fused to VH. FIG. 42F: ID 8996. FolR1 36F2 TCB, classic format.

Figure 43:
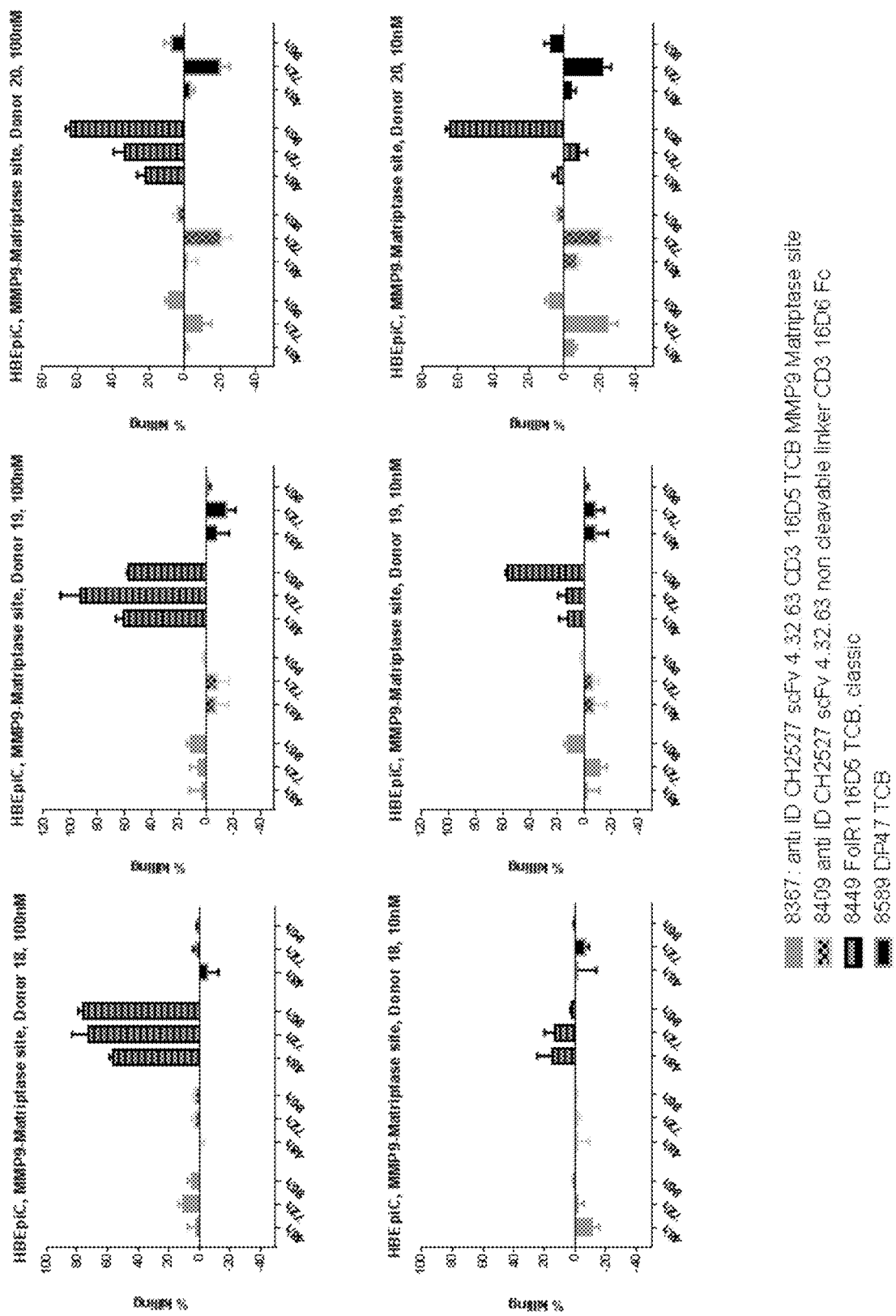

FIG. 43 depicts Human Bronchial Epithelial Cell toxicity mediated by human PBMCs and 100 nM or 10 nM of TCBs. Maximal lysis of the target cells (=100%) was achieved by incubation of target cells with 1% Triton X-100 20 h before LDH readout. Minimal lysis (=0%) refers to target cells co-incubated with effector cells without any TCB. Each point represents the mean value of triplicates. Standard deviation is indicated by error bars.

Figure 44:
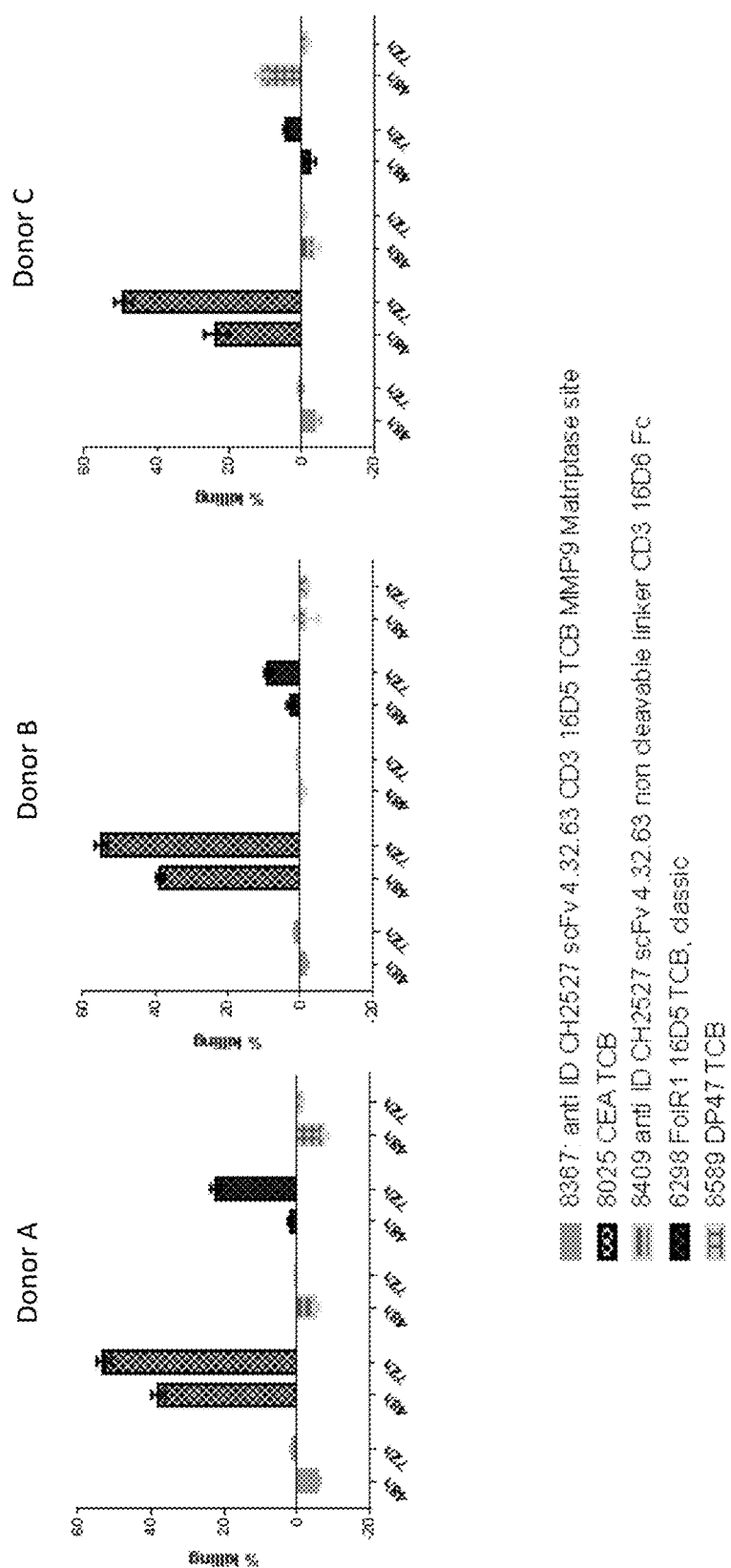

FIG. 44 depicts FolR1 negative target cell (Mkn-45) cytotoxicity mediated by 100 nM of FolR1 TCBs and human PBMCs. Maximal lysis of the target cells (=100%) was achieved by incubation of target cells with 1% Triton X-100 20 h before LDH readout. Minimal lysis (=0%) refers to target cells co-incubated with effector cells without any TCB. Each point represents the mean value of triplicates. Standard deviation is indicated by error bars.

Figure 45A:
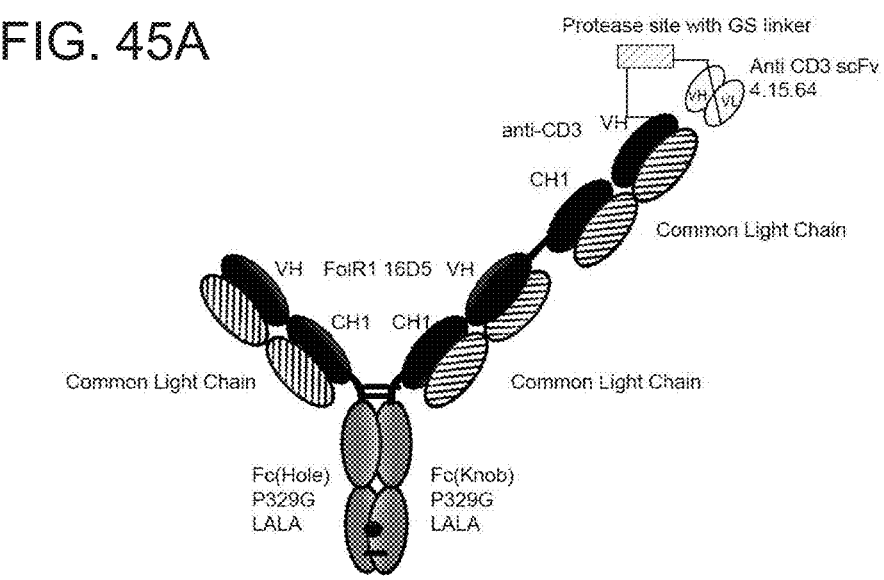
Figure 45B:
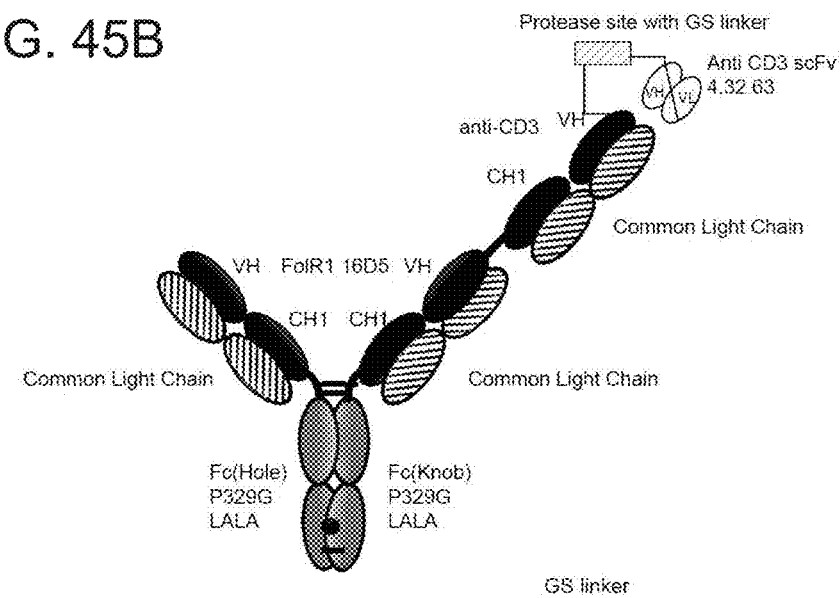
Figure 45C:
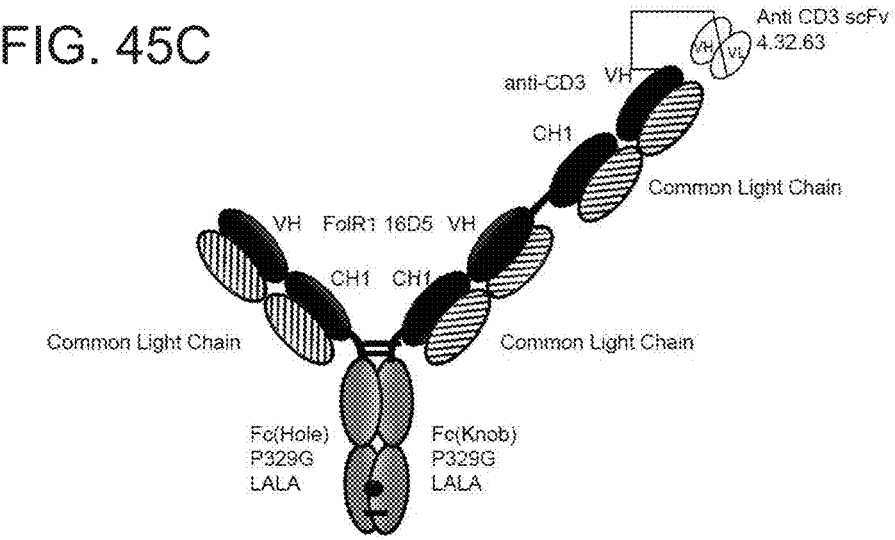
Figure 45D:
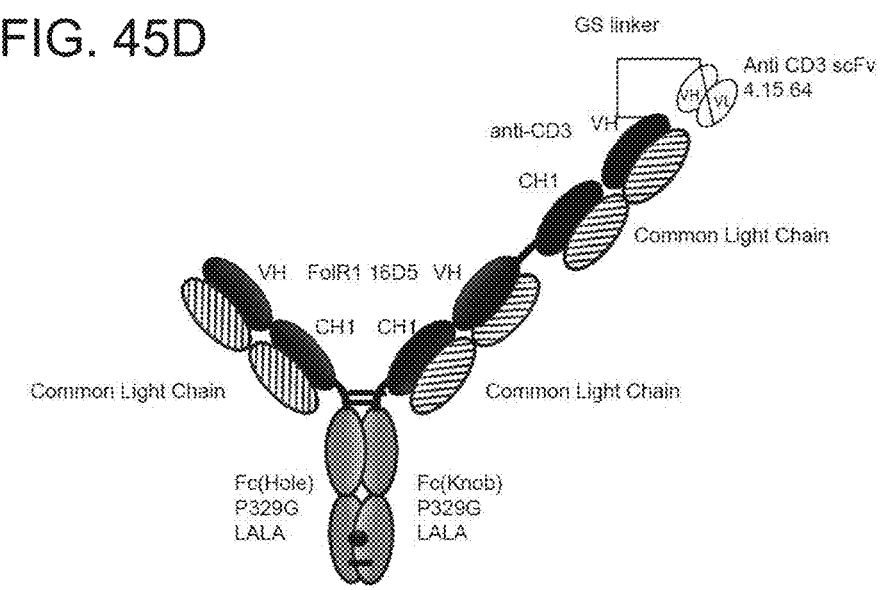
Figure 45E:
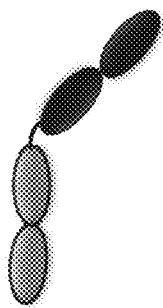
Figure 45F:
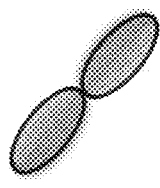
Figure 45G:
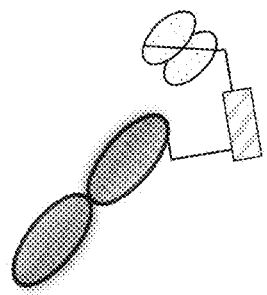
Figure 45H:
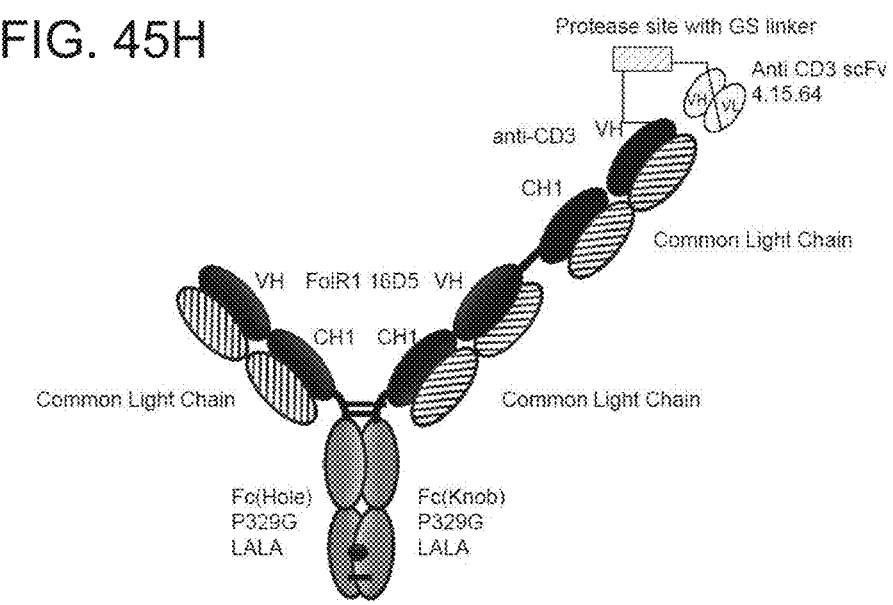
Figure 45I:
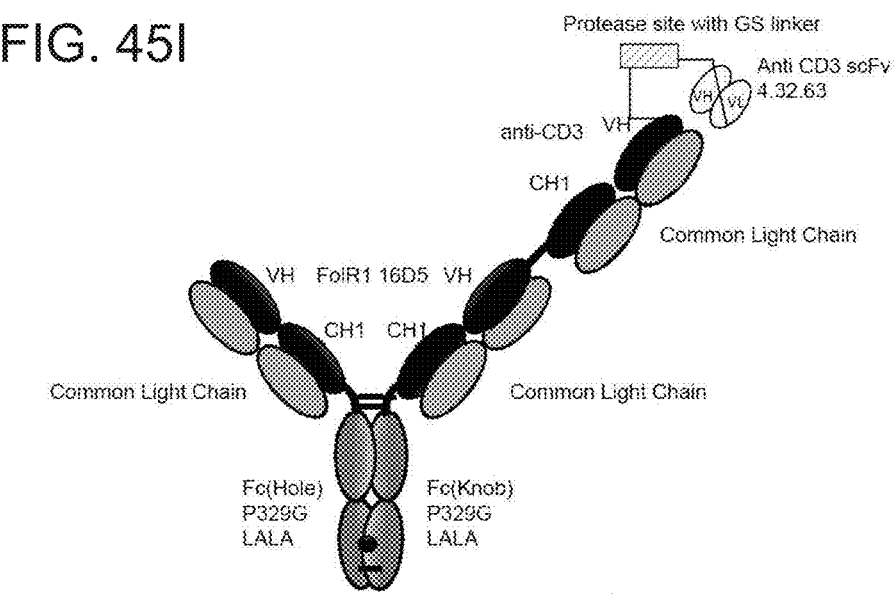
Figure 45J:
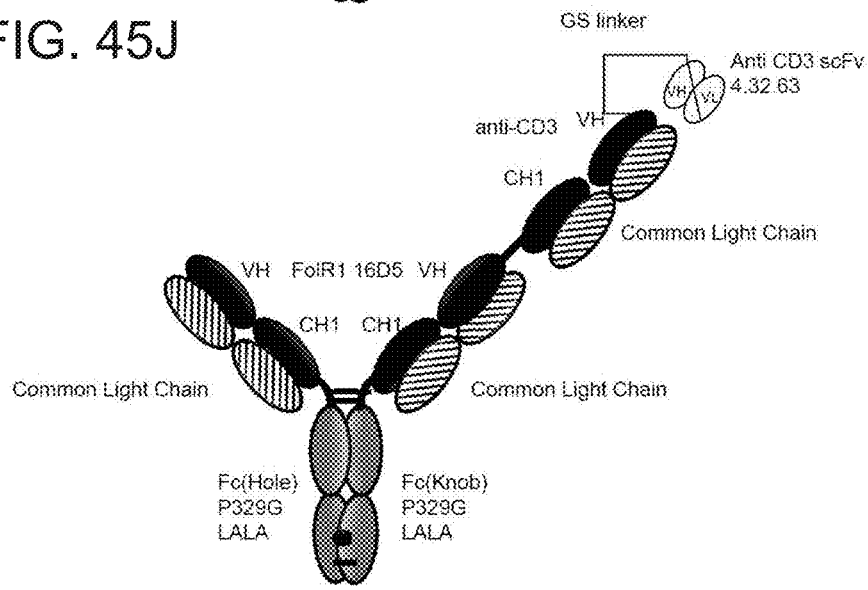
Figure 45K:
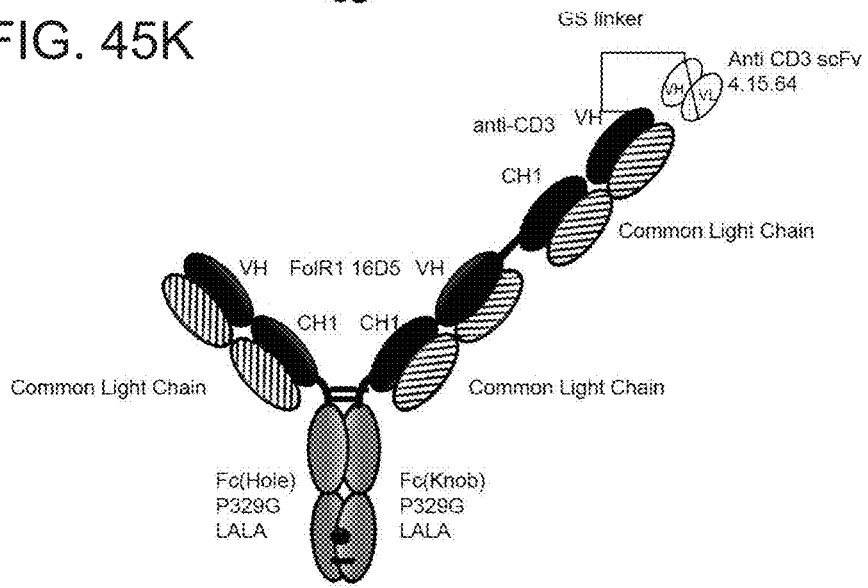
Figure 45L:
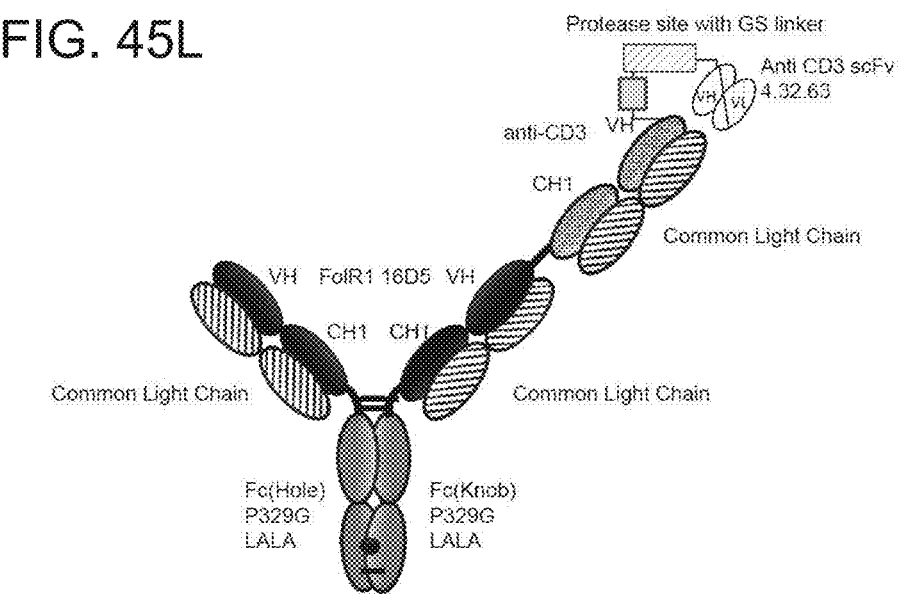
Figure 45M:
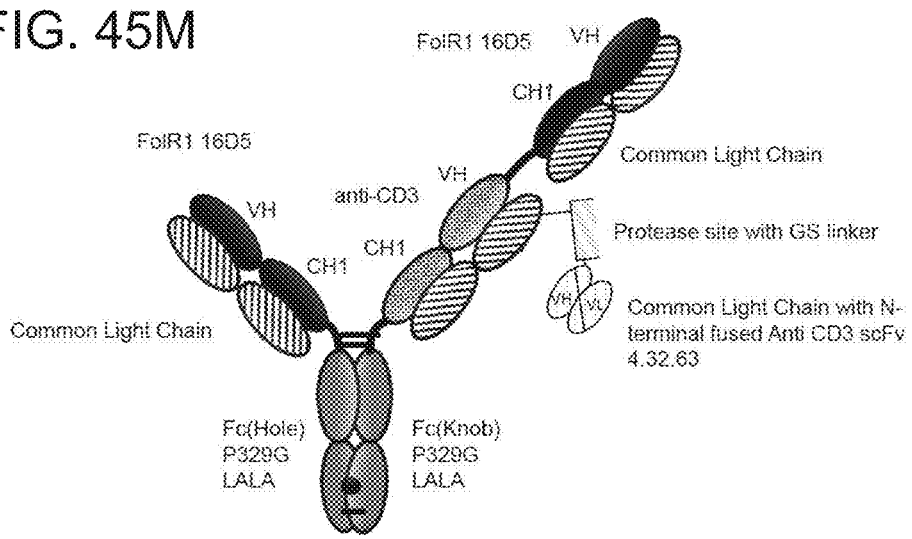
Figure 45N:
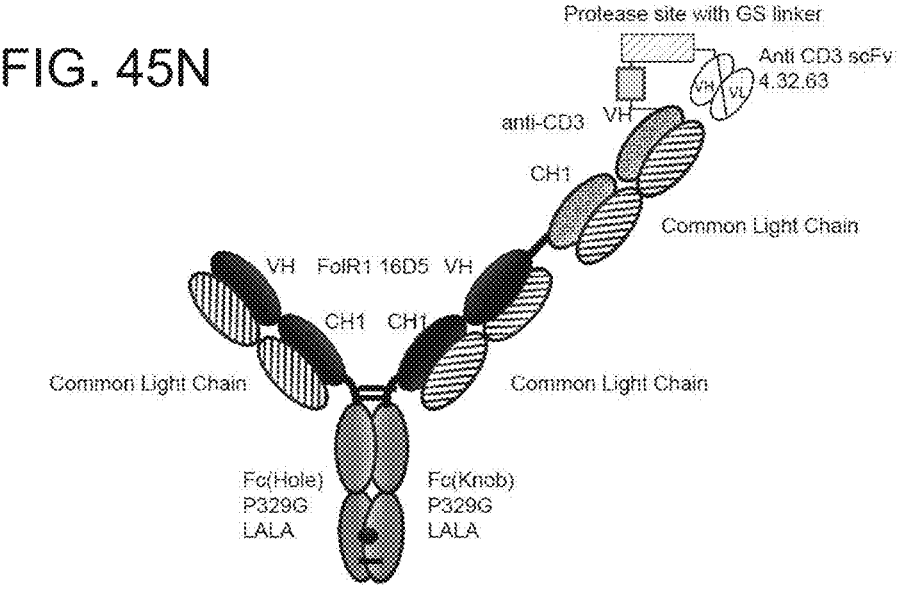

FIG. 45A to FIG. 45N depict schematic diagrams of exemplary antibody constructs.

DETAILED DESCRIPTION

Definitions

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g., fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g., a second antigen binding moiety) to a target site, for example to a specific type of tumor cell or tumor stroma bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" is synonymous with "antigen" and "epitope," and refers to a site (e.g., a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g., FolR1, HER1, HER2, CD3, Mesothelin) can be any native form of the proteins from any vertebrate source, including mammals such as primates (e.g., humans) and rodents (e.g., mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g., splice variants or allelic variants. Exemplary human proteins useful as antigens include, but are not limited to: FolR1, HER1 and CD3, particularly the epsilon subunit of CD3 (see UniProt no. P07766 (version 130), NCBI Ref Seq no. NP_000724.1, SEQ ID NO: 54 for the human sequence; or UniProt no. Q95LI5 (version 49), NCBI GenBank no. BAB71849.1 for the cynomolgus [*Macaca fascicularis*] sequence). In certain embodiments the protease-activatable T cell activating bispecific molecule of the invention binds to an epitope of CD3 or a target cell antigen that is conserved among the CD3 or target antigen from different species. In certain embodiments the protease-activatable T cell activating bispecific molecule of the invention binds to CD3 and FolR1, but does not bind to FolR2 or FolR3. In certain embodiments the protease-activatable T cell activating bispecific molecule of the invention binds to CD3 and HER1. In certain embodiments the protease-activatable T cell activating bispecific molecule of the invention binds to CD3 and Mesothelin. In certain embodiments the protease-activatable T cell activating bispecific molecule of the invention binds to CD3 and HER2. By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The protease-activatable T cell activating bispecific molecules of the invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma.

As used herein, the terms "first" and "second" with respect to antigen binding moieties etc., are used for convenience of distinguishing when there is more than one of each type of moiety. Use of these terms is not intended to confer a specific order or orientation of the protease-activatable T cell activating bispecific molecule unless explicitly so stated.

A "Fab molecule" refers to a protein consisting of the VH and CH1 domain of the heavy chain (the "Fab heavy chain") and the VL and CL domain of the light chain (the "Fab light chain") of an immunoglobulin.

By "fused" is meant that the components (e.g., a Fab molecule and an Fc domain subunit) are linked by peptide bonds, either directly or via one or more peptide linkers.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

By a "crossover" Fab molecule (also termed "Crossfab") is meant a Fab molecule wherein either the variable regions or the constant regions of the Fab heavy and light chain are exchanged, i.e. the crossover Fab molecule comprises a peptide chain composed of the light chain variable region and the heavy chain constant region, and a peptide chain composed of the heavy chain variable region and the light chain constant region. For clarity, in a crossover Fab molecule wherein the variable regions of the Fab light chain and the Fab heavy chain are exchanged, the peptide chain comprising the heavy chain constant region is referred to herein as the "heavy chain" of the crossover Fab molecule. Conversely, in a crossover Fab molecule wherein the constant regions of the Fab light chain and the Fab heavy chain are exchanged, the peptide chain comprising the heavy chain variable region is referred to herein as the "heavy chain" of the crossover Fab molecule.

In contrast thereto, by a "conventional" Fab molecule is meant a Fab molecule in its natural format, i.e. comprising a heavy chain composed of the heavy chain variable and constant regions (VH-CH1), and a light chain composed of the light chain variable and constant regions (VL-CL).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g., $γ_1$ ($IgG_1$), $γ_2$ ($IgG_2$), $γ_3$ ($IgG_3$), $γ_4$ ($IgG_4$), $α_1$ ($IgA_1$) and $α_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g., scFv), and single-domain antibodies. For a review of certain antibody fragments, see Hudson et al., Nat Med 9, 129-134 (2003). For a review of scFv fragments, see e.g., Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g., U.S. Pat. No. 6,248,516 B1). Antibody fragments can be made by various techniques, including but not limited to proteolytic digestion of an intact antibody as well as production by recombinant host cells (e.g., E. coli or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes). e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g., antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g., the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B. and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term "nucleic acid molecule" refers to any one or more nucleic acid segments, e.g., DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator. By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g., ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g., PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, protease-activatable T cell activating bispecific molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

An "idiotype-specific polypeptide" as used herein refers to a polypeptide that recognizes the idiotype of an antigen-binding moiety, e.g., an antigen-binding moiety specific for CD3. The idiotype-specific polypeptide is capable of specifically binding to the variable region of the antigen-binding moiety and thereby reducing or preventing specific binding of the antigen-binding moiety to its cognate antigen. When associated with a molecule that comprises the antigen-binding moiety, the idiotype-specific polypeptide can function as a masking moiety of the molecule. Specifically disclosed herein are anti-idiotype antibodies or anti-idiotype-binding antibody fragments specific for the idiotype of anti-CD3 binding molecules.

"Protease" or "proteolytic enzyme" as used herein refers to any proteolytic enzyme that cleaves the linker at a recognition site and that is expressed by a target cell. Such proteases might be secreted by the target cell or remain associated with the target cell, e.g., on the target cell surface. Examples of proteases include but are not limited to metalloproteinases, e.g., matrix metalloproteinase 1-28 and A Disintegrin And Metalloproteinase (ADAM) 2, 7-12, 15, 17-23, 28-30 and 33, serine proteases, e.g., urokinase-type plasminogen activator and Matriptase, cysteine protease, aspartic proteases, and members of the cathepsin family.

"Protease activatable" as used herein, with respect to the T cell activating bispecific molecule, refers to a T cell activating bispecific molecule having reduced or abrogated ability to activate T cells due to a masking moiety that reduces or abrogates the T cell activating bispecific molecule's ability to bind to CD3. Upon dissociation of the masking moiety by proteolytic cleavage, e.g., by proteolytic cleavage of a linker connecting the masking moiety to the T cell activating bispecific molecule, binding to CD3 is restored and the T cell activating bispecific molecule is thereby activated.

"Reversibly concealing" as used herein refers to the binding of a masking moiety or idiotype-specific polypeptide to an antigen-binding moiety or molecule such as to prevent the antigen-binding moiety or molecule from its antigen, e.g., CD3. This concealing is reversible in that the idiotype-specific polypeptide can be released from the antigen-binding moiety or molecule, e.g., by protease cleavage, and thereby freeing the antigen-binding moiety or molecule to bind to its antigen.

DETAILED DESCRIPTION

In one aspect, the invention relates to a protease-activatable T cell activating bispecific molecule comprising
(a) a first antigen binding moiety capable of specific binding to CD3;
(b) a second antigen binding moiety capable of specific binding to a target cell antigen; and
(c) a masking moiety covalently attached to the T cell bispecific binding molecule through a protease-cleavable linker, wherein the masking moiety is capable of specific binding to the idiotype of the first or the second antigen binding moiety thereby reversibly concealing the first or second antigen binding moiety.

The first antigen binding moiety capable of specific binding to CD3 comprises an idiotype. In one embodiment, the masking moiety of the protease-activatable T cell activating bispecific molecule is covalently attached to the first antigen binding moiety. In one embodiment the masking moiety is covalently attached to the heavy chain variable region of the first antigen binding moiety. In one embodiment the masking moiety is covalently attached to the light chain variable region of the first antigen binding moiety. This covalent bond is separate from the specific binding, which is preferably non-covalent, of the masking moiety to the idiotype first antigen binding site. The idiotype of the first antigen binding moiety comprises its variable region. In one embodiment the masking moiety binds to amino acid residues that make contact with CD3 when the first antigen biding moiety is bound to CD3. In a preferred embodiment, the masking moiety is not the cognate antigen or fragments thereof of the first antigen binding moiety, i.e., the masking moiety is not a CD3 or fragments thereof. In one embodiment the masking moiety is an anti-idiotypic antibody or fragment thereof. In one embodiment, the masking moiety is an anti-idiotypic scFv. Exemplary embodiments of masking moieties which are anti-idiotypic scFv, and protease activatable T cell activating molecules comprising such masking moieties, are described in detail in the examples.

In one embodiment the protease-activatable T cell activating bispecific molecule comprises a second masking moiety reversibly concealing the second antigen binding moiety.

In one embodiment the protease-activatable T cell activating bispecific molecule comprises (i) a first antigen binding moiety which is a Fab molecule capable of specific binding to CD3, and which comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19;

(ii) a second antigen binding moiety which is a Fab molecule capable of specific binding to a target cell antigen.

In one embodiment the first antigen binding moiety comprises a heavy chain variable region comprising an amino acid sequence that is at least about 95%, 96%, 97%, 98%, 99% or 100% identical to an amino acid sequence of SEQ ID NO: 43 and a light chain variable region comprising an amino acid sequence that is at least about 95%, 96%, 97%, 98%, 99% or 100% identical to an amino acid sequence of SEQ ID NO: 55.

In one embodiment the first antigen binding moiety comprises the heavy chain variable region comprising an amino acid sequence of SEQ ID NO: 43 and the light chain variable region comprising an amino acid sequence of SEQ ID NO: 55.

In a specific embodiment the second antigen binding moiety is capable of specific binding to FolR1 and comprises at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In another specific embodiment, the second antigen binding moiety is capable of specific binding to FolR1 and comprises a heavy chain variable region comprising an amino acid sequence that is at least about 95%, 96%, 97%, 98%, 99% or 100% identical to the amino acid sequence of SEQ ID NO: 47 and a light chain variable region comprising an amino acid sequence that is at least about 95%, 96%, 97%, 98%, 99% or 100% identical to the amino acid sequence of SEQ ID NO: 55.

In a specific embodiment the second antigen binding moiety is capable of specific binding to FolR1 and comprises at least one heavy chain complementarity determining region (CDR) selected from the group consisting of SEQ ID NO: 151, SEQ ID NO: 152 and SEQ ID NO: 153 and at least one light chain CDR selected from the group of SEQ ID NO: 154, SEQ ID NO: 155 and SEQ ID NO: 156.

In another specific embodiment, the second antigen binding moiety is capable of specific binding to FolR1 and comprises a heavy chain variable region comprising an amino acid sequence that is at least about 95%, 96%, 97%, 98%, 99% or 100% identical to the amino acid sequence of SEQ ID NO: 157 and a light chain variable region comprising an amino acid sequence that is at least about 95%, 96%, 97%, 98%, 99% or 100% identical to the amino acid sequence of SEQ ID NO: 158.

In another specific embodiment, the second antigen binding moiety is capable of specific binding to HER1 and comprises at least one heavy chain complementarity determining region (CDR) selected from the group consisting of SEQ ID NO: 56, SEQ ID NO: 57 and SEQ ID NO: 58 and at least one light chain CDR selected from the group of SEQ ID NO: 59, SEQ ID NO: 60 and SEQ ID NO: 61.

In another specific embodiment, the second antigen binding moiety is capable of specific binding to HER1 and comprises a heavy chain comprising an amino acid sequence that is at least about 95%, 96%, 97%, 98%, 99% or 100% identical to an amino acid sequence of SEQ ID NO: 32, and a light chain comprising an amino acid sequence that is at least about 95%, 96%, 97%, 98%, 99% or 100% identical to an amino acid sequence of SEQ ID NO: 33.

In another specific embodiment, the second antigen binding moiety is capable of specific binding to HER1 and comprises a heavy chain variable region comprising an amino acid sequence that is at least about 95%, 96%, 97%, 98%, 99% or 100% identical to the amino acid sequence of SEQ ID NO: 115 and a light chain variable region comprising an amino acid sequence that is at least about 95%, 96%, 97%, 98%, 99% or 100% identical to the amino acid sequence of SEQ ID NO: 116.

In a specific embodiment the second antigen binding moiety is capable of specific binding to Mesothelin and comprises at least one heavy chain complementarity determining region (CDR) selected from the group consisting of SEQ ID NO: 107, SEQ ID NO: 108 and SEQ ID NO: 109 and at least one light chain CDR selected from the group of SEQ ID NO: 110, SEQ ID NO: 111 and SEQ ID NO: 112.

In another specific embodiment, the second antigen binding moiety is capable of specific binding Mesothelin and comprises a heavy chain variable region comprising an amino acid sequence that is at least about 95%, 96%, 97%, 98%, 99% or 100% identical to the amino acid sequence of SEQ ID NO: 113 and a light chain variable region comprising an amino acid sequence that is at least about 95%, 96%, 97%, 98%, 99% or 100% identical to the amino acid sequence of SEQ ID NO: 114.

In one embodiment the present invention provides a protease-activatable T cell activating bispecific molecule comprising (i) a first antigen binding moiety which is a Fab molecule capable of specific binding to CD3, comprising at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19;

(ii) a second antigen binding moiety which is a Fab molecule capable of specific binding to FolR1 comprising at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, (ii) a second antigen binding moiety which is a Fab molecule capable of specific binding to FolR1 comprising heavy chain variable region comprising an amino acid sequence that is at least about 95%, 96%, 97%, 98%, 99% or 100% identical to the amino acid sequence of SEQ ID NO: 47 and a light chain variable region comprising an amino acid sequence that is at least about 95%, 96%, 97%, 98%, 99% or 100% identical to the amino acid sequence of SEQ ID NO: 55.

In one embodiment the present invention provides a protease-activatable T cell activating bispecific molecule comprising (i) a first antigen binding moiety which is a Fab molecule capable of specific binding to CD3, comprising at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19;

(ii) a second antigen binding moiety which is a Fab molecule capable of specific binding to FolR1 comprising at least one heavy chain complementarity determining region (CDR) selected from the group consisting of SEQ ID NO: 151, SEQ ID NO: 152 and SEQ ID NO: 153 and at least one light chain CDR selected from the group of SEQ ID NO: 154, SEQ ID NO: 155 and SEQ ID NO: 156.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, (ii) a second antigen binding moiety which is a Fab molecule capable of specific binding to FolR1 comprising heavy chain variable region comprising an amino acid sequence that is at least about 95%, 96%, 97%, 98%, 99% or 100% identical to the amino acid sequence of SEQ ID NO: 157 and a light chain variable region comprising an amino acid sequence that is at least about 95%, 96%, 97%, 98%, 99% or 100% identical to the amino acid sequence of SEQ ID NO: 158.

In one embodiment the present invention provides a protease-activatable T cell activating bispecific molecule comprising (i) a first antigen binding moiety which is a Fab molecule capable of specific binding to CD3, comprising at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19;

(ii) a second antigen binding moiety which is a Fab molecule capable of specific binding to HER1 comprising at least one heavy chain complementarity determining region (CDR) selected from the group consisting of SEQ ID NO: 56, SEQ ID NO: 57 and SEQ ID NO: 58 and at least one light chain CDR selected from the group of SEQ ID NO: 59, SEQ ID NO: 60 and SEQ ID NO: 61.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55.

(ii) a second antigen binding moiety which is a Fab molecule capable of specific binding to HER1 comprising a heavy chain variable region comprising an amino acid sequence that is at least about 95%, 96%, 97%, 98%, 99% or 100% identical to the amino acid sequence of SEQ ID NO: 115 and a light chain variable region comprising an amino acid sequence that is at least about 95%, 96%, 97%, 98%, 99% or 100% identical to the amino acid sequence of SEQ ID NO: 116.

In a particular embodiment, the first antigen binding moiety is a crossover Fab molecule wherein either the variable or the constant regions of the Fab light chain and the Fab heavy chain are exchanged.

In one embodiment the present invention provides a protease-activatable T cell activating bispecific molecule comprising (i) a first antigen binding moiety which is a Fab molecule capable of specific binding to CD3, comprising at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19;

(ii) a second antigen binding moiety which is a Fab molecule capable of specific binding to Mesothelin comprising at least one heavy chain complementarity determining region (CDR) selected from the group consisting of SEQ ID NO: 107, SEQ ID NO: 108 and SEQ ID NO: 109 and at least one light chain CDR selected from the group of SEQ ID NO: 110, SEQ ID NO: 111 and SEQ ID NO: 112.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, (ii) a second antigen binding moiety which is a Fab molecule capable of specific binding to Mesothelin comprising heavy chain variable region comprising an amino acid sequence that is at least about 95%, 96%, 97%, 98%, 99% or 100% identical to the amino acid sequence of SEQ ID NO: 113 and a light chain variable region comprising an amino acid sequence that is at least about 95%, 96%, 97%, 98%, 99% or 100% identical to the amino acid sequence of SEQ ID NO: 114.

In one embodiment, the second antigen binding moiety is a conventional Fab molecule.

In a particular embodiment, the first antigen binding moiety is a crossover Fab molecule wherein the constant regions of the Fab light chain and the Fab heavy chain are exchanged, and the second antigen binding moiety is a conventional Fab molecule. In a further particular embodiment, the first and the second antigen binding moiety are fused to each other, optionally through a peptide linker.

In particular embodiments, the protease-activatable T cell activating bispecific molecule further comprises an Fc domain composed of a first and a second subunit capable of stable association.

In a further particular embodiment, not more than one antigen binding moiety capable of specific binding to CD3 is present in the protease-activatable T cell activating bispecific molecule (i.e. the protease-activatable T cell activating bispecific molecule provides monovalent binding to CD3).

Protease-Activatable T Cell Activating Bispecific Molecule Formats

The components of the protease-activatable T cell activating bispecific molecule can be fused to each other in a variety of configurations. Exemplary configurations are depicted in FIGS. 1A-1E and 5A-5H. Further exemplary configurations are depicted in FIGS. 33A-33K.

In particular embodiments, the protease-activatable T cell activating bispecific molecule comprises an Fc domain composed of a first and a second subunit capable of stable association. In some embodiments, the second antigen binding moiety is fused at the C-terminus of the Fab heavy chain to the N-terminus of the first or the second subunit of the Fc domain.

In one such embodiment, the first antigen binding moiety is fused at the C-terminus of the Fab heavy chain to the N-terminus of the Fab heavy chain of the second antigen binding moiety. In a specific such embodiment, the protease-activatable T cell activating bispecific molecule essentially consists of a first and a second antigen binding moiety, an Fc domain composed of a first and a second subunit, and optionally one or more peptide linkers, wherein the first antigen binding moiety is fused at the C-terminus of the Fab heavy chain to the N-terminus of the Fab heavy chain of the second antigen binding moiety, and the second antigen binding moiety is fused at the C-terminus of the Fab heavy chain to the N-terminus of the first or second subunit of the Fc domain. Optionally, the Fab light chain of the first antigen binding moiety and the Fab light chain of the second antigen binding moiety may additionally be fused to each other.

In another such embodiment, the first antigen binding moiety is fused at the C-terminus of the Fab heavy chain to the N-terminus of the first or second subunit of the Fc domain. In a specific such embodiment, the protease-activatable T cell activating bispecific molecule essentially consists of a first and a second antigen binding moiety, an Fc domain composed of a first and a second subunit, and optionally one or more peptide linkers, wherein the first and the second antigen binding moiety are each fused at the C-terminus of the Fab heavy chain to the N-terminus of one of the subunits of the Fc domain.

In other embodiments, the first antigen binding moiety is fused at the C-terminus of the Fab heavy chain to the N-terminus of the first or second subunit of the Fc domain.

In a particular such embodiment, the second antigen binding moiety is fused at the C-terminus of the Fab heavy chain to the N-terminus of the Fab heavy chain of the first antigen binding moiety. In a specific such embodiment, the protease-activatable T cell activating bispecific molecule essentially consists of a first and a second antigen binding moiety, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first or the second subunit of the Fc domain. Optionally, the Fab light chain of the first antigen binding moiety and the Fab light chain of the second antigen binding moiety may additionally be fused to each other.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally a number between 1 and 10, typically between 2 and 4. A particularly suitable peptide linker for fusing the Fab light chains of the first and the second antigen binding moiety to each other is $(G_4S)_2$. An exemplary peptide linker suitable for connecting the Fab heavy chains of the first and the second antigen binding moiety is EPKSC(D)-$(G_4S)_2$ (SEQ ID NOs 105 and 106). Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

A protease-activatable T cell activating bispecific molecule with a single antigen binding moiety capable of specific binding to a target cell antigen is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have a protease-activatable T cell activating bispecific molecule comprising two or more antigen binding moieties specific for a target cell antigen (see examples in shown in FIGS. 5A-5H), for example to optimize targeting to the target site or to allow crosslinking of target cell antigens.

Accordingly, in certain embodiments, the protease-activatable T cell activating bispecific molecule of the invention further comprises a third antigen binding moiety which is a Fab molecule capable of specific binding to a target cell antigen. In one embodiment, the third antigen binding moiety is a conventional Fab molecule. In one embodiment, the third antigen binding moiety is capable of specific binding to the same target cell antigen as the second antigen binding moiety. In a particular embodiment, the first antigen binding moiety is capable of specific binding to CD3, and the second and third antigen binding moieties are capable of specific binding to a target cell antigen. In a particular embodiment, the second and the third antigen binding moiety are identical (i.e. they comprise the same amino acid sequences).

In a particular embodiment, the first antigen binding moiety is capable of specific binding to CD3, and the second and third antigen binding moieties are capable of specific binding to FolR1, wherein the second and third antigen binding moieties comprise at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In a particular embodiment, the first antigen binding moiety is capable of specific binding to CD3, and comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19; and the second and third antigen binding moieties are capable of specific binding to FolR1, wherein the second and third antigen binding moieties comprise at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In a particular embodiment, the first antigen binding moiety is capable of specific binding to CD3, and comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19; and the second and third antigen binding moieties are capable of specific binding to FolR1, wherein the second and third antigen binding moieties comprise at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In a particular embodiment, the first antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, and the second and third antigen binding moieties are capable of specific binding to FolR1, wherein the second and third antigen binding moieties comprise a heavy chain variable region comprising an amino acid sequence that is at least about 95%, 96%, 97%, 98%, 99% or 100% identical to the amino acid sequence of SEQ ID NO: 47 and a light chain variable region comprising an amino acid sequence that is at least about 95%, 96%, 97%, 98%, 99% or 100% identical to the amino acid sequence of SEQ ID NO: 55.

In one embodiment, the first antigen binding moiety is capable of specific binding to CD3, and the second and third antigen binding moieties are capable of specific binding to HER1, wherein the second and third antigen binding moieties comprise at least one heavy chain complementarity determining region (CDR) selected from the group consisting of SEQ ID NO: 56, SEQ ID NO: 57 and SEQ ID NO: 58 and at least one light chain CDR selected from the group of SEQ ID NO: 59, SEQ ID NO: 60 and SEQ ID NO: 61.

In one embodiment, the first antigen binding moiety is capable of specific binding to CD3, and comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19; and the second and third antigen binding moieties are capable of specific binding to HER1, wherein the second and third antigen binding moieties comprise at least one heavy chain complementarity determining region (CDR) selected from the group consisting of SEQ ID NO: 56, SEQ ID NO: 57 and SEQ ID NO: 58 and at least one light chain CDR selected from the group of SEQ ID NO: 59, SEQ ID NO: 60 and SEQ ID NO: 61.

In one embodiment, the first antigen binding moiety is capable of specific binding to CD3, and comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18 and SEQ ID NO: 19; and the second and third antigen binding moieties are capable of specific binding to HER1, wherein the second and third antigen binding moieties comprise at least one heavy chain complementarity determining region (CDR) selected from the group consisting of SEQ ID NO: 56, SEQ ID NO: 57 and SEQ ID NO: 58 and at least one light chain CDR selected from the group of SEQ ID NO: 59, SEQ ID NO: 60 and SEQ ID NO: 61.

In one embodiment, the first antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, and the second and third antigen binding moieties are capable of specific binding to HER1, wherein the second and third antigen binding moieties comprise a heavy chain variable region comprising an amino acid sequence that is at least about 95%, 96%, 97%, 98%, 99% or 100% identical to the amino acid sequence of SEQ ID NO: 115 and a light chain variable region comprising an amino acid sequence that is at least about 95%, 96%, 97%, 98%, 99% or 100% identical to the amino acid sequence of SEQ ID NO: 116.

In one embodiment, the first antigen binding moiety is capable of specific binding to CD3, and the second and third antigen binding moieties are capable of specific binding to HER2, wherein the second antigen binding moiety comprises at least one heavy chain complementarity determining region (CDR) selected from the group consisting of SEQ ID NO: 142, SEQ ID NO: 143 and SEQ ID NO: 144 and at least one light chain CDR selected from the group of SEQ ID NO: 148, SEQ ID NO: 149 and SEQ ID NO: 150, and wherein the third antigen binding moiety comprises at least one heavy chain complementarity determining region (CDR) selected from the group consisting of SEQ ID NO: 145, SEQ ID NO: 146 and SEQ ID NO: 147 and at least one light chain CDR selected from the group of SEQ ID NO: 148, SEQ ID NO: 149 and SEQ ID NO: 150.

In a particular embodiment, the first antigen binding moiety is capable of specific binding to CD3, and comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19; and the second and third antigen binding moieties are capable of specific binding to HER2, wherein the second antigen binding moiety comprises at least one heavy chain complementarity determining region (CDR) selected from the group consisting of SEQ ID NO: 142, SEQ ID NO: 143 and SEQ ID NO: 144 and at least one light chain CDR selected from the group of SEQ ID NO: 148, SEQ ID NO: 149 and SEQ ID NO: 150, and wherein the third antigen binding moiety comprises at least one heavy chain complementarity determining region (CDR) selected from the group consisting of SEQ ID NO: 145, SEQ ID NO: 146 and SEQ ID NO: 147 and at least one light chain CDR selected from the group of SEQ ID NO: 148, SEQ ID NO: 149 and SEQ ID NO: 150.

In one embodiment, the first antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, and the second and third antigen binding moieties are capable of specific binding to HER2, wherein the second antigen binding moiety comprises a heavy chain variable region comprising an amino acid sequence that is at least about 95%, 96%, 97%, 98%, 99% or 100% identical to the amino acid sequence of SEQ ID NO: 160 and a light chain variable region comprising an amino acid sequence that is at least about 95%, 96%, 97%, 98%, 99% or 100% identical to the amino acid sequence of SEQ ID NO: 161, wherein the third antigen binding moiety comprises a heavy chain variable region comprising an amino acid sequence that is at least about 95%, 96%, 97%, 98%, 99% or 100% identical to the amino acid sequence of SEQ ID NO: 159 and a light chain variable region comprising an amino acid sequence that is at least about 95%. 96%, 97%, 98%, 99% or 100% identical to the amino acid sequence of SEQ ID NO: 161.

In a particular embodiment, the first antigen binding moiety is capable of specific binding to CD3, and the second and third antigen binding moieties are capable of specific binding to Mesothelin, wherein the second and third antigen binding moieties comprise at least one heavy chain complementarity determining region (CDR) selected from the group consisting of SEQ ID NO: 107, SEQ ID NO: 108 and SEQ ID NO: 109 and at least one light chain CDR selected from the group of SEQ ID NO: 110, SEQ ID NO: 111 and SEQ ID NO: 112.

In a particular embodiment, the first antigen binding moiety is capable of specific binding to CD3, and comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18, SEQ ID NO: 19; and the second and third antigen binding moieties are capable of specific binding to Mesothelin, wherein the second and third antigen binding moieties comprise at least one heavy chain complementarity determining region (CDR) selected from the group consisting of SEQ ID NO: 107. SEQ ID NO: 108 and SEQ ID NO: 109 and at least one light chain CDR selected from the group of SEQ ID NO: 110, SEQ ID NO: 11 and SEQ ID NO: 112.

In a particular embodiment, the first antigen binding moiety is capable of specific binding to CD3, and comprises a heavy chain variable region comprising an amino acid sequence that is at least about 95%, 96%, 97%, 98%, 99% or 100% identical to the amino acid sequence of SEQ ID NO: 43, and a light chain variable region comprising an amino acid sequence that is at least about 95%, 96%, 97%, 98%, 99% or 100% identical to the amino acid sequence of SEQ ID NO: 55, and the second and third antigen binding moieties are capable of specific binding to Mesothelin, wherein the second and third antigen binding moieties comprise a heavy chain variable region comprising an amino acid sequence that is at least about 95%, 96%, 97%, 98%, 99% or 100% identical to the amino acid sequence of SEQ ID NO: 113 and a light chain variable region comprising an amino acid sequence that is at least about 95%, 96%, 97%, 98%, 99% or 100% identical to the amino acid sequence of SEQ ID NO: 114.

In one embodiment, the first antigen binding moiety is capable of specific binding to CD3, and the second and third antigen binding moieties are capable of specific binding to HER1, wherein the second and third antigen binding moieties comprise at least one heavy chain complementarity determining region (CDR) selected from the group consisting of SEQ ID NO: 56, SEQ ID NO: 57 and SEQ ID NO: 58 and at least one light chain CDR selected from the group consisting of SEQ ID NO: 59, SEQ ID NO: 60 and SEQ ID NO: 61.

In a particular embodiment, the first antigen binding moiety is capable of specific binding to CD3, and comprises at least one heavy chain complementarity determining region (CDR) selected from the group consisting of SEQ ID NO: 44, SEQ ID NO: 45 and SEQ ID NO: 46 and at least one light chain CDR selected from the group consisting of SEQ ID NO: 17, SEQ ID NO: 18 and SEQ ID NO: 19; and the second and third antigen binding moieties are capable of specific binding to HER1, wherein the second and third antigen binding moieties comprise at least one heavy chain complementarity determining region (CDR) selected from the group consisting of SEQ ID NO: 56, SEQ ID NO: 57 and SEQ ID NO: 58 and at least one light chain CDR selected from the group consisting of SEQ ID NO: 59, SEQ ID NO: 60 and SEQ ID NO: 61.

In one embodiment, the third antigen binding moiety is fused at the C-terminus of the Fab heavy chain to the N-terminus of the first or second subunit of the Fc domain. In a more specific embodiment, the second and the third antigen binding moiety are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second antigen binding moiety. Optionally, the Fab light chain of the first antigen binding moiety and the Fab light chain of the second antigen binding moiety may additionally be fused to each other.

The second and the third antigen binding moiety may be fused to the Fe domain directly or through a peptide linker. In a particular embodiment the second and the third antigen binding moiety are each fused to the Fc domain through an immunoglobulin hinge region. In a specific embodiment, the immunoglobulin hinge region is a human IgG$_1$ hinge region. In one embodiment the second and the third antigen binding moiety and the Fe domain are part of an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG$_4$ subclass immunoglobulin. In a further particular embodiment the immunoglobulin is a human immunoglobulin. In other embodiments the immunoglobulin is a chimeric immunoglobulin or a humanized immunoglobulin. In one embodiment, the protease-activatable T cell activating bispecific molecule essentially consists of an immunoglobulin molecule capable of specific binding to a target cell antigen, and an antigen binding moiety capable of specific binding to CD3 wherein the antigen binding moiety is a Fab molecule, particularly a crossover Fab molecule, fused to the N-terminus of one of the immunoglobulin heavy chains, optionally via a peptide linker.

In a particular embodiment, the first and the third antigen binding moiety are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. In a specific such embodiment, the protease-activatable T cell activating bispecific molecule essentially consists of a first, a second and a third antigen binding moiety, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain. Optionally, the Fab light chain of the first antigen binding moiety and the Fab light chain of the second antigen binding moiety may additionally be fused to each other.

In one embodiment the present invention provides a protease-activatable T cell activating bispecific molecule comprising (i) a first antigen binding moiety which is a Fab molecule capable of specific binding to CD3, comprising the heavy chain complementarity determining region (CDR) 1 of SEQ ID NO: 44, the heavy chain CDR 2 of SEQ ID NO: 45, the heavy chain CDR 3 of SEQ ID NO: 46, the light chain CDR 1 of SEQ ID NO: 17, the light chain CDR 2 of SEQ ID NO: 18 and the light chain CDR 3 of SEQ ID NO: 19, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to FolR1 comprising the heavy chain CDR 1 of SEQ ID NO: 14, the heavy chain CDR 2 of SEQ ID NO: 15, the heavy chain CDR 3 of SEQ ID NO: 16, the light chain CDR 1 of SEQ ID NO: 17, the light chain CDR 2 of SEQ ID NO: 18 and the light chain CDR3 of SEQ ID NO: 19.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to FolR1 comprising heavy chain variable region comprising an amino acid sequence that is at least about 95%, 96%, 97%, 98%, 99% or 100% identical to the amino acid sequence of SEQ ID NO: 47 and a light chain variable region comprising an amino acid sequence that is at least about 95%, 96%, 97%, 98%, 99% or 100% identical to the amino acid sequence of SEQ ID NO: 55.

In one embodiment the present invention provides a protease-activatable T cell activating bispecific molecule comprising (i) a first antigen binding moiety which is a Fab molecule capable of specific binding to CD3, comprising the heavy chain complementarity determining region (CDR) 1 of SEQ ID NO: 44, the heavy chain CDR 2 of SEQ ID NO: 45, the heavy chain CDR 3 of SEQ ID NO: 46, the light chain CDR 1 of SEQ ID NO: 17, the light chain CDR 2 of SEQ ID NO: 18 and the light chain CDR 3 of SEQ ID NO: 19, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to FolR1 comprising the heavy chain CDR 1 of SEQ ID NO: 151, the heavy chain CDR 2 of SEQ ID NO: 152, the heavy chain CDR 3 of SEQ ID NO: 153, the light chain CDR 1 of SEQ ID NO: 154, the light chain CDR 2 of SEQ ID NO: 155 and the light chain CDR3 of SEQ ID NO: 156.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55. wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to FolR1 comprising heavy chain variable region comprising an amino acid sequence that is at least about 95%, %%, 97%, 98%, 99% or 100% identical to the amino acid sequence of SEQ ID NO: 157 and a light chain variable region comprising an amino acid sequence that is at least about 95%, 96%, 97%, 98%, 99% or 100% identical to the amino acid sequence of SEQ ID NO: 158.

In one embodiment the present invention provides a protease-activatable T cell activating bispecific molecule comprising (i) a first antigen binding moiety which is a Fab molecule capable of specific binding to CD3, comprising the heavy chain complementarity determining region (CDR) 1 of SEQ ID NO: 44, the heavy chain CDR 2 of SEQ ID NO: 45, the heavy chain CDR 3 of SEQ ID NO: 46, the light chain CDR 1 of SEQ ID NO: 17, the light chain CDR 2 of SEQ ID NO: 18 and the light chain CDR 3 of SEQ ID NO: 19, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to HER1 comprising the heavy chain CDR 1 of SEQ ID NO: 56, the heavy chain CDR 2 of SEQ ID NO: 57, the heavy chain CDR 3 of SEQ ID NO: 58, the light chain CDR 1 of SEQ ID NO: 59, the light chain CDR 2 of SEQ ID NO: 60 and the light chain CDR3 of SEQ ID NO: 61.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to HER1 comprising a heavy chain variable region comprising an amino acid sequence that is at least about 95%, 96%, 97%, 98%, 99% or 100% identical to the amino acid sequence of SEQ ID NO: 115 and a light chain variable region comprising an amino acid sequence that is at least about 95%. 96%, 97%. 98%, 99% or 100% identical to the amino acid sequence of SEQ ID NO: 116.

In one embodiment the present invention provides a protease-activatable T cell activating bispecific molecule comprising (i) a first antigen binding moiety which is a Fab molecule capable of specific binding to CD3, comprising the heavy chain complementarity determining region (CDR) 1 of SEQ ID NO: 44, the heavy chain CDR 2 of SEQ ID NO: 45, the heavy chain CDR 3 of SEQ ID NO: 46, the light chain CDR 1 of SEQ ID NO: 17. the light chain CDR 2 of SEQ ID NO: 18 and the light chain CDR 3 of SEQ ID NO: 19, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to HER2, wherein the second antigen binding moiety comprises the heavy chain CDR 1 of SEQ ID NO: 142, the heavy chain CDR 2 of SEQ ID NO: 143, the heavy chain CDR 3 of SEQ ID NO: 144, the light chain CDR 1 of SEQ ID NO: 148, the light chain CDR 2 of SEQ ID NO: 149 and the light chain CDR3 of SEQ ID NO: 150, and wherein the third antigen binding moiety comprises the heavy chain CDR 1 of SEQ ID NO: 145, the heavy chain CDR 2 of SEQ ID NO: 146, the heavy chain CDR 3 of SEQ ID NO: 148, the light chain CDR 1 of SEQ ID NO: 148, the light chain CDR 2 of SEQ ID NO: 149 and the light chain CDR3 of SEQ ID NO: 150.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55. wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to HER2, wherein the second antigen binding moiety comprises a heavy chain variable region comprising an amino acid sequence that is at least about 95%, 96%, 97%, 98%, 99% or 100% identical to the amino acid sequence of SEQ ID NO: 160 and a light chain variable region comprising an amino acid sequence that is at least about 95%, 96%, 97%, 98%, 99% or 100% identical to the amino acid sequence of SEQ ID NO: 161, and wherein the third antigen binding moiety comprises a heavy chain variable region comprising an amino acid sequence that is at least about 95%, 96%, 97%, 98%, 99% or 100% identical to the amino acid sequence of SEQ ID NO: 159 and a light chain variable region comprising an amino acid sequence that is at least about 95%. 96%, 97%, 98%, 99% or 100% identical to the amino acid sequence of SEQ ID NO: 161.

In one embodiment the present invention provides a protease-activatable T cell activating bispecific molecule comprising (i) a first antigen binding moiety which is a Fab molecule capable of specific binding to CD3, comprising the heavy chain complementarity determining region (CDR) 1 of SEQ ID NO: 44, the heavy chain CDR 2 of SEQ ID NO: 45, the heavy chain CDR 3 of SEQ ID NO: 46, the light chain CDR 1 of SEQ ID NO: 17, the light chain CDR 2 of SEQ ID NO: 18 and the light chain CDR 3 of SEQ ID NO: 19, wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to Mesothelin comprising the heavy chain CDR 1 of SEQ ID NO: 107, the heavy chain CDR 2 of SEQ ID NO: 108, the heavy chain CDR 3 of SEQ ID NO: 109, the light chain CDR 1 of SEQ ID NO: 110, the light chain CDR 2 of SEQ ID NO: 111 and the light chain CDR3 of SEQ ID NO: 112.

In one embodiment the present invention provides a protease-activatable T cell activating bispecific molecule comprising (i) a first antigen binding moiety which is a Fab molecule capable of specific binding to CD3 comprising a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55. wherein the first antigen binding moiety is a crossover Fab molecule wherein either the variable or the constant regions, particularly the constant regions, of the Fab light chain and the Fab heavy chain are exchanged;

(ii) a second and a third antigen binding moiety each of which is a Fab molecule capable of specific binding to Mesothelin comprising heavy chain variable region comprising an amino acid sequence that is at least about 95%, 96%, 97%, 98%, 99% or 100% identical to the amino acid sequence of SEQ ID NO: 113 and a light chain variable region comprising an amino acid sequence that is at least about 95%, 96%, 97%, 98%, 99% or 100% identical to the amino acid sequence of SEQ ID NO: 114. The protease-activatable T cell activating bispecific molecule according to any of the ten above embodiments may further comprise (iii) an Fc domain composed of a first and a second subunit capable of stable association, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain.

In some of the protease-activatable T cell activating bispecific molecule of the invention, the Fab light chain of the first antigen binding moiety and the Fab light chain of the second antigen binding moiety are fused to each other, optionally via a linker peptide. Depending on the configuration of the first and the second antigen binding moiety, the Fab light chain of the first antigen binding moiety may be fused at its C-terminus to the N-terminus of the Fab light chain of the second antigen binding moiety, or the Fab light chain of the second antigen binding moiety may be fused at its C-terminus to the N-terminus of the Fab light chain of the first antigen binding moiety. Fusion of the Fab light chains of the first and the second antigen binding moiety further reduces mispairing of unmatched Fab heavy and light chains, and also reduces the number of plasmids needed for expression of some of the protease-activatable T cell activating bispecific molecule of the invention.

In certain embodiments the protease-activatable T cell activating bispecific molecule comprises a polypeptide wherein the Fab light chain variable region of the first antigen binding moiety shares a carboxy-terminal peptide bond with the Fab heavy chain constant region of the first antigen binding moiety (i.e. a the first antigen binding moiety comprises a crossover Fab heavy chain, wherein the heavy chain variable region is replaced by a light chain variable region), which in turn shares a carboxy-terminal peptide bond with an Fc domain subunit ($VL_{(1)}$-$CH1_{(1)}$-CH2-CH3(-CH4)), and a polypeptide wherein a the Fab heavy chain of the second antigen binding moiety shares a carboxy-terminal peptide bond with an Fc domain subunit ($VH_{(2)}$-$CH1_{(2)}$-CH2-CH3(-CH4)). In some embodiments the protease-activatable T cell activating bispecific molecule further comprises a polypeptide wherein the Fab heavy chain variable region of the first antigen binding moiety shares a carboxy-terminal peptide bond with the Fab light chain constant region of the first antigen binding moiety ($VH_{(1)}$-$CL_{(1)}$) and the Fab light chain polypeptide of the second antigen binding moiety ($VL_{(2)}$-$CL_{(2)}$). In certain embodiments the polypeptides are covalently linked, e.g., by a disulfide bond.

In alternative embodiments the protease-activatable T cell activating bispecific molecule comprises a polypeptide wherein the Fab heavy chain variable region of the first antigen binding moiety shares a carboxy-terminal peptide bond with the Fab light chain constant region of the first antigen binding moiety (i.e. the first antigen binding moiety comprises a crossover Fab heavy chain, wherein the heavy chain constant region is replaced by a light chain constant region), which in turn shares a carboxy-terminal peptide bond with an Fc domain subunit ($VH_{(1)}$-$CL_{(1)}$-CH2-CH3(-CH4)), and a polypeptide wherein the Fab heavy chain of the second antigen binding moiety shares a carboxy-terminal peptide bond with an Fc domain subunit ($VH_{(2)}$-$CH1_{(1)}$-CH2-CH3(-CH4)). In some embodiments the protease-activatable T cell activating bispecific molecule further comprises a polypeptide wherein the Fab light chain variable region of the first antigen binding moiety shares a carboxy-terminal peptide bond with the Fab heavy chain constant region of the first antigen binding moiety ($VL_{(1)}$-$CH1_{(1)}$) and the Fab light chain polypeptide of the second antigen binding moiety ($VL_{(2)}$-$CL_{(2)}$). In certain embodiments the polypeptides are covalently linked, e.g., by a disulfide bond.

In some embodiments, the protease-activatable T cell activating bispecific molecule comprises a polypeptide wherein the Fab light chain variable region of the first antigen binding moiety shares a carboxy-terminal peptide bond with the Fab heavy chain constant region of the first antigen binding moiety (i.e. the first antigen binding moiety comprises a crossover Fab heavy chain, wherein the heavy chain variable region is replaced by a light chain variable region), which in turn shares a carboxy-terminal peptide bond with the Fab heavy chain of the second antigen binding moiety, which in turn shares a carboxy-terminal peptide bond with an Fc domain subunit ($VL_{(1)}$-$CH1_{(1)}$-$VH_{(2)}$-$CH1_{(2)}$-CH2-CH3(-CH4)). In other embodiments, the protease-activatable T cell activating bispecific molecule comprises a polypeptide wherein the Fab heavy chain variable region of the first antigen binding moiety shares a carboxy-terminal peptide bond with the Fab light chain constant region of the first antigen binding moiety (i.e. the first antigen binding moiety comprises a crossover Fab heavy chain, wherein the heavy chain constant region is replaced by a light chain constant region), which in turn shares a carboxy-terminal peptide bond with the Fab heavy chain of the second antigen binding moiety, which in turn shares a carboxy-terminal peptide bond with an Fc domain subunit ($VH_{(1)}$-$CL_{(1)}$-$VH_{(2)}$-$CH1_{(2)}$-CH2-CH3(-CH4)). In still other embodiments, the protease-activatable T cell activating bispecific molecule comprises a polypeptide wherein the Fab heavy chain of the second antigen binding moiety shares a carboxy-terminal peptide bond with the Fab light chain variable region of the first antigen binding moiety which in turn shares a carboxy-terminal peptide bond with the Fab heavy chain constant region of the first antigen binding moiety (i.e. the first antigen binding moiety comprises a crossover Fab heavy chain, wherein the heavy chain variable region is replaced by a light chain variable region), which in turn shares a carboxy-terminal peptide bond with an Fc domain subunit ($VH_{(2)}$-$CH1_{(2)}$-$VL_{(1)}$-CH1-CH2-CH3(-CH4)). In other embodiments, the protease-activatable T cell activating bispecific molecule comprises a polypeptide wherein the Fab heavy chain of the second antigen binding moiety shares a carboxy-terminal peptide bond with the Fab heavy chain variable region of the first antigen binding moiety which in turn shares a carboxy-terminal peptide bond with the Fab light chain constant region of the first antigen binding moiety (i.e. the first antigen binding moiety comprises a crossover Fab heavy chain, wherein the heavy chain constant region is replaced by a light chain constant region), which in turn shares a carboxy-terminal peptide bond with an Fc domain subunit ($VH_{(2)}$-$CH1_{(2)}$-$VH_{(1)}$-$CL_{(1)}$-CH2-CH3(-CH4)).

In some of these embodiments the protease-activatable T cell activating bispecific molecule further comprises a crossover Fab light chain polypeptide of the first antigen binding moiety, wherein the Fab heavy chain variable region of the first antigen binding moiety shares a carboxy-terminal peptide bond with the Fab light chain constant region of the first antigen binding moiety ($VH_{(1)}$-$CL_{(1)}$), and the Fab light chain polypeptide of the second antigen binding moiety ($VL_{(2)}$-$CL_{(2)}$). In others of these embodiments the protease-activatable T cell activating bispecific molecule further comprises a crossover Fab light chain polypeptide, wherein the Fab light chain variable region of the first antigen binding moiety shares a carboxy-terminal peptide bond with the Fab heavy chain constant region of the first antigen binding moiety ($VL_{(1)}$-$CH1_{(1)}$), and the Fab light chain polypeptide of the second antigen binding moiety ($VL_{(2)}$-$CL_{(2)}$). In still others of these embodiments the protease-activatable T cell activating bispecific molecule further comprises a polypeptide wherein the Fab light chain variable region of the first antigen binding moiety shares a carboxy-terminal peptide bond with the Fab heavy chain constant region of the first antigen binding moiety which in turn shares a carboxy-terminal peptide bond with the Fab light chain polypeptide of the second antigen binding moiety ($VL_{(1)}$-$CH1_{(1)}$-$VL_{(2)}$-$CL_{(2)}$), a polypeptide wherein the Fab heavy chain variable region of the first antigen binding moiety shares a carboxy-terminal peptide bond with the Fab light chain constant region of the first antigen binding moiety which in turn shares a carboxy-terminal peptide bond with the Fab light chain polypeptide of the second antigen binding moiety ($VH_{(1)}$-$CL_{(1)}$-$VL_{(2)}$-$CL_{(2)}$), a polypeptide wherein the Fab light chain polypeptide of the second antigen binding moiety shares a carboxy-terminal peptide bond with the Fab light chain variable region of the first antigen binding moiety which in turn shares a carboxy-terminal peptide bond with the Fab heavy chain constant region of the first antigen binding moiety ($VL_{(2)}$-$CL_{(2)}$-$VL_{(1)}$-$CH1_{(1)}$), or a polypeptide wherein the Fab light chain polypeptide of the second antigen binding moiety shares a carboxy-terminal peptide bond with the Fab heavy chain variable region of the first antigen binding moiety which in turn shares a carboxy-terminal peptide bond with the Fab light chain constant region of the first antigen binding moiety ($VL_{(2)}$-$CL_{(2)}$-$VH_{(1)}$-$CL_{(1)}$).

The protease-activatable T cell activating bispecific molecule according to these embodiments may further comprise (i) an Fc domain subunit polypeptide (CH2-CH3(-CH4)), or (ii) a polypeptide wherein the Fab heavy chain of a third antigen binding moiety shares a carboxy-terminal peptide bond with an Fc domain subunit ($VH_{(3)}$-$CH1_{(3)}$-CH2-CH3 (-CH4)) and the Fab light chain polypeptide of a third antigen binding moiety ($VL_{(3)}$-$CL_{(3)}$). In certain embodiments the polypeptides are covalently linked, e.g., by a disulfide bond.

According to any of the above embodiments, components of the protease-activatable T cell activating bispecific molecule (e.g., antigen binding moiety, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally a number between 1 and 10, typically between 2 and 4.

Fc Domain

The Fc domain of the protease-activatable T cell activating bispecific molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the protease-activatable T cell activating bispecific molecule of the invention comprises not more than one Fc domain.

In one embodiment according the invention the Fc domain of the protease-activatable T cell activating bispecific molecule is an IgG Fc domain. In a particular embodiment the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment the Fc domain is human.

Fc Domain Modifications Promoting Helerodimerization

Protease-activatable T cell activating bispecific molecules according to the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of protease-activatable T cell activating bispecific molecules in recombinant production, it will thus be advantageous to introduce in the Fc domain of the protease-activatable T cell activating bispecific molecule a modification promoting the association of the desired polypeptides.

Accordingly, in particular embodiments the Fc domain of the protease-activatable T cell activating bispecific molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fe domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g., in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in a particular embodiment, in the CH3 domain of the first subunit of the Fc domain of the protease-activatable T cell activating bispecific molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g., by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In a particular embodiment the antigen binding moiety capable of binding to CD3 is fused (optionally via the antigen binding moiety capable of binding to a target cell antigen) to the first subunit of the Fc domain (comprising the "knob" modification). Without wishing to be bound by theory, fusion of the antigen binding moiety capable of binding to CD3 to the knob-containing subunit of the Fc domain will (further) minimize the generation of antigen binding molecules comprising two antigen binding moieties capable of binding to CD3 (steric clash of two knob-containing polypeptides).

In an alternative embodiment a modification promoting association of the first and the second subunit of the Fc domain comprises a modification mediating electrostatic steering effects, e.g., as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Fc Domain Modifications Reducing Fc Receptor Binding and/or Effector Function

The Fc domain confers to the protease-activatable T cell activating bispecific molecule favorable pharmacokinetic properties. including a long serum half-life which contributes to good accumulation in the target tissue and a favorable tissue-blood distribution ratio. At the same time it may, however, lead to undesirable targeting of the protease-activatable T cell activating bispecific molecule to cells expressing Fc receptors rather than to the preferred antigen-bearing cells. Moreover, the co-activation of Fc receptor signaling pathways may lead to cytokine release which, in combination with the T cell activating properties and the long half-life of the antigen binding molecule, results in excessive activation of cytokine receptors and severe side effects upon systemic administration. Activation of (Fc receptor-bearing) immune cells other than T cells may even reduce efficacy of the protease-activatable T cell activating bispecific molecule due to the potential destruction of T cells e.g., by NK cells.

Accordingly, in particular embodiments the Fc domain of the protease-activatable T cell activating bispecific molecules according to the invention exhibits reduced binding affinity to an Fc receptor and/or reduced effector function, as compared to a native $IgG_1$ Fc domain. In one such embodiment the Fc domain (or the protease-activatable T cell activating bispecific molecule comprising said Fc domain) exhibits less than 50%, preferably less than 20%, more preferably less than 10% and most preferably less than 5% of the binding affinity to an Fc receptor, as compared to a native $IgG_1$ Fc domain (or a protease-activatable T cell activating bispecific molecule comprising a native $IgG_1$ Fc domain), and/or less than 50%, preferably less than 20%. more preferably less than 10% and most preferably less than 5% of the effector function, as compared to a native $IgG_1$ Fc domain domain (or a protease-activatable T cell activating bispecific molecule comprising a native $IgG_1$ Fc domain). In one embodiment, the Fc domain domain (or the protease-activatable T cell activating bispecific molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native $IgG_1$ Fc domain domain. Substantially similar binding to FcRn is achieved when the Fc domain (or the protease-activatable T cell activating bispecific molecule comprising said Fc domain) exhibits greater than about 70%, particularly greater than about 80%, more particularly greater than about 90% of the binding affinity of a native $IgG_1$ Fc domain (or the protease-activatable T cell activating bispecific molecule comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the protease-activatable T cell activating bispecific molecule comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the protease-activatable T cell activating bispecific molecule comprising an engineered Fc domain exhibits less than 20%, particularly less than 10%, more particularly less than 5% of the binding affinity to an Fc receptor as compared to a protease-activatable T cell activating bispecific molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the protease-activatable T cell activating bispecific molecule comprising said Fc domain) exhibits greater than about 70% of the binding affinity of a non-engineered form of the Fc domain (or the protease-activatable T cell activating bispecific molecule comprising said non-engineered form of the Fc domain) to FcRn. The Fc domain, or protease-activatable T cell activating bispecific molecules of the invention comprising said Fc domain, may exhibit greater than about 80% and even greater than about 90% of such affinity. In certain embodiments the Ft domain of the protease-activatable T cell activating bispecific molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a protease-activatable T cell activating bispecific molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329. In a more specific embodiment the Fc domain comprises an amino acid substitution at a position selected from the group of L234, L235 and P329. In some embodiments the Fc domain comprises the amino acid substitutions L234A and L235A. In one such embodiment, the Fc domain is an IgG₁ Fc domain, particularly a human IgG₁ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an IgG₁ Fc domain, particularly a human IgG₁ Fc domain. The "P329G LALA" combination of amino acid substitutions almost completely abolishes Fcγ receptor (as well as complement) binding of a human IgG₁ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions. IgG₄ antibodies exhibit reduced binding affinity to Fc receptors and reduced effector functions as compared to IgG₁ antibodies. Hence, in some embodiments the Fc domain of the protease-activatable T cell activating bispecific molecules of the invention is an IgG₄ Fc domain, particularly a human IgG₄ Fc domain. In one embodiment the IgG₄ Fc domain comprises amino acid substitutions at position S228, specifically the amino acid substitution S228P. To further reduce its binding affinity to an Fc receptor and/or its effector function, in one embodiment the IgG₄ Fc domain comprises an amino acid substitution at position L235, specifically the amino acid substitution L235E. In another embodiment, the IgG₄ Fc domain comprises an amino acid substitution at position P329, specifically the amino acid substitution P329G. In a particular embodiment, the IgG₄ Fc domain comprises amino acid substitutions at positions S228, L235 and P329, specifically amino acid substitutions S228P, L235E and P329G. Such IgG₄ Fc domain mutants and their Fcγ receptor binding properties are described in PCT publication no. WO 2012/130831, incorporated herein by reference in its entirety.

In a particular embodiment the Fc domain exhibiting reduced binding affinity to an Fc receptor and/or reduced effector function, as compared to a native IgG₁ Fc domain, is a human IgG₁ Fc domain comprising the amino acid substitutions L234A, L235A and optionally P329G, or a human IgG₄ Fc domain comprising the amino acid substitutions S228P, L235E and optionally P329G.

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g., by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or a protease-activatable T cell activating bispecific molecule comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82. 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96 non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the protease-activatable T cell activating bispecific molecule is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Antigen Binding Moieties

The antigen binding molecule of the invention is bispecific, i.e. it comprises at least two antigen binding moieties capable of specific binding to two distinct antigenic determinants. According to the invention, the antigen binding moieties are Fab molecules (i.e. antigen binding domains composed of a heavy and a light chain, each comprising a variable and a constant region). In one embodiment said Fab molecules are human. In another embodiment said Fab molecules are humanized. In yet another embodiment said Fab molecules comprise human heavy and light chain constant regions.

At least one of the antigen binding moieties is a crossover Fab molecule. Such modification prevent mispairing of heavy and light chains from different Fab molecules, thereby improving the yield and purity of the protease-activatable T cell activating bispecific molecule of the invention in recombinant production. In a particular crossover Fab molecule useful for the protease-activatable T cell activating bispecific molecule of the invention, the constant regions of the Fab light chain and the Fab heavy chain are exchanged. In another crossover Fab molecule useful for the protease-activatable T cell activating bispecific molecule of the invention, the variable regions of the Fab light chain and the Fab heavy chain are exchanged.

In a particular embodiment according to the invention, the protease-activatable T cell activating bispecific molecule is capable of simultaneous binding to a target cell antigen, particularly a tumor cell antigen, and CD3. In one embodiment, the protease-activatable T cell activating bispecific molecule is capable of crosslinking a T cell and a target cell by simultaneous binding to a target cell antigen and CD3. In an even more particular embodiment, such simultaneous binding results in lysis of the target cell, particularly a tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the protease-activatable T cell activating bispecific molecule to CD3 without simultaneous binding to the target cell antigen does not result in T cell activation.

In one embodiment, the protease-activatable T cell activating bispecific molecule is capable of re-directing cytotoxic activity of a T cell to a target cell. In a particular embodiment, said re-direction is independent of MHC-mediated peptide antigen presentation by the target cell and and/or specificity of the T cell.

Particularly, a T cell according to any of the embodiments of the invention is a cytotoxic T cell. In some embodiments the T cell is a CD4$^+$ or a CD8$^+$ T cell, particularly a CD8$^+$ T cell.

CD3 Binding Moiety

The protease-activatable T cell activating bispecific molecule of the invention comprises at least one antigen binding moiety capable of binding to CD3 (also referred to herein as an "CD3 antigen binding moiety" or "first antigen binding moiety"). In a particular embodiment, the protease-activatable T cell activating bispecific molecule comprises not more than one antigen binding moiety capable of specific binding to CD3. In one embodiment the protease-activatable T cell activating bispecific molecule provides monovalent binding to CD3. The CD3 antigen binding is a crossover Fab molecule, i.e. a Fab molecule wherein either the variable or the constant regions of the Fab heavy and light chains are exchanged. In embodiments where there is more than one antigen binding moiety capable of specific binding to a target cell antigen comprised in the protease-activatable T cell activating bispecific molecule, the antigen binding moiety capable of specific binding to CD3 preferably is a crossover Fab molecule and the antigen binding moieties capable of specific binding to a target cell antigen am conventional Fab molecules.

In a particular embodiment CD3 is human CD3 or cynomolgus CD3, most particularly human CD3. In a particular embodiment the CD3 antigen binding moiety is cross-reactive for (i.e. specifically binds to) human and cynomolgus CD3. In some embodiments, the first antigen binding moiety is capable of specific binding to the epsilon subunit of CD3.

The CD3 antigen binding moiety comprises at least one heavy chain complementarity determining region (CDR) selected from the group consisting of SEQ ID NO: 11, SEQ ID NO: 12 and SEQ ID NO: 13 and at least one light chain CDR selected from the group of SEQ ID NO: 17, SEQ ID NO: 18, SEQ ID NO: 19.

In one embodiment the CD3 antigen binding moiety comprises the heavy chain CDR1 of SEQ ID NO: 11, the heavy chain CDR2 of SEQ ID NO: 12, the heavy chain CDR3 of SEQ ID NO: 13, the light chain CDR1 of SEQ ID NO: 17, the light chain CDR2 of SEQ ID NO: 18, and the light chain CDR3 of SEQ ID NO: 19.

In one embodiment the CD3 antigen binding moiety comprises the heavy chain CDR1 of SEQ ID NO: 44, the heavy chain CDR2 of SEQ ID NO: 45, the heavy chain CDR3 of SEQ ID NO: 46, the light chain CDR1 of SEQ ID NO: 17, the light chain CDR2 of SEQ ID NO: 18, and the light chain CDR3 of SEQ ID NO: 19.

In one embodiment the CD3 antigen binding moiety comprises a heavy chain variable region sequence that is at least about 95%, 96%, 97%, 98%, 99% or 100% identical to the amino acid sequence of SEQ ID NO: 43, and a light chain variable region sequence that is at least about 95%, 96%, 97%, 98%, 99% or 100% identical to the amino acid sequence of SEQ ID NO: 55.

In one embodiment the CD3 antigen binding moiety comprises a heavy chain variable region comprising the amino acid sequence of SEQ ID NO: 43 and a light chain variable region comprising the amino acid sequence of SEQ ID NO: 55.

In one embodiment the CD3 antigen binding moiety comprises the heavy chain variable region sequence of SEQ ID NO: 43 and the light chain variable region sequence of SEQ ID NO: 55.

Target Cell Antigen Binding Moiety

The protease-activatable T cell activating bispecific molecule of the invention comprises at least one antigen binding moiety capable of binding to a target cell antigen (also referred to herein as an "target cell antigen binding moiety" or "second" or "third" antigen binding moiety). In certain embodiments, the protease-activatable T cell activating bispecific molecule comprises two antigen binding moieties capable of binding to a target cell antigen. In a particular such embodiment, each of these antigen binding moieties specifically binds to the same antigenic determinant. In an even more particular embodiment, all of these antigen binding moieties are identical. In one embodiment, the protease-activatable T cell activating bispecific molecule comprises an immunoglobulin molecule capable of specific binding to a target cell antigen. In one embodiment the protease-activatable T cell activating bispecific molecule comprises not more than two antigen binding moieties capable of binding to a target cell antigen.

In a preferred embodiment, the target cell antigen binding moiety is a Fab molecule, particularly a conventional Fab molecule that binds to a specific antigenic determinant and is able to direct the Protease-activatable T cell activating bispecific molecule to a target site, for example to a specific type of tumor cell that bears the antigenic determinant.

In certain embodiments the target cell antigen binding moiety specifically binds to a cell surface antigen. In a particular embodiment the target cell antigen binding moiety specifically binds to a Folate Receptor 1 (FolR1) on the surface of a target cell. In another specific such embodiment the target cell antigen binding moiety specifically binds to an epidermal growth factor receptor (EGFR), specifically, a human EGFR, e.g., HER1. In another specific such embodiment the target cell antigen binding moiety specifically binds to HER2. In another specific such embodiment the target cell antigen binding moiety specifically binds to Mesothelin, specifically, to human Mesothelin.

In certain embodiments the target cell antigen binding moiety is directed to an antigen associated with a pathological condition, such as an antigen presented on a tumor cell or on a virus-infected cell. Suitable antigens are cell surface antigens, for example, but not limited to, cell surface receptors. In particular embodiments the antigen is a human antigen. In a specific embodiment the target cell antigen is selected from Folate Receptor 1 (FolR1) and epidermal growth factor receptor (EGFR), specifically, a human EGFR, e.g., HER1. In a further specific embodiment the target cell antigen is HER2. In a further specific embodiment the target cell antigen is Mesothelin.

In some embodiments the protease-activatable T cell activating bispecific molecule comprises at least one antigen binding moiety that is specific for HER1. In one embodiment, the antigen binding moiety that is specific for HER1 comprises at least one heavy chain complementarity determining region (CDR) of selected from the group consisting of SEQ ID NO: 56, SEQ ID NO: 57 and SEQ ID NO: 58 and at least one light chain CDR selected from the group of SEQ ID NO: 59, SEQ ID NO: 60, and SEQ ID NO: 61.

In one embodiment, the antigen binding moiety that is specific for HER1 comprises the heavy chain CDR1 of SEQ ID NO: 56, the heavy chain CDR2 of SEQ ID NO: 57, the heavy chain CDR3 of SEQ ID NO: 58, the light chain CDR1 of SEQ ID NO: 59, the light chain CDR2 of SEQ ID NO: 60, and the light chain CDR3 of SEQ ID NO: 61.

In one embodiment, the antigen binding moiety that is specific for HER1 comprises the heavy chain and light chain CDR sequences of an anti-HER1 antibody disclosed in PCT Application Publication Number WO2006/082515.

In one embodiment the protease-activatable T cell activating bispecific molecule comprising at least one antigen binding moiety that is specific for HER1 comprises at least one of a polypeptide sequence that is at least about 95%, 96%, 97%, 98%, 99% or 100% identical to SEQ ID NO: 32, a polypeptide sequence that is at least about 95%, 96%, 97%, 98%, 99% or 100% identical to SEQ ID NO: 33, a polypeptide sequence that is at least about 95%, 96%, 97%, 98%, 99% or 100% identical to SEQ ID NO: 34. In one embodiment the protease-activatable T cell activating bispecific molecule comprising at least one antigen binding moiety that is specific for HER1 comprises the polypeptide sequence of SEQ ID NO: 32, the polypeptide sequence of SEQ ID NO: 33, and the polypeptide sequence of SEQ ID NO: 34.

In one embodiments the protease-activatable T cell activating bispecific molecule comprising at least one antigen binding moiety that is specific for HER1 further comprises an anti-idiotypic CD3 scFv comprising at least one of the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25. In one embodiment, the anti-idiotypic scFv comprises the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25.

In one embodiments the protease-activatable T cell activating bispecific molecule comprising at least one antigen binding moiety that is specific for HER1 further comprises an anti-idiotypic CD3 scFv comprising at least one of the heavy chain CDR 1 of SEQ ID NO: 26. the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31. In one embodiment, the anti-idiotypic scFv comprises the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31.

In one embodiments the protease-activatable T cell activating bispecific molecule comprising at least one antigen binding moiety that is specific for HER1 further comprises an anti-idiotypic CD3 scFv comprising a polypeptide sequence that is at least about 95%, 96%, 97%, 98%, 99% or 100% identical to SEQ ID NO: 41 or 42. In one embodiment, the anti-idiotypic scFv comprises the polypeptide sequence of SEQ ID NO: 41 or 42.

In one embodiments the protease-activatable T cell activating bispecific molecule comprising at least one antigen binding moiety that is specific for HER1 further comprises an anti-idiotypic HER1 scFv comprising at least one of the heavy chain CDR1 of SEQ ID NO: 48, the heavy chain CDR2 of SEQ ID NO: 49, the heavy chain CDR3 of SEQ ID NO: 50, the light chain CDR1 of SEQ ID NO: 51, the light chain CDR2 of SEQ ID NO: 52, and the light chain CDR3 of SEQ ID NO: 53. In one embodiment, the anti-idiotypic scFv comprises the heavy chain CDR1 of SEQ ID NO: 48, the heavy chain CDR2 of SEQ ID NO: 49, the heavy chain CDR3 of SEQ ID NO: 50, the light chain CDR1 of SEQ ID NO: 51, the light chain CDR2 of SEQ ID NO: 52, and the light chain CDR3 of SEQ ID NO: 53.

In one embodiments the protease-activatable T cell activating bispecific molecule that comprises at least one antigen binding moiety that is specific for HER1 further comprises a linker comprising a polypeptide sequence that is at least about 95%, 96%, 97%, 98%, 99% or 100% identical to SEQ ID NO: 35.

In one embodiment the protease-activatable T cell activating bispecific molecule comprising at least one antigen binding moiety that is specific for HER1 further comprises a linker having a protease recognition site comprising a polypeptide sequence that is at least about 95%, 96%, 97%, 98%, 99% or 100% identical to SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36. In one embodiment, the protease recognition site comprises the polypeptide sequence of SEQ ID NO: 97.

In one embodiments the protease-activatable T cell activating bispecific molecule comprising at least one antigen binding moiety that is specific for HER1 further comprises a linker comprising a polypeptide sequence that is at least about 95%, 96%, 97%, 98%, 99% or 100% identical to SEQ ID NO: 7, 8, 9, 10, 86, 87, 88, 89, 90, 91, 92, 93, 94, 95 or 96. In one embodiment, the linker comprises the polypeptide sequence of SEQ ID NO: 7, 8, 9, 10, 86, 87, 88, 89, 90. 91, 92, 93, 94, 95 or 96. In one embodiment, the linker comprises the polypeptide sequence of SEQ ID NO: 7. In one embodiment, the linker comprises the polypeptide sequence of SEQ ID NO: 86.

In some embodiments the protease-activatable T cell activating bispecific molecule comprises at least one antigen binding moiety that is specific for HER2. In one embodiment, the antigen binding moiety that is specific for HER2 comprises at least one heavy chain complementarity determining region (CDR) of selected from the group consisting of SEQ ID NO: 142, SEQ ID NO: 143 and SEQ ID NO: 144 and at least one light chain CDR selected from the group of SEQ ID NO: 148, SEQ ID NO: 149, and SEQ ID NO: 150. In a further one embodiment, the antigen binding moiety that is specific for HER2 comprises at least one heavy chain complementarity determining region (CDR) of selected from the group consisting of SEQ ID NO: 145, SEQ ID NO: 146 and SEQ ID NO: 147 and at least one light chain CDR selected from the group of SEQ ID NO: 148, SEQ ID NO: 149, and SEQ ID NO: 150.

In one embodiment, the antigen binding moiety that is specific for HER2 comprises the heavy chain CDR1 of SEQ ID NO: 142, the heavy chain CDR2 of SEQ ID NO: 143, the heavy chain CDR3 of SEQ ID NO: 144, the light chain CDR1 of SEQ ID NO: 148, the light chain CDR2 of SEQ ID NO: 149, and the light chain CDR3 of SEQ ID NO: 150. In a further embodiment, the antigen binding moiety that is specific for HER2 comprises the heavy chain CDR1 of SEQ ID NO: 145, the heavy chain CDR2 of SEQ ID NO: 146, the heavy chain CDR3 of SEQ ID NO: 147, the light chain CDR1 of SEQ ID NO: 148, the light chain CDR2 of SEQ ID NO: 149, and the light chain CDR3 of SEQ ID NO: 150.

In one embodiments the protease-activatable T cell activating bispecific molecule comprising at least one antigen binding moiety that is specific for HER2 further comprises an anti-idiotypic CD3 scFv comprising at least one of the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25. In one embodiment, the anti-idiotypic scFv comprises the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25.

In one embodiments the protease-activatable T cell activating bispecific molecule comprising at least one antigen binding moiety that is specific for HER2 further comprises an anti-idiotypic CD3 scFv comprising at least one of the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31. In one embodiment, the anti-idiotypic scFv comprises the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31.

In one embodiments the protease-activatable T cell activating bispecific molecule comprising at least one antigen binding moiety that is specific for HER2 further comprises an anti-idiotypic CD3 scFv comprising a polypeptide sequence that is at least about 95%, 96%, 97%, 98%, 99% or 100% identical to SEQ ID NO: 41 or 42. In one embodiment, the anti-idiotypic scFv comprises the polypeptide sequence of SEQ ID NO: 41 or 42.

In one embodiments the protease-activatable T cell activating bispecific molecule comprising at least one antigen binding moiety that is specific for HER2 further comprises an anti-idiotypic HER2 scFv comprising at least one of the heavy chain CDR1 of SEQ ID NO: 48, the heavy chain CDR2 of SEQ ID NO: 49, the heavy chain CDR3 of SEQ ID NO: 50, the light chain CDR1 of SEQ ID NO: 51, the light chain CDR2 of SEQ ID NO: 52, and the light chain CDR3 of SEQ ID NO: 53. In one embodiment, the anti-idiotypic scFv comprises the heavy chain CDR1 of SEQ ID NO: 48, the heavy chain CDR2 of SEQ ID NO: 49, the heavy chain CDR3 of SEQ ID NO: 50, the light chain CDR1 of SEQ ID NO: 51, the light chain CDR2 of SEQ ID NO: 52, and the light chain CDR3 of SEQ ID NO: 53.

In one embodiments the protease-activatable T cell activating bispecific molecule that comprises at least one antigen binding moiety that is specific for HER2 further comprises a linker comprising a polypeptide sequence that is at least about 95%, 96%, 97%, 98%, 99% or 100% identical to SEQ ID NO: 35.

In one embodiment the protease-activatable T cell activating bispecific molecule comprising at least one antigen binding moiety that is specific for HER2 further comprises a linker having a protease recognition site comprising a polypeptide sequence that is at least about 95%, 96%, 97%, 98%, 99% or 100% identical to SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36. In one embodiment, the protease recognition site comprises the polypeptide sequence of SEQ ID NO: 97.

In one embodiments the protease-activatable T cell activating bispecific molecule comprising at least one antigen binding moiety that is specific for HER2 further comprises a linker comprising a polypeptide sequence that is at least about 95%, 96%, 97%, 98%, 99% or 100% identical to SEQ ID NO: 7, 8, 9, 10, 86, 87, 88, 89, 90, 91, 92, 93, 94, 95 or 96. In one embodiment, the linker comprises the polypeptide sequence of SEQ ID NO: 7, 8, 9, 10, 86, 87, 88, 89, 90. 91, 92, 93, 94, 95 or 96. In one embodiment, the linker comprises the polypeptide sequence of SEQ ID NO: 7. In one embodiment, the linker comprises the polypeptide sequence of SEQ ID NO: 86.

In one embodiment the protease-activatable T cell activating bispecific molecule comprises a polypeptide sequence that is at least about 95%, 96%, 97%, 98%, 99% or 100% identical to SEQ ID NO: 132, a polypeptide sequence that is at least about 95%, 96%, 97%, 98%, 99% or 100% identical to SEQ ID NO: 136, a polypeptide sequence that is at least about 95%, 96%, 97%, 98%, 99% or 100% identical to SEQ ID NO: 81 and a polypeptide sequence that is at least about 95%, 96%, 97%, 98%, 99% or 100% identical to SEQ ID NO: 133.

In one embodiment the protease-activatable T cell activating bispecific molecule comprises the polypeptide sequence of SEQ ID NO: 132, the polypeptide sequence of SEQ ID NO: 136, the polypeptide sequence of SEQ ID NO: 81 and the polypeptide sequence of SEQ ID NO: 133.

In particular embodiments the protease-activatable T cell activating bispecific molecule comprises at least one antigen binding moiety that is specific for FolR1. In one embodiment the FolR1 is a human FolR1. In one embodiment, the protease-activatable T cell activating bispecific molecule comprises at least one antigen binding moiety that is specific for human FolR1 and does not bind to human FolR2 or human FolR3. In one embodiment, the antigen binding moiety that is specific for FolR1 comprises at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

In one embodiment, the antigen binding moiety that is specific for FolR1 comprises the heavy chain CDR1 of SEQ ID NO: 14, the heavy chain CDR2 of SEQ ID NO: 15, the heavy chain CDR3 of SEQ ID NO: 16, the light chain CDR1 of SEQ ID NO: 17, the light chain CDR2 of SEQ ID NO: 18, and the light chain CDR3 of SEQ ID NO: 19.

In a further embodiment, the antigen binding moiety that is specific for FolR1 comprises a heavy chain variable region sequence that is at least about 95%, 96%, 97%, 98%, 99% or 100% identical to SEQ ID NO: 47 and a light chain variable region sequence that is at least about 95%, 96%, 97%, 98%, 99% or 100% identical to SEQ ID NO: 55, or variants thereof that retain functionality.

In one embodiment, the antigen binding moiety that is specific for FolR1 comprises the heavy chain variable region comprising an amino acid sequence of SEQ ID NO: 47 and the light chain variable region comprising an amino acid sequence of SEQ ID NO: 55.

In one embodiment, the antigen binding moiety that is specific for FolR1 comprises at least one heavy chain complementarity determining region (CDR) selected from the group consisting of SEQ ID NO: 151, SEQ ID NO: 152 and SEQ ID NO: 153 and at least one light chain CDR selected from the group of SEQ ID NO: 154, SEQ ID NO: 155 and SEQ ID NO: 156.

In one embodiment, the antigen binding moiety that is specific for FolR1 comprises the heavy chain CDR1 of SEQ ID NO: 151, the heavy chain CDR2 of SEQ ID NO: 152, the heavy chain CDR3 of SEQ ID NO: 153, the light chain CDR1 of SEQ ID NO: 154, the light chain CDR2 of SEQ ID NO: 155, and the light chain CDR3 of SEQ ID NO: 156.

In a further embodiment, the antigen binding moiety that is specific for FolR1 comprises a heavy chain variable region sequence that is at least about 95%, 96%, 97%, 98%, 99% or 100% identical to SEQ ID NO: 157 and a light chain variable region sequence that is at least about 95%, 96%, 97%, 98%, 99% or 100% identical to SEQ ID NO: 158, or variants thereof that retain functionality.

In one embodiment, the antigen binding moiety that is specific for FolR1 comprises the heavy chain variable region comprising an amino acid sequence of SEQ ID NO: 157 and the light chain variable region comprising an amino acid sequence of SEQ ID NO: 158.

In one embodiment the protease-activatable T cell activating bispecific molecule comprises a polypeptide sequence that is at least about 95%, 96%, 97%, 98%, 99% or 100% identical to SEQ ID NO: 2, and a polypeptide sequence that is at least about 95%, 96%, 97%, 98%, 99% or 100% identical to SEQ ID NO: 1.

In one embodiment the protease-activatable T cell activating bispecific molecule comprises the polypeptide sequence of SEQ ID NO: 2, and the polypeptide sequence of SEQ ID NO: 1.

In one embodiments the protease-activatable T cell activating bispecific molecule comprising at least one antigen binding moiety that is specific for FolR1 further comprises an anti-idiotypic CD3 scFv comprising at least one of the heavy chain CDR 1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24. and the light chain CDR3 of SEQ ID NO: 25. In one embodiment, the anti-idiotypic scFv comprises the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25.

In one embodiments the protease-activatable T cell activating bispecific molecule comprising at least one antigen binding moiety that is specific for FolR1 further comprises an anti-idiotypic CD3 scFv comprising at least one of the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31. In one embodiment, the anti-idiotypic scFv comprises the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31.

In one embodiments the protease-activatable T cell activating bispecific molecule comprising at least one antigen binding moiety that is specific for FolR1 further comprises an anti-idiotypic CD3 scFv comprising a polypeptide sequence that is at least about 95%, 96%, 97%, 98%, 99% or 100% identical to SEQ ID NO: 41 or 42. In one embodiment, the anti-idiotypic scFv comprises the polypeptide sequence of SEQ ID NO: 41 or 42.

In one embodiments the protease-activatable T cell activating bispecific molecule comprising at least one antigen binding moiety that is specific for FolR1 further comprises a linker having a protease recognition site comprising a polypeptide sequence that is at least about 95%, 96%, 97%, 98%, 99% or 100% identical to SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36. In one embodiment, the protease recognition site comprises the polypeptide sequence of SEQ ID NO: 97.

In one embodiments the protease-activatable T cell activating bispecific molecule comprising at least one antigen binding moiety that is specific for ForR1 further comprises a linker comprising a polypeptide sequence that is at least about 95%, 96%, 97%, 98%, 99% or 100% identical to SEQ ID NO: 7, 8, 9, 10, 86, 87, 88, 89, 90, 91, 92, 93, 94, 95 or 96. In one embodiment, the linker comprises the polypeptide sequence of SEQ ID NO: 7, 8, 9, 10, 86, 87, 88, 89, 90, 91, 92. 93, 94, 95 or 96. In one embodiment, the linker comprises the polypeptide sequence of SEQ ID NO: 7. In one embodiment, the linker comprises the polypeptide sequence of SEQ ID NO: 86.

In one embodiment the protease-activatable T cell activating bispecific molecule comprises a polypeptide sequence that is at least about 95%, 96%, 97%, 98%, 99% or 100% identical to SEQ ID NO: 1, a polypeptide sequence that is at least about 95%, 96%, 97%, 98%, 99% or 100% identical to SEQ ID NO: 3 and a polypeptide sequence that is at least about 95%, 96%, 97%, 98%, 99% or 100% identical to SEQ ID NO: 72.

In one embodiment the protease-activatable T cell activating bispecific molecule comprises a polypeptide sequence that is at least about 95%, 96%, 97%, 98%, 99% or 100% identical to SEQ ID NO: 1, a polypeptide sequence that is at least about 95%, 96%, 97%, 98%, 99% or 100% identical to SEQ ID NO: 3 and a polypeptide sequence that is at least about 95%, 96%, 97%, 98%, 99% or 100% identical to SEQ ID NO: 72.

In one embodiment the protease-activatable T cell activating bispecific molecule comprises a polypeptide sequence that is at least about 95%, 96%, 97%, 98%, 99% or 100% identical to SEQ ID NO: 1, a polypeptide sequence that is at least about 95%, 96%, 97%, 98%, 99% or 100% identical to SEQ ID NO: 3 and a polypeptide sequence that is at least about 95%, 96%, 97%, 98%, 99% or 100% identical to SEQ ID NO: 85.

In one embodiment the protease-activatable T cell activating bispecific molecule comprises a polypeptide sequence that is at least about 95%, 96%, 97%, 98%, 99% or 100% identical to SEQ ID NO: 1, a polypeptide sequence that is at least about 95%, 96%, 97%, 98%, 99% or 100% identical to SEQ ID NO: 3, a polypeptide sequence that is at least about 95%, 96%, 97%, 98%, 99% or 100% identical to SEQ ID NO: 73 and a polypeptide sequence that is at least about 95%, 96%, 97%, 98%, 99% or 100% identical to SEQ ID NO: 74.

In one embodiment the protease-activatable T cell activating bispecific molecule comprises the polypeptide sequence of SEQ ID NO: 1, the polypeptide sequence of SEQ ID NO: 3 and the polypeptide sequence of SEQ ID NO: 72.

In one embodiment the protease-activatable T cell activating bispecific molecule comprises the polypeptide sequence of SEQ ID NO: 1, the polypeptide sequence of SEQ ID NO: 3 and the polypeptide sequence of SEQ ID NO: 85.

In one embodiment the protease-activatable T cell activating bispecific molecule comprises the polypeptide sequence of SEQ ID NO: 1, the polypeptide sequence of SEQ ID NO: 3, the polypeptide sequence of SEQ ID NO: 73 and the polypeptide sequence of SEQ ID NO: 74.

In one embodiment the protease-activatable T cell activating bispecific molecule comprises a polypeptide sequence that is at least about 95%, 96%, 97%, 98%, 99% or 100% identical to SEQ ID NO: 137, a polypeptide sequence that is at least about 95%, 96%, 97%, 98%, 99% or 100% identical to SEQ ID NO: 139, a polypeptide sequence that is at least about 95%, 96%, 97%, 98%, 99% or 100% identical to SEQ ID NO: 81 and a polypeptide sequence that is at least about 95%, 96%, 97%, 98%, 99% or 100% identical to SEQ ID NO: 138.

In one embodiment the protease-activatable T cell activating bispecific molecule comprises the polypeptide sequence of SEQ ID NO: 137, the polypeptide sequence of SEQ ID NO: 139, the polypeptide sequence of SEQ ID NO: 81 and the polypeptide sequence of SEQ ID NO: 138.

In particular embodiments the protease-activatable T cell activating bispecific molecule comprises at least one antigen binding moiety that is specific for Mesothelin. In one embodiment the Mesothelin is human Mesothelin. In one embodiment, the protease-activatable T cell activating bispecific molecule comprises at least one antigen binding moiety that is specific for human Mesothelin. In one embodiment, the antigen binding moiety that is specific for Mesothelin comprises at least one heavy chain complementarity determining region (CDR) selected from the group consisting of SEQ ID NO: 107, SEQ ID NO: 108 and SEQ ID NO: 109 and at least one light chain CDR selected from the group of SEQ ID NO: 110, SEQ ID NO: 111 and SEQ ID NO: 112.

In one embodiment, the antigen binding moiety that is specific for Mesothelin comprises the heavy chain CDR 1 of SEQ ID NO: 107, the heavy chain CDR2 of SEQ ID NO: 108, the heavy chain CDR3 of SEQ ID NO: 109, the light chain CDR1 of SEQ ID NO: 110, the light chain CDR2 of SEQ ID NO: 111, and the light chain CDR3 of SEQ ID NO: 112.

In a further embodiment, the antigen binding moiety that is specific for Mesothelin comprises a heavy chain variable region sequence that is at least about 95%, 96%, 97%, 98%, 99% or 100% identical to SEQ ID NO: 113 and a light chain variable region sequence that is at least about 95%, 96%, 97%, 98%, 99% or 100% identical to SEQ ID NO: 114, or variants thereof that retain functionality.

In one embodiment, the antigen binding moiety that is specific for Mesothelin comprises the heavy chain variable region comprising the amino acid sequence of SEQ ID NO: 113 and the light chain variable region comprising the amino acid sequence of SEQ ID NO: 114.

In one embodiments the protease-activatable T cell activating bispecific molecule comprising at least one antigen binding moiety that is specific for Mesothelin further comprises an anti-idiotypic CD3 scFv comprising at least one of the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25.

In one embodiment, the anti-idiotypic scFv comprises the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25.

In one embodiments the protease-activatable T cell activating bispecific molecule comprising at least one antigen binding moiety that is specific for Mesothelin further comprises an anti-idiotypic CD3 scFv comprising at least one of the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31.

In one embodiment, the anti-idiotypic scFv comprises the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31.

In one embodiments the protease-activatable T cell activating bispecific molecule comprising at least one antigen binding moiety that is specific for Mesothelin further comprises an anti-idiotypic CD3 scFv comprising a polypeptide sequence that is at least about 95%, 96%, 97%, 98%, 99% or 100% identical to SEQ ID NO: 41 or 42. In one embodiment, the anti-idiotypic scFv comprises the polypeptide sequence of SEQ ID NO: 41 or 42.

In one embodiments the protease-activatable T cell activating bispecific molecule comprising at least one antigen binding moiety that is specific for Mesothelin further comprises a linker having a protease recognition site comprising a polypeptide sequence that is at least about 95%, 96%, 97%, 98%, 99% or 100% identical to SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36, 37, 38, 39, 40, 97, 98, 99, 100, 101, 102, 103, 104, 105 or 106. In one embodiment, the protease recognition site comprises the polypeptide sequence of SEQ ID NO: 36. In one embodiment, the protease recognition site comprises the polypeptide sequence of SEQ ID NO: 97.

In one embodiments the protease-activatable T cell activating bispecific molecule comprising at least one antigen binding moiety that is specific for Mesothelin further comprises a linker comprising a polypeptide sequence that is at least about 95%, 96%, 97%, 98%, 99% or 100% identical to SEQ ID NO: 7, 8, 9, 10, 86, 87, 88, 89, 90, 91, 92, 93, 94, 95 or 96. In one embodiment, the linker comprises the polypeptide sequence of SEQ ID NO: 7, 8, 9, 10, 86, 87, 88, 89, 90, 91, 92, 93, 94, 95 or 96. In one embodiment, the linker comprises the polypeptide sequence of SEQ ID NO: 7. In one embodiment, the linker comprises the polypeptide sequence of SEQ ID NO: 86.

In one embodiment the protease-activatable T cell activating bispecific molecule comprises a polypeptide sequence that is at least about 95%, 96%, 97%, 98%, 99% or 100% identical to SEQ ID NO: 77, a polypeptide sequence that is at least about 95%, 96%, 97%, 98%, 99% or 100% identical to SEQ ID NO: 78, a polypeptide sequence that is at least about 95%, 96%, 97%, 98%, 99% or 100% identical to SEQ ID NO: 81 and a polypeptide sequence that is at least about 95%, 96%, 97%, 98%, 99% or 100% identical to SEQ ID NO: 82.

In one embodiment the protease-activatable T cell activating bispecific molecule comprises a polypeptide sequence that is at least about 95%, 96%, 97%, 98%, 99% or 100% identical to SEQ ID NO: 76, a polypeptide sequence that is at least about 95%, 96%, 97%, 98%, 99% or 100% identical to SEQ ID NO: 77, a polypeptide sequence that is at least about 95%, 96%, 97%, 98%, 99% or 100% identical to SEQ ID NO: 78 and a polypeptide sequence that is at least about 95%, 96%, 97%, 98%, 99% or 100% identical to SEQ ID NO: 79.

In one embodiment the protease-activatable T cell activating bispecific molecule comprises the polypeptide sequence of SEQ ID NO: 77, the polypeptide sequence of SEQ ID NO: 78, the polypeptide sequence of SEQ ID NO: 81 and the polypeptide sequence of SEQ ID NO: 82.

In one embodiment the protease-activatable T cell activating bispecific molecule comprises the polypeptide sequence of SEQ ID NO: 76, the polypeptide sequence of SEQ ID NO: 77, the polypeptide sequence of SEQ ID NO: 78 and the polypeptide sequence of SEQ 1D NO: 79.

In one embodiment, provided is a T cell activating bispecific molecule comprises a polypeptide sequence that is at least about 95%, 96%, 97%, 98%, 99% or 100% identical to SEQ ID NO: 76, a polypeptide sequence that is at least about 95%, 96%, 97%, 98%, 99% or 100% identical to SEQ ID NO: 77, a polypeptide sequence that is at least about 95%, 96%, 97%, 98%, 99% or 100% identical to SEQ ID NO: 78 and a polypeptide sequence that is at least about 95%, 96%, 97%, 98%, 99% or 100% identical to SEQ ID NO: 81.

In one embodiment the T cell activating bispecific molecule comprises a polypeptide sequence that is at least about 95%, 96%, 97%, 98%, 99% or 100% identical to SEQ ID NO: 77, a polypeptide sequence that is at least about 95%, 96%, 97%, 98%, 99% or 100% identical to SEQ ID NO: 78, a polypeptide sequence that is at least about 95%, 96%, 97%, 98%, 99% or 100% identical to SEQ ID NO: 81 and a polypeptide sequence that is at least about 95%, 96%, 97%, 98%, 99% or 100% identical to SEQ ID NO: 84.

In one embodiment the T cell activating bispecific molecule comprises the polypeptide sequence of SEQ ID NO: 76, the polypeptide sequence of SEQ ID NO: 77, the polypeptide sequence of SEQ ID NO: 78 and the polypeptide sequence of SEQ ID NO: 81.

In one embodiment the T cell activating bispecific molecule comprises the polypeptide sequence of SEQ ID NO: 77, the polypeptide sequence of SEQ ID NO: 78, the polypeptide sequence of SEQ ID NO: 81 and the polypeptide sequence of SEQ ID NO: 84.

Masking Moiety

The protease-activatable T cell activating bispecific molecule of the invention comprises at least one masking moiety. Others have tried to mask binding of an antibody by capping the binding moiety with a fragment of the antigen recognized by the binding moiety (e.g., WO2013128194). This approach has several limitations. For example, using the antigen allows for less flexibility in reducing the affinity of the binding moiety. This is so because the affinity has to be high enough to be reliably masked by the antigen mask. Also, dissociated antigen could potentially bind to and interact with its cognate receptor(s) in vivo and cause undesirable signals to the cell expressing such receptor. In contrast, the approach described herein uses an anti-idiotype antibody or fragment thereof as a mask. Two countervailing considerations for designing an effective masking moiety are 1. effectiveness of the masking and 2. reversibility of the masking. If the affinity is too low, masking would be inefficient. However, if the affinity is too high, the masking process might not be readily reversible. It was not predictable whether a high affinity anti-idiotype mask or a low affinity anti-idiotype mask would work better. As described herein, higher affinity masking moieties performed overall better in masking the antigen binding side and, at the same time, could be effectively removed for activation of the molecule. In one embodiment, the anti-idiotype mask has a $K_D$ of 1-8 nM. In one embodiment, anti-idiotype mask has a $K_D$ of 2 nM at 37° C. In one specific embodiment, the masking moiety recognizes the idiotype of the first antigen binding moiety capable of specific binding to a CD3, e.g., a human CD3. In one specific embodiment, the masking moiety recognizes the idiotype of the second antigen binding moiety capable of binding to a target cell antigen.

In one embodiment, the masking moiety masks a CD3-binding moiety and comprises at least one of the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25. In one embodiment, the masking moiety comprises the heavy chain CDR1 of SEQ ID NO: 20, the heavy chain CDR2 of SEQ ID NO: 21, the heavy chain CDR3 of SEQ ID NO: 22, the light chain CDR1 of SEQ ID NO: 23, the light chain CDR2 of SEQ ID NO: 24, and the light chain CDR3 of SEQ ID NO: 25.

In one embodiment, the masking moiety masks a CD3-binding moiety and comprises a polypeptide sequence that is at least about 95%, 96%, 97%, 98%, 99% or 100% identical to SEQ ID NO: 41. In one embodiment, the masking moiety masks a CD3-binding moiety and comprises the polypeptide sequence of SEQ ID NO: 41.

In one preferred embodiment, the masking moiety masks a CD3-binding moiety and comprises at least one of the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31. In one embodiment, the masking moiety comprises the heavy chain CDR1 of SEQ ID NO: 26, the heavy chain CDR2 of SEQ ID NO: 27, the heavy chain CDR3 of SEQ ID NO: 28, the light chain CDR1 of SEQ ID NO: 29, the light chain CDR2 of SEQ ID NO: 30, and the light chain CDR3 of SEQ ID NO: 31. In one embodiment, the masking moiety masks a CD3-binding moiety and comprises a polypeptide sequence that is at least about 95%, 96%, 97%, 98%, 99% or 100% identical to SEQ ID NO: 42. In one preferred embodiment, the masking moiety masks a CD3-binding moiety and comprises the polypeptide sequence of SEQ ID NO: 42.

In one embodiment, the masking moiety masks a HER1-binding moiety and comprises at least one of the heavy chain CDR1 of SEQ ID NO: 48, the heavy chain CDR2 of SEQ ID NO: 49, the heavy chain CDR3 of SEQ ID NO: 50, the light chain CDR1 of SEQ ID NO: 51, the light chain CDR2 of SEQ ID NO: 52, and the light chain CDR3 of SEQ ID NO: 53. In one embodiment, the anti-idiotypic scFv comprises the heavy chain CDR1 of SEQ ID NO: 48, the heavy chain CDR2 of SEQ ID NO: 49, the heavy chain CDR3 of SEQ ID NO: 50, the light chain CDR1 of SEQ ID NO: 51, the light chain CDR2 of SEQ ID NO: 52, and the light chain CDR3 of SEQ ID NO: 53.

In one aspect, the invention relates to an idiotype-specific polypeptide for reversibly concealing antigen binding of an antigen-binding of a molecule. In one embodiment, the invention relates to an idiotype-specific polypeptide for reversibly concealing an anti-CD3 antigen binding site of a molecule. Such idiotype-specific polypeptide for reversibly concealing an anti-CD3 antigen binding site must be capable of specific binding to the anti-CD3 antigen binding site's idiotype and thereby reducing or abrogating binding of the anti-CD3 antigen binding site to CD3. In one embodiment, the invention relates to an idiotype-specific polypeptide for reversibly concealing an anti-HER1 antigen binding site of a molecule. In one embodiment the idiotype-specific polypeptide is an anti-idiotype scFv. In one embodiment the idiotype-specific polypeptide is covalently attached to the molecule through a linker. In one embodiment the idiotype-specific polypeptide is covalently attached to the molecule through more than one linker. In one embodiment the idiotype-specific polypeptide is covalently attached to the molecule through two linkers. In one embodiment the linker is a peptide linker. In one embodiment the linker is a protease-cleavable linker. In one embodiment, the linker comprises the sequence of SEQ ID NO: 7, 8, 9, or 10. In one embodiment, the linker comprises the sequence of SEQ ID NO: 7, 8, 9, 10, 86, 87, 88, 89, 90, 91, 92, 93, 94, 95 or 96. In one embodiment, the linker comprises the polypeptide sequence of SEQ ID NO: 7. In one embodiment, the linker comprises the polypeptide sequence of SEQ ID NO: 86. In one embodiment the peptide linker comprises at least one protease recognition site. In one embodiment, the protease recognition site comprises the polypeptide sequence of SEQ ID NO: 36, 37, 38, 39, 40, 97, 98, 99, 100, 101, 102, 103, 104, 105 or 106. In one preferred embodiment, the protease recognition site comprises the protease recognition sequence RQARVVNG (SEQ ID NO: 36). In further embodiment, the linker comprises more than one protease recognition site. In one preferred embodiment, the protease recognition site comprises the protease recognition sequence VHM-PLFLGPRQARVVNG (SEQ ID NO:97). In one embodiment the protease is selected from the group consisting of metalloproteinase, e.g., matrix metalloproteinase (MMP) 1-28 and A Disintegrin And Metalloproteinase (ADAM) 2, 7-12, 15, 17-23, 28-30 and 33, serine protease, e.g., urokinase-type plasminogen activator and Matriptase, cysteine protease, aspartic protease, and cathepsin protease. In one specific embodiment the protease is MMP9 or MMP2. In a further specific embodiment, the protease is Matriptase.

In one embodiment the molecule which comprises the anti-CD3 antigen binding site is a T-cell activating bispecific molecule. In one particular embodiment the idiotype-specific polypeptide comprises a heavy chain variable region comprising at least one of a heavy chain complementarity determining region (CDR H) 1 amino acid sequence of DYSIH (SEQ ID NO:20); CDR H2 amino acid sequence of WINTETGEPAYADDFKG (SEQ ID NO:21); and a CDR H3 amino acid sequence of PYDYDVLDY (SEQ ID NO:22). In one particular embodiment the idiotype-specific polypeptide comprises a light chain variable region comprising at least one of: a light chain (CDR L)1 amino acid sequence of RASKSVSTSNYSYIH (SEQ ID NO:23); a CDR L2 amino acid sequence of YVSYLES (SEQ ID NO:24); and a CDR L3 amino acid sequence of QHSREFPWT (SEQ ID NO:25). In one particular embodiment the idiotype-specific polypeptide comprises: a heavy chain complementarity determining region (CDR H) 1 amino acid sequence of DYSIH (SEQ ID NO:20); a CDR H2 amino acid sequence of WINTETGEPAYADDFKG (SEQ ID NO:21); a CDR H3 amino acid sequence of PYDYDVLDY (SEQ ID NO:22); and a light chain variable region comprising: a light chain (CDR L)1 amino acid sequence of RASKSVSTSNYSYIH (SEQ ID NO:23); a CDR L2 amino acid sequence of YVSYLES (SEQ ID NO:24); and a CDR L3 amino acid sequence of QHSREFPWT (SEQ ID NO:25). In one particular embodiment the idiotype-specific polypeptide comprises a heavy chain variable region comprising at least one of: a heavy chain complementarity determining region (CDR H) 1 amino acid sequence of SYGVS (SEQ ID NO:26); a CDR H2 amino acid sequence of IIWGDGSTNYHSALIS (SEQ ID NO:27); and a CDR H3 amino acid sequence of GITTVVDDYYAMDY (SEQ ID NO:28). In one particular embodiment the idiotype-specific polypeptide comprises a light chain variable region comprising at least one of: a light chain (CDR L)1 amino acid sequence of RASENIDSYLA (SEQ ID NO:29): a CDR L2 amino acid sequence of AATFLAD (SEQ ID NO:30); and a CDR L3 amino acid sequence of QHYYSTPYT (SEQ ID NO:31). In one particular embodiment the idiotype-specific polypeptide comprises a heavy chain variable region comprising: a heavy chain complementarity determining region (CDR H) 1 amino acid sequence of SYGVS (SEQ ID NO:26); a CDR H2 amino acid sequence of IIWGDGSTNYHSALIS (SEQ ID NO:27); a CDR H3 amino acid sequence of GITTVVDDYYAMDY (SEQ ID NO:28); and a light chain variable region comprising: a light chain (CDR L)1 amino acid sequence of RASENIDSYLA (SEQ ID NO:29); a CDR L2 amino acid sequence of AATFLAD (SEQ ID NO:30); and a CDR L3 amino acid sequence of QHYYSTPYT (SEQ ID NO:31). In one embodiment, the idiotype-specific polypeptide comprises a heavy chain variable region comprising at least one of: a heavy chain complementarity determining region (CDR H) 1 amino acid sequence of SEQ ID NO:48; a CDR H2 amino acid sequence of SEQ ID NO:49; and a CDR H3 amino acid sequence of SEQ ID NO:50. In one embodiment, the idiotype-specific polypeptide comprises a light chain variable region comprising at least one of: a light chain complementarity determining region (CDR L) 1 amino acid sequence of SEQ ID NO:51; a CDR L2 amino acid sequence of SEQ ID NO:52; and a CDR L3 amino acid sequence of SEQ ID NO:53. In one embodiment, the idiotype-specific polypeptide comprises a heavy chain variable region comprising a heavy chain complementarity determining region (CDR H) 1 amino acid sequence of SEQ ID NO:48; a CDR H2 amino acid sequence of SEQ ID NO:49; and a CDR H3 amino acid sequence of SEQ ID NO:50, and a light chain variable region comprising a light chain complementarity determining region (CDR L) 1 amino acid sequence of SEQ ID NO:51; a CDR L2 amino acid sequence of SEQ ID NO:52; and a CDR L3 amino acid sequence of SEQ ID NO:53.

Polynucleotides

The invention further provides isolated polynucleotides encoding a protease-activatable T cell activating bispecific molecule as described herein or a fragment thereof. In some embodiments, said fragment is an antigen binding fragment.

Polynucleotides of the invention include those that are at least about 80%, 85%, 90%, 95%, 96%, 97%, 98%, 99%, or 100% identical to the sequences set forth in SEQ ID NOs 62-71 or SEQ ID NOs including functional fragments or variants thereof. Polynucleotides of the invention further include those that are at least about 80%, 85%, 90%, 95%, 96%, 97%, 98%, 99%, or 100% identical to the sequences set forth in SEQ ID NOs 117-131 including functional fragments or variants thereof. Polynucleotides of the invention further include those that are at least about 80%, 85%, 90%, 95%, 96%, 97%, 98%, 99%, or 100% identical to the sequences set forth in SEQ ID NOs 162-170 including functional fragments or variants thereof.

The polynucleotides encoding protease-activatable T cell activating bispecific molecules of the invention may be expressed as a single polynucleotide that encodes the entire protease-activatable T cell activating bispecific molecule or as multiple (e.g., two or more) polynucleotides that are co-expressed. Polypeptides encoded by polynucleotides that are co-expressed may associate through, e.g., disulfide bonds or other means to form a functional protease-activatable T cell activating bispecific molecule. For example, the light chain portion of an antigen binding moiety may be encoded by a separate polynucleotide from the portion of the protease-activatable T cell activating bispecific molecule comprising the heavy chain portion of the antigen binding moiety, an Fc domain subunit and optionally (part of) another antigen binding moiety. When co-expressed, the heavy chain polypeptides will associate with the light chain polypeptides to form the antigen binding moiety. In another example, the portion of the protease-activatable T cell activating bispecific molecule comprising one of the two Fc domain subunits and optionally (part of) one or more antigen binding moieties could be encoded by a separate polynucleotide from the portion of the protease-activatable T cell activating bispecific molecule comprising the other of the two Fc domain subunits and optionally (part of) an antigen binding moiety. When co-expressed, the Fc domain subunits will associate to form the Fc domain.

In some embodiments, the isolated polynucleotide encodes the entire protease-activatable T cell activating bispecific molecule according to the invention as described herein. In other embodiments, the isolated polynucleotide encodes a polypeptides comprised in the protease-activatable T cell activating bispecific molecule according to the invention as described herein.

In another embodiment, the present invention is directed to an isolated polynucleotide encoding a protease-activatable T cell activating bispecific molecule of the invention or a fragment thereof, wherein the polynucleotide comprises a sequence that encodes a variable region sequence. In another embodiment, the present invention is directed to an isolated polynucleotide encoding a protease-activatable T cell activating bispecific molecule or fragment thereof, wherein the polynucleotide comprises a sequence that encodes a polypeptide sequence as shown in SEQ ID NOs 1, 2, 3, 4, 5, 6, 7, 8, 9, 10, 32, 33, 34, 35, 36, 37, 38, 39, 40, 41, 42, 43, 47, or 55. In another embodiment, the present invention is directed to an isolated polynucleotide encoding a protease-activatable T cell activating bispecific molecule or fragment thereof, wherein the polynucleotide comprises a sequence that encodes a polypeptide sequence as shown in SEQ ID NOs 1, 2, 3, 4, 5, 6, 7, 8, 9, 10, 32, 33, 34, 35, 36, 37, 38, 39, 40, 41, 42, 43, 47, 55, 72, 73, 74, 75, 76, 77, 78, 79, 80, 81, 82, 83, 84, 85. In another embodiment, the present invention is directed to an isolated polynucleotide encoding a protease-activatable T cell activating bispecific molecule or fragment thereof, wherein the polynucleotide comprises a sequence that encodes a polypeptide sequence as shown in SEQ ID NOs 1, 2, 3, 4, 5, 6, 7, 8, 9, 10, 32, 33, 34, 35, 36, 37, 38, 39, 40, 41, 42, 43, 47, 55, 72, 73, 74, 75, 76, 77, 78, 79, 80, 81, 82, 83, 84, 85, 132, 133, 134, 135, 136, 137, 138, 139, 140 or 141. In another embodiment, the invention is further directed to an isolated polynucleotide encoding a protease-activatable T cell activating bispecific molecule of the invention or a fragment thereof, wherein the polynucleotide comprises a sequence that is at least about 80%, 85%, 90%, 95%, 96%, 97%, 98%, or 99% identical to the nucleotide sequence shown in SEQ ID NOs 62, 63, 64, 65, 66, 67, 68, 69, 70, or 71. In another embodiment, the invention is further directed to an isolated polynucleotide encoding a protease-activatable T cell activating bispecific molecule of the invention or a fragment thereof, wherein the polynucleotide comprises a sequence that is at least about 80%, 85%, 90%, 95%, 96%, 97%, 98%, or 99% identical to the nucleotide sequence shown in SEQ ID NOs 62, 63, 64, 65, 66, 67, 68, 69, 70, 71, 117, 118, 119, 120, 121, 122, 123, 124, 125, 126, 127, 128, 129, 130 or 131. In another embodiment, the invention is further directed to an isolated polynucleotide encoding a protease-activatable T cell activating bispecific molecule of the invention or a fragment thereof, wherein the polynucleotide comprises a sequence that is at least about 80%, 85%, 90%, 95%, 96%, 97%, 98%, or 99% identical to the nucleotide sequence shown in SEQ ID NOs 62, 63, 64, 65, 66, 67, 68, 69, 70, 71, 117, 118, 119, 120, 121, 122, 123, 124, 125, 126, 127, 128, 129, 130, 131, 162, 163, 164, 165, 166, 167, 168, 169 or 170. In another embodiment, the invention is directed to an isolated polynucleotide encoding a protease-activatable T cell activating bispecific molecule of the invention or a fragment thereof, wherein the polynucleotide comprises the nucleic acid sequence shown in SEQ ID NOs 62, 63, 64, 65, 66, 67, 68, 69, 70, or 71. In another embodiment, the invention is directed to an isolated polynucleotide encoding a protease-activatable T cell activating bispecific molecule of the invention or a fragment thereof, wherein the polynucleotide comprises the nucleic acid sequence shown in SEQ ID NOs 62, 63, 64, 65, 66, 67, 68, 69, 70, 71, 117, 118, 119, 120, 121, 122, 123, 124, 125, 126, 127, 128, 129, 130 or 131. In another embodiment, the invention is directed to an isolated polynucleotide encoding a protease-activatable T cell activating bispecific molecule of the invention or a fragment thereof, wherein the polynucleotide comprises the nucleic acid sequence shown in SEQ ID NOs 62, 63, 64, 65, 66, 67, 68, 69, 70, 71, 117, 118, 119, 120, 121, 122, 123, 124, 125, 126, 127, 128, 129, 130, 131, 162, 163, 164, 165, 166, 167, 168, 169 or 170. In another embodiment, the invention is directed to an isolated polynucleotide encoding a protease-activatable T cell activating bispecific molecule of the invention or a fragment thereof, wherein the polynucleotide comprises a sequence that encodes a variable region sequence that is at least about 80%, 85%, 90%, 95%, 96%, 97%, 98%, or 99% identical to the amino acid sequence in SEQ ID NOs 43, 47, or 55. The invention encompasses an isolated polynucleotide encoding a protease-activatable T cell activating bispecific molecule of the invention or a fragment thereof, wherein the polynucleotide comprises a sequence that encodes the variable region sequence of SEQ ID NOs SEQ ID NOs 43, 47, or 55 with conservative amino acid substitutions.

In another embodiment, the invention is directed to an isolated polynucleotide encoding a protease-activatable T cell activating bispecific molecule of the invention or a fragment thereof, wherein the polynucleotide comprises a sequence that encodes a variable region sequence that is at least about 80%, 85%, 90%, 95%, 96%, 97%, 98%, or 99% identical to the amino acid sequence in SEQ ID NOs 43, 47, 55, 113, 114, 115 or 116. The invention encompasses an isolated polynucleotide encoding a protease-activatable T cell activating bispecific molecule of the invention or a fragment thereof, wherein the polynucleotide comprises a sequence that encodes the variable region sequence of SEQ ID NOs SEQ ID NOs 43, 47, 55, 113, 114, 115 or 116 with conservative amino acid substitutions.

In another embodiment, the invention is directed to an isolated polynucleotide encoding a protcasc-activatable T cell activating bispecific molecule of the invention or a fragment thereof, wherein the polynucleotide comprises a sequence that encodes a variable region sequence that is at least about 80%, 85%, 90%, 95%, 96%, 97%, 98%, or 99% identical to the amino acid sequence in SEQ ID NOs 43, 47, 55, 113, 114, 115, 116, 157, 158, 159, 160 or 161. The invention encompasses an isolated polynucleotide encoding a protease-activatable T cell activating bispecific molecule of the invention or a fragment thereof, wherein the polynucleotide comprises a sequence that encodes the variable region sequence of SEQ ID NOs SEQ ID NOs 43, 47, 55, 113, 114, 115, 116, 157, 158, 159, 160 or 161 with conservative amino acid substitutions.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

The invention further provides isolated polynucleotides encoding an idiotype-specific polypeptide as described herein or a fragment thereof. In some embodiments, said fragment is an idiotype binding, i.e., anti-idiotype specific antibody or fragment thereof. In one embodiment the idiotype-specific polypeptide is an anti-idiotypic scFv.

The invention also encompasses an isolated polynucleotide encoding an idiotype-specific polypeptide of the invention or a fragment thereof, wherein the polynucleotide comprises a sequence that encodes the polypeptide sequence of one or more of SEQ ID NOs 20, 21, 22, 23, 24, 25, 26, 27, 28, 29, 30, 31, 48, 49, 50, 51, 52, and 53. The invention also encompasses an isolated polynucleotide encoding an idiotype-specific polypeptide of the invention or a fragment thereof, wherein the polynucleotide comprises a sequence that encodes the polypeptide sequence of one or more of SEQ ID NOs 20, 21, 22, 23, 24, 25, 26, 27, 28, 29, 30, 31, 48, 49, 50, 51, 52, and 53 with conservative amino acid substitutions.

The polynucleotides encoding idiotype-specific polypeptides of the invention may be expressed as a single polynucleotide that encodes the entire idiotype-specific polypeptide or as multiple (e.g., two or more) polynucleotides that are co-expressed. Polypeptides encoded by polynucleotides that are co-expressed may associate through, e.g., disulfide bonds or other means to form a functional idiotype-specific polypeptide, e.g., a masking moiety. For example, in one embodiment the idiotype-specific polypeptide is an anti-idiotypic scFv (single chain variable fragment) wherein the light chain variable portion of the anti-idiotypic scFv may be encoded by a separate polynucleotide from the portion of the anti-idiotypic scFv comprising the heavy chain variable portion of the anti-idiotypic scFv. When co-expressed, the heavy chain polypeptides will associate with the light chain polypeptides to form the anti-idiotypic scFv. In some embodiments, the isolated polynucleotide encodes the idiotype-specific polypeptide according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods protease-activatable T cell activating bispecific molecules of the invention may be obtained, for example, by solid-state peptide synthesis (e.g., Merrifield solid phase synthesis) or recombinant production. For recombinant production one or more polynucleotide encoding the protease-activatable T cell activating bispecific molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a protease-activatable T cell activating bispecific molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the protease-activatable T cell activating bispecific molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g., on a single vector, or in separate polynucleotide constructs, e.g., on separate (different) vectors. Furthermore, any vector may contain a single coding region. or may comprise two or more coding regions, e.g., a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the protease-activatable T cell activating bispecific molecule (fragment) of the invention, or variant or derivative thereof. Heterologous coding regions include without limitation specialized elements or motifs, such as a secretory signal peptide or a heterologous functional domain. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g., the immediate early promoter, in conjunction with intron-A), simian virus 40 (e.g., the early promoter), and retroviruses (such as, e.g., Rous sarcoma virus). Other transcription control regions include those derived from vertebrate genes such as actin, heat shock protein, bovine growth hormone and rabbit I-globin, as well as other sequences capable of controlling gene expression in eukaryotic cells. Additional suitable transcription control regions include tissue-specific promoters and enhancers as well as inducible promoters (e.g., promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the protease-activatable T cell activating bispecific molecule is desired, DNA encoding a signal sequence may be placed upstream of the nucleic acid encoding a protease-activatable T cell activating bispecific molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g., a histidine tag) or assist in labeling the protease-activatable T cell activating bispecific molecule may be included within or at the ends of the protease-activatable T cell activating bispecific molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g., has been transformed or transfected with) a vector comprising a polynucleotide that encodes (part of) a protease-activatable T cell activating bispecific molecule of the invention. As used herein, the term "host cell" refers to any kind of cellular system which can be engineered to generate the protease-activatable T cell activating bispecific molecules of the invention or fragments thereof. Host cells suitable for replicating and for supporting expression of protease-activatable T cell activating bispecific molecules are well known in the art.

Such cells may be transfected or transduced as appropriate with the particular expression vector and large quantities of vector containing cells can be grown for seeding large scale fermenters to obtain sufficient quantities of the protease-activatable T cell activating bispecific molecule for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells.

Numerous baculoviral strains have been identified which may be used in conjunction with insect cells, particularly for transfection of *Spodoptera frugiperda* cells. Plant cell cultures can also be utilized as hosts. See e.g., U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a protease-activatable T cell activating bispecific molecule according to the invention is provided, wherein the method comprises culturing a host cell comprising a polynucleotide encoding the protease-activatable T cell activating bispecific molecule, as provided herein, under conditions suitable for expression of the protease-activatable T cell activating bispecific molecule, and recovering the protease-activatable T cell activating bispecific molecule from the host cell (or host cell culture medium).

The components of the protease-activatable T cell activating bispecific molecule are genetically fused to each other. Protease-activatable T cell activating bispecific molecules can be designed such that its components are fused directly to each other or indirectly through a linker sequence. The composition and length of the linker may be determined in accordance with methods well known in the art and may be tested for efficacy. Examples of linker sequences between different components of protease-activatable T cell activating bispecific molecules are found in the sequences provided herein. Additional sequences may also be included to incorporate a cleavage site to separate the individual components of the fusion if desired, for example an endopeptidase recognition sequence.

In certain embodiments the one or more antigen binding moieties of the protease-activatable T cell activating bispecific molecules comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g., Harlow and Lane, "Antibodies, a laboratory manual", Cold Spring Harbor Laboratory, 1988). Non-naturally occurring antibodies can be constructed using solid phase-peptide synthesis, can be produced recombinantly (e.g., as described in U.S. Pat.

No. 4,186,567) or can be obtained, for example, by screening combinatorial libraries comprising variable heavy chains and variable light chains (see e.g., U.S. Pat. No. 5,969,108 to McCafferty).

Any animal species of antibody, antibody fragment, antigen binding domain or variable region can be used in the protease-activatable T cell activating bispecific molecules of the invention. Non-limiting antibodies, antibody fragments, antigen binding domains or variable regions useful in the present invention can be of murine, primate, or human origin. If the protease-activatable T cell activating bispecific molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g., recipient antibody) framework and constant regions with or without retention of critical framework residues (e.g., those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhocycn et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Cuff Opin Pharmacol 5, 368-74 (2001) and Lonberg, Curr Opin Immunol 20, 450-459 (2008). Human variable regions can form part of and be derived from human monoclonal antibodies made by the hybridoma method (see e.g., Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g., Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antigen binding moities useful in the present invention are engineered to have enhanced binding affinity according to, for example, the methods disclosed in U.S. Pat. Appl. Publ. No. 2004/0132066. the entire contents of which are hereby incorporated by reference. The ability of the protease-activatable T cell activating bispecific molecule of the invention to bind to a specific antigenic determinant can be measured either through an enzyme-linked immunosorbent assay (ELISA) or other techniques familiar to one of skill in the art, e.g., surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g., an antibody that competes with the V9 antibody for binding to CD3. In certain embodiments, such a competing antibody binds to the same epitope (e.g., a linear or a conformational epitope) that is bound by the reference antibody. Detailed exemplary methods for mapping an epitope to which an antibody binds are provided in Morris (1996) "Epitope Mapping Protocols." in Methods in Molecular Biology vol. 66 (Humana Press, Totowa, N.J.). In an exemplary competition assay, immobilized antigen (e.g., CD3) is incubated in a solution comprising a first labeled antibody that binds to the antigen (e.g., V9 antibody, described in U.S. Pat. No. 6,054,297) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Protease-activatable T cell activating bispecific molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the protease-activatable T cell activating bispecific molecule binds. For example, for affinity chromatography purification of protease-activatable T cell activating bispecific molecules of the invention, a matrix with protein A or protein G may be used. Sequential Protein A or G affinity chromatography and size exclusion chromatography can be used to isolate a protease-activatable T cell activating bispecific molecule essentially as described in the Examples. The purity of the protease-activatable T cell activating bispecific molecule can be determined by any of a variety of well-known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see, e.g., FIGS. 8-12). Three bands were resolved at approximately Mr 25,000, Mr 50,000 and Mr 75,000, corresponding to the predicted molecular weights of the protease-activatable T cell activating bispecific molecule light chain, heavy chain and heavy chain/light chain fusion protein.

Assays protease-activatable T cell activating bispecific molecules provided herein may be identified, screened for, or characterized for their physical/chemical properties and/or biological activities by various assays known in the art.

Affinity Assays

The affinity of the protease-activatable T cell activating bispecific molecule for an Fc receptor or a target antigen can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of protease-activatable T cell activating bispecific molecules for different receptors or target antigens may be evaluated using cell lines expressing the particular receptor or target antigen, for example by flow cytometry (FACS). A specific illustrative and exemplary embodiment for measuring binding affinity is described in the following and in the Examples below. According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti-human Fab specific antibody (GE Healthcare) that is immobilized on an activated CM5-sensor chip surface as described for the anti Penta-His antibody. The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the protease-activatable T cell activating bispecific molecules of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the protease-activatable T cell activating bispecific molecules provided herein, e.g., for use in any of the below therapeutic methods. In one embodiment, a pharmaceutical composition comprises any of the protease-activatable T cell activating bispecific molecules provided herein and a pharmaceutically acceptable carrier. In another embodiment, a pharmaceutical composition comprises any of the protease-activatable T cell activating bispecific molecules provided herein and at least one additional therapeutic agent, e.g., as described below.

Further provided is a method of producing a protease-activatable T cell activating bispecific molecule of the invention in a form suitable for administration in vivo, the method comprising (a) obtaining a protease-activatable T cell activating bispecific molecule according to the invention, and (b) formulating the protease-activatable T cell activating bispecific molecule with at least one pharmaceutically acceptable carrier, whereby a preparation of protease-activatable T cell activating bispecific molecule is formulated for administration in vivo.

Pharmaceutical compositions of the present invention comprise a therapeutically effective amount of one or more protease-activatable T cell activating bispecific molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one protease-activatable T cell activating bispecific molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g., antibacterial agents, antifungal agents), isotonic agents, absorption delaying agents, salts, preservatives. antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990. pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Protease-activatable T cell activating bispecific molecules of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularily, mucosally, intrapericardially, intraumbilically, intraocularally, orally, topically, locally, by inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the protease-activatable T cell activating bispecific molecules of the invention.

Parenteral compositions include those designed for administration by injection, e.g., subcutaneous, intradermal, intralesional, intravenous, intraarterial intramuscular, intrathecal or intraperitoneal injection. For injection, the protease-activatable T cell activating bispecific molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the protease-activatable T cell activating bispecific molecules may be in powder form for constitution with a suitable vehicle, e.g., sterile pyrogen-free water, before use. Sterile injectable solutions are prepared by incorporating the protease-activatable T cell activating bispecific molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g., films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the protease-activatable T cell activating bispecific molecules may also be formulated as a depot preparation. Such long acting formulations may be administered by implantation (for example subcutaneously or intramuscularly) or by intramuscular injection. Thus, for example, the protease-activatable T cell activating bispecific molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the protease-activatable T cell activating bispecific molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The protease-activatable T cell activating bispecific molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the protease-activatable T cell activating bispecific molecules provided herein may be used in therapeutic methods. Protease-activatable T cell activating bispecific molecules of the invention can be used as immunotherapeutic agents, for example in the treatment of cancers.

For use in therapeutic methods, protease-activatable T cell activating bispecific molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, protease-activatable T cell activating bispecific molecules of the invention for use as a medicament are provided. In further aspects, protease-activatable T cell activating bispecific molecules of the invention for use in treating a disease are provided. In certain embodiments, protease-activatable T cell activating bispecific molecules of the invention for use in a method of treatment are provided. In one embodiment, the invention provides a protease-activatable T cell activating bispecific molecule as described herein for use in the treatment of a disease in an individual in need thereof. In certain embodiments, the invention provides a protease-activatable T cell activating bispecific molecule for use in a method of treating an individual having a disease comprising administering to the individual a therapeutically effective amount of the protease-activatable T cell activating bispecific molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a protease-activatable T cell activating bispecific molecule as described herein for use in inducing lysis of a target cell, particularly a tumor cell. In certain embodiments, the invention provides a protease-activatable T cell activating bispecific molecule for use in a method of inducing lysis of a target cell, particularly a tumor cell, in an individual comprising administering to the individual an effective amount of the protease-activatable T cell activating bispecific molecule to induce lysis of a target cell. An "individual" according to any of the above embodiments is a mammal, preferably a human.

In a further aspect, the invention provides for the use of a protease-activatable T cell activating bispecific molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of a protease-activatable T cell activating bispecific molecule of the invention. In one embodiment a composition is administered to said individual, comprising the protease-activatable T cell activating bispecific molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with a protease-activatable T cell activating bispecific molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of a protease-activatable T cell activating bispecific molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a protease-activatable T cell activating bispecific molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the protease-activatable T cell activating bispecific molecule may not provide a cure but may only provide partial benefit. In some embodiments, a physiological change having some benefit is also considered therapeutically beneficial. Thus, in some embodiments, an amount of protease-activatable T cell activating bispecific molecule that provides a physiological change is considered an "effective amount" or a "therapeutically effective amount". The subject, patient, or individual in need of treatment is typically a mammal, more specifically a human.

In some embodiments, an effective amount of a protease-activatable T cell activating bispecific molecule of the invention is administered to a cell. In other embodiments, a therapeutically effective amount of a protease-activatable T cell activating bispecific molecule of the invention is administered to an individual for the treatment of disease.

For the prevention or treatment of disease, the appropriate dosage of a protease-activatable T cell activating bispecific molecule of the invention (when used alone or in combination with one or more other additional therapeutic agents) will depend on the type of disease to be treated, the route of administration, the body weight of the patient, the type of T cell activating bispecific antigen binding molecule, the severity and course of the disease, whether the T cell activating bispecific antigen binding molecule is administered for preventive or therapeutic purposes, previous or concurrent therapeutic interventions, the patient's clinical history and response to the protease-activatable T cell activating bispecific molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The protease-activatable T cell activating bispecific molecule is suitably administered to the patient at one time or over a series of treatments. Depending on the type and severity of the disease, about 1 μg/kg to 15 mg/kg (e.g., 0.1 mg/kg-10 mg/kg) of protease-activatable T cell activating bispecific molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the T cell activating bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body wright to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the protease-activatable T cell activating bispecific molecule). An initial higher loading dose, followed by one or more lower doses may be administered. However, other dosage regimens may be useful. The progress of this therapy is easily monitored by conventional techniques and assays.

The protease-activatable T cell activating bispecific molecule of the invention will generally be used in an amount effective to achieve the intended purpose. For use to treat or prevent a disease condition, the protease-activatable T cell activating bispecific molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the protease-activatable T cell activating bispecific molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC. In cases of local administration or selective uptake, the effective local concentration of the protease-activatable T cell activating bispecific molecules may not be related to plasma concentration. One having skill in the art will be able to optimize therapeutically effective local dosages without undue experimentation.

A therapeutically effective dose of the protease-activatable T cell activating bispecific molecules described herein will generally provide therapeutic benefit without causing substantial toxicity. Toxicity and therapeutic efficacy of a protease-activatable T cell activating bispecific molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LDs/ED_{50}$. Protease-activatable T cell activating bispecific molecule that exhibit large therapeutic indices are preferred. In one embodiment, the protease-activatable T cell activating bispecific molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety). The attending physician for patients treated with protease-activatable T cell activating bispecific molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The protease-activatable T cell activating bispecific molecules of the invention may be administered in combination with one or more other agents in therapy. For instance, a protease-activatable T cell activating bispecific molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of protease-activatable T cell activating bispecific molecule used, the type of disorder or treatment, and other factors discussed above. The protease-activatable T cell activating bispecific molecule are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the protease-activatable T cell activating bispecific molecule of the invention can occur prior to, simultaneously, and/or following, administration of the additional therapeutic agent and/or adjuvant. Protease-activatable T cell activating bispecific molecules of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a protease-activatable T cell activating bispecific molecule of the invention. The label or package insert indicates that the composition is used for treating the condition of choice. Moreover, the article of manufacture may comprise (a) a first container with a composition contained therein, wherein the composition comprises a protease-activatable T cell activating bispecific molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXEMPLARY EMBODIMENTS

1. A protease-activatable T cell activating bispecific molecule comprising
   (a) a first antigen binding moiety capable of specific binding to CD3;
   (b) a second antigen binding moiety capable of specific binding to a target cell antigen; and
   (c) a masking moiety covalently attached to the T cell bispecific binding molecule through a protease-cleavable linker, wherein the masking moiety is capable of specific binding to the idiotype of the first or the second antigen binding moiety thereby reversibly concealing the first or the second antigen binding moiety.
2. The protease-activatable T cell activating bispecific molecule of embodiment 1, wherein the masking moiety is covalently attached to the first antigen binding moiety and reversibly conceals the first antigen binding moiety.
3. The protease-activatable T cell activating bispecific molecule of embodiment 1 or 2, wherein the masking moiety is covalently attached to the heavy chain variable region of the first antigen binding moiety.
4. The protease-activatable T cell activating bispecific molecule of embodiment 1 or 2, wherein the masking moiety is covalently attached to the light chain variable region of the first antigen binding moiety.
5. The protease-activatable T cell activating bispecific molecule of any one of embodiments 1 to 4, wherein the masking moiety is an anti-idiotypic scFv.
6. The protease-activatable T cell activating bispecific molecule of any one of embodiments 2 to 5, wherein the protease-activatable T cell activating bispecific molecule comprises a second masking moiety reversibly concealing the second antigen binding moiety.
7. The protease-activatable T cell activating bispecific molecule of any one of embodiments 1 to 6, wherein the protease is expressed by the target cell.
8. The protease-activatable T cell activating bispecific molecule of any one of embodiments 1 to 7, wherein the second antigen binding moiety is a crossover Fab molecule wherein either the variable or the constant regions of the Fab light chain and the Fab heavy chain are exchanged.
9. The protease-activatable T cell activating bispecific molecule of any one of embodiments 1 to 8, wherein the second antigen binding moiety is a crossover Fab molecule wherein the constant regions of the Fab light chain and the Fab heavy chain are exchanged.
10. The protease-activatable T cell activating bispecific molecule of any one of embodiments 1 to 9. wherein the first antigen binding moiety is a conventional Fab molecule.
11. The protease-activatable T cell activating bispecific molecule of any one of embodiments 1 to 10, comprising not more than one antigen binding moiety capable of specific binding to CD3.
12. The protease-activatable T cell activating bispecific molecule of any one of embodiments 1 to 11, comprising a third antigen binding moiety which is a Fab molecule capable of specific binding to a target cell antigen.
13. The protease-activatable T cell activating bispecific molecule of embodiment 12, wherein the third antigen binding moiety is identical to the second antigen binding moiety.
14. The protease-activatable T cell activating bispecific molecule of any one of embodiments 1 to 13, wherein the second antigen binding moiety is capable of specific binding to FolR1 or HER1.
15. The protease-activatable T cell activating bispecific molecule of any one of embodiments 1 to 13, wherein the second antigen binding moiety is capable of specific binding to a target cell antigen selected from the group consisting of FolR1, HER1 and Mesothelin.
16. The protease-activatable T cell activating bispecific molecule of any one of embodiments 1 to 13, wherein the second antigen binding moiety is capable of specific binding to a target cell antigen selected from the group consisting of FolR1, HER1, HER2 and Mesothelin.
17. The protease-activatable T cell activating bispecific molecule of any one of embodiments 1 to 16, wherein the first and the second antigen binding moiety are fused to each other, optionally via a peptide linker.
18. The protease-activatable T cell activating bispecific molecule of any one of embodiments 1 to 17, wherein the second antigen binding moiety is fused at the C-terminus of the Fab heavy chain to the N-terminus of the Fab heavy chain of the first antigen binding moiety.
19. The protease-activatable T cell activating bispecific molecule of any one of embodiments 1 to 17, wherein the first antigen binding moiety is fused at the C-terminus of the Fab heavy chain to the N-terminus of the Fab heavy chain of the second antigen binding moiety.
20. The protease-activatable T cell activating bispecific molecule of any one of embodiments 1 to 19, wherein the Fab light chain of the first antigen binding moiety and the Fab light chain of the second antigen binding moiety are fused to each other, optionally via a peptide linker.
21. The protease-activatable T cell activating bispecific molecule of any one of embodiments 1 to 20, additionally comprising an Fc domain composed of a first and a second subunit capable of stable association.
22. The protease-activatable T cell activating bispecific molecule of embodiment 21, wherein the Fc domain is an IgG, specifically an $IgG_1$ or $IgG_4$. Fc domain.
23. The protease-activatable T cell activating bispecific molecule of embodiment 21 or 22, wherein the Fc domain is a human Fc domain.
24. The protease-activatable T cell activating bispecific molecule of any one of embodiments 21 to 23. wherein the Fc domain exhibits reduced binding affinity to an Fc receptor and/or reduced effector function, as compared to a native $IgG_1$ Fc domain.
25. The protease-activatable T cell activating bispecific molecule of embodiment 24, wherein the Fc domain comprises one or more amino acid substitution that reduces binding to an Fc receptor and/or effector function.
26. The protease-activatable T cell activating bispecific molecule of embodiment 25, wherein said one or more amino acid substitution is at one or more position selected from the group of L234, L235, and P329 (Kabat numbering).
27. The protease-activatable T cell activating bispecific molecule of embodiment 26, wherein each subunit of the Fc domain comprises three amino acid substitutions that reduce binding to an activating Fc receptor and/or effector function wherein said amino acid substitutions are L234A, L235A and P329G.
28. The protease-activatable T cell activating bispecific molecule of any one of embodiments 24 to 27, wherein the Fc receptor is an Fcγ receptor.
29. The protease-activatable T cell activating bispecific molecule of any one of embodiments 24 to 28, wherein the effector function is antibody-dependent cell-mediated cytotoxicity (ADCC).
30. The protease-activatable T cell activating bispecific molecule of any one of embodiments 1 to 29, wherein the masking moiety comprises a heavy chain variable region comprising at least one of:
   (a) a heavy chain complementarity determining region (CDR H) 1 amino acid sequence of DYSIH (SEQ ID NO:20);
   (b) a CDR H2 amino acid sequence of WINTETGE-PAYADDFKG (SEQ ID NO:21); and
   (c) a CDR H3 amino acid sequence of PYDYDVLDY (SEQ ID NO:22).

31. The protease-activatable T cell activating bispecific molecule of any one of embodiments 1 to 30, wherein the masking moiety comprises a light chain variable region comprising at least one of:
   (d) a light chain (CDR L)l amino acid sequence of RASKSVSTSNYSYIH (SEQ ID NO:23);
   (e) a CDR L2 amino acid sequence of YVSYLES (SEQ ID NO:24); and
   (f) a CDR L3 amino acid sequence of QHSREFPWT (SEQ ID NO:25).

32. The protease-activatable T cell activating bispecific molecule of any one of embodiments 1 to 31, wherein the masking moiety comprises a heavy chain variable region comprising:
   (a) a heavy chain complementarity determining region (CDR H) 1 amino acid sequence of DYSIH (SEQ ID NO:20);
   (b) a CDR H2 amino acid sequence of WINTETGEPAYADDFKG (SEQ ID NO:21);
   (c) a CDR H3 amino acid sequence of PYDYDVLDY (SEQ ID NO:22); and a light chain variable region comprising:
   (d) a light chain (CDR L)1 amino acid sequence of RASKSVSTSNYSYIH (SEQ ID NO:23);
   (e) a CDR L2 amino acid sequence of YVSYLES (SEQ ID NO:24); and
   (f) a CDR L3 amino acid sequence of QHSREFPWT (SEQ ID NO:25).

33. The protease-activatable T cell activating bispecific molecule of any one of embodiments 1 to 29, wherein the masking moiety comprises a heavy chain variable region comprising at least one of:
   (a) a heavy chain complementarity determining region (CDR H) 1 amino acid sequence of SYGVS (SEQ ID NO:26);
   (b) a CDR H2 amino acid sequence of IIWGDGSTNYHSALIS (SEQ ID NO:27); and
   (c) a CDR H3 amino acid sequence of GITTVVDDYYAMDY (SEQ ID NO:28).

34. The protease-activatable T cell activating bispecific molecule of any one of embodiments 1 to 29 and 33, wherein the masking moiety comprises a light chain variable region comprising at least one of:
   (d) a light chain (CDR L)1 amino acid sequence of RASENIDSYLA (SEQ ID NO:29);
   (e) a CDR L2 amino acid sequence of AATFLAD (SEQ ID NO:30); and
   (f) a CDR L3 amino acid sequence of QHYYSTPYT (SEQ ID NO:31).

35. The protease-activatable T cell activating bispecific molecule of any one of embodiments 1 to 29 and 33 to 34, wherein the masking moiety comprises a heavy chain variable region comprising:
   (a) a heavy chain complementarity determining region (CDR H) 1 amino acid sequence of SYGVS (SEQ ID NO:26);
   (b) a CDR H2 amino acid sequence of IIWGDGSTNYHSALIS (SEQ ID NO:27);
   (c) a CDR H3 amino acid sequence of GITTVVDDYYAMDY (SEQ ID NO:28); and a light chain variable region comprising:
   (d) a light chain (CDR L)1 amino acid sequence of RASENIDSYLA (SEQ ID NO:29);
   (e) a CDR L2 amino acid sequence of AATFLAD (SEQ ID NO:30); and
   (f) a CDR L3 amino acid sequence of QHYYSTPYT (SEQ ID NO:31).

36. The protease-activatable T cell activating bispecific molecule of any one of embodiments 1 to 35, wherein the masking moiety comprises a heavy chain variable region comprising at least one of:
   (a) a heavy chain complementarity determining region (CDR H) 1 amino acid sequence of DYYIN (SEQ ID NO:48);
   (b) a CDR H2 amino acid sequence of VINPDSGGTDYNQNFKG (SEQ ID NO:49); and
   (c) a CDR H3 amino acid sequence of RDSYGFDY (SEQ ID NO:50).

37. The protease-activatable T cell activating bispecific molecule of any one of embodiments 1 to 36, wherein the masking moiety comprises a light chain variable region comprising at least one of:
   (a) a light chain (CDR L)1 amino acid sequence of KASLSVTNDVA (SEQ ID NO:51);
   (b) a CDR L2 amino acid sequence of YASNRNA (SEQ ID NO:52); and
   (c) a CDR L3 amino acid sequence of QQDYTSPPT (SEQ ID NO:53).

38. The protease-activatable T cell activating bispecific molecule of any one of embodiments 1 to 37, wherein the masking moiety comprises a heavy chain variable region comprising:
   a) a heavy chain complementarity determining region (CDR H) 1 amino acid sequence of DYYIN (SEQ ID NO:48);
   b) a CDR H2 amino acid sequence of VINPDSGGTDYNQNFKG (SEQ ID NO:49); and
   c) a CDR H3 amino acid sequence of RDSYGFDY (SEQ ID NO:50); and a light chain variable region comprising:
   d) a light chain (CDR L)1 amino acid sequence of KASLSVTNDVA (SEQ ID NO:51);
   e) a CDR L2 amino acid sequence of YASNRNA (SEQ ID NO:52); and
   f) a CDR L3 amino acid sequence of QQDYTSPPT (SEQ ID NO:53).

39. The protease-activatable T cell activating bispecific molecule of any one of embodiments 1 to 38, wherein the protease cleavable linker comprises at least one protease recognition sequence.

40. The protease-activatable T cell activating bispecific molecule of embodiment 39, wherein the protease cleavable linker comprises a protease recognition sequence.

41. The protease-activatable T cell activating bispecific molecule of embodiment 40, wherein the protease recognition sequence is selected from the group consisting of:

```
                                         (SEQ ID NO: 36)
    (a) RQARVVNG;

(SEQ ID NO: 37)
    (b) VHMPLGFLGPGRSRGSFP;

(SEQ ID NO: 38)
    (c) RQARVVNGXXXXXVPLSLYSG;
    and (SEQ ID NO: 39)
    (d) RQARVVNGVPLSLYSG (SEQ ID NO: 40)
    (e) PLGLWSQ, wherein X is any amino acid.
```

42. The protease-activatable T cell activating bispecific molecule of embodiment 40, wherein the protease recognition sequence is selected from the group consisting of:

(a) RQARVVNG; (SEQ ID NO: 36)

(b) VHMPLGFLGPGRSRGSFP; (SEQ ID NO: 37)

(c) RQARVVNGXXXXXVPLSLYSG; (SEQ ID NO: 38)

(d) RQARVVNGVPLSLYSG; (SEQ ID NO: 39)

(e) PLGLWSQ; (SEQ ID NO: 40)

(f) VHMPLGFLGPRQARVVNG; (SEQ ID NO: 97)

(g) FVGGTG; (SEQ ID NO: 98)

(h) KKAAPVNG; (SEQ ID NO: 99)

(i) PMAKKVNG; (SEQ ID NO: 100)

(j) QARAKVNG; (SEQ ID NO: 101)

(k) VHMPLGFLGP; (SEQ ID NO: 102)

(l) QARAK; (SEQ ID NO: 103)

(m) VHMPLGFLGPPMAKK; (SEQ ID NO: 104)

(n) KKAAP; and (SEQ ID NO: 105)

(o) PMAKK, (SEQ ID NO: 106)

wherein X is any amino acid.

43. The protease-activatable T cell activating bispecific molecule of embodiment 39 or 40, wherein the protease cleavable linker comprises the protease recognition sequence RQARVVNG (SEQ ID NO:36).

44. The protease-activatable T cell activating bispecific molecule of embodiment 39 or 40, wherein the protease cleavable linker comprises the protease recognition sequence VHMPLGFLGPRQARVVNG (SEQ ID NO:97).

45. The protease-activatable T cell activating bispecific molecule of embodiment 39 or 40, wherein the protease cleavable linker comprises the protease recognition sequence RQARVVNG (SEQ ID NO:36) or the protease recognition sequence VHMPLGFLGPRQARVVNG (SEQ ID NO:97).

46. The protease-activatable T cell activating bispecific molecule of any one of embodiments 1 to 45, wherein the protease is selected from the group consisting of metalloproteinase, serine protease, cysteine protease, aspartic proteases, and cathepsin protease.

47. The protease-activatable T cell activating bispecific molecule of embodiment 46, wherein the metalloproteinase is a matrix metalloproteinase (MMP), preferably MMP9 or MMP2.

48. The protease-activatable T cell activating bispecific molecule of embodiment 46, wherein the serine protease is Matriptase.

49. The protease-activatable T cell activating bispecific molecule of any one of embodiments 1 to 48, wherein the first antigen binding moiety comprises at least one heavy chain complementarity determining region (CDR) selected from the group consisting of SEQ ID NO: 44, SEQ ID NO: 45 and SEQ ID NO: 46 and at least one light chain CDR selected from the group of SEQ ID NO: 17, SEQ ID NO: 18 and SEQ ID NO: 19.

50. The protease-activatable T cell activating bispecific molecule of any one of embodiments 1 to 49, wherein the first antigen binding moiety is capable of specific binding to CD3 and comprises a heavy chain variable region comprising:
a) a heavy chain complementarity determining region (CDR H) 1 amino acid sequence of TYAMN (SEQ ID NO:44);
b) a CDR H2 amino acid sequence of RIRSKYNNYATYYADSVKG (SEQ ID NO:45); and
c) a CDR H3 amino acid sequence of HGNFGNSYVSWFAY (SEQ ID NO:46); and a light chain variable region comprising:
d) a light chain (CDR L)1 amino acid sequence of GSSTGAVTTSNYAN (SEQ ID NO:17);
e) a CDR L2 amino acid sequence of GTNKRAP (SEQ ID NO:18); and
f) a CDR L3 amino acid sequence of ALWYSNLWV (SEQ ID NO:19).

51. The protease-activatable T cell activating bispecific molecule of any one of embodiments 1 to 50, wherein the first antigen binding moiety comprises a heavy chain variable region comprising an amino acid sequence that is at least about 95%, 96%, 97%, 98%, 99% or 100% identical to the amino acid sequence of SEQ ID NO: 43 and a light chain variable region comprising an amino acid sequence that is at least about 95%, 96%, 97%, 98%, 99% or 100% identical to the amino acid sequence of SEQ ID NO: 55.

52. The protease-activatable T cell activating bispecific molecule of any one of embodiments 1 to 50, wherein the first antigen binding moiety is capable of specific binding to CD3 and comprises a heavy chain variable region comprising the amino acid sequence of SEQ ID NO: 43 and a light chain variable region comprising the amino acid sequence of SEQ ID NO: 55.

53. The protease-activatable T cell activating bispecific molecule of any one of embodiments 1 to 52, wherein the second antigen binding moiety is capable of specific binding to FolR1 and comprises at least one heavy chain complementarity determining region (CDR) selected from the group consisting of SEQ ID NO: 14, SEQ ID NO: 15 and SEQ ID NO: 16 and at least one light chain CDR selected from the group of SEQ ID NO: 17, SEQ ID NO: 18 and SEQ ID NO: 19.

54. The protease-activatable T cell activating bispecific molecule of any one of embodiments 1 to 53, wherein the second antigen binding moiety is capable of specific binding to FolR1 and comprises a heavy chain variable region comprising:
a) a heavy chain complementarity determining region (CDR H) 1 amino acid sequence of NAWMS (SEQ ID NO:14);
b) a CDR H2 amino acid sequence of RIKSKTDGGTTDYAAPVKG (SEQ ID NO:15); and c) a CDR H3 amino acid sequence of PWEWSWYDY (SEQ ID NO:16); and a light chain variable region comprising:
d) a light chain (CDR L)1 amino acid sequence of GSSTGAVTTSNYAN (SEQ ID NO:17);
e) a CDR L2 amino acid sequence of GTNKRAP (SEQ ID NO:18); and
f) a CDR L3 amino acid sequence of ALWYSNLWV (SEQ ID NO:19).

55. The protease-activatable T cell activating bispecific molecule of any one of embodiments 1 to 54, wherein the second antigen binding moiety comprises a heavy chain variable region comprising an amino acid sequence that is at least about 95%, 96%, 97%, 98%, 99% or 100% identical to the amino acid sequence of SEQ ID NO: 47 and a light chain variable region comprising an amino acid sequence that is at least about 95%, 96%, 97%, 98%, 99% or 100% identical to the amino acid sequence of SEQ ID NO: 55.

56. The protease-activatable T cell activating bispecific molecule of any one of embodiments 1 to 54, wherein the second antigen binding moiety is capable of specific binding to FolR1 and comprises a heavy chain variable region comprising the amino acid sequence of SEQ ID NO: 47 and a light chain variable region comprising the amino acid sequence of SEQ ID NO: 55.

57. The protease-activatable T cell activating bispecific molecule of any one of embodiments 1 to 52, wherein the second antigen binding moiety is capable of specific binding to FolR1 and comprises at least one heavy chain complementarity determining region (CDR) selected from the group consisting of SEQ ID NO: 151, SEQ ID NO: 152 and SEQ ID NO: 153 and at least one light chain CDR selected from the group of SEQ ID NO: 154. SEQ ID NO: 155 and SEQ ID NO: 156.

58. The protease-activatable T cell activating bispecific molecule of any one of embodiments 1 to 52 or 57, wherein the second antigen binding moiety is capable of specific binding to FolR1 and comprises a heavy chain variable region comprising:
a) a heavy chain complementarity determining region (CDR H) 1 amino acid sequence of SYYMH (SEQ ID NO:151);
b) a CDR H2 amino acid sequence of IINPSGGST-SYAQKFQG (SEQ ID NO:152); and
c) a CDR H3 amino acid sequence of SFFTGFHLDY (SEQ ID NO:153); and a light chain variable region comprising:
d) a light chain (CDR L)I amino acid sequence of RASQSVSSSYLA (SEQ ID NO:154);
e) a CDR L2 amino acid sequence of GASSRAT (SEQ ID NO:155); and
f) a CDR L3 amino acid sequence of QQYTNEHYYT (SEQ ID NO:156).

59. The protease-activatable T cell activating bispecific molecule of any one of embodiments 1 to 52, 57 or 58, wherein the second antigen binding moiety comprises a heavy chain variable region comprising an amino acid sequence that is at least about 95%, 96%, 97%, 98%, 99% or 100% identical to the amino acid sequence of SEQ ID NO: 157 and a light chain variable region comprising an amino acid sequence that is at least about 95%, 96%. 97%, 98%, 99% or 100% identical to the amino acid sequence of SEQ ID NO: 158.

60. The protease-activatable T cell activating bispecific molecule of any one of embodiments 1 to 52 or 57 to 59, wherein the second antigen binding moiety wherein the second antigen binding moiety is capable of specific binding to ForR1 and comprises a heavy chain variable region comprising the amino acid sequence of SEQ ID NO: 157 and a light chain variable region comprising the amino acid sequence of SEQ ID NO: 158.

61. The protease-activatable T cell activating bispecific molecule of any one of embodiments 1 to 52, wherein the second antigen binding moiety is capable of specific binding to Mesothelin and comprises at least one heavy chain complementarity determining region (CDR) selected from the group consisting of SEQ ID NO: 107, SEQ ID NO: 108 and SEQ ID NO: 109 and at least one light chain CDR selected from the group of SEQ ID NO: 110, SEQ ID NO: 111 and SEQ ID NO: 112.

62. The protease-activatable T cell activating bispecific molecule of any one of embodiments 1 to 52 or 61, wherein the second antigen binding moiety is capable of specific binding to Mesothelin and comprises a heavy chain variable region comprising:
a) a heavy chain complementarity determining region (CDR H) 1 amino acid sequence of GYTMN (SEQ ID NO:107);
b) a CDR H2 amino acid sequence of LITPYNGAS-SYNQKFRG (SEQ ID NO:108); and
c) a CDR H3 amino acid sequence of GGYDGRGFDY (SEQ ID NO:109); and a light chain variable region comprising:
d) a light chain (CDR L)1 amino acid sequence of SASSSVSYMH (SEQ ID NO:110);
e) a CDR L2 amino acid sequence of DTSKLAS (SEQ ID NO:111); and
f) a CDR L3 amino acid sequence of QQWSKHPLT (SEQ ID NO:112).

63. The protease-activatable T cell activating bispecific molecule of any one of embodiments 1 to 52, 61 or 62, wherein the second antigen binding moiety comprises a heavy chain variable region comprising an amino acid sequence that is at least about 95%, 96%, 97%, 98%, 99% or 100% identical to the amino acid sequence of SEQ ID NO: 113 and a light chain variable region comprising an amino acid sequence that is at least about 95%, 96%, 97%, 98%, 99% or 100% identical to the amino acid sequence of SEQ ID NO: 114.

64. The protease-activatable T cell activating bispecific molecule of any one of embodiments 1 to 52 or 61 to 63, wherein the second antigen binding moiety is capable of specific binding to Mesothelin and comprises a heavy chain variable region comprising the amino acid sequence of SEQ ID NO: 113 and a light chain variable region comprising to the amino acid sequence of SEQ ID NO: 114.

65. The protease-activatable T cell activating bispecific molecule of any one of embodiments 1 to 52, wherein the second antigen binding moiety comprises a heavy chain comprising an amino acid sequence that is at least about 95%, 96%, 97%, 98%, 99% or 100% identical to the amino acid sequence of SEQ ID NO: 32 and a light chain comprising an amino acid sequence that is at least about 95%, 96%, 97%, 98%, 99% or 100% identical to the amino acid sequence of SEQ ID NO: 33.

66. The protease-activatable T cell activating bispecific molecule of any one of embodiments 1 to 52 or 65. wherein the second antigen binding moiety is capable of specific binding to HER1 and comprises a heavy chain variable region comprising the amino acid sequence of SEQ ID NO: 115 and a light chain variable region comprising the amino acid sequence of SEQ ID NO: 116.
67. The protease-activatable T cell activating bispecific molecule of any one of embodiments 1 to 48, comprising
    (a) a first heavy chain comprising the amino acid sequence of SEQ ID NO:2;
    (b) a second heavy chain comprising the amino acid sequence of SEQ ID NO:3; and
    (c) a light chain comprising an amino acid sequence of SEQ ID NO:1.
68. The protease-activatable T cell activating bispecific molecule of any one of embodiments 1 to 48, comprising
    (a) a first heavy chain comprising the amino acid sequence of SEQ ID NO:4;
    (b) a second heavy chain comprising the amino acid sequence of SEQ ID NO:3; and
    (c) a light chain comprising an amino acid sequence of SEQ ID NO:1.
69. The protease-activatable T cell activating bispecific molecule of any one of embodiments 1 to 48, comprising
    a) at least one heavy chain comprising the amino acid sequence of SEQ ID NO:32;
    b) at least one light chain comprising the amino acid sequence of SEQ ID NO:34.
70. The protease-activatable T cell activating bispecific molecule of any one of embodiments 1 to 48, comprising
    (a) a first heavy chain comprising the amino acid sequence of SEQ ID NO:72;
    (b) a second heavy chain comprising the amino acid sequence of SEQ ID NO:3; and
    (c) a light chain comprising an amino acid sequence of SEQ ID NO:1.
71. The protease-activatable T cell activating bispecific molecule of any one of embodiments 1 to 48, comprising
    (a) a first heavy chain comprising the amino acid sequence of SEQ ID NO:85;
    (b) a second heavy chain comprising the amino acid sequence of SEQ ID NO:3; and
    (c) a light chain comprising an amino acid sequence of SEQ ID NO:1.
72. The protease-activatable T cell activating bispecific molecule of any one of embodiments 1 to 48, comprising
    (a) a first heavy chain comprising the amino acid sequence of SEQ ID NO:73;
    (b) a second heavy chain comprising the amino acid sequence of SEQ ID NO:3;
    (c) a first light chain comprising an amino acid sequence of SEQ ID NO:1; and
    (d) a second light chain comprising an amino acid sequence of SEQ ID NO: 74.
73. The protease-activatable T cell activating bispecific molecule of any one of embodiments 1 to 48, comprising
    (a) a first heavy chain comprising the amino acid sequence of SEQ ID NO:77;
    (b) a second heavy chain comprising the amino acid sequence of SEQ ID NO:82;
    (c) a first light chain comprising an amino acid sequence of SEQ ID NO:78; and
    (d) a second light chain comprising an amino acid sequence of SEQ ID NO:81.
74. The protease-activatable T cell activating bispecific molecule of any one of embodiments 1 to 48, comprising
    (a) a first heavy chain comprising the amino acid sequence of SEQ ID NO:76;
    (b) a second heavy chain comprising the amino acid sequence of SEQ ID NO:77;
    (c) a first light chain comprising an amino acid sequence of SEQ ID NO:78; and
    (d) a second light chain comprising an amino acid sequence of SEQ ID NO:79.
75. The protease-activatable T cell activating bispecific molecule of any one of embodiments 1 to 48, comprising
    (a) a first heavy chain comprising the amino acid sequence of SEQ ID NO:132;
    (b) a second heavy chain comprising the amino acid sequence of SEQ ID NO:136;
    (c) a first light chain comprising an amino acid sequence of SEQ ID NO:81; and
    (d) a second light chain comprising an amino acid sequence of SEQ ID NO:133.
76. The protease-activatable T cell activating bispecific molecule of any one of embodiments 1 to 48, comprising
    (a) a first heavy chain comprising the amino acid sequence of SEQ ID NO:137;
    (b) a second heavy chain comprising the amino acid sequence of SEQ ID NO:139;
    (c) a first light chain comprising an amino acid sequence of SEQ ID NO:81; and
    (d) a second light chain comprising an amino acid sequence of SEQ ID NO:138.
77. An idiotype-specific polypeptide for reversibly concealing an anti-CD3 antigen binding site of a molecule.
78. The idiotype-specific polypeptide of embodiment 77, wherein the idiotype-specific polypeptide is an anti-idiotype scFv.
79. The idiotype-specific polypeptide of embodiment 77 or 78, wherein the idiotype-specific polypeptide is covalently attached to the molecule through a linker.
80. The idiotype-specific polypeptide of embodiment 79, wherein the linker is a peptide linker.
81. The idiotype-specific polypeptide of embodiment 79 or 80, wherein the linker is a protease-cleavable linker.
82. The idiotype-specific polypeptide of any one of embodiments 79 to 81, wherein the peptide linker comprises at least one protease recognition site.
83. The idiotype-specific polypeptide of embodiment 82, wherein the protease is selected from the group consisting of metalloproteinase, serine protease, cysteine protease, aspartic proteases, and cathepsin protease.
84. The idiotype-specific polypeptide of embodiment 83, wherein the metalloproteinase is a matrix metalloproteinase (MMP), preferably MMP9 or MMP2.
85. The idiotype-specific polypeptide of embodiment 83, wherein the serine protease is Matriptase.
86. The idiotype-specific polypeptide of embodiment 82, wherein the protease cleavable linker comprises the protease recognition sequence RQARVVNG (SEQ ID NO:36) or the protease recognition sequence VHMPLGFLGPRQARVVNG (SEQ ID NO:97).
87. The idiotype-specific polypeptide of any one of embodiments 77 to 86, wherein the molecule is a T-cell activating bispecific molecule.

88. The idiotype-specific polypeptide of any one of embodiments 77 to 87, comprising a heavy chain variable region comprising at least one of:
   (a) a heavy chain complementarity determining region (CDR H) 1 amino acid sequence of DYSIH (SEQ ID NO:20);
   (b) a CDR H2 amino acid sequence of WINTETGEPAYADDFKG (SEQ ID NO:21); and
   (c) a CDR H3 amino acid sequence of PYDYDVLDY (SEQ ID NO:22).

89. The idiotype-specific polypeptide of any one of embodiments 77 to 88, comprising a light chain variable region comprising at least one of:
   (d) a light chain (CDR L)1 amino acid sequence of RASKSVSTSNYSYIH (SEQ ID NO:23);
   (e) a CDR L2 amino acid sequence of YVSYLES (SEQ ID NO:24); and
   (f) a CDR L3 amino acid sequence of QHSREFPWT (SEQ ID NO:25).

90. The idiotype-specific polypeptide of any one of embodiments 77 to 87, comprising a heavy chain variable region comprising:
   (a) a heavy chain complementarity determining region (CDR H) 1 amino acid sequence of DYSIH (SEQ ID NO:20);
   (b) a CDR H2 amino acid sequence of WINTETGEPAYADDFKG (SEQ ID NO:21);
   (c) a CDR H3 amino acid sequence of PYDYDVLDY (SEQ ID NO:22); and a light chain variable region comprising:
   (d) a light chain (CDR L)1 amino acid sequence of RASKSVSTSNYSYIH (SEQ ID NO:23);
   (e) a CDR L2 amino acid sequence of YVSYLES (SEQ ID NO:24); and
   (f) a CDR L3 amino acid sequence of QHSREFPWT (SEQ ID NO:25).

91. The idiotype-specific polypeptide of any one of embodiments 77 to 87, comprising a heavy chain variable region comprising at least one of:
   (a) a heavy chain complementarity determining region (CDR H) 1 amino acid sequence of SYGVS (SEQ ID NO:26);
   (b) a CDR H2 amino acid sequence of IIWGDGSTNYHSALIS (SEQ ID NO:27); and
   (c) a CDR H3 amino acid sequence of GITTVVDDYYAMDY (SEQ ID NO:28).

92. The idiotype-specific polypeptide of any one of embodiments 77 to 87 and 91, comprising a light chain variable region comprising at least one of:
   (d) a light chain (CDR L)1 amino acid sequence of RASENIDSYLA (SEQ ID NO:29);
   (e) a CDR L2 amino acid sequence of AATFLAD (SEQ ID NO:30); and
   (f) a CDR L3 amino acid sequence of QHYYSTPYT (SEQ ID NO:31).

93. The idiotype-specific polypeptide of any one of embodiments 77 to 87, comprising a heavy chain variable region comprising:
   (a) a heavy chain complementarity determining region (CDR H) 1 amino acid sequence of SYGVS (SEQ ID NO:26);
   (b) a CDR H2 amino acid sequence of IIWGDGSTNYHSALIS (SEQ ID NO:27);
   (c) a CDR H3 amino acid sequence of GITTVVDDYYAMDY (SEQ ID NO:28); and a light chain variable region comprising:
   (d) a light chain (CDR L)1 amino acid sequence of RASENIDSYLA (SEQ ID NO:29);
   (e) a CDR L2 amino acid sequence of AATFLAD (SEQ ID NO:30); and
   (f) a CDR L3 amino acid sequence of QHYYSTPYT (SEQ ID NO:31).

94. The idiotype-specific polypeptide of embodiments 77 to 93, wherein the anti-CD3 antigen binding site comprises a heavy chain variable region comprising the amino acid sequence of SEQ ID NO: 43 and a light chain variable region comprising the amino acid sequence of SEQ ID NO: 55.

95. An isolated polynucleotide encoding the protease-activatable T cell activating bispecific antigen binding molecule of any one of embodiments 1 to 76 or the idiotype-specific polypeptide of any one of embodiments 77 to 94.

96. A polypeptide encoded by the polynucleotide of embodiment 95.

97. A vector, particularly an expression vector, comprising the polynucleotide of embodiment 95.

98. A host cell comprising the polynucleotide of embodiment 95 or the vector of embodiment 97.

99. A method of producing a protease-activatable T cell activating bispecific molecule, comprising the steps of a) culturing the host cell of embodiment 98 under conditions suitable for the expression of the protease-activatable T cell activating bispecific molecule and b) recovering the protease-activatable T cell activating bispecific molecule.

100. A protease-activatable T cell activating bispecific molecule produced by the method of embodiment 99.

101. A method of producing an idiotype-specific polypeptide, comprising the steps of a) culturing the host cell of embodiment 98 under conditions suitable for the expression of the idiotype-specific polypeptide and b) recovering the an idiotype-specific polypeptide.

102. An idiotype-specific polypeptide produced by the method of embodiment 101.

103. A pharmaceutical composition comprising the protease-activatable T cell activating bispecific molecule of any one of embodiments 1 to 76 and a pharmaceutically acceptable carrier.

104. A pharmaceutical composition comprising the idiotype-specific polypeptide of any one of embodiments 77 to 94 and a pharmaceutically acceptable carrier.

105. A protease-activatable T cell activating bispecific molecule of any one of embodiments 1 to 76, the idiotype-specific polypeptide of any one of embodiments 77 to 94 or the composition of embodiment 103 for use as a medicament.

106. The protease-activatable T cell activating bispecific molecule for use according to embodiment 105, wherein the medicament is for treating or delaying progression of cancer, treating or delaying progression of an immune related disease, or enhancing or stimulating an immune response or function in an individual.

107. The protease-activatable T cell activating bispecific molecule of any one of embodiments 1 to 76 or the idiotype-specific polypeptide of any one of embodiments 77 to 94 for use in the treatment of a disease in an individual in need thereof.

108. The protease-activatable T cell activating bispecific molecule or the idiotype-specific polypeptide for use in the treatment of a disease in an individual in need thereof of embodiment 107, wherein the disease is a cancer.

109. Use of the protease-activatable T cell activating bispecific molecule of any one of embodiments 1 to 76 or the idiotype-specific polypeptide of any one of embodiments 77 to 94 for the manufacture of a medicament.

110. The use of embodiment 109, wherein the disease is a cancer.

111. A method of treating a disease in an individual, comprising administering to said individual a therapeutically effective amount of a composition comprising the protease-activatable T cell activating bispecific molecule of any one of embodiments 1 to 76 or composition of embodiment 103.

112. A method for inducing lysis of a target cell, comprising contacting a target cell with the protease-activatable T cell activating bispecific molecule of any one of embodiments 1 to 76 or composition of embodiment 103 in the presence of a T cell.

113. The method of embodiment 112 wherein the target cell is a cancer cell.

114. The method of embodiment 112 or 113, wherein the target cell expresses a protease capable of activating the protease-activatable T cell activating bispecific molecule.

115. An anti-idiotype CD3 antibody or antigen-binding fragment thereof specific for an idiotype of an anti-CD3 antigen-binding molecule, wherein the anti-idiotype CD3 antibody or fragment thereof when bound to the anti-CD3 antigen-binding molecule specifically blocks binding of the anti-CD3 antigen-binding molecule to CD3.

116. The anti-idiotype CD3 antibody or antigen-binding fragment thereof of embodiment 115, wherein the anti-idiotype CD3 antibody or fragment thereof is reversibly associated with the anti-CD3 antigen-binding molecule through a peptide linker comprising a protease recognition site.

117. The anti-idiotype CD3 antibody or antigen-binding fragment thereof of embodiment 115 or 116, wherein the CD3 is a mouse, monkey or human CD3.

118. A method of reducing in vivo toxicity of a T cell activating bispecific molecule comprising attaching an idiotype-specific polypeptide of any one of embodiments 77 to 94 to the T cell activating bispecific molecule with a protease-cleavable linker to form a protease-activatable T cell activating bispecific molecule, wherein the in vivo toxicity of the protease-activatable T cell activating bispecific molecule is reduced compared to toxicity of the T cell activating bispecific molecule.

119. The invention as described hereinbefore.

EXAMPLES

The following are examples of methods and compositions of the invention. It is understood that various other embodiments may be practiced, given the general description provided above.

Example 1

Synthesis of Monovalent Anti-CD3 IgG Molecules with Anti-Idiotypic scFv

Described herein are CD3 binders that are masked with an N-terminally linked anti-idiotypic CD3 scFv. These constructs include a protease recognition site which is recognized by a tumor specific protease. In the presence of protease-expressing tumor cells, the linker connecting the masking moiety will be cleaved and, thereby, CD3 binding by the CD3 binder is recovered. Several monovalent anti-CD3 IgG molecules with various anti-idiotypic scFv were produced and are schematically depicted in FIGS. 1A-1E with their respective ID number. The following molecules were prepared:

Identification No. 7859: monovalent CD3 IgG, (anti-idiotypic scFv 4.15.64-MK062 Matriptase site—CD3-N-terminal fused to CD3 Fab—inert Fc) with N-terminal fused anti CD3 scFv 4.15.64 and protease-cleavable linker.

Identification No. 7860: monovalent CD3 IgG, (anti-idiotypic scFv 4.32.63-MK062 Matriptase site—CD3-N-terminal fused to CD3 Fab—inert Fc) with N-terminal fused anti CD3 scFv 4.32.63 and protease-cleavable linker.

Identification No. 7857: monovalent CD3 IgG, (anti-idiotypic scFv 4.15.64-non-cleavable linker—CD3-N-terminal fused to CD3 Fab—inert Fc) with N-terminal fused anti CD3 scFv 4.15.64 and protease-cleavable linker.

Identification No. 7858: monovalent CD3 IgG, (anti-idiotypic scFv 4.32.63-non-cleavable linker—CD3-N-terminal fused to CD3 Fab—inert Fc) with N-terminal fused anti CD3 scFv 4.32.63 and protease-cleavable linker.

Identification No. 7861: monovalent CD3 IgG, (CD3 Fab-inert Fc) with N-terminal fused anti CD3 scFv 4.15.64/4.32.63 and protease linker.

Anti-idiotypic (ID) binder sequences were obtained by RACE-PCR (rapid amplification of cDNA ends) from RNA of Hybridoma cells. Hybridoma cells were obtained by immunization of mice with CH2527 (VL_7-46(13)/VH_3-23(12)) Fab-fragment. Single chain Fv (ScFv) sequence synthesis was ordered from Invitrogen including the necessary restriction sites for cloning. Six different anti-idiotypic CH2527 binders were compared for their affinities (FIG. 2, result Biacore-Analytics (AG M. Schräml) at 25° C./37° C. (Analyt: MAKCCEA/CD3>rH)) and two of them were cloned as N-terminal fusions at the heavy chain of CD3 Fab—Fc.

The anti-ID single chain Fv DNA sequences were sub-cloned in frame with the CD3 VH chain pre-inserted into the respective recipient mammalian expression vector. Protein expression is driven by an MPSV promoter and a synthetic polyA signal sequence is present at the 3' end of the CDS. In addition each vector contains an EBV OriP sequence.

The molecules were produced by co-transfecting HEK293-EBNA cells growing in suspension with the mammalian expression vectors using polyethylenimine (PEI). The cells were transfected with the corresponding expression vectors in a 1:1:2 ratio ("Fc hole (CH2-CH3)": "common light chain (CLC)": "vector heavy chain knob (scFv-VH-CH1-CH2-CH3)").

For transfection, HEK293 EBNA cells were cultivated in serum free ExCell culture medium containing 6 mM L-glutamine and 250 mg/l G418. For the production in 600 ml tubespin flasks (max. working volume 400 mL) 800 million HEK293 EBNA cells were seeded 24 hours before transfection without G418. For transfection 800 mio cells were centrifuged for 5 min at 210×g and supernatant was replaced by 40 ml pre-warmed CD CHO medium containing 6 mM L-Glutamine.

Expression vectors were mixed with 40 ml CD CHO medium containing 6 mM L-Glutamine to a total amount of 400 µg DNA. After addition of 1080 µl PEI solution (2.7 µg/ml) the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a 5% $CO_2$ atmosphere. After incubation, 320 ml ExCell+6 mM L-glutamine+5 g/L Pepsoy+1.0 mM VPA+3 g/l glucose medium was added and cells were cultivated for 24 hours prior to feeding with 7% Feed 7. After 6-7 days cultivation supernatant was collected for purification by centrifugation for 20-30 min at 210×g (Sigma 8K centrifuge). The solution was sterile filtered (0.22 µm filter) and sodium azide in a final concentration of 0.01% w/v was added. The solution was kept at 4° C. until purification. The secreted protein was purified from cell culture supernatants by affinity chromatography using ProteinA affinity chromatography, followed by one to two size exclusion chromatographic steps.

For affinity chromatography supernatant was loaded on a HiTrap Protein A FF column (CV=5 mL, GE Healthcare) equilibrated with 25 ml 20 mM sodium phosphate, 20 mM sodium citrate, 0.5M sodium chloride, 0.01% Tween-20 pH 7.5. Unbound protein was removed by washing with at least 10 column volumes 20 mM sodium phosphate, 20 mM sodium citrate, 0.5M sodium chloride, 0.01% Tween-20 pH 7.5 and target protein was eluted in 20 column volumes (gradient from 0%-100%) 20 mM sodium citrate, 0.5M sodium chloride, 0.01% Tween-20 pH 2.5. Protein solution was neutralized by adding 1/10 of 2 M Tris pH 10.5. Target protein was concentrated with Amicon®Ultra-15 Ultracel 30K (Merck Millipore Ltd.) to a volume of 4 ml maximum prior loading on a HiLoad Superdex 200 column (GE Healthcare) equilibrated with 20 mM histidine, 140 mM sodium chloride, pH 6.0, 0.01% Tween20.

For analytics after size exclusion chromatography the purity and molecular weight of the molecules in the single fractions were analyzed by SDS-PAGE in the absence of a reducing agent and staining with Coomassie (InstantBlue™, Expedeon). The NuPAGE® Pre-Cast gel system (4-12% Bis-Tris, Invitrogen or 3-8% Tris-Acetate, Invitrogen) was used according to the manufacturer's instruction.

The protein concentration of purified protein samples was determined by measuring the optical density (OD) at 280 nm divided by the molar extinction coefficient calculated on the basis of the amino acid sequence.

Purity and molecular weight of the molecules after the final purification step were analyzed by CE-SDS analyses in the presence and absence of a reducing agent. The Caliper LabChip GXII system (Caliper Lifescience) was used according to the manufacturer's instruction. The aggregate content of the molecules was analyzed using a TSKgel G3000 SW XL analytical size-exclusion column (Tosoh) in 25 mM K2HPO4, 125 mM NaCl, 200 mM L-arginine monohydrocloride, 0.02% (w/v) NaN3, pH 6.7 running buffer at 25° C. The final quality of all molecules was good, with >92% monomer content.

TABLE 2

Summary of production and purification of protease activated monovalent CD3 IgG molecules.

| Molecule | Titer [mg/l] | Yield [mg/l] | Analytical SEC (HMW/Monomer/LMW) [%] |
|---|---|---|---|
| 1 | 12 | 3.38 | 2.21/95.5/2.29 |
| 2 | 9 | 1.75 | 4.86/95.14/0 |
| 3 | 15 | 4.8 | 6.93/93.07/0 |
| 4 | 4.5 | 0.26 | 4.88/95.12/0 |
| 5 | 105.3 | 26.3 | 0/100/0 |

Example 2

Cleavage and Stability of Protease Activated IgGs

Figure 1A:
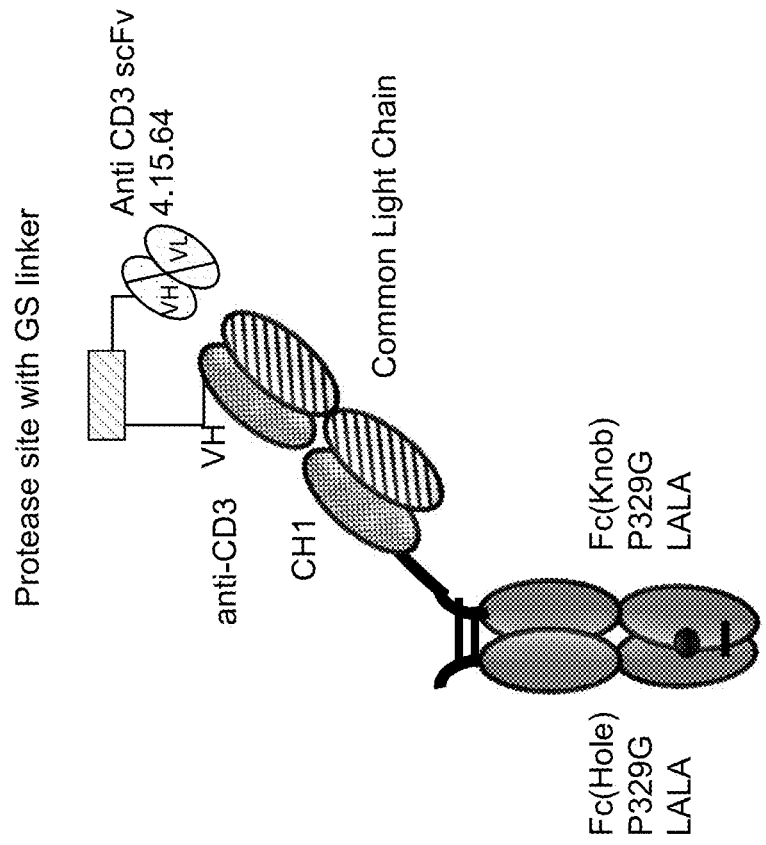
Figure 1B:
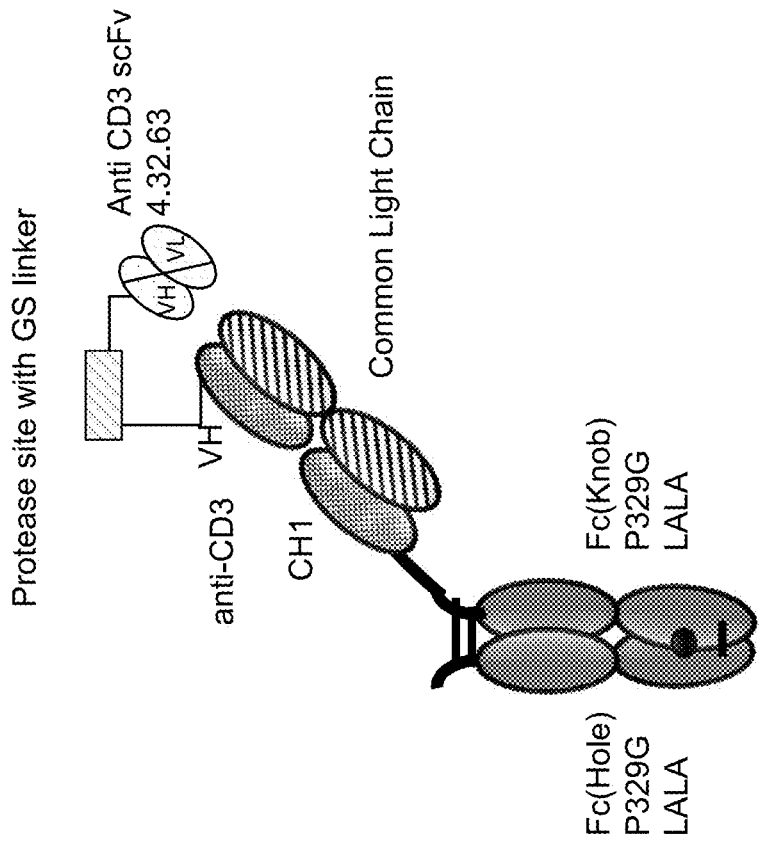
Figure 1C:
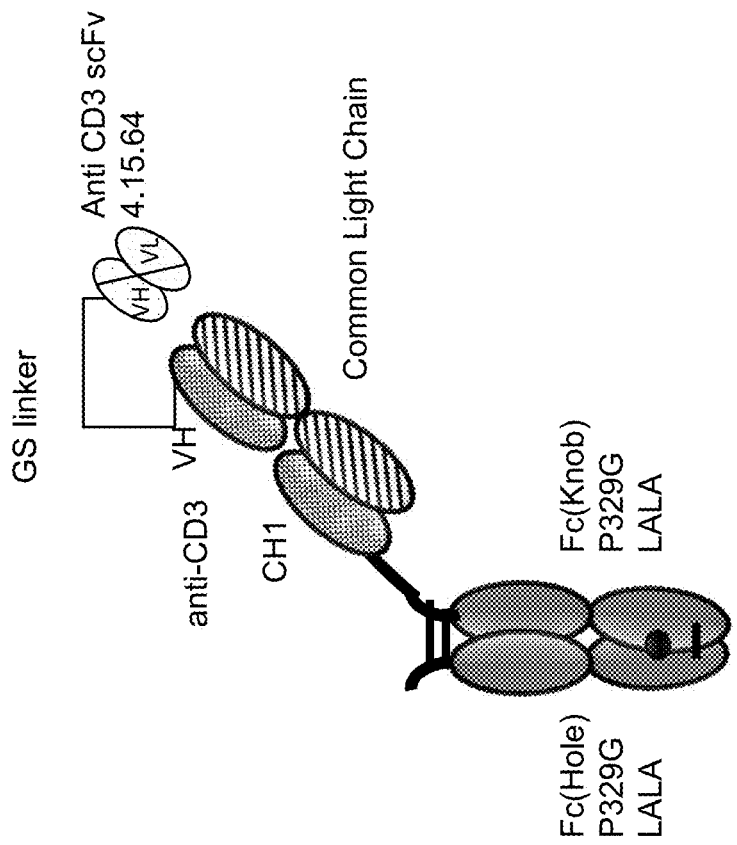
Figure 1D:
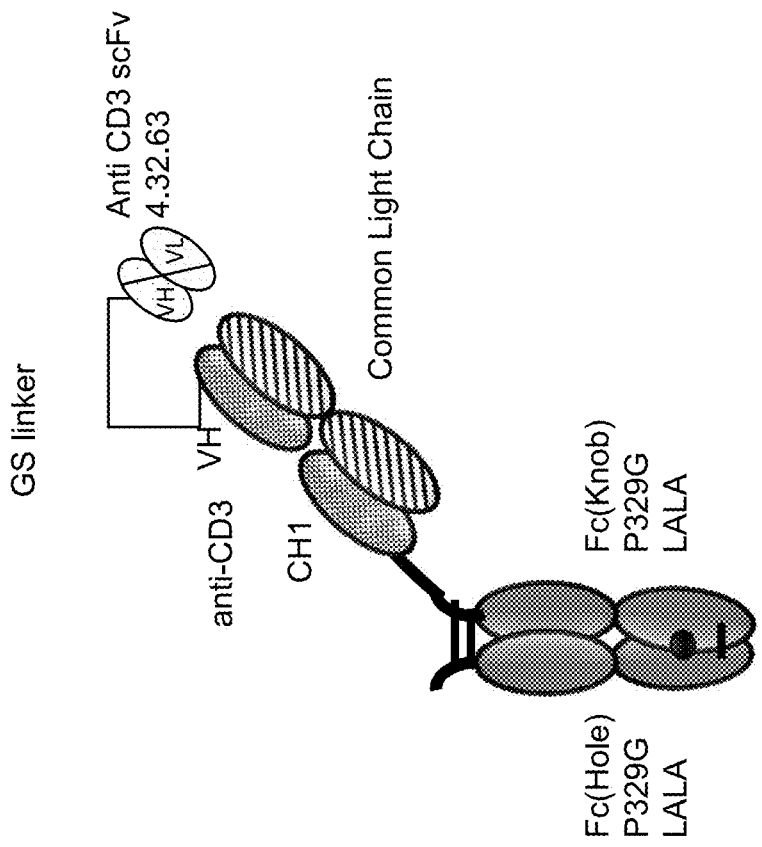
Figure 1E:
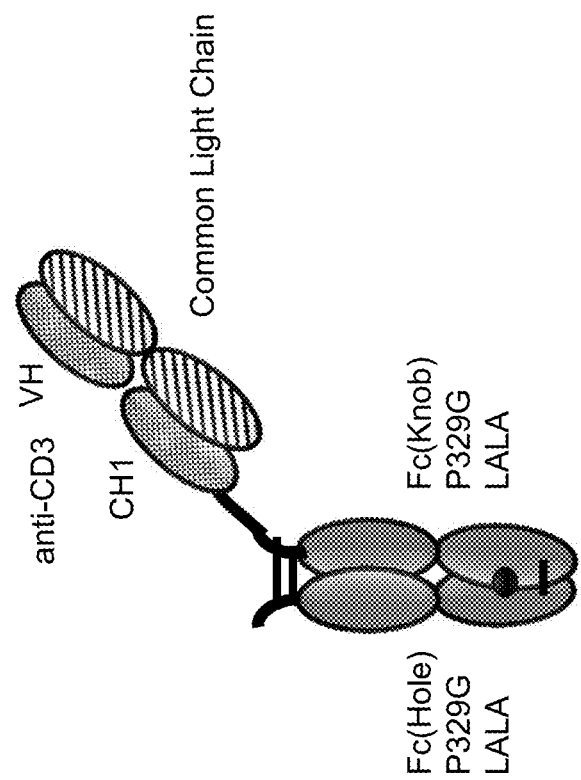
Figure 3B:
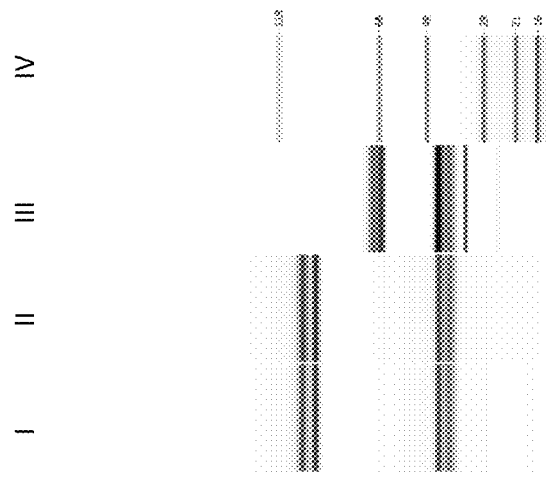
Figure 3A:
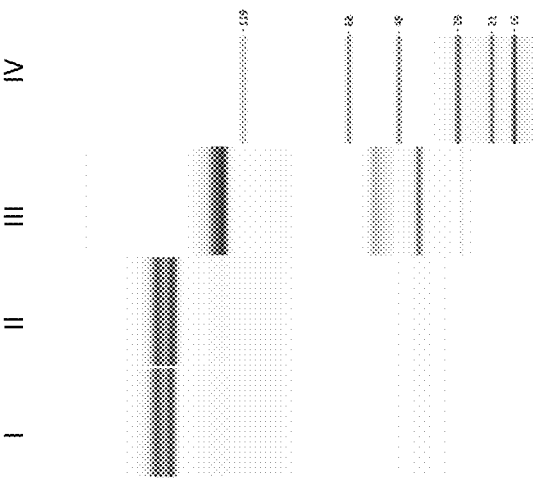

Capillary Electrophoresis of protease activated IgG molecules. Comparison of untreated sample and treated sample showed that the anti-ID scFv was completely cleaved off after treatment with rhMatriptase/ST14 (R&D Systems) indicated by the size shift in the SDS page analysis (FIG. 3). Analysis of samples incubated for 48 h at 37° C. confirmed stability of the molecules in formulation buffer (FIG. 3A-D).

Example 3

Masking Effect of Anti-Idiotypic scFv for CD3 IgG

The efficiency of masking the CD3 binder by N-terminal fusion of an anti-idiotypic CD3 scFv was shown by a Jurkat-NFAT reporter assay. Jurkat-NFAT reporter cells (a human acute lymphatic leukemia reporter cell line with a NFAT promoter-regulated luciferase expression, GloResponse Jurkat NFAT-RE-luc2P, Promega #CS176501) express active firefly luciferase if the NFAT promoter is activated by binding of CD3e. The intensity of the luminescence signal upon addition of luciferase substrate is proportional to the intensity of CD3 activation and signaling. Completely unmasked monovalent CD3 molecules served as a positive control. The treatment was done with rhMatriptase/ST14 (R&D Systems) for 48h at 37° C. In parallel 8 ug/ml Anti human Fc Antibody (BioLegends) were coated in 0.025 ul/well PBS for 48h at 4° C. in white-walled, clear bottom 96-well (flat)-plate (Greiner Bio-One). PBS was removed by pipetting before monovalent IgGs were added at the indicated concentration range of 200 nM—2.56 µM. Plates were incubated for about 30 min at 4° C. Subsequently, Jurkat-NFAT reporter cells were harvested and viability assessed using ViCell.

Figure 4A:
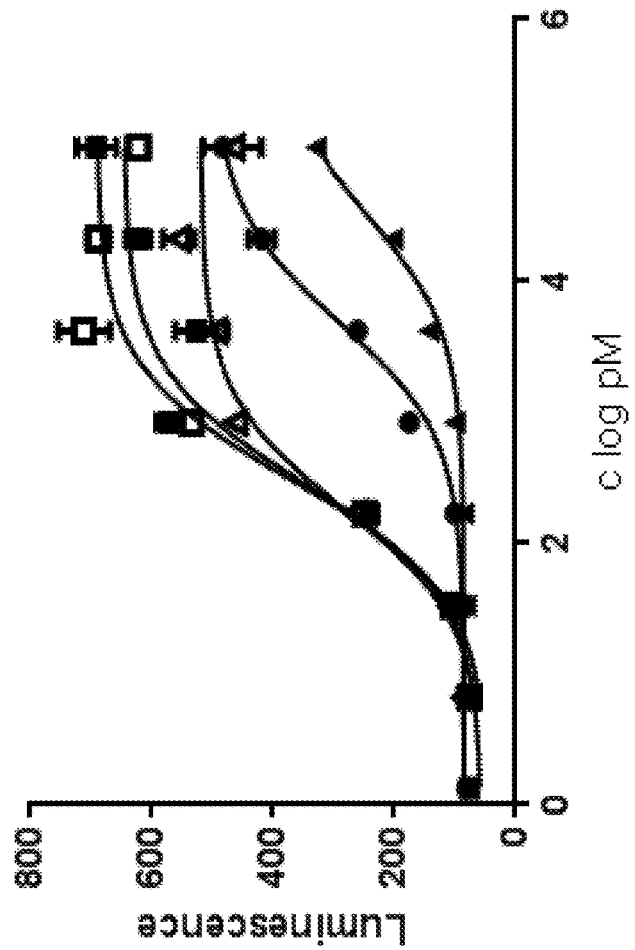
Figure 4B:
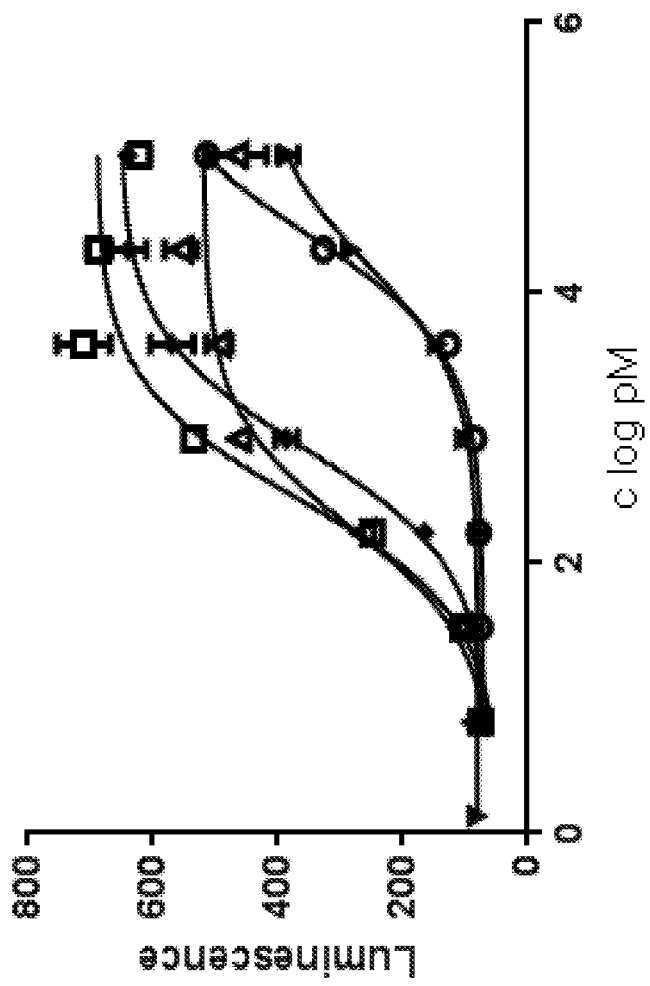

Cells were resuspended in Jurkat medium (RPMI1640, 2 g/l Glucose, 2 g/l $NaHCO_3$, 10% FCS, 25 mM HEPES, 2 mM L-Glutamin, 1×NEAA, 1× Sodium-pyruvate) without Hygromycine and 100 µl per well (25.000 cells/well) were added to the crosslinked monovalent CD3 IgGs. Cells were incubated for 3 h at 37° C. in a humidified incubator. Plates were taken out of the incubator for about 10 min to adapt to room temperature prior to Luminescence read out. 100 µl/well of ONE-Glo solution (1:1 ONE-Glo and assay medium volume per well) were added to wells and incubated for 10 min at room temperature in the dark. Luminescence was detected using WALLAC Victor3 ELISA reader (PerkinElmer2030), 1 sec/well as detection time. 7857 (4.15.64 mask with non-cleavable linker) and 7859 (untreated) show significantly reduced CD3ε binding compared to unmasked (7861) and pretreated molecule (7859 treated) (FIG. 4A). 7760 was included as a control to show that N-terminal linkage does not block CD3 binding itself. 7858 (4.32.63 mask with non-cleavable linker) and 7860 (untreated) show significantly reduced CD3ε binding compared to unmasked (7861) and pretreated molecule (7860 treated) (FIG. 4B). In line with the affinities of the anti-idiotypic CD3 binders the 4.32.63 mask is much more efficient than the 4.15.64. In terms of EC50 values (FIG. 4C) the 4.32.63 masked CD3 binder binds 54 fold less than the unmasked CD3 binder 7861. For the 4.15.64 mask it is only 16 fold less binding than for 7861. Depending on the tumor target and the target binder the best mask can be evaluated.

Example 4

Figure 5D:
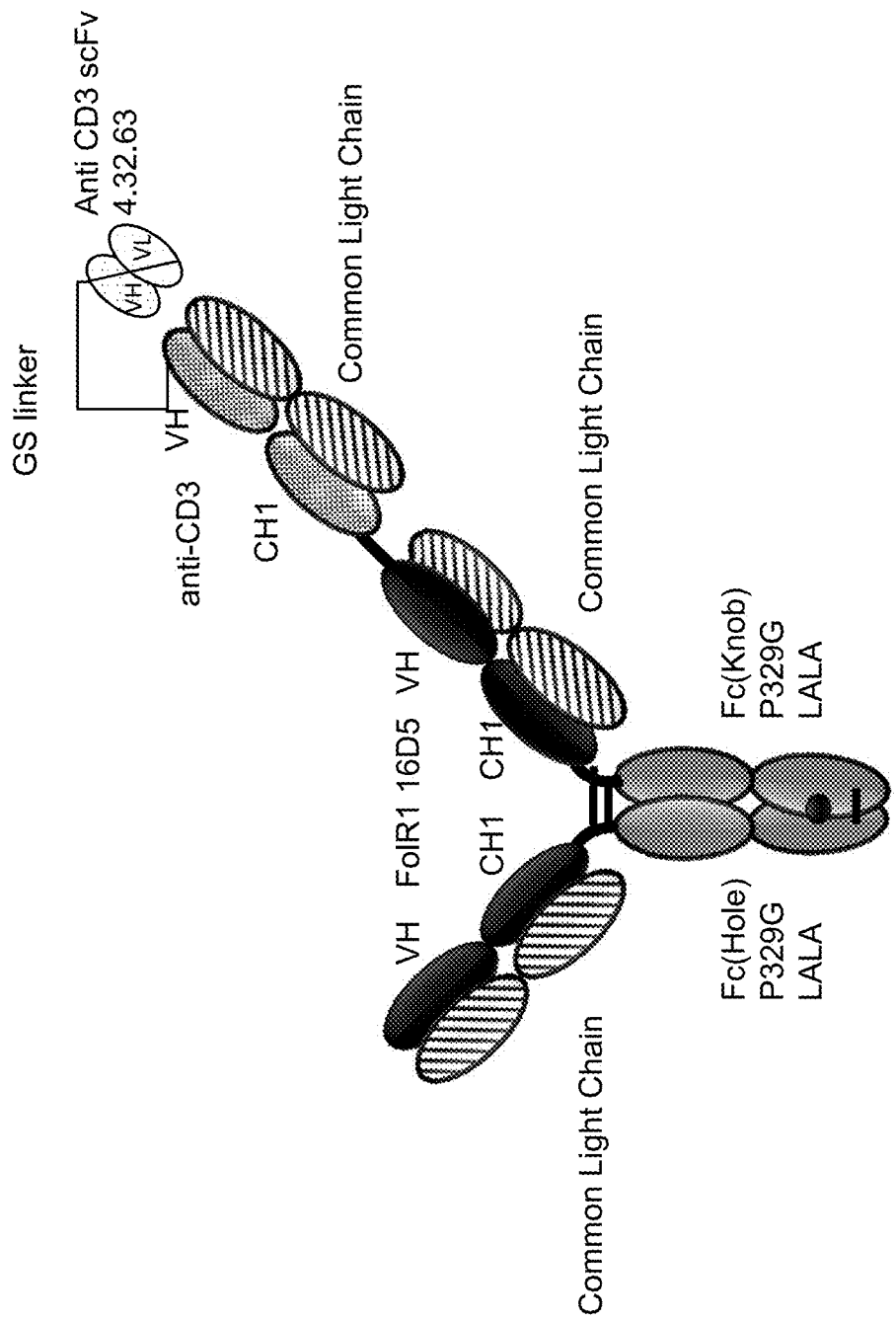
Figure 5E:
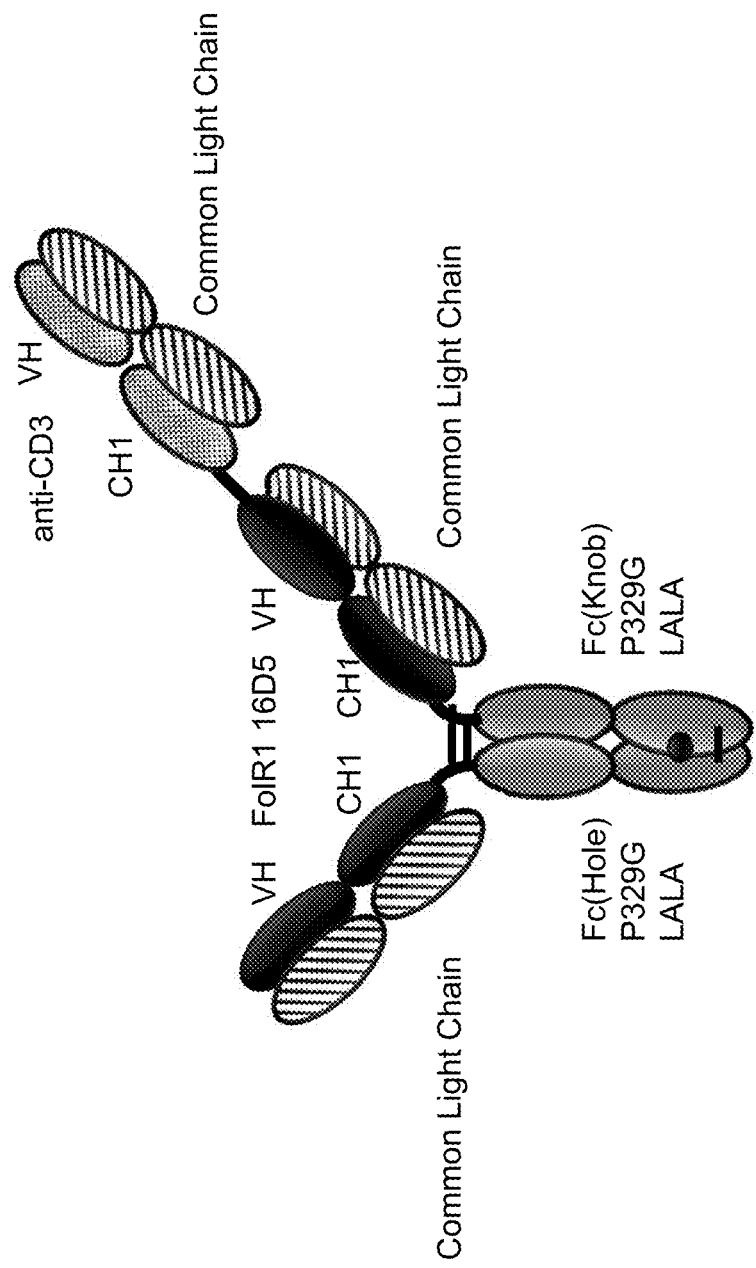
Figure 5F:
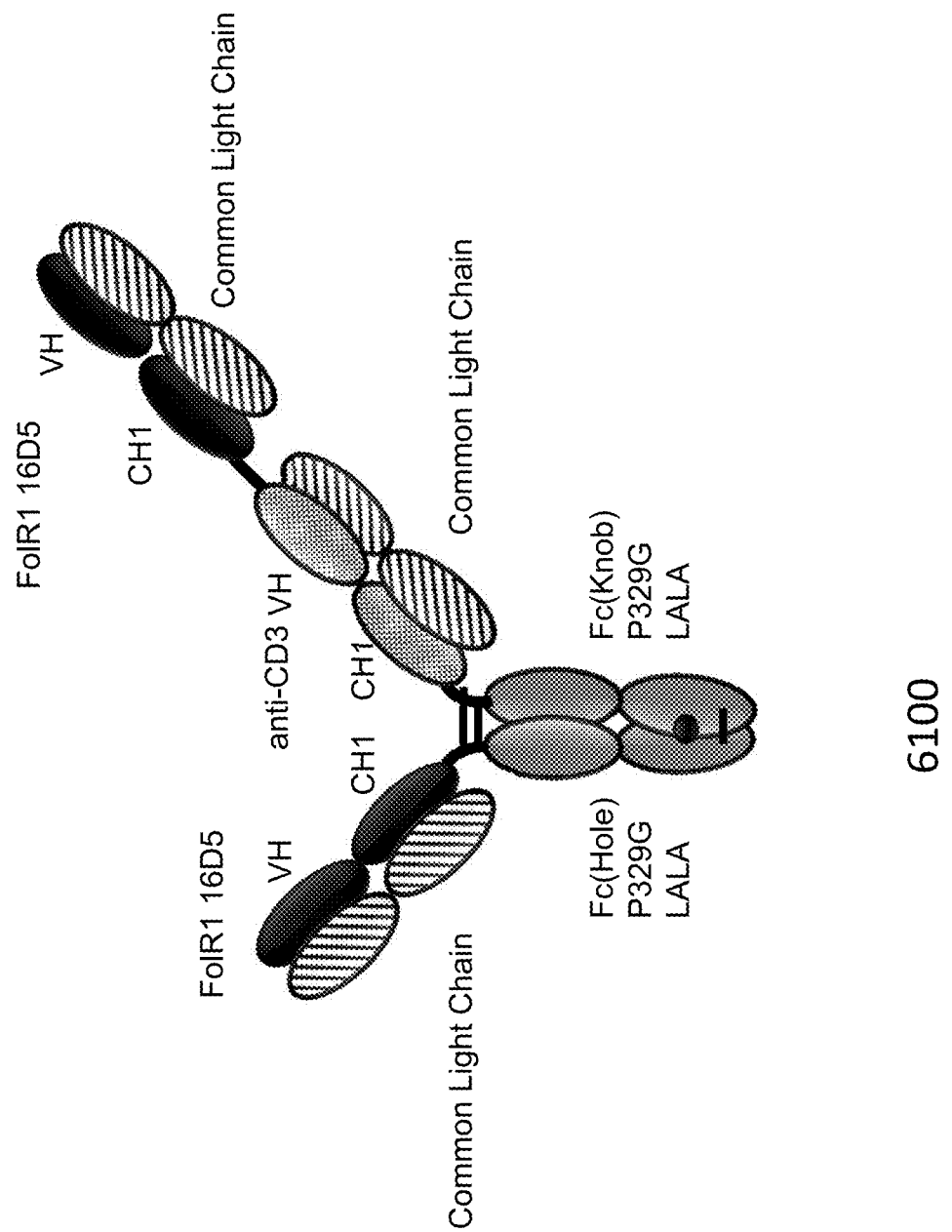
Figure 5G:
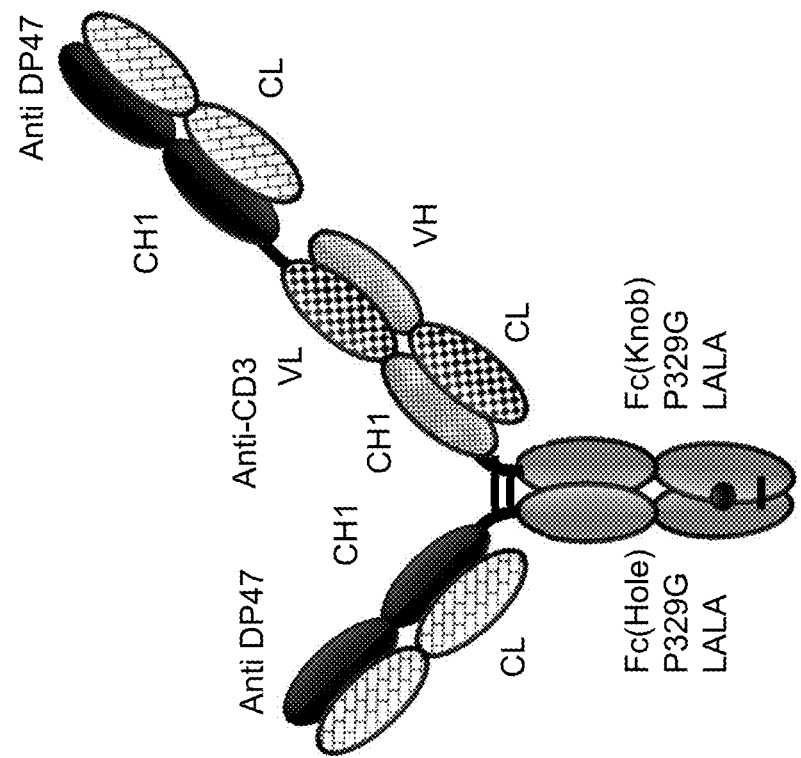
Figure 5H:
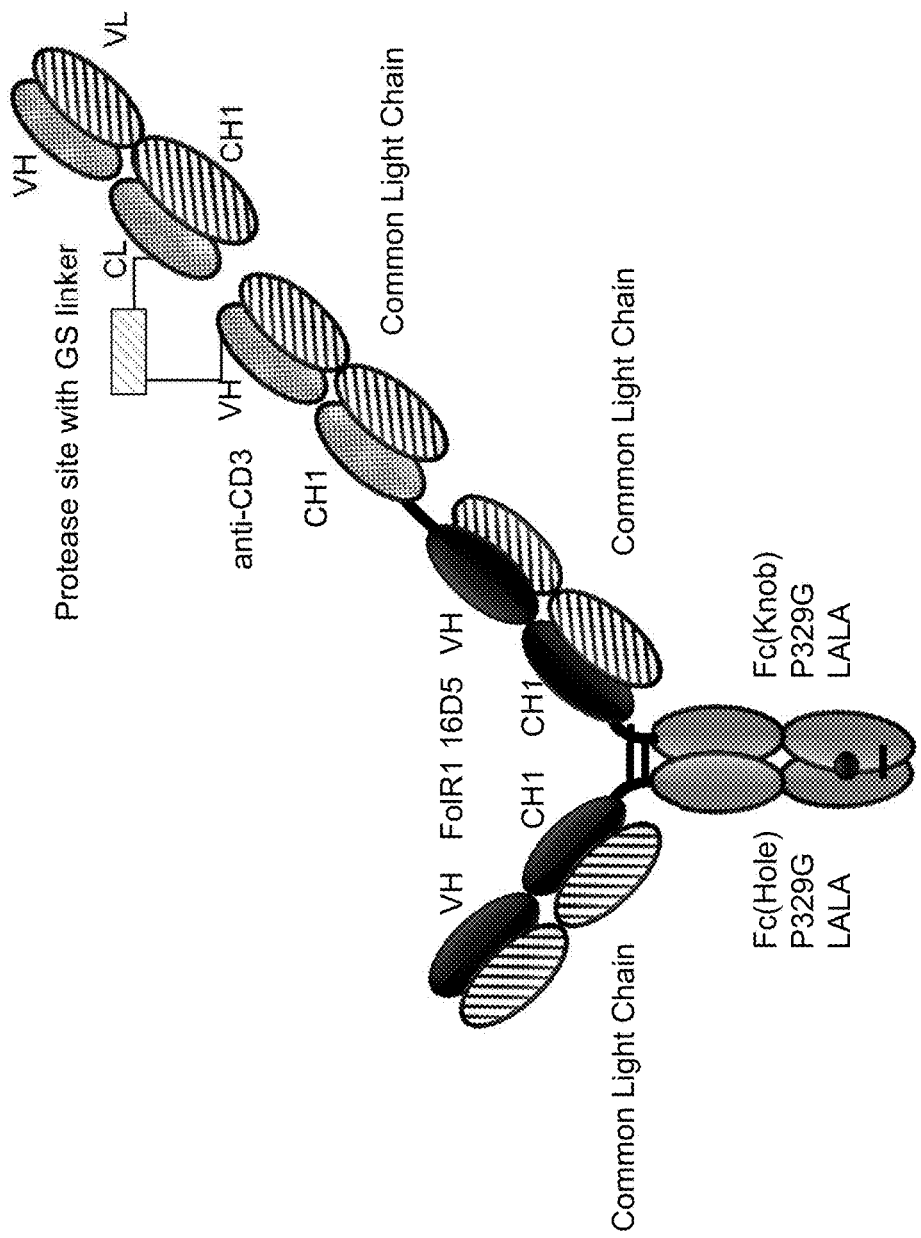

Preparation of Anti FolR1/Anti-CD3 T Cell Bispecific (TCB) Molecules with Anti CD3 scFv Several T cell bispecific (TCB) molecules with various anti-idiotypic scFv were produced and are schematically depicted in FIGS. 5A-5H with their respective ID number. The following molecules were prepared:
- ID7344: FolR1 16D5 2+1 IgG, classic format (anti-idiotypic scFv 4.15.64-MK062 Matriptase site—CD3-N-terminal fused to FolR1 VH—inert Fc) with N-terminal fused anti CD3 scFv 4.15.64 and protease linker (FIG. 5A, SEQ ID NOs 1, 2 and 3).
- ID7496: FolR1 16D5 2+1 IgG, classic format (anti-idiotypic scFv 4.32.63-MK062 Matriptase site—CD3-N-terminal fused to FolR1 VH—inert Fc) with N-terminal fused anti CD3 scFv 4.32.63 and protease linker (FIG. 5C, SEQ ID NOs 1, 3 and 4).
- ID7676: FolR1 16D5 2+1 IgG, classic format (anti-idiotypic scFv 4.15.64-non-cleavable GS linker—CD3-N-terminal fused to FolR1 VH—inert Fc) with N-terminal fused anti CD3 scFv 4.15.64 and protease linker (FIG. 5B, SEQ ID NOs 1, 3 and 6).
- ID7611: FolR1 16D5 2+1 IgG, classic format (anti-idiotypic scFv 4.32.63-non-cleavable GS linker—CD3-N-terminal fused to FolR1 VH—inert Fc) with N-terminal fused anti CD3 scFv 4.32.63 and protease linker (FIG. 5D, SEQ ID NOs 1, 3 and 5).

Anti-idiotypic (ID) binder sequences were obtained by RACE-PCR (rapid amplification of cDNA ends) from RNA of Hybridoma cells. Hybridoma cells were obtained by immunization of mice. Single chain Fv (ScFv) sequence synthesis was ordered at Invitrogen including the necessary restriction sites for cloning. Six different anti-idiotypic CH2527 binders were compared for their affinities (FIG. 2, result Biacore-Analytics (AG M. Schräml) at 25° C./37° C. (Analyt: MAK<CEA/CD3>rH)) and four of them were cloned as N-terminal fusions at the HC of CD3-FolR1 16D5 TCB.

The anti-ID single chain Fv DNA sequences were subcloned in frame with the CD3 VH chain pre-inserted into the respective recipient mammalian expression vector. Protein expression is driven by an MPSV promoter and a synthetic polyA signal sequence is present at the 3' end of the coding sequence (CDS). In addition each vector contains an EBV OriP sequence.

The molecules were produced by co-transfecting HEK293-EBNA cells growing in suspension with the mammalian expression vectors using polyethylenimine (PEI). The cells were transfected with the corresponding expression vectors in a 1:3:2 ratio ("vector heavy chain hole (VH-CH1-CH2-CH3)": "common light chain (CLC)": "vector heavy chain knob (scFv-VH-CH1-VH-CH1-CH2-CH3)").

For transfection HEK293 EBNA cells were cultivated in serum free ExCell culture medium containing 6 mM L-glutamine and 250 mg/l G418. For the production in 600 ml tubespin flasks (max. working volume 400 mL) 800 million HEK293 EBNA cells were seeded 24 hours before transfection without G418. For transfection 800 mio cells were centrifuged for 5 min at 210×g and supernatant was replaced by 40 ml pre-warmed CD CHO medium containing 6 mM L-Glutamine.

Expression vectors were mixed with 40 ml CD CHO medium containing 6 mM L-Glutamine to a total amount of 400 µg DNA. After addition of 1080 µl PEI solution (2.7 µg/ml) the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a 5% $CO_2$ atmosphere. After incubation, 320 ml ExCell+6 mM L-glutamine+5 g/L Pepsoy+1.0 mM VPA+3 g/l glucose medium was added and cells were cultivated for 24 hours prior to feeding with 7% Feed 7. After 6-7 days cultivation supernatant was collected for purification by centrifugation for 20-30 min at 210×g (Sigma 8K centrifuge). The solution was sterile filtered (0.22 µm filter) and sodium azide in a final concentration of 0.01% w/v was added. The solution was kept at 4° C. until purification.

The secreted protein was purified from cell culture supernatants by affinity chromatography using ProteinA affinity chromatography, followed by one to two size exclusion chromatographic steps. For affinity chromatography supernatant was loaded on a HiTrap Protein A FF column (CV=5 mL, GE Healthcare) equilibrated with 25 ml 20 mM sodium phosphate, 20 mM sodium citrate, 0.5M sodium chloride, 0.01% Tween-20 pH 7.5. Unbound protein was removed by washing with at least 10 column volumes 20 mM sodium phosphate, 20 mM sodium citrate, 0.5M sodium chloride, 0.01% Tween-20 pH 7.5 and target protein was eluted in 20 column volumes (gradient from 0%-100%) 20 mM sodium citrate, 0.5M sodium chloride, 0.01% Tween-20 pH 2.5. Protein solution was neutralized by adding 1/10 of 2 M Tris pH 10.5. Target protein was concentrated with Amicon®Ultra-15 Ultracel 30K (Merck Millipore Ltd.) to a volume of 4 ml maximum prior loading on a HiLoad Superdex 200 column (GE Healthcare) equilibrated with 20 mM histidine, 140 mM sodium chloride, pH 6.0, 0.01% Tween20.

For analytics after size exclusion chromatography the purity and molecular weight of the molecules in the single fractions were analyzed by SDS-PAGE in the absence of a reducing agent and staining with Coomassie (InstantBlue™, Expedeon). The NuPAGE® Pre-Cast gel system (4-12% Bis-Tris, Invitrogen or 3-8% Tris-Acetate, Invitrogen) was used according to the manufacturer's instruction.

The protein concentration of purified protein samples was determined by measuring the optical density (OD) at 280 nm divided by the molar extinction coefficient calculated on the basis of the amino acid sequence.

Purity and molecular weight of the molecules after the final purification step were analyzed by CE-SDS analyses in the presence and absence of a reducing agent. The Caliper LabChip GXII system (Caliper Lifescience) was used according to the manufacturer's instruction.

The aggregate content of the molecules was analyzed using a TSKgel G3000 SW XL analytical size-exclusion column (Tosoh) in 25 mM K2HPO4, 125 mM NaCl, 200 mM L-arginine monohydrochloride, 0.02% (w/v) NaN3, pH 6.7 running buffer at 25° C. The final quality of all molecules was good, with >92% monomer content.

TABLE 2

Summary of production and purification of protease activated TCB molecules.

| Molecule | Titer [mg/l] | Yield [mg/l] | Analytical SEC (HMW/Monomer/LMW) [%] |
|---|---|---|---|
| 1 | 33 | 3.7 | 0.98/92.7/6.32 |
| 2 | 11 | 0.55 | 3.76/96.24/0 |
| 3 | 12.9 | 0.89 | 2.9/93.82/2.19 |
| 4 | 6.7 | 0.35 | 4.59/95.41/0 |

Example 5

Transient Expression of Protease Activated TCBs

Figure 6:
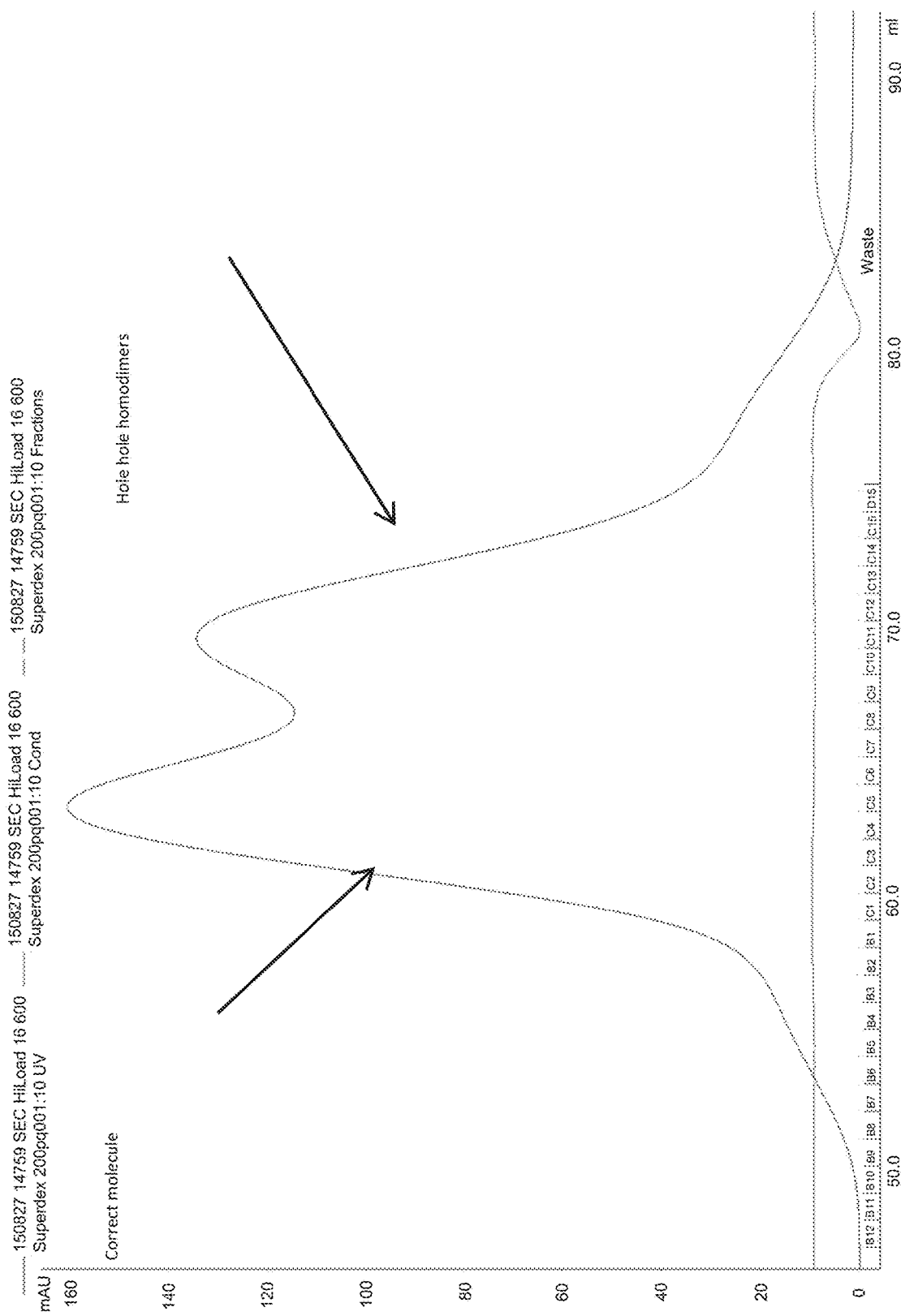
FIG. 6 shows a first plasmid ratios used for transfection by size exclusion chromatography (1 (hole):1 (knob):3 (CLC)).
Figure 7:
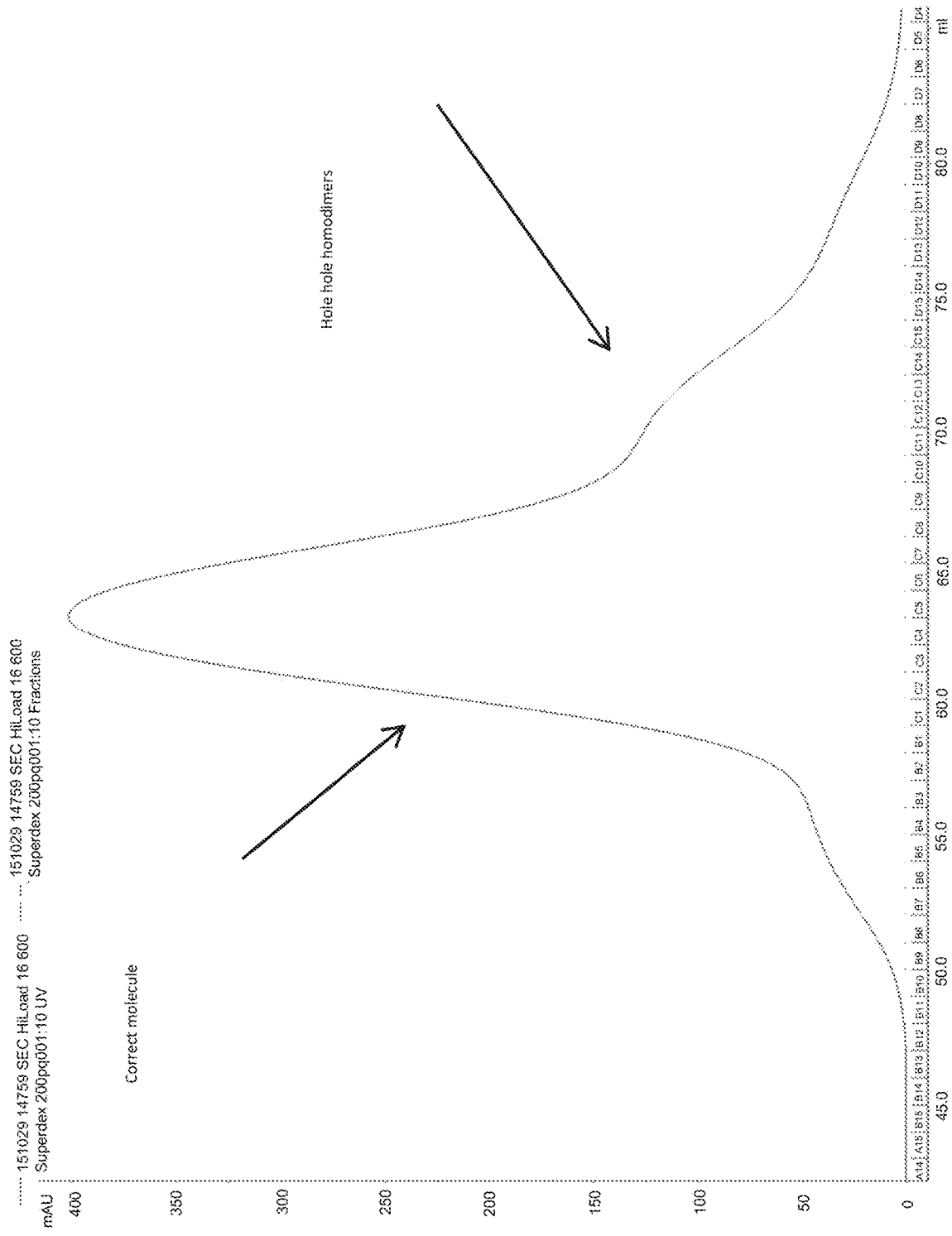
FIG. 7 shows a second plasmid ratios used for transfection by size exclusion chromatography. (1 (hole):2 (knob):3 (CLC)).
Figure 8:
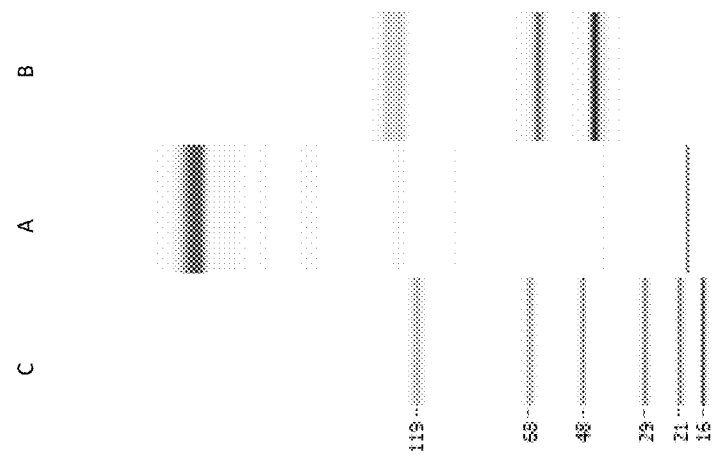
FIG. 8 shows CE-SDS analysis of the TCB molecule depicted in FIG. 5A (ID 7344) (final purified preparation): Lane A=non-reduced, lane B=reduced, lane C=Protein standard.
Figure 9:
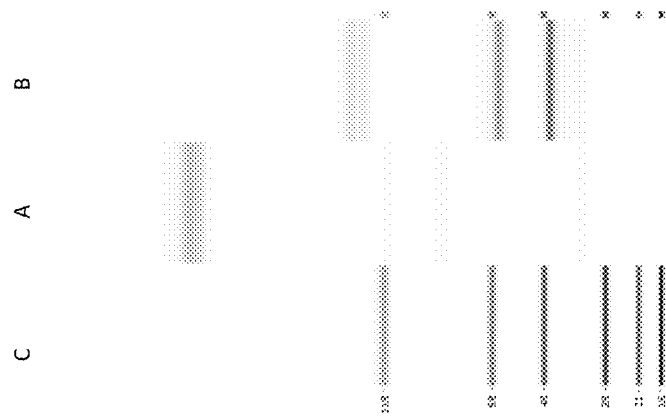
FIG. 9 shows CE-SDS analysis of the TCB molecule depicted in FIG. 5B (ID 7676) (final purified preparation): Lane A=non-reduced, lane B=reduced, lane C=Protein standard.
Figure 10:
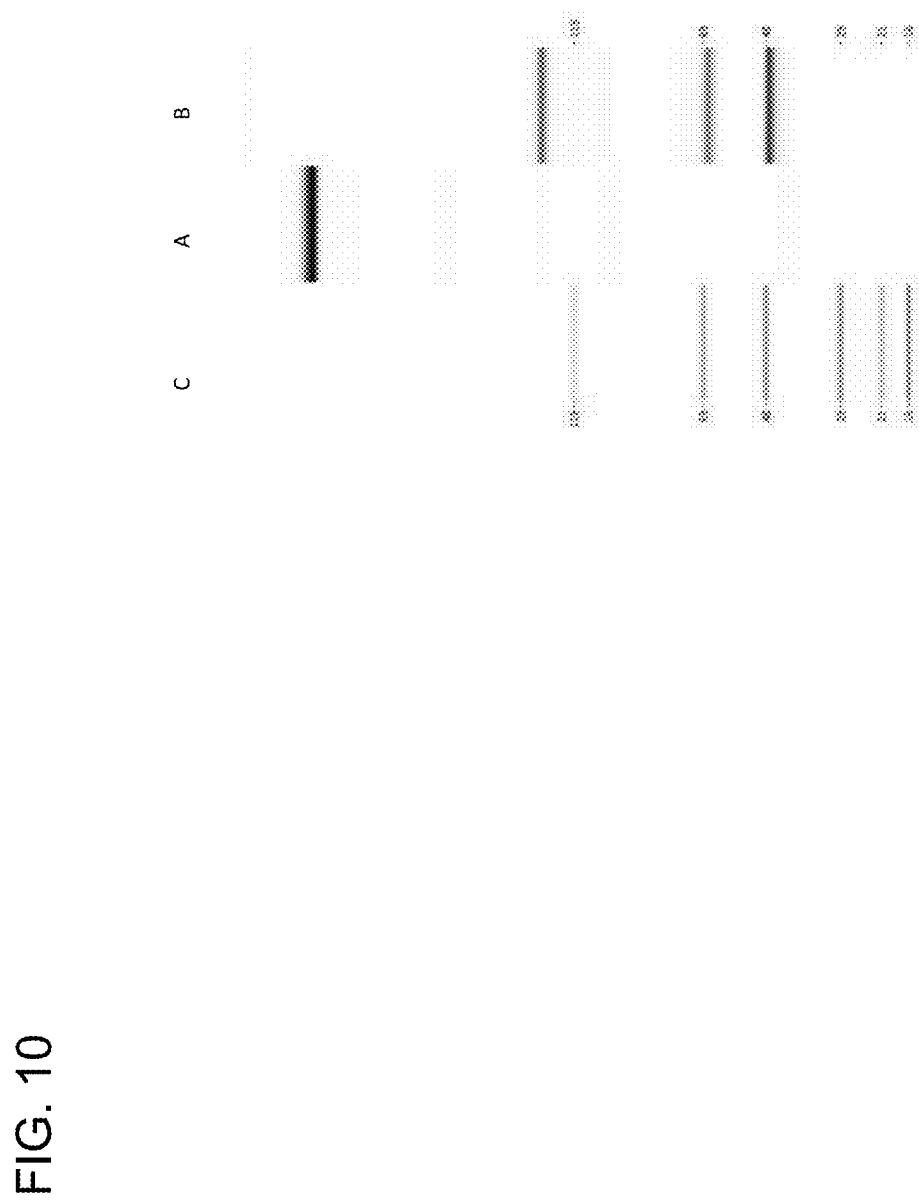
FIG. 10 shows CE-SDS analysis of the TCB molecule depicted in FIG. 5C (ID 7496) (final purified preparation): Lane A=non-reduced, lane B=reduced, lane C=Protein standard.
Figure 11:
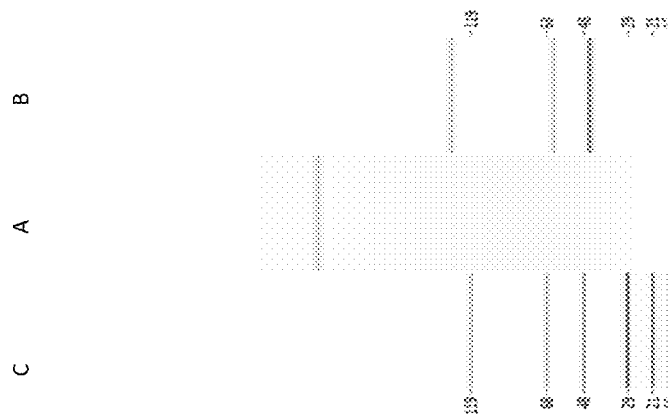
FIG. 11 shows CE-SDS analysis of the TCB molecule depicted in FIG. 5D (ID 7611) (final purified preparation): Lane A=non-reduced, lane B=reduced, lane C=Protein standard.

Different plasmid ratios used for transfection were compared by size exclusion chromatography as the knob chain was suspected to be expressed in lower levels compared to the hole chain and the light chain. As shown in FIGS. 6 and 7, using a plasmid ratio of 1 (hole): 2 (knob): 3 (CLC) (FIG. 7) instead of 1 (hole): 1 (knob): 3 (CLC) (FIG. 6) increased the yield of correct molecule (left peak) and decreased the amount of hole homodimers (right peak).

Example 6

Cleavage and Stability of Protease Activated TCB

Protease activated TCBs were analyzed by capillary electrophoresis. Comparison of untreated sample and treated sample showed that the anti-idiotype scFc moiety was completely cleaved off after treatment with rhMatriptase/ST14. Analysis of samples incubated for 48 h at 37° C. confirmed stability of the molecules in formulation buffer (FIGS. 12A-12D).

Example 7

Cell Killing Using Target Cell Lines that Express Different Levels of FolR1

T-cell-mediated cell killing induced by protease activated TCB molecules was assessed using target cell lines expressing different levels of FolR1 (FIG. 13). Human PBMCs were used as effector cells and cell killing was detected at 48 h of incubation with the protease activated TCB molecules.

Human Peripheral blood mononuclear cells (PBMCs) were isolated from fresh taken blood or from buffy coats obtained from healthy human donors. For fresh blood 50 ml Leucosep tubes (GreinerBioOne) were used for preparation. For enriched lymphocyte preparations (buffy coats) Histopaque-1077 density preparation was used. Blood/buffy coat was diluted 1:1 with sterile PBS and layered over Histopaque gradient (Sigma, #H8889). After centrifugation (450×g, 30 minutes, w/o break, room temperature). the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet resuspended in 2 ml ACK buffer for Erythrocytes lysis. After incubation at 37° C. for about 2-3 minutes the tubes were filled with sterile PBS to 50 ml and centrifuged at 350×g for 10 minutes. This washing step was repeated once prior to resuspension of PBMCs in RPMI1640 medium containing 2% FCS and 1× GlutaMax at 37° C., 5% $CO_2$ in cell incubator until further use. Briefly, adherent target cells were harvested with Trypsin/EDTA, counted, checked for viability and resuspended at $0.4 \times 10^6$ cells/ml in assay medium (RPMI1640, 2% FCS, 1× GlutaMax). Target cells were plated at a density of 20 000 cells/well using round-bottom 96-well plates. For the killing assay, the molecules were added at the indicated concentrations in triplicates. FolR1 16D5 TCB was included as positive control and an untargeted TCB molecule (binding to CD3 but not to a target cell antigen) was included as negative control. PBMCs were added to target cells at final E:T ratio of 10:1. Target cell killing was assessed after 48 h of incubation at 37° C., 5% $CO_2$ by quantification of LDH release into cell supernatants by apoptotic/necrotic cells (LDH detection kit, Roche Applied Science, #11 644 793 001). Maximal lysis of the target cells (=100%) was achieved by incubation of target cells with 1% Triton X-100 1 h before LDH readout. Minimal lysis (=0%) refers to target cells co-incubated with effector cells without any TCB.

The results (FIGS. 14A, 15A, 16, 17, 18A, 19A and 20A) show that the protease activated TCB with anti-idiotypic CD3 scFv moiety N-terminally linked by a non-cleavable linker (#7676 and #7611, FIGS. 5B and D, respectively) were able to significantly reduce cell lysis on Skov3 and HT29 cells. #7611 (FIG. 5D) led to reduced killing on Hela cells while anti-idiotypic CD3 scFv 4.15.64 in #7676 (FIG. 5B) was less efficient in reduction of cell lysis. This is in line with affinities of the anti-idiotypic CD3 scFv N moiety. The higher affinity scFv moiety masks more efficiently.

Comparable potency of treated and untreated TCBs suggests Matriptase expression of Hela and Skov3 cells. Expression of Matriptase seems to be lower in HT29 cells. Treatment of Mkn-45, a FolR1 negative cell line, shows only weak killing with all molecules used herein (FIG. 15A).

Example 8

T-Cell Activation after Co-Incubation of Tumor Cell Lines with Human PBMCs

T-cell activation mediated by protease activated TCB molecules was assessed on Hela, Skov3 and HT29 cells. Human PBMCs were used as effector cells and the T cell activation was detected at 48 h of incubation with target cells and the antibodies. Target cells were plated at a density of 20 000 cells/well using round-bottom 96-well plates. Molecules were added at the indicated concentrations in triplicates. FolR1 16D5 TCB was included as positive control and an untargeted TCB molecule (binding to CD3 but not to a target cell antigen) was included as negative control. PBMCs were added to target cells at final E:T ratio of 10:1. T-cell activation was assessed after 48 h of incubation at 37° C., 5% $CO_2$ by quantification of CD25 and CD69 on CD4 positive and CD8 positive T cells. T cell activation results are consistent with the results observed in the previous example assessing target cell killing (Example 7).

Example 9

T-Cell Activation Mediated by Protease-Activated TCBs and Target Cell Lines Expressing Low Antigen Levels T-cell activation mediated by protease activated TCB molecules was assessed on HT29 cells expressing only low levels of FolR1 (FIG. 13). Human PBMCs isolated from buffy coat were used as effector cells. For enriched lymphocyte preparations (buffy coats) Histopaque-1077 density preparation was used. Buffy coat was diluted 1:1 with sterile PBS and layered over Histopaque gradient (Sigma, #H8889). After centrifugation (450×g, 30 minutes, w/o break, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet resuspended in 2 ml ACK buffer for Erythrocytes lysis. After incubation at 37° C. for about 2-3 minutes the tubes were filled with sterile PBS to 50 ml and centrifuged at 350×g for 10 minutes. This washing step was repeated once prior to resuspension of PBMCs in RPMI1640 medium containing 2% FCS and 1× GlutaMax at 37° C., 5% $CO_2$ in cell incubator until further use. Briefly, adherent target cells were harvested with Trypsin/EDTA, counted, assessed for viability and resuspended at $0.4 \times 10^6$ cells/ml in assay medium (RPMI1640, 2% FCS, 1× GlutaMax). Target cells were plated at a density of 20 000 cells/well using round-bottom 96-well plates. Molecules were added at the indicated concentrations in triplicates. FolR1 16D5 TCB was included as positive control and an untargeted TCB molecule (binding to CD3 but not to a target cell antigen) was included as negative control.

PBMCs were added to target cells at final E:T ratio of 10:1. T-cell activation was assessed after 48 h of incubation at 37° C., 5% $CO_2$ by quantification of CD25 and CD69 on CD4 positive and CD8-positive T cells. The potency of treated protease activated TCB is comparable to 16D5 TCB (6298).

The 16D5 TCB (inverted format) show higher potency than the classic format. Masked TCBs with non-cleavable linker or without Matriptase pre-treatment do not induce T cell activation on this cell line. For cell lines with low or medium FolR1 expression levels both anti-idiotypic scFvs are sufficient in masking the CD3 Fab (FIGS. 22A and B).

Example 10

T-Cell Activation Mediated by Protease Activated TCB with Primary Cell Line HRCEpiC T-cell activation mediated by protease activated TCB molecules was assessed on primary Human Renal Cortical Epithelial Cell (ScienceCell) cells expressing only very little amounts of FolR1 (FIG. 13). Human PBMCs isolated from buffy coat were used as effector cells. For enriched lymphocyte preparations (buffy coats) Histopaque-1077 density preparation was used. Buffy coat was diluted 1:1 with sterile PBS and layered over Histopaque gradient (Sigma, #H8889). After centrifugation (450×g, 30 minutes, without break at room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet resuspended in 2 ml ACK buffer for Erythrocytes lysis. After incubation at 37° C. for about 2-3 minutes the tubes were filled with sterile PBS to 50 ml and centrifuged at 350×g for 10 minutes. This washing step was repeated once prior to resuspension of PBMCs in RPMI1640 medium containing 2% FCS and 1× GlutaMax at 37° C., 5% $CO_2$ in cell incubator until further use. Briefly, adherent target cells were harvested with Trypsin/EDTA, counted, checked for viability and resuspended at $0.4 \times 10^6$ cells/ml in assay medium (RPMI1640, 2% FCS, 1× GlutaMax). Target cells were plated at a density of 20 000 cells/well using round-bottom 96-well plates. Protease activatable TCB molecules were added at the indicated concentrations in triplicates. FolR1 16D5 TCB was included as positive control and an untargeted TCB molecule (binding to CD3 but not to a target cell antigen) was included as negative control. PBMCs were added to target cells at final E:T ratio of 10:1. T-cell activation was assessed after 48 h of incubation at 37° C., 5% $CO_2$ by quantification of CD25 and CD69 on CD4 positive and CD8 positive T cells. Masked 16D5 TCB does not induce T cell activation upon incubation with primary human renal cortical epithelial cells despite low level FolR1 expression at the highest concentration of 10.000 µM of TCB, demonstrating the effectiveness of the anti-idiotype masking moiety. Little T cell activation can be observed for the 16D5 TCBs (inverted and classic format) (FIG. 23).

Example 11

Anti-ID CD3 Fab Masking CD3 Binder of 16D5 TCB. Killing on Ovcar3 Cells

T-cell-mediated target cell killing mediated by protease activated TCB molecules was assessed on OVCAR3 cells (FIG. 24). Human PBMCs were used as effector cells and cell killing was detected at 48 h of incubation with the molecules. Human Peripheral blood mononuclear cells (PBMCs) were isolated from fresh taken blood of a healthy donor. 50 ml Leucosep tubes (GreinerBioOne) were used for preparation. Blood was diluted 1:1 with sterile PBS and layered over Histopaque gradient (Sigma, #H8889). After centrifugation (450×g, 30 minutes, w/o break, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet resuspended in 2 ml ACK buffer for Erythrocytes lysis. After incubation at 37° C. for about 2-3 minutes the tubes were filled with sterile PBS to 50 ml and centrifuged at 350×g for 10 minutes. This washing step was repeated once prior to resuspension of PBMCs in RPMI1640 medium containing 2% FCS and 1× GlutaMax at 37° C., 5% C02 in cell incubator until further use. Briefly, adherent target cells were harvested with Trypsin/EDTA, counted, checked for viability and resuspended at $0.4 \times 10^6$ cells/ml in assay medium (RPMI1640, 2% FCS. 1× GlutaMax). Target cells were plated at a density of 20 000 cells/well using round-bottom 96-well plates. For the killing assay, the molecules were added at the indicated concentrations in triplicates. FolR1 16D5 TCB was included as positive control and an untargeted TCB molecule (binding to CD3 but not to a target cell antigen) was included as negative control. PBMCs were added to target cells at final E:T ratio of 10:1. Target cell killing was assessed after 48 h of incubation at 37° C., 5% $CO_2$ by quantification of LDH release into cell supernatants by apoptotic/necrotic cells (LDH detection kit, Roche Applied Science, #11 644 793 001). Maximal lysis of the target cells (=100%) was achieved by incubation of target cells and PBMCs with 1% Triton X-100 1 h before LDH readout. Minimal lysis (=0%) refers to target cells co-incubated with effector cells without any TCB. The result (FIG. 24) shows that protease activated TCB with anti-idiotypic CD3 4.15.64 crossed Fab N—terminally linked by a non-cleavable linker is not significantly masking the CD3 binder. Further, Ovcar3 cells appear to express Matriptase because untreated molecule also induces killing of these cells.

Example 12

Killing on Skov3 and HeLa Cells with Three Different Human PBMC Donors

T-cell killing mediated by protease activated TCB molecules was assessed on two different cell lines expressing different levels of FolR1 (FIGS. 25-27). Human PBMCs were used as effector cells and cell killing was detected at 48 h of incubation with the molecules. Human Peripheral blood mononuclear cells (PBMCs) were isolated from buffy coats obtained from healthy human donors. For enriched lymphocyte preparations (buffy coats) Histopaque-1077 density preparation was used. Blood/buffy coat was diluted 1:1 with sterile PBS and layered over Histopaque gradient (Sigma, #H8889). After centrifugation (450×g, 30 minutes, w/o break, room temperature), the plasma above the PBMC-containing interphase was discarded and PBMCs transferred in a new falcon tube subsequently filled with 50 ml of PBS. The mixture was centrifuged (400×g. 10 minutes, room temperature), the supernatant discarded and the PBMC pellet resuspended in 2 ml ACK buffer for Erythrocytes lysis. After incubation at 37° C. for about 2-3 minutes the tubes were filled with sterile PBS to 50 ml and centrifuged at 350×g for 10 minutes. This washing step was repeated once prior to resuspension of PBMCs in RPMI1640 medium containing 10% FCS and 1× GlutaMax. PBMCs were resuspended in RPMI1640 medium containing 10% FCS, 1× GlutaMax and 10% DMSO. PBMCs were frozen overnight at −80° C. in Cool Cell boxes before they were transferred to liquid nitrogen. 24 h before assay start, PBMCs were thawed and kept in RPMI1640 medium containing 10% FCS and 1× GlutaMax at 37° C., 5% C02 in cell incubator. The day before assay start adherent target cells were harvested with Trypsin/EDTA, counted, checked for viability and resuspended at $0.4 \times 10^6$ cells/ml in appropriate medium. Target cells were plated at a density of 20 000 cells/well using flat-bottom 96-well plates. On the day of assay start PBMCs were counted and checked for viability. PBMCs were centrifuged at 350 g for 5 min and resuspended in assay medium (RPMI1640, 2% FCS, 1× GlutaMax). The medium of target cells was removed and PBMCs were added to the target cells before diluted antibodies were added at the indicated concentrations in triplicates. FolR1 16D5 TCB was included as positive control and an untargeted TCB molecule (binding to CD3 but not to a target cell antigen) was included as negative control. PBMCs were added to target cells at E:T ratio of 10:1. Target cell killing was assessed after 48 h of incubation at 37° C., 5% $CO_2$ by quantification of LDH release into cell supernatants by apoptotic/necrotic cells (LDH detection kit, Roche Applied Science, #11 644 793 001). Maximal lysis of the target cells (=100%) was achieved by incubation of target cells with 1% Triton X-100 2 h before LDH readout. Minimal lysis (=0%) refers to target cells co-incubated with effector cells without any TCB.

The results (FIGS. 25-27) show that FolR1 TCB with scFv 4.32.63 N-terminally linked by a non-cleavable linker (FIG. 5D) induced reduced killing on Hela cells at concentration of 100 µM and on Skov3 cells at a concentration of 10 nM. FolR1 TCB with scFv 4.15.64 N-terminally linked by a non-cleavable linker (FIG. 5B) was less efficient in reducing killing on Skov3 cells at a concentration of 10 nM. The stronger mask, meaning the anti-idiotypic scFv 4.32.63 with the higher affinity, is more efficient in masking the CD3 binder than the weak anti-idiotypic scFv 4.15.64. Comparable potency of treated and untreated TCBs suggests protease, e.g. Matriptase, expression by Hela and Skov3 cells.

Example 13

Preparation of the HER1 Binding Antibody GA201 Masked with an Anti-Idiotype GA201 scFv The following molecules were prepared in this example:
1: GA201 IgG1 antibody with N-terminal fusion of an anti-idiotypic GA201 scFv and Matrix Metalloprotease site in glycine serine linker (SEQ ID NOs 32 and 34); and
2: HER1-binding IgG1 antibody GA201 (SEQ ID NOs 32 and 33).

Schematic illustrations thereof are shown in FIGS. 28 and 29. The GA201 anti-idiotypic (ID) binder sequence was obtained by RT-PCR (reverse transcription) from RNA of Hybridoma cells using degenerated primers binding to the ends of the variable light and heavy chain, respectively. Hybridoma cells were obtained by immunization of mice. Single chain Fv (scFv) DNA sequence synthesis with flanking singular restriction endonuclease sites was ordered at Geneart and cloned as N-terminal fusion at the GA201 light chain.

A Roche expression vector was used for the construction of all heavy and light chain scFv fusion protein encoding expression plasmids. The vector is composed of the following elements:
a hygromycin resistance gene as a selection marker,
an origin of replication, oriP, of Epstein-Barr virus (EBV),
an origin of replication from the vector pUC18 which allows replication of this plasmid in E. coli
a beta-lactamase gene which confers ampicillin resistance in E. coli,
the immediate early enhancer and promoter from the human cytomegalovirus (HCMV),
the human 1-immunoglobulin polyadenylation ("poly A") signal sequence, and
unique BamHI and XbaI restriction sites.

The molecules were produced by co-transfecting human embryonic kidney 293-F cells growing in suspension with the mammalian expression vectors using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2 \times 10^6$ viable cells/ml on the day of transfection. DNA-293fectin™ complexes were prepared in Opti-MEM I medium (Invitrogen, USA) using 325 µl of 293fectin™ (Invitrogen, Germany) and 250 µg of heavy ("GA201 heavy chain") and light chain ("anti-GA201 VH-VL scFv MMP cleavable linker G4S GA201 light chain" or "GA201 light chain") plasmid DNA in a 1:1 molar ratio for a 250 ml final transfection volume. Antibody containing cell culture supernatants were harvested 7 days after transfection by centrifugation at 14000 g for 30 minutes and filtered through a sterile filter (0.22 µm). Supernatants were stored at −20° C. until purification.

The secreted protein was purified from cell culture supernatants by affinity chromatography using ProteinA affinity chromatography, followed by size exclusion chromatography. Briefly, sterile filtered cell culture supernatants were applied to a HiTrap ProteinA HP (5 ml) column equilibrated with PBS buffer (10 mM Na2HPO4, 1 mM KH2PO4, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 Hiload 120 ml 16/60 gel filtration column (GE Healthcare, Sweden) equilibrated with 20 mM Histidin, 140 mM NaCl, pH 6.0. Fractions containing purified GA201-anti-GA201-scFv or GA201 with less than 5% high molecular weight aggregates were pooled and stored as 1.0 mg/ml aliquots at −80° C.

For Protein analytics after size exclusion chromatography, the purity and molecular weight of the molecules in the single fractions were analyzed by SDS-PAGE in the absence of a reducing agent and staining with Coomassie (InstantBlue™, Expedeon). The NuPAGE® Pre-Cast gel system (4-12% Bis-Tris, Invitrogen or 3-8% Tris-Acetate, Invitrogen) was used according to the manufacturer's instruction.

The protein concentration of purified protein samples was determined by measuring the optical density (OD) at 280 nm divided by the molar extinction coefficient calculated on the basis of the amino acid sequence. Purity and molecular weight of the molecules after the final purification step were analyzed by CE-SDS analyses in the presence and absence of a reducing agent. The Caliper LabChip GXII system (Caliper Lifescience) was used according to the manufacturer's instruction.

The aggregate content of the molecules was analyzed by high-performance SEC using a Superdex 200 analytical size-exclusion column (GE Healthcare, Sweden) in 200 mM KH2PO4, 250 mM KCl, pH 7.0 running buffer at 25° C. 25 μg protein were injected on the column at a flow rate of 0.5 ml/min and eluted isocratic over 50 minutes.

The final purity of all molecules was >95% monomer content as detected by high performance SEC. The molecular weight of the anti-idiotypic scFv masked GA201 was determined by CE-SDS analysis as 216.3 kDa under non reducing conditions (FIG. 1A) and under reducing conditions as 58.3 kDa for the GA201 heavy chain and 60.3 kDa for the scFv linked GA201 light chain (FIG. 30B), respectively. The molecular weight based on the amino acid sequence was calculated as 49.2 kDa for the heavy chain and 51.9 kDa for the scFv fused GA201 light chain, which indicates glycosylation of both chains in HEK293 cells.

TABLE 3

Summary of production and purification of protease-activated GA201 IgG (FIG. 28) and GA201 (FIG. 29) control molecules.

| Molecule | Supernatant | Protein A - Yield | SEC -Yield |
|---|---|---|---|
| 1 | 1.0 L | 1.3 mg | 0.4 mg |
| 2 | 1.0 L | 26.4 mg | 24 mg |

Example 14

Masking Effect of an Anti-Idiotypic scFv for GA201 IgG

The efficiency of masking the HER1 binding of GA201 by N-terminal fusion of an anti-idiotypic GA201 scFv was shown by FACS analysis on HER1 expressing H322M cells and Surface Plasmon Resonance (SPR) analysis on a HER1 coated chip surface. For proteolytic cleavage of GA201-anti-GA201-scFv recombinant active human MMP2 (Calbiochem) was used. 1 mg of GA201 anti-idiotypic scFv fused to GA201 by a glycine serine linker containing a MMP cleavage site was incubated with 1.2 μg MMP2 overnight at 37° C. in PBS.

For FACS analysis of HER1 binding of cleaved and uncleaved GA201-anti-GA201-scFv, the non-small cell lung cancer line H322M was used. Cells were adjusted to 1×10⁶/ml and distributed to a 96-well round-bottom plate. The molecules were added and incubated on ice for 30 minutes. Cells were washed once with FACS buffer (PBS+2% FCS+0.1% sodium azide) and re-suspended with a F(ab')2-goat anti-human IgG Fc secondary antibody FITC conjugate (ThermoFisher Scientific). After another 20 minutes on ice, cells were washed twice and re-suspended in FACS buffer and analyzed in a BD FACS Canto II. 10000 cells were measured and the median of the fluorescence signal was used for analysis. Before MMP-2 cleavage of GA201-anti-GA201-scFv no binding to HER1 on H322M cells was measurable, indicating complete masking of the GA201 binding domains by the anti-idiotypic scFv (FIG. 31). Binding of uncleaved GA201-anti-GA201-scFv was comparable to an unspecific isotype IgG control antibody (FIG. 31). In contrast, MMP cleavage of the anti-idiotypic scFv leads to activation of GA201 and binding to HER1 on H322M cells was restored to similar levels as the unmasked parental antibody GA201 (FIG. 31) To confirm the FACS binding data of masked GA201 binding after MMP cleavage, we also performed a SPR experiment as second analytical method using a Biacore T100 instrument (GE Healthcare Biosciences AB, Uppsala, Sweden). HER1 was immobilized on the surface of a CM5 biosensorchip using standard aminecoupling chemistry. The HER1 extracellular domain was injected in sodium acetate, pH 5.0 at 1 μg/ml. Reference control flow cells were treated in the same way but with vehicle buffer only. GA201-anti-GA201-scFv, before and after an overnight MMP cleavage, and GA201 were diluted in 1×PBS pH 7.4, 0.05% Tween20 Roche Diagnostics GmbH) and injected at increasing concentrations between 3.125 and 50 nM with a flow rate of 30 μl/min. The association phase was 3 minutes and the dissociation time was 10 minutes. HER1 binding was regenerated with an inject of 0.85% phosphoric acid for 30 s at a flow rate of 5 μl/min. Kinetic rate constants and equilibrium dissociation constants were calculated by using the 1:1 Langmuir binding model within the Biaevaluation software. A $K_D$ value of 1 nM for binding of HER1 was determined for the GA201 parental unmasked antibody (FIG. 32). After an overnight MMP-2 incubation of GA201-anti-GA201-scFv, a $K_D$ value of 2 nM was measured with similar $k_a$ and $k_d$ rate constants for association and dissociation as the unmasked control antibody. indicating complete restoration of HER1 binding by protease cleavage (FIG. 32). Uncleaved GA201-anti-GA201-scFv did not show any binding to HER1 in SPR analysis (FIG. 32). In summary, we have demonstrated a complete loss of binding to HER1 by fusion of an anti-idiotypic scFv to the N-terminus of the IgG1 antibody GA201 with two independent analytical methods. Furthermore, binding to HER1 was fully restored by removal of the scFv through protease cleavage in the MMP cleavage site in the glycine serine linker.

Example 15

Preparation of Anti FolR1/Anti-CD3 and antiMesothelin/Anti-CD3 T Cell Bispecific (TCB) Molecules with Anti CD3 scFv Several T cell bispecific (TCB) molecules with various anti-idiotypic scFv were produced and are schematically depicted in FIGS. 33A-33J with their respective ID number. The following molecules were prepared:

- ID 8364: "FolR1 16D5 2+1 IgG, classic format (anti idiotypic scFv 4.32.63-MMP9-MK062 Matriptase site—CD3-N-terminal fused to FolR1 VH—inert Fc) with N-terminal fused anti CD3 scFv 4.32.63 and MMP9-MK062 protease linker" (FIG. 33A, SEQ ID NOs 1, 3 and 72).
- ID 8363: "FolR1 16D5 2+1 IgG, classic format (anti idiotypic scFv 4.32.63-Cathepsin S/B site—CD3-N-terminal fused to FolR1 VH—inert Fc) with N-terminal fused anti CD3 scFv 4.32.63 and Cathepsin S/B protease linker" (FIG. 33B, SEQ ID NOs 1, 3 and 85).
- ID 8365: "FolR1 16D5 2+1 IgG, inverted format, (anti idiotypic scFv 4.32.63-MK062 Matriptase linker—CD3-N-terminal fused to CD3 VL—inert Fc) with N-terminal fused anti CD3 scFv 4.32.63 and MK062 Matriptase linker" (FIG. 33C, SEQ ID NOs 1, 3, 73 and 74).
- ID 8366: "FolR1 16D5 2+1 IgG, inverted format, (anti idiotypic scFv 4.32.63-non-cleavable GS linker—CD3-N-terminal fused to CD3 VL—inert Fc) with N-terminal fused anti CD3 scFv 4.32.63 and non-cleavable GS linker" (FIG. 33D).
- ID 8672: "aMesothelin 2+1 IgG, classic format, MSLN charged variants, CD3 crossed (anti idiotypic scFv 4.32.63-MMP9-MK062 Matriptase—CD3-N-terminal fused to aMesothelin VH—inert Fc) with N-terminal fused anti CD3 scFv 4.32.63 and MMP9-MK062 Matriptase" (FIG. 33E, SEQ ID NOs 77, 78, 81, 82).
- ID 8673: "aMesothelin 2+1 IgG, classic format, MSLN charged variants, CD3 crossed (anti idiotypic scFv 4.32.63-non-cleavable GS linker—CD3-N-terminal fused to aMesothelin VH—inert Fc) with N-terminal fused anti CD3 scFv 4.32.63 non-cleavable GS linker" (FIG. 33F).
- ID 8674: "aMesothelin 2+1 IgG, inverted format, MSLN charged variants, CD3 crossed (anti idiotypic scFv 4.32.63-MMP9-MK062 Matriptase—CD3-N-terminal fused to CD3 VH—inert Fc) with N-terminal fused anti CD3 scFv 4.32.63 and MMP9-MK062 Matriptase" (FIG. 33G, SEQ ID NOs 76, 77, 78, 79).
- ID 8675: "aMesothelin 2+1 IgG, inverted format, MSLN charged variants, CD3 crossed (anti idiotypic scFv 4.32.63-non-cleavable GS linker—CD3-N-terminal fused to CD3 VH—inert Fc) with N-terminal fused anti CD3 scFv 4.32.63 and non-cleavable GS linker" (FIG. 33H).
- ID 8505: "aMesothelin 2+1 IgG, inverted format, MSLN charged variants, CD3 (aMesothelin HC N-terminally fused to CD3 VL—inert Fc)" (FIG. 33I).
- ID 8676: "aMesothelin 2+1 IgG, classic format, MSLN charged variants, CD3 crossed (aMesothelin IgG with CD3-N-terminal fused to aMesothelin VH—inert Fc)" (FIG. 33J)

The variable domains were subcloned in frame with the pre-inserted domains into the respective recipient mammalian expression vector. Protein expression is driven by an MPSV promoter and a synthetic polyA signal sequence is present at the 3' end of the CDS. In addition each vector contains an EBV OriP sequence.

The molecules (except 8505, this molecule was produced by co-transfecting CHO cells growing in suspension with the mammalian expression vectors. Transient transfection was done at Evitria AG (Switzerland).) were produced by co-transfecting HEK293-EBNA cells growing in suspension with the mammalian expression vectors using polyethylenimine (PEI). For transfection HEK293 EBNA cells were cultivated in serum free ExCell culture medium containing 6 mM L-glutamine and 250 mg/l G418. For the production in 600 ml tubespin flasks (max. working volume 400 ml) 800 million HEK293 EBNA cells were seeded 24 hours before transfection without G418. For transfection 800 mio cells were centrifuged for 5 min at 210×g and supernatant was replaced by 40 ml pre-warmed CD CHO medium containing 6 mM L-Glutamine. Expression vectors were mixed with 40 ml CD CHO medium containing 6 mM L-Glutamine to a total amount of 400 µg DNA. After addition of 1080 µl PEI solution (2.7 µg/ml) the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a 5% $CO_2$ atmosphere. After incubation, 320 ml ExCell+6 mM L-glutamine+5 g/L Pepsoy+1.0 mM VPA+3 g/l glucose medium was added and cells were cultivated for 24 hours prior to feeding with 7% Feed 7. After 6-7 days the cultivation supernatant was collected for purification by centrifugation for 20-30 min at 210×g (Sigma 8K centrifuge). The solution was sterile filtered (0.22 µm filter) and sodium azide in a final concentration of 0.01% w/v was added. The solution was kept at 4° C. until purification.

The secreted protein was purified from cell culture supernatants by affinity chromatography using ProteinA affinity chromatography, followed by one to two size exclusion chromatographic steps.

For affinity chromatography supernatant was loaded on a Protein A MabSelectSure (CV=5 mL, GE Healthcare) equilibrated with 20 mM Sodium Citrate, 20 mM Sodium Phosphate, pH 7.5. Unbound protein was removed by washing with at least 10 column volumes 20 mM Sodium Citrate, 20 mM Sodium Phosphate, pH 7.5 and target protein was eluted in 20 column volumes (gradient from 0%-100%) 20 mM Sodium Citrate, 100 mM Sodium Chloride, 100 mM Glycine, pH 3.0. Protein solution was neutralized by adding 1/10 of 0.5 M Na2HPO4 pH 8.0. Target protein was concentrated with Amicon®Ultra-15 Ultracel 30K (Merck Millipore Ltd.) to a volume of 4 ml maximum prior loading on a HiLoad Superdex 200 column (GE Healthcare) equilibrated with 20 mM Histidine, 140 mM NaCl, 0.01% Tween pH 6.0.

The protein concentration of purified protein samples was determined by measuring the optical density (OD) at 280 nm divided by the molar extinction coefficient calculated on the basis of the amino acid sequence.

Purity and molecular weight of the molecules after the final purification step were analyzed by CE-SDS analyses in the presence and absence of a reducing agent. The Caliper LabChip GXII system (Caliper Lifescience) was used according to the manufacturer's instruction.

The aggregate content of the molecules was analyzed using a TSKgel G3000 SW XL analytical size-exclusion column (Tosoh) in 25 mM K2HPO4, 125 mM NaCl, 200 mM L-arginine monohydrocloride, 0.02% (w/v) NaN3, pH 6.7 running buffer at 25° C.

The final quality of all molecules was good, with >95% monomer content.

TABLE 4

Summary of production and purification of protease activated TCB molecules.

| Molecule | Titer [mg/l] | Yield [mg/l] | Analytical SEC (HMW/Monomer/LMW) [%] |
|---|---|---|---|
| 1 (8364) | 34.55 | 1.72 | 0.68/99.32/0 |
| 2 (8363) | 33.75 | 1.59 | 4.02/95.98/0 |
| 3 (8365) | 5.35 | 0.24 | 2.71/96.46/0.83 |
| 4 (8366) | 4.2 | 0.43 | 4.908/96.02/0 |
| 5 (8672) | 13.8 | 1.59 | 3.96/96.04/0 |
| 6 (8673) | 14 | 1.99 | 2.15/97.85/0 |
| 7 (8674) | 3.6 | 0.96 | 6.27/93.73/0 |
| 8 (8675) | 5.2 | 0.59 | 5.81/90.63/3.57 |
| 9 (8505) | 120 | 20.46 | 0.47/99.32/0.22 |
| 10 (8676) | 22.5 | 3.84 | 1.98/96.21/1.81 |

Example 16

Quality Control and Stability—Capillary Electrophoresis SDS Analysis of Different TCB Molecules Purity and molecular weight of the molecules after the final purification step were analyzed by CE-SDS analyses in the presence and absence of a reducing agent. The Caliper LabChip GXII system (Caliper Lifescience) was used according to the manufacturer's instruction. Comparison of untreated molecules (stored at 4° C.), treated molecules (treated with appropriate recombinant protease (R&D Systems) for 24 h at 37° C. and molecule incubated for 72 h at 37° C. (FIGS. 34, 35A, and 35B).

Comparison of the untreated and treated molecule shows complete cleavage of the anti ID scFv after rhMatriptase/ST14 treatment for the inverted format containing MK062 Matriptase linker but incomplete cleavage of MMP9-MK062 Matriptase linker. rhCathepsin B and rhCathepsin S treatment is incomplete as well. The conditions for the purified enzymes have not been optimal. Molecules incubated at 37° C. for 72 h are running on the same height than pure molecules suggesting that the molecules are stable at 37° C. for the time of in vitro assay duration. Pre-stained protein Marker Mark 12 (Invitrogen) was used for estimation of correct molecule weight.

Example 17

Comparison of Different Linkers and Formats of Protean Activated FolR1 TCBs Jurkat NFAT activation assay. Jurkat NFAT activation assay for comparison of different formats and linkers of protease activated TCB. Jurkat-NFAT reporter cell line (Promega) is a human acute lymphatic leukemia reporter cell line with a NFAT promoter, expressing human CD3ε. If the TCB binds the tumor target and the CD3 binder (crosslinkage) binds the CD3ε Luciferase expression can be measured in Luminescence after addition of One-Glo substrate (Promega). 20.000 target cells were seeded in 96-well white walled clear bottom plate (Greiner BioOne) in 50 ul/well Jurkat medium (RPMI1640, 2 g/l Glucose, 2 g/l NaHCO$_3$, 10% FCS, 25 mM HEPES, 2 mM L-Glutamin, 1×NEAA, 1× Sodium-pyruvate) without Hygromycine. Plates were incubated for about 20 hours at 37° C. Jurkat-NFAT reporter cells were harvested and viability was assessed using ViCell. Cells were resuspended in Jurkat medium without Hygromycine and 50 μl per well (50.000 cells/well) were added. The E:T ratio was 2.5:1 (based on cell number seeded). Antibodies were diluted in Jurkat medium without Hygromycine and 50 ul/well were added. Cells were incubated at 37° C. for 6 h in a humidified incubator before they were taken out of the incubator for about 10 min to adapt to room temperature prior to Luminescence read out. 50 μl/well of ONE-Glo solution were added to wells and incubated for 10 min at room temperature in the dark. Luminescence was detected using WALLAC Victor3 ELISA reader (PerkinElmer2030), 1 sec/well as detection time. Comparison of the pretreated protease activated TCB (8364, grey filled squares) and FolR1 TCB (black triangles pointing down) showed that potency after cleavage is recovered completely. No Luminescence was detectable for cells incubated with the masked TCB (containing a GS non-cleavable linker, grey triangles pointing up) and the non-targeted TCB control (empty triangle pointing down) for both cell lines in this concentration range. The dotted line shows the Luminescence of target cells and effector cells without any TCB (FIGS. 36A and 36B).

Example 18

Tumor Cell Cytotoxicity Mediated by Different Formats of Protease Activated TCB T-cell killing mediated by protease activated TCB molecules was assessed on cell lines expressing different levels of FolR1. Human Peripheral blood mononuclear cells (PBMCs) were isolated from buffy coats obtained from healthy human donors. Buffy coat was diluted 1:1 with sterile PBS and layered over Histopaque gradient (Sigma, #H8889). After centrifugation (450×g, 30 minutes, w/o break, room temperature) the PBMC-containing interphase was transferred in a new falcon tube that was subsequently filled with 50 ml of PBS. The mixture was centrifuged (400×g. 10 minutes, room temperature), the supernatant was discarded and the PBMC pellet was resuspended in 2 ml ACK buffer for Erythrocytes lysis. After incubation for about 2-3 minutes at 37° C. the tubes were filled with sterile PBS to 50 ml and centrifuged for 10 minutes at 350×g. This washing step was repeated once prior to resuspension of PBMCs in RPMI1640 medium containing 10% FCS, 1× GlutaMax and 10% DMSO. PBMCs were slowly frozen in CoolCell® Cell Freezing Containers (BioCision) at −80° C. and then transferred to liquid nitrogen. One day before assay start adherent target cells were harvested with Trypsin/EDTA, counted, checked for viability and resuspended in assay medium (RPMI1640, 2% FCS, 1× GlutaMax). Target cells were plated at a density of 20 000 cells/well using 96-well flat-bottom plates and incubated for about 20 h at 37° C. in a humidified incubator. About 20 h before assay start PBMCs were thawed in RPMI1640 medium (10% FCS, 1× GlutaMax). PBMCs were centrifuged at 350 g for 7 min. The pellet was resuspended in fresh medium (RPMI1640, 10% FCS, 1× GlutaMax) and incubated for max 24 h at 37° C. in a humidified incubator. On the day of the assay start PBMCs were harvested and centrifuged at 350 g for 7 min. The pellet was resuspended in assay medium and 0.2 mio PBMCs in 100 ul/well (E:T 10:1, based on the number of seeded target cells) were added to the target cells. The molecules were diluted in assay medium (RPMI1640, 2% FCS, 1× GlutaMax) and 50 ul/well were added at the indicated concentrations in triplicates before the plates were incubated for about 48 h at 37° C. in a humidified incubator. Target cell killing was assessed after 48 h of incubation at 37° C., 5% $CO_2$ by quantification of LDH release into cell supernatants by apoptotic/necrotic cells (LDH detection kit, Roche Applied Science, #11 644 793 001). Maximal lysis of the target cells (=100%) was achieved by incubation of target cells with 1% Triton X-100 20 h before LDH readout. Minimal lysis (=0%) refers to target cells co-incubated with effector cells without any TCB.

The results (FIGS. 37A and 37B) show the comparison of two different formats of the Protease activated TCBs both containing the anti idiotypic CD3 scFv 4.32.63 linked with a MK062 Matriptase linker. The inverted format of the protease activated TCB (8365, grey circles) seems to be more potent in killing (HeLa and Skov-3 target cells) than the classic format of the protease activated TCB (8408, dark grey triangles pointing up). However the inverted molecule containing the non-cleavable linker (8366, light grey squares) is less efficient in masking than the classic molecule (8409, dark grey triangles pointing down).

FIG. 37C HeLa target cell cytotoxicity. Comparison of classic Protease activated TCB containing the anti idiotypic CD3 scFv 4.32.63 and GS linkers with different protease sites. Protease activated TCB containing the MMP9-Matriptase MK062 linker (8364, grey squares) reaches the potency of FolR1 TCB (light grey triangles pointing down) whereas the protease activated TCB containing only Matriptase MK062 (light grey rhomb) is less potent in killing HeLa cells. Molecules containing Cathepsin site (grey circles) or non-cleavable linker (black triangles pointing down) are comparable.

FIG. 37D Skov-3 target cell cytotoxicity. Comparison of classic Protease activated TCB containing the anti idiotypic CD3 scFv 4.32.63 and GS linkers with different protease sites. Protease activated TCB containing the MMP9-Matriptase MK062 linker (8364, grey squares) nearly reaches the potency of FolR1 TCB (light grey triangles pointing down) whereas the protease activated TCB containing only Matriptase MK062 (light grey rhomb) is less potent in killing Skov-3 cells. The molecule containing Cathepsin site (grey circles) is less potent than the molecule containing only the Matriptase MK062 site and the molecule containing the non-cleavable linker (black triangles pointing down) only induces killing below 10% in the indicated concentration range for Skov-3 cells.

Example 19

T-Cell Activation after Co-Incubation of Human Renal Epithelial Cortical Cells or Human Bronchial Epithelial Cells with TCBs and Human PBMCs T-cell activation mediated by protease activated TCB molecules was assessed for HRCEpi (Human renal cortical epithelial cells) and HBEpiC (human bronchial epithelial cells expressing only little amounts of FolR1. Human PBMCs were used as effector cells and T cell activation markers were stained after 48 h of incubation with the molecules and cells. Human Peripheral blood mononuclear cells (PBMCs) were isolated from buffy coats obtained from healthy human donors. Buffy coat was diluted 1:1 with sterile PBS and layered over Histopaque gradient (Sigma, #H8889). After centrifugation (450×g, 30 minutes, w/o break, room temperature) the PBMC-containing interphase was transferred in a new falcon tube subsequently filled with 50 ml of PBS. The mixture was centrifuged (400×g, 10 minutes, room temperature), the supernatant was discarded and the PBMC pellet was resuspended in 2 ml ACK buffer for Erythrocytes lysis. After incubation for about two minutes at 37° C. the tubes were filled with sterile PBS to 50 ml and centrifuged for 10 minutes at 350×g. This washing step was repeated once prior to resuspension of PBMCs in RPMI1640 medium containing 10% FCS, 1× GlutaMax and 10% DMSO. PBMCs were slowly frozen in CoolCell® Cell Freezing Containers (BioCision) at −80° C. and then transferred to liquid nitrogen. One day before the assay was started adherent target cells were harvested with Trypsin/EDTA, counted, checked for viability and resuspended in assay medium (RPMI1640, 2% FCS, 1× GlutaMax). Target cells were plated at a density of 20 000 cells/well using 96-well flat-bottom plates and incubated for about 20 h at 37° C. in a humidified incubator. About 20 h before assay start PBMCs were thawed in RPMI1640 medium (10% FCS, 1× GlutaMax). PBMCs were centrifuged for 7 min at 350 g. The pellet was resuspended in fresh medium (RPMI1640, 10% FCS, 1× GlutaMax) and incubated for max 24 h at 37° C. in a humidified incubator. On the day of the assay start PBMCs were harvested and centrifuged for 7 min at 350 g. The pellet was resuspended in assay medium and 0.2 mio PBMCs in 100 ul/well (E:T 10:1, based on the number of seeded target cells) were added to the target cells. The molecules were diluted in assay medium (RPMI1640, 2% FCS, 1× GlutaMax) and added at the indicated concentrations in triplicates before the plates were incubated for about 48 h at 37° C. in a humidified incubator.

T-cell activation was assessed after 48 h of incubation at 37° C., 5% C02 by quantification of CD25 and CD69 on CD4 positive and CD8 positive T cells. FolR1 16D5 TCB (6298) and an untargeted TCB (binding to CD3 but not to a target cell antigen, 7235) were included as controls. Each point represents the mean value of triplicates of three different human PBMC donors. Standard deviation is indicated in error bars. Unpaired t test was used for statistical analysis. The results show an increase in CD69 for CD8 positive cells for the FolR1 TCB that is significantly higher than the median fluorescence intensity for the protease activated TCBs (FIGS. 38A and 38B).

Example 20

Tumor Cell Cytotoxicity Mediated by Different Formats of Protease Activated Mesothelin (MSLN) TCB T-cell killing mediated by protease activated TCB molecules was assessed on cell lines expressing different levels of Mesothelin (MSLN). Human Peripheral blood mononuclear cells (PBMCs) were isolated from buffy coats obtained from healthy human donors. Buffy coat was diluted 1:1 with sterile PBS and layered over Histopaque gradient (Sigma, #H8889). After centrifugation (450×g, 30 minutes, w/o break, room temperature) the PBMC-containing interphase was transferred in a new falcon tube subsequently filled with 50 ml of PBS. The mixture was centrifuged (400×g, 10 minutes, room temperature), the supernatant was discarded and the PBMC pellet was resuspended in 2 ml ACK buffer for Erythrocytes lysis. After incubation for about two minutes at 37° C. the tubes were filled with sterile PBS to 50 ml and centrifuged for 10 minutes at 350×g. This washing step was repeated once prior to resuspension of PBMCs in RPMI1640 medium containing 10% FCS, 1× GlutaMax and 10% DMSO. PBMCs were slowly frozen in CoolCell® Cell Freezing Containers (BioCision) at −80° C. and then transferred to liquid nitrogen. Adherent target cells were harvested with Trypsin/EDTA, counted, checked for viability and resuspended in assay medium (RPMI1640, 2% FCS, 1× GlutaMax) one day before the assay was started. Target cells were plated at a density of 20 000 cells/well using 96-well flat-bottom plates and incubated for about 20 h at 37° C. in a humidified incubator. PBMCs were thawed in RPMI1640 medium (10% FCS, 1× GlutaMax) about 20 h before assay start. PBMCs were centrifuged for 7 min at 350 g. The pellet was resuspended in fresh medium (RPMI1640, 10% FCS, 1× GlutaMax) and incubated for max 24 h at 37° C. in a humidified incubator. On the day of the assay start PBMCs were harvested and centrifuged for 7 min at 350 g. The pellet was resuspended in assay medium and 0.2 mio PBMCs in 100 ul/well (E:T 10:1, based on the number of seeded target cells) were added to the target cells. The molecules were diluted in assay medium (RPMI1640, 2% FCS, 1× GlutaMax) and added at the indicated concentrations in triplicates before the plates were incubated for about 48 h at 37° C. in a humidified incubator. Target cell killing was assessed after 48 h of incubation at 37° C., 5% $CO_2$ by quantification of LDH release into cell supernatants by apoptotic/necrotic cells (LDH detection kit, Roche Applied Science, #11 644 793 001). Maximal lysis of the target cells (=100%) was achieved by incubation of target cells with 1% Triton X-100 20 h before LDH readout. Minimal lysis (=0%) refers to target cells co-incubated with effector cells without any TCB.

The results (FIGS. 39A and 39B) show target cell killing mediated by Protease activated MSLN TCB (8672) for NCI H596 and AsPC-1 cell lines. The protease activated TCBs nearly reaches the potency of MSLN TCB (8676) for NCI H596 and AsPC-1. The molecule containing the non-cleavable GS linker (8673) does not induce killing in the indicated concentration range for both cell lines.

Example 21

Jurkat-NFAT Reporter Assay to Monitor Target Expression (FOLR1 TCB) and Protease Activity (Protease Activated FOLR1 TCB) in Primary Tumor Samples The intention of this assay was to show tumor target antigen (FolR1) expression and activity of tumor specific proteases like MMP9, Matriptase or Cathepsin in human tumor samples. Jurkat-NFAT reporter cell line (Promega) is a human acute lymphatic leukemia reporter cell line with a NFAT promoter, expressing human CD3ε. Luciferase expression can be measured, if the T cell bispecific molecule binds the tumor target and the CD3ε (crosslinkage). Luminescence is measured after addition of One-Glo substrate (Promega).

Primary tumor samples were received from Indivumed GmbH, Germany. Samples were shipped over night in transport medium. About 24 h after surgery the sample was cut in small pieces. 96-well white walled, flat (clear) bottom plate was prepared by adding 18 ul cold Matrigel (Matrigel (734-1101, Corning/VWR). Plate was incubated for 2 min at 37° C. before tumor pieces were added (triplicates). 33 ul of cold Matrigel were added per well and plate was incubated again for 2 min at 37° C. 50 ul of antibody dilution (in Jurkat medium without Hygromycine but containing 2× Penicillin/Streptomycine) was added per well and plate was incubated for about 48 hours at 37° C., 5% $CO_2$.

Jurkat-NFAT reporter cells were harvested and viability was assessed using ViCell. Cells were centrifuged at 350×g, 7 min before they were resuspended in Jurkat medium without Hygromycine and 50 µl per well (50.000 cells/well) were added. Plate was incubated for 5 h at 37° C. in a humidified incubator before it was taken out for Luminescence read out. 80 ul of each well were transferred into a white walled 96-well plate. 27 µl/well of ONE-Glo solution were added to each well and incubated for 10 min at room temperature in the dark. Luminescence was detected using WALLAC Victor3 ELISA reader (PerkinElmer2030), 1 sec/well as detection time. Jurkat NFAT reporter cells are activated after co-incubation with FolR1 TCB (6298) and Protease activated FolR1 TCB containing MMP9-Matriptase cleavage site (8364). Protease activated FolR1 TCBs (8363, 8408) and control TCBs (8409, 7235) do not induce Luciferase expression. The dotted line indicates the baseline Luminescence for Jurkat NFAT cells co-incubated with tumor (FIG. 40).

Example 22

Serum Stability of Protease Activated TCBs

Capillary electrophoresis of protease activated TCBs after incubation in human serum. Molecules were incubated for 0 or 14 days in human IgG depleted serum at 37° C. in a humidified incubator (5% C02). All molecules were purified by affinity chromatography (ProteinA) and then analyzed by Capillary electrophoresis.

100 ug of each molecule was added either in buffer (Histidine buffer (Bichsel) with 0.01% Tween-20) or in human serum (IgG depleted, SP1839, TL-15216. 16FSP63814). The concentration of the molecules was higher than 2 mg/ml and the final concentration was 0.5 mg/ml. The pretreatment for one molecule (8408) was done with rhMatriptase (R&D Systems) for 24 h at 37° C., 5% C02 in a humidified incubator (otherwise pH of serum could change). The samples for day 0 were directly frozen in liquid nitrogen and stored at −80° C. until analysis. Samples for day 14 were incubated for 14 days at 37° C., 5% C02 in a humidified incubator until they were also snap frozen.

Prior to CE-SDS analysis all samples were purified via HPLC affinity chromatography (Agilent technologies 1200series, column: Upchurch scientific C-130B, packaging material: Applied Biosystems POROS 20A 60 µl, buffer: 10 mM Tris, 50 mM Glycine, 500 mM NaCl pH 8.0 und pH 2.0, injection volume: 100 µl, flow rate 1 ml/min, collection: peak based, neutralization: 0.5 M Na-phosphate pH 8.0 10% volume). Protease activated TCB is stable in human IgG depleted serum for a minimum of 14 days (FIGS. 41A-41C).

Example 23

Design of anti Her2/anti-CD3 and antiFolR1/anti-CD3 T cell bispecific (TCB) molecules with anti CD3 scFv Several T cell bispecific (TCB) molecules designed and are schematically depicted in FIGS. 42A-42F with their respective ID number. The following molecules were designed:

ID 8955: "Herceptarg 2+1 IgG, classic format, Herceptarg charged variants, CD3 crossed (anti idiotypic scFv 4.32.63-MMP9-MK062 Matriptase—CD3-N-terminal fused to Herceptarg VH—inert Fc) with N-terminal fused anti CD3 scFv 4.32.63 and MMP9-MK062 Matriptase "(FIG. 42A, SEQ ID NOs 81, 132, 133 and 136).

ID 827: "Herceptarg 2+1 IgG, classic format, Herceptarg charged variants, CD3 crossed (anti idiotypic scFv 4.32.63-non cleavable GS linker—CD3-N-terminal fused to Herceptarg VH—inert Fc) with N-terminal fused anti CD3 scFv 4.32.63 and non cleavable GS linker "(FIG. 42B, SEQ ID NOs 81, 132, 133 and 135).

ID 8959: "Herceptarg 2+1 IgG, classic format, Herceptarg charged variants, CD3 crossed (Herceptarg IgG with CD3-N-terminal fused to Herceptarg VH—inert Fc)" (FIG. 42C, SEQ ID NOs 81, 132. 133 and 134).

ID 8997: "FolR1 36F2 2+1 IgG, classic format, FolR1 36F2 charged variants, CD3 crossed (anti idiotypic scFv 4.32.63-MMP9-MK062 Matriptase—CD3-N-terminal fused to FolR1 36F2 VH—inert Fc) with N-terminal fused anti CD3 scFv 4.32.63 and MMP9-MK062 Matriptase "(FIG. 42D, SEQ ID NOs 81, 137, 138 and 139).

ID 8998: "FolR1 36F2 2+1 IgG, classic format, FolR1 36F2 charged variants. CD3 crossed (anti idiotypic scFv 4.32.63-non cleavable GS linker—CD3-N-terminal fused to FolR1 36F2 VH—inert Fc) with N-terminal fused anti CD3 scFv 4.32.63 and non cleavable GS linker "(FIG. 42E, SEQ ID NOs 81, 137. 138 and 140).

ID 8996: "FolR1 36F2 2+1 IgG, classic format, FolR1 36F2 charged variants, CD3 crossed (FolR1 36F2 IgG with CD3-N-terminal fused to FolR1 36F2 VH—inert Fc)" (FIG. 42F, SEQ ID NOs 81, 137, 138 and 141).

The variable domains were subcloned in frame with the pre-inserted domains into the respective recipient mammalian expression vector. Protein expression is driven by an MPSV or CMV (for Herceptarg) promoter and a synthetic polyA signal sequence is present at the 3' end of the CDS. In addition each vector contains an EBV OriP sequence.

Example 24

Primary Cell Cytotoxicity Mediated by Protease Activated FolR1 TCB

T-cell killing mediated by protease activated FolR1 TCB molecule was assessed on primary cell lines expressing low levels of FolR1 (FIG. 43). Human Peripheral blood mononuclear cells (PBMCs) were isolated from buffy coats obtained from healthy human donors. Buffy coat was diluted 1:1 with sterile PBS and layered over Histopaque gradient (Sigma, #H8889). After centrifugation (450×g, 30 minutes, w/o break, room temperature) the PBMC-containing interphase was transferred in a new falcon tube that was subsequently filled with 50 ml of PBS. The mixture was centrifuged (400×g, 10 minutes, room temperature), the supernatant was discarded and the PBMC pellet was resuspended in 2 ml ACK buffer for Erythrocytes lysis. After incubation for about 2-3 minutes at 37° C. the tubes were filled with sterile PBS to 50 ml and centrifuged for 10 minutes at 350×g. This washing step was repeated once prior to resuspension of PBMCs in RPMI1640 medium containing 10% FCS, 1× GlutaMax and 10% DMSO. PBMCs were slowly frozen in CoolCell® Cell Freezing Containers (BioCision) at −80° C. and then transferred to liquid nitrogen. One day before assay start adherent target cells were harvested with Trypsin/EDTA, counted, checked for viability and resuspended in assay medium (RPMI1640, 2% FCS, 1× GlutaMax). Target cells were plated at a density of 20 000 cells/well using 96-well flat-bottom plates and incubated for about 20 h at 37° C. in a humidified incubator. About 20 h before assay start PBMCs were thawed in RPMI1640 medium (10% FCS, 1× GlutaMax). PBMCs were centrifuged at 350 g for 7 min. The pellet was resuspended in fresh medium (RPMI1640, 10% FCS, 1× GlutaMax) and incubated for max 24 h at 37° C. in a humidified incubator. On the day of the assay start PBMCs were harvested and centrifuged at 350 g for 7 min. The pellet was resuspended in assay medium and 0.2 mio PBMCs in 100 ul/well (E:T 10:1, based on the number of seeded target cells) were added to the target cells. The molecules were diluted in assay medium (RPMI1640, 2% FCS, 1× GlutaMax) and 50 ul/well were added at the indicated concentrations in triplicates before the plates were incubated for about 48 h, 72 h or 96 h at 37° C. in a humidified incubator. Target cell killing was assessed after 48 h, 72 h and 96 h of incubation at 37° C., 5% $CO_2$ by quantification of LDH release into cell supernatants by apoptotic/necrotic cells (LDH detection kit, Roche Applied Science, #11 644 793 001). Maximal lysis of the target cells (=100%) was achieved by incubation of target cells with 1% Triton X-100 20 h before LDH readout. Minimal lysis (=0%) refers to target cells co-incubated with effector cells without any TCB.

Human Bronchial Epithelial Cell toxicity mediated by human PBMCs and 100 nM or 10 nM of FolR1 TCB is higher compared to Protease activated TCB.

Example 25

FolR1 Negative Target Cell Cytotoxicity Mediated by Protease Activated FolR1 TCB T-cell killing mediated by protease activated FolR1 TCB molecule was assessed on FolR1 negative Mkn-45 cell line (FIG. 44). Human Peripheral blood mononuclear cells (PBMCs) were isolated from buffy coats obtained from healthy human donors. Buffy coat was diluted 1:1 with sterile PBS and layered over Histopaque gradient (Sigma, #H8889). After centrifugation (450×g, 30 minutes, w/o break, room temperature) the PBMC-containing interphase was transferred in a new falcon tube that was subsequently filled with 50 ml of PBS. The mixture was centrifuged (400×g, 10 minutes, room temperature), the supernatant was discarded and the PBMC pellet was resuspended in 2 ml ACK buffer for Erythrocytes lysis. After incubation for about 2-3 minutes at 37° C. the tubes were filled with sterile PBS to 50 ml and centrifuged for 10 minutes at 350×g. This washing step was repeated once prior to resuspension of PBMCs in RPMI1640 medium containing 10% FCS, 1× GlutaMax and 10% DMSO. PBMCs were slowly frozen in CoolCell® Cell Freezing Containers (BioCision) at −80° C. and then transferred to liquid nitrogen. One day before assay start adherent target cells were harvested with Trypsin/EDTA, counted, checked for viability and resuspended in assay medium (RPMI1640, 2% FCS, 1× GlutaMax). Target cells were plated at a density of 20 000 cells/well using 96-well flat-bottom plates and incubated for about 20 h at 37° C. in a humidified incubator. About 20 h before assay start PBMCs were thawed in RPMI1640 medium (10% FCS, 1× GlutaMax). PBMCs were centrifuged at 350 g for 7 min. The pellet was resuspended in fresh medium (RPMI1640, 10% FCS, 1× GlutaMax) and incubated for max 24 h at 37° C. in a humidified incubator. On the day of the assay start PBMCs were harvested and centrifuged at 350 g for 7 min. The pellet was resuspended in assay medium and 0.2 mio PBMCs in 100 ul/well (E:T 10:1, based on the number of seeded target cells) were added to the target cells. The molecules were diluted in assay medium (RPMI1640, 2% FCS, 1× GlutaMax) and 50 ul/well were added at the indicated concentrations in triplicates before the plates were incubated for about 48 h and 72 h at 37° C. in a humidified incubator. Target cell killing was assessed after 48 h, 72 h and 96 h of incubation at 37° C., 5% $CO_2$ by quantification of LDH release into cell supernatants by apoptotic/necrotic cells (LDH detection kit, Roche Applied Science, #11 644 793 001). Maximal lysis of the target cells (=100%) was achieved by incubation of target cells with 1% Triton X-100 20 h before LDH readout. Minimal lysis (=0%) refers to target cells co-incubated with effector cells without any TCB. Protease activated TCB did not induce target cell killing at 100 nM.

EXAMPLARY SEQUENCES

| Construct | Amino acid Sequence | SEQ ID No |
| --- | --- | --- |
| LC Common light chain pETR13197 | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVLGQPKAAPSVTLFPP SSEELQANKATLVCLISDFYPGAVTVAWKADSSPVKAGVETT TPSKQSNNKYAASSYLSLTPEQWKSHRSYSCQVTHEGSTVE KTVAPTECS | 1 |
| anti CD3 (CH2527 VH_3-23(12) VL7-46(13)) scFv15-Matriptase MK062 CH2527 VH3_23-VH12 CH1 FolR1 16D5 VH CH1 hum Fc knob PG LALA, pETR15422 (FIG. 45A) | QIQLVQSGPELKKPGETVRISCKASGYTFTDYSIHWVKQAPG KCLKWMGWINTETGEPAYADDFKGRFAFSLETSASTAYLQI NNLKNEDTATFFCAHPYDYDVLDYWGQGTSVTVSSGGGGS GGGGSGGGGSGGGGSDTVLTQSPASLGVSLGQRATISCRA SKSVSTSNYSYIHWYQQKPGQPPKLLIKYVSYLESGVPARFS GSGSGTDFTLNIHPVEEEDAATYYCQHSREFPWTFGCGTKL EIKGGGGSGGGGSRQARVVNGGGGSGGGGSGGGGSEV QLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVS SASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDGGGGSGGGGSEVQLVES GGGLVKPGGSLRLSCAASGFTFSNAWMSWVRQAPGKGLE WVGRIKSKTDGGTTDYAAPVKGRFTISRDDSKNTLYLQMNS LKTEDTAVYYCTTPWEWSWYDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALGA PIEKTISKAKGQPREPQVYTLPPCRDELTKNQVSLWCLVKGF YPSDIAVEWESNGQPENNYKTTPPVLDSDGSFFLYSKLTVD KSRWQQGNVFSCSVMHEALHNHYTQKSLSLSPGK | 2 |
| FolR1 16D5 VH CH1 Fc hole P329G LALA HRYF, pETR15214 | EVQLVESGGGLVKPGGSLRLSCAASGFTFSNAWMSWVRQA PGKGLEWVGRIKSKTDGGTTDYAAPVKGRFTISRDDSKNTL YLQMNSLKTEDTAVYYCTTPWEWSWYDYWGQGTLVTVSSA STKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPPCPAPEAAGGPSVFL FPPKPKDTLMISRTPEVTCVVVDVSHEDPEVKFNWYVDGVE VHNAKTKPREEQYNSTYRVVSVLTVLHQDWLNGKEYKCKVS NKALGAPIEKTISKAKGQPREPQVCTLPPSRDELTKNQVSLS CAVKGFYPSDIAVEWESNGQPENNYKTTPPVLDSDGSFFLV SKLTVDKSRWQQGNVFSCSVMHEALHNRFTQKSLSLSPGK | 3 |
| anti CD3 (CH2527 VH_3-23(12) VL7-46(13)) scFv 4.32.63 Matriptase MK062 CH2527 VH3_23-VH12 CH1 FolR1 16D5 VH CH1 hum Fc knob PG LALA, pETR15599 (FIG. 45B) | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSGGGGSRQARVVNGGGGSGGGGSGGGGSEV QLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVS SASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDGGGGSGGGGSEVQLVES GGGLVKPGGSLRLSCAASGFTFSNAWMSWVRQAPGKGLE VVVGRIKSKTDGGTTDYAAPVKGRFTISRDDSKNTLYLQMNS LKTEDTAVYYCTTPWEWSWYDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALGA PIEKTISKAKGQPREPQVYTLPPCRDELTKNQVSLWCLVKGF YPSDIAVEWESNGQPENNYKTTPPVLDSDGSFFLYSKLTVD KSRWQQGNVFSCSVMHEALHNHYTQKSLSLSPGK | 4 |

| | | |
|---|---|---|
| anti CD3 (CH2527 VH_3-23(12) VL7-46(13)) scFv 4.32.63 non-cleavable linker CH2527 VH3_23-VH12 CH1 FolR1 16D5 VH CH1 hum Fc knob PG LALA, pETR15603 (FIG. 45C) | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSGGGGSGGGGSGGGGGGSGGGGSGGGGSEV QLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVS SASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDGGGGSGGGGSEVQLVES GGGLVKPGGSLRLSCAASGFTFSNAWMSWVRQAPGKGLE WVGRIKSKTDGGTTDYAAPVKGRFTISRDDSKNTLYLQMNS LKTEDTAVYYCTTPWEWSWYDYVVGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDKTHTCPPCPAPEAAGGPSVFLFPPKPK DTLMISRTPEVTCVVVDVSHEDPEVKFNWYVDGVEVHNAKT KPREEQYNSTYRVVSVLTVLHQDWLNGKEYKCKVSNKALGA PIEKTISKAKGQPREPQVYTLPPCRDELTKNQVSLWCLVKGF YPSDIAVEWESNGQPENNYKTTPPVLDSDGSFFLYSKLTVD KSRWQQGNVFSCSVMHEALHNHYTQKSLSLSPGK | 5 |
| anti CD3 (CH2527 VH_3-23(12) VL7-46(13)) scFv15 non-cleavable linker CH2527 VH3_23-VH12 CH1 FolR1 16D5 VH CH1 hum Fc knob PG LALA, pETR14759 (FIG. 45D) | QIQLVQSGPELKKPGETVRISCKASGYTFTDYSIHWVKQAPG KCLKWMGWINTETGEPAYADDFKGRFAFSLETSASTAYLQI NNLKNEDTATFFCAHPYDYDVLDYWGQGTSVTVSSGGGGS GGGGSGGGGSGGGGSDTVLTQSPASLGVSLGQRATISCRA SKSVSTSNYSIHWYQ QKPGQPPKLLIKYVSYLESGVPARFSGSGSGTDFTLNIHPVE EEDAATYYCQHSREFPWTFGCGTKLEIKGGGGSGGGGSGG GGSGGGGGGGSGGGGSGGGGSEVQLLESGGGLVQPGGS LRLSCAASGFTFSTYAMNWVRQAPGKGLEWVSRIRSKYNN YATYYADSVKGRFTISRDDSKNTLYLQMNSLRAEDTAVYYCV RHGNFGNSYVSWFAYWGQGTLVTVSSASTKGPSVFPLAPS SKSTSGGTAALGCLVKDYFPEPVTVSWNSGALTSGVHTFPA VLQSSGLYSLSSVVIVPSSSLGTQTYICNVNHKPSNTKVDKK VEPKSCDGGGGSGGGGSEVQLVESGGGLVKPGGSLRLSC AASGFTFSNAWMSWVRQAPGKGLEWVGRIKSKTDGGTTDY AAPVKGRFTISRDDSKNTLYLQMNSLKTEDTAVYYCTTPWE WSWYDYWGQGTLVTVSSASTKGPSVFPLAPSSKSTSGGTA ALGCLVKDYFPEPVTVSWNSGALTSGVHTFPAVLQSSGLYS LSSVVTVPSSSLGTQTYICNVNHKPSNTKVDKKVEPKSCDKT HTCPPCPAPEAAGGPSVFLFPPKPKDTLMISRTPEVTCVVVD VSHEDPEVKFNWYVDGVEVHNAKTKPREEQYNSTYRVVSV LTVLHQDWLNGKEYKCKVSNKALGAPIEKTISKAKGQPREPQ VYTLPPCRDELTKNQVSLWCLVKGFYPSDIAVEWESNGQPE NNYKTTPPVLDSDGSFFLYSKLTVDKSRWQQGNVFSCSVM HEALHNHYTQKSLSLSPGK | 6 |
| MK062 Protease linker | GGGGSGGGGSRQARVVNGGGGGSGGGGSGGGGS | 7 |
| Combined NF9/Mat5 linker | GGGGSVHMPLGFLGPGRSRGSFPGGGGS | 8 |
| Combined MK062 MMP9 | GGGGSGGGGSRQARVVNGGGGGSVPLSLYSGGGGSGG GGS | 9 |
| Combined MK062 MMP9 | GGGGSGGGGSRQARVVNGVPLSLYSGGGGSGGGGS | 10 |
| H2527 CDR H1 Kabat | TYAMN | 11 |
| CH2527 CDR H2 Kabat | RIRSKYNNYATYYADSVKG | 12 |
| CH2527 CDR H3 Kabat | HGNFGNSYVSWFAY | 13 |
| FolR1 CDR H1 Kabat | NAWMS | 14 |
| FolR1 CDR H2 Kabat | RIKSKTDGGTTDYAAPVKG | 15 |
| FolR1 CDR H3 Kabat | PWEWSWYDY | 16 |
| CLC CDR1 L1 Kabat | GSSTGAVTTSNYAN | 17 |
| CLC CDR L2 Kabat | GTNKRAP | 18 |
| CLC CDR L3 Kabat | ALWYSNLWV | 19 |

| | | |
|---|---|---|
| Anti-ID 4.15.64 CDR H1 Kabat | DYSIH | 20 |
| Anti-ID 4.15.64 CDR H2 Kabat | WINTETGEPAYADDFKG | 21 |
| Anti-ID 4.15.64 CDR H3 Kabat | PYDYDVLDY | 22 |
| Anti-ID 415.64 CDR L1 Kabat | RASKSVSTSNYSYIH | 23 |
| Anti-ID 4.15.64 CDR L2 Kabat | YVSYLES | 24 |
| Anti-ID 4.15.64 CDR L3 Kabat | QHSREFPWT | 25 |
| Anti-ID 4.32.63 CDR H1 Kabat | SYGVS | 26 |
| Anti-ID 4.32.63 CDR H2 Kabat | IIWGDGSTNYHSALIS | 27 |
| Anti-ID 4.32.63 CDR H3 Kabat | GITTVVDDYYAMDY | 28 |
| Anti-ID 4.32.63 CDR L1 Kabat | RASENIDSYLA | 29 |
| Anti-ID 4.32.63 CDR L2 Kabat | AATFLAD | 30 |
| Anti-ID 4.32.63 CDR L3 Kabat | QHYYSTPYT | 31 |
| anti HER1 (GA201 heavy chain, pUC-Exp-GA201-HC) (FIG. 45E) | QVQLVQSGAEVKKPGSSVKVSCKASGFTFTDYKIHWVRQAP GQGLEWMGYFNPNSGYSTYAQKFQGRVTITADKSTSTAYM ELSSLRSEDTAVYYCARLSPGGYYVMDAWGQGTTVTVSSA STKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDKTHTCPPCPAPELLGGPSVFL FPPKPKDTLMISRTPEVTCVVVDVSHEDPEVKFNWYVDGVE VHNAKTKPREEQYNSTYRVVSVLTVLHQDWLNGKEYKCKVS NKALPAPIEKTISKAKGQPREPQVYTLPPSRDELTKNQVSLT CLVKGFYPSDIAVEWESNGQPENNYKTTPPVLDSDGSFFLY SKLTVDKSRWQQGNVFSCSVMHEALHNHYTQKSLSLSPGK | 32 |
| anti HER1 (GA201 light chain, pUC-Exp-GA201-LC) (FIG. 45F) | DIQMTQSPSSLSASVGDRVTITCRASQGINNYLNWYQQKPG KAPKRLIYNTNNLQTGVPSRFSGSGSGTEFTLTISSLQPEDF ATYYCLQHNSFPTFGQGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 33 |
| anti HER1 (anti-GA201 VH-VL scFv MMP cleavable linker G4S GA201 light chain, pUC-I_GA201_MMP_LC) (FIG. 45G) | EVQLEQSGPVLVKPGTSVKMSCKASGYTFTDYYINWIIQSHG K<u>C</u>LEWIGVINPDSGGTDYNQNFKGKATLTVDKSSTTAYMELT SLTSEDSAVYYCARRDSYGFDYWGQGTTLTVSSGGGGSGG GGSGGGGSGGGGSDIVLTQTPKFLLVPAGDRITMTCKASLS VTNDVAWYQQKPGQSPKLLLYYASNRNAGVPDRFTGSGYG TDFTFTITTLQAEDLAVYFCQQDYTSPPTFG<u>C</u>GTKLEIRGGG GSGGGGSGPLGLWSQGGGGSGGGGSGGGGSGGDIQMTQ SPSSLSASVGDRVTITCRASQGINNYLNWYQQKPGKAPKRLI YNTNNLQTGVPSRFSGSGSGTEFTLTISSLQPEDFATYYCLQ HNSFPTFGQGTKLEIKRTVAAPSVFIFPPSDEQLKSGTASVV CLLNNFYPREAKVQWKVDNALQSGNSQESVTEQDSKDSTY SLSSTLTLSKADYEKHKVYACEVTHQGLSSPVTKSFNRGEC | 34 |
| MMP Protease linker | GGGGSGGGGS<u>PLGLWSQ</u>GGGGSGGGGSGGGGSGG | 35 |
| Protease recognition site 1 | RQARVVNG | 36 |
| Protease recognition site 2 | VHMPLGFLGPGRSRGSFP | 37 |
| Protease recognition site 3 | RQARVVNGXXXXXVPLSLYSG | 38 |

-continued

| | | |
|---|---|---|
| Protease recognition site 4 | RQARVVNGVPLSLYSG | 39 |
| Protease recognition site 5 | PLGLWSQ | 40 |
| 4.15.64 Anti-idiotypic scFv | QIQLVQSGPELKKPGETVRISCKASGYTFTDYSIHWVKQAPG KCLKWMGWINTETGEPAYADDFKGRFAFSLETSASTAYLQI NNLKNEDTATFFCAHPYDYDVLDYWGQGTSVTVSSGGGGS GGGGSGGGGSGGGGSDTVLTQSPASLGVSLGQRATISCRA SKSVSTSNYSYIHWYQQKPGQPPKLLIKYVSYLESGVPARFS GSGSGTDFTLNIHPVEEEDAATYYCQHSREFPWTFGCGTKL EIK | 41 |
| 4.32.63 Anti-idiotypic scFv | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIK | 42 |
| Anti-CD3 variable heavy chain (VH) | EVQLLESGGGLVQPGGSLRLSCAASGFTFSTYAMNWVRQA PGKGLEWVSRIRSKYNNYATYYADSVKGRFTISRDDSKNTLY LQMNSLRAEDTAVYYCVRHGNFGNSYVSWFAYWGQGTLVT VSS | 43 |
| CD3 heavy chain (VH)_CDR1 | TYAMN | 44 |
| CD3 heavy chain (VH)_CDR2 | RIRSKYNNYATYYADSVKG | 45 |
| CD3 heavy chain (VH)_CDR3 | HGNFGNSYVSWFAY | 46 |
| Anti-FolR1 16D5 variable region | EVQLVESGGGLVKPGGSLRLSCAASGFTFSNAWMSWVRQA PGKGLEWVGRIKSKTDGGTTDYAAPVKGRFTISRDDSKNTL YLQMNSLKTEDTAVYYCTTPWEWSWYDYWGQGTLVTVSS | 47 |
| anti-idiotypic GA201 CDR H1 Kabat | DYYIN | 48 |
| anti-idiotypic GA201 CDR H2 Kabat | VINPDSGGTDYNQNFKG | 49 |
| anti-idiotypic GA201 CDR H3 Kabat | RDSYGFDY | 50 |
| anti-idiotypic GA201 CDR L1 Kabat | KASLSVTNDVA | 51 |
| anti-idiotypic GA201 CDR L2 Kabat | YASNRNA | 52 |
| anti-idiotypic GA201 CDR L3 Kabat | QQDYTSPPT | 53 |
| hu CD3E | MQSGTHWRVLGLCLLSVGVWGQDGNEEMGGITIQTPYKVSI SGTTVILTCPQYPGSEILWQHNDKNIGGDEDDKNIGSDEDHL SLKEFSELEQSGYYVCYPRGSKPEDANFYLYLRARVCENC MEMDVMSVATIVIVDICITGGLLLLVYYVVSKNRKAKAKPVTRG AGAGGRQRGQNKERPPPVPNPDYEPIRKGQRDLYSGLNQR RI | 54 |
| LC Common light chain pETR13197 V region | QAVVTQEPSLTVSPGGTVILTCGSSTGAVTTSNYANWVQEK PGQAFRGLIGGTNKRAPGTPARFSGSLLGGKAALTLSGAQP EDEAEYYCALWYSNLWVFGGGTKLTVL | 55 |
| GA201 CDR H1 Kabat | DYKIH | 56 |
| GA201 CDR H2 Kabat | YFNPNSGYSTYAQKFQG | 57 |
| GA201 CDR H3 Kabat | LSPGGYYVMDA | 58 |
| GA201 CDR L1 Kabat | RASQGINNYLN | 59 |
| GA201 CDR L2 Kabat | NTNNLQT | 60 |

| | | |
|---|---|---|
| GA201 CDR L3 Kabat | LQHNSFPT | 61 |

| Construct | DNA Sequence | SEQ ID No |
|---|---|---|
| LC Common light chain pETR13197 | CAGGCCGTCGTGACCCAGGAACCCAGCCTGACAGTGTCTCCTGGC<br>GGCACCGTGACCCTGACATGTGGCAGTTCTACAGGCGCCGTGACC<br>ACCAGCAACTACGCCAACTGGGTGCAGGAAAAGCCCGGCCAGGCC<br>TTCAGAGGACTGATCGGCGGCACCAACAAGAGAGCCCCTGGCACC<br>CCTGCCAGATTCAGCGGATCTCTGCTGGGAGGAAAGGCCGCCCTG<br>ACACTGTCTGGCGCCCAGCCAGAAGATGAGGCCGAGTACTACTGC<br>GCCCTGTGGTACAGCAACCTGTGGGTGTTCGGCGGAGGCACCAAG<br>CTGACAGTCCTAGGTCAACCCAAGGCTGCCCCCAGCGTGACCCTG<br>TTCCCCCCCAGCAGCGAGGAACTGCAGGCCAACAAGGCCACCCTG<br>GTCTGCCTGATCAGCGACTTCTACCCAGGCGCCGTGACCGTGGCC<br>TGGAAGGCCGACAGCAGCCCCGTGAAGGCCGGCGTGGAGACCAC<br>CACCCCCAGCAAGCAGAGCAACAACAAGTACGCCGCCAGCAGCTA<br>CCTGAGCCTGACCCCCGAGCAGTGGAAGAGCCACAGGTCCTACAG<br>CTGCCAGGTGACCCACGAGGGCAGCACCGTGGAGAAAACCGTGG<br>CCCCCACCGAGTGCAGCTGA | 62 |
| anti CD3<br>(CH2527<br>VH_3-23(12)<br>VL7-46(13))<br>scFv15-<br>Matriptase<br>MK062<br>CH2527<br>VH3_23-VH12<br>CH1 FolR1<br>16D5 VH CH1<br>hum Fc knob<br>PG LALA,<br>pETR15422<br>(FIG. 45H) | CAGATCCAGCTGGTGCAGAGCGGCCCTGAGCTGAAGAAACCCGGC<br>GAGACAGTGCGGATCAGCTGCAAGGCCAGCGGCTACACCTTCACC<br>GACTACAGCATCCACTGGGTCAAGCAGGCCCCTGGCAAGTGCCTG<br>AAGTGGATGGGCTGGATCAACACCGAGACAGGCGAGCCCGCCTAC<br>GCCGACGATTTCAAGGGCAGATTCGCCTTCAGCCTGGAAACCAGC<br>GCCAGCACCGCCTACCTGCAGATCAACAACCTGAAGAACGAGGAC<br>ACCGCCACCTTTTTCTGCGCCCACCCCTACGACTACGACGTGCTG<br>GATTATTGGGGCCAGGGCACCAGCGTGACCGTGTCTAGCGGAGGC<br>GGAGGATCTGGCGGCGGAGGAAGTGGCGGAGGGGGATCTGGGG<br>GAGGCGGATCTGATACCGTGCTGACACAGAGCCCTGCCAGCCTGG<br>GAGTGTCCCTGGGACAGAGAGCCACCATCAGCTGTCGGGCCAGCA<br>AGAGCGTGTCCACCAGCAACTACAGCTATATCCACTGGTATCAGCA<br>GAAGCCCGGCCAGCCCCCCAAGCTGCTGATCAAATACGTCCTA<br>CCTGGAAAGCGGCGTGCCCGCCAGATTTTCTGGCTCTGGCAGCGG<br>CACCGACTTCACCCTGAACATCCACCCCGTGGAAGAGGAAGATGC<br>CGCCACCTACTACTGCCAGCACAGCAGAGAGTTCCCTTGGACCTTC<br>GGCTGCGGCACCAAGCTGGAAATCAAAGGCGGGGGAGGCTCCGG<br>AGGCGGCGGAAGTAGACAGGCCAGAGTCGTGAACGGGGGAGGGG<br>GGGGAAGTGGGGCGGAGGCAGTGGGGGGGGAGGATCCGAGGT<br>GCAGCTGCTGGAATCTGGCGGCGGACTGGTGCAGCCTGGCGGAT<br>CTCTGAGACTGAGCTGTGCCGCCAGCGGCTTCACCTTCAGCACCT<br>ACGCCATGAACTGGGTGCGCCAGGCCCCTGGCAAGGCCTGGAAT<br>GGGTGTCCCGGATCAGAAGCAAGTACAACAACTACGCCACCTACTA<br>CGCCGACAGCGTGAAGGGCCGGTTCACCATCAGCCGGGACGACA<br>GCAAGAACACCCTGTACCTGCAGATGAACAGCCTGCGGGCCGAGG<br>ACACCGCCGTGTACTATTGTGTGCGGCACGGCAACTTCGGCAACA<br>GCTATGTGTCTTGGTTTGCCTACTGGGGCCAGGGCACCCTCGTGA<br>CCGTGTCAAGCGCTAGCACAAAGGGCCCTAGCGTGTTCCCTCTGG<br>CCCCCAGCAGCAAGAGCACAAGCGGCGGAACAGCCGCCCTGGGC<br>TGCCTCGTGAAGGACTACTTCCCCGAGCCCGTGACAGTGTCTTGG<br>AACAGCGGAGCCCTGACAAGCGGCGTGCACACCTTCCCTGCCGTG<br>CTGCAGAGCAGCGGCCTGTACTCCCTGAGCAGCGTGGTCACCGTG<br>CCTAGCAGCAGCCTGGGCACCCAGACCTACATCTGCAACGTGAAC<br>CACAAGCCCAGCAACACCAAAGTGGACAAGAAGGTGGAGCCCAA<br>AGCTGTGATGGCGGAGGAGGGTCCGGAGGCGGAGGATCCGAGGT<br>GCAATTGGTTGAATCTGGTGGTGGTCTGGTAAAACCGGGCGGTTC<br>CCTGCGTCTGAGCTGCGCGGCTTCCGGATTCACCTTCTCCAACGC<br>GTGGATGAGCTGGGTTCGCCAGGCCCGGGCAAAGGCCTCGAGT<br>GGGTTGGTCGTATCAAGTCTAAAACTGACGGTGGCACCACGGATTA<br>CGCGGCTCCAGTTAAAGGTCGTTTTACCATTTCCCGCGACGATAGC<br>AAAAACACTCTGTATCTGCAGATGAACTCTCTGAAAACTGAA-<br>GACAC<br>CGCAGTCTACTACTGTACTACCCCGTGGGAATGGTCTTGGTACGAT<br>TATTGGGGCCAGGGCACGCTGGTTACGGTGTCTAGCGCTAGTACC<br>AAGGGCCCCAGCGTGTTCCCCCTGGCACCCAGCAGCAAGAGCACA<br>TCTGGCGGAACAGCCGCTCTGGGCTGTCTGGTGAAAGACTACTTC<br>CCCGAGCCCGTGACCGTGTCTTGGAACTCTGGCGCCCTGACCAGC<br>GGCGTGCACACCTTTCCAGCCGTGCTGCAGAGCAGCGGCCTGTAC<br>TCCCTGTCCTCCGTGGTCACCGTGCCCTCTAGCTCCCTGGGAACA<br>CAGACATATATCTGTAATGTCAATCACAAGCCTTCCAACAC-<br>CAAAGT<br>CGATAAGAAAGTCGAGCCCAAGAGCTGCGACAAAACTCACACATG<br>CCCACCGTGCCCAGCACCTGAAGCTGCAGGGGGACCGTCAGTCTT<br>CCTCTTCCCCCCAAAACCCAAGGACACCCTCATGATCTCCCGGACC<br>CCTGAGGTCACATGCGTGGTGGTGGACGTGAGCCACGAAGACCCT<br>GAGGTCAAGTTCAACTGGTACGTGGACGGCGTGGAGGTGCATAAT<br>GCCAAGACAAAGCCGCGGGAGGAGCAGTACAACAGCACGTACCGT<br>GTGGTCAGCGTCCTCACCGTCCTGCACCAGGACTGGCTGAATGGC<br>AAGGAGTACAAGTGCAAGGTCTCCAACAAAGCCCTCGGCGCCCCC | 63 |

| | | |
|---|---|---|
| | ATCGAGAAAACCATCTCCAAAGCCAAAGGGCAGCCCCGAGAACCA<br>CAGGTGTACACCCTGCCCCCATGCCGGGATGAGCTGACCAAGAAC<br>CAGGTCAGCCTGTGGTGCCTGGTCAAAGGCTTCTATCCCAGCGAC<br>ATCGCCGTGGAGTGGGAGAGCAATGGGCAGCCGGAGAACAACTAC<br>AAGACCACGCCTCCCGTGCTGGACTCCGACGGCTCCTTCTTCCTCT<br>ACAGCAAGCTCACCGTGGACAAGAGCAGGTGGCAGCAGGGGAAC<br>GTCTTCTCATGCTCCGTGATGCATGAGGCTCTGCACAACCACTACA<br>CGCAGAAGAGCCTCTCCCTGTCTCCGGGTAAATGA | |
| FolR1 16D5<br>VH CH1 Fc<br>hole P329G<br>LALA HRYF,<br>pETR15214 | GAGGTGCAATTGGTTGAATCTGGTGGTGGTCTGGTAAAACCGGGC<br>GGTTCCCTGCGTCTGAGCTGCGCGGCTTCCGGATTCACCTTCTCC<br>AACGCGTGGATGAGCTGGGTTCGCCAGGCCCCGGGCAAAGGCCT<br>CGAGTGGGTTGGTCGTATCAAGTCTAAAACTGACGGTGGCACCAC<br>GGATTACGCGGCTCCAGTTAAAGGTCGTTTTACCATTTCCCGCGAC<br>GATAGCAAAAACACTCTGTATCTGCAGATGAACTCTCT-<br>GAAAACTGA<br>AGACACCGCAGTCTACTACTGTACTACCCCGTGGGAATGGTCTTGG<br>TACGATTATTGGGGCCAGGGCACGCTGGTTACGGTGTCTTCCGCT<br>AGCACCAAGGGCCCCTCCGTGTTCCCCCTGGCCCCCAGCAGCAAG<br>AGCACCAGCGGCGGCACAGCCGCTCTGGGCTGCCTGGTCAAGGA<br>CTACTTCCCCGAGCCCGTGACCGTGTCCTGGAACAGCGGAGCCCT<br>GACCTCCGGCGTGCACACCTTCCCCGCCGTGCTGCAGAGTTCTGG<br>CCTGTATAGCCTGAGCAGCGTGGTCACCGTGCCTTCTAGCAGCCT<br>GGGCACCCAGACCTACATCTGCAACGTGAACCACAAGCCCAGCAA<br>CACCAAGGTGGACAAGAAGGTGGAGCCCAAGAGCTGCGACAAGA<br>CTCACACATGCCCACCGTGCCCAGCACCTGAAGCTGCAGGGGGACC<br>GTCAGTCTTCCTCTTCCCCCCAAAACCCAAGGACACCCTCATGATC<br>TCCCGGACCCCTGAGGTCACATGCGTGGTGGTGGACGTGAGCCAC<br>GAAGACCCTGAGGTCAAGTTCAACTGGTACGTGGACGGCGTGGAG<br>GTGCATAATGCCAAGACAAAGCCGCGGGAGGAGCAGTACAACAGC<br>ACGTACCGTGTGGTCAGCGTCCTCACCGTCCTGCACCAGGACTGG<br>CTGAATGGCAAGGAGTACAAGTGCAAGGTCTCCAACAAAGCCCTC<br>GGCGCCCCCATCGAGAAAACCATCTCCAAAGCCAAAGGGCAGCCC<br>CGAGAACCACAGGTGTGCACCCTGCCCCCATCCCGGGATGAGCTG<br>ACCAAGAACCAGGTCAGCCTCTCGTGCGCAGTCAAAGGCTTCTATC<br>CCAGCGACATCGCCGTGGAGTGGGAGAGCAATGGGCAGCCGGAG<br>AACAACTACAAGACCACGCCTCCCGTGCTGGACTCCGACGGCTCC<br>TTCTTCCTCGTGAGCAAGCTCACCGTGGACAAGAGCAGGTGGCA<br>CAGGGGAACGTCTTCTCATGCTCCGTGATGCATGAGGCTCTGCAC<br>AACCGCTTCACGCAGAAGAGCCTCTCCCTGTCTCCGGGTAAATGA | 64 |
| anti CD3<br>(CH2527<br>VH_3-23(12)<br>VL7-46(13))<br>scFv 4.32.63<br>Matriptase<br>MK062<br>CH2527<br>VH3_23-VH12<br>CH1 FolR1<br>16D5 VH CH1<br>hum Fc knob<br>PG LALA,<br>pETR15599<br>(FIG. 45I) | CAAGTGCAGCTGAAAGAGTCCGGCCCTGGACTGGTGGCCCCTAGC<br>CAGAGCCTGAGCATCACCTGTACCGTGTCCGGCTTCAGCCTGACC<br>AGCTACGGCGTGTCATGGGTGCGCCAGCCTCCAGGCAAGTGTCTG<br>GAATGGCTGGGCATCATCTGGGGCGACGGCAGCACCAATTACCAC<br>AGCGCCCTGATCAGCAGACTGAGCATCTCCAAGGACAACAGCAAG<br>AGCCAGGTGTTCCTGAAGCTGAACAGCCTGCAGACCGACGACACC<br>GCCACCTACTACTGCGCCAAGGGCATCACCACCGTGGTGGACGAC<br>TACTACGCTATGGACTACTGGGGCCAGGGCACCAGCGTGACAGTG<br>TCTAGCGGAGGCGGAGGATCTGGCGGCGGAGGAAGTGGCGGAGG<br>GGGATCTGGGGGAGGCGGAAGCGATATCCAGATGACCCAGAGCC<br>CTGCCAGCCTGTCTGCCTCTGTGGGCGAGACAGTGACCATCACAT<br>GCCGGGCCAGCGAGAACATCGACAGCTACCTGGCCTGGTATCAGC<br>AGAAGCAGGGCAAGAGCCCCCAGCTGCTGGTGTACGCCGCCACCT<br>TTCTGGCCGACGATGTGCCCAGCAGATTCAGCGGCAGCGGAAGCG<br>GCACACAGTACAGCCTGAAGATCAACTCCCTGCAGAGCGAGGACG<br>TGGCCCGGTACTACTGCCAGCACTACTACAGCACCCCCTACACCTT<br>CGGCTGCGGCACCAAGCTGGAAATCAAAGGCGGGGAGGCTCCG<br>GAGGCGGCGGAAGTAGACAGGCCAGAGTCGTGAACGGGGGAGGG<br>GGGGGAAGTGGGGCGGAGGCAGTGGGGCGGAGGATCCGAGG<br>TGCAGCTGCTGGAATCTGGCGGCGGACTGGTGCAGCCTGCGGA<br>TCTCTGAGACTGAGCTGTGCCGCCAGCGGCTTCACCTTCAGCACC<br>TACGCCATGAACTGGGTGCGCCAGGCCCCTGGCAAAGGCCTGGAA<br>TGGGTGTCCCGGATCAGAAGCAAGTACAACAACTACGCCACCTACT<br>ACGCCGACAGCGTGAAGGGCCGGTTCACCATCAGCCGGGACGAC<br>AGCAAGAACACCCTGTACCTGCAGATGAACAGCCTGCGGGCCGAG<br>GACACCGCCGTGTACTATTGTGTGCGGCACGGCAACTTCGGCAAC<br>AGCTATGTGTCTTGGTTTGCCTACTGGGGCCAGGGCACCCTCGTG<br>ACCGTGTCAAGCGCTAGCACAAAGGGCCCTAGCGTGTTCCCTCTG<br>GCCCCCAGCAGCAAGAGCACAAGCGGCGGAACAGCCGCCCTGGG<br>CTGCCTCGTGAAGGACTACTTCCCCGAGCCCGTGACAGTGTCTTG<br>GAACAGCGGAGCCCTGACAAGCGGCGTGCACACCTTCCCTGCCGT<br>GCTGCAGAGCAGCGGCCTGTACTCCCTGAGCAGCGTGGTCACCGT<br>GCCTAGCAGCAGCCTGGGCACCCAGACCTACATCTGCAACGTGAA<br>CCACAAGCCCAGCAACACCAAAGTGGACAAGAAGGTGGAGCCCAA<br>GAGCTGTGATGGCGGAGGAGGGTCCGGGGCGGAGGATCCGAG<br>GTGCAATTGGTTGAATCTGGTGGTGGTCTGGTAAAACCGGGCGGT<br>TCCCTGCGTCTGAGCTGCGCGGCTTCCGGGTTCACCTTCTCCAAC<br>GCGTGGATGAGCTGGGTTCGCCAGGCCCCGGGCAAAGGCCTCGA<br>GTGGGTTGGTCGTATCAAGTCTAAAACTGACGGTGGCACCACGGA | 65 |

| | | |
|---|---|---|
| | TTACGCGGCTCCAGTTAAAGGTCGTTTTACCATTTCCCGCGACGAT<br>AGCAAAAACACTCTGTATCTGCAGATGAACTCTCTGAAAACTGAAG<br>ACACCGCAGTCTACTACTGTACTACCCCGTGGGAATGGTCTTGGTA<br>CGATTATTGGGCCAGGGCACGCTGGTTACGGTGTCTAGCGCTAG<br>TACCAAGGGCCCCAGCGTGTTCCCCCTGGCACCCAGCAGCAAGAG<br>CACATCTGGCGGAACAGCCGCTCTGGGCTGTCTGGTGAAAGACTA<br>CTTCCCCGAGCCCGTGACCGTGTCTTGGAACTCTGGCGCCCTGAC<br>CAGCGGCGTGCACACCTTTCCAGCCGTGCTGCAGAGCAGCGGCCT<br>GTACTCCCTGTCCTCCGTGGTCACCGTGCCCTCTAGCTCCCTGGG<br>AACACAGACATATATCTGTAATGTCAATCACAAGCCTTC-<br>CAACACCA<br>AAGTCGATAAGAAAGTCGAGCCCAAGAGCTGCGACAAAACTCACAC<br>ATGCCCACCGTGCCCAGCACCTGAAGCTGCAGGGGGACCGTCAGT<br>CTTCCTCTTCCCCCCAAAACCCAAGGACACCCTCATGATCTCCCGG<br>ACCCCTGAGGTCACATGCGTGGTGGTGGACGTGAGCCACGAAGAC<br>CCTGAGGTCAAGTTCAACTGGTACGTGGACGGCGTGGAGGTGCAT<br>AATGCCAAGACAAAGCCGCGGGAGGAGCAGTACAACAGCACGTAC<br>CGTGTGGTCAGCGTCCTCACCGTCCTGCACCAGGACTGGCTGAAT<br>GGCAAGGAGTACAAGTGCAAGGTCTCCAACAAAGCCCTCGGCGCC<br>CCCATCGAGAAAACCATCTCCAAAGCCAAAGGGCAGCCCCGAGAA<br>CCACAGGTGTACACCCTGCCCCCATGCCCGGGATGAGCTGACCAAG<br>AACCAGGTCAGCCTGTGGTGCCTGGTCAAAGGCTTCTATCCCAGC<br>GACATCGCCGTGGAGTGGGAGAGCAATGGGCAGCCGGAGAACAA<br>CTACAAGACCACGCCTCCCGTGCTGGACTCCGACGGCTCCTTCTT<br>CCTCTACAGCAAGCTCACCGTGGACAAGAGCAGGTGGCAGCAGGG<br>GAACGTCTTCTCATGCTCCGTGATGCATGAGGCTCTGCACAACCAC<br>TACACGCAGAAGAGCCTCTCCCTGTCTCCGGGTAAATGA | |
| anti CD3<br>(CH2527<br>VH_3-23(12))<br>VL7-46(13))<br>scFv 4.32.63<br>non-<br>cleavable<br>linker<br>CH2527<br>VH3_23-VH12<br>CH1 FolR1<br>16D5 VH CH1<br>hum Fc knob<br>PG LALA,<br>pETR15603<br>(FIG. 45J) | CAAGTGCAGCTGAAAGAGTCCGGCCCTGGACTGGTGGCCCCTAGC<br>CAGAGCCTGAGCATCACCTGTACCGTGTCCGGCTTCAGCCTGACC<br>AGCTACGGCGTGTCATGGGTGCGCCAGCCTCCAGGCAAGTGTCTG<br>GAATGGCTGGGCATCATCTGGGGCGACGGCAGCACCAATTACCAC<br>AGCGCCCTGATCAGCAGACTGAGCATCTCCAAGGACAACAGCAAG<br>AGCCAGGTGTTCCTGAAGCTGAACAGCCTGCAGACCGACGACACC<br>GCCACCTACTACTGCGCCAAGGGCATCACCACCGTGGTGGACGAC<br>TACTACGCTATGGACTACTGGGGCCAGGGCACCAGCGTGACAGTG<br>TCTAGCGGAGGCGGAGGATCTGGCGGCGGAGGAAGTGGCGGAGG<br>GGGATCTGGGGGAGGCGGAAGCGATATCCAGATGACCCAGAGCC<br>CTGCCAGCCTGTCTGCCTCTGTGGGCGAGACAGTGACCATCACAT<br>GCCGGGCCAGCGAGAACATCGACAGCTACCTGGCCTGGTATCAGC<br>AGAAGCAGGGCAAGAGCCCCCAGCTGCTGGTGTACGCCGCCACCT<br>TTCTGGCCGACGATGTGCCCAGCAGATTCAGCGGCAGCGGAAGCG<br>GCACACAGTACAGCCTGAAGATCAACTCCCTGCAGAGCGAGGACG<br>TGGCCCGGTACTACTGCCAGCACTACTACAGCACCCCCTACACCTT<br>CGGCTGCGGCACCAAGCTGGAAATCAAAGGCGGGGGAGGCTCCG<br>GAGGCGGCGGAAGTGGAGGCGGCGGAAGTGGCGGAGGCGGAGG<br>GGGGGGAAGTGGGGGCGGAGGCAGTGGGGGGGGAGGATCCGAG<br>GTGCAGCTGCTGGAATCTGGCGGCGGACTGGTGCAGCCTGGCGG<br>ATCTCTGAGACTGAGCTGTGCCGCCAGCGGCTTCACCTTCAGCAC<br>CTACGCCATGAACTGGGTGCGCCAGGCCCCTGGCAAAGGCCTGGA<br>ATGGGTGTCCCGGATCAGAAGCAAGTACAACAACTACGCCACCTAC<br>TACGCCGACAGCGTGAAGGGCCGGTTCACCATCAGCCGGGACGA<br>CAGCAAGAACACCCTGTACCTGCAGATGAACAGCCTGCGGGCCGA<br>GGACACCGCCGTGTACTATTGTGTGCGGCACGGCAACTTCGGCAA<br>CAGCTATGTGTCTTGGTTTGCCTACTGGGGCCAGGGCACCCTCGT<br>GACCGTGTCAAGCGCTAGCACAAAGGGCCCTAGCGTGTTCCCTCT<br>GGCCCCCAGCAGCAAGAGCACAAGCGGCGGAACAGCCGCCCTGG<br>GCTGCCTCGTGAAGGACTACTTCCCCGAGCCCGTGACAGTGTCTT<br>GGAACAGCGGAGCCCTGACAAGCGGCGTGCACACCTTCCCTGCC<br>GTGCTGCAGAGCAGCGGCCTGTACTCCCTGAGCAGCGTGGTCACC<br>GTGCCTAGCAGCAGCCTGGGCACCCAGACCTACATCTGCAACGTG<br>AACCACAAGCCCAGCAACACCAAAGTGGACAAGAAGGTGGAGCCC<br>AAGAGCTGTGATGGCGGAGGAGGGTCCGGAGGCGGAGGCTCCGA<br>GGTGCAATTGGTTGAATCTGGTGGTGGTCTGGTAAAACCGGGCGG<br>TTCCCTGCGTCTGAGCTGCGCGGCTTCCGGATTCACCTTCTCCAAC<br>GCGTGGATGAGCTGGGTTCGCCAGGCCCCGGGCAAAGGCCTCGA<br>GTGGGTTGGTCGTATCAAGTCTAAAACTGACGGTGGCACCACGGA<br>TTACGCGGCTCCAGTTAAAGGTCGTTTTACCATTTCCCGCGACGAT<br>AGCAAAAACACTCTGTATCTGCAGATGAACTCTCTGAAAACTGAAG<br>ACACCGCAGTCTACTACTGTACTACCCCGTGGGAATGGTCTTGGTA<br>CGATTATTGGGCCAGGGCACGCTGGTTACGGTGTCTAGCGCTAG<br>TACCAAGGGCCCCAGCGTGTTCCCCCTGGCACCCAGCAGCAAGAG<br>CACATCTGGCGGAACAGCCGCTCTGGGCTGTCTGGTGAAAGACTA<br>CTTCCCCGAGCCCGTGACCGTGTCTTGGAACTCTGGCGCCCTGAC<br>CAGCGGCGTGCACACCTTTCCAGCCGTGCTGCAGAGC<br>AGCGGCCTGTACTCCCTGTCCTCCGTGGTCACCGTGCCCTCTAGC<br>TCCCTGGGAACACAGACATATATCTGTAATGTCAAT-<br>CACAAGCCTTC | 66 |

| | | |
|---|---|---|
| | CAACACCAAAGTCGATAAGAAAGTCGAGCCCAAGAGCTGCGACAA<br>AACTCACACATGCCCACCGTGCCCAGCACCTGAAGCTGCAGGGGG<br>ACCGTCAGTCTTCCTCTTCCCCCAAAACCCAAGGACACCCTCATG<br>ATCTCCCGGACCCCTGAGGTCACATGCGTGGTGGTGGACGTGAGC<br>CACGAAGACCCTGAGGTCAAGTTCAACTGGTACGTGGACGGCGTG<br>GAGGTGCATAATGCCAAGACAAAGCCGCGGGAGGAGCAGTACAAC<br>AGCACGTACCGTGTGGTCAGCGTCCTCACCGTCCTGCACCAGGAC<br>TGGCTGAATGGCAAGGAGTACAAGTGCAAGGTCTCCAACAAAGCC<br>CTCGGCGCCCCCATCGAGAAAACCATCTCCAAAGCCAAAGGGCAG<br>CCCCGAGAACCACAGGTGTACACCCTGCCCCCATGCCGGGATGAG<br>CTGACCAAGAACCAGGTCAGCCTGTGGTGCCTGGTCAAAGGCTTC<br>TATCCCAGCGACATCGCCGTGGAGTGGGAGAGCAATGGGCAGCC<br>GGAGAACAACTACAAGACCACGCCTCCCGTGCTGGACTCCGACGG<br>CTCCTTCTTCCTCTACAGCAAGCTCACCGTGGACAAGAGCAGGTGG<br>CAGCAGGGGAACGTCTTCTCATGCTCCGTGATGCATGAGGCTCTG<br>CACAACCACTACACGCAGAAGAGCCTCTCCCTGTCTCCGGGTAAAT<br>GA | |
| anti CD3<br>(CH2527<br>VH_3-23(12)<br>VL7-46(13))<br>scFv15 non-<br>cleavable<br>linker<br>CH2527<br>VH3_23-VH12<br>CH1_FolR1<br>16D5 VH CH1<br>hum Fc knob<br>PG LALA,<br>pETR14759<br>(FIG. 45K) | CAGATCCAGCTGGTGCAGAGCGGCCCTGAGCTGAAGAAACCCGGC<br>GAGACAGTGCGGATCAGCTGCAAGGCCAGCGGCTACACCTTCACC<br>GACTACAGCATCCACTGGGTCAAGCAGGCCCCTGGCAAGTGCCTG<br>AAGTGGATGGGCTGGATCAACACCGAGACAGGCGAGCCCGCCTAC<br>GCCGACGATTTCAAGGGCAGATTCGCCTTCAGCCTGGAAACCAGC<br>GCCAGCACCGCCTACCTGCAGATCAACACCTGAAGAACGAGGAC<br>ACCGCCACCTTTTTCTGCGCCACCCCTACGACTACGACGTGCTG<br>GATTATTGGGGCCAGGGCACCAGCGTGACCGTGTCTAGCGGAGGC<br>GGAGGATCTGGCGGCGGAGGAAGTGGCGGAGGGGGATCTGGGG<br>GAGGCGGATCTGATACCGTGCTGACACAGAGCCCTGCCAGCCTGG<br>GAGTGTCCCTGGGACAGAGAGCCACCATCAGCTGTCGGGCCAGCA<br>AGAGCGTGTCCACCAGCAACTACAGCTATATCCACTGGTATCAGCA<br>GAAGCCCGGCCAGCCCCCAAGCTGCTGATCAAATACGTGTCCTA<br>CCTGGAAAGCGGCGTGCCCGCCAGATTTTCTGGCTCTGGCAGCGG<br>CACCGACTTCACCCTGAACATCCACCCCGTGGAAGAGGAAGATGC<br>CGCCACCTACTACTGCCAGCACAGCAGAGAGTTCCCTTGGACCTTC<br>GGCTGCGGCACCAAGCTGGAAATCAAAGGCGGGGGAGGCTCCGG<br>AGGCGGCGGAAGTGGAGGCGGCGAAGTGGCGGAGGCGGAGGG<br>GGGGGAAGTGGGGCGGAGGCAGTGGGGGGGAGGATCCGAGG<br>TGCAGCTGCTGGAATCTGGCGGCGGACTGGTGCAGCCTGGCGGA<br>TCTCTGAGACTGAGCTGTGCCGCCAGCGGCTTCACCTTCAGCACC<br>TACGCCATGAACTGGGTGCGCCAGGCCCTGGCAAAGGCCTGGAA<br>TGGGTGTCCCGGATCAGAAGCAAGTACAACAACTACGCCACCTACT<br>ACGCCGACAGCGTGAAGGGCCGGTTCACCATCAGCCGGGACGAC<br>AGCAAGAACACCCTGTACCTGCAGATGAACAGCCTGCGGGCCGAG<br>GACACCGCCGTGTACTATTGTGTGCGGCACGGCAACTTCGGCAAC<br>AGCTATGTGCTTGGTTTGCCTACTGGGGCCAGGGCACCCTCGTG<br>ACCGTGTCAAGCGCTAGCACAAAGGGCCCTAGCGTGTTCCCTCTG<br>GCCCCCAGCAGCAAGAGCACAAGCGGCGGAACAGCCGCCCTGGG<br>CTGCCTCGTGAAGGACTACTTCCCCGAGCCCGTGACAGTGTCTTG<br>GAACAGCGGAGCCCTGACAAGCGGCGTGCACACCTTCCCTGCCGT<br>GCTGCAGAGCAGCGGCCTGTACTCCCTGAGCAGCGTGGTCACCGT<br>GCCTAGCAGCAGCCTGGGCACCCAGACCTACATCTGCAACGTGAA<br>CCACAAGCCCAGCAACACCAAAGTGGACAAGAAGGTGGAGCCCAA<br>GAGCTGTGATGGCGGAGGAGGGTCCGGAGGCGGAGGCTCCGAGG<br>TGCAATTGGTTGAATCTGGTGGTGGTCTGGTAAAACCGGGCGGTTC<br>CCTGCGTCTGAGCTGCGCGGCTTCCGGATTCACCTTCTCCAACGC<br>GTGGATGAGCTGGGTTCGCCAGGCCCCGGGCAAAGGCCTCGAGT<br>GGGTTGGTCGTATCAAGTCTAAAACTGACGGTGGCACCACGGATTA<br>CGCGGCTCCAGTTAAAGGTCGTTTTACCATTTCCCGCGACGATAGC<br>AAAAACACTCTGTATCTGCAGATGAACTCTCTGAAAACTGAA-<br>GACAC<br>CGCAGTCTACTACTGTACTACCCCGTGGGAATGGTCTTGGTACGAT<br>TATTGGGGCCAGGGCACGCTGGTTACGGTGTCTAGCGCTAGTACC<br>AAGGGCCCCAGCGTGTTCCCCCTGGCACCCAGCAGCAAGAGCACA<br>TCTGGCGGAACAGCCGCTCTGGGCTGTCTGGTGAAAGACTACTTC<br>CCCGAGCCCGTGACCGTGTCTTGGAACTCTGGCGCCCTGACCAGC<br>GGCGTGCACACCTTTCCAGCCGTGCTGCAGAGCAGCGGCCTGTAC<br>TCCCTGTCCTCCGTGGTCACCGTGCCCTCTAGCTCCCTGGGAACA<br>CAGACATATATCTGTAATGTCAATCACAAGCCTTCCAACAC-<br>CAAAGT<br>CGATAAGAAAGTCGAGCCCAAGAGCTGCGACAAAACTCACACATG<br>CCCACCGTGCCCAGCACCTGAAGCTGCAGGGGGACCGTCAGTCTT<br>CCTCTTCCCCCCAAAACCCAAGGACACCCTCATGATCTCCCGGACC<br>CCTGAGGTCACATGCGTGGTGGTGGACGTGAGCCACGAAGACCCT<br>GAGGTCAAGTTCAACTGGTACGTGGACGGCGTGGAGGTGCATAAT<br>GCCAAGACAAAGCCGCGGGAGGAGCAGTACAACAGCACGTACCGT<br>GTGGTCAGCGTCCTCACCGTCCTGCACCAGGACTGGCTGAATGGC<br>AAGGAGTACAAGTGCAAGGTCTCCAACAAAGCCCTCGGCGCCCCC<br>ATCGAGAAAACCATCTCCAAAGCCAAAGGGCAGCCCCGAGAACCA<br>CAGGTGTACACCCTGCCCCCATGCCGGGATGAGCTGACCAAGAAC<br>CAGGTCAGCCTGTGGTGCCTGGTCAAAGGCTTCTATCCCAGCGAC | 67 |

| | | |
|---|---|---|
| | ATCGCCGTGGAGTGGGAGAGCAATGGGCAGCCGGAGAACAACTAC<br>AAGACCACGCCTCCCGTGCTGGACTCCGACGGCTCCTTCTTCCTCT<br>ACAGCAAGCTCACCGTGGACAAGAGCAGGTGGCAGCAGGGGAAC<br>GTCTTCTCATGCTCCGTGATGCATGAGGCTCTGCACAACCACTACA<br>CGCAGAAGAGCCTCTCCCTGTCTCCGGGTAAATGA | |
| MK062 Protease linker | GGCGGGGGAGGCTCCGGAGGCGGCGGAAGTAGACAGGCCAGAG<br>TCGTGAACGGGGGAGGGGGGGAAGTGGGGGCGGAGGCAGTGG<br>GGGCGGAGGATCC | 68 |
| anti HER1 (GA201 heavy chain, pUC-Exp-GA201-HC) | CAGGTGCAGCTGGTCCAGAGCGGCGCCGAGGTGAAGAAACCCGG<br>GTCCCTCTGTCAAGGTGTCATGCAAGGCTAGCGGATTCACCTTTACA<br>GACTACAAAATCCACTGGGTTAGGCAGGCACCTGGCCAAGGACTC<br>GAATGGATGGGGTATTTCAACCCAAATTCCGGCTACTCTACCTATG<br>CCCAGAAGTTTCAGGGAAGAGTGACTATTACAGCTGATAAGAGTAC<br>CAGCACTGCATACATGGAGCTGTCCTCTCTTCGCTCAGAGGACACC<br>GCCGTCTACTATTGTGCTCGGCTGAGCCCCGGTGGCTACTATGTG<br>ATGGATGCATGGGGGCAGGGAACAACCGTAACAGTGTCCTCTGCG<br>TCGACTAAGGGCCCTTCAGTTTTTCCACTCGCCCCCAGTAGCAAGT<br>CCACATCTGGGGTACCGCTGCCCTGGGCTGCCTTGTGAAAGACT<br>ATTTCCCTGAACCAGTCACTGTGTCATGGAATAGCGGAGCCCTGAC<br>CTCCGGTGTACACACATTCCCCGCTGTGTTGCAGTCTAGTGGCCTG<br>TACAGCCTCTCCTCTGTTGTGACCGTCCCTTCAAGCTCCCTGGGGA<br>CACAGACCTATATCTGTAACGTGAATCATAAGC-<br>CATCTAACACTAAA<br>GTAGATAAAAAAGTGGAGCCCAAGAGTTGCGACAAAACACACACCT<br>GTCCCCCTTGCCCAGCCCCCGAGCTTCTGGGAGGCCCTAGCGTCT<br>TTCTCTMCCACCCAAGCCTAAGGATACTCTGATGATATCCAGGAC<br>CCCAGAAGTTACATGCGTGGTCGTGGACGTCTCACACGAGGACCC<br>CGAAGTGAAATTTAACTGGTACGTTGATGGTGTGGAAGTCCATAAT<br>GCCAAGACCAAGCCTAGAGAGGAGCAATACAACAGTACATATCGC<br>GTGGTAAGCGTGTTGACCGTTCTCCACCAGGACTGGCTCAATGGG<br>AAAGAATACAAGTGTAAAGTGTCCAACAAAGCTCTGCCAGCACCCA<br>TCGAGAAGACTATTTCTAAGGCCAAAGGCCAGCCCCGGGAGCCTC<br>AGGTCTATACACTTCCACCCTCAAGGGATGAACTGACCAAGAACCA<br>AGTGAGCTTGACTTGCCTGGTAAAGGGGTTCTACCCTTCCGACATC<br>GCTGTGGAGTGGGAGTCTAATGGACAACCAGAAAACAATTACAAAA<br>CCACACCCCCTGTCCTCGACAGTGATGGCAGCTTTTTCCTGTATAG<br>CAAACTTACCGTTGACAAGTCCAGATGGCAGCAGGGAAACGTGTTC<br>TCATGTAGCGTCATGCACGAAGCTTTGCATAACCACTACACACAGA<br>AAAGCCTCAGCCTGAGTCCAGGGAAG | 69 |
| anti HER1 (GA201 light chain, pUC-Exp-GA201-LC) | GACATCCAAATGACCCAGTCACCTAGTAGCCTCTCCGCCTCTGTTG<br>GCGACAGGGTGACAATTACATGCAGAGCTTCACAGGGTATCAACAA<br>TTACCTGAACTGGTATCAGCAGAAACCAGGGAAGGCCCCCAAGCG<br>CTTGATATATAACACCAATAACCTGCAAACTGGCGTCCTAGCCGG<br>TTCTCCGGATCTGGTAGTGGCACCGAATTTACACTCACCATCAGCT<br>CCCTGCAGCCAGAGGATTCGCCACATACTATTGTCTTCAGCATAA<br>TTCTTTCCCCACCTTTGGGCAAGGAACTAAACTGGAGATTAAGCGT<br>ACTGTCGCCGCTCCCTCTGTGTTCATTTTTCCTCCAAGTGATGAGC<br>AGCTCAAAAGCGGTACCGCATCCGTTGTGTGCCTGCTTAACAACTT<br>CTATCCCCGGGAAGCCAAGGTCCAATGGAAGGTGGACAATGCTCT<br>GCAGTCAGGAAACAGTCAGGAGAGCGTAACCGAGCAGGATTCCAA<br>AGACTCTACTTACTCATTGAGCTCCACCCTGACACTCTCTAAGGCA<br>GACTATGAAAAGCATAAAGTGTACGCCTGTGAGGTTACCCACCAGG<br>GCCTGAGTAGCCCTGTGACAAAGTCCTTCAATAGGGGAGAGTGC | 70 |
| HER1 (anti-GA201 VH-VL scFv MMP cleavable linker G4S GA201 light chain, pUC-I_GA201_MMP_LC) | GAGGTTCAGCTGGAGCAGTCAGGACCTGTGCTGGTGAAGCCTGGG<br>ACTTCAGTGAAGATGTCCTGTAAGGCTTCTGGATACACATTCACTG<br>ACTACTATATAAACTGGATAATACAGAGCCATGGAAAGTGTCTT-<br>GAG<br>TGGATTGGAGTTATTAATCCTGACAGCGGTGGTACTGACTACAACC<br>AGAACTTCAAGGGCAAGGCCACATTGACTGTTGACAAGTCCTCCAC<br>CACAGCCTACATGGAACTCACTAGCCTGACATCTGAGGACTCTGCA<br>GTCTATTATTGTGCAAGAAGGGATTCTTACGGCTTTGACTACTGGG<br>GCCAAGGCACCACTCTCACAGTCTCCTCAGGCGGAGGTGGCTCAG<br>GGGGAGGCGGTAGCGGCGGAGGTGGCTCAGGGGGAGGCGGTAG<br>CGACATTGTGCTGACCCAGACTCCCAAATTCCTGCTTGTGCCAGCA<br>GGAGACAGGATTACCATGACCTGCAAGGCCAGTCTGAGTGTGACT<br>AATGATGTAGCTTGGTATCAACAGAAACCAGGGCAGTCTCCTAAAC<br>TGCTGTTATACTATGCATCCAATCGCAACGCTGGAGTCCCTGATCG<br>CTTCACTGGCAGTGGATATGGGACGGATTTCACTTTCACCATCACC<br>ACTTTGCAGGCTGAAGACCTGGCAGTTTATTTCTGTCAGCAGGATT<br>ATACCTCTCCTCCGACGTTCGGTTGTGGCACCAAGCTAGAAATCCG<br>TGGTGGCGGCGGTTCTGGCGGAGGGGGTTCTGGCCCCCTGGGGC<br>TATGGAGCCAGGGTGGCGGCGGTTCTGGCGGAGGGGGTTCTGGC<br>GGTGGTGGCTCTGGCGGTGACATCCAAATGACCCAGTCACCTAGT<br>AGCCTCTCCGCCTCTGTTGGCGACAGGGTGACAATTACATGCAGA<br>GCTTCACAGGGTATCAACAATTACCTGAACTGGTATCAGCAGAAAC<br>CAGGGAAGGCCCCCAAGCGCTTGATATATAACACCAATAACCTGCA | 71 |

-continued

```
AACTGGCGTCCCTAGCCGGTTCTCCGGATCTGGTAGTGGCACCGA
ATTTACACTCACCATCAGCTCCCTGCAGCCAGAGGATTTCGCCACA
TACTATTGTCTTCAGCATAATTCTTTCCC-
CACCTTTGGGCAAGGAAC
TAAACTGGAGATTAAGCGTACTGTCGCCGCTCCCTCTGTGTTCATT
TTTCCTCCAAGTGATGAGCAGCTCAAAAGCGGTACCGCATCCGTTG
TGTGCCTGCTTAACAACTTCTATCCCCGGGAAGCCAAGGTCCAATG
GAAGGTGGACAATGCTCTGCAGTCAGGAAACAGTCAGGAGAGCGT
AACCGAGCAGGATTCCAAAGACTCTACTTACTCATTGAGCTCCACC
CTGACACTCTCTAAGGCAGACTATGAAAAGCATAAAGTGTACGCCT
GTGAGGTTACCCACCAGGGCCTGAGTAGCCCTGTGACAAAGTCCT
TCAATAGGGGAGAGTGC
```

| Construct | Amino acid Sequence | SEQ ID No |
|---|---|---|
| anti CD3 (CH2527 VH_3-23(12) VL7-46(13)) scFv 4.32.63 MMP9 Matriptase MK062 CH2527 VH3_23-VH12 CH1 FolR1 16D5 VH CH1 hum Fc knob PG LALA, pETR16546 (FIG. 45L) | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSVHMPLGFLGPRQARVVNGGGGGSGGGGSEVQ LLESGGGLVQPGGSLRLSCAASGFTFSTYAMNWVRQAPGK GLEWVSRIRSKYNNYATYYADSVKGRFTISRDDSKNTLYLQ MNSLRAEDTAVYYCVRHGNFGNSYVSWFAYWGQGTLVTVS SASTKGPSVFPLAPSSKSTSGGTAALGCLVKDYFPEPVTVS WNSGALTSGVHTFPAVLQSSGLYSLSSVVIVPSSSLGTQTYI CNVNHKPSNTKVDKKVEPKSCDGGGGSGGGGSEVQLVES GGGLVKPGGSLRLSCAASGFTFSNAWMSWVRQAPGKGLE WVGRIKSKTDGGTTDYAAPVKGRFTISRDDSKNTLYLQMNS LKTEDTAVYYCTTPWEWSWYDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDKTHTCPPCPAPEAAGGpSVFLFPPKpK DTLMISRTPEVTCVVVDVSHEDPEVKFNWYVDGVEVHNAKT KPREEQYNSTYRVVSVLTVLHQDWLNGKEYKCKVSNKALGA PIEKTISKAKGQPREPQVYTLPPCRDELTKNQVSLWCLVKGF YPSDIAVEWESNGQPENNYKTTPPVLDSDGSFFLYSKLTVD KSRWQQGNVFSCSVMHEALHNHYTQKSLSLSPGK | 72 |
| FolR1 16D5 HC CH2527-VH3_23-12 HC Fc knob PG LALA, pCON999 (FIG. 45M) | EVQLVESGGGLVKPGGSLRLSCAASGFTFSNAWMSWVRQA PGKGLEWVGRIKSKTDGGTTDYAAPVKGRFTISRDDSKNTL YLQMNSLKTEDTAVYYCTTPWEWSWYDYWGQGTLVTVSSA STKGPSVFPLAPSSKSTSGGTAALGCLVKDYFPEPVTVSWN SGALTSGVHTFPAVLQSSGLYSLSSVVTVPSSSLGTQTYICN VNHKPSNTKVDKKVEPKSCDGGGGSGGGGSEVQLLESGG GLVQPGGSLRLSCAASGFTFSTYAMNWVRQAPGKGLEWVS RIRSKYNNYATYYADSVKGRFTISRDDSKNTLYLQMNSLRAE DTAVYYCVRHGNFGNSYVSWFAYWGQGTLVTVSSASTKGP SVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPEAAGGPSVFLFPPKP KDTLMISRTPEVTCVVVDVSHEDPEVKFNWYVDGVEVHNAK TKPREEQYNSTYRVVSVLTVLHQDWLNGKEYKCKVSNKALG APIEKTISKAKGQPREPQVYTLPPCRDELTKNQVSLWCLVKG FYPSDIAVEWESNGQPENNYKTTPPVLDSDGSFFLYSKLTVD KSRWQQGNVFSCSVMHEALHNHYTQKSLSLSPGK | 73 |
| anti ID CD3 scFv 4.32.63 MK062 protease site CD3 VL CLambda, pETR16544 | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSGGGGSRQARVVNGGGGGSGGGGSGGGGSQA VVTQEPSLTVSPGGTVTLTCGSSTGAVTTSNYANWVQEKPG QAFRGLIGGTNKRAPGTPARFSGSLLGGKAALTLSGAQPED EAEYYCALWYSNLWVFGGGTKLTVLGQPKAAPSVTLFPPSS EELQANKATLVCLISDFYPGAVTVAWKADSSPVKAGVETTTP SKQSNNKYAASSYLSLTPEQWKSHRSYSCQVTHEGSTVEKT VAPTECS | 74 |
| anti ID CD3 scFv 4.32.63 non-cleavable linker CD3 VL CLambda, pETR16545 | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT | 75 |

|  |  |  |
|---|---|---|
|  | CRASENIDSYLAWYQQKQGKSPQLLVYAATFLADDVPSRFS<br>GSGSGTQYSLKINSLQSEDVARYYCQHYYSTPYTFGCGTKL<br>EIKGGGGSGGGGSGGGGSGGGGSGGGGGGGSGGGGSGGGGSQ<br>AVVTQEPSLTVSPGGTVTLICGSSTGAVTTSNYANWVQEKP<br>GQAFRGLIGGTNKRAPGTPARFSGSLLGGKAALTLSGAQPE<br>DEAEYYCALWYSNLWVFGGGTKLTVLGQPKAAPSVTLFPPS<br>SEELQANKATLVCLISDFYPGAVTVAWKADSSPVKAGVETTT<br>PSKQSNNKYAASSYLSLTPEQWKSHRSYSCQVTHEGSTVE<br>KTVAPTECS |  |
| aMSLN RG7787 VH<br>CH1 EE CD3 CH2527-<br>VH3_23-12 VL CH1 Fc<br>knob PG LALA,<br>pETR15445 | QVQLVQSGAEVKKPGASVKVSCKASGYSFTGYTMNWVRQA<br>PGQGLEWMGLITPYNGASSYNQKFRGKATMTVDTSTSTVY<br>MELSSLRSEDTAVYYCARGGYDGRGFDYWGQGTLVTVSSA<br>STKGPSVFPLAPSSKSTSGGTAALGCLVEDYFPEPVTVSWN<br>SGALTSGVHTFPAVLQSSGLYSLSSVVTVPSSSLGTQTYICN<br>VNHKPSNTKVDEKVEPKSCDGGGGSGGGGSQAVVTQEPSL<br>TVSPGGTVTLTCGSSTGAVTTSNYANWVQEKPGQAFRGLIG<br>GINKRAPGTPARFSGSLLGGKAALTLSGAQPEDEAEYYCAL<br>WYSNLWVFGGGTKLTVLSSASTKGPSVFPLAPSSKSTSGGT<br>AALGCLVKDYFPEPVTVSWNSGALTSGVHTFPAVLQSSGLY<br>SLSSVVTVPSSSLGTQTYICNVNHKPSNTKVDKKVEPKSCDK<br>THTCPPCPAPEAAGGPSVFLFPPKPKDTLMISRTPEVTCVVV<br>DVSHEDPEVKFNWYVDGVEVHNAKTKPREEQYNSTYRVVS<br>VLTVLHQDWLNGKEYKCKVSNKALGAPIEKTISKAKGQPREP<br>QVYTLPPCRDELTKNQVSLWCLVKGFYPSDIAVEWESNGQP<br>ENNYKTTPPVLDSDGSFFLYSKLTVDKSRWQQGNVFSCSV<br>MHEALHNHYTQKSLSLSPGK | 76 |
| aMSLN RG7787 VH<br>CH1EE Fc hole P329G<br>LALA, pETR15444 | QVQLVQSGAEVKKPGASVKVSCKASGYSFTGYTMNWVRQA<br>PGQGLEWMGLITPYNGASSYNQKFRGKATMTVDTSTSTVY<br>MELSSLRSEDTAVYYCARGGYDGRGFDYWGQGTLVTVSSA<br>STKGPSVFPLAPSSKSTSGGTAALGCLVEDYFPEPVTVSWN<br>SGALTSGVHTFPAVLQSSGLYSLSSVVTVPSSSLGTQTYICN<br>VNHKPSNTKVDEKVEPKSCDKTHTCPPCPAPEAAGGPSVFL<br>FPPKPKDTLMISRTPEVTCVVVDVSHEDPEVKFNWYVDGVE<br>VHNAKTKPREEQYNSTYRVVSVLTVLHQDWLNGKEYKCKVS<br>NKALGAPIEKTISKAKGQPREPQVCTLPPSRDELTKNQVSLS<br>CAVKGFYPSDIAVEWESNGQPENNYKTTPPVLDSDGSFFLV<br>SKLTVDKSRWQQGNVFSCSVMHEALHNHYTQKSLSLSPGK | 77 |
| aMSLN RG7787 VL Ck<br>RK, pETR15443 | DIQMTQSPSSLSASVGDRVTITCSASSSVSYMHWYQQKSGK<br>APKWYDTSKLASGVPSRFSGSGSGTDFTLTISSLQPEDFAT<br>YYCQQWSKHPLTFGQGTKLEIKRTVAAPSVFIFPPSDRKLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC | 78 |
| anti ID CH2527 4.32.63<br>CD3 CH2527 VH 23-12<br>Ck, MMP9-MK062 site,<br>pETR16758 | QVQLKESGPGLVAPSQSLSITCTVSGFSLTSYGVSWVIRQPP<br>GKCLEWLGIIWGDGSTNYHSALISRLSISKDNSKSQVFLKLNS<br>LQTDDTATYYCAKGITTVVDDYYAMDYWGQGTSVTVSSGG<br>GGSGGGGSGGGGSGGGGSDIQMTQSPASLSASVGETVTIT<br>CRASENIDSYLAWYQQKQGKSPQLLVYAATFLADDVPSRFS<br>GSGSGTQYSLKINSLQSEDVARYYCQHYYSTPYTFGCGTKL<br>EIKGGGGSVHMPLGFLGPRQARVVNGGGGGSGGGGSEVQ<br>LLESGGGLVQPGGSLRLSCAASGFTFSTYAMNWVIRQAPG<br>GLEWVSRIRSKYNNYATYYADSVKGRFTISRDDSKNTLYLQ<br>MNSLRAEDTAVYYCVRHGNFGNSYVSWFAYWGQGTLVTVS<br>SASVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC | 79 |
| anti ID CH2527 4.32.63<br>CD3 CH2527 VH 23-12<br>Ck, non-cleavable<br>linker, pETR16759 | QVQLKESGPGLVAPSQSLSITCTVSGFSLTSYGVSWVRQPP<br>GKCLEWLGIIWGDGSTNYHSALISRLSISKDNSKSQVFLKLNS<br>LQTDDTATYYCAKGITTVVDDYYAMDYWGQGTSVTVSSGG<br>GGSGGGGSGGGGSGGGGSDIQMTQSPASLSASVGETVTIT<br>CRASENIDSYLAWYQQKQGKSPQLLVYAATFLADDVPSRFS<br>GSGSGTQYSLKINSLQSEDVARYYCQHYYSTPYTFGCGTKL<br>EIKGGGGSGGGGSGGGGSGGGGGGGSGGGGSGGGGSEV<br>QLLESGGGLVQPGGSLRLSCAASGFTFSTYAMNWVIRQAPG<br>KGLEWVSRIRSKYNNYATYYADSVKGRFTISRDDSKNTLYLQ<br>MNSLRAEDTAVYYCVRHGNFGNSYVSWFAYWGQGTLVTVS<br>SASVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC | 80 |
| CD3 CH2527 VH 23-<br>12 - Ck, pETR13811 | EVQLLESGGGLVQPGGSLRLSCAASGFTFSTYAMNWVRQA<br>PGKGLEWVSRIRSKYNNYATYYADSVKGRFTISRDDSKNTLY<br>LQMNSLRAEDTAVYYCVRHGNFGNSYVSWFAYWGQGTLVT<br>VSSASVAAPSVFIFPPSDEQLKSGTASVVCLLNNFYPREAKV | 81 |

| | | |
|---|---|---|
| | QWKVDNALQSGNSQESVTEQDSKDSTYSLSSTLTLSKADYE KHKVYACEVTHQGLSSPVTKSFNRGEC | |
| anti CD3 (CH2527 VH_3-23(12) VL7-46(13)) scFv 4.32.63 MMP9 Matriptase MK062 aMSLN VH CH1 EE CH2527-VL7_46-13 CH1 hum Fc knob PG LALA, pETR16751 | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSVHMPLGFLGPRQARVVNGGGGGSGGGGSQAV VTQEPSLTVSPGGTVTLTCGSSTGAVTTSNYANWVQEKPG QAFRGLIGGTNKRAPGTPARFSGSLLGGKAALTLSGAQPED EAEYYCALWYSNLWVFGGGTKLTVLSSASTKGPSVFPLAPS SKSTSGGTAALGCLVKDYFPEPVTVSWNSGALTSGVHTFPA VLQSSGLYSLSSVVTVPSSSLGTQTYICNVNHKPSNTKVDKK VEPKSCDGGGSGGGGSQVQLVQSGAEVKKPGASVKVSC KASGYSFTGYTMNVVVRQAPGQGLEWMGLITPYNGASSYNQ KFRGKATMTVDTSTSTVYMELSSLRSEDTAVYYCARGGYDG RGFDYWGQGTLVTVSSASTKGPSVFPLAPSSKSTSGGTAAL GCLVEDYFPEPVTVSWNSGALTSGVHTFPAVLQSSGLYSLS SVVTVPSSSLGTQTYICNVNHKPSNTKVDEKVEPKSCDKTHT CPPCPAPEAAGGPSVFLFPPKPKDTLMISRTPEVTCVVVDVS HEDPEVKFNWYVDGVEVHNAKTKPREEQYNSTYRVVSVLT VLHQDWLNGKEYKCKVSNKALGAPIEKTISKAKGQPREPQV YTLPPCRDELTKNQVSLWCLVKGFYPSDIAVEWESNGQPEN NYKTTPPVLDSDGSFFLYSKLTVDKSRWQQGNVFSCSVMH EALHNHYTQKSLSLSPGK | 82 |
| anti CD3 (CH2527 VH_3-23(12) VL7-46(13)) scFv 4.32.63 non-cleavable linker aMSLN VH CH1 EE CH2527-VL7_46-13 CH1 hum Fc knob PG LALA, pETR16752 | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSGGGGSGGGGSGGGGGGGSGGGGSGGGGSQ AVVTQEPSLTVSPGGTVTLTCGSSTGAVTTSNYANWVQEKP GQAFRGLIGGINKRAPGTPARFSGSLLGGKAALTLSGAQIDE DEAEYYCALWYSNLWVFGGGTKLTVLSSASTKGPSVFPLAP SSKSTSGGTAALGCLVKDYFPEPVTVSWNSGALTSGVHTFP AVLQSSGLYSLSSVVTVPSSSLGTQTYICNVNHKPSNTKVDK KVEPKSCDGGGSGGGGSQVQLVQSGAEVKKPGASVKVS CKASGYSFTGYTMNWVRQAPGQGLEWMGLITPYNGASSYN QKFRGKATMTVDTS,TSTVYMELSSLRSEDTAVYYCARGGYD GRGFDYWGQGTLVTVSSASTKGPSVFPLAPSSKSTSGGTA ALGCLVEDYFPEPVTVSWNSGALTSGVHTFPAVLQSSGLYS LSSVVTVPSSSLGTQTYICNVNHKPSNTKVDEKVEPKSCDKT HTCPPCPAPEAAGGPSVFLFPPKPKDTLMISRTPEVTCVVVD VSHEDPEVKFNWYVDGVEVHNAKTKPREEQYNSTYRVVSV LTVLHQDWLNGKEYKCKVSNKALGAPIEKTISKAKGQPREPQ VYTLPPCRDELTKNQVSLWCLVKGFYPSDIAVEWESNGQPE NNYKTTPPVLDSDGSFFLYSKLTVDKSRWQQGNVFSCSVM HEALHNHYTQKSLSLSPGK | 83 |
| CH2527 XFab aMSLN RG7787 HC EE Fc knob PG LALA, pETR16764 | QAVVTQEPSLIVSPGGTVTLICGSSTGAVTTSNYANWVQEK PGQAFRGLIGGTNKRAPGTPARFSGSLLGGKAALTLSGAQP EDEAEYYCALWYSNLWVFGGGTKLTVLSSASTKGPSVFPLA PSSKSTSGGTAALGCLVKDYFPEPVTVSWNSGALTSGVHTF PAVLQSSGLYSLSSVVTVPSSSLGTQTYICNVNHKPSNTKVD KKVEPKSCDGGGSGGGGSQVQLVQSGAEVKKPGASVKV SCKASGYSFTGYTMNWVRQAPGQGLEWMGLITPYNGASSY NQKFRGKATMTVDTSTSTVYMELSSLRSEDTAVYYCARGGY DGRGFDYWGQGTLVTVSSASTKGPSVFPLAPSSKSTSGGT AALGCLVEDYFPEPVTVSWNSGALTSGVHTFPAVLQSSGLY SLSSVVTVPSSSLGTQTYICNVNHKPSNTKVDEKVEPKSCDK THTCPPCPAPEAAGGPSVFLFPPKPKDTLMISRTPEVTCVVV DVSHEDPEVKFNWYVDGVEVHNAKTKPREEQYNSTYRVVS VLTVLHQDWLNGKEYKCKVSNKALGAPIEKTISKAKGQPREP QVYTLPPCRDELTKNQVSLWCLVKGFYPSDIAVEWESNGQP ENNYKTTPPVLDSDGSFFLYSKLTVDKSRWQQGNVFSCSV MHEALHNHYTQKSLSLSPGK | 84 |
| anti CD3 (CH2527 VH_3-23(12) VL7-46(13)) scFv 4.32.63 Cathepsin S/B site CH2527 VH3_23-VH12 CH1 FolR1 16D5 VH CH1 hum Fc knob PG LALA, pETR16550 | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSGGGGSGGGGSFVGGTGGGSGGGGSGGSEV QLLESGGGLVQPGGSLRLSCAASGFTFSTYAMNWVRQAPG | 85 |

| | | |
|---|---|---|
| | KGLEWVSRIRSKYNNYATYYADSVKGRFTISRDDSKNTLYLQ<br>MNSLRAEDTAVYYCVRHGNFGNSYVSWFAYWGQGTLVTVS<br>SASTKGPSVFPLAPSSKSTSGGTAALGCLVKDYFPEPVTVS<br>WNSGALTSGVHTFPAVLQSSGLYSLSSVVIVPSSSLGTQTYI<br>CNVNHKPSNTKVDKKVEPKSCDGGGGSGGGGSEVQLVES<br>GGGLVKPGGSLRLSCAASGFTFSNAWMSWVRQAPGKGLE<br>WVGRIKSKTDGGTTDYAAPVKGRFTISRDDSKNTLYLQMNS<br>LKTEDTAVYYCTTPWEWSWYDYWGQGTLVTVSSASTKGPS<br>VFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKKVEPKSCDKTHTCPPCPAPEAAGGPSVFLFPPKPK<br>DTLMISRTPEVTCVVVDVSHEDPEVKFNWYVDGVEVHNAKT<br>KPREEQYNSTYRVVSVLTVLHQDWLNGKEYKCKVSNKALGA<br>PIEKTISKAKGQPREPQVYTLPPCRDELTKNQVSLWCLVKGF<br>YPSDIAVEWESNGQPENNYKTTPPVLDSDGSFFLYSKLTVD<br>KSRWQQGNVFSCSVMHEALHNHYTQKSLSLSPGK | |
| Combined MMP9<br>MK062, 33 AA for CD3 | GGGGSVHMPLGFLGPRQARVVNGGGGGSGGGGS | 86 |
| Combined MMP9<br>MK062, 35 AA for Her1 | GGGGSVHMPLGFLGPRQARVVNGGGGGSGGGGSGG | 87 |
| Cathepsin S/B | GGGGSGGGGSGGGGSFVGGTGGGGGSGGGGSGGS | 88 |
| KKAAPVNG | GGGGSGGGGSKKAAPVNGGGGGSGGGGSGGGGS | 89 |
| PMAKKVNG | GGGGSGGGGSPMAKKVNGGGGGSGGGGSGGGGS | 90 |
| QARAKVNG | GGGGSGGGGSQARAKVNGGGGGSGGGGSGGGGS | 91 |
| MMP9 | GGGGSGGGGSVHMPLGFLGPGGGGSGGGGSGGS | 92 |
| QARAK | GGGGSGGGGSQARAKGGGGSGGGGSGGGGSGGS | 93 |
| MMP9-PMAKK | GGGGSVHMPLGFLGPPMAKKGGGGSGGGGSGGS | 94 |
| KKAAP | GGGGSGGGGSKKAAPGGGGSGGGGSGGGGSGGS | 95 |
| PMAKK | GGGGSGGGGSPMAKKGGGGSGGGGSGGGGSGGS | 96 |
| Protease recognition<br>site 6 | VHMPLGFLGPRQARVVNG | 97 |
| Protease recognition<br>site 7 | FVGGTG | 98 |
| Protease recognition<br>site 8 | KKAAPVNG | 99 |
| Protease recognition<br>site 9 | PMAKKVNG | 100 |
| Protease recognition<br>site 10 | QARAKVNG | 101 |
| Protease recognition<br>site 11 | VHMPLGFLGP | 102 |
| Protease recognition<br>site 12 | QARAK | 103 |
| Protease recognition<br>site 13 | VHMPLGFLGPPMAKK | 104 |
| Protease recognition<br>site 14 | KKAAP | 105 |
| Protease recognition<br>site 15 | PMAKK | 106 |
| aMSLN CDR H1 Kabat | GYTMN | 107 |
| aMSLN CDR H2 Kabat | LITPYNGASSYNQKFRG | 108 |
| aMSLN CDR H3 Kabat | GGYDGRGFDY | 109 |
| aMSLN CDR L1 Kabat | SASSSVSYMH | 110 |

| | | |
|---|---|---|
| aMSLN CDR L2 Kabat | DTSKLAS | 111 |
| aMSLN CDR L3 Kabat | QQWSKHPLT | 112 |
| aMSLN VH | QVQLVQSGAEVKKPGASVKVSCKASGYSFTGYTMNWVRQA PGQGLEWMGLITPYNGASSYNQKFRGKATMTVDTSTSTVY MELSSLRSEDTAVYYCARGGYDGRGFDYWGQGTLVTVSS | 113 |
| aMSLN VL | DIQMTQSPSSLSASVGDRVTITCSASSSVSYMHWYQQKSGK APKWYDTSKLASGVPSRFSGSGSGTDFTLTISSLQPEDFAT YYCQQWSKHPLTFGQGTKLEIK | 114 |
| aHER1 VH | QVQLVQSGAEVKKPGSSVKVSCKASGFTFTDYKIHWVRQAP GQGLEWMGYFNPNSGYSTYAQKFQGRVTITADKSTSTAYM ELSSLRSEDTAVYYCARLSPGGYYVMDAWGQGTTVTVSS | 115 |
| aHER1 VL | DIQNATQSPSKSASVGDRVTITCRASQGINNYLNWYQQKPGKA PKRLEYNTNNWTGVPSRFSGSGSGTERITESSWPEDFATYYC LQHNSFPTFGQGTKLEIK | 116 |

| Construct | DNA Sequence | SEQ ID No |
|---|---|---|
| LC Common light chain pETR13197 | CAGGCCGTCGTGACCCAGGAACCCAGCCTGACAGTGTCTCCTGGC GGCACCGTGACCCTGACATGTGGCAGTTCTACAGGCGCCGTGACC ACCAGCAACTACGCCAACTGGGTGCAGGAAAAGCCCGGCCAGGCC TTCAGAGGACTGATCGGCGGCACCAACAAGAGAGCCCCTGGCACC CCTGCCAGATTCAGCGGATCTCTGCTGGGAGGAAAGGCCGCCCTG ACACTGTCTGGCGCCCAGCCAGAAGATGAGGCCGAGTACTACTGC GCCCTGTGGTACAGCAACCTGTGGGTGTTCGGCGGAGGCACCAAG CTGACAGTCCTAGGTCAACCCAAGGCTGCCCCCAGCGTGACCCTG TTCCCCCCCAGCAGCGAGGAACTGCAGGCCAACAAGGCCACCCTG GTCTGCCTGATCAGCGACTTCTACCCAGGCGCCGTGACCGTGGCC TGGAAGGCCGACAGCAGCCCCGTGAAGGCCGGCGTGGAGACCAC CACCCCCAGCAAGCAGAGCAACAACAAGTACGCCGCCAGCAGCTA CCTGAGCCTGACCCCCGAGCAGTGGAAGAGCCACAGGTCCTACAG CTGCCAGGTGACCCACGAGGGCAGCACCGTGGAGAAAACCGTGG CCCCCACCGAGTGCAGCTGA | 117 |
| anti CD3 (CH2527 VH_3-23(12) VL7-46(13)) scFv 4.32.63 MMP9 Matriptase MK062 CH2527 VH3_23-VH12 CH1 FolR1 16D5 VH CH1 hum Fc knob PG LALA, pETR16546 (FIG. 45N) | CAAGTGCAGCTGAAAGAGTCCGGCCCTGGACTGGTGGCCCCTAGC CAGAGCCTGAGCATCACCTGTACCGTGTCCGGCTTCAGCCTGACC AGCTACGGCGTGTCATGGGTGCGCCAGCCTCCAGGCAAGTGTCTG GAATGGCTGGGCATCATCTGGGGCGACGGCAGCACCAATTACCAC AGCGCCCTGATCAGCAGACTGAGCATCTCCAAGGACAACAGCAAG AGCCAGGTGTTCCTGAAGCTGAACAGCCTGCAGACCGACGACACC GCCACCTACTACTGCGCCAAGGGCATCACCACCGTGGTGGACGAC TACTACGCTATGGACTACTGGGGCCAGGGCACCAGCGTGACAGTG TCTAGCGGAGGCGGAGGATCTGGCGGCGGAGGAAGTGGCGGAGG GGGATCTGGGGGAGGCGGAAGCGATATCCAGATGACCCAGAGCC CTGCCAGCCTGTCTGCCTCTGTGGGCGAGACAGTGACCATCACAT GCCGGGCCAGCGAGAACATCGACAGCTACCTGGCCTGGTATCAGC AGAAGCAGGGCAAGAGCCCCCAGCTGCTGGTGTACGCCGCCACCT TCTGGCCGACGATGTGCCCAGCAGATTCAGCGGCAGCGGAAGCG GCACAGATTACAGCCTGAAGATCAACTCCCTGCAGAGCGAGGACG TGGCCCGGTACTACTGCCAGCACTACTACAGCACCCCCTACACCTT CGGCTGCGGCACCAAGCTGGAAATCAAAGGAGGCGGCGGAAGTG TGCACATGCCCCTGGGCTTCCTGGGCCCCAGACAGGCCAGAGTCG TGAACGGGGGGGGCGGAGGCAGTGGGGGGGGAGGATCCGAGGT GCAGCTGCTGGAATCTGGCGGCGGACTGGTGCAGCCTGGCGGAT CTCTGAGACTGAGCTGTGCCGCCAGCGGCTTCACCTTCAGCACCT ACGCCATGAACTGGGTGCGCCAGGCCCCTGGCAAAGGCCTGGAAT GGGTGTCCCGGATCAGAAGCAAGTACAACAACTACGCCACCTACTA CGCCGACAGCGTGAAGGGCCGGTTCACCATCAGCCGGGACGACA GCAAGAACACCCTGTACCTGCAGATGAACAGCCTGCGGGCCGAGG ACACCGCCGTGTACTATTGTGCGCGGCACGGCAACTTCGGCAACA GCTATGTGCTTGGTTTGCCTACTGGGGCCAGGGCACCCTCGTGA CCGTGTCAAGCGCTAGCACAAAGGGCCCTAGCGTGTTCCCTCTGG CCCCCAGCAGCAAGAGCACAAGCGGCGGAACAGCCGCCCTGGGC TGCCTCGTGAAGGACTACTTCCCCGAGCCCGTGACAGTGTCTTGG AACAGCGGAGCCCTGACAAGCGGCGTGCACACCTTCCCTGCCGTG CTGCAGAGCAGCGGCCTGTACTCCCTGAGCAGCGTGGTCACCGTG CCTAGCAGCAGCCTGGGCACCCAGACCTACATCTGCAACGTGAAC CACAAGCCCAGCAACACCAAGGTGGACAAGAAGGTGGAGCCCAAG AGCTGTGATGGCGGAGGAGGGTCCGGGGGCGGAGGATCCGAGGT GCAATTGGTTGAATCTGGTGGTGGTCTGGTAAAACCGGCGGTTC CCTGCGTCTGAGCTGCGCGGCTTCCGGGTTCACCTTCTCCAACGC GTGGATGAGCTGGGTTCGCCAGGCCCCGGGCAAAGGCCTGGAGT GGGTTGGTCGTATCAAGTCTAAAACTGACGGTGGCACCACGGATTA CGCGGCTCCAGTTAAAGGTCGTTTTACCATTTCCCGCGACGATAGC AAAAACACTCTGTATCTGCAGATGAACTCTCTGAAAACTGAA- GACAC | 118 |

| | | |
|---|---|---|
| | CGCAGTCTACTACTGTACTACCCCGTGGGAATGGTCTTGGTACGAT<br>TATTGGGGCCAGGGCACGCTGGTTACGGTGTCTAGCGCTAGTACC<br>AAGGGCCCCAGCGTGTTCCCCCTGGCACCCAGCAGCAAGAGCACA<br>TCTGGCGGAACAGCCGCTCTGGGCTGTCTGGTGAAAGACTACTTC<br>CCCGAGCCCGTGACCGTGTCTTGGAACTCTGGCGCCCTGACCAGC<br>GGCGTGCACACCTTTCCAGCCGTGCTGCAGAGCAGCGGCCTGTAC<br>TCCCTGTCCTCCGTGGTCACCGTGCCCTCTAGCTCCCTGGGAACA<br>CAGACATATATCTGTAATGTCAATCACAAGCCTTCCAACAC-<br>CAAAGT<br>CGATAAGAAAGTCGAGCCCAAGAGCTGCGACAAAACTCACACATG<br>CCCACCGTGCCCAGCACCTGAAGCTGCAGGGGACCGTCAGTCTT<br>CCTCTTCCCCCCAAAACCCAAGGACACCCTCATGATCTCCCGGACC<br>CCTGAGGTCACATGCGTGGTGGTGGACGTGAGCCACGAAGACCCT<br>GAGGTCAAGTTCAACTGGTACGTGGACGGCGTGGAGGTGCATAAT<br>GCCAAGACAAAGCCGCGGGAGGAGCAGTACAACAGCACGTACCGT<br>GTGGTCAGCGTCCTCACCGTCCTGCACCAGGACTGGCTGAATGGC<br>AAGGAGTACAAGTGCAAGGTCTCCAACAAAGCCCTCGGCGCCCCC<br>ATCGAGAAAACCATCTCCAAAGCCAAAGGGCAGCCCCGAGAACCA<br>CAGGTGTACACCCTGCCCCCATGCCGGGATGAGCTGACCAAGAAC<br>CAGGTCAGCCTGTGGTGCCTGGTCAAAGGCTTCTATCCCAGCGAC<br>ATCGCCGTGGAGTGGGAGAGCAATGGGCAGCCGGAGAACAACTAC<br>AAGACCACGCCTCCCGTGCTGGACTCCGACGGCTCCTTCTTCCTCT<br>ACAGCAAGCTCACCGTGGACAAGAGCAGGTGGCAGCAGGGGAAC<br>GTCTTCTCATGCTCCGTGATGCATGAGGCTCTGCACAACCACTACA<br>CGCAGAAGAGCCTCTCCCTGTCTCCGGGTAAATGA | |
| FolR1 16D5<br>HC CH2527-<br>VH3_23-12<br>HC Fc knob<br>PG LALA,<br>pCON999 | GAGGTGCAATTGGTTGAATCTGGTGGTGGTCTGGTAAAACCGGGC<br>GGTTCCCTGCGTCTGAGCTGCGCGGCTTCCGGATTCACCTTCTCC<br>AACGCGTGGATGAGCTGGGTTCGCAGGCCCCGGGCAAAGGCCT<br>CGAGTGGGTTGGTCGTATCAAGTCTAAAACTGACGGTGGCACCAC<br>GGATTACGCGGCTCCAGTTAAAGGTCGTTTTACCATTTCCCGCGAC<br>GATAGCAAAAACACTCTGTATCTGCAGATGAACTCTCT-<br>GAAAACTGA<br>AGACACCGCAGTCTACTACTGTACTACCCCGTGGGAATGGTCTTGG<br>TACGATTATTGGGGCCAGGGCACGCTGGTTACGGTGTCTTCCGCT<br>AGCACAAAGGGCCCCAGCGTGTTCCCTCTGGCCCCCAGCAGCAAG<br>AGCACAAGCGGCGGAACAGCCGCCCTGGGCTGCCTCGTGAAGGA<br>CTACTTCCCCGAGCCCGTGACAGTGTCTTGGAACAGCGGAGCCCT<br>GACAAGCGGCGTGCACACTTTCCCTGCCGTGCTGCAGAGCAGCGG<br>CCTGTACTCCCTGAGCAGCGTGGTCACCGTGCCTAGCAGCAGCCT<br>GGGCACCCAGACCTACATCTGCAACGTGAACCACAAGCCCAGCAA<br>CACCAAAGTGGACAAGAAGGTGGAGCCCAAGAGCTGTGATGGCTG<br>AGGAGGGTCCGGAGGCGAGGATCCGAGGTGCAGCTGCTGGAAT<br>CTGGCGGCGGACTGGTGCAGCCTGGCGGATCTCTGAGACTGAGCT<br>GTGCCGCCAGCGGCTTCACCTTCAGCACCTACGCCATGAACTGGG<br>TGCGCCAGGCCCCTGGCAAAGGCCTGGAATGGGTGTCCGGATCA<br>GAAGCAAGTACAACAACTACGCCACCTACTACGCCGACAGCGTGA<br>AGGGCCGGTTCACCATCAGCCGGGACGACAGCAAGAACACCCTGT<br>ACCTGCAGATGAACAGCCTGCGGGCCGAGGACACCGCCGTGTACT<br>ATTGTGTGCGGCACGGCAACTTCGGCAACAGCTATGTGTCTTGGTT<br>TGCCTACTGGGGCCAGGGCACCCTCGTGACCGTGTCAAGCGCTAG<br>TACCAAGGGCCCCAGCGTGTTCCCCCTGGCACCCAGCAGCAAGAG<br>CACATCTGGCGGAACAGCCGCTCTGGGCTGTCTGGTGAAAGACTA<br>CTTCCCCGAGCCCGTGACCGTGTCTTGGAACTCTGGCGCCCTGAC<br>CAGCGGCGTGCACACCTTTCCAGCCGTGCTGCAGAGCAGCGGCCT<br>GTACTCCCTGTCCTCCGTGGTCACCGTGCCCTCTAGCTCCCTGGG<br>AACACAGACATATATCTGTAATGTCAATCACAAGCCTTC-<br>CAACACCA<br>AAGTCGATAAGAAAGTCGAGCCCAAGAGCTGCGACAAAACTCACAC<br>ATGCCCACCGTGCCCAGCAGCTGAAGCTGCAGGGGACCGTCAGT<br>CTTCCTCTTCCCCCCAAAACCCAAGGACACCCTCATGATCTCCCGG<br>ACCCCTGAGGTCACATGCGTGGTGGTGGACGTGAGCCACGAAGAC<br>CCTGAGGTCAAGTTCAACTGGTACGTGGACGGCGTGGAGGTGCAT<br>AATGCCAAGACAAAGCCGCGGGAGGAGCAGTACAACAGCACGTAC<br>CGTGTGGTCAGCGTCCTCACCGTCCTGCACCAGGACTGGCTGAAT<br>GGCAAGGAGTACAAGTGCAAGGTCTCCAACAAAGCCCTCGGCGCC<br>CCCATCGAGAAAACCATCTCCAAAGCCAAAGGGCAGCCCCGAGAA<br>CCACAGGTGTACACCCTGCCCCCATGCCGGGATGAGCTGACCAAG<br>AACCAGGTCAGCCTGTGGTGCCTGGTCAAAGGCTTCTATCCCAGC<br>GACATCGCCGTGGAGTGGGAGAGCAATGGGCAGCCGGAGAACAA<br>CTACAAGACCACGCCTCCCGTGCTGGACTCCGACGGCTCCTTCTT<br>CCTCTACAGCAAGCTCACCGTGGACAAGAGCAGGTGGCAGCAGGG<br>GAACGTCTTCTCATGCTCCGTGATGCATGAGGCTCTGCACAACCAC<br>TACACGCAGAAGAGCCTCTCCCTGTCTCCGGGTAAATGA | 119 |
| anti ID CD3<br>scFv 4.32.63<br>MK062<br>protease site<br>CD3 VL | CAAGTGCAGCTGAAAGAGTCCGGCCCTGGACTGGTGGCCCCTAGC<br>CAGAGCCTGAGCATCACCTGTACCGTGTCCGGCTTCAGCCTGACC<br>AGCTACGCGTGTCATGGGTGCGCCAGCCTCCAGGCAAGTGTCTG<br>GAATGGCTGGGCATCATCTGGGGCGACGGCAGCACCAATTACCAC<br>AGCGCCCTGATCAGCAGACTGAGCATCTCCAAGGACAACAGCAAG | 120 |

-continued

| | | |
|---|---|---|
| CLambda,<br>pETR16544 | AGCCAGGTGTTCCTGAAGCTGAACAGCCTGCAGACCGACGACACC<br>GCCACCTACTACTGCGCCAAGGGCATCACCACCGTGGTGGACGAC<br>TACTACGCTATGGACTACTGGGGCCAGGGCACCAGCGTGACAGTG<br>TCTAGCGGAGGCGGAGGATCTGGCGGCGGAGGAAGTGGCGGAGG<br>GGGATCTGGGGGAGGCGGAAGCGATATCCAGATGACCCAGAGCC<br>CTGCCAGCCTGTCTGCCTCTGTGGGCGAGACAGTGACCATCACAT<br>GCCGGGCCAGCGAGAACATCGACAGCTACCTGGCCTGGTATCAGC<br>AGAAGCAGGGCAAGAGCCCCCAGCTGCTGGTGTACGCCGCCACCT<br>TTCTGGCCGACGATGTGCCCAGCAGATTCAGCGGCAGCGGAAGCG<br>GCACACAGTACAGCCTGAAGATCAACTCCCTGCAGAGCGAGGACG<br>TGGCCCGGTACTACTGCCAGCACTACTACAGCACCCCCTACACCTT<br>CGGCTGCGGCACCAAGCTGGAAATCAAAGGCGGGGAGGCTCCG<br>GAGGCGGCGGAAGTAGACAGGCCAGAGTCGTGAACGGGGGAGGG<br>GGGGGAAGTGGGGCGGAGGCAGTGGGGCGGAGGATCCCAGG<br>CCGTCGTGACCCAGGAACCCAGCCTGACAGTGTCTCCTGGCGGCA<br>CCGTGACCCTGACATGTGGCAGTTCTACAGGCGCCGTGACCACCA<br>GCAACTACGCCAACTGGGTGCAGGAAAAGCCCGGCCAGGCCTTCA<br>GAGGACTGATCGGCGGCACCAACAAGAGAGCCCCTGGCACCCCT<br>GCCAGATTCAGCGGATCTCTGCTGGGAGGAAAGGCCGCCCTGACA<br>CTGTCTGGCGCCCAGCCAGAAGATGAGGCCGAGTACTACTGCGCC<br>CTGTGGTACAGCAACCTGTGGGTGTTCGGCGGAGGCACCAAGCTG<br>ACAGTCCTAGGTCAACCCAAGGCTGCCCCCAGCGTGACCCTGTTC<br>CCCCCCAGCAGCGAGGAACTGCAGGCCAACAAGGCCACCCTGGT<br>CTGCCTGATCAGCGACTTCTACCCAGGCGCCGTGACCGTGGCCTG<br>GAAGGCCGACAGCAGCCCCGTGAAGGCCGGCGTGGAGACCACCA<br>CCCCCAGCAAGCAGAGCAACAACAAGTACGCCGCCAGCAGCTACC<br>TGAGCCTGACCCCCGAGCAGTGGAAGAGCCACAGGTCCTACAGCT<br>GCCAGGTGACCCACGAGGGCAGCACCGTGGAGAAAACCGTGGCC<br>CCCACCGAGTGCAGCTGA | |
| anti ID CD3<br>scFv 4.32.63<br>non-cleavable<br>linker CD3 VL<br>CLambda,<br>pETR16545 | CAAGTGCAGCTGAAAGAGTCCGGCCCTGGACTGGTGGCCCCTAGC<br>CAGAGCCTGAGCATCACCTGTACCGTGTCCGGCTTCAGCCTGACC<br>AGCTACGGCGTGTCATGGGTGCGCCAGCCTCCAGGCAAGTGTCTG<br>GAATGGCTGGGCATCATCTGGGGCGACGGCAGCACCAATTACCAC<br>AGCGCCCTGATCAGCAGACTGAGCATCTCCAAGGACAACAGCAAG<br>AGCCAGGTGTTCCTGAAGCTGAACAGCCTGCAGACCGACGACACC<br>GCCACCTACTACTGCGCCAAGGGCATCACCACCGTGGTGGACGAC<br>TACTACGCTATGGACTACTGGGGCCAGGGCACCAGCGTGACAGTG<br>TCTAGCGGAGGCGGAGGATCTGGCGGCGGAGGAAGTGGCGGAGG<br>GGGATCTGGGGGAGGCGGAAGCGATATCCAGATGACCCAGAGCC<br>CTGCCAGCCTGTCTGCCTCTGTGGGCGAGACAGTGACCATCACAT<br>GCCGGGCCAGCGAGAACATCGACAGCTACCTGGCCTGGTATCAGC<br>AGAAGCAGGGCAAGAGCCCCCAGCTGCTGGTGTACGCCGCCACCT<br>TTCTGGCCGACGATGTGCCCAGCAGATTCAGCGGCAGCGGAAGCG<br>GCACACAGTACAGCCTGAAGATCAACTCCCTGCAGAGCGAGGACG<br>TGGCCCGGTACTACTGCCAGCACTACTACAGCACCCCCTACACCTT<br>CGGCTGCGGCACCAAGCTGGAAATCAAAGGCGGGGAGGCTCCG<br>GAGGCGGCGGAAGTGGAGGCGGCGGAAGTGGCGGAGGCGGAGG<br>GGGGGGAAGTGGGGCGGAGGCAGTGGGGGGGAGGATCCCAG<br>GCCGTCGTGACCCAGGAACCCAGCCTGACAGTGTCTCCTGGCGGC<br>ACCGTGACCCTGACATGTGGCAGTTCTACAGGCGCCGTGACCACC<br>AGCAACTACGCCAACTGGGTGCAGGAAAAGCCCGGCCAGGCCTTC<br>AGAGGACTGATCGGCGGCACCAACAAGAGAGCCCCTGGCACCCCT<br>GCCAGATTCAGCGGATCTCTGCTGGGAGGAAAGGCCGCCCTGACA<br>CTGTCTGGCGCCCAGCCAGAAGATGAGGCCGAGTACTACTGCGCC<br>CTGTGGTACAGCAACCTGTGGGTGTTCGGCGGAGGCACCAAGCTG<br>ACAGTCCTAGGTCAACCCAAGGCTGCCCCCAGCGTGACCCTGTTC<br>CCCCCCAGCAGCGAGGAACTGCAGGCCAACAAGGCCACCCTGGT<br>CTGCCTGATCAGCGACTTCTACCCAGGCGCCGTGACCGTGGCCTG<br>GAAGGCCGACAGCAGCCCCGTGAAGGCCGGCGTGGAGACCACCA<br>CCCCCAGCAAGCAGAGCAACAACAAGTACGCCGCCAGCAGCTACC<br>TGAGCCTGACCCCCGAGCAGTGGAAGAGCCACAGGTCCTACAGCT<br>GCCAGGTGACCCACGAGGGCAGCACCGTGGAGAAAACCGTGGCC<br>CCCACCGAGTGCAGCTGA | 121 |
| aMSLN<br>RG7787 VH<br>CH1 EE CD3<br>CH2527-<br>VH3_23-12<br>VL CH1 Fc<br>knob PG<br>LALA,<br>pET R15445 | CAGGTGCAGCTGGTGCAGTCTGGCGCCGAAGTGAAGAAACCAGGC<br>GCCAGCGTGAAGGTGTCCTGCAAGGCCAGCGGCTACAGCTTCACC<br>GGCTACACCATGAACTGGGTGCGCCAGGCTCCTGGACAGGGCCTG<br>GAATGGATGGGCCTGATCACCCCCTACAACGGCGCCAGCAGCTAC<br>AACCAGAAGTTCCGGGGCAAGGCCACCATGACCGTGGACACCAGC<br>ACCTCCACCGTGTATATGGAACTGAGCAGCCTGCGGAGCGAGGAC<br>ACCGCCGTGTACTATTGTGCCAGAGGCGGCTACGACGGCAGAGGC<br>TTCGATTATTGGGGCCAGGGCACCCTCGTGACCGTGTCCTCTGCA<br>GCACCAAGGGCCCCTCCGTGTTTCCTCTGGCCCCTTCCAGCAAGT<br>CCACCTCTGGCGGAACTGCCGCTCTGGGCTGCCTGGTGGAAGATT<br>ACTTCCCCGAGCCCGTGACCGTGTCCTGGAATTCTGGCGCTCTGA<br>CCTCCGGCGTGCACACCTTTCCAGCTGTGCTGCAGTCCTCCGGCC<br>TGTACTCCCTGTCCTCCGTCGTGACAGTGCCCTCCAGCTCTCTGGG<br>CACCCAGACCTACATCTGCAACGTGAACCACAAGCCCTCCAACACC | 122 |

| | | |
|---|---|---|
| | AAGGTGGACGAGAAGGTGGAACCCAAGTCCTGCGACGGTGGCGG<br>AGGTTCCGGAGGCGGAGGATCCCAGGCTGTCGTGACCCAGGAAC<br>CCTCCCTGACAGTGTCTCCTGGCGGCACCGTGACCCTGACCTGTG<br>GATCTTCTACCGGCGCTGTGACCACCTCCAACTACGCCAATTGGGT<br>GCAGGAAAAGCCCGGCCAGGCCTTCAGAGGACTGATCGGCGGCA<br>CCAACAAGAGAGCCCTGGCACCCCTGCCAGATTCTCCGGTTCTC<br>TGCTGGGCGGCAAGGCTGCCCTGACTCTGTCTGGTGCTCAGCCTG<br>AGGACGAGGCCGAGTACTACTGCGCCCTGTGGTACTCCAACCTGT<br>GGGTGTTCGGCGGAGGCACCAAGCTGACCGTGCTGTCCAGCGCTT<br>CCACCAAGGGACCCAGTGTGTTCCCCCTGGCCCCCAGCTCCAAGT<br>CTACATCCGGTGGCACAGCTGCCCTGGGATGTCTCGTGAAGGACT<br>ACTTTCCTGAGCCTGTGACAGTGTCTTGGAACAGCGGAGCCCTGA<br>CCAGCGGAGTGCACACATTCCCTGCAGTGCTGCAGAGCAGCGGCC<br>TGTATAGCCTGAGCAGCGTCGTGACCGTGCCTTCCTCTAGCCTGG<br>GAACACAGACATATATCTGTAATGTGAATCAT-<br>AAGCCCAGTAATACC<br>AAAGTGGATAAGAAAGTGGAACCTAAGAGCTGCGATAAGACCCACA<br>CCTGTCCCCCTGCCCTGCTCCTGAAGCTGCTGGTGGCCCTAGCG<br>TGTTCCTGTTCCCCCCAAAGCCCAAGGACACCCTGATGATCTCCCG<br>GACCCCCGAAGTGACCTGCGTGGTGGTGGATGTGTCCCACGAGGA<br>CCCTGAAGTGAAGTTCAATTGGTACGTGGACGGCGTGGAAGTGCA<br>CAACGCCAAGACCAAGCCTAGAGAGGAACAGTACAACTCCACCTA<br>CCGGGTGGTGTCCGTGCTGACAGTGCTGCACCAGGACTGGCTGAA<br>CGGCAAAGAGTACAAGTGCAAGGTGTCCAACAAGGCCCTGGGCGC<br>TCCCATCGAAAAGACCATCTCCAAGGCCAAGGGCCAGCCCCGGGA<br>ACCCCAGGTGTACACCCTGCCCCCATGCCGGGATGAGCTGACCAA<br>GAACCAGGTCAGCCTGTGGTGCCTGGTCAAAGGCTTCTATCCCAG<br>CGACATCGCCGTGGAGTGGGAGAGCAATGGGCAGCCGGAGAACA<br>ACTACAAGACCACGCCTCCCGTGCTGGACTCCGACGGCTCCTTCTT<br>CCTCTACAGCAAGCTCACCGTGGACAAGAGCAGGTGGCAGCAGGG<br>GAACGTCTTCTCATGCTCCGTGATGCATGAGGCTCTGCACAACCAC<br>TACACGCAGAAGAGCCTCTCCCTGTCTCCGGGTAAATGA | |
| aMSLN<br>RG7787 VH<br>CH1 EE Fc<br>hole P329G<br>LALA,<br>pETR15444 | CAGGTGCAGCTGGTGCAGTCTGGCGCCGAAGTGAAGAAACCAGGC<br>GCCAGCGTGAAGGTGTCCTGCAAGGCCAGCGGCTACAGCTTCACC<br>GGCTACACCATGAACTGGGTGCGCCAGGCTCCTGGACAGGGCCTG<br>GAATGGATGGGCCTGATCACCCCCTACAACGGCGCCAGCAGCTAC<br>AACCAGAAGTTCCGGGGCAAGGCCACCATGACCGTGGACACCAGC<br>ACCTCCACCGTGTATATGGAACTGAGCAGCCTGCGGAGCGAGGAC<br>ACCGCCGTGTACTATTGTGCCAGAGGCGGCTACGACGGCAGAGGC<br>TTCGATTATTGGGGCCAGGGCACCCTCGTGACCGTGTCCTCTGCTA<br>GCACCAAGGGCCCCTCCGTGTTCCCCCTGGCCCCCAGCAGCAAGA<br>GCACCAGCGGCGGCACAGCCGCTCTGGGCTGCCTGGTCGAGGAC<br>TACTTCCCCGAGCCCGTGACCGTGTCCTGGAACAGCGGAGCCCTG<br>ACCTCCGGCGTGCACACCTTCCCCGCCGTGCTGCAGAGTTCTGGC<br>CTGTATAGCCTGAGCAGCGTGGTCACCGTGCCTTCTAGCAGCCTG<br>GGCACCCAGACCTACATCTGCAACGTGAACCACAAGCCCAGCAAC<br>ACCAAGGTGGACGAGAAGGTGGAGCCCAAGAGCTGCGACAAAACT<br>CACACATGCCCACCGTGCCCAGCACCTGAAGCTGCAGGGGGACC<br>GTCAGTCTTCCTCTTCCCCCCAAAACCCAAGGACACCCTCATGATC<br>TCCCGGACCCCTGAGGTCACATGCGTGGTGGTGGACGTGAGCCAC<br>GAAGACCCTGAGGTCAAGTTCAACTGGTACGTGGACGGCGTGGAG<br>GTGCATAATGCCAAGACAAAGCCGCGGGAGGAGCAGTACAACAGC<br>ACGTACCGTGTGGTCAGCGTCCTCACCGTCCTGCACCAGGACTGG<br>CTGAATGGCAAGGAGTACAAGTGCAAGGTCTCCAACAAAGCCCTC<br>GGCGCCCCCATCGAGAAAACCATCTCCAAAGCCAAAGGGCAGCCC<br>CGAGAACCACAGGTGTGCACCCTGCCCCCATCCCGGGATGAGCTG<br>ACCAAGAACCAGGTCAGCCTCTCGTGCGCAGTCAAAGGCTTCTATC<br>CCAGCGACATCGCCGTGGAGTGGGAGAGCAATGGGCAGCCGGAG<br>AACAACTACAAGACCACGCCTCCCGTGCTGGACTCCGACGGCTCC<br>TTCTTCCTCGTGAGCAAGCTCACCGTGGACAAGAGCAGGTGGCAG<br>CAGGGGAACGTCTTCTCATGCTCCGTGATGCATGAGGCTCTGCAC<br>AACCACTACACGCAGAAGAGCCTCTCCCTGTCTCCGGGTAAATGA | 123 |
| aMSLN<br>RG7787 VL<br>Ck RK,<br>pETR15443 | GACATCCAGATGACCCAGAGCCCCAGCAGCCTGTCTGCCAGCGTG<br>GGCGACAGAGTGACCATCACCTGTAGCGCCAGCAGCAGCGTGTCC<br>TACATGCACTGGTATCAGCAGAAGTCCGGCAAGGCCCCCAAGCTG<br>CTGATCTACGACACCAGCAAGCTGGCCTCCGGCGTGCCCAGCAGA<br>TTTTCTGGCAGCGGCTCCGGCACCGACTTCACCCTGACAATCAGCT<br>CCCTCCAGCCCGAGGACTTCGCCACCTACTACTGCCAGCAGTGGT<br>CCAAGCACCCCCTGACCTTTGGCCAGGGCACCAAGCTGGAAATCA<br>AGCGTACGGTGGCTGCACCATCTGTCTTCATCTTCCCGCCATCTGA<br>TGAGCAGTTGAAATCTGGAACTGCCTCTGTTGTGTGCCTGCTGAAT<br>AACTTCTATCCCAGAGAGGCCAAAGTACAGTGGAAGGTGGATAACG<br>CCCTCCAATCGGGTAACTCCCAGGAGAGTGTCACAGAGCAGGACA<br>GCAAGGACAGCACCTACAGCCTCAGCAGCACCCTGACGCTGAGCA<br>AAGCAGACTACGAGAAACACAAAGTCTACGCCTGCGAAGTCACCCA<br>TCAGGGCCTGAGCTCGCCCGTCACAAAGAGCTTCAACAGGGGAGA<br>GTGTTAG | 124 |

| | | |
|---|---|---|
| anti ID CH2527 4.32.63 CD3 CH2527 VH 23-12 Ck, MMP9-MK062 site, pETR16758 | CAAGTGCAGCTGAAAGAGTCCGGCCCTGGACTGGTGGCCCCTAGC CAGAGCCTGAGCATCACCTGTACCGTGTCCGGCTTCAGCCTGACC AGCTACGGCGTGTCATGGGTGCGCCAGCCTCCAGGCAAGTGTCTG GAATGGCTGGGCATCATCTGGGGCGACGGCAGCACCAATTACCAC AGCGCCCTGATCAGCAGACTGAGCATCTCCAAGGACAACAGCAAG AGCCAGGTGTTCCTGAAGCTGAACAGCCTGCAGACCGACGACACC GCCACCTACTACTGCGCCAAGGGCATCACCACCGTGGTGGACGAC TACTACGCTATGGACTACTGGGGCCAGGGCACCAGCGTGACAGTG TCTAGCGGAGGCGGAGGATCTGGCGGCGGAGGAAGTGGCGGAGG GGGATCTGGGGGAGGCGGAAGCGATATCCAGATGACCCAGAGCC CTGCCAGCCTGTCTGCCTCTGTGGGCGAGACAGTGACCATCACAT GCCGGGCCAGCGAGAACATCGACAGCTACCTGGCCTGGTATCAGC AGAAGCAGGGCAAGAGCCCCCAGCTGCTGGTGTACGCCGCCACCT TTCTGGCCGACGATGTGCCCAGCAGATTCAGCGGCAGCGGAAGCG GCACACAGTACAGCCTGAAGATCAACTCCCTGCAGAGCGAGGACG TGGCCCGGTACTACTGCCAGCACTACTACAGCACCCCCTACACCTT CGGCTGCGGCACCAAGCTGGAAATCAAAGGAGGCGGCGGAAGTG TGCACATGCCCCTGGGCTTCCTGGGCCCCAGACAGGCCAGAGTCG TGAACGGGGGGGGCGGAGGCAGTGGGGGGGGAGGATCCGAGGT GCAGCTGCTGGAATCTGGCGGCGGACTGGTGCAGCCTGGCGGAT CTCTGAGACTGAGCTGTGCCGCCAGCGGCTTCACCTTCAGCACCT ACGCCATGAACTGGGTGCGCCAGGCCCCTGGCAAAGGCCTGGAAT GGGTGTCCCGGATCAGAAGCAAGTACAACAACTACGCCACCTACTA CGCCGACAGCGTGAAGGGCCGGTTCACCATCAGCCGGGACGACA GCAAGAACACCCTGTACCTGCAGATGAACAGCCTGCGGGCCGAGG ACACCGCCGTGTACTATTGTGTGCGGCACGGCAACTTCGGCAACA GCTATGTGTCTTGGTTTGCCTACTGGGGCCAGGGCACCCTCGTGA CCGTGTCAAGCGCTAGCGTGGCCGCTCCCTCCGTGTTCATCTTCC CACCTTCCGACGAGCAGCTGAAGTCCGGCACCGCTrCTGTCGTGT GCCTGCTGAACAACTTCTACCCCCGCGAGGCCAAGGTGCAGTGGA AGGTGGACAACGCCCTGCAGTCCGGCAACAGCCAGGAATCCGTGA CCGAGCAGGACTCCAAGGACAGCACCTACTCCCTGTCCTCCACCC TGACCCTGTCCAAGGCCGACTACGAGAAGCACAAGGTGTACGCCT GCGAAGTGACCCACCAGGGCCTGTCTAGCCCCGTGACCAAGTCTT TCAACCGGGGCGAGTGCTGA | 125 |
| anti ID CH2527 4.32.63 CD3 CH2527 VH 23-12 Ck, non-cleavable linker, pETR16759 | CAAGTGCAGCTGAAAGAGTCCGGCCCTGGACTGGTGGCCCCTAGC CAGAGCCTGAGCATCACCTGTACCGTGTCCGGCTTCAGCCTGACC AGCTACGGCGTGTCATGGGTGCGCCAGCCTCCAGGCAAGTGTCTG GAATGGCTGGGCATCATCTGGGGCGACGGCAGCACCAATTACCAC AGCGCCCTGATCAGCAGACTGAGCATCTCCAAGGACAACAGCAAG AGCCAGGTGTTCCTGAAGCTGAACAGCCTGCAGACCGACGACACC GCCACCTACTACTGCGCCAAGGGCATCACCACCGTGGTGGACGAC TACTACGCTATGGACTACTGGGGCCAGGGCACCAGCGTGACAGTG TCTAGCGGAGGCGGAGGATCTGGCGGCGGAGGAAGTGGCGGAGG GGGATCTGGGGGAGGCGGAAGCGATATCCAGATGACCCAGAGCC CTGCCAGCCTGTCTGCCTCTGTGGGCGAGACAGTGACCATCACAT GCCGGGCCAGCGAGAACATCGACAGCTACCTGGCCTGGTATCAGC AGAAGCAGGGCAAGAGCCCCCAGCTGCTGGTGTACGCCGCCACCT TTCTGGCCGACGATGTGCCCAGCAGATTCAGCGGCAGCGGAAGCG GCACACAGTACAGCCTGAAGATCAACTCCCTGCAGAGCGAGGACG TGGCCCGGTACTACTGCCAGCACTACTACAGCACCCCCTACACCTT CGGCTGCGGCACCAAGCTGGAAATCAAAGGCGGGGGAGGCTCCG GAGGCGGCGGAAGTGGAGGCGGCGGAAGTGGCGGAGGCGGAGG GGGGGAAGTGGGGGCGGAGGCAGTGGGGGGGGAGGATCCGAG GTGCAGCTGCTGGAATCTGGCGGCGGACTGGTGCAGCCTGGCGG ATCTCTGAGACTGAGCTGTGCCGCCAGCGGCTTCACCTTCAGCAC CTACGCCATGAACTGGGTGCGCCAGGCCCCTGGCAAAGGCCTGGA ATGGGTGTCCCGGATCAGAAGCAAGTACAACAACTACGCCACCTAC TACGCCGACAGCGTGAAGGGCCGGTTCACCATCAGCCGGGACGA CAGCAAGAACACCCTGTACCTGCAGATGAACAGCCTGCGGGCCGA GGACACCGCCGTGTACTATTGTGTGCGGCACGGCAACTTCGGCAA CAGCTATGTGTCTTGGTTTGCCTACTGGGGCCAGGGCACCCTCGT GACCGTGTCAAGCGCTAGCGTGGCCGCTCCCTCCGTGTTCATCTT CCCACCTTCCGACGAGCAGCTGAAGTCCGGCACCGCTTCTGTCGT GTGCCTGCTGAACAACTTCTACCCCCGCGAGGCCAAGGTGCAGTG GAAGGTGGACAACGCCCTGCAGTCCGGCAACAGCCAGGAATCCGT GACCGAGCAGGACTCCAAGGACAGCACCTACTCCCTGTCCTCCAC CCTGACCCTGTCCAAGGCCGACTACGAGAAGCACAAGGTGTACGC CTGCGAAGTGACCCACCAGGGCCTGTCTAGCCCCGTGACCAAGTC TTTCAACCGGGGCGAGTGCTGA | 126 |
| CD3 CH2527 VH 23-12 - Ck, pETR13811 | GAAGTGCAGCTGCTGGAATCCGGCGGAGGACTGGTGCAGCCTGG CGGATCTCTGAGACTGTCTTGTGCCGCCTCCGGCTTCACCTTCTCC ACCTACGCCATGAACTGGGTGCGACAGGCTCCTGGCAAGGGCCTG GAATGGGTGTCCCGGATCAGATCCAAGTACAACAACTACGCCACCT ACTACGCCGACTCCGTGAAGGGCCGGTTCACCATCTCTCGGGACG ACTCCAAGAACACCCTGTACCTGCAGATGAACTCCCTGCGCGCCG AGGACACCGCCGTGTACTATTGTGTGCGGCACGGCAACTTCGGCA | 127 |

| | | |
|---|---|---|
| | ACTCCTATGTGTCTTGGTTTGCCTACTGGGGCCAGGGCACCCTCGT<br>GACCGTGTCATCTGCTAGCGTGGCCGCTCCCTCCGTGTTCATCTTC<br>CCACCTTCCGACGAGCAGCTGAAGTCCGGCACCGCTTCTGTCGTG<br>TGCCTGCTGAACAACTTCTACCCCCGCGAGGCCAAGGTGCAGTGG<br>AAGGTGGACAACGCCCTGCAGTCCGGCAACAGCCAGGAATCCGTG<br>ACCGAGCAGGACTCCAAGGACAGCACCTACTCCCTGTCCTCCACC<br>CTGACCCTGTCCAAGGCCGACTACGAGAAGCACAAGGTGTACGCC<br>TGCGAAGTGACCCACCAGGGCCTGTCTAGCCCCGTGACCAAGTCT<br>TTCAACCGGGGCGAGTGCTGA | |
| anti CD3<br>(CH2527<br>VH_3-23(12)<br>VL7-46(13))<br>scFv 4.32.63<br>MMP9<br>Matriptase<br>MK062<br>aMSLN VH<br>CH1 EE<br>CH2527-<br>VL7_46-13<br>CH1_hum Fc<br>knob PG<br>LALA,<br>pETR16751 | CAAGTGCAGCTGAAAGAGTCCGGCCCTGGACTGGTGGCCCCTAGC<br>CAGAGCCTGAGCATCACCTGTACCGTGTCCGGCTTCAGCCTGACC<br>AGCTACGGCGTGTCATGGGTGCGCCAGCCTCCAGGCAAGTGTCTG<br>GAATGGCTGGGCATCATCTGGGGCGACGGCAGCACCAATTACCAC<br>AGCGCCCTGATCAGCAGACTGAGCATCTCCAAGGACAACAGCAAG<br>AGCCAGGTGTTCCTGAAGCTGAACAGCCTGCAGACCGACGACACC<br>GCCACCTACTACTGCGCCAAGGGCATCACCACCGTGGTGGACGAC<br>TACTACGCTATGGACTACTGGGGCCAGGGCACCACCAGCGTGACAGTG<br>TCTAGCGGAGGCGGAGGATCTGGCGGCGGAGGAAGTGGCGGAGG<br>GGGATCTGGGGGAGGCGGAAGCGATATCCAGATGACCCAGAGCC<br>CTGCCAGCCTGTCTGCCTCTGTGGGCGAGACAGTGACCATCACAT<br>GCCGGGCCAGCGAGAACATCGACAGCTACCTGGCCTGGTATCAGC<br>AGAAGCAGGGCAAGAGCCCCAGCTGCTGGTGTACGCCGCCACCT<br>TTCTGGCCGACGATGTGCCCAGCAGATTCAGCGGCAGCGGAAGCG<br>GCACACAGTACACCCTGAAGATCAACTCCCTGCAGAGCGAGGACG<br>TGGCCCCGGTACTACTGCCAGCACTACTACAGCACCCCCTACACCTT<br>CGGCTGCGGCACCAAGCTGGAAATCAAAGGAGGCGGCGGAAGTG<br>TGCACATGCCCCTGGGCTTCCTGGGCCCCAGACAGGCCAGAGTCG<br>TGAACGGGGGGGGCGGAGGCAGTGGGGGGGAGGATCCCAGGC<br>CGTCGTGACCCAGGAACCCAGCCTGACAGTGTCTCCTGGCGGCAC<br>CGTGACCCTGACATGTGGCAGTTCTACAGGCGCCGTGACCACCAG<br>CAACTACGCCAACTGGGTGCAGGAAAAGCCCGGCCAGGCCTTCAG<br>AGGACTGATCGGCGGCACCAACAAGAGAGCCCCTGGCACCCCTGC<br>CAGATTCAGCGGATCTCTGCTGGGAGGAAAGGCCGCCCTGACACT<br>GTCTGGCGCCCAGCCAGAAGATGAGGCCGAGTACTACTGCGCCCT<br>GTGGTACAGCAACCTGTGGGTGTTCGGCGGAGGCACCAAGCTGAC<br>AGTGCTGAGCAGCGCTTCCACCAAGGGACCCAGTGTGTTCCCCCT<br>GGCCCCCAGCTCCAAGTCTACATCCGGTGGCACAGCTGCCCTGGG<br>ATGTCTCGTGAAGGACTACTTTCCTGAGCCTGTGACAGTGTCTTGG<br>AACAGCGGAGCCCTGACCAGCGGAGTGCACACATTCCCTGCAGTG<br>CTGCAGAGCAGCGGCCTGTATAGCCTGAGCAGCGTCGTGACCGTG<br>CCTTCCTCTAGCCTGGGAACACAGACATATATCTGTAATGT-<br>GAATCA<br>TAAGCCCAGTAATACCAAAGTGGATAAGAAAGTGGAACCTAAGAGC<br>TGCGATGGCGGAGGAGGGTCCGGAGGCGGAGGGTCCCAGGTGCA<br>GCTGGTGCAGTCTGGCGCCGAAGTGAAGAAACCAGGCGCCAGCG<br>TGAAGGTGTCCTGCAAGGCCAGCGGCTACAGCTTCACCGGCTACA<br>CCATGAACTGGGTGCGCCAGGCTCCTGGACAGGGCCTGGAATGGA<br>TGGGCCTGATCACCCCCTACAACGGCGCCAGCAGCTACAACCAGA<br>AGTTCCGGGGCAAGGCCACCATGACCGTGGACACCAGCACCTCCA<br>CCGTGTATATGGAACTGAGCAGCCTGCGGAGCGAGGACACCGCCG<br>TGTACTATTGTGCCAGAGGCGGCTACGACGGCAGAGGCTTCGATT<br>ATTGGGGCCAGGGCACCCTCGTGACCGTGTCCTCTGCTAGCACCA<br>AGGGCCCCTCCGTGTTCCCCCTGGCCCCCAGCAGCAAGAGCACCA<br>GCGGCGGCACAGCCGCTCTGGGCTGCCTGGTCGAGGACTACTTC<br>CCCGAGCCCGTGACCGTGTCCTGGAACAGCGGAGCCCTGACCTCC<br>GGCGTGCACACCTTCCCCGCCGTGCTGCAGAGTTCTGGCCTGTAT<br>AGCCTGAGCAGCGTGGTCACCGTGCCTTCTAGCAGCCTGGGCACC<br>CAGACCTACATCTGCAACGTGAACCACAAGCCCAGCAACACCAAG<br>GTGGACGAGAAGGTGGAGCCCAAGAGCTGCGACAAAACTCACACA<br>TGCCCACCGTGCCCAGCACCTGAAGCTGCAGGGGACCGTCAGTC<br>TTCCTCTTCCCCCCAAAACCCAAGGACACCCTCATGATCTCCCGGA<br>CCCCTGAGGTCACATGCGTGGTGGTGGACGTGAGCCACGAAGACC<br>CTGAGGTCAAGTTCAACTGGTACGTGGACGGCGTGGAGGTGCATA<br>ATGCCAAGACAAAGCCGCGGGAGGAGCAGTACAACAGCACGTACC<br>GTGTGGTCAGCGTCCTCACCGTCCTGCACCAGGACTGGCTGAATG<br>GCAAGGAGTACAAGTGCAAGGTCTCCAACAAAGCCCTCGGCGCCC<br>CCATCGAGAAAACCATCTCCAAAGCCAAAGGGCAGCCCCGAGAAC<br>CACAGGTGTACACCCTGCCCCCATGCCCGGGATGAGCTGACCAAGA<br>ACCAGGTCAGCCTGTGGTGCCTGGTCAAAGGCTTCTATCCCAGCG<br>ACATCGCCGTGGAGTGGGAGAGCAATGGGCAGCCGGAGAACACT<br>ACAAGACCACGCCTCCCGTGCTGGACTCCGACGGCTCCTTCTTCC<br>TCTACAGCAAGCTCACCGTGGACAAGAGCAGGTGGCAGCAGGGGA<br>ACGTCTTCTCATGCTCCGTGATGCATGAGGCTCTGCACAACCACTA<br>CACGCAGAAGAGCCTCTCCCTGTCTCCGGGTAAATGA | 128 |
| anti CD3<br>(CH2527<br>VH_3-23(12)<br>VL7-46(13)) | CAAGTGCAGCTGAAAGAGTCCGGCCCTGGACTGGTGGCCCCTAGC<br>CAGAGCCTGAGCATCACCTGTACCGTGTCCGGCTTCAGCCTGACC<br>AGCTACGGCGTGTCATGGGTGCGCCAGCCTCCAGGCAAGTGTCTG<br>GAATGGCTGGGCATCATCTGGGGCGACGGCAGCACCAATTACCAC | 129 |

| | | |
|---|---|---|
| scFv 4.32.63 non-cleavable linker aMSLN VH CH1 EE CH2527-VL7_46-13 CH1 hum Fc knob PG LALA, pETR16752 | AGCGCCCTGATCAGCAGACTGAGCATCTCCAAGGACAACAGCAAG<br>AGCCAGGTGTTCCTGAAGCTGAACAGCCTGCAGACCGACGACACC<br>GCCACCTACTACTGCGCCAAGGGCATCACCACCGTGGTGGACGAC<br>TACTACGCTATGGACTACTGGGGCCAGGGCACCAGCGTGACAGTG<br>TCTAGCGGAGGCGGAGGATCTGGCGGCGGAGGAAGTGGCGGAGG<br>GGGATCTGGGGGAGGCGGAAGCGATATCCAGATGACCCAGAGCC<br>CTGCCAGCCTGTCTGCCTCTGTGGGCGAGACAGTGACCATCACAT<br>GCCGGGCCAGCGAGAACATCGACAGCTACCTGGCCTGGTATCAGC<br>AGAAGCAGGGCAAGAGCCCCCAGCTGCTGGTGTACGCCGCCACCT<br>TTCTGGCCGACGATGTGCCCAGCAGATTCAGCGGCAGCGGAAGCG<br>GCACACAGTACAGCCTGAAGATCAACTCCCTGCAGAGCGAGGACG<br>TGGCCCGGTACTACTGCCAGCACTACTACAGCACCCCCTACACCTT<br>CGGCTGCGGCACCAAGCTGGAAATCAAAGGCGGGGGAGGCTCCG<br>GAGGCGGCGGAAGTGGAGGCGGCGAAGTGGCGGAGGCGGAGG<br>GGGGGGAAGTGGGGGCGGAGGCAGTGGGGGGGGAGGATCCCAG<br>GCCGTCGTGACCCAGGAACCCAGCCTGACAGTGTCTCCTGGCGGC<br>ACCGTGACCCTGACATGTGGCAGTTCTACAGGCGCCGTGACCACC<br>AGCAACTACGCCAACTGGGTGCAGGAAAAGCCCGGCCAGGCCTTC<br>AGAGGACTGATCGGCGGCACCAACAAGAGAGCCCCTGGCACCCCT<br>GCCAGATTCAGCGGATCTCTGCTGGGAGGAAAGGCCGCCCTGACA<br>CTGTCTGGCGCCCAGCCAGAAGATGAGGCCGAGTACTACTGCGCC<br>CTGTGGTACAGCAACCTGTGGGTGTTCGGCGGAGGCACCAAGCTG<br>ACAGTGCTGAGCAGCGCTTCCACCAAGGGACCCAGTGTGTTCCCC<br>CTGGCCCCCAGCTCCAAGTCTACATCCGGTGGCACAGCTGCCCTG<br>GGATGTCTCGTGAAGGACTACTTTCCTGAGCCTGTGACAGTGTCTT<br>GGAACAGCGGAGCCCTGACCAGCGGAGTGCACACATTCCCTGCAG<br>TGCTGCAGAGCAGCGGCCTGTATAGCCTGAGCAGCGTCGTGACCG<br>TGCCTTCCTCTAGCCTGGGAACACAGACATATATCTGTAATGT-<br>GAAT<br>CATAAGCCCAGTAATACCAAAGTGGATAAGAAAGTGGAACCTAAGA<br>GCTGCGATGGCGGAGGAGGGTCCGGAGGCGGAGGGTCCCAGGT<br>GCAGCTGGTGCAGTCTGGCGCCGAAGTGAAGAAACCAGGCGCCA<br>GCGTGAAGGTGTCCTGCAAGGCCAGCGGCTACAGCTTCACCGGCT<br>ACACCATGAACTGGGTGCGCCAGGCTCCTGGACAGGGCCTGGAAT<br>GGATGGGCCTGATCACCCCCTACAACGGCGCCAGCAGCTACAACC<br>AGAAGTTCCGGGGCAAGGCCACCATGACCGTGGACACCAGCACCT<br>CCACCGTGTATATGGAACTGAGCAGCCTGCGGAGCGAGGACACCG<br>CCGTGTACTATTGTGCCAGAGGCGGCTACGACGGCAGAGGCTTCG<br>ATTATTGGGGCCAGGGCACCCTCGTGACCGTGTCCTCTGCTAGCA<br>CCAAGGGCCCCTCCGTGTTCCCCCTGGCCCCCAGCAGCAAGAGCA<br>CCAGCGGCGGCACAGCCGCTCTGGGCTGCCTGGTCGAGGACTAC<br>TTCCCCGAGCCCGTGACCGTGTCCTGGAACAGCGGAGCCCTGACC<br>TCCGGCGTGCACACCTTCCCCGCCGTGCTGCAGAGTTCTGGCCTG<br>TATAGCCTGAGCAGCGTGGTCACCGTGCCTTCTAGCAGCCTGGGC<br>ACCCAGACCTACATCTGCAACGTGAACCACAAGCCCAGCAACACCA<br>AGGTGGACGAGAAGGTGGAGCCCAAGAGCTGCGACAAAACTCACA<br>CATGCCCACCGTGCCCAGCACCTGAAGCTGCAGGGGACCGTCA<br>GTCTTCCTCTTCCCCCCAAAACCCAAGGACACCCTCATGATCTCCC<br>GGACCCCTGAGGTCACATGCGTGGTGGTGGACGTGAGCCACGAA<br>GACCCTGAGGTCAAGTTCAACTGGTACGTGGACGGCGTGGAGGTG<br>CATAATGCCAAGACAAAGCCGCGGGAGGAGCAGTACAACAGCACG<br>TACCGTGTGGTCAGCGTCCTCACCGTCCTGCACCAGGACTGGCTG<br>AATGGCAAGGAGTACAAGTGCAAGGTCTCCAACAAAGCCCTCGGC<br>GCCCCCATCGAGAAAACCATCTCCAAAGCCAAAGGGCAGCCCCGA<br>GAACCACAGGTGTACACCCTGCCCCCATGCCGGGATGAGCTGACC<br>AAGAACCAGGTCAGCCTGTGGTGCCTGGTCAAAGGCTTCTATCCCA<br>GCGACATCGCCGTGGAGTGGGAGAGCAATGGGCAGCCGGAGAAC<br>AACTACAAGACCACGCCTCCCGTGCTGGACTCCGACGGCTCCTTC<br>TTCCTCTACAGCAAGCTCACCGTGGACAAGAGCAGGTGGCAGCAG<br>GGGAACGTCTTCTCATGCTCCGTGATGCATGAGGCTCTGCACAACC<br>ACTACACGCAGAAGAGCCTCTCCCTGTCTCCGGGTAAATGA | |
| CH2527 XFab aMSLN RG7787 HC EE Fc knob PG LALA, pETR16764 | CAGGCCGTCGTGACCCAGGAACCCAGCCTGACAGTGTCTCCTGGC<br>GGCACCGTGACCCTGACATGTGGCAGTTCTACAGGCGCCGTGACC<br>ACCAGCAACTACGCCAACTGGGTGCAGGAAAAGCCCGGCCAGGCC<br>TTCAGAGGACTGATCGGCGGCACCAACAAGAGAGCCCCTGGCACC<br>CCTGCCAGATTCTCCGGTTCTCTGCTGGGCGGCAAGGCTGCCCTG<br>ACTCTGTCTGGTGCTCAGCCTGAGGACGAGGCCGAGTACTACTGC<br>GCCCTGTGGTACTCCAACCTGTGGGTGTTCGGCGGAGGCACCAAG<br>CTGACCGTGCTGTCCAGCGCTTCCACCAAGGGACCCAGTGTGTTC<br>CCCCTGGCCCCCAGCTCCAAGTCTACATCCGGTGGCACAGCTGCC<br>CTGGGATGTCTCGTGAAGGACTACTTTCCTGAGCCTGTGACAGTGT<br>CTTGGAACAGCGGAGCCCTGACCAGCGGAGTGCACACATTCCCTG<br>CAGTGCTGCAGAGCAGCGGCCTGTATAGCCTGAGCAGCGTCGTGA<br>CCGTGCCTTCCTCTAGCCTGGGAACACAGACATATATCTGTAATGT<br>GAATCATAAGCCCAGTAATACCAAAGTGGATAAGAAAGTGGAACCT<br>AAGAGCTGCGATGGCGGAGGAGGGTCCGGAGGCGGAGGGTCCCA<br>GGTGCAGCTGGTGCAGTCTGGCGCCGAAGTGAAGAAACCAGGCG<br>CCAGCGTGAAGGTGTCCTGCAAGGCCAGCGGCTACAGCTTCACCG<br>GCTACACCATGAACTGGGTGCGCCAGGCTCCTGGACAGGGCCTGG | 130 |

| | | |
|---|---|---|
| | AATGGATGGGCCTGATCACCCCCTACAACGGCGCCAGCAGCTACA | |
| | ACCAGAAGTTCCGGGGCAAGGCCACCATGACCGTGGACACCAGCA | |
| | CCTCCACCGTGTATATGGAACTGAGCAGCCTGCGGAGCGAGGACA | |
| | CCGCCGTGTACTATTGTGCCAGAGGCGGCTACGACGGCAGAGGCT | |
| | TCGATTATTGGGGCCAGGGCACCCTCGTGACCGTGTCCTCTGCTA | |
| | GCACCAAGGGCCCCTCCGTGTTCCCCCTGGCCCCCAGCAGCAAGA | |
| | GCACCAGCGGCGGCACAGCCGCTCTGGGCTGCCTGGTCGAGGAC | |
| | TACTTCCCCGAGCCCGTGACCGTGTCCTGGAACAGCGGAGCCCTG | |
| | ACCTCCGGCGTGCACACCTTCCCCGCCGTGCTGCAGAGTTCTGGC | |
| | CTGTATAGCCTGAGCAGCGTGGTCACCGTGCCTTCTAGCAGCCTG | |
| | GGCACCCAGACCTACATCTGCAACGTGAACCACAAGCCCAGCAAC | |
| | ACCAAGGTGGACGAGAAGGTGGAGCCCAAGAGCTGCGACAAAACT | |
| | CACACATGCCCACCGTGCCCAGCACCTGAAGCTGCAGGGGGACC | |
| | GTCAGTCTTCCTCTTCCCCCCAAAACCCAAGGACACCCTCATGATC | |
| | TCCCGGACCCCTGAGGTCACATGCGTGGTGGTGGACGTGAGCCAC | |
| | GAAGACCCTGAGGTCAAGTTCAACTGGTACGTGGACGGCGTGGAG | |
| | GTGCATAATGCCAAGACAAAGCCGCGGGAGGAGCAGTACAACAGC | |
| | ACGTACCGTGTGGTCAGCGTCCTCACCGTCCTGCACCAGGACTGG | |
| | CTGAATGGCAAGGAGTACAAGTGCAAGGTCTCCAACAAAGCCCTC | |
| | GGCGCCCCCATCGAGAAAACCATCTCCAAAGCCAAGGGCAGCCC | |
| | CGAGAACCACAGGTGTACACCCTGCCCCCATGCCGGGATGAGCTG | |
| | ACCAAGAACCAGGTCAGCCTGTGGTGCCTGGTCAAAGGCTTCTATC | |
| | CCAGCGACATCGCCGTGGAGTGGGAGAGCAATGGGCAGCCGGAG | |
| | AACAACTACAAGACCACGCCTCCCGTGCTGGACTCCGACGGCTCC | |
| | TTCTTCCTCTACAGCAAGCTCACCGTGGACAAGAGCAGGTGGCAG | |
| | CAGGGGAACGTCTTCTCATGCTCCGTGATGCATGAGGCTCTGCAC | |
| | AACCACTACACGCAGAAGAGCCTCTCCCTGTCTCCGGGTAAATGA | |
| anti CD3 (CH2527 VH_3-23(12) VL7-46(13)) scFv 4.32.63 Cathepsin S/B site CH2527 VH3_23-VH12 CH1 FolR1 16D5 VH CH1 hum Fc knob PG LALA, pETR16550 | CAAGTGCAGCTGAAAGAGTCCGGCCCTGGACTGGTGGCCCCTAGC CAGAGCCTGAGCATCACCTGTACCGTGTCCGGCTTCAGCCTGACC AGCTACGGCGTGTCATGGGTGCGCCAGCCTCCAGGCAAGTGTCTG GAATGGCTGGGCATCATCTGGGGCGACGGCAGCACCAATTACCAC AGCGCCCCTGATCAGCAGACTGAGCATCTCCAAGGACAACAGCAAG AGCCAGGTGTTCCTGAAGCTGAACAGCCTGCAGACCGACGACACC GCCACCTACTACTGCGCCAAGGGCATCACCACCGTGGTGGACGAC TACTACGCTATGGACTACTGGGGCCAGGGCACCAGCGTGACAGTG TCTAGCGGAGGCGGAGGATCTGGCGGCGGAGGAAGTGGCGGAGG GGGATCTGGGGGAGGCGGAAGCGGATATCCAGATGACCCAGAGCC CTGCCAGCCTGTCTGCCTCTGTGGGCGAGACAGTGACCATCACAT GCCGGGCCAGCGAGAACATCGACAGCTACCTGGCCTGGTATCAGC AGAAGCAGGGCAAGAGCCCCCAGCTGCTGGTGTACGCCGCCACCT TTCTGGCCGACGATGTGCCCAGCAGATTCAGCGGCAGCGGAAGCG GCACACAGTACAGCCTGAAGATCAACTCCCTGCAGAGCGAGGACG TGGCCCGGTACTACTGCCAGCACTACTACAGCACCCCCTACACCTT CGGCTGCGGCACCAAGCTGGAAATCAAAGGCGGGGGAGGCTCCG GAGGCGGCGGAAGTGGAGGCGGCGGAAGTTTCGTGGGGGGGAC CGGGGGCGGAGGCAGTGGGGGGGAGGATCCGGGGGATCCGAG GTGCAGCTGCTGGAATCTGGCGGCGGACTGGTGCAGCCTGGCGG ATCTCTGAGACTGAGCTGTGCCGCCAGCGGCTTCACCTTCAGCAC CTACGCCATGAACTGGGTGCGCCAGGCCCCTGGCAAAGGCCTGGA ATGGGTGTCCCGGATCAGAAGCAAGTACAACAACTACGCCACCTAC TACGCCGACAGCGTGAAGGGCCGGTTCACCATCAGCCGGGACGA CAGCAAGAACACCCTGTACCTGCAGATGAACAGCCTGCGGGCCGA GGACACCGCCGTGTACTATTGTGTGCGGCACGGCAACTTCGGCAA CAGCTATGTGTCTTGGTTTGCCTACTGGGGCCAGGGCACCCTCGT GACCGTGTCAAGCGCTAGCACAAAGGGCCCTAGCGTGTTCCCTCT GGCCCCCAGCAGCAAGAGCACAAGCGGCGGAACAGCCGCCCTGG GCTGCCTCGTGAAGGACTACTTCCCCGAGCCCGTGACAGTGTCTT GGAACAGCGGAGCCCTGACAAGCGGCGTGCACACCTTCCCTGCC GTGCTGCAGAGCAGCGGCCTGTACTCCCTGAGCAGCGTGGTCACC GTGCCTAGCAGCAGCCTGGGCACCCAGACCTACATCTGCAACGTG AACCACAAGCCCAGCAACACCAAAGTGGACAAGAAGGTGGAGCCC AAGAGCTGTGATGGCGGAGGAGGGTCCGGGGGCGGAGGATCCGA GGTGCAATTGGTTGAATCTGGTGGTGGTCTGGTAAAACCGGGCGG TTCCCTGCGTCTGAGCTGCGCGGCTTCCGGGTTCACCTTCTCCAAC GCGTGGATGAGCTGGGTTCGCCAGGCCCCGGGCAAAGGCCTCGA GTGGGTTGGTCGTATCAAGTCTAAAACTGACGGTGGCACCACGGA TTACGCGGCTCCAGTTAAAGGTCGTTTTACCATTTCCCGCGACGAT AGCAAAAACACTCTGTATCTGCAGATGAACTCTCTGAAAACTGAAG ACACCGCAGTCTACTACTGTACTACCCCGTGGGAATGGTCTTGGTA CGATTATTGGGGCCAGGGCACGCTGGTTACGGTGTCTAGCGCTAG TACCAAGGGCCCCAGCGTGTTCCCCCTGGCACCCAGCAGCAAGAG CACATCTGGCGGAACAGCCGCTCTGGGCTGTCTGGTGAAAGACTA CTTCCCCGAGCCCGTGACCGTGTCTTGGAACTCTGGCGCCCTGAC CAGCGGCGTGCACACCTTCCAGCCGTGCTGCAGAGCAGCGGCCT GTACTCCCTGTCCTCCGTGGTCACCGTGCCCTCTAGCTCCCTGGG AACACAGACATATATCTGTAATGTCAATCACAAGCCTTC- CAACACCA AAGTCGATAAGAAAGTCGAGCCCAAGAGCTGCGACAAAACTCACAC ATGCCCACCGTGCCCAGCACCTGAAGCTGCAGGGGGACCGTCAGT | 131 |

-continued

```
CTTCCTCTTCCCCCCAAAACCCAAGGACACCCTCATGATCTCCCGG
ACCCCTGAGGTCACATGCGTGGTGGTGGACGTGAGCCACGAAGAC
CCTGAGGTCAAGTTCAACTGGTACGTGGACGGCGTGGAGGTGCAT
AATGCCAAGACAAAGCCGCGGGAGGAGCAGTACAACAGCACGTAC
CGTGTGGTCAGCGTCCTCACCGTCCTGCACCAGGACTGGCTGAAT
GGCAAGGAGTACAAGTGCAAGGTCTCCAACAAAGCCCTCGGCGCC
CCCATCGAGAAAACCATCTCCAAAGCCAAAGGGCAGCCCCGAGAA
CCACAGGTGTACACCCTGCCCCCATGCCGGGATGAGCTGACCAAG
AACCAGGTCAGCCTGTGGTGCCTGGTCAAAGGCTTCTATCCCAGC
GACATCGCCGTGGAGTGGGAGAGCAATGGGCAGCCGGAGAACAA
CTACAAGACCACGCCTCCCGTGCTGGACTCCGACGGCTCCTTCTT
CCTCTACAGCAAGCTCACCGTGGACAAGAGCAGGTGGCAGCAGGG
GAACGTCTTCTCATGCTCCGTGATGCATGAGGCTCTGCACAACCAC
TACACGCAGAAGAGCCTCTCCCTGTCTCCGGGTAAATGA
```

| Construct | Amino acid Sequence | SEQ ID No |
|---|---|---|
| pETR16859 Omnitarg aff.mat variant Fab cv - Fc hole PG LALA | EVQLVESGGGLVQPGGSLRLSCAASGFTFNDYTMDWVRQA PGKGLEWVADVNPNSGGSIVNRRFKGRFTLSVDRSKNTLYL QMNSLRAEDTAVYYCARNLGPFFYFDYWGQGTLVTVSSAS TKGPSVFPLAPSSKSTSGGTAALGCLVEDYFPEPVTVSWNS GALTSGVHTFPAVLQSSGLYSLSSVVTVPSSSLGTQTYICNV NHKPSNTKVDEKVEPKSCDKTHTCPPCPAPEAAGGPSVFLF PPKPKDTLMISRTPEVTCVVVDVSHEDPEVKFNWYVDGVEV HNAKTKPREEQYNSTYRVVSVLTVLHQDWLNGKEYKCKVS NKALGAPIEKTISKAKGQPREPQVCTLPPSRDELTKNQVSLS CAVKGFYPSDIAVEWESNGQPENNYKTTPPVLDSDGSFFLV SKLTVDKSRWQQGNVFSCSVMHEALHNHYTQKSLSLSPGK | 132 |
| pETR16860 Herceptarg common CLkRK | DIQMTQSPSSLSASVGDRVTITCKASQDVSTAVAWYQQKPG KAPKLLIYSASFRYTGVPSRFSGSRSGTDFTLTISSLQPEDFA TYYCQQHYTTPPTFGQGTKVEIKRTVAAPSVFIFPPSDRKLK SGTASVVCLLNNFYPREAKVQWKVDNALQSGNSQESVTEQ DSKDSTYSLSSTLTLSKADYEKHKVYACEVTHQGLSSPVTKS FNRGEC | 133 |
| pETR17605 CD3 X Fab Herceptin HC charged variants Fc knob PG LALA | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVLSSASTKGPSVFPLA PSSKSTSGGTAALGCLVKDYFPEPVTVSWNSGALTSGVHTF PAVLQSSGLYSLSSVVTVPSSSLGTQTYICNVNHKPSNTKVD KKVEPKSCDGGGSGGGGSEVQLVESGGGLVQPGGSLRL SCAASGFNIKDTYIHWVRQAPGKGLEWVARIYPTNGYTRYA DSVKGRFTISADTSKNTAYLQMNSLRAEDTAVYYCSRWGGE GFYAMDYVVGQGTLVTVSSASTKGPSVFPLAPSSKSTSGGT AALGCLVEDYFPEPVTVSWNSGALTSGVHTFPAVLQSSGLY SLSSVVTVPSSSLGTQTYICNVNHKPSNTKVDEKVEPKSCDK THTCPPCPAPEAAGGPSVFLFPPKPKDTLMISRTPEVTCVVV DVSHEDPEVKFNWYVDGVEVHNAKTKPREEQYNSTYRVVS VLTVLHQDWLNGKEYKCKVSNKALGAPIEKTISKAKGQPREP QVYTLPPCRDELTKNQVSLWCLVKGFYPSDIAVEWESNGQP ENNYKTTPPVLDSDGSFFLYSKLTVDKSRWQQGNVFSCSV MHEALHNHYTQKSLSLSPGK | 134 |
| pETR17606 anti CD3 (CH2527 VH_3-23(12) VL7-46(13)) scFv 4.32.63 non cleavable linker aHerceptin VH CH1 EE 0H2527-VL7_46-13 CH1 hum Fc knob PG LALA | QVQLKESGPGLVAPSQSLSITCTVSGFSLTSYGVSWVRQPP GKCLEWLGIIWGDGSTNYHSALISRLSISKDNSKSQVFLKLNS LQTDDTATYYCAKGITTVVDDYYAMDYWGQGTSVTVSSGG GGSGGGGSGGGGSDIQMTQSPASLSASVGETVTIT CRASENIDSYLAWYQQKQGKSPQLLVYAATFLADDVPSRFS GSGSGTQYSLKINSLQSEDVARYYCQHYYSTPYTFGCGTKL EIKGGGGSGGGGSGGGGSGGGGGGSGGGGSGGGGSQ AVVTQEPSLTVSPGGTVTLTCGSSTGAVTTSNYANWVQEKP GQAFRGLIGGTNKRAPGTPARFSGSLLGGKAALTLSGAQPE DEAEYYCALWYSNLWVFGGGTKLTVLSSASTKGPSVFPLAP SSKSTSGGTAALGCLVKDYFPEPVTVSWNSGALTSGVHTFP AVLQSSGLYSLSSVVTVPSSSLGTQTYICNVNHKPSNTKVDK KVEPKSCDGGGSGGGGSEVQLVESGGGLVQPGGSLRLS CAASGFNIKDTYIHWVRQAPGKGLEWVARIYPTNGYTRYAD SVKGRFTISADTSKNTAYLQMNSLRAEDTAVYYCSRWGGEG FYAMDYWGQGTLVTVSSASTKGPSVFPLAPSSKSTSGGTA LGCLVEDYFPEPVTVSWNSGALTSGVHTFPAVLQSSGLYSL SSVVTVPSSSLGTQTYICNVNHKPSNTKVDEKVEPKSCDKTH TCPPCPAPEAAGGPSVFLFPPKPKDTLMISRTPEVTCVVVDV SHEDPEVKFNWYVDGVEVHNAKTKPREEQYNSTYRVVSVL TVLHQDWLNGKEYKCKVSNKALGAPIEKTISKAKGQPREPQ | 135 |

-continued

| | VYTLPPCRDELTKNQVSLWCLVKGFYPSDIAVEWESNGQPE<br>NNYKTTPPVLDSDGSFFLYSKLTVDKSRWQQGNVFSCSVM<br>HEALHNHYTQKSLSLSPGK | |
|---|---|---|
| pETR17607 anti CD3<br>(CH2527 VH_3-23(12)<br>VL7-46(13)) scFv<br>4.32.63 MMP9<br>Matriptase MK062<br>aHerceptin VH CH1 EE<br>CH2527-VL7_46-13<br>CH1 hum Fc knob PG<br>LALA | QVQLKESGPGLVAPSQSLSITCTVSGFSLTSYGVSWVRQPP<br>GKCLEWLGIIWGDGSTNYHSALISRLSISKDNSKSQVFLKLNS<br>LQTDDTATYYCAKGITTVVDDYYAMDYWGQGTSVTVSSGG<br>GGSGGGGSGGGGSGGGGSDIQMTQSPASLSASVGETVTIT<br>CRASENIDSYLAWYQQKQGKSPQLLVYAATFLADDVPSRFS<br>GSGSGTQYSLKINSLQSEDVARYYCQHYYSTPYTFGCGTKL<br>EIKGGGGSVHMPLGFLGPRQARVVNGGGGSGGGGSQAV<br>VTQEPSLTVSPGGTVTLTCGSSTGAVTTSNYANWVQEKPG<br>QAFRGLIGGTNKRAPGTPARFSGSLLGGKAALTLSGAQPED<br>EAEYYCALWYSNLWVFGGGTKLTVLSSASTKGPSVFPLAPS<br>SKSTSGGTAALGCLVKDYFPEPVTVSWNSGALTSGVHTFPA<br>VLQSSGLYSLSSVVTVPSSSLGTQTYICNVNHKPSNTKVDKK<br>VEPKSCDGGGGSGGGGSEVQLVESGGGLVQPGGSLRLSC<br>AASGFNIKDTYIHWVRQAPGKGLEWVARIYPTNGYTRYADS<br>VKGRFTISADTSKNTAYLQMNSLRAEDTAVYYCSRWGGEGF<br>YAMDYWGQGTLVTVSSASTKGPSVFPLAPSSKSTSGGTAAL<br>GCLVEDYFPEPVTVSWNSGALTSGVHTFPAVLQSSGLYSLS<br>SVVTVPSSSLGTQTYICNVNHKPSNTKVDEKVEPKSCDKTHT<br>CPPCPAPEAAGGPSVFLFPPKPKDTLMISRTPEVTCVVVDVS<br>HEDPEVKFNWYVDGVEVHNAKTKPREEQYNSTYRVVSVLT<br>VLHQDWLNGKEYKCKVSNKALGAPIEKTISKAKGQPREPQV<br>YTLPPCRDELTKNQVSLWCLVKGFYPSDIAVEWESNGQPEN<br>NYKTTPPVLDSDGSFFLYSKLTVDKSRWQQGNVFSCSVMH<br>EALHNHYTQKSLSLSPGK | 136 |
| FolR1 36F2 VH CH1 EE<br>Fc hole PG LALA<br>pETR14797 | QVQLVQSGAEVKKPGASVKVSCKASGYTFTSYYMHWVRQA<br>PGQGLEWMGIINPSGGSTYAQKFQGRVTMTHDTSTSTVY<br>MELSSLRSEDTAVYYCARSFFTGFHLDYWGQGTLVTVSSAS<br>TKGPSVFPLAPSSKSTSGGTAALGCLVEDYFPEPVTVSWNS<br>GALTSGVHTFPAVLQSSGLYSLSSVVTVPSSSLGTQTYICNV<br>NHKPSNTKVDEKVEPKSCDKTHTCPPCPAPEAAGGPSVFLF<br>PPKPKDTLMISRTPEVTCVVVDVSHEDPEVKFNWYVDGVEV<br>HNAKTKPREEQYNSTYRVVSVLTVLHQDWLNGKEYKCKVS<br>NKALGAPIEKTISKAKGQPREPQVCTLPPSRDELTKNQVSLS<br>CAVKGFYPSDIAVEWESNGQPENNYKTTPPVLDSDGSFFLV<br>SKLTVDKSRWQQGNVFSCSVMHEALHNHYTQKSLSLSPGK | 137 |
| FolR1 36F2 VL Ck RK,<br>pETR14798 | EIVLTQSPGTLSLSPGERATLSCRASQSVSSSYLAWYQQKP<br>GQAPRLLIYGASSRATGIPDRFSGSGSGTDFTLTISRLEPEDF<br>AVYYCQQYTNEHYYTFGQGTKVEIKRTVAAPSVFIFPPSDRK<br>LKSGTASVVCLLNNFYPREAKVQWKVDNALQSGNSQESVTE<br>QDSKDSTYSLSSTLTLSKADYEKHKVYACEVTHQGLSSPVTK<br>SFNRGEC | 138 |
| anti CD3 (CH2527<br>VH_3-23(12) VL7-<br>46(13)) scFv 4.32.63<br>MMP9 Matriptase<br>MK062 aFolR1 36F2<br>VH CH1 EE 0H2527-<br>VL7_46-13 CH1 hum Fc<br>knob PG LALA<br>pETR17621 | QVQLKESGPGLVAPSQSLSITCTVSGFSLTSYGVSWVRQPP<br>GKCLEWLGIIWGDGSTNYHSALISRLSISKDNSKSQVFLKLNS<br>LQTDDTATYYCAKGITTVVDDYYAMDYWGQGTSVTVSSGG<br>GGSGGGGSGGGGSGGGGSDIQMTQSPASLSASVGETVTIT<br>CRASENIDSYLAWYQQKQGKSPQLLVYAATFLADDVPSRFS<br>GSGSGTQYSLKINSLQSEDVARYYCQHYYSTPYTFGCGTKL<br>EIKGGGGSVHMPLGFLGPRQARVVNGGGGSGGGGSQAV<br>VTQEPSLTVSPGGTVTLTCGSSTGAVTTSNYANWVQEKPG<br>QAFRGLIGGTNKRAPGTPARFSGSLLGGKAALTLSGAQPED<br>EAEYYCALWYSNLWVFGGGTKLTVLSSASTKGPSVFPLAPS<br>SKSTSGGTAALGCLVKDYFPEPVTVSWNSGALTSGVHTFPA<br>VLQSSGLYSLSSVVTVPSSSLGTQTYICNVNHKPSNTKVDKK<br>VEPKSCDGGGGSGGGGSQVQLVQSGAEVKKPGASVKVSC<br>KASGYTFTSYYMHWVRQAPGQGLEWMGIINPSGGSTYAQ<br>KFQGRVTMTHDTSTSTVYMELSSLRSEDTAVYYCARSFFTG<br>FHLDYWGQGTLVTVSSASTKGPSVFPLAPSSKSTSGGTAAL<br>GCLVEDYFPEPVTVSWNSGALTSGVHTFPAVLQSSGLYSLS<br>SVVTVPSSSLGTQTYICNVNHKPSNTKVDEKVEPKSCDKTHT<br>CPPCPAPEAAGGPSVFLFPPKPKDTLMISRTPEVTCVVVDVS<br>HEDPEVKFNWYVDGVEVHNAKTKPREEQYNSTYRVVSVLT<br>VLHQDWLNGKEYKCKVSNKALGAPIEKTISKAKGQPREPQV<br>YTLPPCRDELTKNQVSLWCLVKGFYPSDIAVEWESNGQPEN<br>NYKTTPPVLDSDGSFFLYSKLTVDKSRWQQGNVFSCSVMH<br>EALHNHYTQKSLSLSPGK | 139 |
| anti CD3 (CH2527<br>VH_3-23(12) VL7-<br>46(13)) scFv 4.32.63<br>non cleavable linker<br>aFolR1 36F2 VH CH1<br>EE CH2527-VL7_46-13 | QVQLKESGPGLVAPSQSLSITCTVSGFSLTSYGVSWVRQPP<br>GKCLEWLGIIWGDGSTNYHSALISRLSISKDNSKSQVFLKLNS<br>LQTDDTATYYCAKGITTVVDDYYAMDYWGQGTSVTVSSGG<br>GGSGGGGSGGGGSGGGGSDIQMTQSPASLSASVGETVTIT<br>CRASENIDSYLAWYQQKQGKSPQLLVYAATFLADDVPSRFS<br>GSGSGTQYSLKINSLQSEDVARYYCQHYYSTPYTFGCGTKL | 140 |

| | | |
|---|---|---|
| CH1 hum Fc knob PG LALA pETR17622 | EIKGGGGSGGGGSGGGGSGGGGGGSGGGGSGGGGSQ AVVTQEPSLTVSPGGTVTLTCGSSTGAVTTSNYANWVQEKP GQAFRGLIGGTNKRAPGTPARFSGSLLGGKAALTLSGAQPE DEAEYYCALWYSNLWVFGGGTKLTVLSSASTKGPSVFPLAP SSKSTSGGTAALGCLVKDYFPEPVTVSWNSGALTSGVHTFP AVLQSSGLYSLSSVVTVPSSSLGTQTYICNVNHKPSNTKVDK KVEPKSCDGGGGSGGGGSQVQLVQSGAEVKKPGASVKVS CKASGYTFTSYYMHWVRQAPGQGLEWMGIINPSGGSTSYA QKFQGRVTMTHDTSTSTVYMELSSLRSEDTAVYYCARSFFT GFHLDYWGQGTLVTVSSASTKGPSVFPLAPSSKSTSGGTAA LGCLVEDYFPEPVTVSWNSGALTSGVHTFPAVLQSSGLYSL SSVVTVPSSSLGTQTYICNVNHKPSNTKVDEKVEPKSCDKTH TCPPCPAPEAAGGPSVFLFPPKPKDTLMISRTPEVTCVVVDV SHEDPEVKFNWYVDGVEVHNAKTKPREEQYNSTYRVVSVL TVLHQDWLNGKEYKCKVSNKALGAPIEKTISKAKGQPREPQ VYTLPPCRDELTKNQVSLWCLVKGFYPSDIAVEWESNGQPE NNYKTTPPVLDSDGSFFLYSKLTVDKSRWQQGNVFSCSVM HEALHNHYTQKSLSLSPGK | |
| FolR1 36F2 classic format: CH2527 XFab 36F2 HC EE Fc knob PG LALA pETR17623 | QAVVTQEPSLTVSPGGTVTLTCGSSTGAVTTSNYANWVQEK PGQAFRGLIGGTNKRAPGTPARFSGSLLGGKAALTLSGAQP EDEAEYYCALWYSNLWVFGGGTKLTVLSSASTKGPSVFPLA PSSKSTSGGTAALGCLVKDYFPEPVTVSWNSGALTSGVHTF PAVLQSSGLYSLSSVVTVPSSSLGTQTYICNVNHKPSNTKVD KKVEPKSCDGGGGSGGGGSQVQLVQSGAEVKKPGASVK VSCKASGYTFTSYYMHWVRQAPGQGLEWMGIINPSGGSTSY AQKFQGRVTMTHDTSTSTVYMELSSLRSEDTAVYYCARSFF TGFHLDYWGQGTLVTVSSASTKGPSVFPLAPSSKSTSGGTA ALGCLVEDYFPEPVTVSWNSGALTSGVHTFPAVLQSSGLYS LSSVVTVPSSSLGTQTYICNVNHKPSNTKVDEKVEPKSCDKT HTCPPCPAPEAAGGPSVFLFPPKPKDTLMISRTPEVTCVVVD VSHEDPEVKFNWYVDGVEVHNAKTKPREEQYNSTYRVVSV LTVLHQDWLNGKEYKCKVSNKALGAPIEKTISKAKGQPREPQ VYTLPPCRDELTKNQVSLWCLVKGFYPSDIAVEWESNGQPE NNYKTTPPVLDSDGSFFLYSKLTVDKSRWQQGNVFSCSVM HEALHNHYTQKSLSLSPGK | 141 |
| Herceptin/Omnitarg CDR H1 Kabat | DYTMD | 142 |
| Herceptin/Omnitarg CDR H2 Kabat | DVNPNSGGSIVNRRFKG | 143 |
| Herceptin/Omnitarg CDR H3 Kabat | NLGPFFYFDY | 144 |
| Perjeta CDR H1 Kabat | TSNYANW | 145 |
| Perjeta CDR H2 Kabat | GTNKRAPGTPARFSGSLLGG | 146 |
| Perjeta CDR H3 Kabat | TKLTV | 147 |
| CLC CDR L1 Kabat | KASQDVSTAVA | 148 |
| CLC CDR L2 Kabat | SASFRYT | 149 |
| CLC CDR L3 Kabat | QQHYTTPPT | 150 |
| 36F2 CDR H1 Kabat | SYYMH | 151 |
| 36F2 CDR H2 Kabat | IINPSGGSTSYAQKFQG | 152 |
| 36F2 CDR H3 Kabat | SFFTGFHLDY | 153 |
| 36F2 CDR L1 Kabat | RASQSVSSSYLA | 154 |
| 36F2 CDR L2 Kabat | GASSRAT | 155 |
| 36F2 CDR L3 Kabat | QQYTNEHYYT | 156 |
| Anti-FolR1 36F2 variable region VH | QVQLVQSGAEVKKPGASVKVSCKASGYTFTSYYMHWVRQA PGQGLEWMGIINPSGGSTSYAQKFQGRVTMTHDTSTSTVY MELSSLRSEDTAVYYCARSFFTGFHLDYWGQGTLVTVSS | 157 |
| Anti-FolR1 36F2 variable region VL | EIVLTQSPGTLSLSPGERATLSCRASQSVSSSYLAWYQQKP GQAPRLLIYGASSRATGIPDRFSGSGSGTDFTLTISRLEPEDF AVYYCQQYTNEHYYTFGQGTKVEIK | 158 |

| | | SEQ ID No |
|---|---|---|
| Herceptarg variable region VH1 | EVQLVESGGGLVQPGGSLRLSCAASGFTFNDYTMDWVRQA PGKGLEWVADVNPNSGGSIVNRRFKGRFTLSVDRSKNTLYL QMNSLRAEDTAVYYCARNLGPFFYFDYWGQGTLVTVSS | 159 |
| Herceptarg variable region VH2 | EVQLVESGGGLVQPGGSLRLSCAASGFNIKDTYIHWVRQAP GKGLEWVARIYPTNGYTRYADSVKGRFTISADTSKNTAYLQ MNSLRAEDTAVYYCSRWGGEGFYAMDYWGQGTLVTVSS | 160 |
| Herceptarg common variable region VL | DIQMTQSPSSLSASVGDRVTITCKASQDVSTAVAWYQQKPG KAPKLLIYSASFRYTGVPSRFSGSRSGTDFTLTISSLQPEDFA TYYCQQHYTTPPTFGQGTKVEIK | 161 |

| Construct | DNA Sequence | SEQ ID No |
|---|---|---|
| pETR16859 Omnitarg aff.mat variant Fab cv - Fc hole PG LALA | GAAGTTCAGCTGGTTGAAAGCGGTGGTGGTCTGGTTCAGCCTGGT GGTAGCCTGCGTCTGAGCTGTGCAGCAAGCGGTTTTACCTTTAACG ATTATACCATGGATTGGGTTCGTCAGGCACCGGGTAAAGGTCTGGA ATGGGTTGCAGATGTTAATCCGAATAGCGGTGGTAGCATTGTTAAC CGTCGTTTTAAAGGTCGTTTTACCCTGAGCGTTGATCGTAGCAAAA ATACCCTGTATCTGCAAATGAATAGTCTGCGTGCAGAGGATACCGC AGTGTATTATTGTGCACGTAACCTGGGTCCGTTCTTCTACTTTGATT ATTGGGGTCAGGGCACCCTGGTTACCGTTAGCAGCGCTAGCACCA AGGGCCCCTCCGTGTTCCCCCTGGCCCCCAGCAGCAAGAGCACCA GCGGCGGCACAGCCGCTCTGGGCTGCCTGGTCGAGGACTACTTC CCCGAGCCCGTGACCGTGTCCTGGAACAGCGGAGCCCTGACCTCC GGCGTGCACACCTTCCCCGCCGTGCTGCAGAGTTCTGGCCTGTAT AGCCTGAGCAGCGTGGTCACCGTGCCTTCTAGCAGCCTGGGCACC CAGACCTACATCTGCAACGTGAACCACAAGCCCAGCAACACCAAG GTGGACGAGAAGGTGGAGCCCAAGAGCTGCGACAAAACTCACACA TGCCCACCGTGCCCAGCACCTGAAGCTGCAGGGGACCGTCAGTC TTCCTCTTCCCCCCAAAACCCAAGGACACCCTCATGATCTCCCGGA CCCCTGAGGTCACATGCGTGGTGGTGGACGTGAGCCACGAAGACC CTGAGGTCAAGTTCAACTGGTACGTGGACGGCGTGGAGGTGCATA ATGCCAAGACAAAGCCGCGGGAGGAGCAGTACAACAGCACGTACC GTGTGGTCAGCGTCCTCACCGTCCTGCACCAGGACTGGCTGAATG GCAAGGAGTACAAGTGCAAGGTCTCCAACAAAGCCCTCGGCGCCC CCATCGAGAAAACCATCTCCAAAGCCAAAGGGCAGCCCCGAGAAC CACAGGTGTGCACCCTGCCCCCATCCCGGGATGAGCTGACCAAGA ACCAGGTCAGCCTCTCGTGCGCAGTCAAAGGCTTCTATCCCAGCG ACATCGCCGTGGAGTGGGAGAGCAATGGGCAGCCGGAGAACAACT ACAAGACCACGCCTCCCGTGCTGGACTCCGACGGCTCCTTCTTCC TCGTGAGCAAGCTCACCGTGGACAAGAGCAGGTGGCAGCAGGGG AACGTCTTCTCATGCTCCGTGATGCATGAGGCTCTGCACAACCACT ACACGCAGAAGAGCCTCTCCCTGTCTCCGGGTAAATGA | 162 |
| pETR16860 Herceptarg common CLkRK | GACATCCAGATGACCCAGAGCCCCAGCAGCCTGTCTGCCAGCGTG GGCGACAGAGTGACCATCACATGCAAGGCCAGCCAGGACGTGTCC ACAGCCGTGGCCTGGTATCAGCAGAAGCCTGGCAAGGCCCCCAAG CTGCTGATCTACAGCGCCAGCTTCCGGTACACCGGCGTGCCCAGC AGATTCAGCGGCAGCAGATCCGGCACCGACTTCACCCTGACCATC AGCTCCCTGCAGCCCGAGGACTTCGCCACCTACTACTGCCAGCAG CACTACACCACCCCCCCCACATTTGGCCAGGGCACCAAGGTGGAA ATCAAGCGTACGGTGGCTGCACCATCTGTCTTCATCTTCCCGCCAT CTGATCGGAAGTTGAAATCTGGAACTGCCTCTGTTGTGTGCCTGCT GAATAACTTCTATCCCAGAGAGGCCAAAGTACAGTGGAAGGTGGAT AACGCCCTCCAATCGGGTAACTCCCAGGAGAGTGTCACAGAGCAG GACAGCAAGGACAGCACCTACAGCCTCAGCAGCACCCTGACGCTG AGCAAAGCAGACTACGAGAAACACAAAGTCTACGCCTGCGAAGTCA CCCATCAGGGCCTGAGCTCGCCCGTCACAAAGAGCTTCAACAGGG GAGAGTGTTAG | 163 |
| pETR17606 anti CD3 (CH2527 VH_3-23(12) VL7-46(13)) scFv 4.32.63 non cleavable linker aHerceptin VH CH1 EE CH2527- VL7_46-13 CH1 hum Fc knob PG LALA | CAAGTGCAGCTGAAAGAGTCCGGCCCTGGACTGGTGGCCCCTAGC CAGAGCCTGAGCATCACCTGTACCGTGTCCGGCTTCAGCCTGACC AGCTACGGCGTGTCATGGGTGCGCCAGCCTCCAGGCAAGTGTCTG GAATGGCTGGGCATCATCTGGGGCGACGGCAGCACCAATTACCAC AGCGCCCTGATCAGCAGACTGAGCATCTCCAAGGACAACAGCAAG AGCCAGGTGTTCCTGAAGCTGAACAGCCTGCAGACCGACGACACC GCCACCTACTACTGCGCCAAGGGCATCACCACCGTGGTGGACGAC TACTACGCTATGGACTACTGGGGCCAGGGCACCAGCGTGACAGTG TCTAGCGGAGGCGGAGGATCTGGCGGCGGAGGAAGTGGCGGAGG GGATCTGGGGAGGCGGAAGCGATATCCAGATGACCCAGAGCC CTGCCAGCCTGTCTGCCTCTGTGGGCGAGACAGTGACCATCACAT GCGGGCCAGCGAGAACATCGACAGCTACCTGGCCTGGTATCAGC AGAAGCAGGGCAAGAGCCCCAGCTGCTGGTGTACGCCGCCACCT TTCTGGCCGACGATGTGCCCAGCAGATTCAGCGGCAGCGGAAGCG GCACACAGTACAGCCTGAAGATCAACTCCCTGCAGAGCGAGGACA TGGCCCCGGTACTACTGCCAGCACTACTACAGCACCCCCTACACCTT | 164 |

-continued

```
                      CGGCTGCGGCACCAAGCTGGAAATCAAAGGCGGGGGAGGCTCCG
                      GAGGCGGCGGAAGTGGAGGCGGCGGAAGTGGCGGAGGCGGAGG
                      GGGGGGAAGTGGGGGCGGAGGCAGTGGGGGGGGAGGATCCCAG
                      GCCGTCGTGACCCAGGAACCCAGCCTGACAGTGTCTCCTGGCGGC
                      ACCGTGACCCTGACATGTGGCAGTTCTACAGGCGCCGTGACCACC
                      AGCAACTACGCCAACTGGGTGCAGGAAAAGCCCGGCCAGGCCTTC
                      AGAGGACTGATCGGCGGCACCAACAAGAGAGCCCCTGGCACCCCT
                      GCCAGATTCAGCGGATCTCTGCTGGGAGGAAAGGCCGCCCTGACA
                      CTGTCTGGCGCCCAGCCAGAAGATGAGGCCGAGTACTACTGCGCC
                      CTGTGGTACAGCAACCTGTGGGTGTTCGGCGGAGGCACCAAGCTG
                      ACAGTGCTGAGCAGCGCTTCCACCAAGGGACCCAGTGTGTTCCCC
                      CTGGCCCCAGCTCCAAGTCTACATCCGGTGGCACAGCTGCCCTG
                      GGATGTCTCGTGAAGGACTACTTTCCTGAGCCTGTGACAGTGTCTT
                      GGAACAGCGGAGCCCTGACCAGCGGAGTGCACACATTCCCTGCAG
                      TGCTGCAGAGCAGCGGCCTGTATAGCCTGAGCAGCGTCGTGACCG
                      TGCCTTCCTCTAGCCTGGGAACACAGACATATATCTGTAATGTGAAT
                      CATAAGCCCAGTAATACCAAAGTGGATAAGAAAGTGGAACCTAAGA
                      GCTGCGATGGCGGAGGAGGGTCCGGAGGCGGAGGGTCCGAGGT
                      CCAGCTGGTCGAGTCTGGAGGAGGACTGGTGCAGCCAGGCGGAT
                      CTCTGAGACTGAGCTGCGCCGCCAGCGGATTCAACATCAAGGACA
                      CCTACATCCACTGGGTGAGGCAGGCCCCTGGAAAGGGACTGGAGT
                      GGGTGGCCAGAATCTACCCCACCAACGGCTACAAGATACGCCG
                      ACAGCGTGAAGGGCAGATTCACCATCAGCGCCGACACCAGCAAGA
                      ACACCGCCTACCTGCAGATGAACAGCCTGAGAGCCGAGGACACAG
                      CCGTGTACTACTGCTCTAGATGGGGAGGCGAGGGCTTCTACGCCA
                      TGGACTACTGGGGACAGGGCACACTGGTGACCGTGTCCAGCGCTA
                      GCACCAAGGGCCCCTCCGTGTTCCCCCTGGCCCCAGCAGCAAGA
                      GCACCAGCGGCGGCACAGCCGCTCTGGGCTGCCTGGTCGAGGAC
                      TACTTCCCCGAGCCCGTGACCGTGTCCTGGAACAGCGGAGCCCTG
                      ACCTCCGGCGTGCACACCTTCCCCGCCGTGCTGCAGAGTTCTGGC
                      CTGTATAGCCTGAGCAGCGTGGTCACCGTGCCTTCTAGCAGCCTG
                      GGCACCCAGACCTACATCTGCAACGTGAACCACAAGCCCAGCAAC
                      ACCAAGGTGGACGAGAAGGTGGAGCCCAAGAGCTGCGACAAAACT
                      CACACACATGCCCACCGTGCCCAGCACCTGAAGCTGCAGGGGGACC
                      GTCAGTCTTCCTCTTCCCCCCAAAACCCAAGGACACCCTCATGATC
                      TCCCGGACCCCTGAGGTCACATGCGTGGTGGTGGACGTGAGCCAC
                      GAAGACCCTGAGGTCAAGTTCAACTGGTACGTGGACGGCGTGGAG
                      GTGCATAATGCCAAGACAAAGCCGCGGGAGGAGCAGTACAACAGC
                      ACGTACCGTGTGGTCAGCGTCCTCACCGTCCTGCACCAGGACTGG
                      CTGAATGGCAAGGAGTACAAGTGCAAGGTCTCCAACAAAGCCCTC
                      GGCGCCCCCATCGAGAAAACCATCTCCAAAGCCAAAGGGCAGCCC
                      CGAGAACCACAGGTGTACACCCTGCCCCCATGCCGGGATGAGCTG
                      ACCAAGAACCAGGTCAGCCTGTGGTGCCTGGTCAAAGGCTTCTATC
                      CCAGCGACATCGCCGTGGAGTGGGAGAGCAATGGGCAGCCGGAG
                      AACAACTACAAGACCACGCCTCCCGTGCTGGACTCCGACGGCTCC
                      TTCTTCCTCTACAGCAAGCTCACCGTGGACAAGAGCAGGTGGCAG
                      CAGGGGAACGTCTTCTCATGCTCCGTGATGCATGAGGCTCTGCAC
                      AACCACTACACGCAGAAGAGCCTCTCCCTGTCTCCGGGTAAATGA
```

| pETR17607 | CAAGTGCAGCTGAAAGAGTCCGGCCCTGGACTGGTGGCCCCCTAGC | 165 |
|---|---|---|
| anti CD3 | CAGAGCCTGAGCATCACCTGTACCGTGTCCGGCTTCAGCCTGACC | |
| (CH2527 | AGCTACGGCGTGTCATGGGTGCGCCAGCCTCCAGGCAAGTGTCTG | |
| VH_3-23(12) | GAATGGCTGGGCATCATCTGGGGCGACGGCAGCACCAATTACCAC | |
| VL7-46(13)) | AGCGCCCTGATCAGCAGACTGAGCATCTCCAAGGACAACAGCAAG | |
| scFv 4.32.63 | AGCCAGGTGTTCCTGAAGCTGAACAGCCTGCAGACCGACGACACC | |
| MMP9 | GCCACCTACTACTGCGCCAAGGGCATCACCACCGTGGTGGACGAC | |
| Matriptase | TACTACGCTATGGACTACTGGGGCCAGGGCACCAGCGTGACAGTG | |
| MK062 | TCTAGCGGAGGCGGAGGATCTGGCGGCGGAGGAAGTGGCGGAGG | |
| aHerceptin VH | GGGATCTGGGGAGGCGGAAGCGATATCCAGATGACCCAGAGCC | |
| CH1 EE | CTGCCAGCCTGTCTGCCTCTGTGGGCGAGACAGTGACCATCACAT | |
| CH2527- | GCCGGGCCAGCGAGAACATCGACAGCTACCTGGCCTGGTATCAGC | |
| VL7_46-13 | AGAAGCAGGGCAAGAGCCCCCAGCTGCTGGTATACGCCGCCACCT | |
| CH1 hum Fc | TTCTGGCCGACGATGTGCCCAGCAGATTCAGCGGCAGCGGAAGCG | |
| knob PG | GCACACAGTACAGCCTGAAGATCAACTCCCTGCAGAGCGAGGACG | |
| LALA | TGGCCCGGTACTACTGCCAGCACTACTACAGCACCCCTACACCTT | |
| | CGGCTGCGGCACCAAGCTGGAAATCAAAGGAGGCGGCGGAAGTG | |
| | TGCACATGCCCCTGGGCTTCCTGGGCCCCAGACAGGCCAGAGTCG | |
| | TGAACGGGGGGGCGGAGGCAGTGGGGGGGGAGGATCCCAGGC | |
| | CGTCGTGACCCAGGAACCCAGCCTGACAGTGTCTCCTGGCGGCAC | |
| | CGTGACCCTGACATGTGGCAGTTCTACAGGCGCCGTGACCACCAG | |
| | CAACTACGCCAACTGGGTGCAGGAAAAGCCCGGCCAGGCCTTCAG | |
| | AGGACTGATCGGCGGCACCAACAAGAGAGCCCCTGGCACCCCTGC | |
| | CAGATTCAGCGGATCTCTGCTGGGAGGAAAGGCCGCCCTGACACT | |
| | GTCTGGCGCCCAGCCAGAAGATGAGGCCGAGTACTACTGCGCCCT | |
| | GTGGTACAGCAACCTGTGGGTGTTCGGCGGAGGCACCAAGCTGAC | |
| | AGTGCTGAGCAGCGCTTCCACCAAGGGACCCAGTGTGTTCCCCCT | |
| | GGCCCCAGCTCCAAGTCTACATCCGGTGGCACAGCTGCCCTGGG | |
| | ATGTCTCGTGAAGGACTACTTTCCTGAGCCTGTGACAGTGTCTTGG | |
| | AACAGCGGAGCCCTGACCAGCGGAGTGCACACATTCCCTGCAGTG | |

| | | |
|---|---|---|
| | CTGCAGAGCAGCGGCCTGTATAGCCTGAGCAGCGTCGTGACCGTG<br>CCTTCCTCTAGCCTGGGAACACAGACATATATCTGTAATGTGAATCA<br>TAAGCCCAGTAATACCAAAGTGGATAAGAAAGTGGAACCTAAGAGC<br>TGCGATGGCGGAGGAGGGTCCGGAGGCGGAGGGTCCGAGGTCCA<br>GCTGGTCGAGTCTGGAGGAGGACTGGTGCAGCCAGGCGGATCTCT<br>GAGACTGAGCTGCGCCGCCAGCGGATTCAACATCAAGGACACCTA<br>CATCCACTGGGTGAGGCAGGCCCCTGGAAAGGGACTGGAGTGGG<br>TGGCCAGAATCTACCCCACCAACGGCTACACAAGATACGCCGACA<br>GCGTGAAGGGCAGATTCACCATCAGCGCCGACACCAGCAAGAACA<br>CCGCCTACCTGCAGATGAACAGCCTGAGAGCCGAGGACACAGCCG<br>TGTACTACTGCTCTAGATGGGGAGGCGAGGGCTTCTACGCCATGG<br>ACTACTGGGGACAGGGCACACTGGTGACCGTGTCCAGCGCTAGCA<br>CCAAGGGCCCCTCCGTGTTCCCCCTGGCCCCCAGCAGCAAGAGCA<br>CCAGCGGCGGCACAGCCGCTCTGGGCTGCCTGGTCGAGGACTAC<br>TTCCCCGAGCCCGTGACCGTGTCCTGGAACAGCGGAGCCCTGACC<br>TCCGGCGTGCACACCTTCCCCGCCGTGCTGCAGAGTTCTGGCCTG<br>TATAGCCTGAGCAGCGTGGTCACCGTGCCTTCTAGCAGCCTGGGC<br>ACCCAGACCTACATCTGCAACGTGAACCACAAGCCCAGCAACACCA<br>AGGTGGACGAGAAGGTGGAGCCCAAGAGCTGCGACAAAACTCACA<br>CATGCCCACCGTGCCCAGCACCTGAAGCTGCAGGGGGACCGTCA<br>GTCTTCCTCTTCCCCCCAAAACCCAAGGACACCCTCATGATCTCCC<br>GGACCCCTGAGGTCACATGCGTGGTGGTGGACGTGAGCCACGAA<br>GACCCTGAGGTCAAGTTCAACTGGTACGTGGACGGCGTGGAGGTG<br>CATAATGCCAAGACAAAGCCGCGGGAGGAGCAGTACAACAGCACG<br>TACCGTGTGGTCAGCGTCCTCACCGTCCTGCACCAGGACTGGCTG<br>AATGGCAAGGAGTACAAGTGCAAGGTCTCCAACAAAGCCCTCGGC<br>GCCCCCATCGAGAAAACCATCTCCAAAGCCAAAGGGCAGCCCCGA<br>GAACCACAGGTGTACACCCTGCCCCCATGCCGGGATGAGCTGACC<br>AAGAACCAGGTCAGCCTGTGGTGCCTGGTCAAAGGCTTCTATCCCA<br>GCGACATCGCCGTGGAGTGGGAGAGCAATGGGCAGCCGGAGAAC<br>AACTACAAGACCACGCCTCCCGTGCTGGACTCCGACGGCTCCTTC<br>TTCCTCTACAGCAAGCTCACCGTGGACAAGAGCAGGTGGCAGCAG<br>GGGAACGTCTTCTCATGCTCCGTGATGCATGAGGCTCTGCACAACC<br>ACTACACGCAGAAGAGCCTCTCCCTGTCTCCGGGTAAATGA | |
| FolR1 36F2<br>VH CH1 EE<br>Fc hole PG<br>LALA<br>pETR14797 | CAGGTGCAATTGGTTCAATCGGTGCTGAAGTAAAAAAACCGGGCG<br>CTTCCGTTAAAGTGAGCTGCAAAGCATCCGGATACACCTTCACTTC<br>CTATTACATGCACTGGGTTCGTCAAGCCCCGGGCCAGGGTCTGGA<br>ATGGATGGGCATCATTAACCCAAGCGGTGGCTCTACCTCCTACGC<br>GCAGAAATTCCAGGGTCGCGTCACGATGACCCATGACACTAGCAC<br>CTCTACCGTTTATATGGAGCTGTCCAGCCTGCGTTCTGAAGATACT<br>GCAGTGTACTACTGTGCACGCTCTTTCTTCACTGGTTTCCATCTGG<br>ACTATTGGGGTCAAGGCACCCTCGTAACGGTTTCTTCTGCTAGCAC<br>CAAGGGCCCCTCCGTGTTCCCCCTGGCCCCCAGCAGCAAGAGCAC<br>CAGCGGCGGCACAGCCGCTCTGGGCTGCCTGGTCGAGGACTACTT<br>CCCCGAGCCCGTGACCGTGTCCTGGAACAGCGGAGCCCTGACCTC<br>CGGCGTGCACACCTTCCCCGCCGTGCTGCAGAGTTCTGGCCTGTA<br>TAGCCTGAGCAGCGTGGTCACCGTGCCTTCTAGCAGCCTGGGCAC<br>CCAGACCTACATCTGCAACGTGAACCACAAGCCCAGCAACACCAA<br>GGTGGACGAGAAGGTGGAGCCCAAGAGCTGCGACAAAACTCACAC<br>ATGCCCACCGTGCCCAGCACCTGAAGCTGCAGGGGGACCGTCAGT<br>CTTCCTCTTCCCCCCAAAACCCAAGGACACCCTCATGATCTCCCGG<br>ACCCCTGAGGTCACATGCGTGGTGGTGGACGTGAGCCACGAAGAC<br>CCTGAGGTCAAGTTCAACTGGTACGTGGACGGCGTGGAGGTGCAT<br>AATGCCAAGACAAAGCCGCGGGAGGAGCAGTACAACAGCACGTAC<br>CGTGTGGTCAGCGTCCTCACCGTCCTGCACCAGGACTGGCTGAAT<br>GGCAAGGAGTACAAGTGCAAGGTCTCCAACAAAGCCCTCGGCGCC<br>CCCATCGAGAAAACCATCTCCAAAGCCAAAGGGCAGCCCCGAGAA<br>CCACAGGTGTGCACCCTGCCCCCATCCCGGGATGAGCTGACCAAG<br>AACCAGGTCAGCCTCTCGTGCGCAGTCAAAGGCTTCTATCCCAGC<br>GACATCGCCGTGGAGTGGGAGAGCAATGGGCAGCCGGAGAACAA<br>CTACAAGACCACGCCTCCCGTGCTGGACTCCGACGGCTCCTTCTT<br>CCTCGTGAGCAAGCTCACCGTGGACAAGAGCAGGTGGCAGCAGG<br>GGAACGTCTTCTCATGCTCCGTGATGCATGAGGCTCTGCACAACCA<br>CTACACGCAGAAGAGCCTCTCCCTGTCTCCGGGTAAATGA | 166 |
| FolR1 36F2<br>VL Ck RK,<br>pETR14798 | GAAATCGTGTTAACGCAGTCTCCAGGCACCCTGTCTTTGTCTCCAG<br>GGGAAAGAGCCACCCTCTCTTGCAGGGCCAGTCAGAGTGTTAGCA<br>GCAGCTACTTAGCCTGGTACCAGCAGAAACCTGGCCAGGCTCCCA<br>GGCTCCTCATCTATGGAGCATCCAGCAGGGCCACTGGCATCCCAG<br>ACAGGTTCAGTGGCAGTGGATCCGGGACAGACTTCACTCTCACCAT<br>CAGCAGACTGGAGCCTGAAGATTTTGCAGTGTATTACTGTCAGCAG<br>TATACCAACGAACATTATTATACGTTCGGCCAGGGGACCAAAGTGG<br>AAATCAAACGTACGGTGGCTGCACCATCTGTCTTCATCTTCCCGCC<br>ATCTGATCGGAAGTTGAAATCTGGAACTGCCTCTGTTGTGTGCCTG<br>CTGAATAACTTCTATCCCAGAGAGGCAAAGTACAGTGGAAGGTGG<br>ATAACGCCCTCCAATCGGGTAACTCCCAGGAGAGTGTCACAGAGC<br>AGGACAGCAAGGACAGCACCTACAGCCTCAGCAGCACCCTGACGC<br>TGAGCAAAGCAGACTACGAGAAACACAAAGTCTACGCCTGCGAAGT | 167 |

| | | |
|---|---|---|
| | CACCCATCAGGGCCTGAGCTCGCCCGTCACAAAGAGCTTCAACAG<br>GGGAGAGTGTTAG | |
| anti CD3<br>(CH2527<br>VH_3-23(12)<br>VL7-46(13))<br>scFv 4.32.63<br>MMP9<br>Matriptase<br>MK062<br>aFolR1 36F2<br>VH CH1 EE<br>CH2527-<br>VL7_46-13<br>CH1 hum Fc<br>knob PG<br>LALA<br>pETR17621 | CAAGTGCAGCTGAAAGAGTCCGGCCCTGGACTGGTGGCCCCTAGC<br>CAGAGCCTGAGCATCACCTGTACCGTGTCCGGCTTCAGCCTGACC<br>AGCTACGGCGTGTCATGGGTGCGCCAGCCTCCAGGCAAGTGTCTG<br>GAATGGCTGGGCATCATCTGGGGCGACGGCAGCACCAATTACCAC<br>AGCGCCCTGATCAGCAGACTGAGCATCTCCAAGGACAACAGCAAG<br>AGCCAGGTGTTCCTGAAGCTGAACAGCCTGCAGACCGACGACACC<br>GCCACCTACTACTGCGCCAAGGGCATCACCACCGTGGTGGACGAC<br>TACTACGCTATGGACTACTGGGGCCAGGGCACCAGCGTGACAGTG<br>TCTAGCGGAGGCGGAGGATCTGGCGGCGGAGGAAGTGGCGGAGG<br>GGGATCTGGGGGAGGCGGAAGCGATATCCAGATGACCCAGAGCC<br>CTGCCAGCCTGTCTGCCTCTGTGGGCGAGACAGTGACCATCACAT<br>GCCGGGCCAGCGAGAACATCGACAGCTACCTGGCCTGGTATCAGC<br>AGAAGCAGGGCAAGAGCCCCAGCTGCTGGTGTACGCCGCCACCT<br>TTCTGGCCGACGATGTGCCCAGCAGATTCAGCGGCAGCGGAAGCG<br>GCACAGACTACAGCCTGAAGATCAACTCCCTGCAGAGCGAGGACG<br>TGGCCCGGTACTACTGCCAGCACTACTACAGCACCCCCTACACCTT<br>CGGCTGCGGCACCAAGCTGGAAATCAAAGGAGGCGGCGGAAGTG<br>TGCACATGCCCCTGGGCTTCCTGGGCCCCAGACAGGCCAGAGTCG<br>TGAACGGGGGGGGCGGAGGCAGTGGGGGGGAGGATCCCAGGC<br>CGTCGTGACCCAGGAACCCAGCCTGACAGTGTCTCCTGGCGGCAC<br>CGTGACCCTGACATGTGGCAGTTCTACAGGCGCCGTGACCACCAG<br>CAACTACGCCAACTGGGTGCAGGAAAAGCCCGGCCAGGCCTTCAG<br>AGGACTGATCGGCGGCACCAACAAGAGAGCCCCTGGCACCCCTGC<br>CAGATTCAGCGGATCTCTGCTGGGAGGAAAGGCCGCCCTGACACT<br>GTCTGGCGCCCAGCCAGAAGATGAGGCCGAGTACTACTGCGCCCT<br>GTGGTACAGCAACCTGTGGGTGTTCGGCGGAGGCACCAAGCTGAC<br>AGTGCTGAGCAGCGCTTCCACCAAGGGACCCAGTGTGTTCCCCCT<br>GGCCCCCAGCTCCAAGTCTACATCCGGTGGCACAGCTGCCCTGGG<br>ATGTCTCGTGAAGGACTACTTTCCTGAGCCTGTGACAGTGTCTTGG<br>AACAGCGGAGCCCTGACCAGCGGAGTGCACACATTCCCTGCAGTG<br>CTGCAGAGCAGCGGCCTGTATAGCCTGAGCAGCGTCGTGACCGTG<br>CCTTCCTCTAGCCTGGGAACACAGACATATATCTGTAATGTGAATCA<br>TAAGCCCAGTAATACCAAAGTGGATAAGAAAGTGGAACCTAAGAGC<br>TGCGATGGCGGAGGAGGGTCCGGAGGCGGAGGGTCCCAGGTGCA<br>ATTGGTTCAATCTGGTGCTGAAGTAAAAAAACCGGGCGCTTCCGTT<br>AAAGTGAGCTGCAAAGCATCCGGATACACCTTCACTTCCTATTACAT<br>GCACTGGGTTCGTCAAGCCCCGGGCCAGGGTCTGGAATGGATGG<br>GCATCATTAACCCAAGCGGTGGCTCTACCTCCTACGCGCAGAAATT<br>CCAGGGTCGCGTCACGATGACCCATGACACTAGCACCTCTACCGT<br>TTATATGGAGCTGTCCAGCCTGCGTTCTGAAGATACTGCAGTGTAC<br>TACTGTGCACGCTCTTTCTTCACTGGTTTCCATCTGGACTATTGGG<br>GTCAAGGCACCCTCGTAACGGTTTCTTCTGCTAGCACCAAGGGCC<br>CCTCCGTGTTCCCCCTGGCCCCCAGCAGCAAGAGCACCAGCGGC<br>GGCACAGCCGCTCTGGGCTGCCTGGTCGAGGACTACTTCCCCGAG<br>CCCGTGACCGTGTCCTGGAACAGCGGAGCCCTGACCTCCGGCGT<br>GCACACCTTCCCCGCCGTGCTGCAGAGTTCTGGCCTGTATAGCCT<br>GAGCAGCGTGGTCACCGTGCCTTCTAGCAGCCTGGGCACCCAGAC<br>CTACATCTGCAACGTGAACCACAAGCCCAGCAACACCAAGGTGGA<br>CGAGAAGGTGGAGCCCAAGAGCTGCGACAAAACTCACACATGCCC<br>ACCGTGCCCAGCACCTGAAGCTGCAGGGGGACCGTCAGTCTTCCT<br>CTTCCCCCCAAAACCCAAGGACACCCTCATGATCTCCCGGACCCCT<br>GAGGTCACATGCGTGGTGGTGGACGTGAGCCACGAAGACCCTGAG<br>GTCAAGTTCAACTGGTACGTGGACGGCGTGGAGGTGCATAATGCC<br>AAGACAAAGCCGCGGGAGGAGCAGTACAACAGCACGTACCGTGTG<br>GTCAGCGTCCTCACCGTCCTGCACCAGGACTGGCTGAATGGCAAG<br>GAGTACAAGTGCAAGGTCTCCAACAAAGCCCTCGGCGCCCCCATC<br>GAGAAAACCATCTCCAAAGCCAAAGGGCAGCCCCGAGAACCACAG<br>GTGTACACCCTGCCCCCATGCCGGGATGAGCTGACCAAGAACCAG<br>GTCAGCCTGTGGTGCCTGGTCAAAGGCTTCTATCCCAGCGACATC<br>GCCGTGGAGTGGGAGAGCAATGGGCAGCCGGAGAACAACTACAA<br>GACCACGCCTCCCGTGCTGGACTCCGACGGCTCCTTCTTCCTCTA<br>CAGCAAGCTCACCGTGGACAAGAGCAGGTGGCAGCAGGGGAACG<br>TCTTCTCATGCTCCGTGATGCATGAGGCTCTGCACAACCACTACAC<br>GCAGAAGAGCCTCTCCCTGTCTCCGGGTAAATGA | 168 |
| anti CD3<br>(CH2527<br>VH_3-23(12)<br>VL7-46(13))<br>scFv 4.32.63<br>non cleavable<br>linker aFolR1<br>36F2 VH CH1<br>EE CH2527-<br>VL7_46-13<br>CH1 hum Fc | AGAGTCCGGCCCTGGACTGGTGGCCCCTAGCCAGAGCCTGAGCAT<br>CACCTGTACCGTGTCCGGCTTCAGCCTGACCAGCTACGGCGTGTC<br>ATGGGTGCGCCAGCCTCCAGGCAAGTGTCTGGAATGGCTGGGCAT<br>CATCTGGGGCGACGGCAGCACCAATTACCACAGCGCCCTGATCAG<br>CAGACTGAGCATCTCCAAGGACAACAGCAAGAGCCAGGTGTTCCT<br>GAAGCTGAACAGCCTGCAGACCGACGACACCGCCACCTACTACTG<br>CGCCAAGGGCATCACCACCGTGGTGGACGACTACTACGCTATGGA<br>CTACTGGGGCCAGGGCACCAGCGTGACAGTGTCTAGCGGAGGCG<br>GAGGATCTGGCGGCGGAGGAAGTGGCGGAGGGGGATCTGGGGG<br>AGGCGGAAGCGATATCCAGATGACCCAGAGCCCTGCCAGCCTGTC<br>TGCCTCTGTGGGCGAGACAGTGACCATCACATGCCGGGCCAGCGA | 169 |

| | | |
|---|---|---|
| knob PG LALA pETR17622 | GAACATCGACAGCTACCTGGCCTGGTATCAGCAGAAGCAGGGCAA<br>GAGCCCCCAGCTGCTGGTGTACGCCGCCACCTTTCTGGCCGACGA<br>TGTGCCCAGCAGATTCAGCGGCAGCGGAAGCGGCACACAGTACAG<br>CCTGAAGATCAACTCCCTGCAGAGCGAGGACGTGGCCCGGTACTA<br>CTGCCAGCACTACAGCACCCCCTACACCTTCGGCTGCGGCAC<br>CAAGCTGGAAATCAAAGGCGGGGGAGGCTCCGGAGGCGGCGGAA<br>GTGGAGGCGGCGGAAGTGGCGGAGGCGGAGGGGGGGAAGTGG<br>GGGCGGAGGCAGTGGGGGGGAGGATCCCAGGCCGTCGTGACC<br>CAGGAACCCAGCCTGACAGTGTCTCCTGGCGGCACCGTGACCCTG<br>ACATGTGGCAGTTCTACAGGCGCCGTGACCACCAGCAACTACGCC<br>AACTGGGTGCAGGAAAAGCCCGGCCAGGCCTTCAGAGGACTGATC<br>GGCGGCACCAACAAGAGAGCCCCTGGCACCCCTGCCAGATTCAGC<br>GGATCTCTGCTGGGAGGAAAGGCCGCCCTGACACTGTCTGGCGCC<br>CAGCCAGAAGATGAGGCCGAGTACTACTGCGCCCTGTGGTACAGC<br>AACCTGTGGGTGTTCGGCGGAGGCACCAAGCTGACAGTGCTGAGC<br>AGCGCTTCCACCAAGGGACCCAGTGTGTTCCCCCTGGCCCCCAGC<br>TCCAAGTCTACATCCGGTGGCACAGCTGCCCTGGGATGTCTCGTG<br>AAGGACTACTTTCCTGAGCCTGTGACAGTGTCTTGGAACAGCGGAG<br>CCCTGACCAGCGGAGTGCACACATTCCCTGCAGTGCTGCAGAGCA<br>GCGGCCTGTATAGCCTGAGCAGCGTCGTGACCGTGCCTTCCTCTA<br>GCCTGGGAACACAGACATATATCTGTAATGTGAATCATAAGCCCAG<br>TAATACCAAAGTGGATAAGAAAGTGGAACCTAAGAGCTGCGATGGC<br>GGAGGAGGGTCTGGAGGCGGAGGGTCCCAGGTGCAATTGGTTCA<br>ATCTGGTGCTGAAGTAAAAAAACCGGGCGCTTCCGTTAAAGTGAGC<br>TGCAAAGCATCCGGATACACCTTCACTTCCTATTACATGCACTGGG<br>TTCGTCAAGCCCCGGGCCAGGGTCTGGAATGGATGGGCATCATTA<br>ACCCAAGCGGTGGCTCTACCTCCTACGCGCAGAAATTCCAGGGTC<br>GCGTCACGATGACCCATGACACTAGCACCTCTACCGTTTATATGGA<br>GCTGTCCAGCCTGCGTTCTGAAGATACTGCAGTGTACTACTGTGCA<br>CGCTCTTTCTTCACTGGTTTCCATCTGGACTATTGGGGTCAAGGCA<br>CCCTCGTAACGGTTTCTTCTGCTAGCACCAAGGGCCCCTCCGTGTT<br>CCCCCTGGCCCCCAGCAGCAAGAGCACCAGCGGCGGCACAGCCG<br>CTCTGGGCTGCCTGGTCGAGGACTACTTCCCCGAGCCCGTGACCG<br>TGTCCTGGAACAGCGGAGCCCTGACCTCCGGCGTGCACACCTTCC<br>CCGCCGTGCTGCAGAGTTCTGGCCTGTATAGCCTGAGCAGCGTGG<br>TCACCGTGCCTTCTAGCAGCCTGGGCACCCAGACCTACATCTGCAA<br>CGTGAACCACAAGCCCAGCAACACCAAGGTGGACGAGAAGGTGGA<br>GCCCAAGAGCTGCGACAAAACTCACACATGCCCACCGTGCCCAGC<br>ACCTGAAGCTGCAGGGGGACCGTCAGTCTTCCTCTTCCCCCCAAA<br>ACCCAAGGACACCCTCATGATCTCCCGGACCCCTGAGGTCACATG<br>CGTGGTGGTGGACGTGAGCCACGAAGACCCTGAGGTCAAGTTCAA<br>CTGGTACGTGGACGGCGTGGAGGTGCATAATGCCAAGACAAAGCC<br>GCGGGAGGAGCAGTACAACAGCACGTACCGTGTGGTCAGCGTCCT<br>CACCGTCCTGCACCAGGACTGGCTGAATGGCAAGGAGTACAAGTG<br>CAAGGTCTCCAACAAAGCCCTCGGCGCCCCCATCGAGAAAACCAT<br>CTCCAAAGCCAAAGGGCAGCCCCGAGAACCACAGGTGTACACCCT<br>GCCCCCATGCCCGGATGAGCTGACCAAGAACCAGGTCAGCCTGTG<br>GTGCCTGGTCAAAGGCTTCTATCCCAGCGACATCGCCGTGGAGTG<br>GGAGAGCAATGGGCAGCCGGAGAACAACTACAAGACCACGCCTCC<br>CGTGCTGGACTCCGACGGCTCCTTCTTCCTCTACAGCAAGCTCACC<br>GTGGACAAGAGCAGGTGGCAGCAGGGGAACGTCTTCTCATGCTCC<br>GTGATGCATGAGGCTCTGCACAACCACTACACGCAGAAGAGCCTC<br>TCCCTGTCTCCGGGTAAATGA | |
| FolR1 36F2 classic format: 0H2527 XFab 36F2 HC EE Fc knob PG LALA pETR17623 | CAGGCCGTCGTGACCCAGGAACCCAGCCTGACAGTGTCTCCTGGC<br>GGCACCGTGACCCTGACATGTGGCAGTTCTACAGGCGCCGTGACC<br>ACCAGCAACTACGCCAACTGGGTGCAGGAAAAGCCCGGCCAGGCC<br>TTCAGAGGACTGATCGGCGGCACCAACAAGAGAGCCCCTGGCACC<br>CCTGCCAGATTCAGCGGATCTCTGCTGGGAGGAAAGGCCGCCCTG<br>ACACTGTCTGGCGCCCAGCCAGAAGATGAGGCCGAGTACTACTGC<br>GCCCTGTGGTACAGCAACCTGTGGGTGTTCGGCGGAGGCACCAAG<br>CTGACAGTGCTGAGCAGCGCTTCCACCAAGGGACCCAGTGTGTTC<br>CCCCTGGCCCCCAGCTCCAAGTCTACATCCGGTGGCACAGCTGCC<br>CTGGGATGTCTCGTGAAGGACTACTTTCCTGAGCCTGTGACAGTGT<br>CTTGGAACAGCGGAGCCCTGACCAGCGGAGTGCACACATTCCCTG<br>CAGTGCTGCAGAGCAGCGGCCTGTATAGCCTGAGCAGCGTCGTGA<br>CCGTGCCTTCCTCTAGCCTGGGAACACAGACATATATCTGTAATGT<br>GAATCATAAGCCCAGTAATACCAAAGTGGATAAGAAAGTGGAACCT<br>AAGAGCTGCGATGCGGAGGAGGGTCTGGAGGCGGAGGGTCCCA<br>GGTGCAATTGGTTCAATCTGGTGCTGAAGTAAAAAAACCGGGCGCT<br>TCCGTTAAAGTGAGCTGCAAAGCATCCGGATACACCTTCACTTCCT<br>ATTACATGCACTGGGTTCGTCAAGCCCCGGGCCAGGGTCTGGAAT<br>GGATGGGCATCATTAACCCAAGCGGTGGCTCTACCTCCTACGCGC<br>AGAAATTCCAGGGTCGCGTCACGATGACCCATGACACTAGCACCTC<br>TACCGTTTATATGGAGCTGTCCAGCCTGCGTTCTGAAGATACTGCA<br>GTGTACTACTGTGCACGCTCTTTCTTCACTGGTTTCCATCTGGACTA<br>TTGGGGTCAAGGCACCCTCGTAACGGTTTCTTCTGCTAGCACCAAG<br>GGCCCCTCCGTGTTCCCCCTGGCCCCCAGCAGCAAGAGCACCAGC<br>GGCGGCACAGCCGCTCTGGGCTGCCTGGTCGAGGACTACTTCCCC | 170 |

```
                    GAGCCCGTGACCGTGTCCTGGAACAGCGGAGCCCTGACCTCCGG
                    CGTGCACACCTTCCCCGCCGTGCTGCAGAGTTCTGGCCTGTATAG
                    CCTGAGCAGCGTGGTCACCGTGCCTTCTAGCAGCCTGGGCACCCA
                    GACCTACATCTGCAACGTGAACCACAAGCCCAGCAACACCAAGGT
                    GGACGAGAAGGTGGAGCCCAAGAGCTGCGACAAAACTCACACATG
                    CCCACCGTGCCCAGCACCTGAAGCTGCAGGGGGACCGTCAGTCTT
                    CCTCTTCCCCCCAAAACCCAAGGACACCCTCATGATCTCCCGGACC
                    CCTGAGGTCACATGCGTGGTGGTGGACGTGAGCCACGAAGACCCT
                    GAGGTCAAGTTCAACTGGTACGTGGACGGCGTGGAGGTGCATAAT
                    GCCAAGACAAAGCCGCGGGAGGAGCAGTACAACAGCACGTACCGT
                    GTGGTCAGCGTCCTCACCGTCCTGCACCAGGACTGGCTGAATGGC
                    AAGGAGTACAAGTGCAAGGTCTCCAACAAAGCCCTCGGCGCCCCC
                    ATCGAGAAAACCATCTCCAAAGCCAAAGGGCAGCCCCGAGAACCA
                    CAGGTGTACACCCTGCCCCCATGCCGGGATGAGCTGACCAAGAAC
                    CAGGTCAGCCTGTGGTGCCTGGTCAAAGGCTTCTATCCCAGCGAC
                    ATCGCCGTGGAGTGGGAGAGCAATGGGCAGCCGGAGAACAACTAC
                    AAGACCACGCCTCCCGTGCTGGACTCCGACGGCTCCTTCTTCCTCT
                    ACAGCAAGCTCACCGTGGACAAGAGCAGGTGGCAGCAGGGGAAC
                    GTCTTCTCATGCTCCGTGATGCATGAGGCTCTGCACAACCACTACA
                    CGCAGAAGAGCCTCTCCCTGTCTCCGGGTAAATGA
```

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An idiotype-specific polypeptide covalently attached through a linker to a T cell activating bispecific molecule comprising an anti-CD3 antigen-binding site, the idiotype-specific polypeptide specifically binding to an idiotype of the anti-CD3 antigen-binding site to reversibly conceal the anti-CD3 antigen-binding site, wherein the linker is a protease-cleavable linker comprising a protease recognition site of SEQ ID NO: 106.

2. The idiotype-specific polypeptide of claim 1, wherein the idiotype-specific polypeptide is an anti-idiotype scFv.

3. The idiotype-specific polypeptide of claim 1, wherein the linker is a peptide linker.

4. A pharmaceutical composition comprising the idiotype-specific polypeptide of claim 1 and a pharmaceutically acceptable carrier.

5. The idiotype-specific polypeptide of claim 1, wherein the protease-cleavable linker comprises the protease recognition sequence of SEQ ID NO: 106.

* * * * *

UNITED STATES PATENT AND TRADEMARK OFFICE
CERTIFICATE OF CORRECTION

PATENT NO. : 11,242,390 B2
APPLICATION NO. : 16/138417
DATED : February 8, 2022
INVENTOR(S) : Peter Bruenker et al.

It is certified that error appears in the above-identified patent and that said Letters Patent is hereby corrected as shown below:

On the Title Page

Delete the title page and replace with the attached title page showing the corrected number of claims.

In the Specification

Column 2, Line 11, replace "(19%))" with --(1996))--.

Column 4, Line 25, replace "GITIVVD" with --GITTVVD--;
  Line 41, replace "IWGDGSTNYH" with --IIWGDGSTNYH--;
  Line 43, replace "GTITVVD" with --GITTVVD--.

Column 6, Line 7, replace "NO: 17. SEQ" with --NO: 17, SEQ--;
  Line 54, replace "95%. 96%," with --95%, 96%,--.

Column 7, Line 12, replace "95%. 96%," with --95%, 96%,--;
  Line 65, replace "96%. 97%," with --96%, 97%,--.

Column 8, Line 25, replace "95%. %%," with --95%, 96%,--;
  Line 34, replace "NO: 56. SEQ" with --NO: 56, SEQ--;
  Line 41, replace "95%, %%," with --95%, 96%,--;
  Line 44, replace "95%, %%," with --95%, 96%,--.

Column 11, Line 39, replace "IWGDGSTNYH" with --IIWGGSTNYH--;
  Line 41, replace "GITIVVD" with --GITTVVD--;
  Line 57, replace "IWGDGSTNYH" with --IIWGDGSTNYH--;
  Line 59, replace "GITVVD" with --GITTVVD--.

Column 14, Line 2, replace "(H)" with --(II)--.

Signed and Sealed this
Twenty-seventh Day of August, 2024

Katherine Kelly Vidal
*Director of the United States Patent and Trademark Office*

Column 15, Line 61, replace "74%" with --7496--.

Column 16, Line 11, replace "74%" with --7496--;
　　　　Line 40, replace "mask. cleavable" with --mask, cleavable--;
　　　　Line 48, replace "mask. cleavable" with --mask, cleavable--.

Column 17, Line 3, replace "mask. cleavable" with --mask, cleavable--;
　　　　Line 20, replace "mask. cleavable" with --mask, cleavable--;
　　　　Line 45, replace "10:1. effectors" with --10:1, effectors--.

Column 19, Line 9, replace "CD3e" with --CD3ε--;
　　　　Line 13, replace "(Promega). The FolR1 TCB" with --(Promega). ¶ The FolR1 TCB--;
　　　　Line 63, replace "CD8'" with --CD8$^+$--.

Column 20, Line 9, replace "H5%" with --H596--.

Column 21, Line 23, replace "Typically. a" with --Typically, a--.

Column 26, Line 24, replace "(isotypes). e.g.," with --(isotypes), e.g.,--;
　　　　Line 40, replace "Kahat" with --Kabat--.

Column 29, Line 7, replace "and B. and" with --and B, and--.

Column 38, Line 31, replace "(G$_4$5)$_2$" with --(G$_4$S)$_2$--.

Column 41, Line 38, replace "95%. 96%," with --95%, 96%,--;
　　　　Line 61, replace "107. SEQ" with --107, SEQ--;
　　　　Line 63, replace "NO: 11" with --NO: 111--.

Column 42, Line 55, replace "Fe" with --Fc--;
　　　　Line 61, replace "Fe" with --Fc--.

Column 44, Line 44, replace "55. wherein" with --55, wherein--;
　　　　Line 52, replace "95%, %%," with --95%, 96%,--.

Column 45, Line 34, replace "95%. 96%," with --95%, 96%,--;
　　　　Line 35, replace "97%. 98%," with --97%, 98%,--;
　　　　Line 45, replace "17. the" with --17, the--.

Column 46, Line 8, replace "55. wherein" with --55, wherein--;
　　　　Line 28, replace "95%. 96%," with --95%, 96%,--;
　　　　Line 61, replace "55. wherein" with --55, wherein--.

Column 48, Line 5, replace "(VH$_{(2)}$-CH$_{(1)}$-" with --(VH$_{(2)}$-CH1$_{(2)}$- --;
　　　　Line 51, replace "CH1-CH2" with --CH1$_{(1)}$-CH2--.

Column 50, Line 19, replace "Helerodimerization" with --Heterodimerization--.

Column 51, Line 55, replace "properties. including" with --properties, including--.

Column 52, Line 16, replace "20%." with --20%,--.

Column 53, Line 26, replace "Ft" with --Fc--.

Column 55, Line 17, replace "82. 1499-1502" with --82, 1499-1502--;
    Line 23, replace "CytoTox 96" with --CytoTox 96®--.

Column 56, Line 53, replace "antigen am" with --antigen are--.

Column 58, Line 63, replace "NO: 26. the" with --NO: 26, the--.

Column 59, Line 55, replace "90. 91," with --90, 91,--.

Column 61, Line 31, replace "90. 91," with --90, 91,--.

Column 62, Line 38, replace "NO: 24. the" with --NO: 24, the--.

Column 63, Line 43, replace "92. 93," with --92, 93,--.

Column 68, Line 51, replace "PLFLGPRQARVVNG" with --PLGFLGPRQARVVNG--.

Column 72, Line 13, replace "protcase-activatable" with --protease-activatable--.

Column 73, Line 52, replace "reaction. or" with --reaction, or--.

Column 74, Line 29, replace "rabbit I-globin," with --rabbit â-globin,--.

Column 75, Line 66, replace "Viral" with --Virol--.

Column 76, Line 1, replace "Rcprod" with --Reprod--.

Column 77, Line 38, replace "Verhocycn" with --Verhoeyen--;
    Line 49, replace "Cuff" with --Curr--.

Column 78, Line 6, replace "2004/0132066. the" with --2004/0132066, the--;
    Line 25, replace "Protocols.”" with --Protocols,”--.

Column 80, Line 65-66, replace "preservatives. antioxidants" with --preservatives, antioxidants--.

Column 86, Line 10, replace "body wright" with --body weight--.

Column 87, Line 3, replace "LDs/ED$_{50}$." with --LD$_{50}$/ED$_{50}$ .--;

CERTIFICATE OF CORRECTION (continued)
U.S. Pat. No. 11,242,390 B2

Line 51, replace "agent. an inhibitor" with --agent, an inhibitor--.

Column 89, Line 36, replace "9. wherein" with --9, wherein--.

Column 90, Line 30, replace "23. wherein" with --23, wherein--.

Column 95, Line 21, replace "54. wherein" with --54, wherein--;
Line 35, replace "154. SEQ" with --154, SEQ--;
Line 49, replace "(CDR L)I" with --(CDR L)1--;
Line 63, replace "96%. 97%," with --96%, 97%,--.

Column 96, Line 64-65, replace "65. wherein" with --65, wherein--.

Column 102, Line 41, replace "MAKCCEA" with --MAK<CEA--.

Column 103, Line 56, replace "with >92% monomer" with --with ≥ 92% monomer--.

Column 104, Line 37, replace "CD3e" with --CD3ε--;
Line 48, replace "-2.56 μM." with -- -2.56pM--.

Column 106, Line 3, replace "mg / l" with --mg/1--;
Line 53, replace "Tris-Acetate. Invitrogen)" with --Tris-Acetate, Invitrogen)--.

Column 107, Line 2, replace "with >92% monomer" with --with ≥ 92% monomer--;
Line 61, replace "temperature). the" with --temperature), the--.

Column 110, Line 1, replace "cells/mi" with --cells/ml--;
Line 15, replace "10.000 μM" with --10.000 pM--;
Line 46, replace "C02" with --$CO_2$--;
Line 50, replace "FCS. 1×" with --FCS, 1×--.

Column 111, Line 24, replace "400xg. 10" with --400xg, 10--;
Line 64, replace "100 μM" with --100 pM--.

Column 113, Line 9, replace "Hiload" with --HiLoad--;
Line 37, replace ">95%" with --≥ 95%--.

Column 114, Line 26, replace "(FIG. 31) To confirm the" with --(FIG. 31) ¶ To confirm the--;
Line 50, replace "antibody. indicating" with --antibody, indicating--.

Column 116, Line 65, replace ">95%" with --≥ 95%--.

Column 117, Line 50, replace "Protean" with --Protease--.

Column 118, Line 38, replace "(400xg. 10" with --(400xg, 10--.

CERTIFICATE OF CORRECTION (continued)
U.S. Pat. No. 11,242,390 B2

Column 120, Line 29, replace "C02" with --$CO_2$--.

Column 121, Line 45, replace "samples. Jurkat-NFAT" with --samples. ¶ Jurkat-NFAT--.

Column 122, Line 24, replace "C02" with --CO2--;
    Line 29, replace "TL-15216." with --TL-15216,--;
    Line 34, replace "C02" with --CO2--;
    Line 36, replace "C02" with --CO2--;
    Line 64, replace "ID 827" with --ID 8957--.

Column 123, Line 5, replace "132. 133" with --132, 133--;
    Line 15, replace "variants. CD3" with --variants, CD3--;
    Line 19, replace "137. 138" with --137, 138--.

Columns 125-126, SEQ ID No 4, Amino Acid Sequence, replace
    "VVVGRIKSKTDGGTTDYAAPVKGRFTISRDDSKNTLYLQMNS" with
    --WVGRIKSKTDGGTTDYAAPVKGRFTISRDDSKNTLYLQMNS--.

Columns 127-128, SEQ ID No 5, Amino Acid Sequence, replace
"LKTEDTAVYYCTTPWEWSWYDYVVGQGTLVTVSSASTKGPS" with
-- LKTEDTAVYYCTTPWEWSWYDYWGQGTLVTVSSASTKGPS--.

Columns 127-128, SEQ ID No 6, Construct, replace "CH1 FolR1 1605 VH" with
    --CH1 FolR1 16D5 VH--.

Columns 127-128, SEQ ID No 6, Amino Acid Sequence, replace
    "VLQSSGLYSLSSVVIVPSSSLGTQTYICNVNHKPSNTKVDKK" with
    --VLQSSGLYSLSSVVTVPSSSLGTQTYICNVNHKPSNTKVDKK--.

Columns 129-130, SEQ ID No 23, Construct, replace "415.64" with --4.15.64--.

Columns 131-132, SEQ ID No 54, Amino Acid Sequence, replace
    "MQSGTHWRVLGLCLLSVGVWGQDGNEEMGGITIQTPYKVSI" with
    --MQSGTHWRVLGLCLLSVGVWGQDGNEEMGGITQTPYKVSI--;
    replace "MEMDVMSVATIVIVDICITGGLLLLVYYVVSKNRKAKAKPVTRG" with
    --MEMDVMSVATIVIVDICITGGLLLLVYYWSKNRKAKAKPVTRG--.

Columns 137-138, SEQ ID No 66, DNA Sequence, delete line space after
    "GAATGGCTGGGCATCATCTGGGGCGACGGCAGCACCAATTACCAC".

Columns 141-142, SEQ ID No 69, DNA Sequence, replace
    "TTCTCTMCCACCCAAGCCTAAGC ⎯ ⎯ ⎯ ⎯ TCTGATGATATCCAGGAC" with
    --TTCTCTTCCCACCCAAGCCTAAGGATACTCTGATGATATCCAGGAC--.

Columns 143-144, SEQ ID No 72, Amino Acid Sequence, replace
    "WNSGALTSGVHTFPAVLQSSGLYSLSSVVIVPSSSLGTQTYI" with

CERTIFICATE OF CORRECTION (continued)
U.S. Pat. No. 11,242,390 B2

--WNSGALTSGVHTFPAVLQSSGLYSLSSVVTVPSSSLGTQTYI--;
replace "NTKVDKKVEPKSCDKTHTCPPCPAPEAAGGPSVFLFPPKpK" with
--NTKVDKKVEPKSCDKTHTCPPCPAPEAAGGPSVFLFPPKPK--.

Columns 143-144, SEQ ID No 75, Amino Acid Sequence, replace
"QVQLKESGPGLVAPSQSLSITCTVSGFSLTSYGVSWVIRQPP" with
--QVQLKESGPGLVAPSQSLSITCTVSGFSLTSYGVSWVRQPP--.

Columns 145-146, SEQ ID No 75, Amino Acid Sequence, replace
"AVVTQEPSLTVSPGGTVTLICGSSTGAVTTSNYANWVQEKP" with
--AVVTQEPSLTVSPGGTVTLTCGSSTGAVTTSNYANWVQEKP--.

Columns 145-146, SEQ ID No 76, Amino Acid Sequence, replace
"GINKRAPGTPARFSGSLLGGKAALTLSGAQPEDEAEYYCAL" with
--GTNKRAPGTPARFSGSLLGGKAALTLSGAQPEDEAEYYCAL--.

Columns 145-146, SEQ ID No 78, Amino Acid Sequence, replace
"APKWYDTSKLASGVPSRFSGSGSGTDFTLTISSLOPEDFAT" with
--APKLLIYDTSKLASGVPSRFSGSGSGTDFTLTISSLQPEDFAT--.

Columns 145-146, SEQ ID No 79, Amino Acid Sequence, replace
"QVQLKESGPGLVAPSQSLSITCTVSGFSLTSYGVSWVIRQPP" with
--QVQLKESGPGLVAPSQSLSITCTVSGFSLTSYGVSWVRQPP--;
replace "LLESGGGLVQPGGSLRLSCAASGFTFSTYAMNWVIRQAPGK" with
--LLESGGGLVQPGGSLRLSCAASGFTFSTYAMNWVRQAPGK--.

Columns 145-146, SEQ ID No 80, Amino Acid Sequence, replace
"QLLESGGGLVQPGGSLRLSCAASGFTFSTYAMNWVRQAPG" with
--QLLESGGGLVQPGGSLRLSCAASGFTFSTYAMNWVIRQAPG--;
replace "KGLEWVSRIRSKYNNYATYVADSVKGRFTISRDDSKNTLYLQ" with
--KGLEWVSRIRSKYNNYATYYADSVKGRFTISRDDSKNTLYLQ--.

Columns 147-148, SEQ ID No 82, Amino Acid Sequence, replace
"KASGYSFTGYTMNVVVRQAPGQGLEWMGLITPYNGASSYNQ" with
--KASGYSFTGYTMNWVRQAPGQGLEWMGLITPYNGASSYNQ--;
replace "KFRGKATMTVDTSTSTVYMELSSLRSEDTAVYYCARGGyDG" with
--KFRGKATMTVDTSTSTVYMELSSLRSEDTAVYYCARGGYDG--.

Columns 147-148, SEQ ID No 83, Amino Acid Sequence, replace
"GQAFRGLIGGINKRAPGTPARFSGSLLGGKAALTLSGAQIDE" with
--GQAFRGLIGGTNKRAPGTPARFSGSLLGGKAALTLSGAQPE--;
replace "QKFRGKATMTVDTS, TSTVYMELSSLRSEDTAVYYCARGGYD" with
--QKFRGKATMTVDTSTSTVYMELSSLRSEDTAVYYCARGGYD--.

Columns 147-148, SEQ ID No 84, Amino Acid Sequence, replace
"QAVVTQEPSLIVSPGGTVTLICGSSTGAVTTSNYANWVQEK" with

CERTIFICATE OF CORRECTION (continued)
U.S. Pat. No. 11,242,390 B2

--QAVVTQEPSLTVSPGGTVTLTCGSSTGAVTTSNYANWVQEK--.

Columns 149-150, SEQ ID No 85, Amino Acid Sequence, replace
"WNSGALTSGVHTFPAVLQSSGLYSLSSVVIVPSSSLGTQTY1" with
--WNSGALTSGVHTFPAVLQSSGLYSLSSVVTVPSSSLGTQTYI--.

Columns 151-152, SEQ ID No 114, Amino Acid Sequence, replace
"APKWYDTSKLASGVPSRFSGSGSGTDFTLTISSLOPEDFAT" with
--APKLLIYDTSKLASGVPSRFSGSGSGTDFTLTISSLOPEDFAT--.

Columns 151-152, SEQ ID No 116, Amino Acid Sequence, replace
"DIQNATQSPSKSASVGDRVTITCRASQGINNYLNWYQQKPGKA" with
--DIQMTQSPSSLSASVGDRVTITCRASQGINNYLNWYQQKPGKA--;
replace "PKRLEYNTNNWTGVPSRFSGSGSGTERITESSWPEDFATYYC" with
--PKRLIYNTNNLQTGVPSRFSGSGSGTEFTLTISSLOPEDFATYYC--.

Columns 153-154, SEQ ID No 119, DNA Sequence, replace
"ATGCCCACCGTGCCCAGCAQCTGAAGCTGCAGGGGGACCGTCAGT" with
--ATGCCCACCGTGCCCAGCACCTGAAGCTGCAGGGGGACCGTCAGT--.

Columns 159-160, SEQ ID No 125, DNA Sequence, replace
"CACCTTCCGACGAGCAGCTGAAGTCCGGCACCGCTrCTGTCGTGT" with
-- CACCTTCCGACGAGCAGCTGAAGTCCGGCACCGCTTCTGTCGTGT--.

Columns 167-168, SEQ ID No 134, Amino Acid Sequence, replace
"GFYAMDYVVGQGTLVTVSSASTKGPSVFPLAPSSKSTSGGT" with
--GFYAMDYWGQGTLVTVSSASTKGPSVFPLAPSSKSTSGGT--.

Columns 167-168, SEQ ID No 135, Construct, replace "CH1 EE 0H2527" with --CH1 EE CH2527--.

Columns 169-170, SEQ ID No 139, Construct, replace "VH CH1 EE 0H2527" with --VH CH1 EE CH2527--.

Columns 181-182, SEQ ID No 170, Construct, replace "0H2527 XFab" with --CH2527 XFab--.

In the Claims

Column 400, Claim 5, delete Claim 5.

(12) United States Patent
Bruenker et al.

(10) Patent No.: US 11,242,390 B2
(45) Date of Patent: Feb. 8, 2022

(54) PROTEASE-ACTIVATED T CELL BISPECIFIC MOLECULES

(71) Applicant: Hoffmann-La Roche Inc., Little Falls, NJ (US)

(72) Inventors: Peter Bruenker, Hittnau (CH); Rebecca Croasdale-Wood, Preston (GB); Christian Klein, Bonstetten (CH); Juergen Michael Schanzer, Munich (DE); Kay-Gunnar Stubenrauch, Penzberg (DE); Pablo Umana, Wollerau (CH); Martina Geiger, Obfelden (CH); Eric Sullivan, Pleasanton, CA (US); Jigar Patel, Pleasanton, CA (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/138,417

(22) Filed: Sep. 21, 2018

(65) Prior Publication Data

US 2019/0119383 A1    Apr. 25, 2019

Related U.S. Application Data

(63) Continuation of application No. PCT/EP2017/056556, filed on Mar. 20, 2017.

(60) Provisional application No. 62/433,327, filed on Dec. 13, 2016.

(30) Foreign Application Priority Data

Mar. 22, 2016    (EP) .................................. 16161740

(51) Int. Cl.
*C07K 16/28* (2006.01)
*A61P 35/00* (2006.01)
*C07K 16/42* (2006.01)
*A61K 39/00* (2006.01)

(52) U.S. Cl.
CPC .......... *C07K 16/2809* (2013.01); *A61P 35/00* (2018.01); *C07K 16/28* (2013.01); *C07K 16/2863* (2013.01); *C07K 16/4208* (2013.01); *A61K 2039/505* (2013.01); *C07K 2317/31* (2013.01); *C07K 2317/524* (2013.01); *C07K 2317/526* (2013.01); *C07K 2317/55* (2013.01); *C07K 2317/622* (2013.01); *C07K 2317/64* (2013.01); *C07K 2317/71* (2013.01); *C07K 2317/73* (2013.01); *C07K 2319/50* (2013.01)

(58) Field of Classification Search
CPC ............ C07K 16/2809; C07K 16/4208; C07K 16/28; C07K 16/2863; C07K 2317/526; C07K 2317/524; C07K 2317/31; C07K 2317/55; C07K 2317/64; C07K 2317/71; C07K 2319/50; C07K 2317/73; C07K 2317/622; C07K 7/06; C07K 7/08; A61P 35/00; A61K 2039/505

See application file for complete search history.

(56) References Cited

U.S. PATENT DOCUMENTS

| | | |
|---|---|---|
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,809,185 B1 | 10/2004 | Schoonjans et al. |
| 7,332,581 B2 | 2/2008 | Presta |
| 7,695,936 B2 | 4/2010 | Carter et al. |
| 8,227,577 B2 | 7/2012 | Klein et al. |
| 8,242,247 B2 | 8/2012 | Klein et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,969,526 B2 | 3/2015 | Baehner et al. |
| 9,068,008 B2 | 6/2015 | Mossner et al. |

(Continued)

FOREIGN PATENT DOCUMENTS

| | | |
|---|---|---|
| EP | 0404097 B1 | 9/1996 |
| EP | 1870459 A1 | 12/2007 |

(Continued)

OTHER PUBLICATIONS

Paul, Fundamental Immunology, 3rd Edition, pp. 292-295 (Year: 1993).*

(Continued)

*Primary Examiner* — Phuong Huynh

(74) *Attorney, Agent, or Firm* — Clark & Elbing LLP; Karen L. Elbing

(57) ABSTRACT

The present invention generally relates to novel protease-activatable T cell activating bispecific molecules and idiotype-specific polypeptides. The present invention also relates to polynucleotides encoding such protease-activatable T cell activating bispecific molecules and idiotype-specific polypeptides, and vectors and host cells comprising such polynucleotides. The invention further relates to methods for producing the protease-activatable T cell activating bispecific molecules and idiotype-specific polypeptides of the invention, and to methods of using these protease-activatable T cell activating bispecific molecules and idiotype-specific polypeptides in the treatment of disease.

4 Claims, 95 Drawing Sheets

Specification includes a Sequence Listing.